US012698507B2

(12) United States Patent
Sung et al.

(10) Patent No.: US 12,698,507 B2
(45) Date of Patent: Aug. 4, 2026

(54) METHODS AND COMPOSITIONS FOR CONFERRING AND/OR ENHANCING HERBICIDE TOLERANCE USING PROTOPORPHYRINOGEN IX OXIDASE OF VARIOUS CYANOBACTERIA OR VARIANT THEREOF

(71) Applicant: FarmHannong Co., Ltd., Seoul (KR)

(72) Inventors: Soon-Kee Sung, Daejeon (KR); Young Ock Ahn, Daejeon (KR); Joo Yong Woo, Daejeon (KR); Joonseon Yoon, Daejeon (KR); Hanul Kim, Daejeon (KR); Myoung-Ki Hong, Daejeon (KR); Joonghyuk Park, Daejeon (KR)

(73) Assignee: FARMHANNONG CO., LTD., Seoul (KR)

( * ) Notice: Subject to any disclaimer, the term of this patent is extended or adjusted under 35 U.S.C. 154(b) by 897 days.

(21) Appl. No.: 17/611,248

(22) PCT Filed: Jun. 12, 2020

(86) PCT No.: PCT/KR2020/007679
§ 371 (c)(1),
(2) Date: Nov. 15, 2021

(87) PCT Pub. No.: WO2020/251313
PCT Pub. Date: Dec. 17, 2020

(65) Prior Publication Data
US 2023/0175004 A1 Jun. 8, 2023

(30) Foreign Application Priority Data
Jun. 14, 2019 (KR) ........................ 10-2019-0071028

(51) Int. Cl.
*C12N 15/82* (2006.01)
*C12N 9/02* (2006.01)

(52) U.S. Cl.
CPC ......... *C12N 15/8274* (2013.01); *C12N 9/001* (2013.01); *C12Y 103/03004* (2013.01)

(58) Field of Classification Search
CPC ................................................. C12N 15/8274
USPC ....................................................... 800/278
See application file for complete search history.

(56) References Cited

U.S. PATENT DOCUMENTS

| | | | |
|---|---|---|---|
| 6,308,458 B1 | 10/2001 | Volrath et al. | |
| 10,392,630 B2 | 8/2019 | Aponte et al. | |
| 10,844,395 B2 * | 11/2020 | Sung ........................ | C12N 1/12 |
| 11,124,803 B2 | 9/2021 | Larue et al. | |

FOREIGN PATENT DOCUMENTS

| | | | |
|---|---|---|---|
| AU | 2018385130 | 7/2020 | |
| CA | 3024985 | 12/2017 | |
| CN | 101688219 | 3/2010 | |
| CN | 101998988 | 3/2011 | |
| CN | 107466321 | 12/2017 | |
| CN | 109476709 | 3/2019 | |
| CN | 109641940 | 4/2019 | |
| CN | 111727245 | 9/2020 | |
| CN | 117897378 | 4/2024 | |
| JP | 2014-504855 | 2/2014 | |
| KR | 20160073340 | 6/2016 | |
| KR | 20170142120 | * 12/2017 | |
| UY | 38011 | 2/2019 | |
| WO | 2008-153927 | 12/2008 | |
| WO | 2015/092706 | 6/2015 | |
| WO | 2017/217794 | 12/2017 | |
| WO | WO-2017217793 A1 * | 12/2017 | ........... C07K 14/195 |

OTHER PUBLICATIONS

Liang et al. GenBank Accession No. CP032152 (Year: 2018).*
Witkowski et al. Biochemistry 38:11643-11650 (Year: 1999).*
KIPO, PCT Search Report & Written Opinion of PCT/KR2020/007679 dated Mar. 4, 2021.
NCBI, GenBank AHB88054.1, protoporphyrinogen oxidase HemY [*Thermosynechococcus* sp. NK55a], Feb. 28, 2014.
Ujjana B. Nandihalli et al., "Relationships between Molecular Properties and Biological Activities of 0-Phenyl Pyrrolidino- and Piperidinocarbamate Herbicides", J, Agric. Food Chem. 1002, 40, 1993-2000.
Canadian Intellectual Property Office, Office Action of the corresponding Canadian Patent Application No. 3,143,319 dated Jan. 27, 2023.
Xin Liu et al., "Mutation of Protoporphyrinogen IX Oxidase Gene Causes Spotted and Rolled Leaf and Its Overexpression Generates Herbicide Resistance in Rice", Int. J. Mol. Sci. 2022, 23, 5781, May 21, 2022, https://doi.org/10.3390/ijms23105781.
UniProt Accession No. A0A3M2FF80, Protoporphyrinogen oxidase, Feb. 13, 2019.
SIPO, Office Action of CN 202080043536.5 dated Jun. 12, 2024.
GenBank: RMH63851.1: Mag: protoporphyrinogen oxidase [Cyanobacteria bacterium J003] (Oct. 29, 2018).
GenBank: BAY51976.1: protoporphyrinogen oxidase [Thermostichus vulcanus NIES-2134] (Oct. 25, 2017).
SIPO, Office Action of the corresponding Chinese Patent Application No. 202080043536.5., dated Feb. 13, 2025, total 11 pages.

* cited by examiner

*Primary Examiner* — Li Zheng
(74) *Attorney, Agent, or Firm* — LEX IP MEISTER, PLLC

(57) ABSTRACT

Provided are protoporphyrinogen IX oxidases derived from various organism or variants thereof, and uses of the same for conferring and/or enhancing herbicide tolerance of a plant and/or an alga.

20 Claims, 38 Drawing Sheets
Specification includes a Sequence Listing.

【Figure 1】
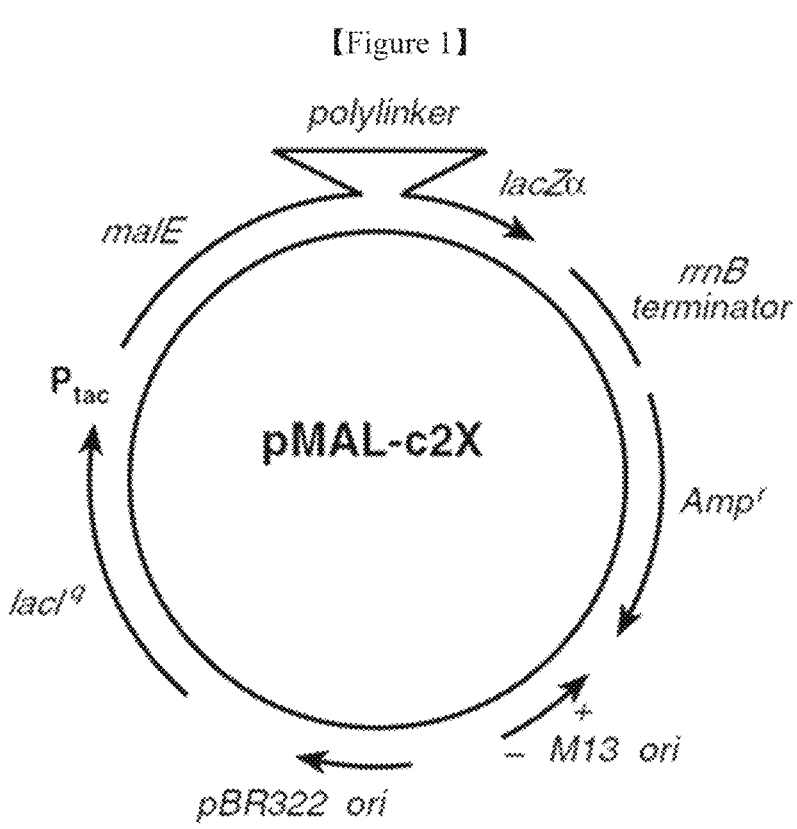

【Figure 2】
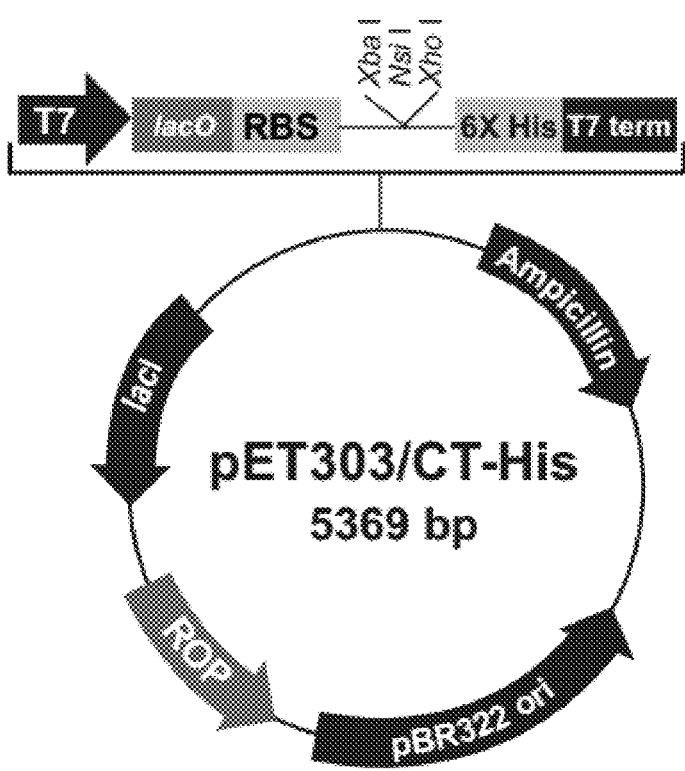
Comments for pET303 CT-His
5369 nucleotides
T7 promoter: bases 20-36
T7 promoter priming site: bases 20-39
lac operator (lacO): bases 39-63
Ribosome binding site (RBS): bases 95-100
6X His Tag: bases 119-136
T7 reverse priming site: bases 186-206
T7 transcription termination region: bases 147-277
F1 origin: bases 287-742
bla promoter: bases 775-879
Ampicillin (bla) resistance gene: bases 874-1734
pBR322 origin: bases 1945-2678 (c)
ROP ORF: bases 2920-3011 (c)
lacI ORF: bases 3914-5032 (c)

【Figure 3】
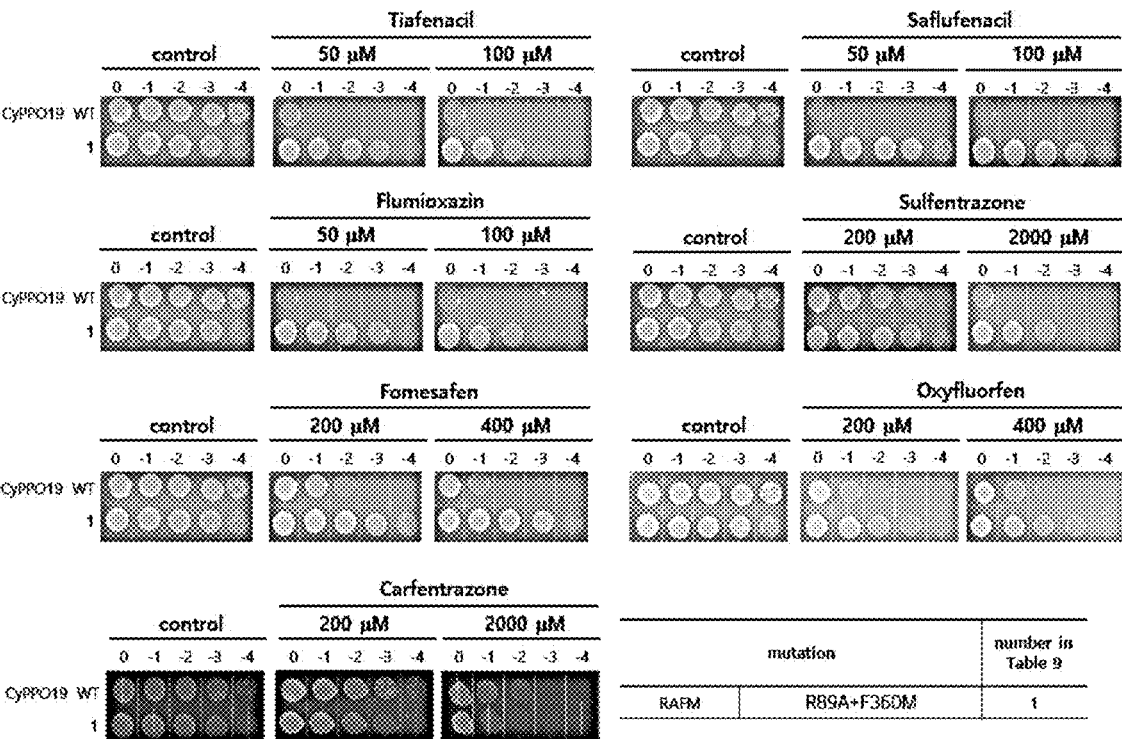

【Figure 4】
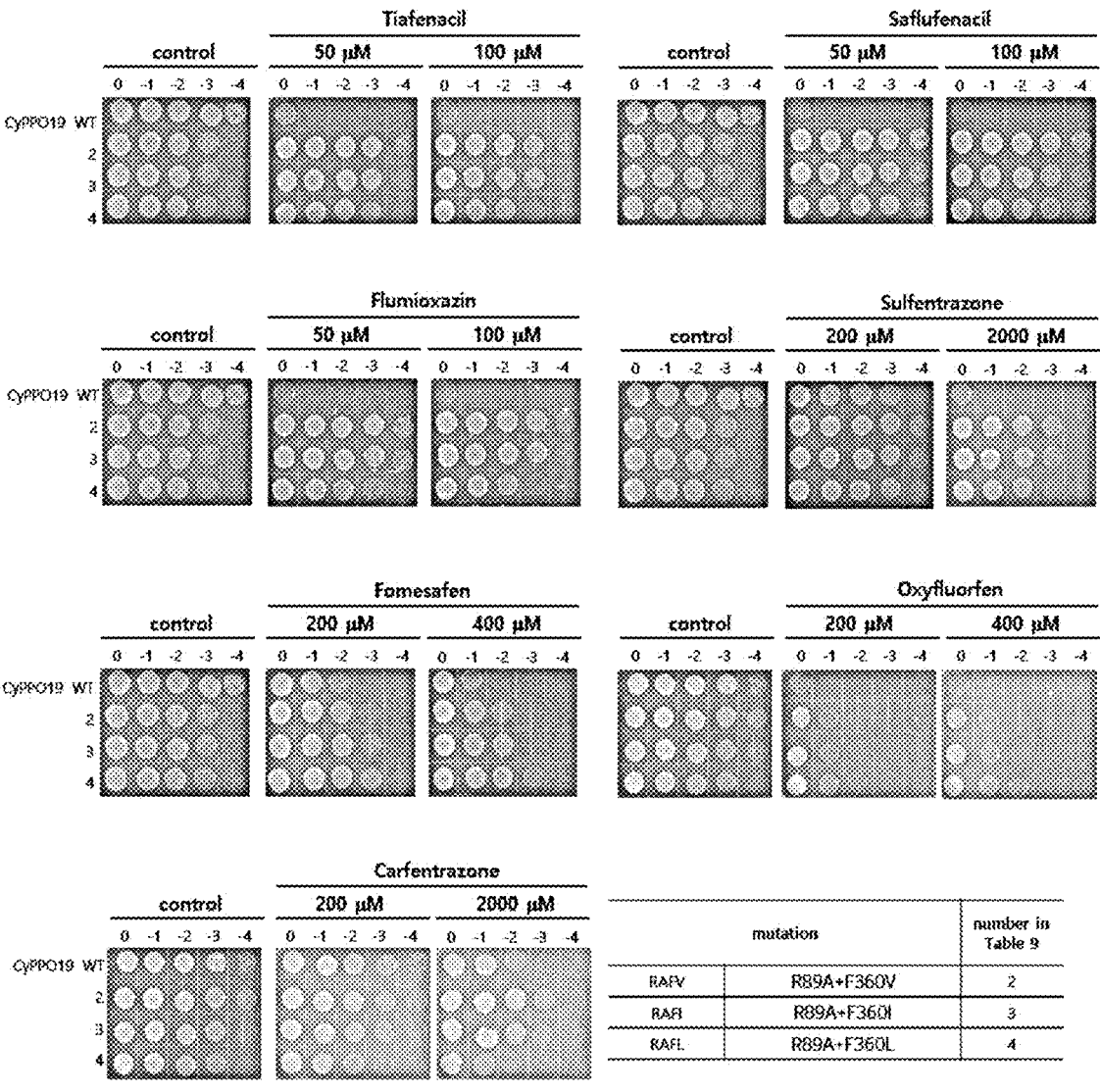

【Figure 5】
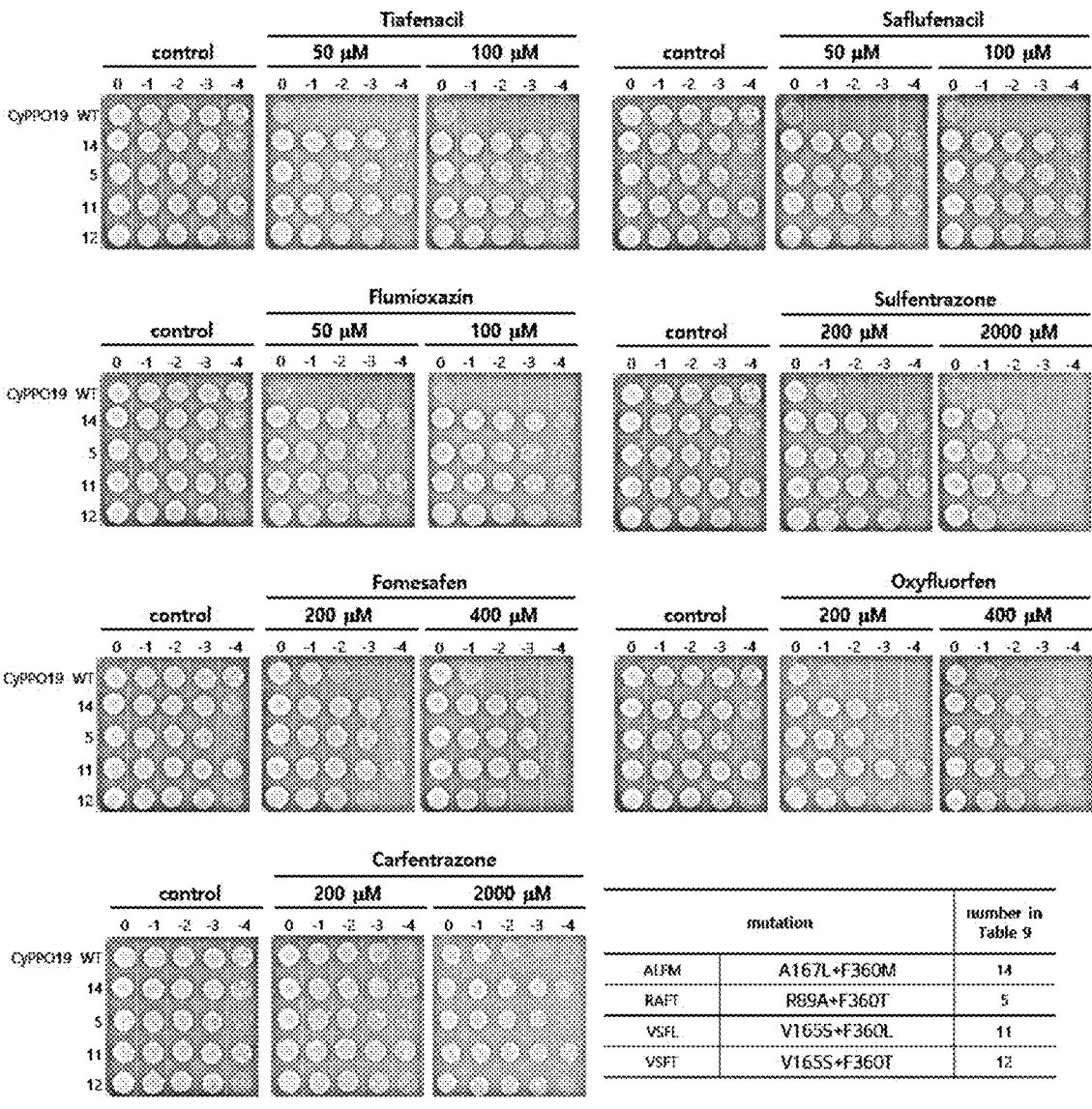

【Figure 6】
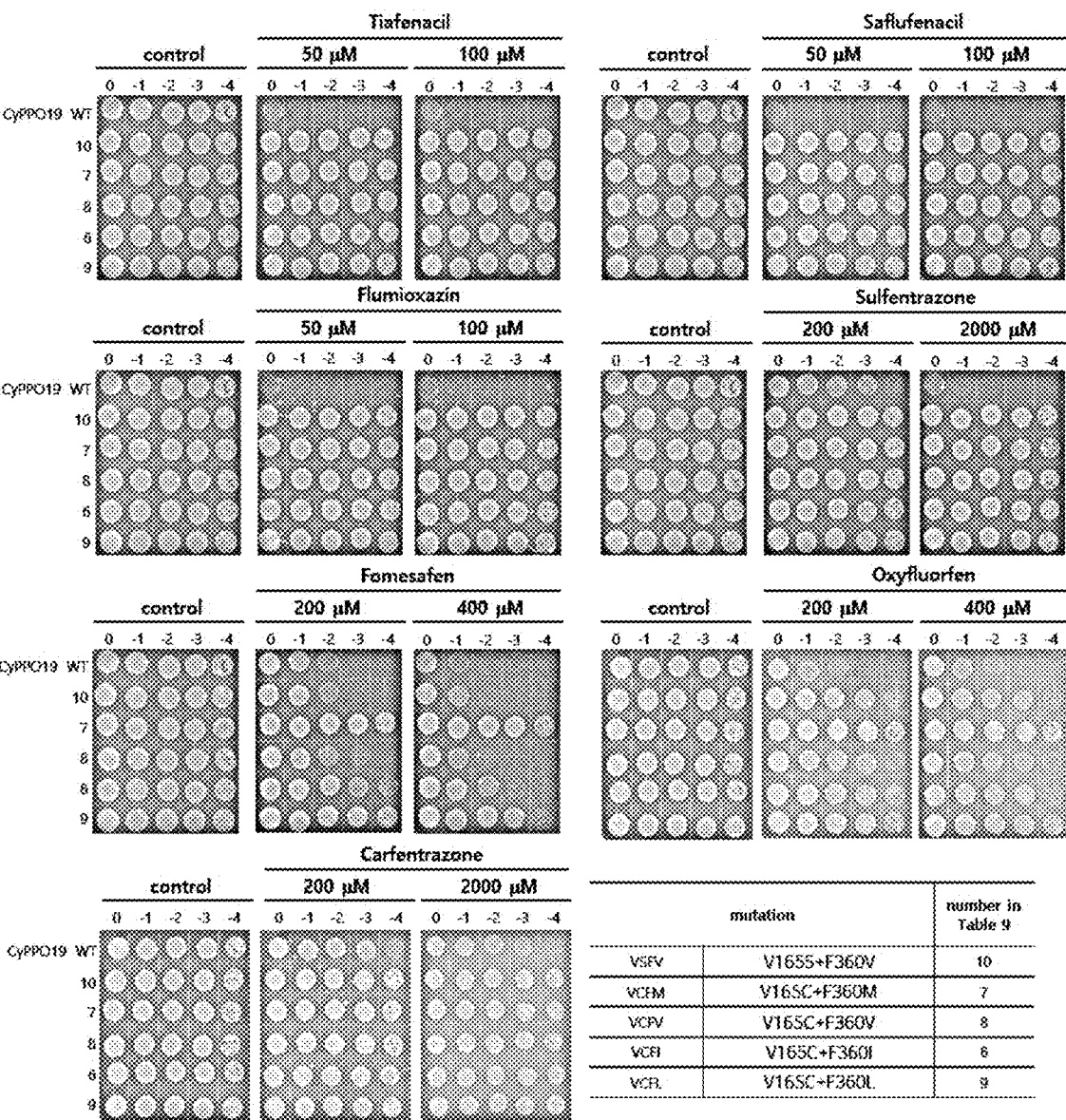

【Figure 7】
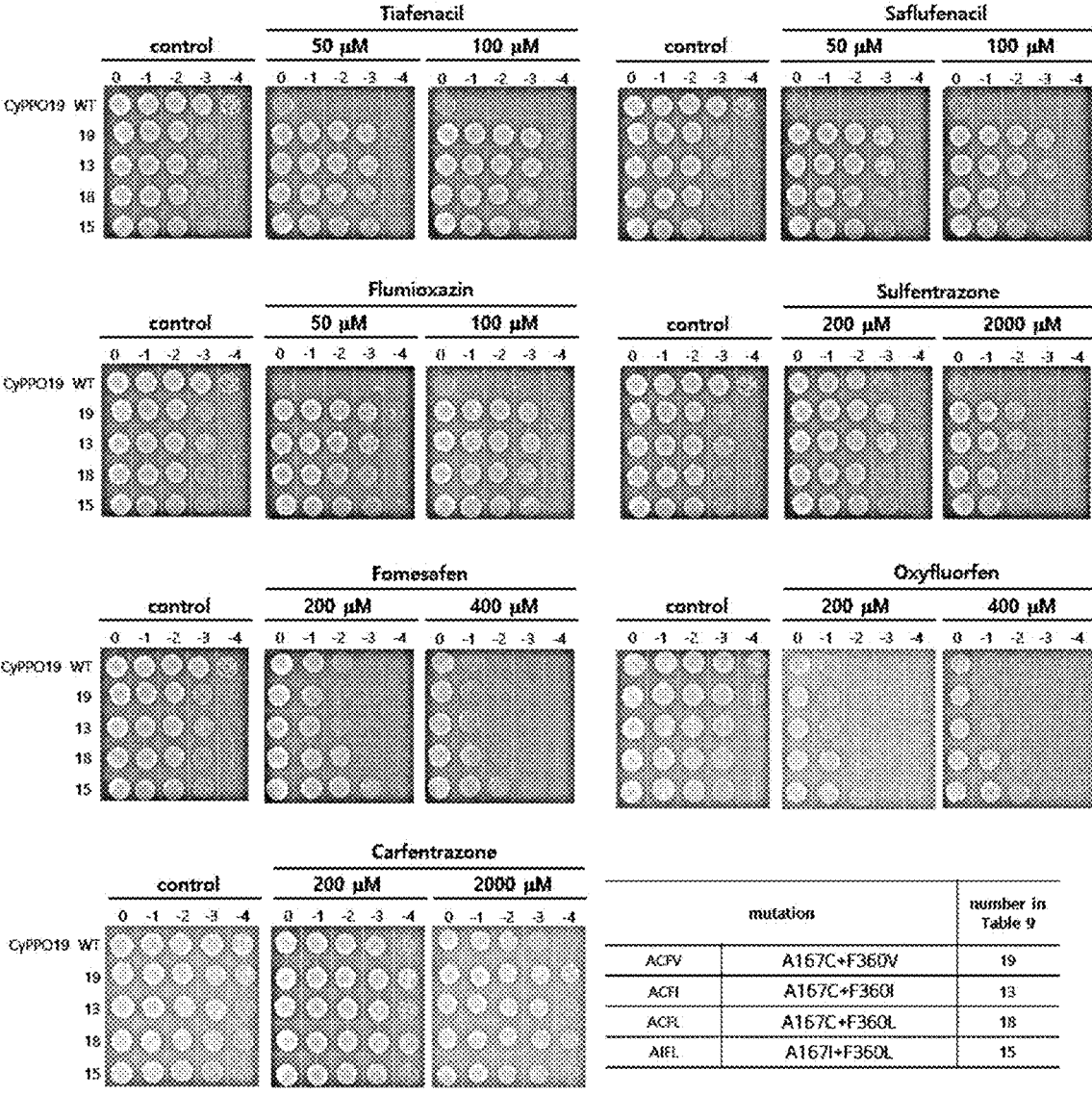

【Figure 8】
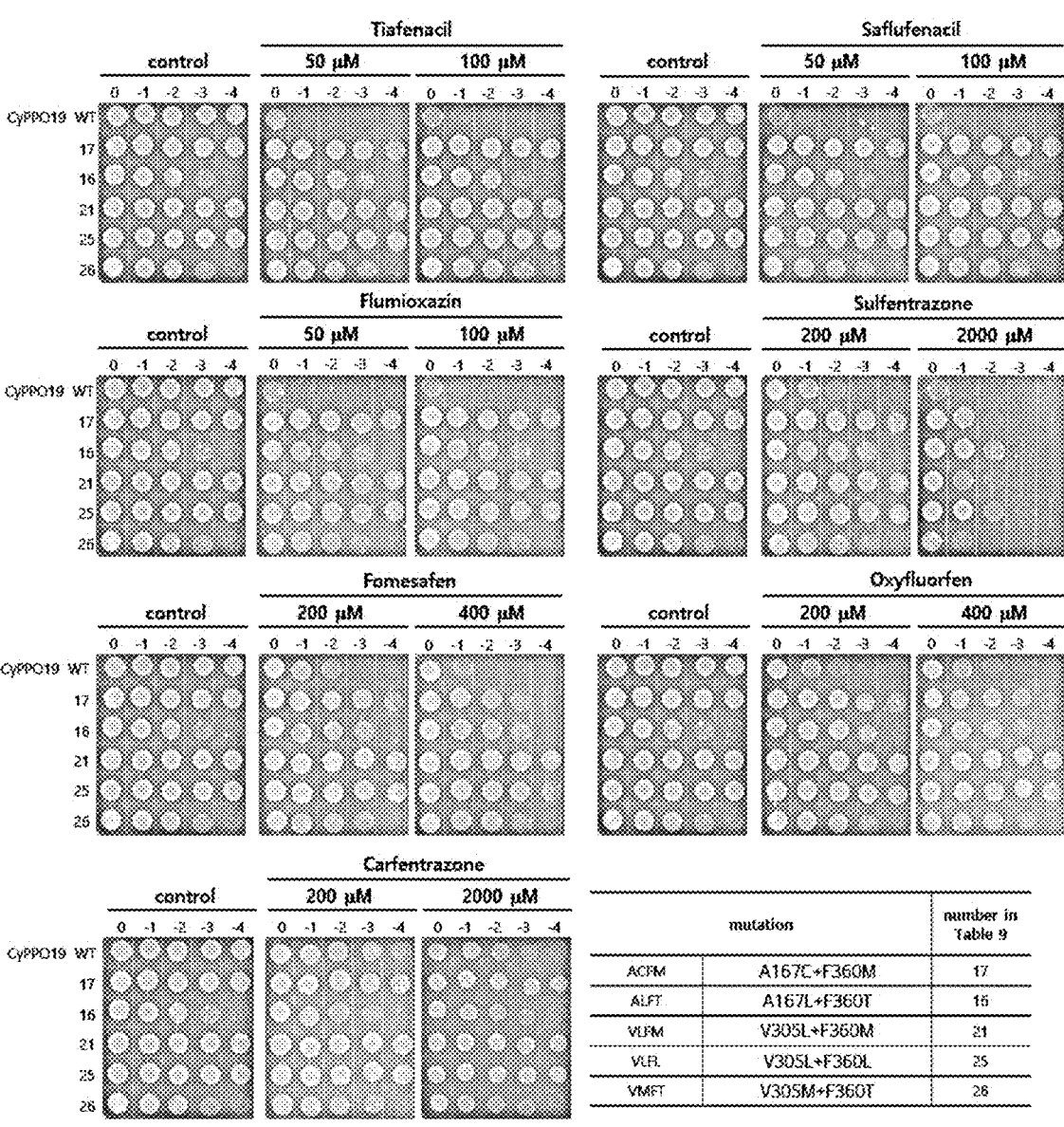

【Figure 9】
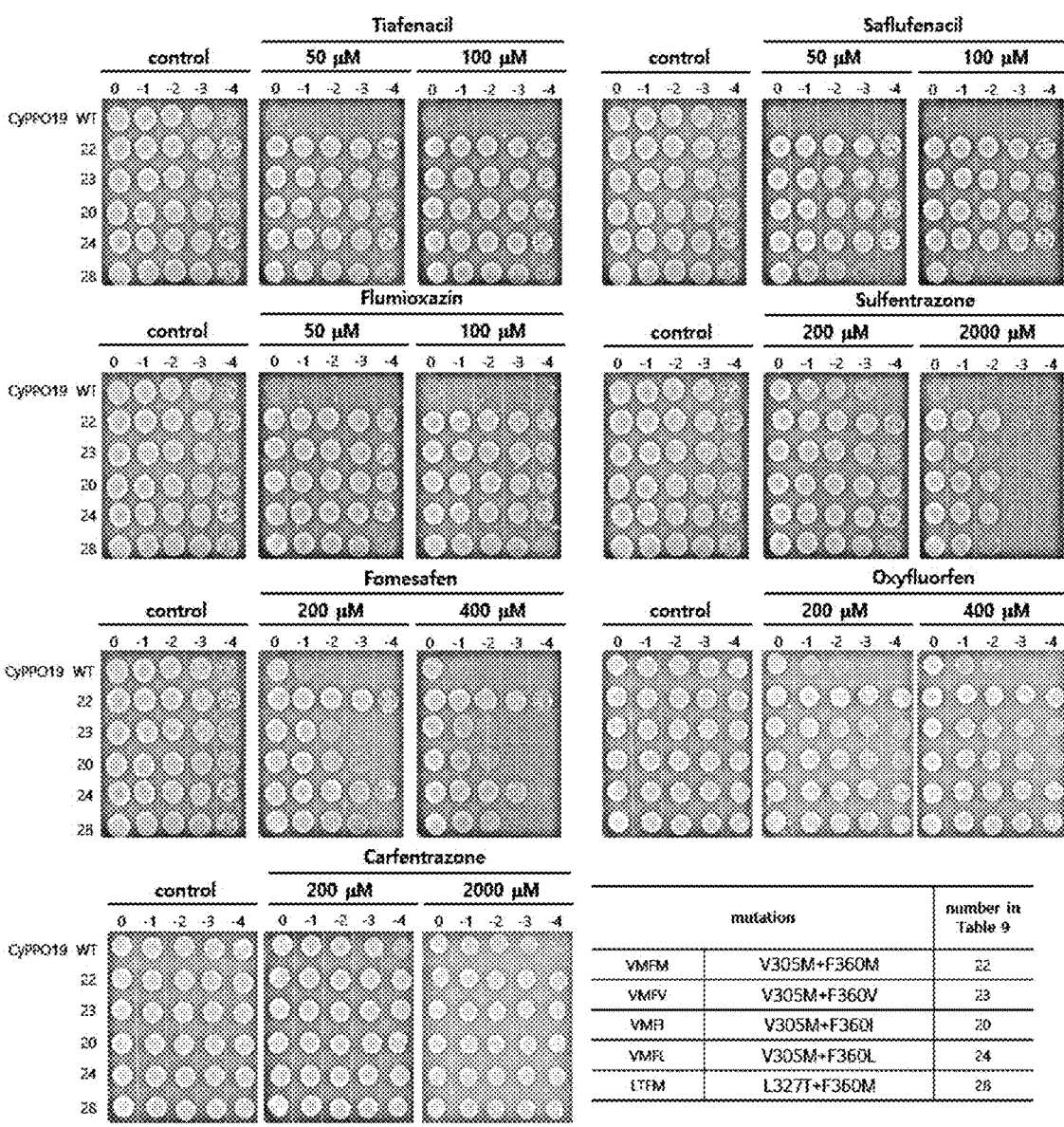

【Figure 10】
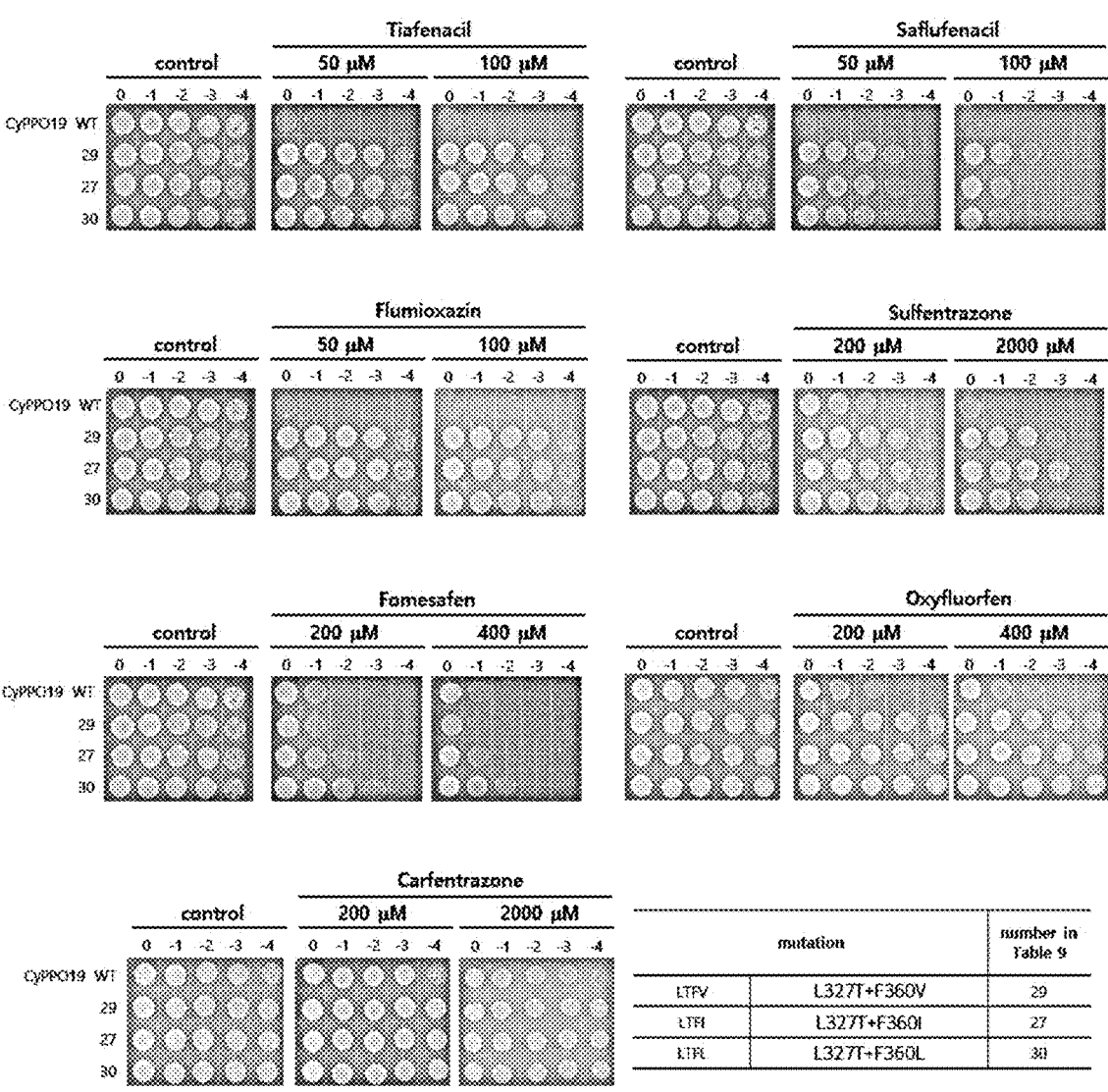

【Figure 11】
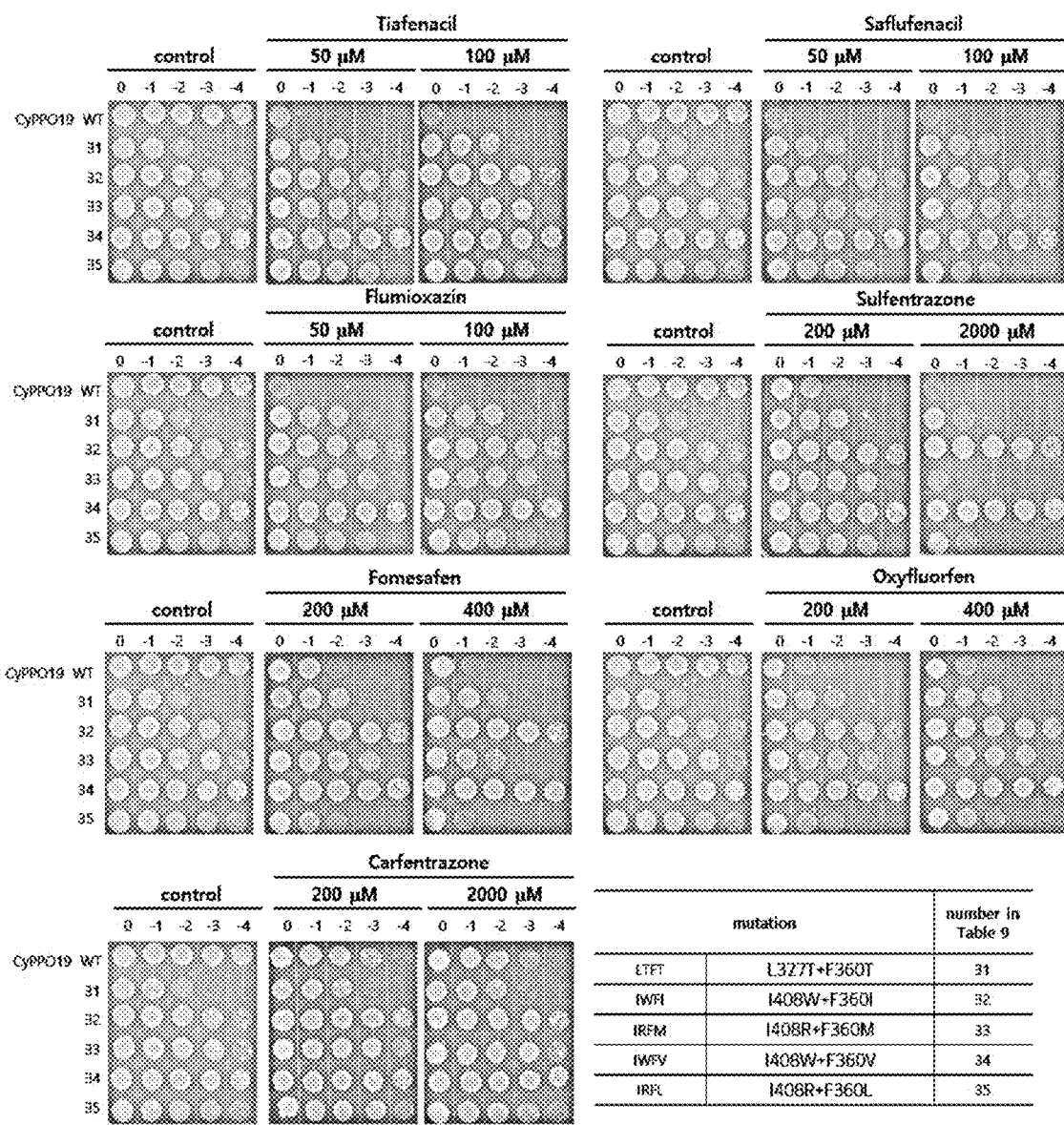

【Figure 12】
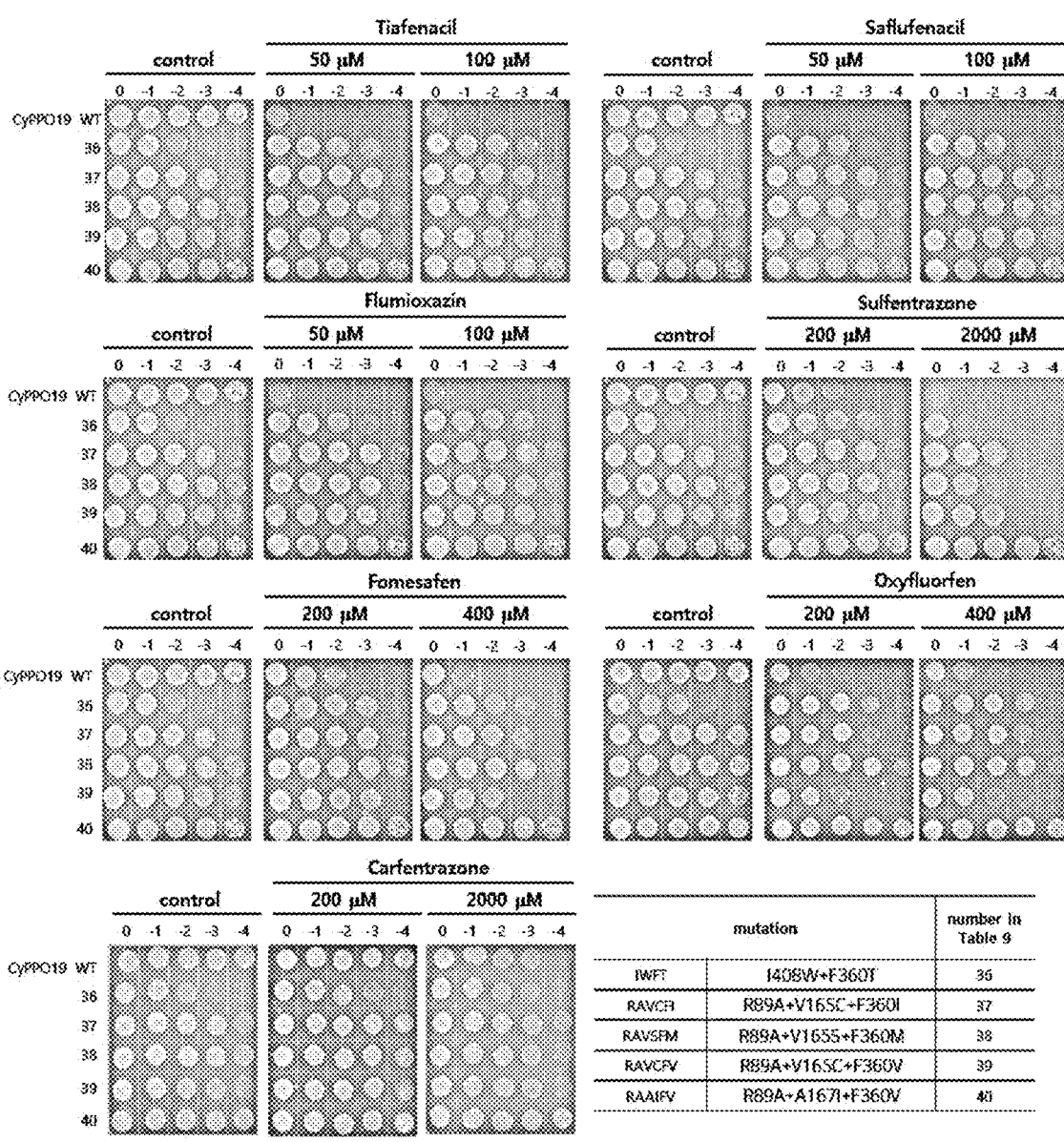

【Figure 13】
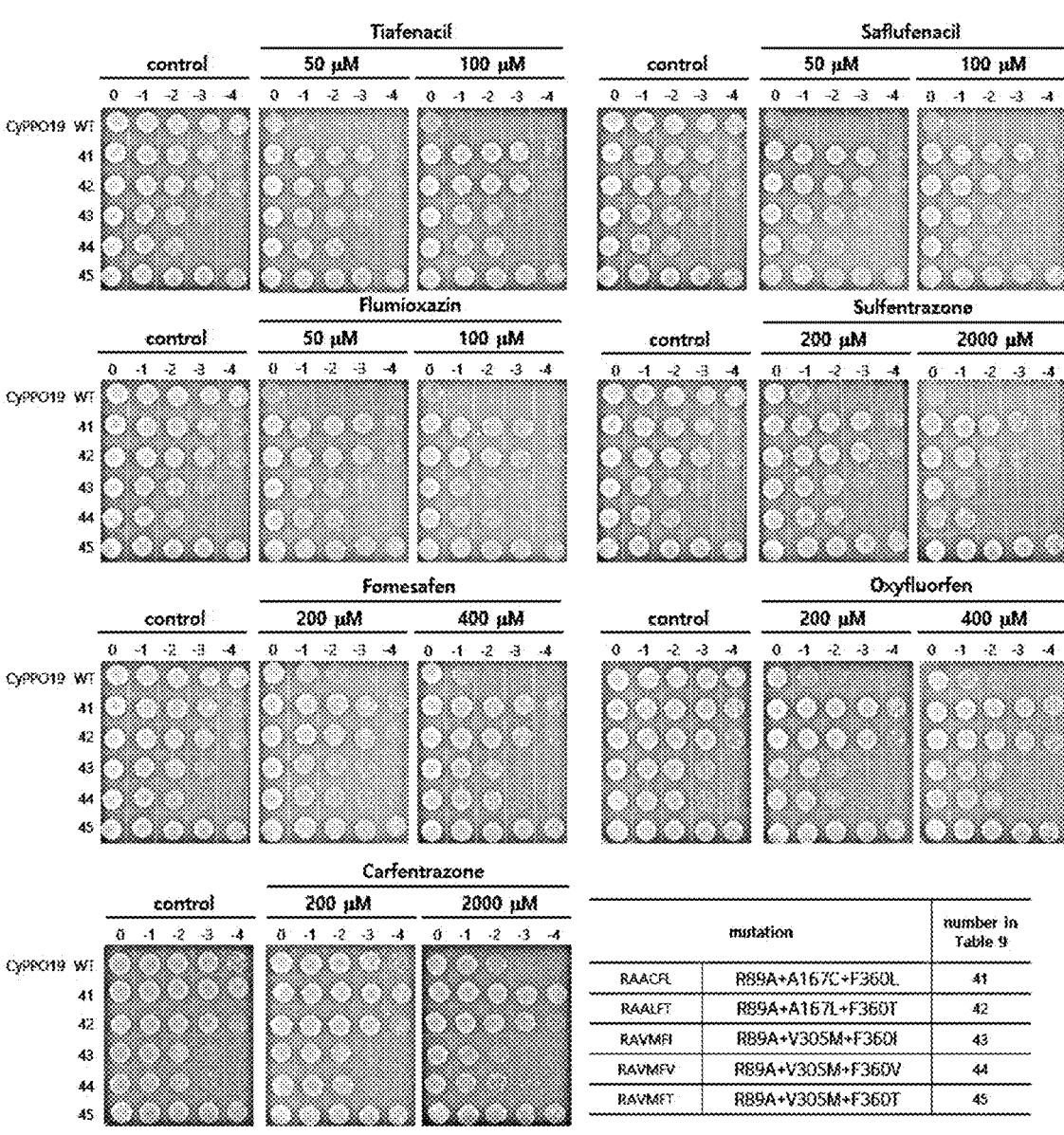

【Figure 14】
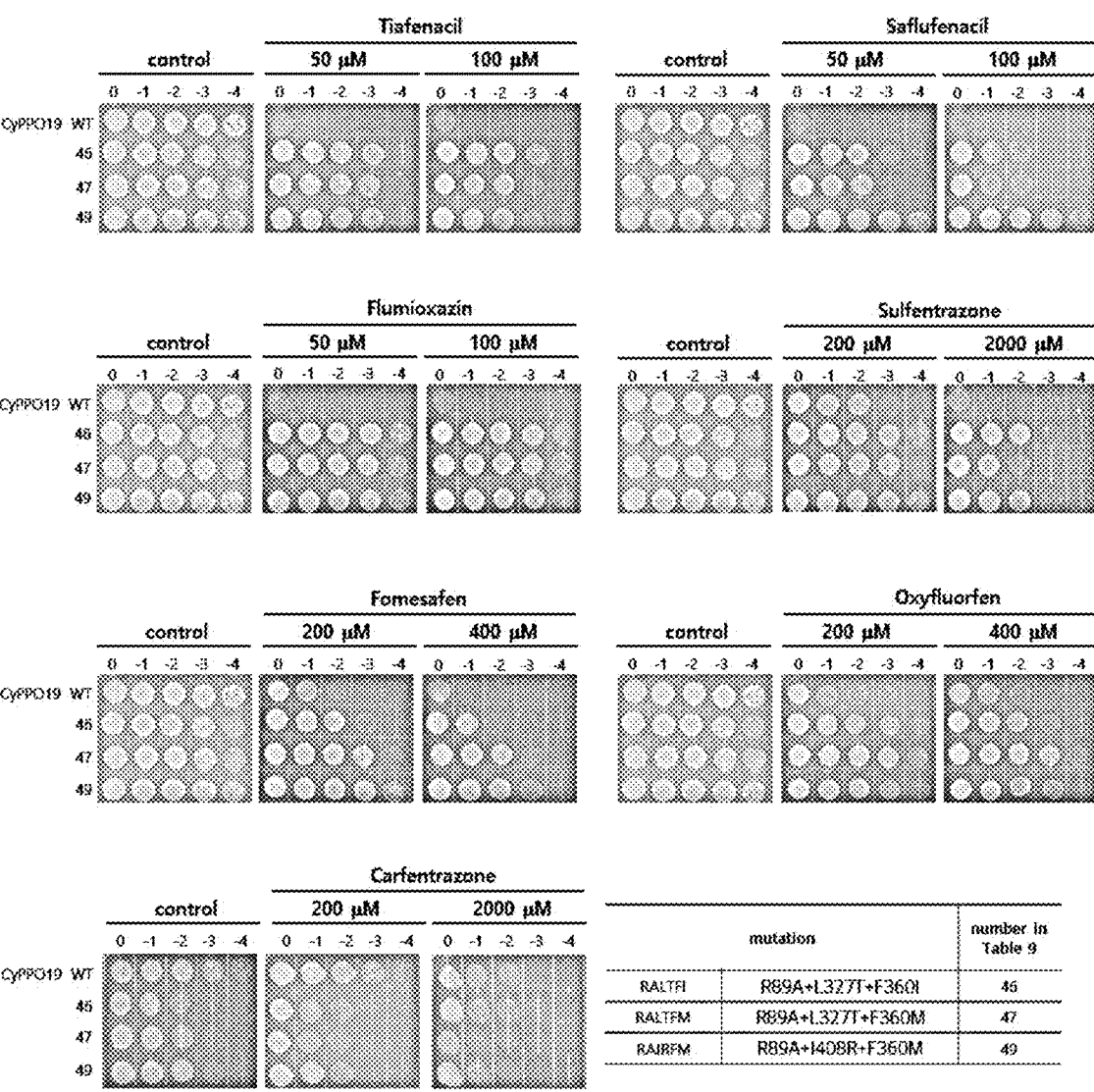

[Figure 15]
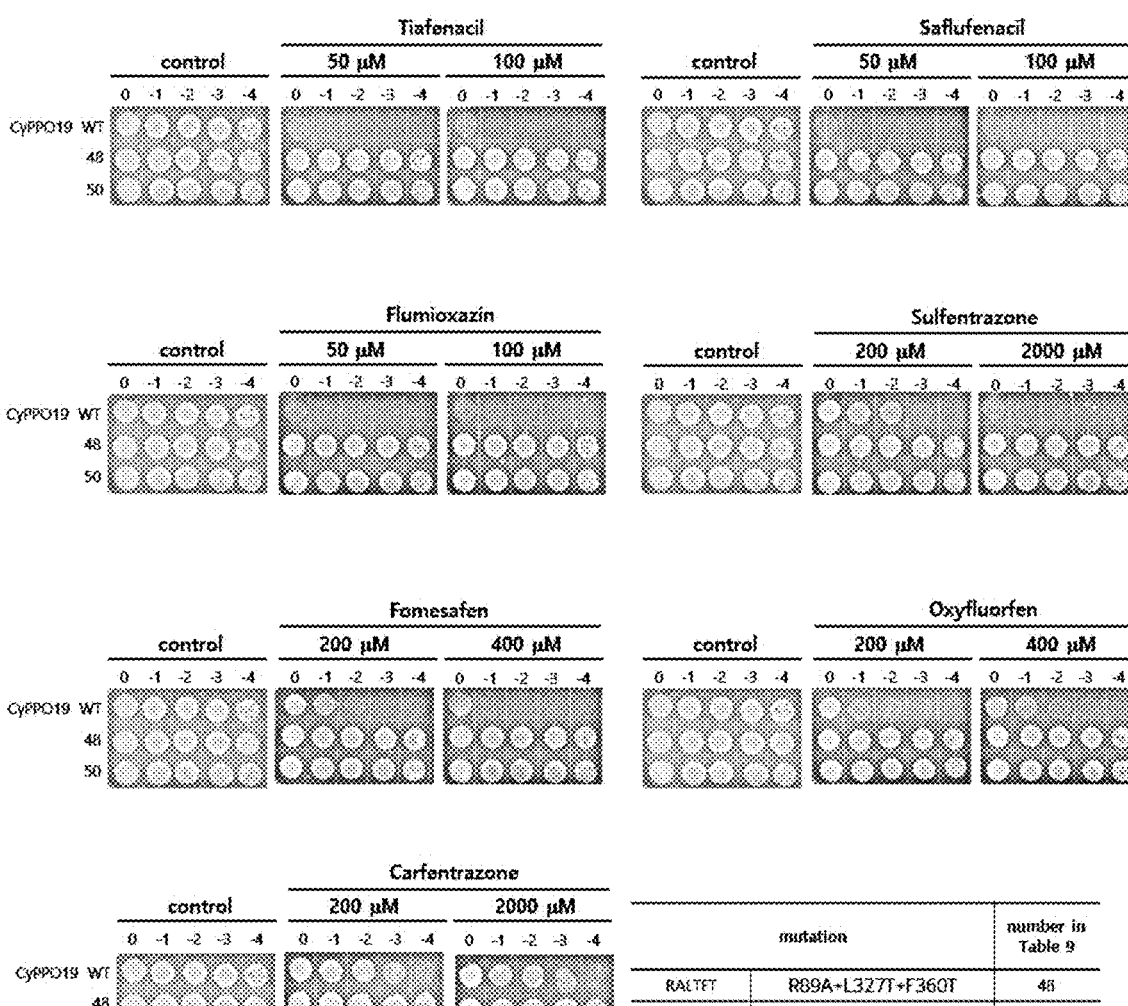

【Figure 16】
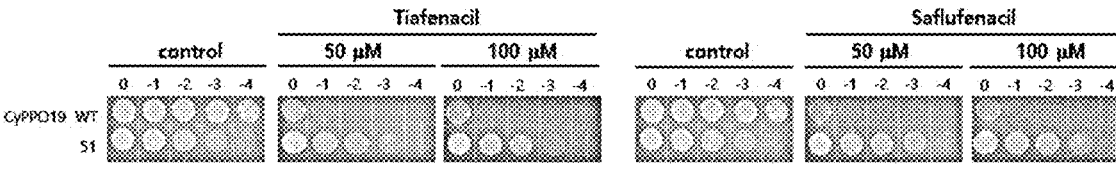
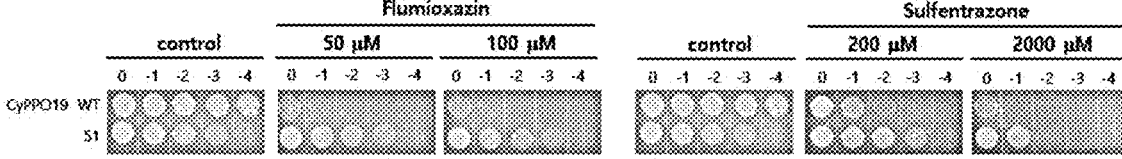
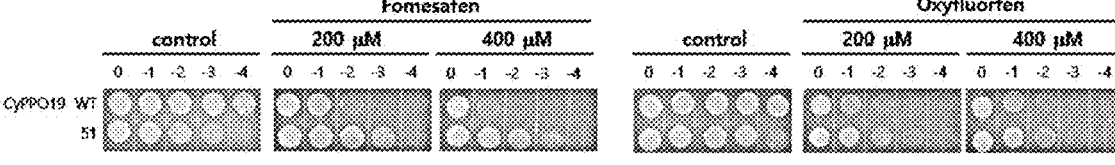
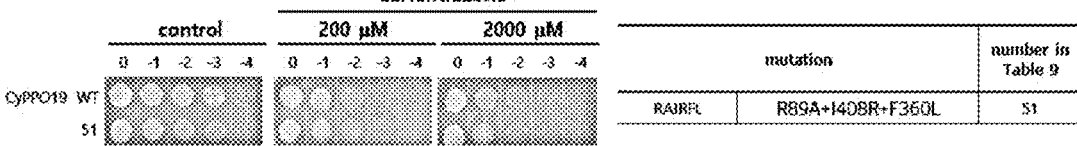

[Figure 17]
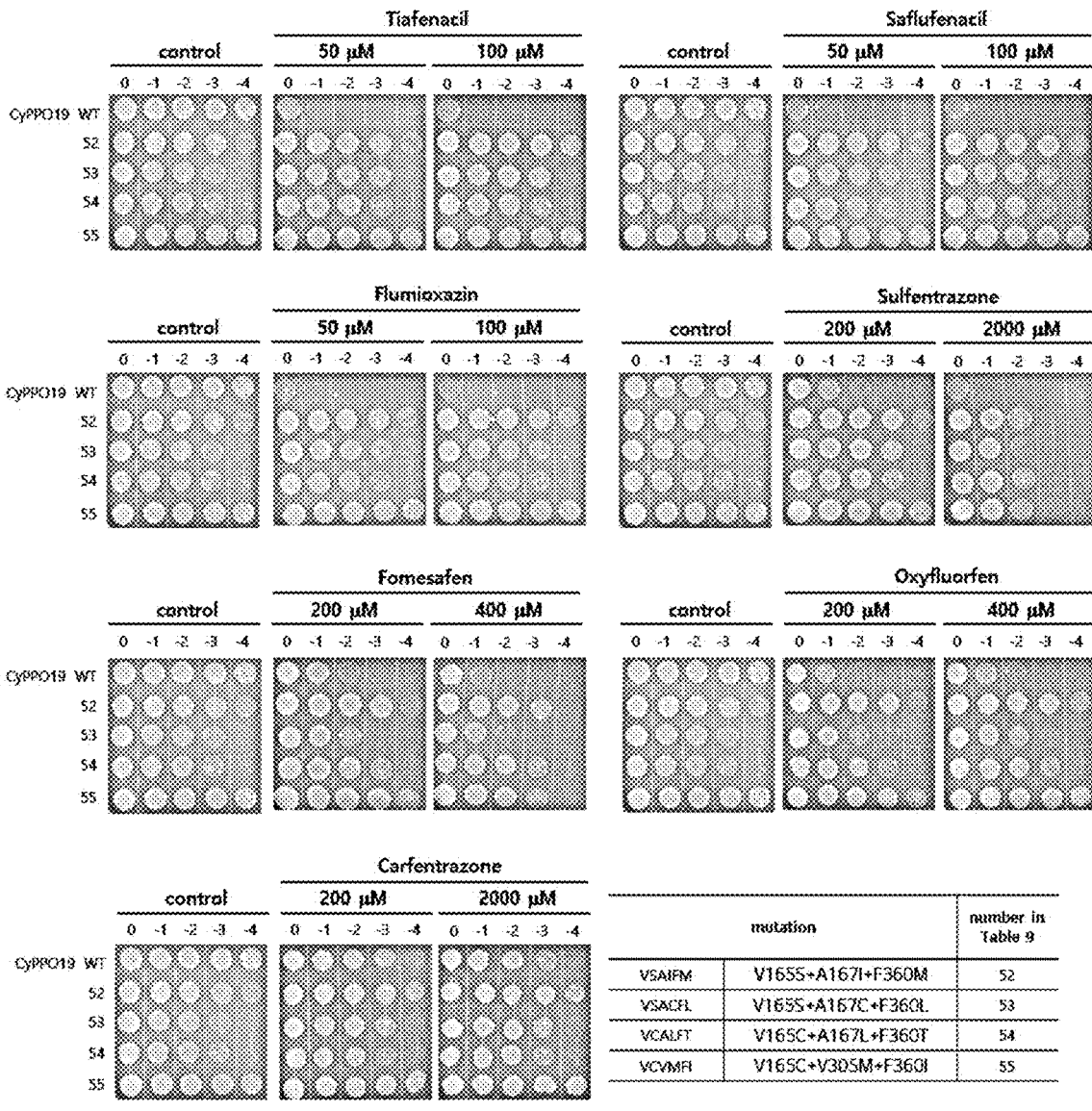

【Figure 18】
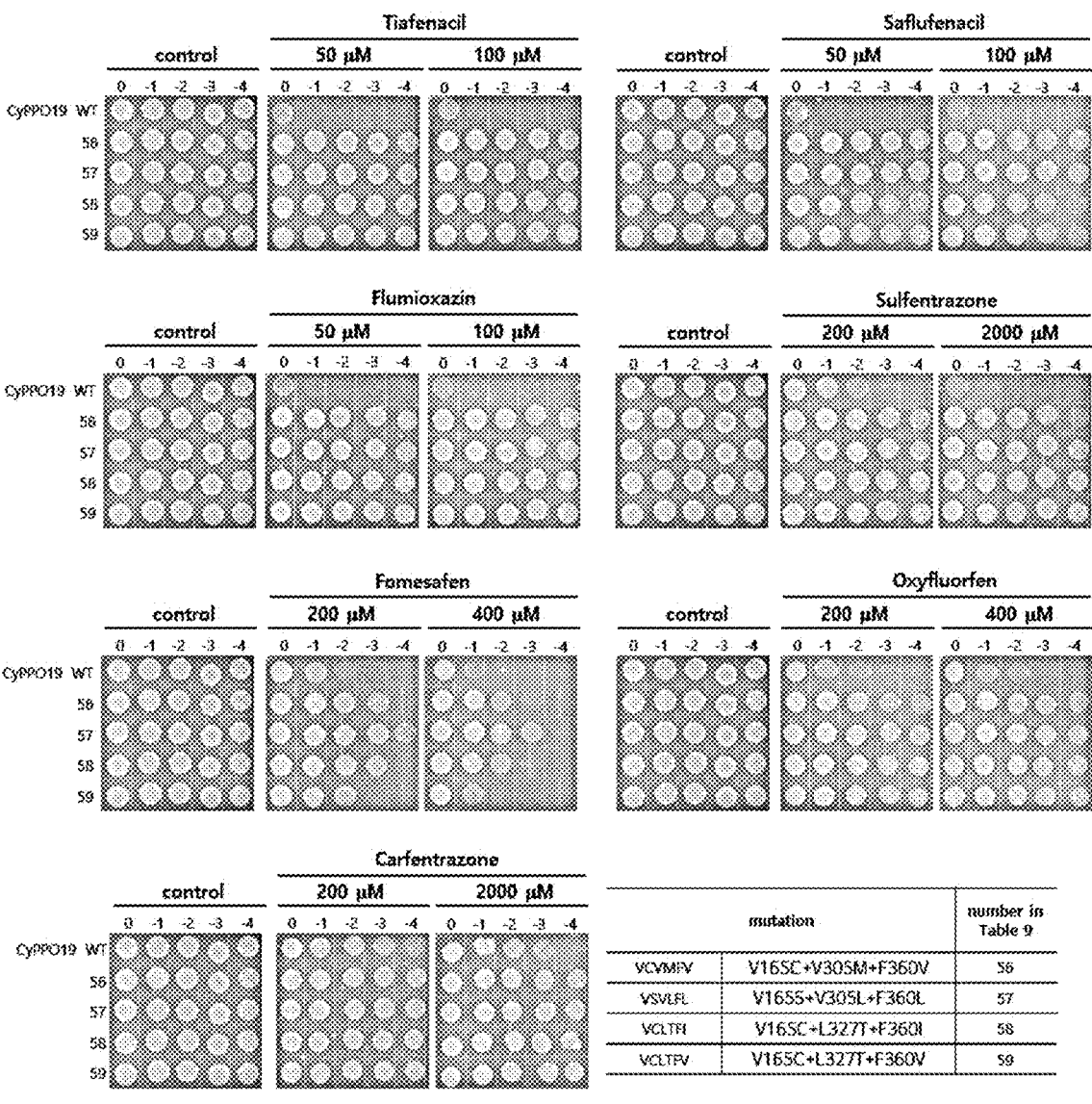
| mutation | | number in Table 9 |
|---|---|---|
| VCVMFV | V16SC+V30SM+F360V | 56 |
| VSVLFL | V16SS+V30SL+F360L | 57 |
| VCLTFI | V16SC+L327T+F360I | 58 |
| VCLTFV | V16SC+L327T+F360V | 59 |

[Figure 19]
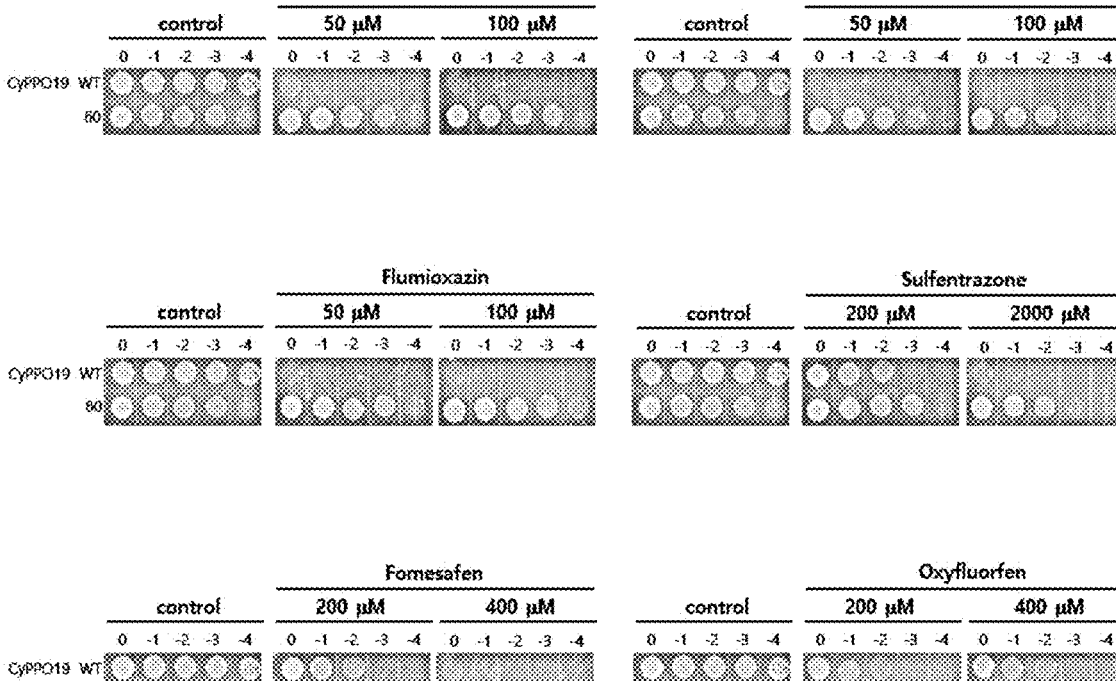
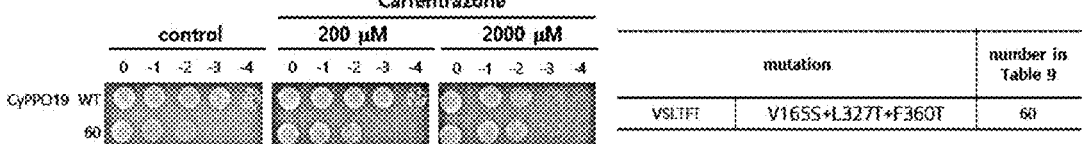

【Figure 20】
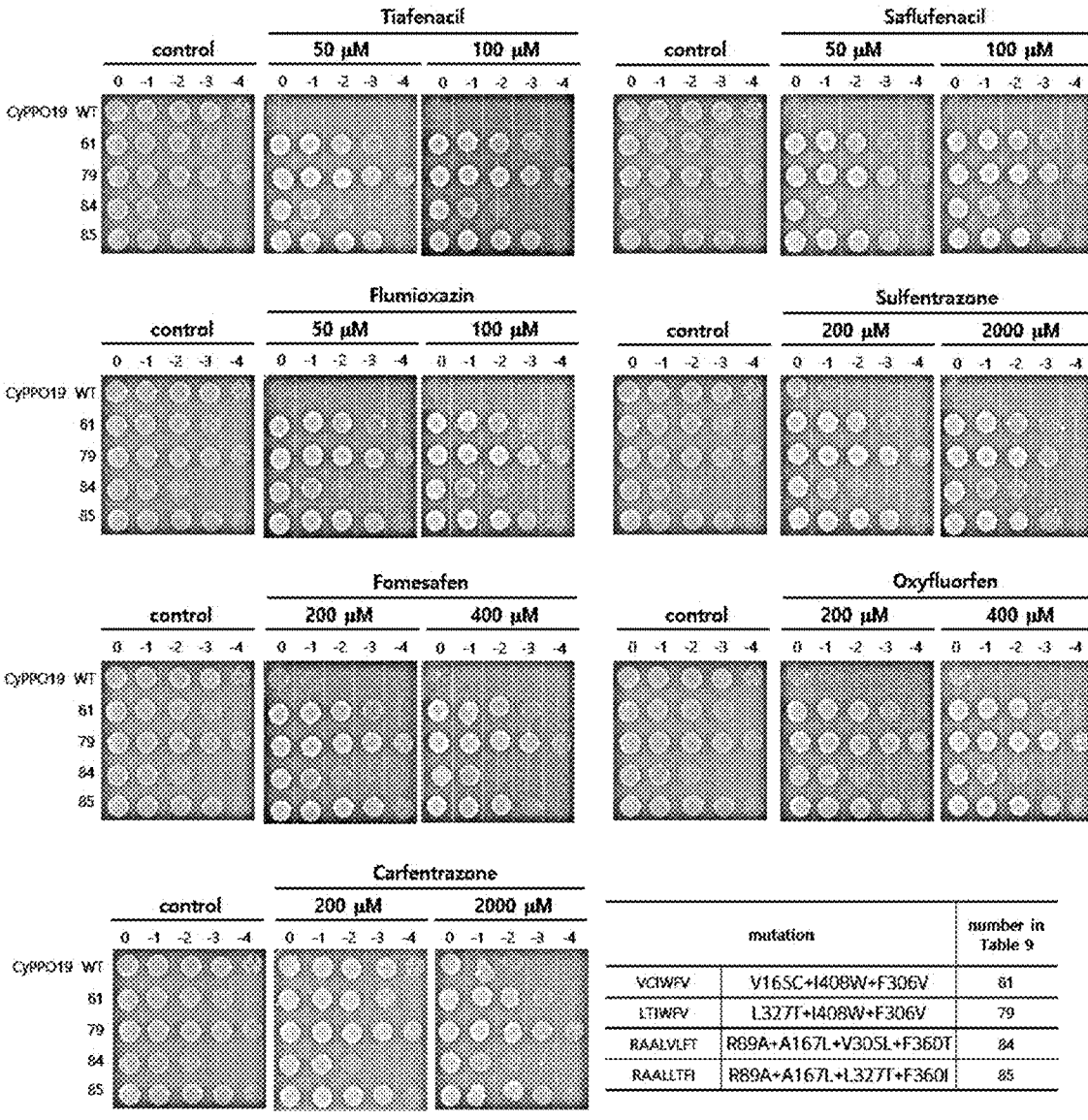

【Figure 21】
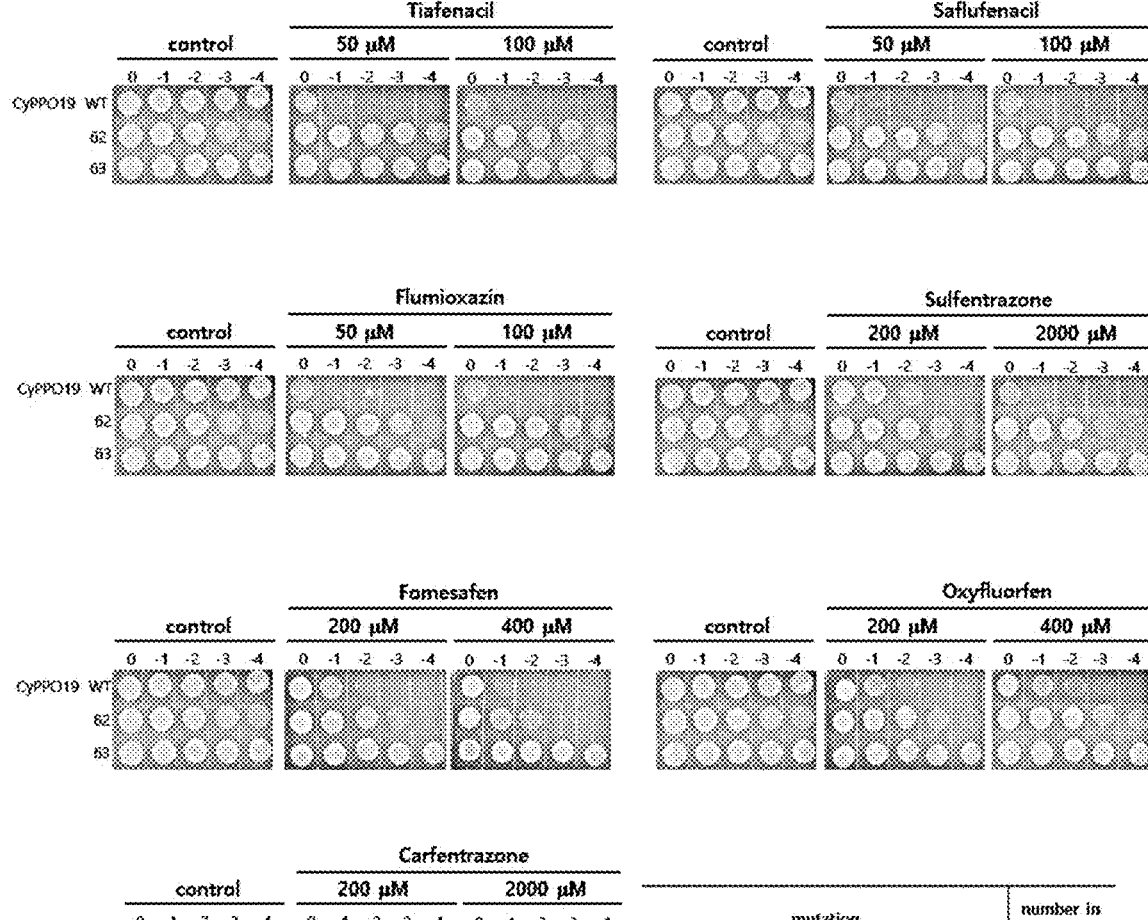

【Figure 22】
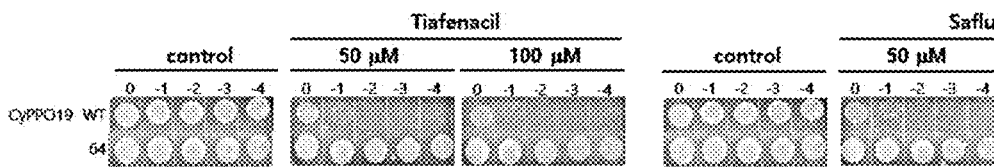
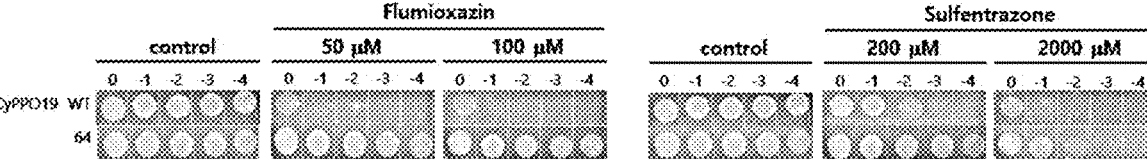
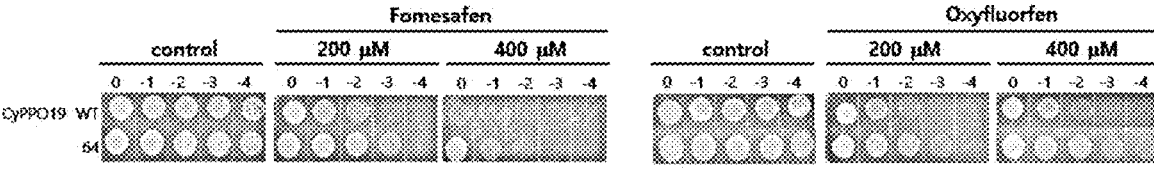
| | mutation | | number in Table 9 |
|---|---|---|---|
| ACVLFV | A167C+V305L+F360V | | 64 |

【Figure 23】
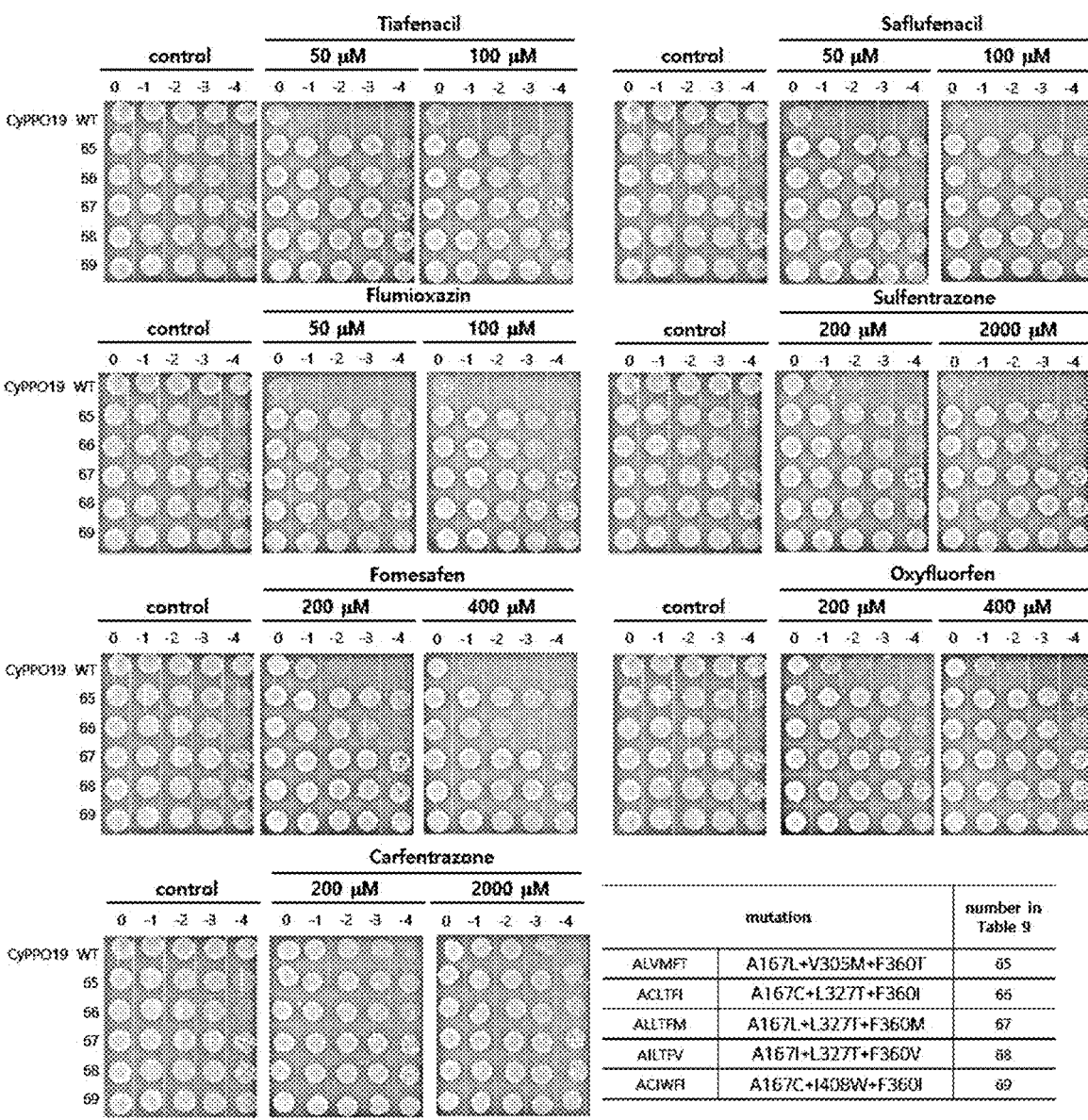
| mutation | | number in Table 9 |
|---|---|---|
| ALVMFT | A167L+V305M+F360T | 65 |
| ACLTFI | A167C+L327T+F360I | 66 |
| ALLTFM | A167L+L327T+F360M | 67 |
| AILTFV | A167I+L327T+F360V | 68 |
| ACIWFI | A167C+I408W+F360I | 69 |

【Figure 24】
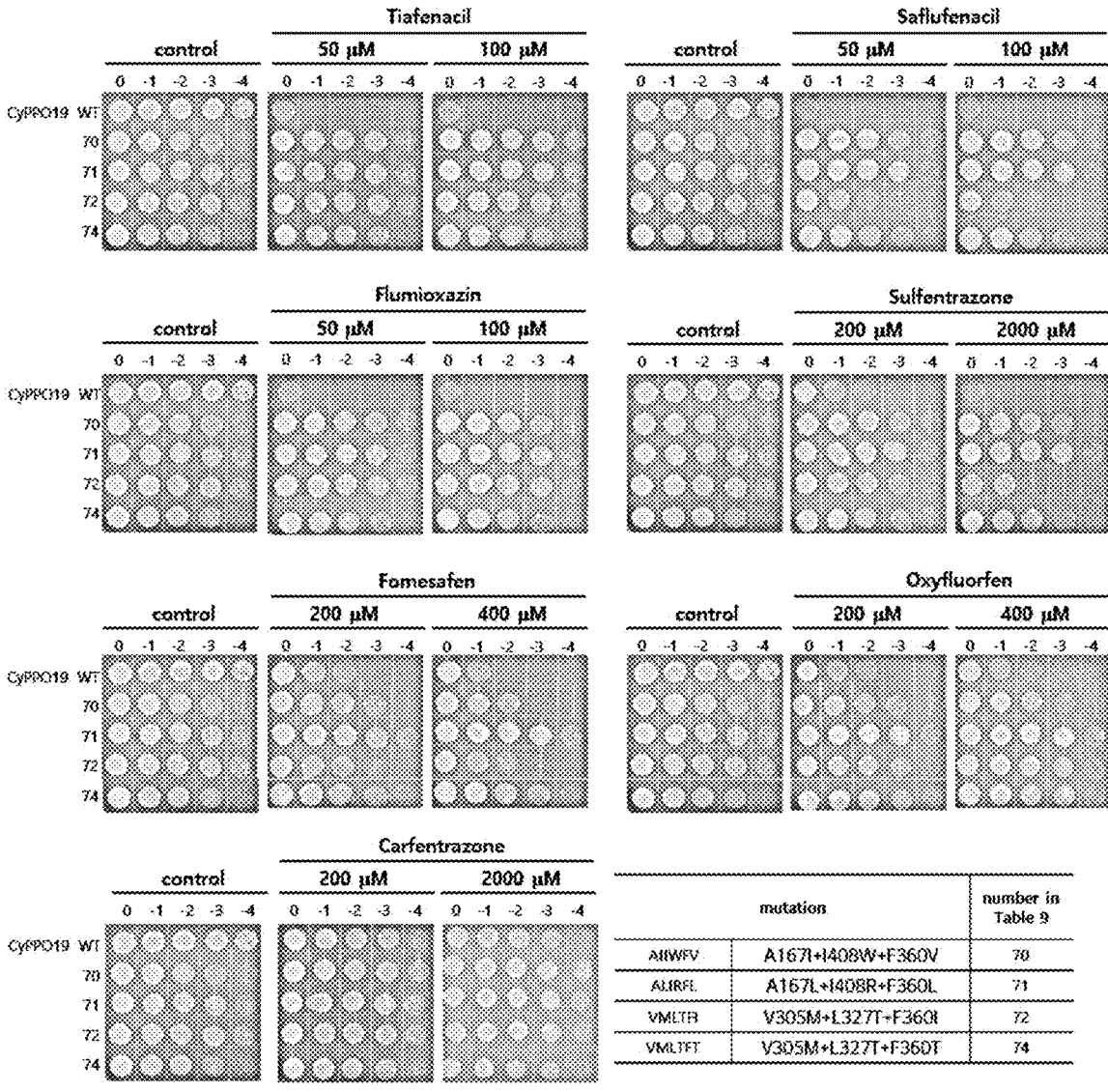

【Figure 25】
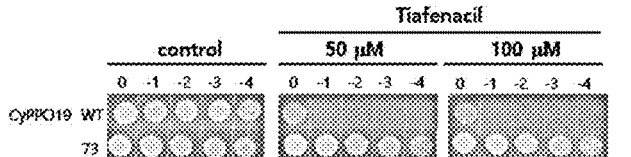
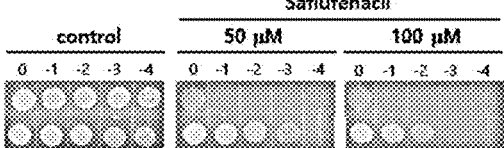
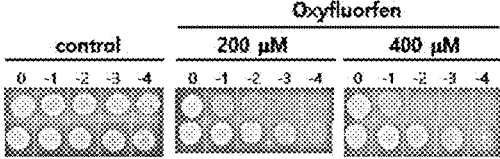
| | mutation | number in Table 9 |
|---|---|---|
| VLLTPV | V305M+L327T+F360V | 73 |

【Figure 26】
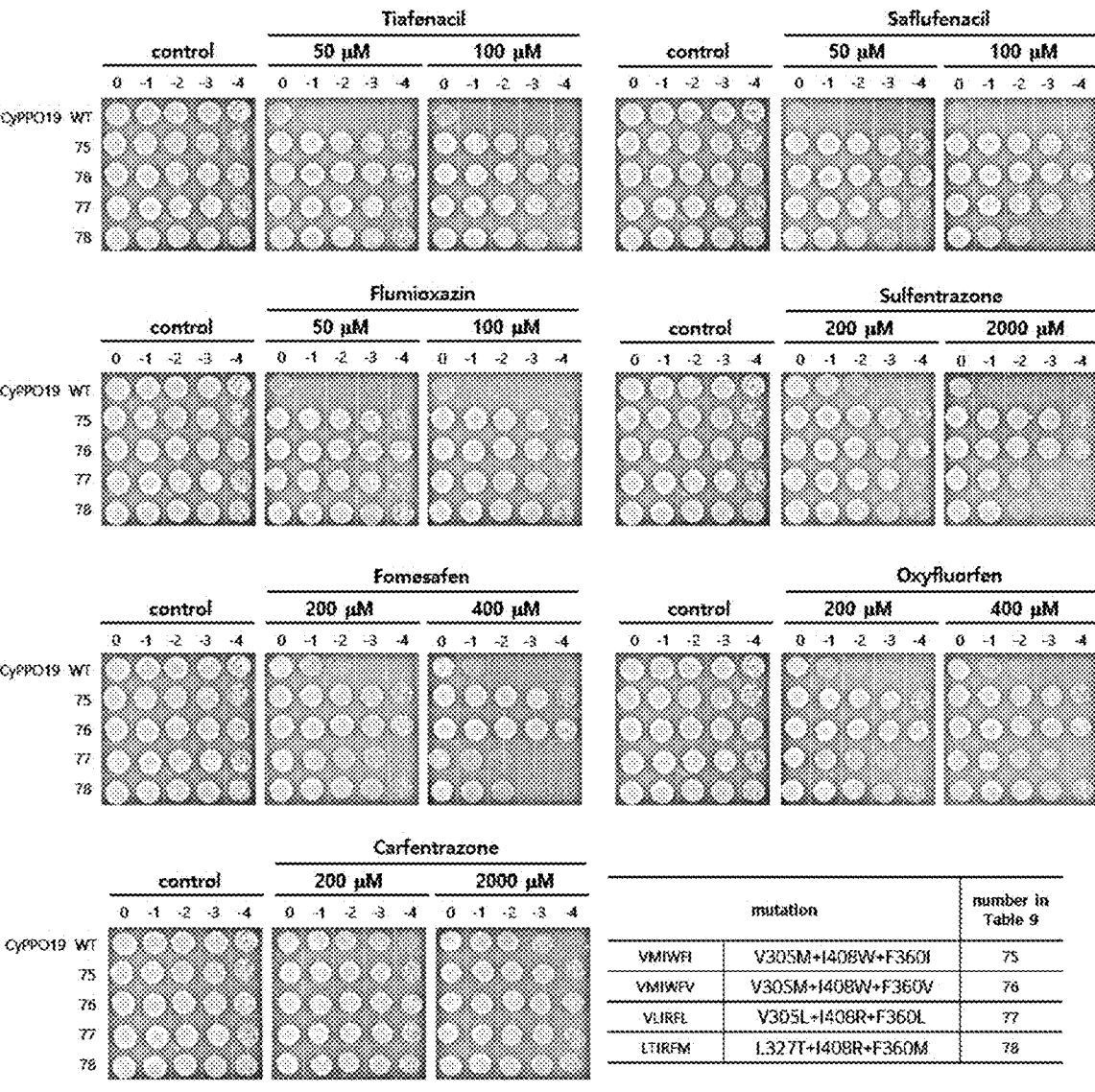
| mutation | | number in Table 9 |
|---|---|---|
| VMIWFI | V305M+I408W+F360I | 75 |
| VMIWFV | V305M+I408W+F360V | 76 |
| VLIRFL | V305L+I408R+F360L | 77 |
| LTIRFM | L327T+I408R+F360M | 78 |

【Figure 27】
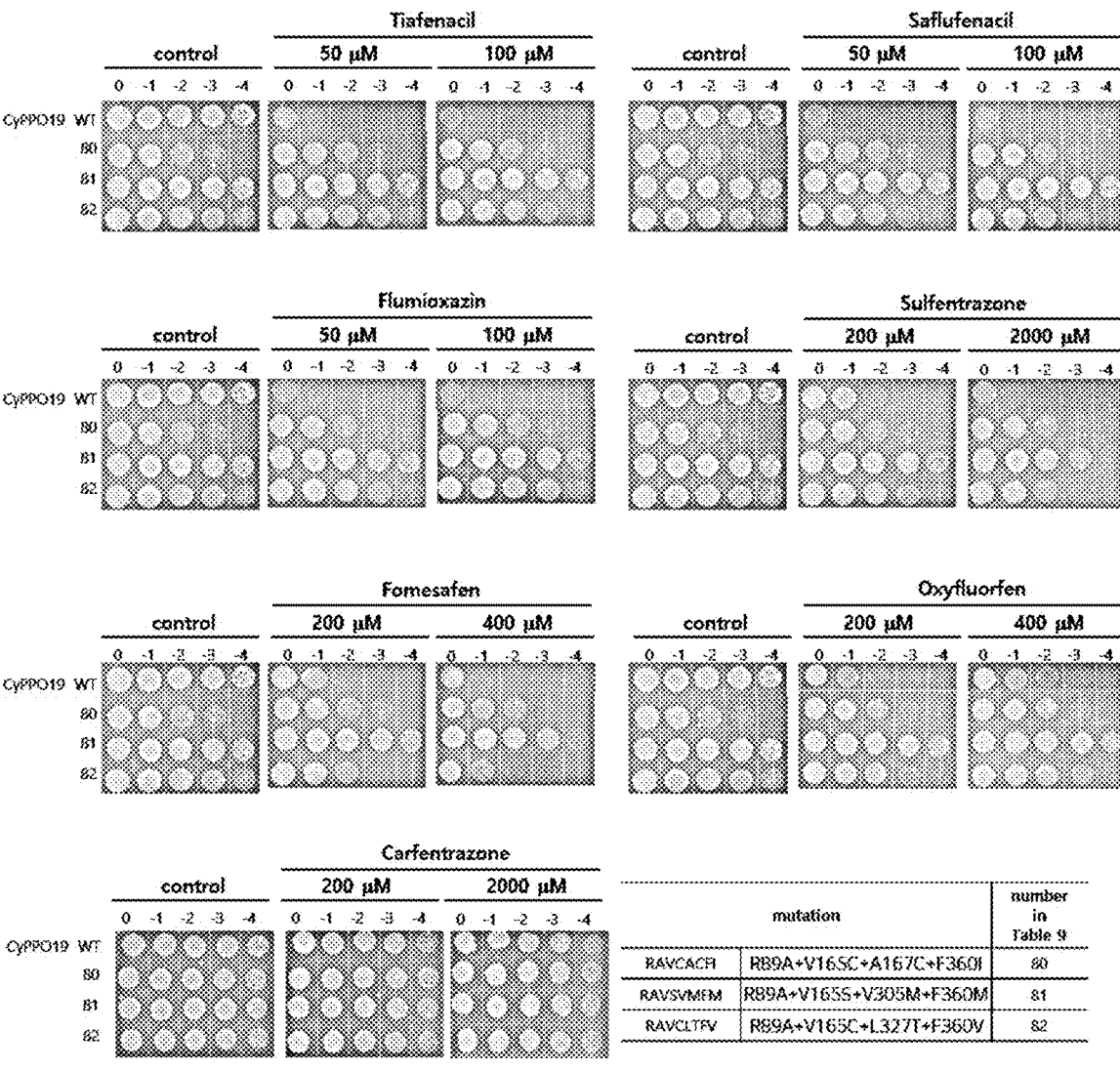

[Figure 28]
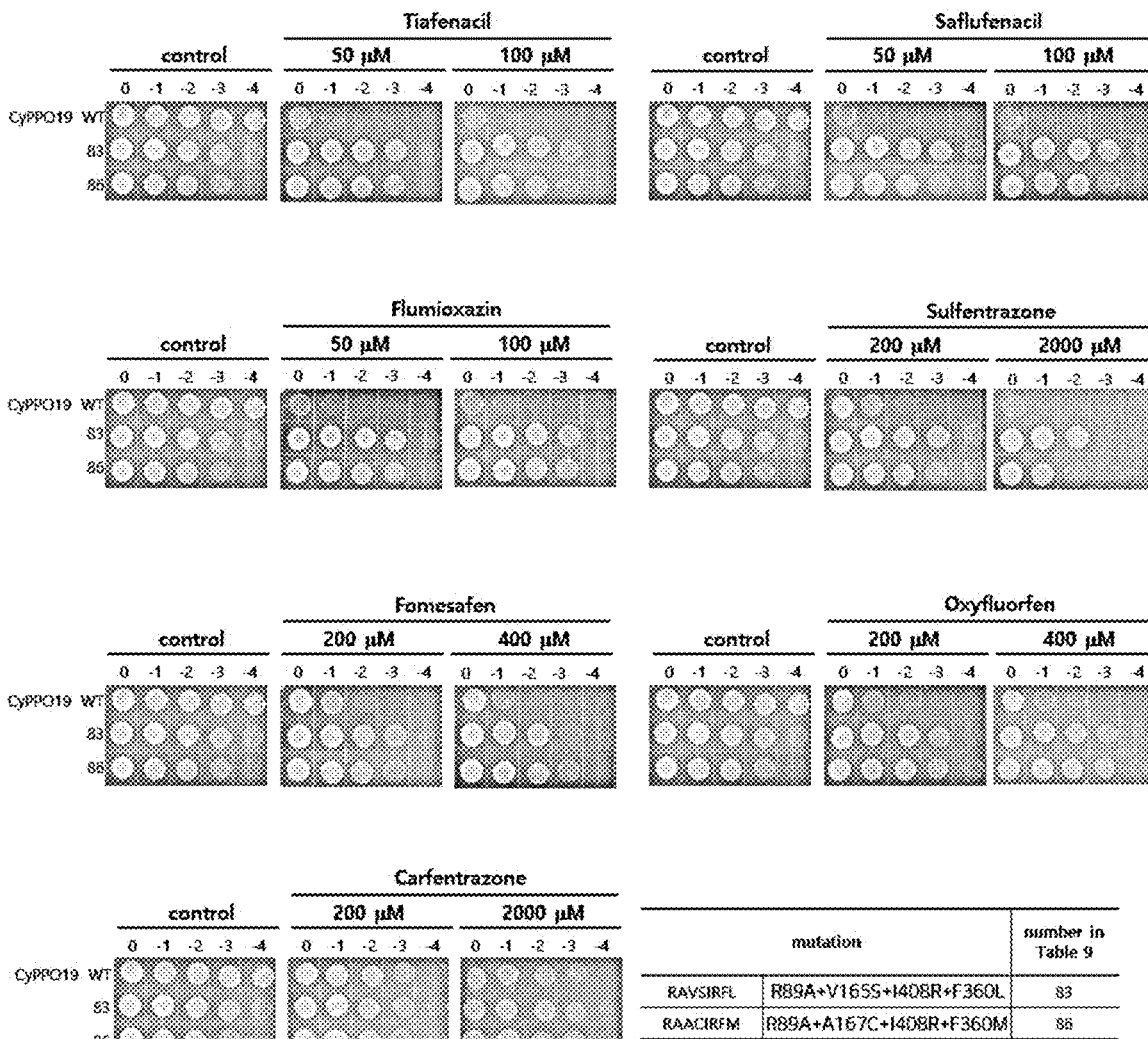

【Figure 29】
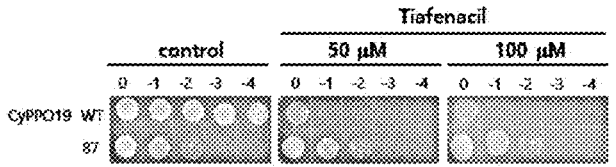
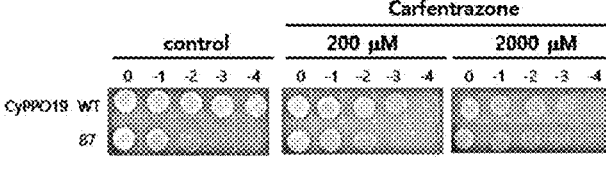
| mutation | | number in Table 9 |
|---|---|---|
| VCAIVMFV | V16SC+A167I+V30SM+F360V | 87 |

【Figure 30】
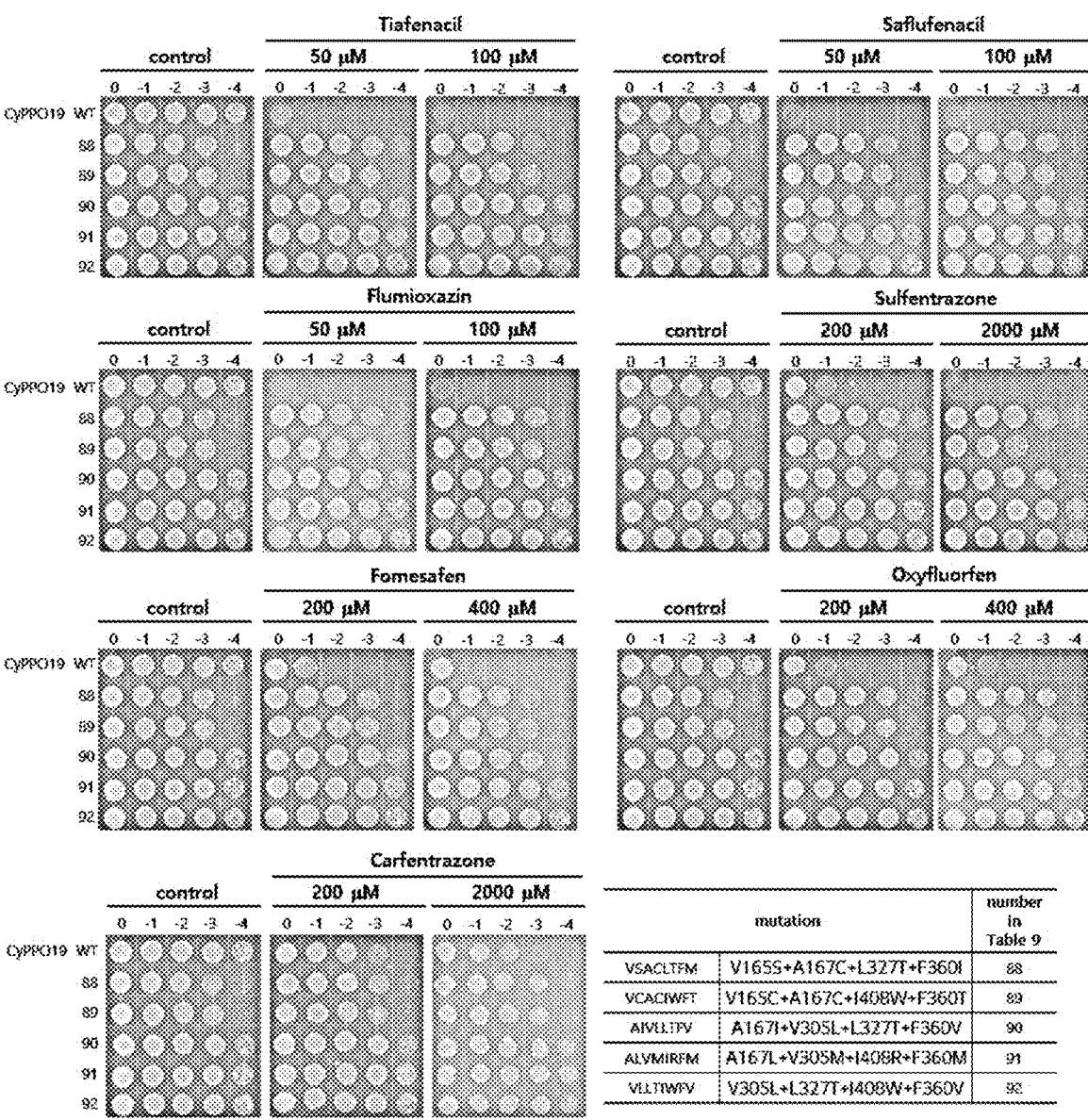
| | mutation | | number in Table 9 |
|---|---|---|---|
| VSACLTFM | V165S+A167C+L327T+F360I | | 88 |
| VCACIWFT | V165C+A167C+I408W+F360T | | 89 |
| AIVLLTFV | A167I+V305L+L327T+F360V | | 90 |
| ALVMIRFM | A167L+V305M+I408R+F360M | | 91 |
| VLLTIWFV | V305L+L327T+I408W+F360V | | 92 |

【Figure 31】
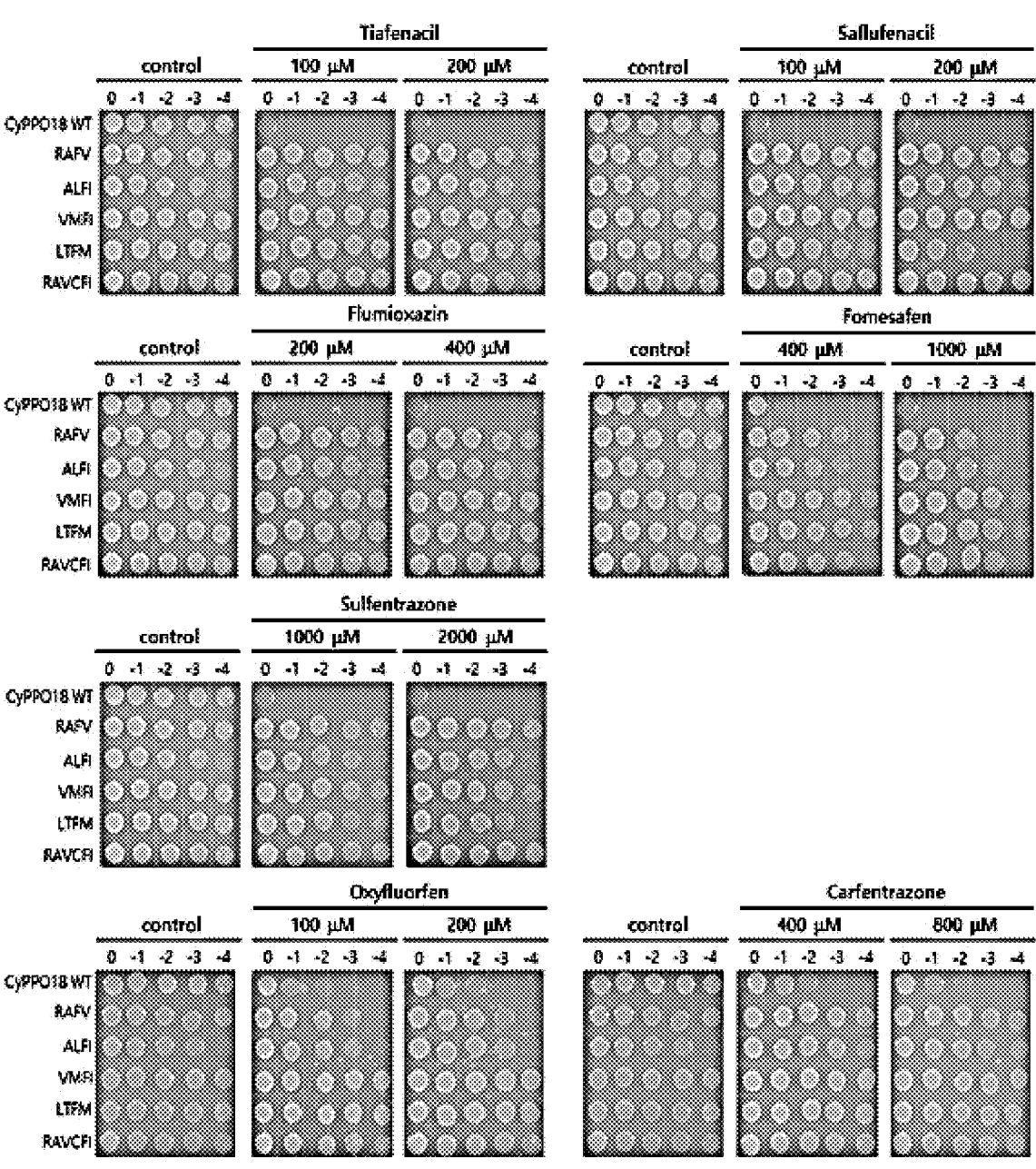

【Figure 32】
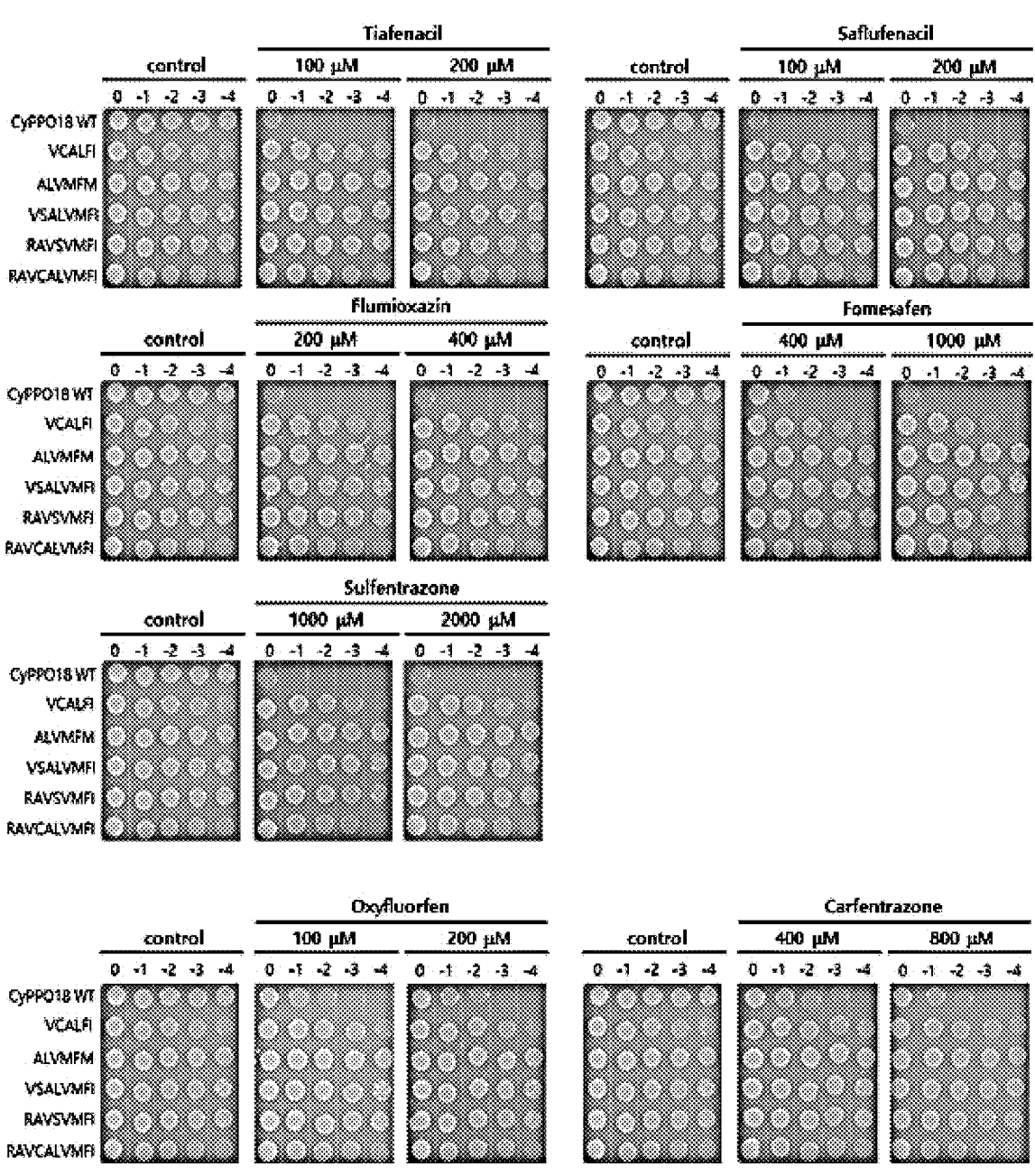

【Figure 33】
Vector for Fusion Protein of PPO and MBP(Maltose binding protein)
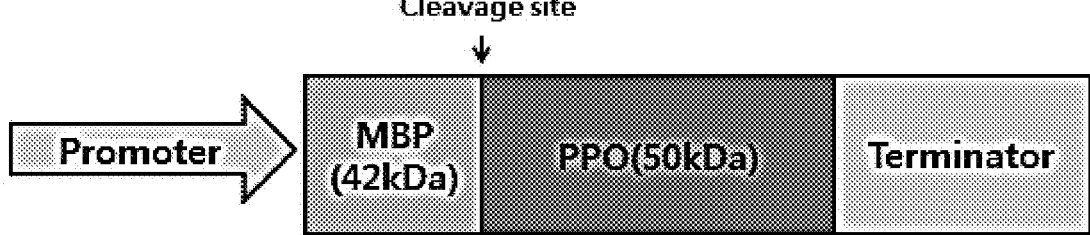

[Figure 34]
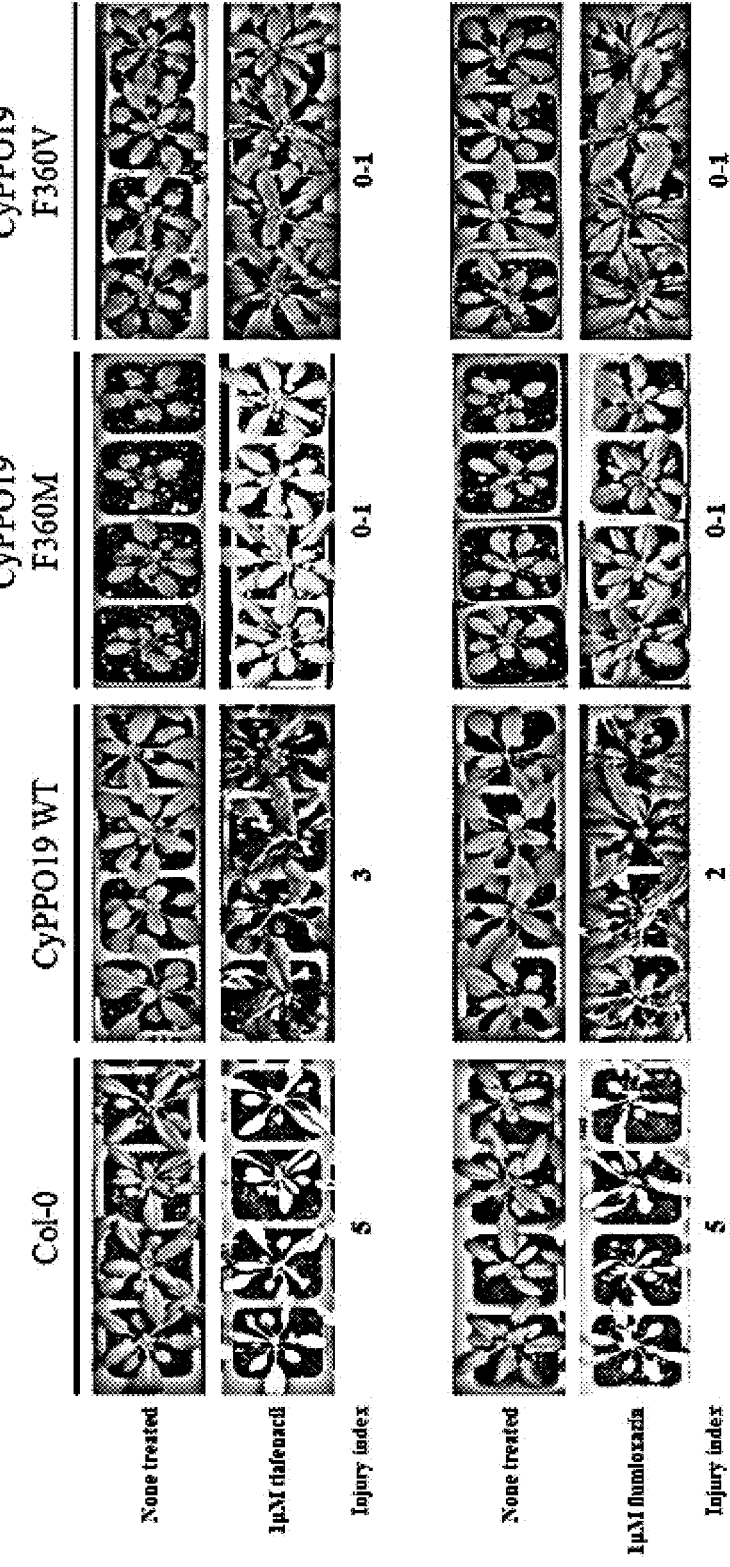

[Figure 35]
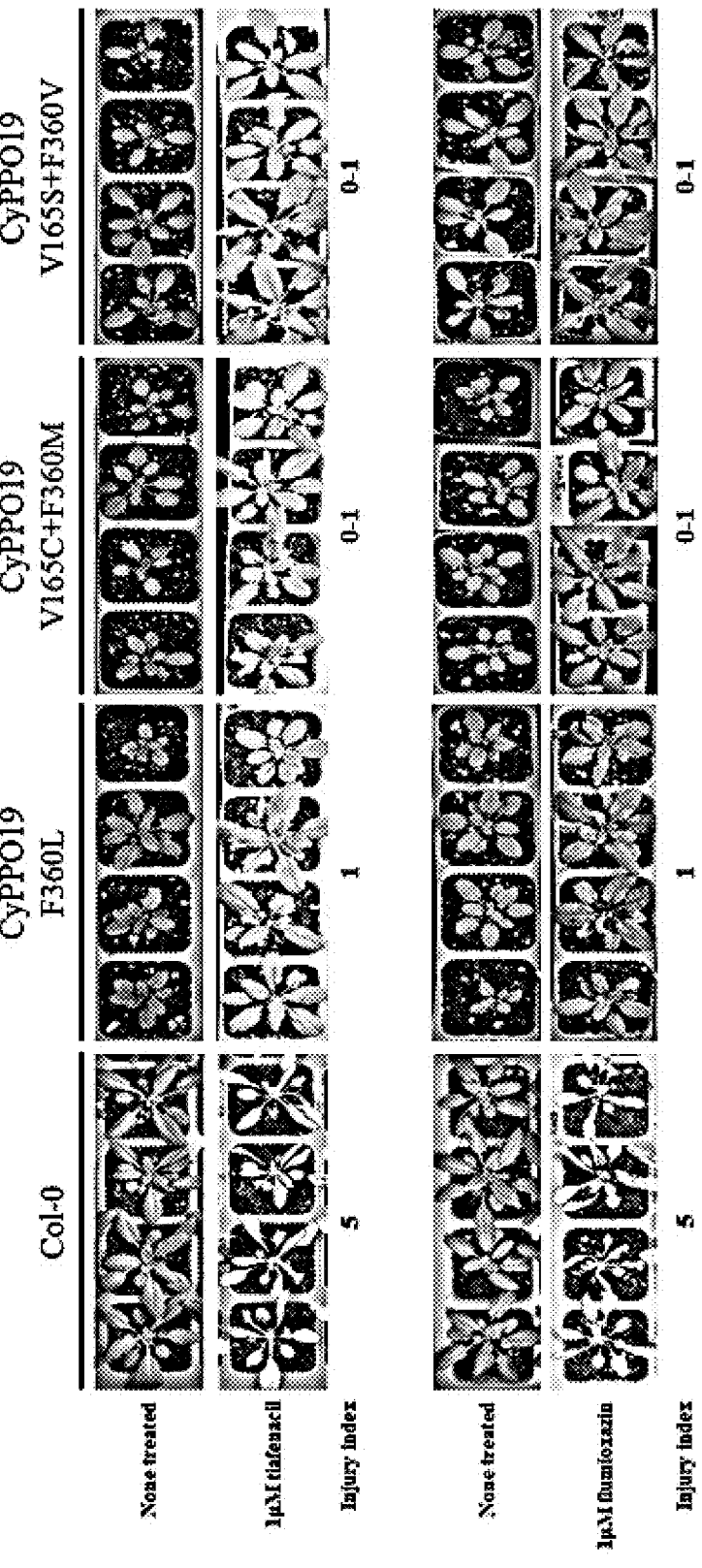

[Figure 36]
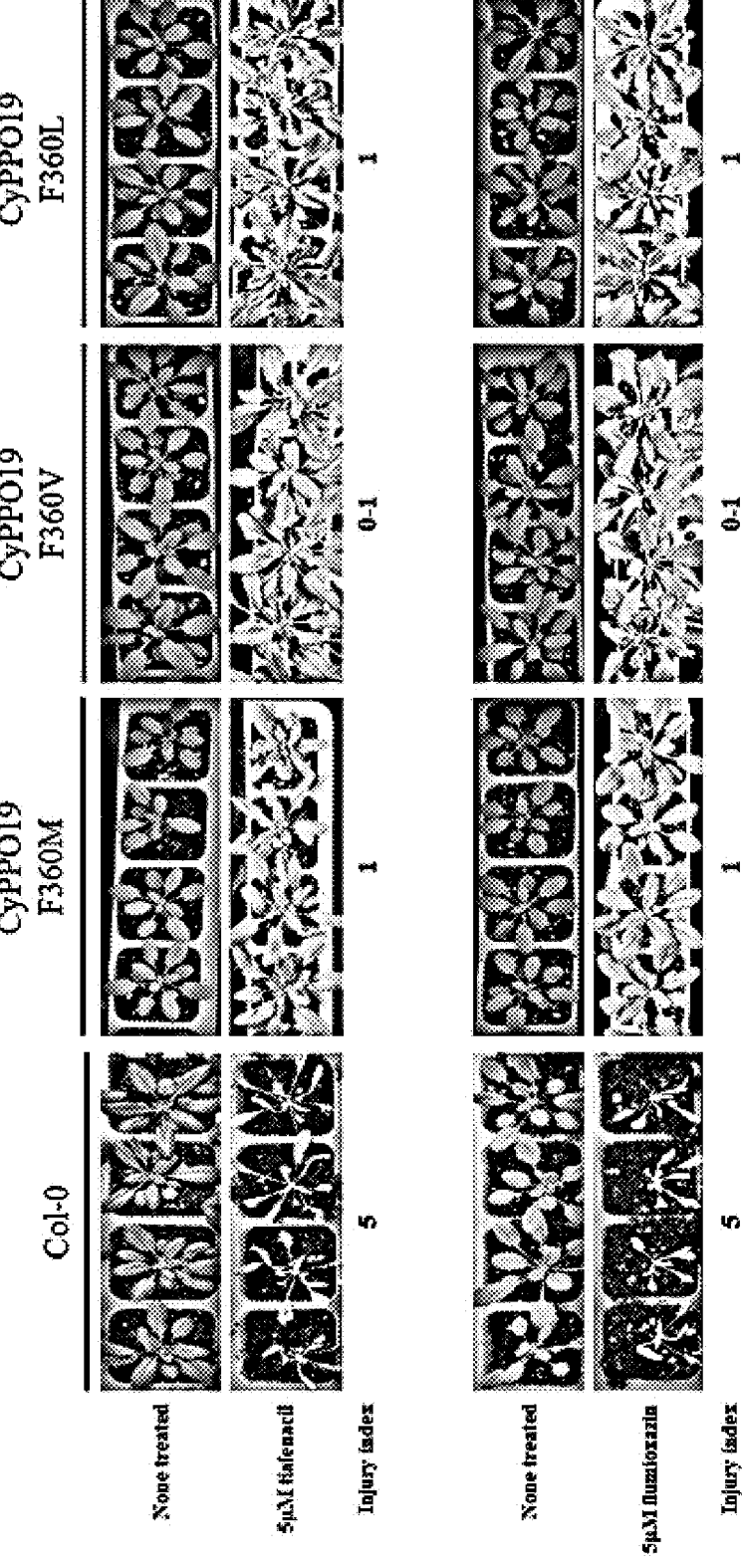

[Figure 37]
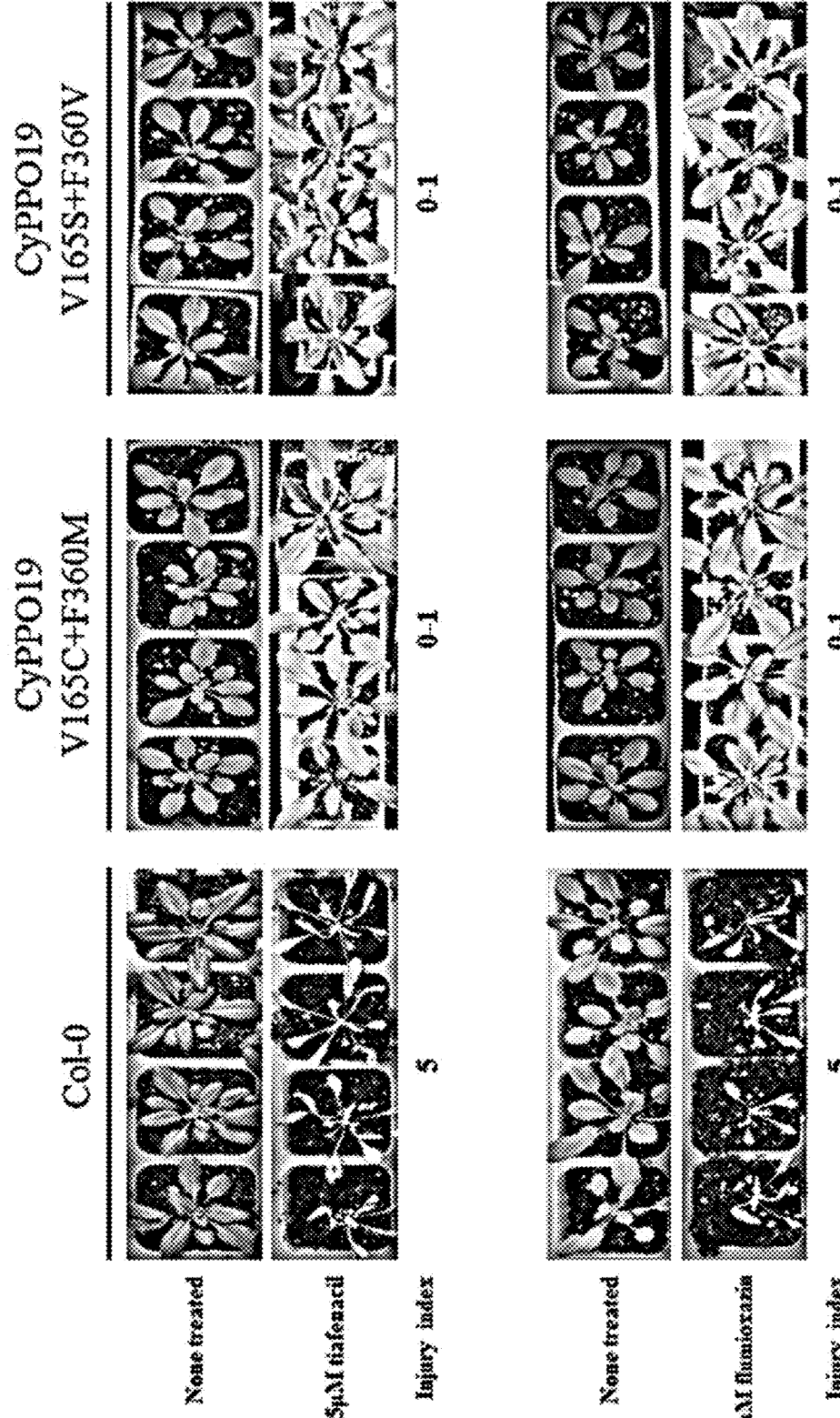

【Figure 38】
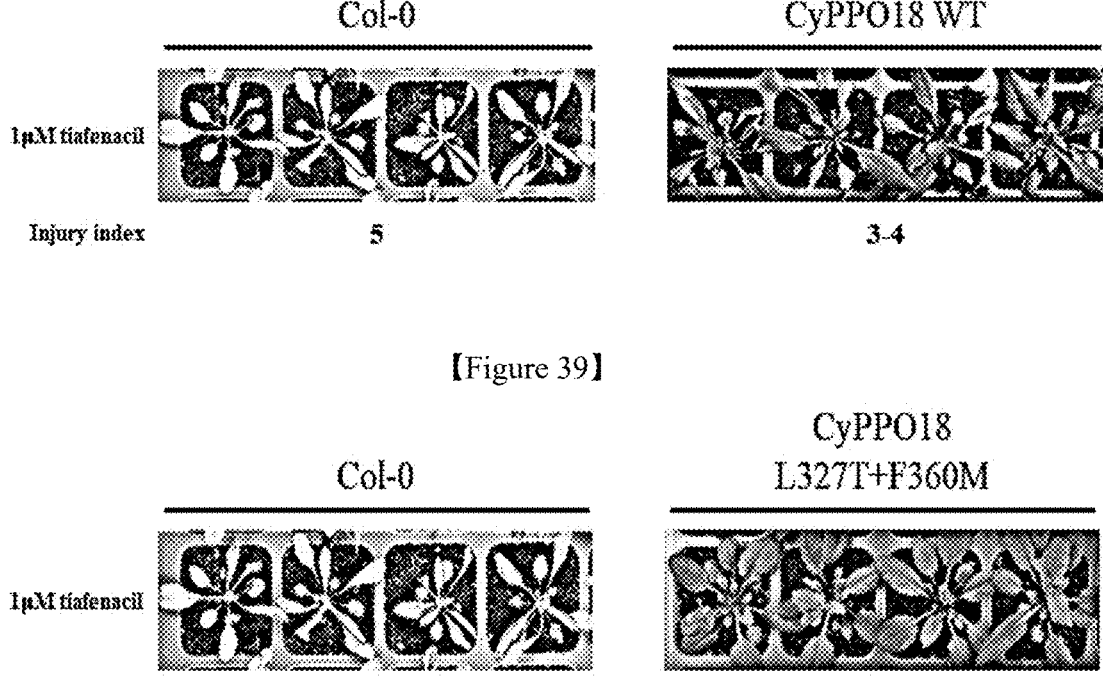
Col-0
CyPPO18 WT
1μM tiafenacil
Injury index     5     3-4
【Figure 39】
Col-0
CyPPO18
L327T+F360M
1μM tiafenacil
Injury index     5     0-1

SEQUENCE LISTING

```
<160> NUMBER OF SEQ ID NOS: 302

<210> SEQ ID NO 1
<211> LENGTH: 467
<212> TYPE: PRT
<213> ORGANISM: Artificial Sequence
<220> FEATURE:
<223> OTHER INFORMATION: Synthetic_PPO of Thermosynechococcus elongatus
      PKUAC-SCTE542 (comprising GenBank No. CP032152.1)

<400> SEQUENCE: 1

Met Ser Glu Val Asp Val Ala Ile Val Gly Gly Gly Leu Ser Gly Leu
1               5                   10                  15

Ser Leu Ala Trp Arg Leu Gln Gln Ser Ala Pro Gln Tyr Ser Val Val
            20                  25                  30

Leu Leu Glu Ala Ser Asp Arg Leu Gly Gly Asn Ile Thr Thr Gln Thr
        35                  40                  45

Ala Glu Gly Phe Val Trp Glu Leu Gly Pro Asn Ser Phe Ala Pro Thr
    50                  55                  60

Pro Ala Leu Leu Gln Leu Ile Ala Glu Val Gly Leu Gln Ser Glu Leu
65                  70                  75                  80

Ile Arg Gly Asp Arg His Leu Pro Arg Tyr Ile Tyr Trp Arg Gly Gln
                85                  90                  95

Leu Tyr Pro Leu Gln Pro Thr Arg Pro Leu Ala Leu Ala Thr Ser Asn
            100                 105                 110

Leu Leu Ser Pro Trp Gly Lys Val Arg Ala Ala Leu Gly Ala Leu Gly
            115                 120                 125

Phe Val Pro Pro Tyr Leu Gly Ser Gly Asp Glu Ser Val Asn Ser Phe
        130                 135                 140

Phe Arg Arg His Leu Gly Gln Glu Val Ala Glu Arg Leu Val Ala Pro
145                 150                 155                 160

Phe Val Ser Gly Val Tyr Ala Gly Asp Pro Gln Gln Leu Ser Ala Ala
                165                 170                 175

Ala Ala Phe Arg Arg Ile Ala Gln Leu Glu Lys Leu Gly Gly Gly Leu
            180                 185                 190

Ile Ala Gly Ala Leu His Leu Arg Arg Gln Gln Ala Pro Lys Pro Lys
            195                 200                 205

Pro Pro Thr Ser Val Gln Met Arg Pro Gly Glu Leu Gly Ser Phe Lys
    210                 215                 220

Glu Gly Leu Ala Ala Leu Pro Arg Ala Ile Ala Gln Gln Leu Lys Ala
225                 230                 235                 240

Pro Ile His Leu Gln Thr Pro Val Gln Glu Ile Thr Pro Asp Pro Lys
                245                 250                 255

Gly Gly Tyr Leu Leu Arg Ser Gly Glu Gln Thr Trp Arg Ala Arg Ser
            260                 265                 270

Val Val Leu Ala Thr Pro Ala Tyr Gln Thr Ala Glu Leu Val Ala Pro
        275                 280                 285

Phe Gln Pro Ala Ile Ala Arg Val Leu Ala Thr Ile Pro Tyr Pro Thr
    290                 295                 300
```

```
Val Ala Cys Val Val Leu Ala Tyr Pro Ala Gly Leu Gly Arg Ser Val
305                 310                 315                 320

Arg Pro Gly Phe Gly Val Leu Ile Pro Arg Ser Gln Gly Ile Arg Thr
                325                 330                 335

Leu Gly Thr Ile Trp Ser Ser Cys Leu Phe Pro Gln Arg Thr Pro Ala
                340                 345                 350

Gly Trp Gln Val Phe Thr Ser Phe Ile Gly Gly Ala Thr Asp Pro Asp
                355                 360                 365

Leu Ala Ser Leu Ser Glu Glu Ala Ile Val Gln Gln Val Gln Gln Asp
    370                 375                 380

Leu Asn Arg Leu Leu Asp Leu Pro Ala Ala Lys Ala Arg Leu Leu Gly
385                 390                 395                 400

Met Lys Val Trp Arg Arg Ala Ile Pro Gln Tyr Met Val Gly Tyr Pro
                405                 410                 415

Glu Gln Trp Gln Gln Val Thr His Ala Leu Ser Gln Thr Pro Gly Leu
                420                 425                 430

Phe Leu Cys Ser Asn Tyr Ala Glu Gly Val Ala Leu Gly Asp Arg Val
                435                 440                 445

Glu His Gly Asn Arg Thr Ala Ala Ala Val Ala Ala Tyr Leu Ser Gly
    450                 455                 460

Gly Gln Pro
465

<210> SEQ ID NO 2
<211> LENGTH: 465
<212> TYPE: PRT
<213> ORGANISM: Artificial Sequence
<220> FEATURE:
<223> OTHER INFORMATION: Synthetic_PPO of Cyanobacteria bacterium J003
      (GenBank: RMH63851.1)

<400> SEQUENCE: 2

Met Met Glu Val Asp Val Ala Ile Val Gly Gly Gly Leu Ser Gly Leu
1                   5                   10                  15

Ser Val Ala Trp Arg Leu Gln Gln Ser Ala Pro Gln Tyr Ser Gly Val
                20                  25                  30

Leu Leu Glu Ala Ser Asp Arg Leu Gly Gly Asn Ile Thr Thr Gln Gly
                35                  40                  45

Ala Glu Gly Phe Val Trp Glu Leu Gly Pro Asn Ser Phe Ala Pro Thr
    50                  55                  60

Pro Ala Leu Leu Gln Leu Ile Ala Glu Val Gly Leu His Ser Glu Leu
65                  70                  75                  80

Ile Arg Gly Asp Arg His Leu Pro Arg Tyr Ile Tyr Trp Arg Gly Glu
                85                  90                  95

Leu Tyr Pro Leu Glu Pro Thr Arg Pro Leu Ala Leu Ala Thr Ser Asn
                100                 105                 110

Leu Leu Ser Pro Trp Gly Lys Val Arg Ala Ala Leu Gly Ala Leu Gly
                115                 120                 125

Phe Val Pro Pro Tyr Leu Gly Ser Gly Asp Glu Ser Val Asn Ser Phe
    130                 135                 140

Phe Arg Arg His Leu Gly Gln Glu Val Ala Glu Arg Leu Val Ala Pro
145                 150                 155                 160

Phe Val Ser Gly Val Tyr Ala Gly Asp Pro Gln Gln Leu Ser Ala Ala
                165                 170                 175

Ala Ala Phe Arg Arg Ile Ala Gln Leu Glu Lys Leu Gly Gly Gly Leu
                180                 185                 190
```

```
Ile Ala Gly Ala Leu Arg Leu Arg Arg Gln Gln Pro Pro Lys Pro Arg
        195                 200                 205

Pro Pro Ala Glu Val Gln Met Arg Pro Gly Glu Leu Gly Ser Phe Lys
    210                 215                 220

Glu Gly Leu Ala Ala Leu Pro Arg Ala Ile Ala Gln Gln Leu Lys Ala
225                 230                 235                 240

Pro Val His Leu Gln Thr Pro Val Glu Ala Ile Thr Pro Glu Pro Asn
                245                 250                 255

Gly Gly Tyr Leu Leu Arg Ser Gly Glu Gln Thr Trp Gln Ala Arg Ser
                260                 265                 270

Val Val Leu Ala Thr Pro Ala Tyr Gln Thr Ala Ala Leu Val Ala Pro
        275                 280                 285

Phe Gln Pro Ala Ile Ala Arg Val Leu Ala Ala Ile Pro Tyr Pro Thr
    290                 295                 300

Val Ala Cys Val Val Leu Ala Tyr Pro Ala Gly Leu Gly Arg Ser Val
305                 310                 315                 320

Arg Pro Gly Phe Gly Val Leu Ile Pro Arg Gly Gln Gly Ile Arg Thr
                325                 330                 335

Leu Gly Thr Ile Trp Ser Ser Cys Leu Phe Pro Gln Arg Thr Pro Ala
                340                 345                 350

Gly Trp Gln Val Phe Thr Ser Phe Ile Gly Gly Ala Thr Asp Pro Asp
        355                 360                 365

Leu Ala Ser Leu Arg Glu Glu Ala Ile Val Gln Gln Val Gln Gln Asp
    370                 375                 380

Leu Thr Arg Leu Leu Asp Leu Pro Ala Ala Lys Ala Arg Leu Leu Gly
385                 390                 395                 400

Met Lys Val Trp Arg Arg Ala Ile Pro Gln Tyr Leu Val Gly Tyr Pro
                405                 410                 415

Gln Gln Trp Gln Gln Val Thr His Ala Leu Ser His Thr Pro Gly Leu
                420                 425                 430

Phe Leu Cys Ser Asn Tyr Ala Glu Gly Val Ala Leu Gly Asp Arg Val
        435                 440                 445

Glu His Gly Asn Arg Thr Ala Ala Ala Val Ala Ala Tyr Leu Ser Gly
    450                 455                 460

Gly
465

<210> SEQ ID NO 3
<211> LENGTH: 467
<212> TYPE: PRT
<213> ORGANISM: Artificial Sequence
<220> FEATURE:
<223> OTHER INFORMATION: Synthetic_PPO of Thermosynechococcus vulcanus
      NIES-2134 (BAY51976)

<400> SEQUENCE: 3

Met Ile Glu Val Asp Val Ala Ile Val Gly Gly Gly Leu Ser Gly Leu
1               5                   10                  15

Ser Val Ala Trp Arg Leu Gln Arg Ser Ala Pro His Tyr Ser Gly Val
                20                  25                  30

Leu Leu Glu Ala Ser Asp Arg Leu Gly Gly Asn Ile Thr Thr Gln Ala
        35                  40                  45

Ala Glu Gly Phe Val Trp Glu Leu Gly Pro Asn Ser Phe Ala Pro Thr
    50                  55                  60

Pro Ala Leu Leu Gln Leu Ile Ala Glu Val Gly Leu His Ser Glu Leu
```

-continued

```
65                  70                  75                  80

Ile Arg Gly Asp Arg His Leu Pro Arg Tyr Ile Tyr Trp Arg Gly Glu
                85                  90                  95

Leu Tyr Pro Leu Glu Pro Thr Arg Pro Leu Ala Leu Ala Thr Ser Asn
                100                 105                 110

Leu Leu Ser Pro Trp Gly Lys Val Arg Ala Ala Leu Gly Ala Leu Gly
                115                 120                 125

Phe Val Pro Pro Tyr Leu Gly Ser Gly Asp Glu Ser Val Asp Ser Phe
                130                 135                 140

Phe Arg Arg His Leu Gly Gln Glu Val Ala Glu Arg Leu Val Ala Pro
145                 150                 155                 160

Phe Val Ser Gly Val Tyr Ala Gly Asp Pro Gln Gln Leu Ser Ala Ala
                165                 170                 175

Ala Ala Phe Arg Arg Ile Ala Gln Leu Glu Lys Leu Gly Gly Ser Leu
                180                 185                 190

Ile Ala Gly Ala Leu Arg Leu Arg Arg Gln Gln Pro Pro Gln Pro Lys
                195                 200                 205

Pro Pro Ala Gln Val Gln Met Arg Pro Gly Glu Leu Gly Ser Phe Arg
                210                 215                 220

Glu Gly Leu Ala Ala Leu Pro Arg Ala Ile Ala Gln Gln Leu Lys Ala
225                 230                 235                 240

Pro Leu His Leu Gln Thr Pro Val Glu Ala Ile Thr Pro Glu Pro Lys
                245                 250                 255

Gly Gly Tyr Leu Leu Arg Ser Gly Glu Gln Thr Trp His Ala Arg Ser
                260                 265                 270

Val Val Leu Ala Thr Pro Ala Tyr Gln Ser Ala Glu Leu Val Ala Pro
                275                 280                 285

Phe Gln Pro Ala Ile Ala Arg Ala Leu Ala Thr Ile Pro Tyr Pro Thr
                290                 295                 300

Val Ala Cys Val Val Leu Ala Tyr Pro Ala Gly Leu Gly Arg Ser Val
305                 310                 315                 320

Arg Pro Gly Phe Gly Val Leu Val Pro Arg Gly Gln Gly Ile Arg Thr
                325                 330                 335

Leu Gly Thr Ile Trp Ser Ser Cys Leu Phe Pro Gln Arg Thr Pro Ala
                340                 345                 350

Gly Trp Gln Val Phe Thr Ser Phe Ile Gly Gly Ala Thr Asp Pro Asp
                355                 360                 365

Leu Ala Ser Leu Arg Glu Glu Ala Ile Val Glu Gln Val Gln Gln Asp
                370                 375                 380

Leu Thr Arg Leu Leu Asp Leu Pro Ala Ala Lys Ala Arg Leu Leu Gly
385                 390                 395                 400

Met Lys Val Trp Arg Arg Ala Ile Pro Gln Tyr Ile Val Gly Tyr Pro
                405                 410                 415

Gln Gln Trp Gln Gln Leu Thr His Ala Leu Thr Gln Thr Pro Gly Leu
                420                 425                 430

Phe Leu Cys Ser Asn Tyr Ala Glu Gly Val Ala Leu Gly Asp Arg Val
                435                 440                 445

Glu His Gly Asn Arg Thr Ala Ala Ala Val Ala Ala Tyr Leu Ala Gly
                450                 455                 460

Gly Gln Ser
465
```

<210> SEQ ID NO 4

<211> LENGTH: 476
<212> TYPE: PRT
<213> ORGANISM: Artificial Sequence
<220> FEATURE:
<223> OTHER INFORMATION: Synthetic_PPO of Synechococcus lividus
(WP_099798264)

<400> SEQUENCE: 4

Met Ser Glu Pro Ile Val Val Asp Val Ala Val Val Gly Ala Gly Leu
1               5                   10                  15

Ser Gly Leu Ser Val Ala Trp Arg Leu Gln Gln Val Ala Pro Gln Tyr
            20                  25                  30

Lys Val Val Val Leu Glu Ala Ser Asp Arg Leu Gly Gly Asn Ile Thr
        35                  40                  45

Thr Glu Ala Arg Asp Gly Phe Val Trp Glu Leu Gly Pro Asn Ser Phe
    50                  55                  60

Ala Pro Thr Pro Ala Leu Leu His Leu Ile Ala Glu Val Gly Leu Gln
65                  70                  75                  80

Asp Gln Leu Leu Arg Gly Asp Arg Arg Leu Pro Arg Tyr Ile Tyr Trp
                85                  90                  95

Arg Gly Lys Leu His Pro Leu Glu Pro Thr Arg Pro Leu Ala Leu Ala
            100                 105                 110

Thr Ser Gly Leu Leu Ser Pro Trp Gly Lys Leu Arg Ala Ala Leu Gly
        115                 120                 125

Ala Phe Gly Phe Val Pro Pro Tyr Leu Arg Asp Ala Asp Glu Ser Val
        130                 135                 140

Ser Ser Phe Phe Gln Arg His Leu Gly Lys Glu Val Ala Glu Arg Leu
145                 150                 155                 160

Val Ala Pro Phe Val Ser Gly Val Tyr Ala Gly Asp Pro Gln Gln Leu
                165                 170                 175

Ser Ala Ala Ala Ala Phe Arg Arg Ile Val Gln Leu Glu Gln Leu Gly
            180                 185                 190

Gly Ala Leu Ile Pro Gly Ala Leu Arg Leu Arg Arg Gln Gln Pro Pro
        195                 200                 205

Lys Pro Thr Pro Pro Lys Gly Leu Glu Met Arg Pro Gly Glu Leu Gly
    210                 215                 220

Ser Phe Gln Glu Gly Leu Ser Ala Leu Pro Arg Ala Ile Ala His His
225                 230                 235                 240

Leu Ala Ala Pro Ile His Leu Gln Thr Ala Leu His Gln Leu Thr Pro
                245                 250                 255

Glu Leu Ser Gly Gly Tyr Thr Leu Ser Ala Thr Thr Pro Asp Gly Glu
            260                 265                 270

Gln Ala Trp Arg Ala Arg Ser Val Val Leu Ala Thr Pro Ala Tyr Val
            275                 280                 285

Thr Ala Asp Leu Leu Arg Pro Trp Gln Pro Thr Ile Ala Ala Gly Leu
    290                 295                 300

Glu Ala Ile Pro Tyr Pro Ala Val Ala Cys Val Val Leu Ala Tyr Pro
305                 310                 315                 320

Ala Ala Val Gly Val Thr Ala Arg Pro Gly Phe Gly Val Leu Ile Pro
            325                 330                 335

Arg Thr Gln Gly Leu Arg Thr Leu Gly Thr Ile Trp Ser Ser Cys Leu
        340                 345                 350

Phe Pro Glu Arg Thr Pro Ser Gly Trp Gln Val Phe Thr Ser Phe Ile
        355                 360                 365

Gly Gly Ala Thr Asp Pro Glu Leu Ala Thr Leu Glu Pro Glu Ala Ile

-continued

```
            370             375             380

Val Gln Gln Val Gln Gln Asp Leu Glu His Met Leu Ala Leu Pro Pro
385             390             395             400

Ala Lys Ala Arg Leu Leu Gly Met Lys Leu Trp Arg Arg Ala Ile Pro
            405             410             415

Gln Tyr Thr Leu Gly Tyr Pro Gln Gln Trp Gln Gln Ile Thr His Ala
            420             425             430

Leu Lys His Leu Pro Gly Leu Phe Leu Cys Ser Asn Tyr Ala Ala Gly
            435             440             445

Val Ala Leu Gly Asp Arg Val Glu His Gly Tyr Asn Thr Ala Ala Ala
            450             455             460

Val Asp Ala Tyr Leu Gly Gly Thr Tyr Gly Ser Val
465             470             475

<210> SEQ ID NO 5
<211> LENGTH: 484
<212> TYPE: PRT
<213> ORGANISM: Artificial Sequence
<220> FEATURE:
<223> OTHER INFORMATION: Synthetic_PPO of Microcoleaceae bacterium
      UBA10368 (HBK97224)

<400> SEQUENCE: 5

Met Thr Asn Val Val Asp Thr Leu Ile Val Gly Ala Gly Ile Ser Gly
1               5               10              15

Leu Ser Leu Ala His Ala Leu Gln Lys Gln Ala Lys Thr Ala Pro Pro
            20              25              30

Leu Lys Ile Leu Val Ala Glu Ser Gln Gly Arg Val Gly Gly Asn Ile
            35              40              45

Thr Thr Gln Thr Asp Gly Gly Phe Leu Trp Glu Glu Gly Pro Asn Ser
            50              55              60

Phe Ala Pro Thr Pro Glu Leu Met Lys Leu Ala Val Asp Val Gly Leu
65              70              75              80

Lys Gln Glu Leu Ile Phe Ala Asp Arg Lys Leu Pro Arg Tyr Val Tyr
            85              90              95

Trp Gln Gly Lys Leu Gln Pro Val Pro Met Thr Pro Gln Ala Met Ile
            100             105             110

Gln Ser Gln Leu Leu Ser Phe Pro Gly Lys Leu Arg Ala Leu Val Gly
            115             120             125

Ala Leu Gly Phe Val Gly Pro Ala Met Gly Ser Gln Leu Ser Gln Gln
            130             135             140

Gly Gly Glu Glu Thr Val Ser Gln Phe Phe Arg Arg His Leu Gly Thr
145             150             155             160

Glu Val Met Gln Arg Leu Val Glu Pro Phe Val Ser Gly Val Tyr Ala
            165             170             175

Gly Asp Pro Gln Gln Leu Ser Ala Ala Ala Phe Gly Arg Val Thr
            180             185             190

Gln Met Ala Asp Val Gly Gly Gly Leu Val Ala Gly Ala Leu Leu Ser
            195             200             205

Ala Arg Lys Arg Pro Lys Lys Leu Pro Val Asp Pro Asn Ile Pro Gln
            210             215             220

Thr Lys Pro Gly Glu Leu Gly Ser Phe Lys Gln Gly Leu Lys Ala Leu
225             230             235             240

Pro Glu Ala Ile Ala Ala Gln Leu Gly Asp Arg Leu Lys Leu Asn Trp
            245             250             255
```

-continued

```
His Leu Thr Arg Leu Gln Arg Thr Glu Arg Gln Thr Tyr Ile Ala Glu
            260             265             270

Phe Ala Thr Pro Asp Gly Gln Gln Gln Val Glu Ala Arg Thr Val Val
        275             280             285

Leu Thr Thr Pro Ala Tyr Ile Thr Ala Glu Leu Leu Ala Pro Leu Gln
        290             295             300

Pro Glu Val Ser Ser Ala Leu Gln Ala Val Thr Tyr Pro Thr Val Ala
305             310             315             320

Cys Val Val Leu Ala Tyr Pro Leu Ser Asp Val Lys Gly Lys Leu Val
            325             330             335

Gly Phe Gly Asn Leu Ile Pro Arg Gly Gln Gly Ile Arg Thr Leu Gly
            340             345             350

Thr Ile Trp Thr Ser Ser Leu Phe Pro Asp Arg Ala Pro Ala Gly Trp
            355             360             365

Gln Thr Leu Ser Asn Tyr Ile Gly Gly Ala Thr Asp Ser Asp Ile Ala
        370             375             380

Asn Leu Asp Pro Glu Gln Ile Val Gly Glu Val His Arg Asp Leu Ser
385             390             395             400

Arg Ile Leu Leu Lys Pro Leu Ala Ala Gln Pro Lys Val Leu Ala Val
            405             410             415

Asn Leu Trp Lys Arg Ala Ile Pro Gln Tyr Asn Leu Gly His Leu Pro
            420             425             430

Arg Leu Gln Gln Val Glu Asn Gly Leu Lys Ser Leu Pro Gly Val Tyr
            435             440             445

Leu Cys Ser Asn Tyr Val Gly Gly Val Ala Leu Gly Asp Cys Val Arg
        450             455             460

Trp Gly Phe Glu Arg Ala Ile Glu Val Ser Glu Tyr Leu Gln Glu Thr
465             470             475             480

Gly His Arg Ala

<210> SEQ ID NO 6
<211> LENGTH: 476
<212> TYPE: PRT
<213> ORGANISM: Artificial Sequence
<220> FEATURE:
<223> OTHER INFORMATION: Synthetic_PPO of Microcoleaceae bacterium
      UBA11344 (HAT14741.1)
<220> FEATURE:
<221> NAME/KEY: VARIANT
<222> LOCATION: (51)..(52)
<223> OTHER INFORMATION: Synthetic_Xaa at positions 51-52 is any
      naturally-occurring amino acid

<400> SEQUENCE: 6

Met Thr Asn Ile Val Asp Thr Leu Ile Val Gly Ala Gly Ile Ser Gly
1               5               10              15

Leu Ser Leu Ala His Ala Leu Gln Lys Gln Ala Lys Thr Ala Pro Pro
            20              25              30

Leu Lys Ile Leu Val Ala Glu Ser Arg Gly Arg Val Gly Gly Asn Ile
        35              40              45

Thr Thr Xaa Xaa Glu Glu Gly Pro Asn Ser Phe Met Pro Thr Pro Glu
        50              55              60

Leu Met Lys Leu Ala Val Asp Val Gly Leu Lys Gln Glu Leu Ile Phe
65              70              75              80

Ala Asp Arg Lys Leu Pro Arg Tyr Ile Tyr Trp Gln Gly Lys Leu Gln
            85              90              95

Pro Val Pro Met Thr Pro Gln Ala Met Ile Gln Ser Gln Leu Leu Ser
```

-continued

```
               100                 105                 110
Phe Pro Gly Lys Leu Arg Ala Leu Phe Gly Ala Leu Gly Phe Val Gly
               115                 120                 125

Ser Ala Met Gly Ser Gln Leu Ser Gln Gln Gly Gly Glu Glu Thr Val
           130                 135                 140

Ser Gln Phe Phe Arg Arg His Leu Gly Thr Glu Val Met Gln Arg Leu
145                 150                 155                 160

Val Glu Pro Phe Val Ser Gly Val Tyr Ala Gly Asp Pro Gln Gln Leu
               165                 170                 175

Ser Ala Ala Ala Phe Gly Arg Val Thr Gln Met Ala Asp Val Gly
               180                 185                 190

Gly Gly Leu Val Ala Gly Ala Leu Leu Ser Ala Arg Lys Arg Pro Lys
               195                 200                 205

Lys Leu Pro Val Asp Pro Asn Ile Pro Gln Thr Lys Pro Gly Glu Leu
           210                 215                 220

Gly Ser Phe Lys Gln Gly Leu Lys Ala Leu Pro Glu Ala Ile Ala Ala
225                 230                 235                 240

Gln Leu Gly Asp Arg Leu Lys Leu Asn Trp His Leu Thr Arg Leu Gln
               245                 250                 255

Arg Thr Glu Arg Gln Thr Tyr Ile Ala Glu Phe Ala Thr Pro Asp Gly
               260                 265                 270

Gln Gln Gln Val Glu Ala Arg Thr Val Val Leu Thr Thr Pro Ala Tyr
           275                 280                 285

Ile Thr Ala Glu Leu Leu Ala Pro Leu Gln Pro Glu Val Ser Ser Ala
           290                 295                 300

Leu Gln Ala Val Thr Tyr Pro Thr Val Ala Cys Val Val Leu Ala Tyr
305                 310                 315                 320

Pro Leu Ser Asp Val Lys Gly Lys Leu Val Gly Phe Gly Asn Leu Ile
               325                 330                 335

Pro Arg Gly Gln Gly Ile Arg Thr Leu Gly Thr Ile Trp Thr Ser Ser
               340                 345                 350

Leu Phe Pro Asp Arg Ala Pro Ala Gly Trp Gln Thr Leu Ser Asn Tyr
               355                 360                 365

Ile Gly Gly Ala Thr Asp Ser Asp Ile Ala Asn Leu Asp Pro Glu Gln
           370                 375                 380

Ile Val Gly Glu Val His Arg Asp Leu Ser Arg Met Leu Leu Lys Pro
385                 390                 395                 400

Leu Val Ala Gln Pro Lys Val Leu Ala Val Asn Leu Trp Lys Arg Ala
               405                 410                 415

Ile Pro Gln Tyr Asn Leu Gly His Ile Gln Arg Leu Gln Gln Val Glu
               420                 425                 430

Asn Gly Leu Lys Ser Leu Pro Gly Val Tyr Leu Cys Ser Asn Tyr Val
               435                 440                 445

Gly Gly Ile Ala Leu Gly Asp Cys Val Arg Trp Gly Phe Glu Arg Ala
           450                 455                 460

Ile Glu Val Ser Glu Tyr Leu Gln Glu Thr Gly Arg
465                 470                 475
```

```
<210> SEQ ID NO 7
<211> LENGTH: 491
<212> TYPE: PRT
<213> ORGANISM: Artificial Sequence
<220> FEATURE:
<223> OTHER INFORMATION: Synthetic_PPO of Oscillatoriales cyanobacterium
      (TAE85894)
```

<400> SEQUENCE: 7

```
Met Glu Val Leu Asp Thr Leu Ile Val Gly Ala Gly Ile Ser Gly Leu
1               5                   10                  15

Ser Leu Ala His Ala Leu Gln Lys Glu Ala Arg Ile Ala Ser Pro Arg
            20                  25                  30

Ala Ile Leu Val Ala Glu Ser Gln Gly Arg Val Gly Gly Asn Ile Thr
        35                  40                  45

Thr Ala Thr Gly Glu Gly Phe Leu Trp Glu Glu Gly Pro Asn Ser Phe
        50                  55                  60

Ser Pro Thr Pro Glu Leu Leu Lys Leu Ala Val Asp Val Gly Leu Lys
65                  70                  75                  80

Gln Glu Leu Ile Phe Ala Asp Arg Lys Leu Pro Arg Tyr Val Tyr Trp
                85                  90                  95

Asp Lys Lys Leu Gln Pro Val Pro Met Thr Pro Gly Ala Met Ile Gln
            100                 105                 110

Ser Gly Leu Leu Ser Phe Pro Gly Lys Leu Arg Ala Leu Phe Gly Ala
            115                 120                 125

Leu Gly Phe Val Ala Pro Ala Met Gly Ser Gln Leu Ser Gln Gln Gly
        130                 135                 140

Asp Glu Glu Thr Val Ser Gln Phe Phe Arg Arg His Leu Gly Lys Glu
145                 150                 155                 160

Val Met Gln Arg Leu Val Glu Pro Phe Val Ser Gly Val Tyr Ala Gly
                165                 170                 175

Asp Pro Gln Gln Leu Ser Ala Ala Ala Ala Phe Gly Arg Val Thr Lys
            180                 185                 190

Met Ala Asp Ala Gly Gly Ser Leu Val Ala Gly Ala Leu Leu Ser Ala
            195                 200                 205

Arg Lys Lys Lys Pro Gln Pro Pro Leu Gly Lys Gly Gly Leu Asn Ala
        210                 215                 220

Leu Ala Asp Pro Asn Ile Pro Lys Thr Lys Arg Gly Glu Leu Gly Ser
225                 230                 235                 240

Phe Lys Gly Gly Leu Lys Ala Leu Pro Glu Ala Ile Ala Ala Ser Leu
                245                 250                 255

Gly Asp Arg Val Lys Leu Asn Trp His Leu Thr Arg Leu Asp Arg Thr
            260                 265                 270

Glu Arg Glu Thr Tyr Ile Ala Val Phe Ser Thr Pro Asp Gly Gln Gln
        275                 280                 285

Glu Ile Glu Ala Arg Thr Val Val Leu Thr Thr Pro Ala Tyr Val Thr
        290                 295                 300

Ala Glu Leu Leu Gln Pro Leu Gln Pro Ser Val Ser Ser Ala Leu Gln
305                 310                 315                 320

Ala Phe Thr Tyr Pro Thr Val Ala Ser Val Val Leu Ala Tyr Pro Met
                325                 330                 335

Ser Asp Val Lys Gly Lys Leu Val Gly Phe Gly Asn Leu Ile Pro Arg
            340                 345                 350

Gly Gln Gly Ile Arg Thr Leu Gly Thr Ile Trp Thr Ser Ser Leu Phe
            355                 360                 365

Pro Asp Arg Ala Pro Ala Gly Trp Gln Thr Leu Thr Ser Tyr Ile Gly
        370                 375                 380

Gly Ala Thr Asp Ser Gly Ile Gly Asn Leu Asp Ala Glu Gln Ile Val
385                 390                 395                 400

Gly Glu Val His Arg Asp Leu Ser Arg Ile Leu Leu Lys Pro Glu Ala
```

-continued

```
                405                 410                 415

Ala Gln Pro Lys Val Leu Thr Val Lys Leu Trp Lys Arg Ala Ile Pro
            420                 425                 430

Gln Tyr Asn Leu Gly Tyr Phe Asp Arg Leu Gln Gln Ile Asp Arg Gly
            435                 440                 445

Leu Lys Ser Leu Pro Gly Leu Tyr Leu Cys Ser Asn Tyr Leu Gly Gly
        450                 455                 460

Val Ala Leu Gly Asp Cys Val Arg Arg Gly Phe Glu Arg Ala Gln Glu
465                 470                 475                 480

Val Gly Glu Tyr Leu Asn Asp Ser Phe Glu Phe
                485                 490

<210> SEQ ID NO 8
<211> LENGTH: 467
<212> TYPE: PRT
<213> ORGANISM: Artificial Sequence
<220> FEATURE:
<223> OTHER INFORMATION: Synthetic_PPO of Cyanobacteria bacterium
      UBA8156 (HAN47127.1)

<400> SEQUENCE: 8

Met Asp Asp Arg Gln Gly Glu Pro Thr Glu Val Leu Val Val Gly Ala
1               5                   10                  15

Gly Ile Cys Gly Leu Thr Val Ala His Gly Leu Ala Gln Arg Gly Val
            20                  25                  30

Ala Cys Arg Val Val Glu Ala Ser Asp Arg Val Gly Gly Ala Ile Val
            35                  40                  45

Thr Arg Arg Glu His Gly Phe Gln Trp Glu Glu Gly Pro Asn Ser Phe
        50                  55                  60

Ser Pro Thr Pro Glu Leu Leu Ala Leu Ala Ile Ala Met Gly Leu Arg
65                  70                  75                  80

Asp Glu Leu Ile Leu Ala Asp Arg Arg Leu Pro Arg Tyr Val Trp Trp
                85                  90                  95

Gln Asn Arg Leu Gln Ala Val Pro Met Ala Pro Pro Gly Leu Leu Thr
            100                 105                 110

Thr Gly Leu Leu Ser Pro Trp Gly Lys Leu Arg Ala Ala Val Gly Ala
        115                 120                 125

Leu Gly Phe Val Pro Pro Ser Phe Ala Ala Asp Glu Thr Val Gly Ser
        130                 135                 140

Phe Phe Arg Arg His Leu Gly Pro Glu Val Leu Thr Arg Leu Ala Ala
145                 150                 155                 160

Pro Phe Val Ser Gly Val Tyr Ala Gly Asp Pro Glu Ala Leu Ser Ile
            165                 170                 175

Gly Ala Ala Phe Pro Arg Val Thr Ala Ile Glu Ala Met Gly Gly Gly
            180                 185                 190

Leu Val Ala Gly Phe Ile Gln Ala Leu Arg Gln Arg Gly Ala Pro Asp
        195                 200                 205

Pro His Leu Pro Gln Thr Lys Pro Gly Glu Leu Gly Ser Phe Arg Glu
        210                 215                 220

Gly Ile Glu Ala Leu Pro Arg Ala Ile Ala Ala Asp Leu Ala Gln Arg
225                 230                 235                 240

Gly Val Thr Leu Thr Leu Asn Gln Ala Leu Thr Arg Leu Glu Pro Thr
                245                 250                 255

Gly Asp Arg Trp Arg Ala Val Leu Ala Ser Gly Glu Glu Leu Glu Ala
            260                 265                 270
```

-continued

Arg Ser Val Val Leu Ala Val Pro Ala Trp Ala Ala Ala Lys Ile Leu
        275                 280                 285

Gln Gln Thr Pro Glu Thr Ala Asp Trp Val Ala Asp Leu Glu Arg Ile
        290                 295                 300

Pro Tyr Pro Ala Val Ala Cys Ala Val Leu Ala Tyr Pro Asp Gly Asp
305                 310                 315                 320

Leu Arg Gln Pro Leu Arg Gly Phe Gly His Leu Val Pro Arg Gly Gln
                325                 330                 335

Gly Ile Arg Thr Leu Gly Thr Ile Trp Ala Ser Ser Leu Phe Pro Gly
                340                 345                 350

Arg Ala Pro Ala Gly Tyr Thr Leu Leu Leu Asn Phe Ile Gly Gly Thr
                355                 360                 365

Thr Asp Pro Thr Leu Ala Gln Leu Asp Ala Gly Ala Ile Ala Gln Ala
        370                 375                 380

Val His Gln Asp Leu Arg Gln Ile Leu Val Gln Pro Thr Ala Ala Pro
385                 390                 395                 400

Pro Lys Val Leu Ala Val Asn Leu Trp Arg Arg Ala Ile Pro Gln Phe
                405                 410                 415

Thr Val Gly His Gln Gly Arg Leu Ala Arg Leu Ala Ala Gly Leu Pro
                420                 425                 430

Pro Gly Leu Val Leu Ala Gly Asn Tyr Arg Gly Gly Val Ala Leu Gly
                435                 440                 445

Asp Cys Val Arg His Gly Leu Ala Val Ala Ala Gln Val Ala Ala Phe
        450                 455                 460

Leu Glu Arg
465

<210> SEQ ID NO 9
<211> LENGTH: 469
<212> TYPE: PRT
<213> ORGANISM: Artificial Sequence
<220> FEATURE:
<223> OTHER INFORMATION: Synthetic_PPO of Rubidibacter lacunae
      (WP_022605844)

<400> SEQUENCE: 9

Met Leu Asp Thr Leu Val Val Gly Ala Gly Leu Ser Gly Leu Ser Val
1               5                   10                  15

Ala Arg Ser Leu Gln Met Ala Gly Arg Asn Val Leu Val Ala Glu Ala
                20                  25                  30

Gln Glu Arg Val Gly Gly Asn Ile Leu Thr Gln Gln Ser Asp Asp Gly
                35                  40                  45

Phe Gln Trp Glu Glu Gly Pro Asn Ser Phe Ser Pro Asn Arg Glu Leu
        50                  55                  60

Leu Glu Leu Ala Val Gly Val Gly Leu Arg Asp Lys Leu Ile Phe Ala
65                  70                  75                  80

Asp Arg Arg Leu Pro Arg Phe Val Tyr Trp Arg Asn Ser Leu His Pro
                85                  90                  95

Val Pro Met Ser Pro Pro Arg Ala Val Thr Thr Ser Leu Leu Ser Pro
                100                 105                 110

Leu Gly Lys Leu Arg Ala Val Ala Gly Ala Ile Gly Phe Val Pro Pro
        115                 120                 125

Ala Leu Ser Asp Glu Glu Ser Val Ala Glu Phe Phe Thr Arg His Leu
        130                 135                 140

Gly Ser Glu Val Ala Glu Arg Leu Val Ala Pro Phe Val Ser Gly Val
145                 150                 155                 160

```
Tyr Ala Gly Asp Val Glu Arg Leu Ser Val Ser Ser Ala Phe Arg Gln
                165                 170                 175

Val Ala Lys Leu Ser Glu Val Gly Gly Gly Leu Leu Ala Gly Ala Leu
                180                 185                 190

Leu Thr Arg Arg Gly Lys Ser Gly Pro Pro Gln Lys Leu Pro Pro Arg
                195                 200                 205

Val Asp Pro Asn Leu Pro Arg Val Gln Arg Gly Glu Leu Gly Ser Phe
            210                 215                 220

Val Gly Gly Leu Lys Met Leu Pro Glu Ala Ile Ala Ala Lys Leu Gly
        225                 230                 235                 240

Thr Lys Leu Lys Leu His Trp Thr Leu Glu His Leu Val Arg Cys Glu
                245                 250                 255

Gly Gly Tyr Arg Ala Glu Phe Ala Thr Pro Glu Gly Gln Gln Gln Ile
                260                 265                 270

Glu Val Arg Ser Leu Val Leu Ala Thr Pro Ala Tyr Arg Cys Ala Arg
                275                 280                 285

Val Leu Gln Ser Leu Ala Pro Ser Ala Cys Gln Ala Leu Ser Glu Met
            290                 295                 300

Pro Tyr Pro Ala Val Ala Cys Val Val Leu Ala Tyr Pro Ser Ser Ala
    305                 310                 315                 320

Phe Ser Ser Pro Leu Gln Gly Phe Gly Asn Leu Ile Pro Arg Gly Gln
                325                 330                 335

Gly Ile Arg Thr Leu Gly Thr Ile Trp Ser Ser Ala Leu Phe Pro Gly
                340                 345                 350

Arg Thr Pro Pro Gly Trp Glu Ile Leu Thr Ser Phe Ile Gly Gly Ala
                355                 360                 365

Thr Asp Pro Glu Leu Gly Thr Leu Ser Ala Gln Gln Ile Val Ala Glu
            370                 375                 380

Val Arg Arg Asp Leu Gln Arg Val Leu Val Asp Lys Glu Pro Asn Thr
    385                 390                 395                 400

Glu Pro Arg Val Leu Ala Ala Lys Val Trp Pro Arg Ala Ile Pro Gln
                405                 410                 415

Tyr Val Leu Gly His Ser Asp Arg Leu Asn Arg Ile Gln Ile Asp Leu
                420                 425                 430

Asp Arg Leu Pro Gly Leu Tyr Leu Cys Ser Asn Phe Thr Asp Gly Val
                435                 440                 445

Ala Leu Gly Asp Cys Val Arg Arg Gly Phe Glu Thr Ala Glu Ala Ile
            450                 455                 460

Gly Gln Tyr Leu Asn
465
```

```
<210> SEQ ID NO 10
<211> LENGTH: 471
<212> TYPE: PRT
<213> ORGANISM: Artificial Sequence
<220> FEATURE:
<223> OTHER INFORMATION: Synthetic_PPO of Hydrocoleum sp. CS-953
      (WP_094676324)
<220> FEATURE:
<221> NAME/KEY: VARIANT
<222> LOCATION: (32)
<223> OTHER INFORMATION: Xaa at position 32 is any naturally-occurring
      amino acid
<220> FEATURE:
<221> NAME/KEY: VARIANT
<222> LOCATION: (462)
<223> OTHER INFORMATION: Xaa at position 462 is any naturally-occurring
      amino acid
```

-continued

<400> SEQUENCE: 10

Met Leu Lys Leu Ala Val Asp Val Gly Leu Lys Gln Asp Leu Ile Phe
1               5                   10                  15

Ala Asp Arg Lys Leu Pro Arg Tyr Val Tyr Trp Asn Gly Gln Leu Xaa
                20                  25                  30

Leu Val Ala Glu Ser Gln Asn Arg Val Gly Gly Asn Ile Thr Thr Val
            35                  40                  45

Ser Gln Gly Asp Phe Ile Trp Glu Glu Gly Pro Asn Ser Phe Ser Pro
        50                  55                  60

Thr Pro Glu Leu Leu Lys Leu Ala Val Asp Val Gly Leu Lys Gln Asp
65                  70                  75                  80

Leu Ile Phe Ala Asp Arg Lys Leu Pro Arg Tyr Val Tyr Trp Asn Gly
                85                  90                  95

Gln Leu Leu Pro Val Pro Met Gly Pro Thr Ala Met Leu Gln Ser Lys
            100                 105                 110

Leu Leu Ser Asp Ser Gly Lys Leu Arg Ala Leu Val Gly Ala Leu Gly
        115                 120                 125

Phe Val Pro Pro Ala Val Gly Thr Gly Leu Ser Gln Gln Gly Gly Glu
    130                 135                 140

Glu Thr Val Ser Gln Phe Phe Gln Arg His Leu Gly Val Glu Val Met
145                 150                 155                 160

Gln Arg Leu Val Glu Pro Phe Val Ser Gly Val Tyr Ala Gly Asp Pro
                165                 170                 175

Ser Gln Leu Ser Ala Thr Ala Ala Phe Ser Arg Val Ala Arg Met Ala
            180                 185                 190

Asp Ile Gly Gly Gly Leu Leu Ala Gly Ala Val Leu Ser Ala Lys Arg
            195                 200                 205

Asn Pro Lys Ser Lys Val Ala Ala Asp Pro Asn Ile Pro Lys Thr Lys
        210                 215                 220

Pro Gly Glu Leu Gly Ser Phe Arg Gly Gly Leu Glu Ala Leu Pro Lys
225                 230                 235                 240

Ala Ile Ala Thr Tyr Leu Gly Glu Ala Val Lys Leu Asn Trp His Leu
                245                 250                 255

Ile Gly Ile Arg Arg Thr Glu Gln Gln Thr Tyr Ile Ala Glu Phe Ser
            260                 265                 270

Thr Pro Asn Gly Ser Glu Gln Ile Glu Thr Arg Thr Ile Ala Leu Ser
        275                 280                 285

Thr Pro Ala Tyr Phe Cys Ser Glu Leu Phe Lys Pro Leu Leu Pro Glu
    290                 295                 300

Ile Ala Ser Thr Phe Asp Glu Phe Tyr Tyr Pro Thr Val Ala Cys Val
305                 310                 315                 320

Val Leu Ala Tyr Pro Val Ser Ser Ile Lys Ala Lys Ile Asp Gly Phe
                325                 330                 335

Gly Asn Leu Ile Pro Arg Gly Gln Gly Ile Arg Thr Leu Gly Thr Ile
            340                 345                 350

Trp Ser Ser Ala Leu Phe Pro Gly Arg Thr Pro Pro Gly Trp Gln Val
            355                 360                 365

Phe Thr Asn Phe Ile Gly Gly Ala Thr Asp Pro Gly Ile Ser Gln Leu
    370                 375                 380

Asp Ser Glu Ala Ile Val Ser Arg Val His Gln Asp Leu Gly Gln Thr
385                 390                 395                 400

Leu Leu Lys Gln Asp Ala Glu Gln Pro Lys Val Leu Ala Val His Leu

```
                    405                 410                 415

Trp Ser Arg Ala Ile Pro Gln Tyr Asn Leu Gly His Asn Ser Arg Leu
        420                 425                 430

Asp Gln Ile Asn His Gly Leu Lys Ser Trp Pro Gly Val Tyr Leu Cys
            435                 440                 445

Ser Asn Tyr Ile Gly Gly Val Ala Leu Gly Asp Cys Val Xaa Tyr Ile
        450                 455                 460

Lys Thr Leu Gly Lys Leu Tyr
465                 470

<210> SEQ ID NO 11
<211> LENGTH: 487
<212> TYPE: PRT
<213> ORGANISM: Artificial Sequence
<220> FEATURE:
<223> OTHER INFORMATION: Synthetic_PPO of Oscillatoriales cyanobacterium
      (TAE55813)

<400> SEQUENCE: 11

Met Glu Val Leu Asp Thr Leu Ile Val Gly Ala Gly Ile Ser Gly Leu
1               5                   10                  15

Ser Leu Ala His Ala Leu Gln Lys Glu Ala Thr Ser Ala Ser Pro Arg
            20                  25                  30

Ala Ile Leu Val Ala Glu Ser Gln Gly Arg Val Gly Gly Asn Ile Thr
            35                  40                  45

Thr Ala Thr Gly Glu Gly Phe Leu Trp Glu Glu Gly Pro Asn Ser Phe
        50                  55                  60

Ser Pro Thr Pro Glu Leu Leu Lys Leu Ala Val Asp Val Gly Leu Lys
65                  70                  75                  80

Gln Glu Leu Ile Phe Ala Asp Arg Lys Leu Pro Arg Tyr Val Tyr Trp
                85                  90                  95

Glu Lys Lys Leu Gln Pro Val Pro Met Thr Pro Gly Ala Met Ile Gln
            100                 105                 110

Ser Gln Leu Leu Ser Phe Pro Gly Lys Leu Arg Ala Leu Phe Gly Ala
        115                 120                 125

Leu Gly Phe Val Gly Pro Ala Met Gly Ser Gln Leu Ser Gln Gln Gly
        130                 135                 140

Asp Glu Glu Thr Val Ser Gln Phe Phe Arg Arg His Leu Gly Lys Glu
145                 150                 155                 160

Val Met Gln Arg Leu Val Glu Pro Phe Val Ser Gly Val Tyr Ala Gly
                165                 170                 175

Asp Pro Gln Gln Leu Ser Ala Ala Ala Phe Gly Arg Val Thr Lys
            180                 185                 190

Met Ala Asp Ala Gly Gly Gly Leu Val Ala Gly Ala Leu Leu Ser Ala
            195                 200                 205

Arg Lys Arg Pro Pro Gln Pro Pro Leu Thr Lys Gly Gly Leu Lys Thr
        210                 215                 220

Val Ala Asp Pro Asn Ile Pro Lys Thr Lys Pro Gly Glu Leu Gly Ser
225                 230                 235                 240

Phe Lys Gly Gly Leu Gln Ala Leu Pro Glu Ala Ile Ala Ala Asn Leu
                245                 250                 255

Gly Asp Arg Leu Lys Leu Asn Trp His Leu Thr Arg Leu Asp Arg Thr
            260                 265                 270

Glu Arg Asp Thr Tyr Ile Ala Val Phe Ser Thr Pro Asp Gly Gln Gln
        275                 280                 285
```

-continued

```
Glu Val Glu Ala Arg Thr Val Val Leu Thr Thr Pro Ala Tyr Val Thr
    290                 295                 300

Ala Glu Leu Leu Glu Pro Leu Gln Pro Ser Val Ser Ser Ala Leu Gln
305                 310                 315                 320

Ala Phe Thr Tyr Pro Thr Val Ala Ser Val Val Leu Ala Tyr Pro Met
                325                 330                 335

Ser Asp Leu Lys Gly Lys Leu Val Gly Phe Gly Asn Leu Ile Pro Arg
            340                 345                 350

Gly Gln Gly Ile Arg Thr Leu Gly Thr Ile Trp Thr Ser Ser Leu Phe
            355                 360                 365

Ala Asp Arg Ala Pro Ala Gly Trp Gln Thr Leu Thr Ser Tyr Ile Gly
    370                 375                 380

Gly Ala Thr Asp Ser Gly Ile Gly Asn Leu Asp Ala Glu Gln Ile Val
385                 390                 395                 400

Gly Glu Val His Arg Asp Leu Ser Gln Ile Leu Leu Lys Pro Glu Ala
                405                 410                 415

Ala Gln Pro Lys Val Leu Thr Val Lys Ile Trp Lys Arg Ala Ile Pro
            420                 425                 430

Gln Tyr Asn Leu Gly His Phe Asp Arg Leu Gln Gln Ile Asp Arg Gly
            435                 440                 445

Leu Lys Ser Leu Pro Gly Leu Tyr Leu Cys Thr Asn Tyr Phe Gly Gly
    450                 455                 460

Val Ala Leu Gly Asp Cys Val Arg Arg Gly Phe Glu Arg Ala Gln Glu
465                 470                 475                 480

Val Asp Glu Tyr Leu Asn Gly
                485
```

```
<210> SEQ ID NO 12
<211> LENGTH: 475
<212> TYPE: PRT
<213> ORGANISM: Artificial Sequence
<220> FEATURE:
<223> OTHER INFORMATION: Synthetic_PPO of Crinalium epipsammum
      (WP_015202233)

<400> SEQUENCE: 12
```

```
Met Val Asp Thr Leu Ile Ile Gly Ala Gly Ile Ser Gly Leu Ser Leu
1               5                   10                  15

Ala Tyr Ala Leu His Gln Asp Gly Arg Lys Val Leu Leu Cys Glu Arg
            20                  25                  30

Gln Glu Arg Val Gly Gly Asn Ile Thr Thr Gly Lys Ala Gly Gly Phe
        35                  40                  45

Leu Trp Glu Glu Gly Pro Thr Ser Phe Thr Pro Thr Pro Ala Leu Leu
    50                  55                  60

Lys Leu Ala Val Asp Val Gly Leu Arg Glu Glu Leu Val Leu Ala Asp
65                  70                  75                  80

His Arg Leu Pro Arg Phe Val Tyr Trp Lys Gly Gln Leu Leu Pro Val
                85                  90                  95

Pro Met Ser Pro Pro Ser Ala Val Thr Ser Lys Leu Leu Ser Leu Ser
            100                 105                 110

Gly Lys Phe Arg Ala Leu Val Gly Ala Leu Gly Phe Ile Pro Pro Ala
            115                 120                 125

Ile Gly Asn His Leu Ser Gln Gln Gly Gly Glu Glu Thr Val Ala Gln
    130                 135                 140

Phe Phe Lys Arg His Leu Gly Thr Glu Val Ala Glu Arg Leu Val Ala
145                 150                 155                 160
```

-continued

```
Pro Phe Val Ser Gly Val Tyr Ala Gly Asp Val His Gln Leu Ser Ala
            165                 170                 175

Arg Ser Ala Phe Arg Arg Ile Ala Gln Leu Glu Asn Val Gly Gly Gly
            180                 185                 190

Leu Val Ser Gly Ala Ile Leu Ser Arg Lys Gln Arg Gln Gln Gln Lys
            195                 200                 205

Pro Pro Thr Asp Pro Ser Leu Pro Thr Val Arg Arg Gly Glu Leu Gly
    210                 215                 220

Ser Phe Lys Glu Gly Leu Gln Ser Leu Pro Lys Ala Ile Ala Ser His
225                 230                 235                 240

Leu Gly Glu Asn Ile Lys Leu Asn Trp Thr Leu Thr Glu Leu Arg Gln
            245                 250                 255

Thr Ala Asn Gln Thr Tyr Ile Ala Glu Phe Ser Thr Pro Glu Gly Ser
            260                 265                 270

Gln Gln Val Glu Ala Arg Thr Val Val Leu Thr Thr Pro Ala Tyr Val
            275                 280                 285

Thr Ala Glu Leu Leu His Asn Leu Ala Pro Asn Ala Ser Ile Ala Leu
    290                 295                 300

Lys Glu Ile Pro Tyr Pro Ser Val Ala Cys Val Val Leu Ala Tyr Pro
305                 310                 315                 320

Asp Asp Ala Leu Lys Phe Pro Leu Lys Gly Phe Gly Asn Leu Ile Pro
            325                 330                 335

Arg Gly Gln Gly Ile Arg Thr Leu Gly Thr Ile Trp Ser Ser Ser Leu
            340                 345                 350

Phe Pro Gly Arg Ala Pro Gln Gly Trp Gln Met Leu Thr Asn Phe Ile
            355                 360                 365

Gly Gly Ala Thr Asp Pro Glu Val Gly Asn Leu Asp Asn Glu Gln Leu
    370                 375                 380

Val Gln Ala Val His Lys Asp Leu Gln Arg Val Leu Leu Lys Lys Asp
385                 390                 395                 400

Val Pro Pro Lys Ala Ile Ala Val His Leu Trp Lys Arg Ala Ile Pro
            405                 410                 415

Gln Tyr Thr Leu Gly His His Leu Arg Leu Ala Gln Ile Asn Gln Asp
            420                 425                 430

Leu Ala Gln Leu Pro Gly Leu Tyr Leu Cys Ser Asn Tyr Thr Asp Gly
            435                 440                 445

Val Ser Leu Gly Asp Cys Val Gln Arg Ala Tyr Asp Gln Leu Pro Ile
    450                 455                 460

Ile Asn Lys Gln Leu Ser Ile Ile Asn Asp Asn
465                 470                 475

<210> SEQ ID NO 13
<211> LENGTH: 487
<212> TYPE: PRT
<213> ORGANISM: Artificial Sequence
<220> FEATURE:
<223> OTHER INFORMATION: Synthetic_PPO of Oscillatoriales cyanobacterium
      (TAE70643)

<400> SEQUENCE: 13

Met Glu Val Leu Asp Thr Leu Ile Val Gly Ala Gly Ile Ser Gly Leu
1               5                   10                  15

Ser Leu Ala His Ala Leu Gln Lys Glu Ala Thr Ser Ala Ser Pro Arg
            20                  25                  30

Ala Ile Leu Val Ala Glu Ser Gln Gly Arg Val Gly Gly Asn Ile Thr
```

```
                 35                      40                      45

Thr Ala Thr Gly Glu Gly Phe Leu Trp Glu Glu Gly Pro Asn Ser Phe
     50                      55                      60

Ser Pro Thr Pro Glu Leu Leu Lys Leu Ala Val Asp Val Gly Leu Lys
65                      70                      75                      80

Gln Glu Leu Ile Phe Ala Asp Arg Lys Leu Pro Arg Phe Val Tyr Trp
                 85                      90                      95

Glu Lys Lys Leu Gln Pro Val Pro Met Thr Pro Gly Ala Met Ile Gln
                 100                     105                     110

Ser Gln Leu Leu Ser Phe Pro Gly Lys Leu Arg Ala Leu Phe Gly Ala
                 115                     120                     125

Leu Gly Phe Val Gly Pro Ala Met Gly Ser Gln Leu Ser Gln Gln Gly
     130                     135                     140

Asp Glu Glu Thr Val Ser Gln Phe Phe Arg Arg His Leu Gly Lys Glu
145                     150                     155                     160

Val Met Gln Arg Leu Val Glu Pro Phe Val Ser Gly Val Tyr Ala Gly
                 165                     170                     175

Asp Pro Gln Gln Leu Ser Ala Ala Ala Phe Gly Arg Val Thr Lys
                 180                     185                     190

Met Ala Asp Ala Gly Gly Gly Leu Val Ala Gly Ala Leu Leu Ser Ala
                 195                     200                     205

Arg Lys Arg Pro Pro Gln Pro Pro Leu Thr Lys Gly Gly Leu Lys Thr
     210                     215                     220

Val Ala Asp Pro Asn Ile Pro Lys Thr Lys Pro Gly Glu Leu Gly Ser
225                     230                     235                     240

Phe Lys Gly Gly Leu Gln Ala Leu Pro Glu Ala Ile Ala Ala Asn Leu
                 245                     250                     255

Gly Asp Arg Leu Lys Leu Asn Trp His Leu Thr Arg Leu Asp Arg Thr
                 260                     265                     270

Glu Arg Asp Thr Tyr Ile Ala Val Phe Ser Thr Pro Asp Gly Gln Gln
                 275                     280                     285

Glu Val Glu Ala Arg Thr Val Val Leu Thr Thr Pro Ala Tyr Val Thr
     290                     295                     300

Ala Glu Leu Leu Glu Pro Leu Gln Pro Ser Val Ser Ser Ala Leu Gln
305                     310                     315                     320

Ala Phe Thr Tyr Pro Thr Val Ala Ser Val Val Leu Ala Tyr Pro Met
                 325                     330                     335

Ser Asp Leu Lys Gly Lys Leu Val Gly Phe Gly Asn Leu Ile Pro Arg
                 340                     345                     350

Gly Gln Gly Ile Arg Thr Leu Gly Thr Ile Trp Thr Ser Ser Leu Phe
                 355                     360                     365

Ala Asp Arg Ala Pro Ala Gly Trp Gln Thr Leu Thr Ser Tyr Ile Gly
     370                     375                     380

Gly Ala Thr Asp Ser Gly Ile Gly Asn Leu Asp Ala Glu Gln Ile Val
385                     390                     395                     400

Gly Glu Val His Arg Asp Leu Ser Gln Ile Leu Leu Lys Pro Glu Ala
                 405                     410                     415

Ala Gln Pro Lys Val Leu Thr Val Lys Ile Trp Lys Arg Ala Ile Pro
                 420                     425                     430

Gln Tyr Asn Leu Gly His Phe Asp Arg Leu Gln Gln Ile Asp Arg Gly
                 435                     440                     445

Leu Lys Ser Leu Pro Gly Leu Tyr Leu Cys Thr Asn Tyr Phe Gly Gly
     450                     455                     460
```

-continued

```
Val Ala Leu Gly Asp Cys Val Arg Arg Gly Phe Glu Arg Ala Gln Glu
465                 470                 475                 480

Val Asp Glu Tyr Leu Asn Gly
                485

<210> SEQ ID NO 14
<211> LENGTH: 487
<212> TYPE: PRT
<213> ORGANISM: Artificial Sequence
<220> FEATURE:
<223> OTHER INFORMATION: Synthetic_PPO of Oscillatoriales cyanobacterium
      (TAE14532)

<400> SEQUENCE: 14

Met Glu Val Leu Asp Thr Leu Ile Val Gly Ala Gly Ile Ser Gly Leu
1               5                   10                  15

Ser Leu Ala His Ala Leu Gln Lys Glu Ala Arg Ser Ala Ser Pro Arg
                20                  25                  30

Ala Ile Leu Val Ala Glu Ser Gln Gly Arg Val Gly Gly Asn Ile Thr
            35                  40                  45

Thr Ala Thr Gly Glu Gly Phe Leu Trp Glu Glu Gly Pro Asn Ser Phe
        50                  55                  60

Ser Pro Thr Pro Glu Leu Leu Lys Leu Ala Val Asp Val Gly Leu Lys
65                  70                  75                  80

Gln Glu Leu Ile Phe Ala Asp Arg Lys Leu Pro Arg Phe Val Tyr Trp
                85                  90                  95

Glu Lys Lys Leu Gln Pro Val Pro Met Thr Pro Gly Ala Met Ile Gln
            100                 105                 110

Ser Gln Leu Leu Ser Phe Pro Gly Lys Leu Arg Ala Leu Phe Gly Ala
        115                 120                 125

Leu Gly Phe Val Gly Pro Ala Met Gly Ser Gln Leu Ser Gln Gln Gly
    130                 135                 140

Asp Glu Glu Thr Val Ser Gln Phe Phe Arg Arg His Leu Gly Lys Glu
145                 150                 155                 160

Val Met Gln Arg Leu Val Glu Pro Phe Val Ser Gly Val Tyr Ala Gly
                165                 170                 175

Asp Pro Gln Gln Leu Ser Ala Ala Ala Phe Gly Arg Val Thr Lys
            180                 185                 190

Met Ala Asp Ala Gly Gly Gly Leu Val Ala Gly Ala Leu Leu Ser Ala
        195                 200                 205

Arg Lys Arg Pro Pro Gln Pro Pro Leu Thr Lys Gly Gly Leu Lys Thr
    210                 215                 220

Val Ala Asp Pro Asn Ile Pro Lys Thr Lys Pro Gly Glu Leu Gly Ser
225                 230                 235                 240

Phe Lys Gly Gly Leu Lys Ala Leu Pro Glu Ala Ile Ala Ala Asn Leu
                245                 250                 255

Gly Asp Arg Leu Lys Leu Asn Trp His Leu Thr Arg Leu Asp Arg Thr
            260                 265                 270

Glu Arg Asp Thr Tyr Ile Ala Val Phe Ser Thr Pro Asp Gly Gln Gln
        275                 280                 285

Glu Val Glu Ala Arg Thr Val Val Leu Thr Thr Pro Ala Tyr Val Thr
    290                 295                 300

Ala Glu Leu Leu Glu Pro Leu Gln Pro Ser Val Ser Ser Ala Leu Gln
305                 310                 315                 320

Ala Phe Thr Tyr Pro Thr Val Ala Ser Val Val Leu Ala Tyr Pro Met
```

-continued

```
              325                330                335

Ser Asp Leu Lys Gly Lys Leu Val Gly Phe Gly Asn Leu Ile Pro Arg
              340                345                350

Gly Gln Gly Ile Arg Thr Leu Gly Thr Ile Trp Thr Ser Ser Leu Phe
              355                360                365

Ala Asp Arg Ala Pro Ala Gly Trp Gln Thr Leu Thr Ser Tyr Ile Gly
              370                375                380

Gly Ala Thr Asp Ser Gly Ile Gly Asn Leu Asp Ala Glu Gln Ile Val
385                390                395                400

Gly Glu Val His Arg Asp Leu Ser Gln Ile Leu Leu Lys Pro Glu Ala
              405                410                415

Ala Gln Pro Lys Val Leu Thr Val Lys Ile Trp Lys Arg Ala Ile Pro
              420                425                430

Gln Tyr Asn Leu Gly His Phe Asp Arg Leu Glu Gln Ile Asn Arg Gly
              435                440                445

Leu Lys Ser Leu Pro Gly Leu Tyr Leu Cys Thr Asn Tyr Phe Gly Gly
              450                455                460

Val Ala Leu Gly Asp Cys Val Arg Arg Gly Phe Glu Arg Ala Gln Glu
465                470                475                480

Val Asp Glu Tyr Leu Asn Gly
              485

<210> SEQ ID NO 15
<211> LENGTH: 478
<212> TYPE: PRT
<213> ORGANISM: Artificial Sequence
<220> FEATURE:
<223> OTHER INFORMATION: Synthetic_PPO of Cyanobacteria bacterium
      QS_8_64_29 (PSP16006)

<400> SEQUENCE: 15

Met Leu Asp Ala Leu Val Val Gly Ala Gly Ile Ser Gly Leu Ser Leu
1                5                10                15

Gly Arg Thr Leu Gln Gln Gln Gln His Ser Leu Leu Val Ala Glu Arg
              20                25                30

Gln Pro Gln Val Gly Gly Asn Ile Thr Thr Ser Ser Thr Gly Glu Phe
              35                40                45

Leu Trp Glu Glu Gly Pro Asn Ser Phe Ser Pro Ala Arg Glu Leu Leu
              50                55                60

Glu Leu Ala Val Asp Ala Gly Leu Arg Glu Glu Leu Val Leu Ala Asp
65                70                75                80

Arg Gln Leu Pro Arg Tyr Ile Tyr Trp Arg Gly Arg Leu Gln Pro Val
              85                90                95

Pro Met Arg Pro Ser Ala Ala Leu Lys Thr Gln Leu Leu Ser Pro Ser
              100                105                110

Gly Lys Leu Arg Ala Leu Ala Gly Ala Leu Gly Phe Val Pro Pro Ala
              115                120                125

Val Gly Glu Ala Val Ser Gln Gln Gly Gly Glu Glu Thr Val Ala Gln
              130                135                140

Phe Phe Gln Arg His Leu Gly Arg Glu Val Thr Glu Arg Leu Val Ala
145                150                155                160

Pro Phe Val Ser Gly Val Tyr Ala Gly Asp Val Arg Gln Leu Ser Ala
              165                170                175

Gln Ala Ala Phe Arg Arg Val Thr Gln Leu Ala Asp Arg Gly Gly Gly
              180                185                190
```

```
Leu Leu Pro Gly Ala Leu Leu Gly Arg Gln Ala Ala Pro Gln Arg Pro
    195                 200                 205

Ala Thr Ser Gln Thr Gln Leu Pro Gln Thr Gln Ser Gly Glu Leu Gly
    210                 215                 220

Ser Phe Arg Thr Gly Leu Gln Ala Leu Pro Asn Ala Ile Ala Glu Arg
225                 230                 235                 240

Leu Gly Asp Ala Leu Arg Cys Asn Trp Ala Leu Ser Gln Leu Gln Arg
                245                 250                 255

Thr Glu Arg Asp Ser Tyr Leu Ala Thr Phe Gln Thr Pro Gln Gly Pro
                260                 265                 270

Gln Gln Val Glu Ala Arg Ala Val Val Leu Thr Thr Pro Ala Tyr Thr
    275                 280                 285

Ser Ala Glu Leu Leu Arg Pro Leu His Ala Arg Ala Ser Gln Arg Leu
    290                 295                 300

Ala Ala Ile Pro Tyr Pro Pro Val Ala Ser Val Val Leu Ala Tyr Pro
305                 310                 315                 320

Gln Gln Ala Leu Gly Gly Ala Leu Arg Gly Phe Gly Asn Leu Asn Pro
                325                 330                 335

Arg Gly Gln Gly Ile Arg Thr Leu Gly Thr Ile Trp Ser Ser Ala Leu
                340                 345                 350

Phe Ala Gly Arg Ala Pro Ala Gly Trp Glu Ile Leu Thr Ser Phe Ile
                355                 360                 365

Gly Gly Ala Thr Asp Pro Glu Ile Ala Arg Leu Asp Glu Asp Arg Ile
    370                 375                 380

Val Gln Ala Val His Ala Asp Leu Arg Gln Val Leu Leu Ala Arg Tyr
385                 390                 395                 400

Val Ala Pro Lys Val Leu Ala Val Arg Leu Trp His Arg Ala Ile Pro
                405                 410                 415

Gln Tyr Ala Ile Gly His Gln Ala Gln Met Gln Ala Leu Glu Ala Glu
                420                 425                 430

Leu Ala Glu Leu Pro Gly Leu Phe Leu Cys Ser Asn Tyr Leu Asp Gly
            435                 440                 445

Val Ser Leu Gly Asp Cys Ile Arg Arg Gly Phe Glu Arg Ala His Thr
    450                 455                 460

Val Ser His Tyr Leu Gln Ala Pro Ala Ala Ala Pro Ala Ala
465                 470                 475
```

```
<210> SEQ ID NO 16
<211> LENGTH: 479
<212> TYPE: PRT
<213> ORGANISM: Artificial Sequence
<220> FEATURE:
<223> OTHER INFORMATION: Synthetic_PPO of Lyngbya aestuarii
      (WP_023067908)

<400> SEQUENCE: 16

Met Thr His Val Leu Asp Ser Leu Ile Val Gly Ala Gly Ile Ser Gly
1               5                   10                  15

Leu Ser Leu Ala His Ser Leu Leu Arg Asn Pro Asn Pro Gln Leu Ser
                20                  25                  30

Leu Asn Ile Leu Val Ser Glu His Gln Gly Arg Val Gly Gly Asn Ile
            35                  40                  45

Thr Thr Val Ser Gln Gly Glu Phe Leu Trp Glu Glu Gly Pro Asn Ser
    50                  55                  60

Phe Ser Pro Thr Pro Glu Leu Leu Lys Leu Ala Val Glu Val Gly Leu
65                  70                  75                  80
```

```
Lys Ser Glu Phe Val Phe Ala Asp Arg Lys Leu Pro Arg Tyr Val Tyr
                85              90              95

Trp Asn Ser Gln Leu Met Pro Val Pro Met Ser Pro Pro Ala Leu Leu
            100             105             110

Ser Thr Lys Leu Leu Ser Pro Gly Gly Lys Leu Arg Ala Leu Thr Gly
        115             120             125

Ala Leu Gly Phe Val Arg Pro Ala Met Gly Gln Ala Leu Ser Gln Gln
    130             135             140

Asn Gly Glu Glu Thr Ile Ser Gln Phe Phe Glu Arg His Leu Gly Ser
145             150             155             160

Glu Val Leu Lys Arg Leu Val Glu Pro Phe Val Ser Gly Val Tyr Ala
                165             170             175

Gly Asp Pro Gln Gln Leu Glu Ile Ser Ser Ala Phe Ala Arg Val Ala
            180             185             190

Arg Met Ala Tyr Ser Gly Gly Leu Val Ala Gly Ala Val Leu Ser
        195             200             205

Arg Gly Gln Asn Lys Ser Ser Arg Ser Pro Ala Asp Pro Ser Ile Pro
    210             215             220

Gln Thr Lys Arg Gly Glu Leu Gly Ser Phe Arg Gln Gly Ile Gly Ala
225             230             235             240

Leu Pro Asn Ala Ile Ala Gln Gln Leu Gly Asp Gln Leu Lys Leu Asn
            245             250             255

Trp Gln Leu Thr Arg Leu Glu Arg Thr Glu Asn Gln Thr Tyr Arg Ala
            260             265             270

Glu Phe Ser Thr Pro Asp Gly Val Gln Gln Val Glu Thr Arg Thr Val
        275             280             285

Val Leu Thr Thr Pro Ala Tyr Val Thr Ala Glu Ile Leu Lys Pro Leu
    290             295             300

Gln Leu Gln Val Ser Gln Thr Leu Thr Glu Ile Pro Tyr Pro Pro Val
305             310             315             320

Ala Cys Val Val Leu Ala Tyr Pro Val Ser Ala Phe Lys Gln Lys Leu
            325             330             335

Thr Gly Phe Gly Asn Leu Val Pro Arg Gly Gln Gly Ile Arg Thr Leu
            340             345             350

Gly Thr Ile Trp Thr Ser Ser Leu Phe Pro Gly Arg Ala Pro Gln Gly
        355             360             365

Trp Gln Val Leu Thr Ser Tyr Ile Gly Gly Ala Thr Asp Pro Glu Ile
    370             375             380

Gly Glu Leu Glu Asp Asp Gln Ile Val Glu Ala Val His Gln Asp Leu
385             390             395             400

Arg Arg Ile Leu Leu Lys Glu Asp Ile Ser Pro Lys Val Leu Ala Val
            405             410             415

His Leu Trp Lys Arg Ala Ile Pro Gln Tyr Asn Leu Gly His Gln Gln
            420             425             430

Arg Leu Gln Gln Val Asn Glu Gly Leu Glu Ala Met Pro Gly Leu Tyr
        435             440             445

Leu Cys Ser Asn Tyr Ile Asp Gly Val Ala Leu Gly Asp Cys Val Arg
    450             455             460

Arg Ser Ile Gly Gln Ala Asn Glu Ile Leu Ser Phe Leu Asp Gln
465             470             475
```

<210> SEQ ID NO 17
<211> LENGTH: 481

<212> TYPE: PRT
<213> ORGANISM: Artificial Sequence
<220> FEATURE:
<223> OTHER INFORMATION: Synthetic_PPO of Tychonema bourrellyi
     (WP_096831359)

<400> SEQUENCE: 17

Met Thr Asn Val Val Asp Ser Leu Ile Val Gly Ala Gly Ile Thr Gly
1               5                   10                  15

Leu Ser Leu Ala His Ala Leu His Lys Glu Ala Lys Thr Gly Thr Pro
            20                  25                  30

Val Lys Ile Leu Val Ala Glu Ser Leu Gly Arg Val Gly Gly Asn Ile
        35                  40                  45

Thr Thr Cys Thr Gly Asn Gly Phe Leu Trp Glu Glu Gly Pro Asn Ser
    50                  55                  60

Phe Ser Pro Thr Val Glu Leu Met Lys Leu Ala Val Asp Val Gly Leu
65                  70                  75                  80

Lys Glu Glu Leu Ile Phe Ala Asp Arg Lys Leu Pro Arg Phe Val Tyr
                85                  90                  95

Trp Gln Asn Lys Leu Gln Pro Val Pro Met Thr Pro Gln Ala Met Ile
            100                 105                 110

Gln Ser Gln Leu Leu Ser Phe Pro Gly Lys Leu Arg Ala Leu Phe Gly
        115                 120                 125

Ala Leu Gly Phe Val Ala Pro Ala Met Gly Ala Thr Leu Ser Gln Gln
    130                 135                 140

Gly Gly Gln Glu Thr Ile Ser Gln Phe Phe Arg Arg His Leu Gly Thr
145                 150                 155                 160

Glu Val Met Gln Arg Leu Val Glu Pro Phe Val Ser Gly Val Tyr Ala
                165                 170                 175

Gly Asp Pro Glu Gln Leu Ser Ala Ala Ala Ala Phe Gly Arg Val Thr
            180                 185                 190

Arg Met Ala Asp Leu Gly Gly Gly Leu Val Ala Gly Ala Leu Leu Gly
            195                 200                 205

Ala Arg Lys Gly Pro Lys Lys Met Pro Ala Asp Pro Asn Ile Pro Lys
    210                 215                 220

Thr Lys Pro Gly Glu Leu Gly Ser Phe Lys Gly Gly Leu Lys Ala Leu
225                 230                 235                 240

Pro Glu Ala Ile Ala Ala Gln Leu Gly Asp Arg Leu Lys Leu Asn Trp
                245                 250                 255

His Leu Thr Gly Leu His Arg Thr Glu Asn Lys Thr Tyr Ile Ala Glu
            260                 265                 270

Phe Ser Thr Pro Asp Gly Pro Gln Gln Val Glu Thr Arg Thr Val Val
            275                 280                 285

Leu Thr Thr Pro Ala Tyr Val Thr Ala Asp Trp Phe Gln Ser Leu Gln
    290                 295                 300

Pro Glu Val Ser Thr Ala Leu Gln Ala Phe Thr Tyr Pro Thr Val Ala
305                 310                 315                 320

Cys Val Val Leu Ala Tyr Pro Lys Ser Asp Val Lys Glu Lys Met Val
                325                 330                 335

Gly Phe Gly Asn Leu Ile Pro Arg Gly Gln Gly Ile Arg Thr Leu Gly
            340                 345                 350

Thr Ile Trp Ser Ser Ser Leu Phe Ala Asn Arg Ala Pro Ala Gly Trp
            355                 360                 365

Gln Thr Leu Thr Ser Phe Ile Gly Gly Ala Thr Asp Ser Gly Ile Ala
    370                 375                 380

```
Asn Leu Asp Ala Glu Gln Ile Val Ala Gln Val His Arg Asp Leu Ser
385                 390                 395                 400

Arg Ile Leu Leu Lys Pro Asp Val Pro Gln Pro Lys Val Leu Ala Val
                405                 410                 415

Lys Val Trp Lys Gln Ala Ile Pro Gln Tyr Asn Leu Gly His Phe Asp
                420                 425                 430

Arg Leu Glu Gln Ile Asp Arg Gly Leu Lys Ser Leu Pro Gly Val Tyr
            435                 440                 445

Leu Cys Ser Asn Tyr Leu Gly Gly Val Ala Leu Gly Asp Cys Val Arg
        450                 455                 460

Leu Gly Leu Glu Arg Ala Ile Glu Val Ser Lys Tyr Leu Gln Glu Thr
465                 470                 475                 480

Ser

<210> SEQ ID NO 18
<211> LENGTH: 481
<212> TYPE: PRT
<213> ORGANISM: Artificial Sequence
<220> FEATURE:
<223> OTHER INFORMATION: Synthetic_PPO of Oscillatoriales cyanobacterium
      (TAG91209)

<400> SEQUENCE: 18

Met Thr Asn Val Val Asp Thr Leu Ile Val Gly Ala Gly Ile Thr Gly
1                   5                   10                  15

Leu Ser Leu Ala His Ala Leu Gln Lys Glu Ala Lys Thr Gly Thr Pro
                20                  25                  30

Val Lys Ile Leu Val Ala Glu Ser Leu Gly Arg Val Gly Gly Asn Ile
            35                  40                  45

Thr Thr Cys Thr Gly Asn Gly Phe Leu Trp Glu Glu Gly Pro Asn Ser
        50                  55                  60

Phe Ser Pro Thr Ala Glu Leu Met Lys Leu Ala Val Asp Val Gly Leu
65                  70                  75                  80

Lys Glu Glu Leu Ile Phe Ala Asp Arg Lys Leu Pro Arg Phe Val Tyr
                85                  90                  95

Trp Gln Asn Lys Leu Gln Pro Val Pro Met Thr Pro Gln Ala Met Ile
                100                 105                 110

Gln Ser Gln Leu Leu Ser Phe Pro Gly Lys Leu Arg Ala Leu Phe Gly
            115                 120                 125

Ala Leu Gly Phe Val Ala Pro Ala Met Gly Ala Thr Leu Ser Gln Gln
        130                 135                 140

Gly Gly Gln Glu Thr Val Ser Gln Phe Phe Gly Arg His Leu Gly Thr
145                 150                 155                 160

Glu Val Met Gln Arg Leu Val Glu Pro Phe Val Ser Gly Val Tyr Ala
                165                 170                 175

Gly Asp Pro Gln Gln Leu Ser Ala Ala Ala Phe Gly Arg Val Thr
            180                 185                 190

Arg Met Ala Asp Leu Gly Gly Gly Leu Val Ala Gly Ala Leu Leu Gly
        195                 200                 205

Ala Arg Lys Ala Pro Lys Lys Met Pro Ala Asp Pro Asn Val Pro Lys
        210                 215                 220

Thr Lys Pro Gly Glu Leu Gly Ser Phe Lys Gly Gly Leu Lys Ala Leu
225                 230                 235                 240

Pro Glu Ala Ile Ala Ala Gln Leu Gly Asp Arg Leu Lys Leu Asn Trp
            245                 250                 255
```

```
His Leu Thr Gly Leu His Arg Thr Glu Asn Lys Thr Tyr Ile Ala Glu
            260                 265                 270

Phe Ser Thr Pro Asp Gly Pro Gln Gln Val Glu Thr Arg Thr Val Val
            275                 280                 285

Leu Thr Thr Pro Ala Tyr Val Thr Ala Asp Leu Phe Gln Ser Leu Gln
            290                 295                 300

Pro Glu Val Ser Ser Ala Leu Gln Ala Phe Thr Tyr Pro Thr Val Ala
305                 310                 315                 320

Cys Val Val Leu Ala Tyr Pro Lys Ser Asp Val Lys Glu Lys Met Val
            325                 330                 335

Gly Phe Gly Asn Leu Ile Pro Arg Gly Gln Gly Ile Arg Thr Leu Gly
            340                 345                 350

Thr Ile Trp Thr Ser Ser Leu Phe Ala Asn Arg Ala Pro Ala Gly Trp
            355                 360                 365

Gln Thr Leu Thr Ser Tyr Ile Gly Gly Ala Thr Asp Ser Gly Ile Gly
            370                 375                 380

Asn Leu Asp Ala Glu Gln Ile Val Gly Glu Val His Arg Asp Leu Ser
385                 390                 395                 400

Arg Ile Leu Leu Lys Pro Asn Val Pro Gln Pro Lys Val Leu Ala Val
            405                 410                 415

Lys Val Trp Lys Gln Ala Ile Pro Gln Tyr Asn Leu Gly His Phe Asp
            420                 425                 430

Arg Leu Glu Arg Ile Asp Arg Gly Leu Lys Ser Leu Pro Gly Val Tyr
            435                 440                 445

Leu Cys Ser Asn Tyr Val Gly Gly Val Ala Leu Gly Asp Cys Val Arg
            450                 455                 460

Leu Gly Phe Glu Arg Ala Ile Glu Val Ser Glu Tyr Leu Gln Ala Thr
465                 470                 475                 480

Ser
```

<210> SEQ ID NO 19
<211> LENGTH: 466
<212> TYPE: PRT
<213> ORGANISM: Artificial Sequence
<220> FEATURE:
<223> OTHER INFORMATION: Synthetic_PPO of Cyanobacteria bacterium
      SW_9_44_58 (PSO49761)

<400> SEQUENCE: 19

```
Met Leu Asp Thr Leu Ile Val Gly Ala Gly Ile Ser Gly Leu Ser Thr
1               5                   10                  15

Ala Tyr Arg Leu His Gln Gly Gln Arg Gln Ile Leu Val Ala Glu Gln
            20                  25                  30

Arg Asp Arg Val Gly Gly Asn Ile Ala Thr Glu His Gln Gly Glu Phe
            35                  40                  45

Leu Trp Glu Glu Gly Pro Asn Ser Phe Ser Pro Thr Pro Glu Leu Leu
            50                  55                  60

Lys Leu Ala Val Asp Ala Gly Leu Lys Asn Asp Phe Val Phe Ala Asp
65                  70                  75                  80

Arg Asn Leu Pro Arg Tyr Val Tyr Trp Gln Gly Lys Leu Arg Pro Val
            85                  90                  95

Pro Met Ser Pro Pro Ala Ala Val Lys Ser Gln Leu Leu Ser Pro Trp
            100                 105                 110

Gly Lys Leu Arg Ala Leu Ala Gly Ala Leu Gly Phe Val Ser Pro Asn
            115                 120                 125
```

-continued

```
Val Glu Gly Lys Glu Glu Thr Val Ala Asp Phe Phe Thr Arg His Leu
    130             135                 140

Gly Glu Glu Val Ala Gln Arg Leu Val Ala Pro Phe Val Ser Gly Val
145             150                 155                 160

Tyr Ala Gly Asp Val His Arg Leu Ser Ala Gln Ala Ala Phe Gly Arg
                165                 170                 175

Val Thr Gln Leu Ala Asp Val Gly Gly Gly Leu Val Ala Gly Ala Val
            180                 185                 190

Leu Ser Arg Gly Lys Arg Lys Gln Ser Ser Ser Thr Val Thr Glu Asn
        195                 200                 205

Ala Asp Ile Pro Lys Thr Lys Ser Gly Glu Leu Gly Ser Phe Arg Glu
    210                 215                 220

Gly Leu Gln Met Leu Pro Arg Ala Ile Ala Ser Lys Leu Gly Glu Ser
225                 230                 235                 240

Val Lys Leu Asn Trp Gln Leu Asn Asn Ile Ser Pro His Pro Glu Gln
            245                 250                 255

Gly Tyr Ile Ala Ala Phe Ser Thr Pro Glu Gly Glu Gln Ser Val Glu
            260                 265                 270

Ala Lys Ser Ile Val Leu Thr Thr Pro Ala His Val Thr Ala Pro Ile
        275                 280                 285

Ile Gln Thr Leu Ser Pro Leu Thr Ser Thr Ala Leu Gln Asp Ile Ser
    290                 295                 300

Tyr Pro Pro Val Ala Cys Val Ile Leu Ala Tyr Pro Asp Glu Ala Leu
305                 310                 315                 320

Arg Phe Ser Leu Lys Gly Phe Gly Asn Leu Val Pro Arg Asn Gln Gly
            325                 330                 335

Leu Arg Thr Leu Gly Thr Ile Trp Ala Ser Thr Leu Phe Pro Gly Arg
            340                 345                 350

Ala Pro Gln Gly Trp His Ile Leu Thr Asn Phe Ile Gly Gly Ala Thr
            355                 360                 365

Asp Pro Glu Ile Ala Gln Leu Ser Glu Glu Gln Ile Ile Asp Gln Val
    370                 375                 380

His Gln Asp Leu Gln Lys Val Leu Leu Lys Ser Asp Thr Asn Pro Lys
385                 390                 395                 400

Pro Leu Ala Val His Leu Trp Ser Lys Ala Ile Pro Gln Tyr Thr Leu
            405                 410                 415

Gly His Leu Asp Arg Leu Glu Thr Ile Arg Asn Ser Leu Lys Ser Cys
            420                 425                 430

Pro Gly Leu Phe Leu Cys Ser Asn Tyr Leu Asp Gly Val Ser Leu Gly
        435                 440                 445

Asp Cys Val Arg Arg Gly Glu Glu Thr Ala Gln Ala Val Leu Asp Tyr
    450                 455                 460

Leu Gly
465
```

```
<210> SEQ ID NO 20
<211> LENGTH: 482
<212> TYPE: PRT
<213> ORGANISM: Artificial Sequence
<220> FEATURE:
<223> OTHER INFORMATION: Synthetic_PPO of Trichodesmium erythraeum
      (WP_011611816)

<400> SEQUENCE: 20

Met Thr Glu Ile Leu Asp Val Leu Val Val Gly Ala Gly Ile Ser Gly
```

```
1                5                    10                   15
Leu Ser Leu Ala His Lys Leu Thr Lys Leu Ser Asn Asn Ser Pro Leu
            20               25               30

Lys Ile Leu Val Ala Glu Ser Gln Asn Arg Val Gly Gly Asn Ile Thr
            35               40               45

Thr Val Ser Gln Gly Glu Phe Leu Trp Glu Glu Gly Pro Asn Ser Phe
        50               55               60

Ser Pro Thr Pro Glu Leu Leu Lys Leu Ala Val Asp Val Gly Leu Lys
65               70               75               80

Glu Asp Leu Ile Phe Ala Asp Arg Lys Leu Pro Arg Tyr Val Tyr Trp
                85               90               95

Asn Gly Gln Leu Leu Pro Val Pro Met Ser Pro Lys Ala Met Leu Gln
            100              105              110

Ser Gln Leu Leu Ser Asn Thr Gly Lys Leu Arg Ala Leu Val Gly Ala
            115              120              125

Leu Gly Phe Val Pro Pro Val Val Gly Met Asp Leu Ser Gln Glu Gly
        130              135              140

Gly Glu Glu Thr Val Ser Gln Phe Phe Gln Arg His Leu Gly Lys Glu
145              150              155              160

Val Met Glu Arg Leu Val Glu Pro Phe Val Ser Gly Val Tyr Ala Gly
            165              170              175

Asp Pro Ser Gln Leu Ser Ala Thr Ala Ala Phe Ser Lys Val Ala Arg
            180              185              190

Met Ala Asp Leu Gly Gly Gly Leu Leu Ala Gly Ala Val Leu Ser Ala
            195              200              205

Gln Arg Asn Pro Lys Ser Lys Ala Ala Ala Asn Ser Asn Ile Pro Lys
        210              215              220

Thr Lys Pro Gly Glu Leu Gly Ser Phe Arg Arg Gly Leu Glu Val Leu
225              230              235              240

Pro Lys Ala Ile Ala Thr Tyr Leu Gly Gln Ala Val Lys Leu Asn Trp
                245              250              255

Ser Leu Val Gly Leu Arg Pro Thr Glu Lys Gln Thr Tyr Ile Ala Glu
            260              265              270

Phe Ser Thr Pro Asn Gly Ser Gln Gln Ile Glu Thr Arg Thr Ile Ala
        275              280              285

Leu Ser Ser Pro Ala Tyr Ala Cys Ala Lys Leu Phe Arg Pro Leu Leu
        290              295              300

Pro Glu Ile Ala Gly Thr Leu Asp Glu Phe Tyr Tyr Pro Thr Val Ala
305              310              315              320

Cys Val Val Leu Ala Tyr Pro Val Ser Ser Ile Lys Ala Lys Ile Asp
                325              330              335

Gly Phe Gly Asn Leu Ile Pro Arg Gly Gln Gly Ile Arg Thr Leu Gly
            340              345              350

Thr Ile Trp Ser Ser Ala Leu Phe Ser Gly Arg Thr Pro Leu Gly Trp
            355              360              365

Gln Ile Phe Thr Asn Tyr Ile Gly Gly Ala Thr Asp Pro Glu Ile Ser
        370              375              380

His Leu Asp Ser Glu Ala Ile Val Ala Gln Val His Gln Asp Leu Cys
385              390              395              400

Gln Thr Leu Leu Asn Gln Asn Pro Glu Lys Pro Lys Val Leu Ala Val
            405              410              415

His Ile Trp Ser Arg Ala Ile Pro Gln Tyr Asn Leu Gly Tyr Ser Ser
            420              425              430
```

```
Arg Leu Ala Gln Ile Asn His Gly Leu Lys Ser Trp Pro Gly Val Tyr
        435                 440                 445

Leu Cys Ser Asn Tyr Ile Gly Gly Val Ala Leu Gly Asp Cys Val Arg
    450                 455                 460

Arg Ser Ile Glu Val Ala Thr Asp Ile Tyr Ser Gly Met Gly Phe Gly
465                 470                 475                 480

Glu Leu

<210> SEQ ID NO 21
<211> LENGTH: 498
<212> TYPE: PRT
<213> ORGANISM: Artificial Sequence
<220> FEATURE:
<223> OTHER INFORMATION: Synthetic_PPO of Geitlerinema sp. PCC 9228
      (WP_071516524.1)

<400> SEQUENCE: 21

Met Asn Ala Ile Ala Glu Asn Gly Asn Glu Ala Asn Glu Ala Ser Pro
1               5                   10                  15

Val Trp Val Asp Thr Leu Ile Val Gly Gly Ile Ser Gly Leu Ser
        20                  25                  30

Val Ala His Ala Leu Val Asn Cys Asp Arg Ser Val Asp Asn Ile Leu
        35                  40                  45

Leu Ala Glu Ser Gln Pro Arg Val Gly Gly Ser Val Thr Ser Ala Ser
    50                  55                  60

Ser Glu Gly Phe Leu Tyr Glu Glu Gly Pro Asn Ser Phe Ser Pro Thr
65                  70                  75                  80

Pro Glu Leu Leu Gln Leu Ala Val Asp Val Gly Leu Lys Asp Glu Leu
                85                  90                  95

Ile Leu Ala Asp Arg Arg Leu Pro Arg Tyr Val Tyr Trp Gln Gly Arg
                100                 105                 110

Leu Ile Ala Leu Pro Asn Ser Pro Pro Ser Ala Val Thr Ser Pro Ile
        115                 120                 125

Leu Ser Pro Val Gly Lys Leu Arg Ala Leu Leu Gly Ala Leu Gly Phe
    130                 135                 140

Val Pro Pro His Val Thr Ser Glu Pro Glu Ser Val Ser Asp Phe Ile
145                 150                 155                 160

Arg Arg His Leu Gly Pro Glu Val Leu Gln Lys Leu Val Glu Pro Phe
                165                 170                 175

Thr Ser Gly Val Tyr Ala Gly Asn Pro Asp Glu Leu Glu Ala Ala Ser
            180                 185                 190

Ala Phe Ala Arg Ile Ala Arg Leu Glu Lys Val Gly Gly Ser Leu Val
        195                 200                 205

Ala Gly Ala Ile Leu Ser Arg Arg Gln Ala Pro Thr Gln Lys Lys Asn
    210                 215                 220

Arg Asp Arg Asn Leu Pro Lys Thr Gln Arg Gly Gln Leu Gly Ser Phe
225                 230                 235                 240

Gln Arg Gly Leu Gln Ser Leu Pro Glu Ala Ile Ala Gly Lys Leu Gly
            245                 250                 255

Ser Arg Val Arg Val Asn Trp Gln Ala Lys Ser Ile Gly Lys Thr Glu
            260                 265                 270

Gly Gly Asn Tyr Leu Val Glu Phe Ala Thr Pro Gln Gly His Gln Gln
        275                 280                 285

Val Glu Ala Arg Ser Leu Val Leu Ala Thr Pro Ala Tyr Val Thr Ala
    290                 295                 300
```

-continued

```
Asn Leu Leu Lys Ser Tyr Pro His Val Asn Ser Gln Gln Gln Gln Ala
305             310         315             320

Ile Gln Ala Leu Glu Ser Ile Pro Tyr Pro Pro Val Ala Cys Val Val
            325             330             335

Leu Gly Tyr Pro Ser Ser Ala Phe Lys Lys Gln Pro Leu His Gly Phe
            340             345             350

Gly Asn Leu Ile Pro Arg Gly Gln Gly Ile Arg Thr Leu Gly Thr Ile
            355             360             365

Trp Gly Ser Ser Leu Phe Pro Gly Arg Ala Pro Glu Gly Trp Glu Leu
            370             375             380

Leu Leu Asn Phe Ile Gly Gly Thr Thr Asp Pro Glu Ile Ala Asn Leu
385             390             395             400

Asp Gln Glu Gln Ile Ala Gln Leu Val His Arg Asp Leu Cys Gln Thr
            405             410             415

Leu Leu Arg Glu Asp Lys Gln Pro Lys Val Leu Gln Val His Leu Trp
            420             425             430

Lys Gln Ala Ile Pro Gln Tyr Thr Ile Gly His Gly Ser Arg Leu Ala
            435             440             445

Ala Ile Asp Ala Gly Val Arg Ser Leu Pro Gly Leu Phe Leu Cys Ser
            450             455             460

Asn Tyr Ser Asp Gly Val Ala Met Gly Asp Cys Ala Arg Arg Gly Tyr
465             470             475             480

Glu Leu Ala Pro Arg Val Ala Glu Tyr Leu Gln Pro Gly Ser Tyr Lys
            485             490             495

Phe Val
```

```
<210> SEQ ID NO 22
<211> LENGTH: 496
<212> TYPE: PRT
<213> ORGANISM: Artificial Sequence
<220> FEATURE:
<223> OTHER INFORMATION: Synthetic_PPO of Oscillatoriales cyanobacterium
      (TAD79992.1)

<400> SEQUENCE: 22
```

```
Met Val Val Ala Thr Pro Gly Ala Val Glu Ser Ser Val Ala Arg Ser
1               5               10              15

Asn Pro Ile Asp Leu Leu Ile Val Gly Ala Gly Leu Thr Gly Leu Ser
            20              25              30

Ala Ala Gln Arg Phe Val Arg Gln Ser Pro Gly Arg Ser Cys Leu Val
            35              40              45

Val Glu Ala Gln Asp Arg Val Gly Gly Asn Ile Thr Thr Arg Ser Gly
            50              55              60

Asn Gly Phe Leu Trp Glu Glu Gly Pro Asn Ser Phe Ala Pro Thr Pro
65              70              75              80

Glu Leu Leu Gln Leu Ala Val Glu Val Gly Leu Lys Asp Gln Leu Val
            85              90              95

Phe Ala Asp Gly Lys Leu Pro Arg Phe Val Tyr Trp Asp Gly Arg Leu
            100             105             110

Gln Ala Ile Pro Met Ser Pro Gly Ala Phe Trp Asn Ser Thr Leu Leu
            115             120             125

Ser Asp Arg Gly Lys Ala Arg Leu Leu Leu Gly Ala Ala Gly Phe Val
            130             135             140

Pro Pro Ile Leu Gly Ala Thr Val Gln Ala Arg Gly Gly Glu Glu Thr
145             150             155             160
```

```
Val Arg Glu Phe Phe Thr Arg His Leu Gly Gln Glu Thr Met Glu Arg
            165                 170                 175

Met Val Asp Pro Phe Ile Ser Gly Val Tyr Ala Gly Asp Pro Asp Ala
            180                 185                 190

Leu Ser Ala Ser Ala Ala Phe Arg Lys Met Ala Ala Met Gln Ala Ala
            195                 200                 205

Gly Gly Gly Leu Ala Ala Gly Ala Ile Arg Thr Leu Leu Ala Lys Arg
        210                 215                 220

Arg Ala Ala Lys Thr Ala Pro Pro Ala Asp Pro Asn Leu Pro Lys Pro
225                 230                 235                 240

Lys Ser Gly Glu Leu Gly Ser Phe Arg Glu Gly Leu Gln Met Leu Pro
            245                 250                 255

Glu Ala Val Ala Lys Glu Leu Gly Asp Arg Val Lys Leu Gly Trp Arg
            260                 265                 270

Val Glu Ala Ile Ala Arg Ser Ser Asn Gly Asp Tyr Thr Val Asp Leu
            275                 280                 285

Ala Thr Pro Asp Gly Pro Arg Gln Ile Thr Thr Arg Ala Ile Val Leu
        290                 295                 300

Ala Thr Pro Ala Pro Ala Thr Ala Asn Leu Leu Gln Pro Leu Ala Pro
305                 310                 315                 320

Ala Ala Ser Ala Ala Leu His Ala Ile Pro Tyr Pro Ala Val Ala Cys
            325                 330                 335

Val Ile Leu Ala Tyr Pro Glu Thr Ala Phe Ala Gln Ser Leu Arg Gly
            340                 345                 350

Phe Gly Asn Leu Ile Pro Arg Ser Leu Gly Leu Gln Thr Leu Gly Thr
            355                 360                 365

Ile Trp Ala Ser Ser Leu Phe Ala Gly Arg Ala Pro Gln Gly Trp Ala
        370                 375                 380

His Leu Ile Asn Phe Ile Gly Gly Ala Gln Asn Pro Gly Leu Ile Asn
385                 390                 395                 400

Lys Thr Glu Ala Glu Ile Ala Asp Ile Val His Gly Asp Val Arg Arg
            405                 410                 415

Ile Leu Leu Lys Glu Asp Val Ala Pro Lys Val Leu Ser Val Lys Leu
            420                 425                 430

Trp Arg Arg Ala Ile Pro Gln Tyr Thr Ile Gly His Ala Asp Arg Leu
            435                 440                 445

Ala Thr Leu His Arg Glu Leu Ala Ala Trp Pro Gly Leu Phe Pro Cys
        450                 455                 460

Ser Asn Tyr Glu Gly Gly Val Ala Leu Gly Asp Cys Val Arg His Gly
465                 470                 475                 480

Trp Asp Gln Ala Ala Glu Val Asp Arg Tyr Leu Ala Gln Leu Pro Val
            485                 490                 495
```

<210> SEQ ID NO 23
<211> LENGTH: 481
<212> TYPE: PRT
<213> ORGANISM: Artificial Sequence
<220> FEATURE:
<223> OTHER INFORMATION: Synthetic_PPO of Oscillatoriales cyanobacterium
    (TAD82603.1)

<400> SEQUENCE: 23

```
Met Thr Asn Arg Val Asp Thr Leu Ile Val Gly Ala Gly Ile Thr Gly
1               5                   10                  15

Leu Ser Leu Ala His Ala Leu His Lys Glu Ala Lys Thr Gly Glu Pro
```

-continued

```
                20                    25                    30
Leu Lys Ile Leu Val Ala Glu Ser Gln Gly Arg Val Gly Gly Asn Ile
            35                    40                    45
Thr Thr Ser Thr Gly His Gly Phe Leu Trp Glu Glu Gly Pro Asn Ser
        50                    55                    60
Phe Ser Pro Thr Pro Glu Leu Met Lys Leu Ala Val Asp Val Gly Leu
65                    70                    75                    80
Lys Gln Glu Leu Met Phe Ala Asp Arg Gln Leu Pro Arg Phe Val Tyr
                85                    90                    95
Trp Gln Asn Lys Leu Gln Pro Val Pro Met Thr Pro Gly Ala Met Ile
                100                   105                   110
Gln Ser Gly Leu Leu Ser Phe Pro Gly Lys Leu Arg Ala Leu Phe Gly
            115                   120                   125
Ala Leu Gly Phe Val Ala Pro Val Met Gly Ala Thr Leu Ser Gln Gln
            130                   135                   140
Gly Glu Glu Glu Thr Val Ser Gln Phe Phe Arg Arg His Leu Gly Thr
145                   150                   155                   160
Glu Val Met Gln Arg Leu Val Glu Pro Phe Val Ser Gly Val Tyr Ala
                165                   170                   175
Gly Asp Pro Gln Gln Leu Ser Ala Ala Ala Ala Phe Gly Arg Val Thr
                180                   185                   190
Lys Met Ala Asp Ala Gly Gly Gly Leu Val Ala Gly Ala Leu Leu Ser
                195                   200                   205
Ala Arg Lys Arg Pro Lys Lys Met Pro Pro Asp Pro Asn Ile Pro Gln
        210                   215                   220
Thr Lys Pro Gly Glu Leu Gly Ser Phe Lys Gly Gly Leu Met Ala Leu
225                   230                   235                   240
Pro Glu Ala Ile Ala Ala Ser Leu Gly Asp Arg Leu Lys Leu Asn Trp
                245                   250                   255
His Leu Thr Gly Leu His Arg Thr Glu Asn Lys Thr Tyr Ile Ala Glu
                260                   265                   270
Phe Ser Thr Pro His Gly Pro Gln Gln Ile Glu Thr Arg Thr Val Val
            275                   280                   285
Leu Thr Thr Pro Ala Tyr Val Ala Ala Asp Leu Leu Gln Ser Leu Gln
        290                   295                   300
Pro Glu Val Ser Ser Thr Leu Gln Gly Phe Thr Tyr Pro Thr Val Ala
305                   310                   315                   320
Cys Val Val Leu Ala Tyr Pro Leu Ser Asp Val Lys Gly Lys Leu Val
            325                   330                   335
Gly Phe Gly Asn Leu Ile Pro Arg Gly Gln Gly Ile Arg Thr Leu Gly
            340                   345                   350
Thr Ile Trp Thr Ser Ser Leu Phe Ala Asp Arg Ala Pro Ala Gly Trp
            355                   360                   365
Gln Thr Leu Thr Ser Tyr Ile Gly Gly Ala Thr Asp Ser Gly Ile Gly
        370                   375                   380
Asn Leu Asp Pro Glu Glu Ile Val Ala Glu Val His Arg Asp Leu Ser
385                   390                   395                   400
Arg Ile Leu Leu Lys Pro Asn Val Pro Gln Pro Lys Val Leu Ala Val
                405                   410                   415
Lys Leu Trp Lys Gln Ala Ile Pro Gln Tyr Asn Leu Gly His Leu Asp
                420                   425                   430
Arg Leu Gln Gln Ile Asp Arg Gly Leu Lys Ser Leu Pro Gly Met Tyr
            435                   440                   445
```

-continued

```
Leu Cys Ser Asn Tyr Val Gly Gly Val Ala Leu Gly Asp Cys Val Arg
    450                 455                 460

Leu Gly Leu Glu Lys Ala Ile Ala Val Ser Lys Tyr Leu Gln Glu Thr
465                 470                 475                 480

Ser

<210> SEQ ID NO 24
<211> LENGTH: 481
<212> TYPE: PRT
<213> ORGANISM: Artificial Sequence
<220> FEATURE:
<223> OTHER INFORMATION: Synthetic_PPO of Oscillatoriales cyanobacterium
      (TAD95528.1)

<400> SEQUENCE: 24

Met Thr Asn Arg Val Asp Thr Leu Ile Val Gly Ala Gly Ile Thr Gly
1               5                   10                  15

Leu Ser Leu Ala His Ala Leu His Lys Glu Ala Lys Thr Gly Glu Pro
            20                  25                  30

Leu Lys Ile Leu Val Ala Glu Ser Gln Gly Arg Val Gly Gly Asn Ile
        35                  40                  45

Thr Thr Ser Thr Gly His Gly Phe Leu Trp Glu Glu Gly Pro Asn Ser
    50                  55                  60

Phe Ser Pro Thr Pro Glu Leu Met Lys Leu Ala Val Asp Val Gly Leu
65                  70                  75                  80

Lys Gln Glu Leu Met Phe Ala Asp Arg Gln Leu Pro Arg Phe Val Tyr
            85                  90                  95

Trp Gln Asn Lys Leu Gln Pro Val Pro Met Thr Pro Gly Ala Met Ile
            100                 105                 110

Gln Ser Gly Leu Leu Ser Phe Pro Gly Lys Leu Arg Ala Leu Phe Gly
        115                 120                 125

Ala Leu Gly Phe Val Ala Pro Val Met Gly Ala Thr Leu Ser Gln Gln
    130                 135                 140

Gly Glu Glu Glu Thr Val Ser Gln Phe Phe Arg Arg His Leu Gly Thr
145                 150                 155                 160

Glu Val Met Gln Arg Leu Val Glu Pro Phe Val Ser Gly Val Tyr Ala
            165                 170                 175

Gly Asp Pro Gln Gln Leu Ser Ala Ala Ala Phe Gly Arg Val Thr
            180                 185                 190

Lys Met Ala Asp Ala Gly Gly Gly Leu Val Ala Gly Ala Leu Leu Ser
        195                 200                 205

Ala Arg Lys Arg Pro Lys Lys Met Pro Pro Asp Pro Asn Ile Pro Gln
    210                 215                 220

Thr Lys Pro Gly Glu Leu Gly Ser Phe Lys Gly Gly Leu Met Ala Leu
225                 230                 235                 240

Pro Glu Ala Ile Ala Ala Ser Leu Gly Asp Arg Leu Lys Leu Asn Trp
            245                 250                 255

His Leu Thr Gly Leu His Arg Thr Glu Asn Lys Thr Tyr Ile Ala Gln
            260                 265                 270

Phe Ser Thr Pro Asp Gly Pro Gln Gln Ile Glu Thr Arg Thr Val Val
            275                 280                 285

Leu Thr Thr Pro Ala Tyr Val Ala Ala Asp Leu Leu Gln Ser Leu Gln
    290                 295                 300

Pro Glu Val Ser Ser Thr Leu Gln Gly Phe Thr Tyr Pro Thr Val Ala
305                 310                 315                 320
```

```
Cys Val Val Leu Ala Tyr Pro Leu Ser Asp Val Lys Gly Lys Leu Val
            325             330             335

Gly Phe Gly Asn Leu Ile Pro Arg Gly Gln Gly Ile Arg Thr Leu Gly
            340             345             350

Thr Ile Trp Thr Ser Ser Leu Phe Ala Asp Arg Ala Pro Ala Gly Trp
            355             360             365

Gln Thr Leu Thr Ser Tyr Ile Gly Gly Ala Thr Asp Ser Gly Ile Gly
        370             375             380

Asn Leu Asp Pro Glu Glu Ile Val Ala Glu Val His Arg Asp Leu Ser
385             390             395             400

Arg Ile Leu Leu Lys Pro Asn Val Pro Gln Pro Lys Val Leu Ala Val
            405             410             415

Lys Leu Trp Lys Gln Ala Ile Pro Gln Tyr Asn Leu Gly His Leu Asp
            420             425             430

Arg Leu Gln Gln Ile Asp Arg Gly Leu Lys Ser Leu Pro Gly Met Tyr
            435             440             445

Leu Cys Ser Asn Tyr Val Gly Gly Val Ala Leu Gly Asp Cys Val Arg
        450             455             460

Leu Gly Leu Glu Lys Ala Ile Ala Val Ser Lys Tyr Leu Gln Glu Thr
465             470             475             480

Ser
```

```
<210> SEQ ID NO 25
<211> LENGTH: 479
<212> TYPE: PRT
<213> ORGANISM: Artificial Sequence
<220> FEATURE:
<223> OTHER INFORMATION: Synthetic_PPO of Limnothrix sp. PR1529
      (WP_099534595.1)

<400> SEQUENCE: 25
```

```
Met Asp Val Leu Ile Val Gly Ala Gly Leu Thr Gly Leu Ser Ala Ala
1               5               10              15

His Arg Leu Val Asn His Pro Gly Asn Arg Gly Arg Ser Thr Leu Val
            20              25              30

Val Glu Ala Gln Asn Arg Val Gly Gly Asn Ile Thr Thr Arg Ser Ala
            35              40              45

Asp Gly Phe Leu Trp Glu Glu Gly Pro Asn Ser Phe Ala Pro Thr Pro
        50              55              60

Glu Leu Leu Lys Leu Ala Val Glu Val Gly Leu Lys Asp Glu Leu Val
65              70              75              80

Phe Ala Asp Gly Lys Leu Pro Arg Phe Val Tyr Trp Asp Gly Arg Leu
            85              90              95

Gln Ala Ile Pro Met Ser Pro Gly Ala Phe Trp Asn Ser Thr Leu Leu
            100             105             110

Ser Asp Arg Gly Lys Ala Arg Leu Leu Leu Gly Ala Ala Gly Phe Val
            115             120             125

Pro Pro Ile Val Gly Ala Ala Ile Ser Ala Arg Gly Gly Glu Glu Thr
        130             135             140

Val Arg Glu Phe Phe Thr Arg His Leu Gly Gln Glu Ala Met Glu Arg
145             150             155             160

Leu Val Asp Pro Phe Ile Ser Gly Val Tyr Ala Gly Asp Pro Asn Ala
            165             170             175

Leu Ser Ala Ser Ala Ala Phe Arg Lys Met Ala Ala Met Gln Ala Ala
            180             185             190
```

```
Gly Gly Gly Leu Gly Ala Gly Ala Ala Arg Ile Leu Trp Ala Lys Arg
        195                 200                 205

Gln Ala Ala Lys Gln Ala Pro Pro Ala Asp Pro Arg Leu Pro Lys Pro
    210                 215                 220

Lys Ser Gly Glu Leu Gly Ser Phe Arg Glu Gly Leu Gln Ala Leu Pro
225                 230                 235                 240

Glu Ala Val Ala Ser Gly Leu Gly Asp Arg Val Lys Leu Gly Trp Gln
                245                 250                 255

Val Glu Ala Ile Ala Arg Asp Pro Gln Gly Val Tyr Gln Val Ala Ile
                260                 265                 270

Ala Ser Pro Asp Gly Pro Gln Gln Ile Thr Ala Arg Ser Ile Ile Leu
        275                 280                 285

Ala Thr Pro Ala Pro Val Thr Ala Gln Leu Leu Glu Pro Leu Ala Pro
        290                 295                 300

Arg Ala Ser Thr Ala Leu Asn Ala Ile Pro Tyr Pro Ala Val Ala Cys
305                 310                 315                 320

Val Ile Leu Ala Tyr Pro Glu Thr Ala Phe Ser Gln Ser Leu Arg Gly
                325                 330                 335

Phe Gly Asn Leu Ile Pro Arg Ser Leu Gly Leu Gln Thr Leu Gly Thr
                340                 345                 350

Ile Trp Ala Ser Ser Leu Phe Ala Gly Arg Ala Pro Gln Gly Trp Ala
        355                 360                 365

His Leu Ile Asn Phe Ile Gly Gly Ala Gln Asn Pro Thr Leu Ile His
    370                 375                 380

Lys Thr Glu Asp Glu Ile Ala Gln Met Val His Ala Asp Val Arg Arg
385                 390                 395                 400

Ile Leu Leu Lys Gln Asp Val Pro Pro Lys Val Leu Ser Val Lys Leu
                405                 410                 415

Trp Arg Arg Ala Ile Pro Gln Tyr Thr Ile Gly His Gly Ser Arg Leu
                420                 425                 430

Ala Thr Leu His Gln Glu Leu Gln His Trp Pro Gly Leu Phe Ala Cys
        435                 440                 445

Ser Asn Tyr Glu Gly Gly Val Ala Leu Gly Asp Cys Val Arg His Gly
    450                 455                 460

Trp Glu Gln Ala Asp Ala Ile Glu Gln Phe Leu Gly Ser Arg Val
465                 470                 475
```

```
<210> SEQ ID NO 26
<211> LENGTH: 490
<212> TYPE: PRT
<213> ORGANISM: Artificial Sequence
<220> FEATURE:
<223> OTHER INFORMATION: Synthetic_PPO of Planktothricoides sp. SR001
      (WP_054468037.1)

<400> SEQUENCE: 26
```

```
Met Asn Ser Thr Asp Leu Ala Asn Pro Ser Thr Thr Leu Asp Thr Leu
1               5                   10                  15

Ile Val Gly Ala Gly Ile Thr Gly Leu Ser Leu Ala Gln Ala Leu Gln
        20                  25                  30

Gln Asp Arg Lys Arg Gly Arg Gln Ser Gly Gln Ile Leu Leu Thr Glu
        35                  40                  45

Ser Gln Glu Arg Val Gly Gly Arg Ile Val Thr Gln Ser Gln Asp Gly
    50                  55                  60

Phe Leu Trp Glu Glu Gly Pro Asn Ser Cys Leu Pro Thr Pro Glu Phe
```

-continued

```
65              70              75              80

Leu Lys Leu Ala Val Asp Val Gly Leu Lys Asp Glu Leu Val Leu Ala
                85              90              95

Asp Arg Arg Leu Pro Arg Tyr Val Tyr Leu Gln Gly Glu Leu Ile Pro
                100             105             110

Val Pro Met Ser Pro Pro Ala Phe Phe Gln Thr Lys Leu Leu Ser Asp
                115             120             125

Trp Gly Lys Leu Arg Ala Ile Ala Gly Ala Leu Gly Phe Val Pro Pro
        130             135             140

Ala Ile Gly Ala Thr Leu Ser Ala Gln Gly Asp Glu Glu Thr Val Ala
145             150             155             160

Gln Phe Phe Gly Arg His Leu Gly Gln Glu Val Leu Glu Arg Leu Val
                165             170             175

Gln Pro Phe Val Ser Gly Val Tyr Ala Gly Asp Pro Asn Gln Leu Ser
                180             185             190

Ala Ser Ala Ala Phe Gly Lys Val Thr Lys Met Ala Asp Ile Gly Gly
                195             200             205

Gly Leu Ala Ala Gly Ala Ile Leu Ser Leu Ala Lys Asn Gly Arg Ala
        210             215             220

Lys Lys Thr Val Asp Pro Ser Leu Pro Lys Val Gln Arg Gly Glu Leu
225             230             235             240

Ala Ser Phe Arg Gln Gly Leu Glu Ala Leu Pro Lys Ala Ile Ala Ala
                245             250             255

Gln Leu Gly Asp Val Val Lys Leu Gly Trp His Leu Ile Gln Ile Lys
                260             265             270

Pro Thr Glu His Gln Thr Tyr Leu Ala Glu Phe Ser Thr Pro Gln Gly
                275             280             285

Pro Ala Arg Ile Glu Thr Arg Ser Met Val Leu Thr Thr Pro Ser Tyr
        290             295             300

Val Ser Ala Asp Leu Leu Ala Asn Leu Cys Pro Val Ala Ser Gln Gly
305             310             315             320

Leu Ala Lys Ile Pro Tyr Pro Ala Val Ala Cys Val Val Leu Gly Tyr
                325             330             335

Pro Glu Ser Ala Phe Lys Thr Ser Val Ser Ser Gly Phe Gly Asn Leu
                340             345             350

Ile Pro Arg Gly Gln Gly Ile Arg Thr Leu Gly Thr Ile Trp Ser Ser
        355             360             365

Ser Leu Phe Pro Asn Arg Ala Pro Ala Gly Trp Arg Leu Leu Leu Asn
        370             375             380

Phe Ile Gly Gly Thr Thr Asp Leu Ala Ile Ala Gln Leu Ser Gln Glu
385             390             395             400

Glu Ile Val Gln Ile Val His Arg Asp Leu Gln Lys Thr Leu Leu Lys
                405             410             415

Gln Asp Ile Pro Pro Lys Val Leu Ala Val His Leu Trp Lys Arg Ala
                420             425             430

Ile Pro Gln Tyr Pro Leu Gly His His Gln Asn Leu Ala Gln Ile His
        435             440             445

His Ser Leu Gln Gln Arg Pro Gly Leu Phe Leu Cys Gly Asn Tyr Thr
        450             455             460

Asp Gly Val Ala Val Gly Asp Cys Ile Arg Arg Gly Gln Glu Cys Ala
465             470             475             480

Ala Asp Val Val Lys Tyr Leu Asp Gln Gly
                485             490
```

<210> SEQ ID NO 27
<211> LENGTH: 479
<212> TYPE: PRT
<213> ORGANISM: Artificial Sequence
<220> FEATURE:
<223> OTHER INFORMATION: Synthetic_PPO of Limnothrix sp. CACIAM 69d
      (RFP59749.1)

<400> SEQUENCE: 27

Met Asp Val Leu Ile Val Gly Ala Gly Leu Thr Gly Leu Ser Ala Ala
1               5                   10                  15

His Arg Leu Val Asn His Pro Gly Asn Arg Gly Arg Ser Thr Leu Val
            20                  25                  30

Val Glu Ala Gln Asn Arg Val Gly Gly Asn Ile Thr Thr Arg Ser Ala
        35                  40                  45

Asp Gly Phe Leu Trp Glu Glu Gly Pro Asn Ser Phe Ala Pro Thr Pro
    50                  55                  60

Glu Leu Leu Lys Leu Ser Val Glu Val Gly Leu Gln Asp Glu Leu Val
65                  70                  75                  80

Phe Ala Asp Gly Lys Leu Pro Arg Phe Val Tyr Trp Asp Gly Arg Leu
                85                  90                  95

Gln Ala Ile Pro Met Ser Pro Gly Ala Phe Trp Asn Ser Thr Leu Leu
            100                 105                 110

Ser Asp Arg Gly Lys Ala Arg Leu Leu Leu Gly Ala Ala Gly Phe Val
            115                 120                 125

Pro Pro Ile Val Gly Ala Ala Ile Ser Ala Arg Gly Gly Glu Glu Thr
    130                 135                 140

Val Arg Glu Phe Phe Thr Arg His Leu Gly Gln Glu Ala Met Glu Arg
145                 150                 155                 160

Leu Val Asp Pro Phe Ile Ser Gly Val Tyr Ala Gly Asp Pro Asn Ala
                165                 170                 175

Leu Ser Ala Ser Ala Ala Phe Arg Lys Met Ala Ala Met Gln Ala Ala
            180                 185                 190

Gly Gly Gly Leu Gly Ala Gly Ala Ala Arg Ile Leu Trp Ala Lys Arg
            195                 200                 205

Gln Ala Ala Lys Gln Ala Pro Pro Ala Asp Pro Arg Leu Pro Lys Pro
    210                 215                 220

Lys Ser Gly Glu Leu Gly Ser Phe Arg Glu Gly Leu Gln Ala Leu Pro
225                 230                 235                 240

Glu Ala Val Ala Ser Gly Leu Gly Asp Arg Val Lys Leu Gly Trp Gln
                245                 250                 255

Val Glu Ala Ile Ala Arg Asp Pro Gln Gly Thr Tyr Gln Val Thr Ile
            260                 265                 270

Ala Ser Pro Asp Gly Pro Gln Arg Ile Thr Ala Arg Ser Ile Ile Leu
            275                 280                 285

Ala Thr Pro Ala Pro Val Thr Ala Gln Leu Leu Glu Pro Leu Ala Pro
    290                 295                 300

Arg Ala Ser Thr Ala Leu Asn Ala Ile Pro Tyr Pro Ala Val Ala Cys
305                 310                 315                 320

Val Ile Leu Ala Tyr Pro Glu Thr Ala Phe Ala Gln Ser Leu Arg Gly
                325                 330                 335

Phe Gly Asn Leu Ile Pro Arg Ser Leu Gly Leu Gln Thr Leu Gly Thr
            340                 345                 350

Ile Trp Ala Ser Ser Leu Phe Ala Gly Arg Ala Pro Gln Gly Trp Ala

-continued

```
              355                 360                 365

His Leu Ile Asn Phe Ile Gly Gly Ala Gln Asn Pro Thr Leu Ile His
    370                 375                 380

Lys Thr Glu Asp Glu Ile Ala Gln Met Val His Ala Asp Val Arg Gln
385                 390                 395                 400

Ile Leu Leu Lys Gln Asp Val Pro Pro Lys Val Leu Ser Val Lys Leu
                405                 410                 415

Trp Arg Arg Ala Ile Pro Gln Tyr Thr Ile Gly His Gly Ser Arg Leu
                420                 425                 430

Ala Thr Leu His Gln Glu Leu Gln His Trp Pro Gly Leu Phe Ala Cys
                435                 440                 445

Ser Asn Tyr Glu Gly Gly Val Ala Leu Gly Asp Cys Val Arg His Gly
    450                 455                 460

Trp Glu Gln Ala Asp Ala Ile Glu Gln Phe Leu Gly Ser Arg Val
465                 470                 475

<210> SEQ ID NO 28
<211> LENGTH: 478
<212> TYPE: PRT
<213> ORGANISM: Artificial Sequence
<220> FEATURE:
<223> OTHER INFORMATION: Synthetic_PPO of Okeania hirsute
      (WP_124155207.1)

<400> SEQUENCE: 28

Met Thr Glu Val Leu Asp Val Leu Val Val Gly Ala Gly Ile Ser Gly
1               5                   10                  15

Leu Ser Leu Ala His Ala Leu Thr Lys Leu Gly Asn Asn Ser Pro Leu
                20                  25                  30

Lys Ile Leu Val Ala Glu Ser Gln Asn Arg Val Gly Gly Asn Ile Thr
            35                  40                  45

Thr Val Ser Leu Gly Asp Phe Leu Trp Glu Glu Gly Pro Asn Ser Phe
    50                  55                  60

Ser Pro Thr Pro Glu Phe Leu Lys Leu Ala Val Asp Val Gly Leu Lys
65                  70                  75                  80

Gln Glu Leu Val Phe Ala Asp Arg Lys Leu Pro Arg Tyr Val Tyr Trp
                85                  90                  95

Asn Gly Gln Leu Leu Pro Val Pro Met Ser Pro Thr Ala Met Leu Gln
                100                 105                 110

Ser Lys Leu Leu Ser Asp Ala Gly Lys Leu Arg Ala Leu Val Gly Ala
            115                 120                 125

Leu Gly Phe Val Ser Pro Ala Ile Gly Asn Leu Ser Gly Gln Gly Gly
    130                 135                 140

Glu Glu Thr Val Ser Gln Phe Phe Gln Arg His Leu Gly Pro Glu Val
145                 150                 155                 160

Met Gln Arg Leu Val Glu Pro Phe Val Ser Gly Val Tyr Ala Gly Asp
                165                 170                 175

Pro Ser Gln Leu Ser Ala Ser Ala Ala Phe Ala Lys Val Ala Arg Met
                180                 185                 190

Ala Asp Leu Gly Gly Gly Leu Val Ala Gly Ala Leu Leu Ser Ala Lys
            195                 200                 205

Lys Asn Arg Lys Phe Lys Val Ala Pro Asp Pro Asn Ile Pro Lys Thr
    210                 215                 220

Lys Thr Gly Glu Leu Gly Ser Phe Arg Gly Gly Leu Glu Ala Leu Pro
225                 230                 235                 240
```

```
Lys Ala Ile Ala Ser Tyr Leu Gly Glu Ala Val Lys Leu Asn Trp His
                245                 250                 255

Leu Thr Asn Ile Arg Arg Thr Glu Gln Gln Thr Tyr Ile Ala Glu Phe
                260                 265                 270

Ser Thr Pro Asn Gly Pro Glu Gln Ile Glu Thr Arg Thr Ile Ser Leu
                275                 280                 285

Ser Thr Pro Ala Arg Val Cys Ala Glu Leu Phe Lys Thr Leu Gln Pro
                290                 295                 300

Glu Ile Ala Ser Ile Phe Asn Glu Phe Tyr Tyr Pro Pro Val Ala Cys
305                 310                 315                 320

Val Val Leu Ala Tyr Pro Asp Thr Ser Ile Lys Val Lys Ile Asp Gly
                325                 330                 335

Phe Gly Asn Leu Ile Pro Arg Gly Gln Gly Ile Arg Thr Leu Gly Ser
                340                 345                 350

Ile Trp Ser Ser Thr Leu Phe Ser Gly Arg Thr Pro Pro Gly Trp Gln
                355                 360                 365

Ile Phe Thr Asn Phe Ile Gly Gly Ala Thr Asp Pro Glu Ile Ala Asn
                370                 375                 380

Leu Asp Ser Glu Ala Ile Val Gln Gln Val His Gln Asp Leu Cys Gln
385                 390                 395                 400

Thr Leu Leu Lys Gln Asn Ala Glu Gln Pro Lys Val Leu Ala Val His
                405                 410                 415

Leu Trp Ser Arg Ala Ile Pro Gln Tyr Asn Leu Gly His Asn Ser Lys
                420                 425                 430

Leu Glu Glu Ile Asn Asn Gly Leu Lys Ser Leu Pro Gly Leu Tyr Leu
                435                 440                 445

Cys Ser Asn Tyr Ile Gly Gly Ile Ala Leu Gly Asp Cys Val Arg Arg
        450                 455                 460

Gly Thr Glu Val Ala Thr Glu Ile Tyr Gln Gly Leu Gln Thr
465                 470                 475
```

```
<210> SEQ ID NO 29
<211> LENGTH: 478
<212> TYPE: PRT
<213> ORGANISM: Artificial Sequence
<220> FEATURE:
<223> OTHER INFORMATION: Synthetic_PPO of Okeania hirsute
      (WP_124145785.1)

<400> SEQUENCE: 29
```

```
Met Thr Glu Val Leu Asp Val Leu Val Val Gly Ala Gly Ile Ser Gly
1               5                   10                  15

Leu Ser Leu Ala His Ala Leu Thr Lys Leu Gly Asn Asn Ser Pro Leu
                20                  25                  30

Lys Ile Leu Val Ala Glu Ser Gln Asn Arg Val Gly Gly Asn Ile Thr
                35                  40                  45

Thr Val Ser Leu Gly Asp Phe Leu Trp Glu Glu Gly Pro Asn Ser Phe
        50                  55                  60

Ser Pro Thr Pro Glu Phe Leu Lys Leu Ala Val Asp Val Gly Leu Lys
65                  70                  75                  80

Glu Glu Leu Ile Phe Ala Asp Arg Lys Leu Pro Arg Tyr Val Tyr Trp
                85                  90                  95

Asn Gly Gln Leu Leu Pro Val Pro Met Ser Pro Lys Ala Met Leu Gln
                100                 105                 110

Ser Lys Leu Leu Ser Asp Gly Gly Lys Leu Arg Ala Leu Val Gly Ala
                115                 120                 125
```

```
Leu Gly Phe Val Ser Pro Ala Ile Gly Asp Leu Ser Glu Gln Gly Gly
    130                 135                 140

Glu Glu Thr Val Ser Gln Phe Phe Gln Arg His Leu Gly Ala Glu Val
145                 150                 155                 160

Met Gln Arg Leu Val Glu Pro Phe Val Ser Gly Val Tyr Ala Gly Asp
                165                 170                 175

Pro Gly Gln Leu Ser Ala Asn Ala Ala Phe Ala Lys Val Ala Arg Met
                180                 185                 190

Ala Asp Leu Gly Gly Gly Leu Val Ala Gly Ala Leu Leu Ser Ala Lys
                195                 200                 205

Lys Asn Arg Lys Phe Lys Val Ala Pro Asp Pro Asn Ile Pro Lys Thr
    210                 215                 220

Lys Thr Gly Glu Leu Gly Ser Phe Arg Gly Gly Leu Glu Ala Leu Pro
225                 230                 235                 240

Lys Ala Ile Ala Ser Tyr Leu Gly Glu Ala Val Lys Leu Asn Trp His
                245                 250                 255

Leu Thr Gly Ile Arg Arg Thr Glu Gln Gln Thr Tyr Ile Ala Glu Phe
                260                 265                 270

Ser Thr Pro Asn Gly Thr Glu Gln Ile Glu Thr Arg Thr Ile Ser Leu
            275                 280                 285

Ser Thr Pro Ala Arg Val Cys Ser Glu Leu Phe Thr Thr Leu Gln Pro
    290                 295                 300

Glu Ile Ala Ser Ile Phe Asn Glu Phe Tyr Tyr Pro Thr Val Ala Cys
305                 310                 315                 320

Val Val Leu Ala Tyr Pro Asp Thr Ser Ile Lys Val Lys Ile Asp Gly
                325                 330                 335

Phe Gly Asn Leu Ile Pro Arg Gly Gln Gly Ile Arg Thr Leu Gly Ser
                340                 345                 350

Ile Trp Ser Ser Thr Leu Phe Ser Gly Arg Thr Pro Pro Gly Trp Gln
            355                 360                 365

Ile Phe Thr Asn Phe Ile Gly Gly Ala Thr Asp Pro Glu Ile Ala Asn
    370                 375                 380

Leu Asp Ser Glu Ala Ile Val Gln Gln Val His Gln Asp Leu Cys Gln
385                 390                 395                 400

Thr Leu Leu Lys Gln Asn Ala Glu Gln Pro Lys Val Leu Ala Val His
                405                 410                 415

Leu Trp Ser Arg Ala Ile Pro Gln Tyr Asn Leu Gly His Asn Ser Lys
            420                 425                 430

Leu Glu Glu Ile Asn Asn Gly Leu Lys Ser Leu Pro Gly Leu Tyr Leu
            435                 440                 445

Cys Ser Asn Tyr Ile Gly Gly Ile Ala Leu Gly Asp Cys Val Arg Ser
    450                 455                 460

Gly Thr Glu Val Ala Thr Lys Ile Tyr Gln Gly Leu Gln Val
465                 470                 475
```

<210> SEQ ID NO 30
<211> LENGTH: 490
<212> TYPE: PRT
<213> ORGANISM: Artificial Sequence
<220> FEATURE:
<223> OTHER INFORMATION: Synthetic_PPO of Desertifilum sp. IPPAS B-1220
      (WP_069967861.1)

<400> SEQUENCE: 30

Met Ser Phe Thr Asp Leu Ala Thr Pro Ser His Pro Leu Asp Thr Leu

```
1                 5                    10                   15

Val Ile Gly Ala Gly Ile Ser Gly Leu Ser Leu Ala Phe Thr Leu Gln
              20                   25                   30

Gln Arg Gln Thr Gln Val Leu Val Cys Glu Ser Gln Asn Arg Ile Gly
              35                   40                   45

Gly Asn Ile Thr Thr Gly Gln Ala Asp Gly Phe Leu Trp Glu Glu Gly
        50                   55                   60

Pro Asn Ser Phe Ala Pro Thr Pro Ala Leu Leu Arg Leu Ile Val Asp
65                   70                   75                   80

Ala Gly Leu Glu Lys Asp Met Ile Leu Ala Asp Arg Arg Leu Pro Arg
                  85                   90                   95

Phe Val Tyr Arg Gln Gly Arg Leu Gln Ala Ile Pro Met Ser Pro Pro
              100                  105                  110

Ala Ala Ile Gly Thr Pro Leu Leu Ser Trp Pro Gly Lys Leu Arg Ala
              115                  120                  125

Gly Leu Gly Ala Ile Gly Phe Val Arg Pro Pro Leu Gly Glu Gln Phe
        130                  135                  140

Ser Gln Gln Gly Ser Glu Glu Thr Val Ala Gln Phe Phe Gln Arg His
145                  150                  155                  160

Leu Gly Glu Glu Val Met Glu Arg Leu Val Thr Pro Phe Val Ser Gly
                  165                  170                  175

Val Tyr Ala Gly Asp Val Asn Gln Leu Ser Ala Ala Ala Phe Arg
              180                  185                  190

Arg Ile Ala Gln Leu Glu Gly Val Gly Gly Gly Leu Val Ala Gly Ala
              195                  200                  205

Ile Leu Ser Arg Met Lys Ala Lys Ser Gln Pro Gln Val Pro Val Asp
        210                  215                  220

Pro Ser Leu Pro Lys Thr Arg Pro Gly Glu Leu Gly Ser Phe Gln Gln
225                  230                  235                  240

Gly Leu Gln Met Leu Pro Gln Ala Leu Ala Ala Lys Leu Gly Asp Ala
                  245                  250                  255

Val Arg Leu Asn Trp Arg Leu Leu Gln Ile Thr Pro Thr Thr Arg Gln
              260                  265                  270

Ser Tyr Ile Ala Glu Phe Gly Thr Pro Glu Gly Thr Gln Ile Val Glu
              275                  280                  285

Ala Arg His Val Val Leu Thr Thr Pro Ala Tyr Ile Thr Ala Glu Ile
        290                  295                  300

Val Glu Ala Ile Ala Pro Leu Ala Ser Gln Ala Leu Arg Ala Ile Glu
305                  310                  315                  320

Tyr Pro Pro Val Ala Asn Val Val Leu Ala Tyr Pro Glu Ser Ala Leu
              325                  330                  335

Lys Gln Pro Leu Lys Gly Phe Gly His Leu Ile Pro Arg Ser Glu Gly
              340                  345                  350

Ile Arg Thr Leu Gly Thr Ile Trp Ser Ser Ser Leu Phe Pro Gly Arg
              355                  360                  365

Val Pro Pro Gly Trp Gln Leu Leu Thr Asn Tyr Ile Gly Gly Ala Thr
        370                  375                  380

Asp Pro Gly Ile Leu Asp Leu Asp Arg Asp Ser Arg Ser Asn Leu Asp
385                  390                  395                  400

Gly Asn Pro Ile Ala Gln Ala Val His Gln Asp Ile Arg Arg Ile Leu
              405                  410                  415

Leu Gln Gln Glu Val Gln Pro Lys Val Leu Ala Val His Leu Trp Lys
              420                  425                  430
```

-continued

```
Arg Ala Ile Pro Gln Tyr Asn Leu Gly His His Gln Arg Leu Gln Thr
        435                 440                 445

Ile Phe Gln Ser Leu Ala Pro Phe Pro Gly Leu His Ile Cys Ser Asn
        450                 455                 460

Tyr Thr Asp Gly Val Ala Leu Gly Asp Cys Val Arg Arg Ala Gln Glu
465                 470                 475                 480

Leu Ala Asp Ile Leu Thr Gln Lys Thr Arg
                485                 490

<210> SEQ ID NO 31
<211> LENGTH: 489
<212> TYPE: PRT
<213> ORGANISM: Artificial Sequence
<220> FEATURE:
<223> OTHER INFORMATION: Synthetic_PPO of Synechococcus sp. 65AY6Li
      (PIK93057.1)

<400> SEQUENCE: 31

Met Glu Ala Ala Val Asn Pro Ala Thr Pro Glu Pro Leu Asn Ala Glu
1               5                   10                  15

Val Val Val Ile Gly Ala Gly Ile Ser Gly Leu Thr Leu Ala Trp Arg
                20                  25                  30

Leu Gln Gln Gly Leu Ser Ala Arg Gly Gly Ser Pro Gln Ala Val Leu
        35                  40                  45

Leu Ala Glu Ala Ser Ser Arg Val Gly Gly Cys Ile Ser Thr Gln Ser
        50                  55                  60

Lys Asp Gly Tyr Cys Trp Glu Glu Gly Pro Asn Ser Phe Thr Pro Thr
65                  70                  75                  80

Pro Ala Leu Leu Asn Leu Ile Ala Glu Val Gly Leu Thr Asp Gln Leu
                85                  90                  95

Val Leu Ala Asp Ala Lys Leu Pro Arg Tyr Ile Tyr Trp Glu Lys Glu
                100                 105                 110

Leu Leu Pro Val Pro Leu Ser Pro Ala Ala Ala Leu Ser Ser Arg Leu
        115                 120                 125

Leu Ser Val Gly Gly Lys Leu Arg Ala Leu Gln Gly Leu Leu Gly Phe
        130                 135                 140

Val Pro Pro Pro Gly Arg Glu Glu Thr Val Arg Gln Phe Phe Arg
145                 150                 155                 160

Arg Gln Leu Gly Ser Glu Val Ala Glu Arg Leu Val Glu Pro Phe Thr
                165                 170                 175

Ser Gly Val Tyr Ala Gly Asp Pro Asp Gln Leu Ser Ala Val Ala Ala
                180                 185                 190

Phe Pro Arg Val Ala Gly Leu Glu Glu Arg Tyr Gly Ser Leu Phe Ala
        195                 200                 205

Gly Ala Leu Gln Ala Leu Arg Gln Arg Pro Gln Pro Ser Pro Ala Ala
        210                 215                 220

Ile Gln Pro Pro Pro Lys Arg Gly Gln Leu Gly Asn Leu Arg Gln Gly
225                 230                 235                 240

Leu Gln Gln Leu Pro Glu Ala Leu Ala Gln Lys Leu Gly Asp Ser Leu
                245                 250                 255

Arg Leu Gly Trp Arg Ala Val Gln Leu Lys Arg Glu Gly Glu Leu Tyr
                260                 265                 270

Trp Val Gly Phe Glu Thr Pro Glu Gly Ser Arg Trp Val Ala Ala Arg
        275                 280                 285

Gln Val Val Leu Ala Leu Pro Ala Tyr Glu Ala Ala Ala Leu Leu Gln
```

```
          290              295              300

Glu Leu Asn Pro Pro Ala Ser Gln Leu Leu Ala Glu Ile Leu Tyr Pro
305              310              315              320

Pro Val Ala Val Val Ala Leu Ala Tyr Pro Gln Glu Ala Leu Pro Gln
                 325              330              335

Pro Leu Arg Gly Phe Gly His Leu Ile Pro Arg Ser Gln Gly Leu Arg
                 340              345              350

Thr Leu Gly Thr Ile Trp Ala Ser Cys Leu Phe Pro Glu Arg Ala Pro
                 355              360              365

Gln Gly Tyr His Ser Phe Leu Ser Phe Leu Gly Gly Ala Thr Asp Ala
                 370              375              380

Ala Leu Ala Arg Arg Arg Gly Ile Pro Pro Ile Pro Ala Leu Ser Pro
385              390              395              400

Glu Glu Arg Ala Gln Ile Ala His Ala Glu Leu Ser Gln Val Leu Leu
                 405              410              415

Thr Arg Arg Val Glu Pro Ile Tyr Leu Gly Glu Arg Leu Trp Pro Arg
                 420              425              430

Ala Ile Pro Gln Tyr Thr Leu Gly His Arg Gln Arg Ile Ala Gln Val
                 435              440              445

Gln Ala His Leu Ala Ser Gln Thr Pro Gly Ile Trp Val Cys Ala Asn
                 450              455              460

Tyr Leu Asp Gly Val Ala Leu Gly Asp Cys Val Arg Arg Ala Glu Ala
465              470              475              480

Leu Ala Gln Gln Leu Leu Ser Gln Val
                 485
```

<210> SEQ ID NO 32
<211> LENGTH: 489
<212> TYPE: PRT
<213> ORGANISM: Artificial Sequence
<220> FEATURE:
<223> OTHER INFORMATION: Synthetic_PPO of Synechococcus sp. 65AY6A5
      (PIK88626.1)

<400> SEQUENCE: 32

```
Met Glu Ala Ala Val Asn Pro Ala Thr Pro Glu Pro Leu Asn Ala Glu
1               5               10               15

Val Val Val Ile Gly Ala Gly Ile Ser Gly Leu Thr Leu Ala Trp Arg
                 20               25               30

Leu Gln Gln Gly Leu Ser Ala Arg Gly Gly Ser Pro Gln Ala Val Leu
         35               40               45

Leu Ala Glu Ala Ser Ser Arg Val Gly Gly Cys Ile Ser Thr Gln Ser
         50               55               60

Lys Asp Gly Tyr Arg Trp Glu Glu Gly Pro Asn Ser Phe Thr Pro Thr
65               70               75               80

Pro Ala Leu Leu Asn Leu Ile Ala Glu Val Gly Leu Thr Asp Gln Leu
                 85               90               95

Val Leu Ala Asp Ala Lys Leu Pro Arg Tyr Ile Tyr Trp Glu Gly Ala
                 100              105              110

Leu Leu Pro Val Pro Leu Ser Pro Ala Ala Ala Leu Gly Ser Arg Leu
         115              120              125

Leu Ser Val Gly Gly Lys Leu Arg Ala Leu Gln Gly Leu Leu Gly Phe
         130              135              140

Val Pro Pro Pro Pro Gly Arg Glu Glu Thr Val Arg Gln Phe Phe Arg
145              150              155              160
```

```
Arg Gln Leu Gly Ser Glu Val Ala Glu Arg Leu Val Glu Pro Phe Thr
            165                 170                 175

Ser Gly Val Tyr Ala Gly Asp Pro Asp Gln Leu Ser Ala Val Ala Ala
            180                 185                 190

Phe Pro Arg Val Ala Gly Leu Glu Glu Arg Tyr Gly Ser Leu Phe Ala
            195                 200                 205

Gly Ala Leu Gln Ala Leu Arg Gln Arg Pro Gln Pro Ser Pro Ala Ala
        210                 215                 220

Ile Gln Pro Pro Pro Lys Arg Gly Gln Leu Gly Asn Leu Arg Gln Gly
225                 230                 235                 240

Leu Gln Gln Leu Pro Glu Ala Leu Ala Gln Lys Leu Gly Asp Ser Leu
            245                 250                 255

Arg Leu Gly Trp Arg Ala Leu Gln Leu Lys Arg Ala Gly Glu Leu Tyr
            260                 265                 270

Trp Val Gly Phe Glu Thr Pro Glu Gly Ser Arg Trp Val Ala Ala Arg
            275                 280                 285

Gln Val Val Leu Ala Leu Pro Ala Tyr Glu Ala Ala Ala Leu Leu Gln
        290                 295                 300

Glu Leu Asn Pro Pro Ala Ser Gln Leu Leu Ala Glu Ile Leu Tyr Pro
305                 310                 315                 320

Pro Val Ala Val Val Ala Leu Ala Tyr Pro Gln Glu Ala Leu Pro Gln
            325                 330                 335

Pro Leu Arg Gly Phe Gly His Leu Ile Pro Arg Ser Gln Gly Leu Arg
            340                 345                 350

Thr Leu Gly Thr Ile Trp Ala Ser Cys Leu Phe Pro Glu Arg Ala Pro
            355                 360                 365

Gln Gly Tyr His Ser Phe Leu Ser Phe Leu Gly Gly Ala Thr Asp Ala
        370                 375                 380

Ala Leu Ala Arg Gln Gln Gly Ile Pro Pro Ile Pro Ala Leu Ser Pro
385                 390                 395                 400

Glu Glu Arg Ala Gln Ile Ala His Ala Glu Leu Ser Gln Val Leu Leu
            405                 410                 415

Thr Arg Arg Ala Glu Pro Val Tyr Leu Gly Glu Arg Leu Trp Pro Arg
            420                 425                 430

Ala Ile Pro Gln Tyr Thr Leu Gly His Arg Gln Arg Ile Ala Gln Val
            435                 440                 445

Gln Ala His Leu Ala Ser Gln Thr Pro Gly Ile Trp Val Cys Ala Asn
        450                 455                 460

Tyr Leu Asp Gly Val Ala Leu Gly Asp Cys Val Arg Arg Ala Glu Ala
465                 470                 475                 480

Leu Ala Gln Gln Leu Leu Ser Gln Val
            485
```

```
<210> SEQ ID NO 33
<211> LENGTH: 489
<212> TYPE: PRT
<213> ORGANISM: Artificial Sequence
<220> FEATURE:
<223> OTHER INFORMATION: Synthetic_PPO of Synechococcus sp. 60AY4M2
      (PIK94415.1)

<400> SEQUENCE: 33

Met Glu Ala Ala Val Asn Pro Ala Thr Pro Glu Pro Leu Asn Ala Glu
1               5                   10                  15

Val Val Val Ile Gly Ala Gly Ile Ser Gly Leu Thr Leu Ala Trp Arg
            20                  25                  30
```

```
Leu Gln Gln Gly Leu Ser Ala Arg Gly Gly Ser Pro Gln Ala Val Leu
        35              40              45

Leu Ala Glu Ala Ser Ser Arg Val Gly Gly Cys Ile Ser Thr Gln Ser
        50              55              60

Lys Asp Gly Tyr Arg Trp Glu Glu Gly Pro Asn Ser Phe Thr Pro Thr
65              70              75              80

Pro Ala Leu Leu Asn Leu Ile Ala Glu Val Gly Leu Ala Asp Gln Leu
                85              90              95

Val Leu Ala Asp Ala Lys Leu Pro Arg Tyr Ile Tyr Trp Glu Gly Ala
                100             105             110

Leu Leu Pro Val Pro Leu Ser Pro Ala Ala Ala Leu Gly Ser Arg Leu
        115             120             125

Leu Ser Val Gly Gly Lys Leu Arg Ala Leu Gln Gly Leu Leu Gly Phe
        130             135             140

Val Pro Pro Pro Gly Arg Glu Glu Thr Val Arg Gln Phe Phe Arg
145             150             155             160

Arg Gln Leu Gly Ser Glu Val Ala Glu Arg Leu Val Glu Pro Phe Thr
                165             170             175

Ser Gly Val Tyr Ala Gly Asp Pro Asp Gln Leu Ser Ala Val Ala Ala
                180             185             190

Phe Pro Arg Val Ala Gly Leu Glu Glu Arg Tyr Gly Ser Leu Phe Ala
        195             200             205

Gly Ala Leu Gln Ala Leu Arg Gln Arg Pro Gln Pro Ser Pro Ala Ala
        210             215             220

Ile Gln Pro Pro Pro Lys Arg Gly Gln Leu Gly Asn Leu Arg Gln Gly
225             230             235             240

Leu Gln Gln Leu Pro Glu Ala Leu Ala Gln Lys Leu Gly Asp Ser Leu
                245             250             255

Arg Leu Gly Trp Arg Ala Leu Gln Leu Lys Arg Ala Gly Glu Leu Tyr
                260             265             270

Trp Val Gly Phe Glu Thr Pro Glu Gly Ser Arg Trp Val Ala Ala Arg
        275             280             285

Gln Val Val Leu Ala Leu Pro Ala Tyr Glu Ala Ala Ala Leu Leu Gln
        290             295             300

Glu Leu Asn Pro Pro Ala Ser Gln Leu Leu Ala Glu Ile Leu Tyr Pro
305             310             315             320

Pro Val Ala Val Val Ala Leu Ala Tyr Pro Gln Glu Ala Leu Pro Gln
                325             330             335

Pro Leu Arg Gly Phe Gly His Leu Ile Pro Arg Ser Gln Gly Leu Arg
                340             345             350

Thr Leu Gly Thr Ile Trp Ala Ser Cys Leu Phe Pro Glu Arg Ala Pro
        355             360             365

Gln Gly Tyr His Ser Phe Leu Ser Phe Leu Gly Gly Ala Thr Asp Ala
        370             375             380

Ala Leu Ala Arg Gln Gln Gly Ile Pro Pro Ile Pro Ala Leu Ser Pro
385             390             395             400

Glu Glu Arg Ala Gln Ile Ala His Ala Glu Leu Ser Gln Val Leu Leu
                405             410             415

Thr Arg Arg Ala Glu Pro Val Tyr Leu Gly Glu Arg Leu Trp Pro Arg
                420             425             430

Ala Ile Pro Gln Tyr Thr Leu Gly His Arg Gln Arg Ile Ala Gln Val
        435             440             445
```

-continued

```
Gln Ala His Leu Ala Ser Gln Thr Pro Gly Ile Trp Val Cys Ala Asn
    450                 455                 460

Tyr Leu Asp Gly Val Ala Leu Gly Asp Cys Val Arg Arg Ala Glu Ala
465                 470                 475                 480

Leu Ala Gln Gln Leu Phe Ser Gln Val
                485

<210> SEQ ID NO 34
<211> LENGTH: 489
<212> TYPE: PRT
<213> ORGANISM: Artificial Sequence
<220> FEATURE:
<223> OTHER INFORMATION: Synthetic_PPO of Synechococcus sp. 63AY4M1
      (PIK96673.1)

<400> SEQUENCE: 34

Met Glu Ala Ala Val Asn Pro Ala Thr Pro Glu Pro Leu Asn Ala Glu
1               5                   10                  15

Val Val Val Ile Gly Ala Gly Ile Ser Gly Leu Thr Leu Ala Trp Arg
                20                  25                  30

Leu Gln Gln Gly Leu Ser Ala Arg Gly Gly Ser Pro Gln Ala Val Leu
        35                  40                  45

Leu Ala Glu Ala Ser Ser Arg Val Gly Gly Cys Ile Ser Thr Gln Ser
    50                  55                  60

Lys Asp Gly Tyr Arg Trp Glu Glu Gly Pro Asn Ser Phe Thr Pro Thr
65                  70                  75                  80

Pro Ala Leu Leu Asn Leu Ile Ala Glu Val Gly Leu Ala Asp Gln Leu
                85                  90                  95

Val Leu Ala Asp Ala Lys Leu Pro Arg Tyr Ile Tyr Trp Glu Gly Ala
                100                 105                 110

Leu Leu Pro Val Pro Leu Ser Pro Ala Ala Ala Leu Gly Ser Arg Leu
                115                 120                 125

Leu Ser Val Gly Gly Lys Leu Arg Ala Leu Gln Gly Leu Leu Gly Phe
    130                 135                 140

Val Pro Pro Pro Gly Arg Glu Glu Thr Val Arg Gln Phe Phe Arg
145                 150                 155                 160

Arg Gln Leu Gly Ser Glu Val Ala Glu Arg Leu Val Glu Pro Phe Thr
                165                 170                 175

Ser Gly Val Tyr Ala Gly Asp Pro Asp Gln Leu Ser Ala Val Ala Ala
                180                 185                 190

Phe Pro Arg Val Ala Gly Leu Glu Glu Arg Tyr Gly Ser Leu Phe Ala
                195                 200                 205

Gly Ala Leu Gln Ala Leu Arg Gln Arg Pro Gln Pro Ser Pro Ala Ala
    210                 215                 220

Ile Gln Pro Pro Pro Lys Arg Gly Gln Leu Gly Asn Leu Arg Gln Gly
225                 230                 235                 240

Leu Gln Gln Leu Pro Glu Ala Leu Ala Gln Lys Leu Gly Asp Ser Leu
                245                 250                 255

Arg Leu Gly Trp Arg Ala Leu Gln Leu Lys Arg Ala Gly Glu Leu Tyr
                260                 265                 270

Trp Val Gly Phe Glu Thr Pro Glu Gly Ser Arg Trp Val Ala Ala Arg
        275                 280                 285

Gln Val Val Leu Ala Leu Pro Ala Tyr Glu Ala Ala Ala Leu Leu Gln
    290                 295                 300

Glu Leu Asn Pro Pro Ala Ser Gln Leu Leu Ala Glu Ile Leu Tyr Pro
305                 310                 315                 320
```

```
Pro Val Ala Val Val Ala Leu Ala Tyr Pro Gln Glu Ala Leu Pro Gln
                325                 330                 335

Pro Leu Arg Gly Phe Gly His Leu Ile Pro Arg Ser Gln Gly Leu Arg
                340                 345                 350

Thr Leu Gly Thr Ile Trp Ala Ser Cys Leu Phe Pro Glu Arg Ala Pro
                355                 360                 365

Gln Gly Tyr His Ser Phe Leu Ser Phe Leu Gly Gly Ala Thr Asp Ala
            370                 375                 380

Ala Leu Ala Arg Arg Arg Gly Ile Pro Pro Ile Pro Ala Leu Ser Pro
385                 390                 395                 400

Glu Glu Arg Ala Gln Ile Ala His Ala Glu Leu Ser Gln Val Leu Leu
                405                 410                 415

Thr Arg Arg Ala Glu Pro Val Tyr Leu Gly Glu Arg Leu Trp Pro Arg
                420                 425                 430

Ala Ile Pro Gln Tyr Thr Leu Gly His Arg Gln Arg Ile Ala Gln Val
                435                 440                 445

Gln Ala His Leu Ala Ser Gln Thr Pro Gly Ile Trp Val Cys Ala Asn
            450                 455                 460

Tyr Leu Asp Gly Val Ala Leu Gly Asp Cys Val Arg Arg Ala Glu Ala
465                 470                 475                 480

Leu Ala Gln Gln Leu Phe Ser Gln Val
                485

<210> SEQ ID NO 35
<211> LENGTH: 489
<212> TYPE: PRT
<213> ORGANISM: Artificial Sequence
<220> FEATURE:
<223> OTHER INFORMATION: Synthetic_PPO of Synechococcus sp. 63AY4M2
      (PIK85371.1)

<400> SEQUENCE: 35

Met Glu Ala Ala Val Asn Pro Ala Thr Pro Glu Pro Leu Asn Ala Glu
1               5                   10                  15

Val Val Val Ile Gly Ala Gly Ile Ser Gly Leu Thr Leu Ala Trp Arg
                20                  25                  30

Leu Gln Gln Gly Leu Ser Ala Arg Gly Gly Ser Pro Gln Ala Val Leu
            35                  40                  45

Leu Ala Glu Ala Ser Ser Arg Val Gly Gly Cys Ile Ser Thr Gln Ser
        50                  55                  60

Lys Asp Gly Tyr Arg Trp Glu Glu Gly Pro Asn Ser Phe Thr Pro Thr
65                  70                  75                  80

Pro Ala Leu Leu Asn Leu Ile Ala Glu Val Gly Leu Thr Asp Gln Leu
                85                  90                  95

Val Leu Ala Asp Ala Lys Leu Pro Arg Tyr Ile Tyr Trp Glu Gly Ala
                100                 105                 110

Leu Leu Pro Val Pro Leu Ser Pro Ala Ala Ala Leu Gly Ser Arg Leu
            115                 120                 125

Leu Ser Val Gly Gly Lys Leu Arg Ala Leu Gln Gly Leu Leu Gly Phe
        130                 135                 140

Val Pro Pro Pro Gly Arg Glu Glu Thr Val Arg Gln Phe Phe Arg
145                 150                 155                 160

Arg Gln Leu Gly Ser Glu Val Ala Glu Arg Leu Val Glu Pro Phe Thr
                165                 170                 175

Ser Gly Val Tyr Ala Gly Asp Pro Asp Gln Leu Ser Ala Val Ala Ala
```

-continued

```
                180                 185                 190

Phe Pro Arg Val Ala Gly Leu Glu Glu Arg Tyr Gly Ser Leu Phe Ala
        195                 200                 205

Gly Ala Leu Gln Ala Leu Arg Gln Arg Pro Gln Pro Ser Pro Ala Ala
        210                 215                 220

Ile Gln Pro Pro Pro Lys Arg Gly Gln Leu Gly Asn Leu Arg Gln Gly
225                 230                 235                 240

Leu Gln Gln Leu Pro Glu Ala Leu Ala Gln Lys Leu Gly Asp Ser Leu
                245                 250                 255

Arg Leu Gly Trp Arg Ala Leu Gln Leu Lys Arg Ala Gly Glu Leu Tyr
                260                 265                 270

Trp Val Gly Phe Glu Thr Pro Glu Gly Ser Arg Trp Val Ala Ala Arg
                275                 280                 285

Gln Val Val Leu Ala Leu Pro Ala Tyr Glu Ala Ala Ala Leu Leu Gln
        290                 295                 300

Glu Leu Asn Pro Pro Ala Ser Gln Leu Leu Ala Glu Ile Leu Tyr Pro
305                 310                 315                 320

Pro Val Ala Val Val Ala Leu Ala Tyr Pro Gln Glu Ala Leu Pro Gln
                325                 330                 335

Pro Leu Arg Gly Phe Gly His Leu Ile Pro Arg Ser Gln Gly Leu Arg
                340                 345                 350

Thr Leu Gly Thr Ile Trp Ala Ser Cys Leu Phe Pro Glu Arg Ala Pro
                355                 360                 365

Gln Gly Tyr His Ser Phe Leu Ser Phe Leu Gly Gly Ala Thr Asp Ala
        370                 375                 380

Ala Leu Ala Arg Arg Arg Gly Ile Pro Pro Ile Pro Ala Leu Ser Pro
385                 390                 395                 400

Glu Glu Arg Ala Gln Ile Ala His Ala Glu Leu Ser Gln Val Leu Leu
                405                 410                 415

Thr Arg Arg Ala Glu Pro Val Tyr Leu Gly Glu Arg Leu Trp Pro Arg
                420                 425                 430

Ala Ile Pro Gln Tyr Thr Leu Gly His Arg Gln Arg Ile Ala Gln Val
        435                 440                 445

Gln Ala His Leu Ala Ser Gln Thr Pro Gly Ile Trp Val Cys Ala Asn
        450                 455                 460

Tyr Leu Asp Gly Val Ala Leu Gly Asp Cys Val Arg Arg Ala Glu Ala
465                 470                 475                 480

Leu Ala Gln Gln Leu Phe Ser Gln Val
                485
```

```
<210> SEQ ID NO 36
<211> LENGTH: 485
<212> TYPE: PRT
<213> ORGANISM: Artificial Sequence
<220> FEATURE:
<223> OTHER INFORMATION: Synthetic_PPO of Cyanobacteria bacterium J007
      (RMH78328.1)

<400> SEQUENCE: 36

Met Ser Glu Pro Ala Asn Pro Ser Thr Leu Leu Asp Thr Leu Val Val
1               5                   10                  15

Gly Ala Gly Ile Thr Gly Leu Thr Leu Ala Phe Asp Leu Gln Gln Lys
                20                  25                  30

Ser Ser Gly Thr Ala His Ser Ala Lys Val Leu Val Ala Glu Ser Gln
        35                  40                  45
```

```
Ala Arg Val Gly Gly Arg Ile Val Thr Ala Ser Gly Asp Gly Phe Leu
    50                  55                  60

Trp Glu Glu Gly Pro Asn Ser Phe Ala Pro Thr Pro Glu Leu Leu Gln
65                  70                  75                  80

Leu Ala Val Glu Val Gly Leu Lys Asp Lys Leu Val Phe Ala Asp Gly
                85                  90                  95

Lys Leu Pro Arg Phe Val Tyr Trp Gln Gly Glu Leu Met Pro Val Pro
                100                 105                 110

Met Ser Pro Pro Ala Ile Ile Ser Ser Lys Leu Leu Thr Trp Arg Gly
                115                 120                 125

Lys Leu Arg Ala Phe Phe Gly Ala Leu Gly Phe Val Pro Pro Ala Met
    130                 135                 140

Ala Asp Val Gly Ser Glu Glu Thr Val Ala Ser Phe Phe Glu Arg His
145                 150                 155                 160

Leu Gly Arg Glu Val Leu Gln Arg Leu Val Glu Pro Phe Val Ser Gly
                165                 170                 175

Val Tyr Ala Gly Asp Pro Arg Gln Leu Ser Ala Arg Ala Ala Phe Gly
                180                 185                 190

Arg Val Ala Arg Met Ala Glu Ala Gly Gly Gly Leu Val Ala Gly Ala
                195                 200                 205

Val Arg Thr Ser Arg Gln Lys Pro Lys Thr Lys Val Thr Pro Asp Pro
    210                 215                 220

Asn Val Pro Gln Pro Lys Arg Gly Gln Leu Gly Ser Phe Arg Gln Gly
225                 230                 235                 240

Leu Ala Thr Leu Pro Glu Ala Ile Ala Asp Arg Leu Gly Asp Ala Val
                245                 250                 255

Gln Leu Asn Trp His Leu Ile Arg Val Arg Pro Thr Glu Arg His Thr
                260                 265                 270

Tyr Ile Ala Glu Phe Ser Thr Pro Asp Gly Pro Lys Arg Val Glu Ala
                275                 280                 285

Arg Ser Val Val Leu Thr Thr Pro Thr Tyr Val Thr Ala Asp Leu Phe
    290                 295                 300

Asp Pro Leu His Gly Glu Ile Ala Arg Ala Leu Arg Gly Phe Val Tyr
305                 310                 315                 320

Pro Ser Val Ala Cys Val Val Leu Gly Tyr Pro Thr Ser Ala Leu Lys
                325                 330                 335

Arg Pro Leu Asn Gly Phe Gly Asn Leu Ile Pro Arg Asn Gln Gly Ile
                340                 345                 350

Arg Thr Leu Gly Thr Ile Trp Ser Ser Ser Leu Phe Ser Gly Arg Ala
                355                 360                 365

Pro Glu Gly Trp Asn Leu Leu Ile Asn Phe Ile Gly Gly Thr Gly Asp
    370                 375                 380

Pro Ala Ile Ala Glu Leu Glu Lys Asp Glu Ile Val Arg Val Val His
385                 390                 395                 400

Arg Asp Leu Leu Lys Thr Leu Leu Ala Arg Asp Val Asp Pro Lys Val
                405                 410                 415

Leu Ala Val His Leu Trp Lys Arg Ala Ile Pro Gln Tyr Cys Leu Gly
                420                 425                 430

His His Gln Arg Trp Glu Gln Ile Asp Arg Gly Leu Gln Glu Phe Pro
                435                 440                 445

Gly Leu Tyr Leu Cys Gly Asn Tyr Ser Asp Gly Val Ala Val Gly Asp
    450                 455                 460

Cys Val Arg Arg Ala Arg Asp Arg Ala Ala Glu Ile Arg Gln Tyr Leu
```

```
         465              470              475              480
Ala Ser Ala Thr Val
                485

<210> SEQ ID NO 37
<211> LENGTH: 468
<212> TYPE: PRT
<213> ORGANISM: Artificial Sequence
<220> FEATURE:
<223> OTHER INFORMATION: Synthetic_PPO of Spirulina major
      (WP_072619201.1)

<400> SEQUENCE: 37

Met Leu Asp Ser Leu Ile Val Gly Ala Gly Leu Ser Gly Leu Thr Val
1               5                   10                  15

Ala His Thr Leu Gln Gln Arg Asp Arg Asn Ile Leu Val Ala Glu Ala
                20                  25                  30

Ser Pro Asp Val Gly Gly Asn Ile Ile Ser Arg Gln Gln Gly Glu Phe
            35                  40                  45

Leu Trp Glu Glu Gly Pro Asn Ser Phe Gln Pro Asn Pro Thr Leu Leu
        50                  55                  60

Lys Leu Ala Val Asp Val Gly Leu Lys Asp Asp Leu Val Phe Ala Asp
65                  70                  75                  80

Arg Lys Leu Pro Arg Trp Val Tyr Trp Gln Gly Arg Leu Leu Ala Val
                85                  90                  95

Pro Met Ser Pro Gly Thr Ala Val Arg Ser Pro Leu Leu Ser Val Pro
                100                 105                 110

Gly Lys Leu Arg Ala Leu Phe Gly Ala Leu Gly Phe Val Pro Pro Leu
            115                 120                 125

Val Gly Ser His Ile Gln Ala Gln Gly Gly Asp Glu Thr Ile Trp Gln
            130                 135                 140

Phe Ile Asn Arg His Leu Gly Pro Glu Val Ala Glu Arg Leu Ile Ser
145                 150                 155                 160

Pro Phe Val Ser Gly Val Tyr Ala Gly Asp Val His Ala Leu Ser Met
                165                 170                 175

Ala Ala Ala Phe Arg Lys Ile Tyr Arg Leu Glu Thr Leu Gly Gly Gly
            180                 185                 190

Leu Val Ala Gly Ala Met Arg Ser Arg Gln Gly Lys Ala Asp Arg
            195                 200                 205

Pro Ala Val Asp Pro Asn Leu Pro Thr Thr Lys Pro Gly Gln Leu Gly
            210                 215                 220

Ser Phe Arg Glu Gly Met Val Met Leu Pro Asn Ala Ile Ala Ala Arg
225                 230                 235                 240

Leu Gly Asp Arg Leu Arg Cys Arg Trp Thr Leu Thr Gln Ile Glu Pro
                245                 250                 255

Leu Glu Gln Gly Tyr Arg Ala His Phe Asp Thr Pro Asp Gly Gly Gln
            260                 265                 270

Thr Ile Glu Thr Arg Thr Leu Val Leu Ala Ile Pro Ala His Arg Val
            275                 280                 285

Ala Pro Leu Leu Ala Pro Leu Met Pro Glu Leu Ser Thr Thr Leu Gln
    290                 295                 300

Ala Ile Pro Tyr Pro Ala Val Ala Cys Thr Val Met Ala Tyr Pro Lys
305                 310                 315                 320

Thr Ala Leu Val Arg Ser Leu His Gly Phe Gly Asn Leu Asn Pro Arg
                325                 330                 335
```

```
Ser Gln Gly Ile Arg Thr Leu Gly Thr Ile Trp Ser Ser Thr Leu Phe
        340             345             350

Pro Gly Arg Ala Pro Glu Gly Trp Val Met Leu Ser Ser Phe Ile Gly
        355             360             365

Gly Ser Thr Asp Pro Ala Val Ala Thr Met Asp Glu Gly Ala Ile Ala
    370             375             380

Gln Ala Val His Gln Asp Leu Ser Asn Ile Leu Val Lys Pro Asp Ser
385             390             395             400

Thr Pro Lys Val Leu Ala Val Lys Leu Trp Ser Lys Ala Ile Pro Gln
                405             410             415

Tyr Thr Leu Gly His Cys Asp Arg Leu Ser Val Met Ala Glu His Leu
        420             425             430

Lys Ala His Pro His Leu Thr Leu Cys Ser Asn Tyr Thr Asp Gly Val
        435             440             445

Ala Leu Gly Asp Cys Ile Arg Arg Gly Ile Glu Ala Gly Glu Ala Ile
    450             455             460

Asp Gln Gln Leu
465
```

<210> SEQ ID NO 38
<211> LENGTH: 463
<212> TYPE: PRT
<213> ORGANISM: Artificial Sequence
<220> FEATURE:
<223> OTHER INFORMATION: Synthetic_PPO of Euhalothece sp. KZN 001
       (PNW65677.1)

<400> SEQUENCE: 38

```
Met Val Glu Thr Leu Ile Val Gly Ala Gly Ile Ser Gly Leu Thr Thr
1               5               10              15

Ala Tyr Arg Leu His Glu Gln Gln His Glu Val Met Val Ala Glu Lys
        20              25              30

Asn Asp Arg Ala Gly Gly Asn Ile Thr Ser Lys Ala Ser Gly Gly Phe
        35              40              45

Leu Trp Glu Glu Gly Pro Asn Ser Phe Ser Pro Thr Pro Glu Leu Leu
    50              55              60

Lys Leu Ala Val Asp Val Gly Leu Lys Asp Glu Phe Val Phe Ala Asp
65              70              75              80

Pro Thr Leu Pro Arg Tyr Val Tyr Trp Gln Gly Lys Leu Leu Pro Val
                85              90              95

Pro Met Ser Pro Pro Ser Ala Val Lys Ser Gln Leu Leu Ser Pro Leu
        100             105             110

Gly Lys Leu Arg Ala Leu Thr Gly Ala Ile Gly Phe Val Pro Pro Lys
        115             120             125

Val Ala Thr Glu Glu Glu Thr Val Ala Glu Phe Phe Thr Arg His Leu
        130             135             140

Gly Ser Glu Val Ala Gln Arg Leu Val Ser Pro Phe Val Ser Gly Val
145             150             155             160

Tyr Ala Gly Asp Val Ala Asn Leu Ser Ala Ser Ala Ala Phe Gly Arg
                165             170             175

Val Thr Gln Leu Ala Asp Val Gly Gly Gly Leu Val Ala Gly Ala Ile
        180             185             190

Leu Ser Arg Gly Lys Lys Lys Ala Thr Thr Glu Val Asp Pro Glu
        195             200             205

Ile Pro Lys Thr Arg Ser Gly Glu Leu Gly Ser Phe Arg Glu Gly Leu
    210             215             220
```

```
Gln Gln Leu Pro Ser Ser Ile Ala Arg Lys Leu Gly Glu Ala Val Lys
225                 230                 235                 240

Phe Asn Trp Glu Leu Lys Gln Ile Ser Gln Thr Ser Glu Ala Gly Tyr
                245                 250                 255

Ile Ala Thr Phe Ser Thr Pro Glu Gly Glu Gln Asn Val Glu Ala Gln
                260                 265                 270

Gln Ile Ile Leu Thr Thr Pro Ala Tyr Val Ser Ala Pro Ile Leu Gln
                275                 280                 285

Asp Leu Ser Pro Glu Ala Ser Gln Ala Leu Arg Glu Ile Tyr Tyr Pro
        290                 295                 300

Pro Val Ala Cys Val Val Leu Ala Tyr Pro Asp Glu Ala Phe Ser Val
305                 310                 315                 320

Pro Leu Asp Gly Phe Gly Asn Leu Asn Pro Arg Ser Glu Gly Val Arg
                325                 330                 335

Thr Leu Gly Thr Ile Trp Ser Ser Thr Leu Phe Ser Gly Arg Thr Pro
                340                 345                 350

Gln Gly Trp Gln Ile Leu Thr Asn Phe Ile Gly Gly Ala Thr Asp Pro
                355                 360                 365

Glu Ile Ala Gln Leu Ser Glu Glu Glu Ile Val Gln Gln Val His Gln
        370                 375                 380

Asp Leu Gln Lys Thr Ile Val Lys Pro Asn Thr Thr Pro Lys Pro Leu
385                 390                 395                 400

Ala Val His Leu Trp Ser Gln Ala Ile Pro Gln Tyr Thr Leu Gly His
                405                 410                 415

Leu Asp Arg Ile Ala Arg Ile Lys Glu Ser Leu Lys Pro Phe Ser Gly
                420                 425                 430

Leu Phe Leu Ser Ser Asn Tyr Leu Asp Gly Val Ala Leu Gly Asp Cys
                435                 440                 445

Val Arg Arg Gly Glu Glu Thr Ala Ala Gln Ile Leu Asn Lys Lys
        450                 455                 460
```

```
<210> SEQ ID NO 39
<211> LENGTH: 461
<212> TYPE: PRT
<213> ORGANISM: Artificial Sequence
<220> FEATURE:
<223> OTHER INFORMATION: Synthetic_PPO of Dactylococcopsis salina
      (WP_015230904.1)

<400> SEQUENCE: 39
```

```
Met Val Glu Thr Leu Ile Val Gly Ala Gly Ile Ser Gly Leu Thr Thr
1               5                   10                  15

Ala Tyr Arg Leu His Glu Gln Gln His Glu Val Met Val Ala Glu Lys
                20                  25                  30

Asn Asp Arg Ala Gly Gly Asn Ile Thr Ser Lys Ala Ser Gly Gly Phe
        35                  40                  45

Leu Trp Glu Glu Gly Pro Asn Ser Phe Ser Pro Thr Pro Glu Leu Leu
        50                  55                  60

Lys Leu Ala Val Asp Val Gly Leu Lys Asp Glu Phe Val Phe Ala Asp
65                  70                  75                  80

Pro Thr Leu Pro Arg Tyr Val Tyr Trp Gln Gly Lys Leu Leu Pro Val
                85                  90                  95

Pro Met Ser Pro Pro Ala Ala Val Lys Ser Gln Leu Leu Ser Pro Leu
                100                 105                 110

Gly Lys Leu Arg Ala Leu Thr Gly Ala Ile Gly Phe Val Pro Pro Lys
```

-continued

```
          115                 120                 125

Val Ala Thr Glu Glu Glu Thr Val Ala Glu Phe Phe Thr Arg His Leu
    130                 135                 140

Gly Ser Glu Val Ala Gln Arg Leu Val Ser Pro Phe Val Ser Gly Val
145                 150                 155                 160

Tyr Ala Gly Asp Val Ala Asn Leu Ser Ala Ser Ala Ala Phe Ala Arg
                165                 170                 175

Val Thr Gln Leu Ala Asp Val Gly Gly Gly Leu Val Ala Gly Ala Ile
            180                 185                 190

Leu Ser Arg Gly Lys Lys Lys Lys Ala Thr Thr Glu Val Asn Ser Glu
            195                 200                 205

Ile Pro Lys Thr Arg Ser Gly Glu Leu Gly Ser Phe Arg Glu Gly Leu
    210                 215                 220

Gln Gln Leu Pro Ser Ser Ile Ala Arg Lys Leu Gly Glu Ala Val Lys
225                 230                 235                 240

Phe Asn Trp Glu Leu Lys Gln Ile Ser Gln Thr Ser Glu Ala Gly Tyr
                245                 250                 255

Ile Ala Thr Phe Ser Thr Pro Glu Gly Glu Gln Asn Val Glu Ala Gln
                260                 265                 270

Gln Ile Ile Leu Thr Thr Pro Ala Tyr Val Asn Ala Pro Ile Leu Gln
    275                 280                 285

Asp Leu Ser Pro Glu Ala Ser Gln Ala Leu Arg Glu Ile Asp Tyr Pro
    290                 295                 300

Pro Val Ala Cys Val Val Leu Ala Tyr Pro Asp Glu Ala Phe Ser Val
305                 310                 315                 320

Pro Leu Asp Gly Phe Gly Asn Leu Asn Pro Arg Ser Glu Gly Val Arg
                325                 330                 335

Thr Leu Gly Thr Ile Trp Ser Ser Thr Leu Phe Ser Gly Arg Thr Pro
            340                 345                 350

Gln Gly Trp Gln Ile Leu Thr Asn Phe Ile Gly Gly Ala Thr Asp Pro
            355                 360                 365

Glu Ile Ala Gln Leu Ser Glu Glu Glu Ile Val Gln Gln Val His Gln
    370                 375                 380

Asp Leu Gln Lys Thr Ile Val Lys Pro Asn Thr Thr Pro Lys Pro Leu
385                 390                 395                 400

Ala Val His Leu Trp Ser Gln Ala Ile Pro Gln Tyr Thr Leu Gly His
                405                 410                 415

Leu Asp Arg Ile Ala Arg Ile Lys Glu Ser Leu Lys Pro Phe Ser Gly
            420                 425                 430

Leu Phe Leu Ser Ser Asn Tyr Leu Asp Gly Val Ala Leu Gly Asp Cys
            435                 440                 445

Val Arg Arg Gly Glu Glu Thr Ala Ala Gln Ile Leu Arg
    450                 455                 460
```

<210> SEQ ID NO 40
<211> LENGTH: 467
<212> TYPE: PRT
<213> ORGANISM: Artificial Sequence
<220> FEATURE:
<223> OTHER INFORMATION: Synthetic_PPO of Synechococcus sp. PCC 7336
      (WP_017328280.1)

<400> SEQUENCE: 40

```
Met Gly Ser His Thr Pro Asp Ile Leu Ile Leu Gly Ala Gly Ile Ser
1               5                   10                  15
```

-continued

```
Gly Leu Ser Ala Ala Phe Arg Leu His Gln Gln Gln Gln Asp Leu Leu
            20                  25                  30

Val Ala Glu Arg Ala Glu Arg Val Gly Gly Val Ile Thr Thr Arg Ala
            35                  40                  45

Gln Asp Gly Phe Arg Trp Glu Glu Gly Pro Asn Ser Phe Thr Pro Ser
    50                  55                  60

Pro Ala Leu Leu Asn Leu Ile Ala Asp Ala Gly Ile Ala Asp Arg Leu
65                  70                  75                  80

Leu Trp Ala Asp Gly Lys Leu Pro Arg Phe Val Tyr Leu Glu Gly Lys
                85                  90                  95

Leu Thr Leu Val Pro Met Thr Pro Pro Asp Leu Ile Lys Ser Asn Leu
            100                 105                 110

Leu Ser Phe Gly Ala Lys Leu Arg Ala Leu Leu Gly Ile Leu Gly Phe
            115                 120                 125

Thr Ala Lys Ala Pro Asp Lys Glu Glu Thr Val Glu Glu Phe Phe Ala
    130                 135                 140

Arg Gln Leu Gly Pro Gln Val Val Glu Arg Leu Val Gly Pro Phe Thr
145                 150                 155                 160

Ser Gly Val Tyr Ala Gly Asp Thr Gln Gln Leu Ser Ala Thr Ala Ala
                165                 170                 175

Phe Ser Lys Val Ala Asp Leu Glu Arg Lys Tyr Gly Ser Ile Ile Ala
            180                 185                 190

Gly Ile Ile Arg Ser Pro Lys Ser Pro Lys Pro Ile Ser Ala Lys
            195                 200                 205

Ile Asp Pro Leu Pro Lys Arg Gly Gln Leu Gly Asn Phe Val Glu Gly
    210                 215                 220

Leu Gln Glu Leu Pro Asp Ala Ile Ala Gln Gln Leu Gly Asp Ala Val
225                 230                 235                 240

Lys Leu Gln Trp Glu Ala Ala Glu Ile Val Lys Glu Gly Asp Arg Tyr
                245                 250                 255

Arg Thr Thr Phe Gln Thr Pro Ser Gly Pro Gln Thr Val Ser Ser Lys
            260                 265                 270

Ala Ile Leu Leu Ala Val Pro Ala Tyr Arg Ala Ala Pro Leu Leu Lys
            275                 280                 285

Ser Leu Asp Thr Ala Leu Ala Asp Glu Leu Ala Ala Ile Pro Tyr Pro
    290                 295                 300

His Val Gly Ala Val Thr Leu Ala Tyr Pro Ala Asp Ala Leu Pro Gln
305                 310                 315                 320

Pro Phe Ala Gly Phe Gly Gln Leu Phe Pro Arg Gly Gln Gly Ile Arg
            325                 330                 335

Thr Leu Gly Thr Ile Trp Thr Ser Ser Leu Phe Pro Gly Arg Ala Pro
            340                 345                 350

Ala Gly Tyr Gln Cys Thr Leu Ser Tyr Ile Gly Gly Ala Thr Asp Pro
            355                 360                 365

Asp Ile Ala Gln Met Thr Asp Glu Ala Leu Ala Arg Thr Val His Gln
    370                 375                 380

Asp Leu Ser Lys Thr Leu Leu Val Lys Glu Ala Glu Pro Arg Val Met
385                 390                 395                 400

Gly Val Arg Arg Trp Pro Arg Ala Ile Pro Gln Tyr Thr Leu Gly His
                405                 410                 415

Arg Gln Arg Leu Ala Arg Ile Asp Glu Leu Leu Ala Asp Tyr Ser Gly
            420                 425                 430

Leu Val Leu Cys Thr Asn Tyr Leu Asp Gly Val Ala Leu Gly Asp Cys
```

-continued

```
          435                440                445

Val Arg Arg Gly Glu Ala Arg Ala Ala Asp Leu Val Glu Trp Leu Ala
    450                455                460

Gln Ala Glu
465
```

```
<210> SEQ ID NO 41
<211> LENGTH: 484
<212> TYPE: PRT
<213> ORGANISM: Artificial Sequence
<220> FEATURE:
<223> OTHER INFORMATION: Synthetic_PPO of Arthrospira sp. O9.13F
      (WP_111891435)
<220> FEATURE:
<221> NAME/KEY: VARIANT
<222> LOCATION: (444)
<223> OTHER INFORMATION: Xaa at position 444 is any naturally-occurring
      amino acid

<400> SEQUENCE: 41

Met Thr Asn Leu Val Asp Ser Leu Ile Val Gly Ala Gly Ile Ser Gly
1               5                  10                 15

Leu Ser Leu Ala Tyr Ser Leu Asn Arg Glu Lys Ser Val Arg Glu Pro
            20                 25                 30

Leu Lys Val Leu Val Thr Glu Ser Gln Asn Arg Val Gly Gly Asn Ile
        35                 40                 45

Thr Thr Gly Arg Ala Asp Asp Phe Leu Trp Glu Glu Gly Pro Asn Ser
    50                 55                 60

Phe Ala Pro Thr Pro Glu Leu Leu Gly Leu Ala Val Asp Leu Gly Leu
65                 70                 75                 80

Lys Glu Glu Leu Ile Phe Ala Asp Arg Lys Leu Pro Arg Tyr Val Tyr
                85                 90                 95

Trp Asn Leu Met Leu His Pro Val Pro Met Asn Pro Pro Ala Leu Leu
            100                105                110

Ser Ser Glu Leu Ile Ser Ala Arg Gly Lys Leu Arg Ala Ala Leu Gly
            115                120                125

Ala Ile Gly Phe Val Pro Pro Pro Val Gly Ala His Leu Ser Gln Gln
    130                135                140

Gly Gly Glu Glu Thr Ile Thr Gln Phe Phe Asp Arg His Leu Gly Ser
145                150                155                160

Glu Val Leu Glu Arg Leu Val Gln Pro Phe Val Ser Gly Val Tyr Ala
                165                170                175

Gly Asp Pro Gln Gln Leu Ala Val Arg Ser Ala Phe Ser Arg Ile Val
            180                185                190

Ala Ala Glu Glu Ala Gly Gly Gly Leu Leu Pro Gly Phe Val Arg Ser
            195                200                205

Arg Leu Asn Lys Lys Ala Pro Val Ser Thr Pro Asp Pro Asn Ile Pro
    210                215                220

Lys Thr Arg Pro Gly Glu Leu Gly Ser Phe Arg Tyr Gly Leu Gln Thr
225                230                235                240

Leu Pro Glu Thr Leu Ala Ser Lys Leu Gly Asp Arg Val Lys Leu Asn
                245                250                255

Trp Thr Ile Asp Arg Phe Tyr Pro Thr Asp His Gln Thr Tyr Ile Ala
            260                265                270

Glu Phe Ser Thr Pro Asp Gly Pro Gln Gln Val Glu Ala Arg Thr Leu
    275                280                285

Ala Leu Met Thr Pro Ala His Val Ser Ala Arg Leu Leu Gln Pro Leu
```

-continued

```
                 290                  295                  300

His Ser Pro Ile Ala Thr Ala Leu Ser Gln Ile Pro Tyr Pro Pro Val
305                  310                  315                  320

Ala Cys Val Val Leu Ala Tyr Pro Lys Ser Ala Leu Lys Gln Gln Leu
                 325                  330                  335

Lys Gly Phe Gly Asn Leu Ile Pro Arg Arg Gln Gly Ile Arg Thr Leu
                 340                  345                  350

Gly Thr Ile Trp Thr Ser Ser Leu Phe Pro Gly Arg Ala Pro Glu Ser
                 355                  360                  365

Trp Gln Val Leu Ser Asn Tyr Ile Gly Gly Ala Thr Asp Pro Glu Ile
                 370                  375                  380

Gly Glu Met Asp Asp Asp Gln Ile Val Ala Ala Val His Gln Asp Leu
385                  390                  395                  400

Arg Gln Ile Leu Leu Ala Glu Asp Val Pro Pro Lys Val Leu Ala Val
                 405                  410                  415

His Leu Trp Arg Arg Ala Ile Pro Gln Tyr Thr Leu Gly His Gln Asn
                 420                  425                  430

Arg Leu Asn Cys Ile Asp Ala Gly Leu Arg Ser Xaa Pro Gly Leu Tyr
                 435                  440                  445

Leu Cys Ser Asn Tyr Ile Asp Gly Val Ser Val Gly Asp Cys Val Arg
                 450                  455                  460

Arg Gly Gln Gln Trp Ala Ser Lys Ile Gln Ser His Leu His Asp Cys
465                  470                  475                  480

Gln Thr Ala Asn

<210> SEQ ID NO 42
<211> LENGTH: 484
<212> TYPE: PRT
<213> ORGANISM: Artificial Sequence
<220> FEATURE:
<223> OTHER INFORMATION: Synthetic_PPO of Arthrospira platensis
      (WP_006622155)

<400> SEQUENCE: 42

Met Thr Asn Leu Val Asp Ser Leu Ile Val Gly Ala Gly Ile Ser Gly
1                5                   10                   15

Leu Ser Leu Ala Tyr Ser Leu Asn Arg Glu Lys Ser Val Arg Glu Pro
                 20                  25                   30

Leu Lys Val Leu Val Thr Glu Ser Gln Asn Arg Val Gly Gly Asn Ile
                 35                  40                   45

Thr Thr Gly Arg Ala Asp Asp Phe Leu Trp Glu Glu Gly Pro Asn Ser
                 50                  55                   60

Phe Ala Pro Thr Pro Glu Leu Leu Gly Leu Ala Val Asp Leu Gly Leu
65                   70                  75                   80

Lys Glu Glu Leu Ile Phe Ala Asp Arg Lys Leu Pro Arg Tyr Val Tyr
                 85                  90                   95

Trp Asn Leu Met Leu His Pro Val Pro Met Asn Pro Pro Ala Leu Leu
                 100                 105                  110

Ser Ser Glu Leu Ile Ser Ala Arg Gly Lys Leu Arg Ala Ala Leu Gly
                 115                 120                  125

Ala Ile Gly Phe Val Pro Pro Val Gly Ala His Leu Ser Gln Gln
                 130                 135                  140

Gly Gly Glu Glu Thr Ile Thr Gln Phe Phe Asp Arg His Leu Gly Ser
145                  150                 155                  160

Glu Val Leu Glu Arg Leu Val Gln Pro Phe Val Ser Gly Val Tyr Ala
```

-continued

```
                165              170              175

Gly Asp Pro Gln Gln Leu Ala Val Arg Ser Ala Phe Ser Arg Ile Val
            180              185              190

Ala Ala Glu Glu Ala Gly Gly Gly Leu Leu Pro Gly Phe Val Arg Ser
            195              200              205

Arg Leu Asn Lys Lys Ala Pro Val Ser Thr Pro Asp Pro Asn Ile Pro
    210              215              220

Lys Thr Arg Pro Gly Glu Leu Gly Ser Phe Arg Tyr Gly Leu Gln Thr
225              230              235              240

Leu Pro Glu Thr Leu Ala Ser Lys Leu Gly Asp Arg Val Lys Leu Asn
            245              250              255

Trp Thr Ile Asp Arg Phe Tyr Pro Thr Asp His Gln Thr Tyr Ile Ala
            260              265              270

Glu Phe Ser Thr Pro Asp Gly Pro Gln Gln Val Glu Ala Arg Thr Leu
            275              280              285

Ala Leu Met Thr Pro Ala His Val Ser Ala Arg Leu Leu Gln Pro Leu
    290              295              300

His Ser Pro Ile Ala Thr Ala Leu Ser Gln Ile Pro Tyr Pro Pro Val
305              310              315              320

Ala Cys Val Val Leu Ala Tyr Pro Lys Ser Ala Leu Lys Gln Gln Leu
            325              330              335

Lys Gly Phe Gly Asn Leu Ile Pro Arg His Gln Gly Ile Arg Thr Leu
            340              345              350

Gly Thr Ile Trp Thr Ser Ser Leu Phe Pro Gly Arg Ala Pro Glu Ser
            355              360              365

Trp Gln Val Leu Ser Asn Tyr Ile Gly Gly Ala Thr Asp Pro Glu Ile
    370              375              380

Gly Glu Met Asp Asp Asp Gln Ile Val Ala Ala Val His Gln Asp Leu
385              390              395              400

Arg Gln Ile Leu Leu Ala Glu Asp Val Pro Pro Lys Val Leu Ala Val
            405              410              415

His Leu Trp Arg Arg Ala Ile Pro Gln Tyr Thr Leu Gly His Gln Asn
            420              425              430

Arg Leu Asn Cys Ile Asp Ala Gly Leu Arg Ser Leu Pro Gly Leu Tyr
            435              440              445

Leu Cys Ser Asn Tyr Ile Asp Gly Val Ser Val Gly Asp Cys Val Arg
    450              455              460

Arg Gly Gln Gln Trp Ala Ser Lys Ile Gln Ser His Leu His Asp Cys
465              470              475              480

Gln Thr Ala Asn
```

```
<210> SEQ ID NO 43
<211> LENGTH: 483
<212> TYPE: PRT
<213> ORGANISM: Artificial Sequence
<220> FEATURE:
<223> OTHER INFORMATION: Synthetic_PPO of Arthrospira platensis
      (WP_006617829)

<400> SEQUENCE: 43

Met Thr Asn Leu Val Asp Ser Leu Ile Val Gly Ala Gly Ile Ser Gly
1               5               10              15

Leu Ser Leu Ala His Ser Leu Asn Arg Glu Lys Asn Pro Arg Ser Pro
            20              25              30

Leu Lys Val Leu Val Thr Glu Ser Gln Asn Arg Val Gly Gly Asn Ile
```

```
          35                    40                    45

Thr Thr Gly Arg Ala Ser Asp Phe Leu Trp Glu Glu Gly Pro Asn Ser
    50                    55                    60

Phe Ala Pro Thr Pro Glu Leu Leu Gly Leu Ala Val Asp Leu Gly Leu
65                    70                    75                    80

Lys Gln Glu Leu Ile Phe Ala Asp Arg Lys Leu Pro Arg Tyr Val Tyr
                85                    90                    95

Trp Asn His Lys Leu His Pro Val Pro Met Thr Pro Pro Ala Leu Leu
            100                   105                   110

Ser Ser Gln Leu Ile Ser Pro Arg Gly Lys Leu Arg Ala Ala Leu Gly
            115                   120                   125

Ala Ile Gly Phe Val Pro Pro Pro Val Gly Ala His Leu Ser Gln Gln
    130                   135                   140

Arg Gly Glu Glu Thr Ile Thr Gln Phe Phe His Arg His Leu Gly Ser
145                   150                   155                   160

Glu Val Leu Glu Arg Leu Val Gln Pro Phe Val Ser Gly Val Tyr Ala
            165                   170                   175

Gly Asp Pro Gln Gln Leu Ala Val Arg Ser Ala Phe Ser Arg Leu Val
            180                   185                   190

Ala Ala Glu Asp Ala Gly Gly Ala Leu Leu Pro Gly Phe Val Arg Ser
            195                   200                   205

Arg Leu Asn Lys Lys Ala Thr Lys Asp Thr Thr Ala Asp Pro Asn Ile
    210                   215                   220

Pro Lys Thr Arg Pro Gly Glu Leu Gly Ser Phe Arg Tyr Gly Leu Glu
225                   230                   235                   240

Thr Leu Pro Glu Thr Leu Ala Ser Lys Leu Gly Asp Arg Val Lys Leu
            245                   250                   255

Asn Trp Thr Leu Asp Arg Phe Tyr Pro Thr Asp His Gln Thr Tyr Ile
            260                   265                   270

Ala Glu Phe Ser Thr Pro Asp Gly Pro Gln Gln Val Glu Thr Arg Thr
            275                   280                   285

Leu Ala Leu Met Thr Pro Ala His Val Ser Ala Arg Leu Leu Gln Pro
    290                   295                   300

Leu His Ser Gln Ile Ala Ser Ala Leu Ser Gln Ile Pro Tyr Pro Pro
305                   310                   315                   320

Val Ala Cys Val Val Leu Ala Tyr Pro Lys Ser Ala Leu Lys Gln Gln
            325                   330                   335

Leu Lys Gly Phe Gly Asn Leu Ile Pro Arg His Gln Gly Ile Arg Thr
            340                   345                   350

Leu Gly Thr Ile Trp Thr Ser Ser Leu Phe Pro Gly Arg Ala Pro Glu
            355                   360                   365

Ser Trp Gln Val Leu Ser Asn Tyr Ile Gly Gly Ala Thr Asp Pro Glu
    370                   375                   380

Ile Gly Glu Met Asp Asp Asp Gln Ile Val Ala Ala Val His Gln Asp
385                   390                   395                   400

Leu Arg Gln Ile Leu Leu Ala Glu Asp Val Pro Pro Lys Val Leu Ala
            405                   410                   415

Val His Leu Trp Arg Arg Ala Ile Pro Gln Tyr Thr Leu Gly His Gln
            420                   425                   430

Asp Arg Leu Asn Ser Ile Asn Ala Gly Leu Arg Ser Leu Pro Gly Leu
            435                   440                   445

Tyr Leu Cys Ser Asn Tyr Ile Asp Gly Val Ser Val Gly Asp Cys Val
    450                   455                   460
```

Arg Arg Gly Gln Gln Trp Ala Ser Gln Ile Gln Ser His Leu His Pro
465                 470                 475                 480

Thr Ala Asn

<210> SEQ ID NO 44
<211> LENGTH: 478
<212> TYPE: PRT
<213> ORGANISM: Artificial Sequence
<220> FEATURE:
<223> OTHER INFORMATION: Synthetic_PPO of Pseudanabaena sp. BC1403
      (WP_103669271.1)

<400> SEQUENCE: 44

Met Thr Ile Thr Pro Pro Ser Glu Asn Asn Gln Pro Ile Asp Val Leu
1               5                   10                  15

Val Val Gly Ala Gly Ile Ser Gly Leu Thr Ile Ala His Glu Leu Ala
                20                  25                  30

Ile Ser Lys Lys Tyr Ser Val Leu Val Ala Glu Ala Gln Asp Arg Val
            35                  40                  45

Gly Gly Ala Ile Thr Ser Ala Lys Asn Asp Glu Gly Tyr Gln Trp Glu
        50                  55                  60

Glu Gly Pro Asn Ser Phe Gln Pro Ala Pro Glu Leu Leu Arg Leu Ala
65                  70                  75                  80

Val Gln Val Gly Leu Lys Asp Glu Leu Val Leu Ala Asp Gly Lys Leu
                85                  90                  95

Pro Arg Phe Val Phe Leu Asn Gly Lys Leu Asn Ala Leu Pro Met Thr
                100                 105                 110

Pro Ala Ser Ala Ile Ala Ser Lys Ile Leu Thr Trp Gly Gly Lys Ile
            115                 120                 125

Arg Leu Ala Leu Gly Ala Ile Gly Phe Ala Arg Pro Ala Met Ala Gly
            130                 135                 140

Glu Glu Ser Val Asp Gln Phe Phe Ser Arg Leu Leu Gly Arg Gln Ala
145                 150                 155                 160

Val Glu Arg Leu Val Ala Pro Phe Ile Ser Gly Val Tyr Ala Gly Asp
                165                 170                 175

Pro Lys Arg Leu Ser Ala Lys Ala Ala Phe Ser Lys Ile Ala Arg Leu
            180                 185                 190

Glu Thr Tyr Gly Gly Leu Ile Ala Gly Ala Ile Leu Ser Ser Lys Gln
            195                 200                 205

Arg Lys Ala Glu Lys Ile Asn Asp Pro Asn Ile Pro Lys Thr Lys Ala
        210                 215                 220

Gly Glu Leu Gly Ser Phe Arg Gln Gly Ile Lys Met Leu Pro Glu Ala
225                 230                 235                 240

Ile Ala Thr Lys Leu Arg Glu Gln Gly Ser Ala Ile Lys Gln Gln Trp
                245                 250                 255

Thr Leu Arg Ser Leu Glu Lys Gln Gly Glu Val Tyr Ile Ser Lys Phe
            260                 265                 270

Asp Thr Pro Thr Gly Glu Glu Thr Val Thr Ser Arg Ser Ile Val Leu
            275                 280                 285

Ala Thr Pro Ala Tyr Val Thr Ala Lys Leu Leu Gln Asp Tyr Leu Pro
        290                 295                 300

Ala Ala Ser Gln Ala Leu Asn Glu Ile Phe Tyr Pro Thr Val Ala Cys
305                 310                 315                 320

Val Val Leu Ala Tyr Pro Lys Ser Glu Phe Ala Tyr Asp Met Lys Gly
                325                 330                 335

-continued

```
Phe Gly Asn Leu Ile Pro Arg Thr Gln Gly Val Arg Thr Leu Gly Thr
        340                 345                 350

Ile Trp Ser Ser Ser Leu Phe Thr Gly Arg Ala Pro Glu Gly Trp Gln
        355                 360                 365

Leu Leu Leu Asn Phe Ile Gly Gly Thr Leu Asp Pro Ala Leu Ala Lys
        370                 375                 380

Leu Ser Glu Pro Glu Ile Ile Ala Ala Val His Gln Asp Leu Lys Lys
385                 390                 395                 400

Thr Ile Leu Arg Pro Asp Thr Lys Ala Glu Pro Lys Ala Ile Ala Val
                405                 410                 415

His Val Trp Asp Lys Ala Ile Pro Gln Tyr Glu Ile Gly His Leu Glu
                420                 425                 430

Arg Leu Ala Ile Val Glu Ala Glu Leu Gln Lys Ser Gln Gly Leu Tyr
                435                 440                 445

Val Ser Ala Asn Phe Ile Gly Gly Val Ala Leu Gly Asp Cys Ile Lys
        450                 455                 460

Arg Ser Leu Gln Glu Ala Asn Lys Ile Asp Ala Tyr Leu Lys
465                 470                 475
```

```
<210> SEQ ID NO 45
<211> LENGTH: 478
<212> TYPE: PRT
<213> ORGANISM: Artificial Sequence
<220> FEATURE:
<223> OTHER INFORMATION: Synthetic_PPO of Pseudanabaena sp. 'Roaring
      Creek' (WP_055076288)

<400> SEQUENCE: 45
```

```
Met Thr Ser Ala Gln Ile Pro Glu Val Asn Pro Leu Asp Val Leu Val
1                   5                   10                  15

Val Gly Ala Gly Ile Ser Gly Leu Thr Ile Ala His Glu Leu Ala Ile
                20                  25                  30

Ala Lys Asn Tyr Arg Val Leu Val Ala Glu Thr Gln Asp Arg Val Gly
        35                  40                  45

Gly Ala Ile Thr Ser Ala Lys Asn Asp Asp Gly Tyr Gln Trp Glu Glu
        50                  55                  60

Gly Pro Asn Ser Phe Gln Pro Ala Pro Glu Leu Leu Arg Leu Ala Val
65                  70                  75                  80

Glu Val Gly Leu Lys Asp Glu Leu Val Leu Ala Asp Gly Lys Leu Pro
                85                  90                  95

Arg Phe Val Phe Leu Asn Gly Lys Leu Asn Ala Leu Pro Met Ser Pro
                100                 105                 110

Pro Thr Ala Ile Ala Ser Arg Ile Leu Thr Trp Gly Gly Lys Ile Arg
        115                 120                 125

Leu Ala Leu Gly Ala Met Gly Phe Ala Arg Pro Ala Met Ala Gly Glu
        130                 135                 140

Glu Ser Val Asp Arg Phe Phe Ser Arg Leu Leu Gly Arg Gln Ala Val
145                 150                 155                 160

Asp Arg Leu Val Ala Pro Phe Ile Ser Gly Val Tyr Ala Gly Asp Pro
                165                 170                 175

Lys Arg Leu Ser Ala Lys Ala Ala Phe Ala Lys Ile Ala Lys Leu Glu
                180                 185                 190

Thr Tyr Gly Gly Leu Leu Ala Gly Ala Ile Leu Ser Ser Lys Glu Arg
        195                 200                 205

Lys Gln Lys Leu Asn Asp Pro Arg Ile Pro Lys Thr Lys Ala Gly Glu
```

-continued

```
        210                 215                 220

Leu Gly Ser Phe Arg Glu Gly Ile Lys Met Leu Pro Glu Ala Ile Ala
225                 230                 235                 240

Ala Lys Leu Arg Ala Gln Gly Thr Ala Val Lys Gln Gln Trp Thr Leu
                245                 250                 255

Arg Ser Leu Glu Lys Gln Gly Gly Ile Tyr Ile Ser Lys Phe Asp Thr
                260                 265                 270

Pro Thr Gly Glu Glu Ile Val Thr Ser Arg Ser Val Val Leu Ser Thr
            275                 280                 285

Pro Ala Tyr Val Thr Ala Lys Leu Leu Gln Asp Tyr Leu Pro Ala Ala
            290                 295                 300

Ser Gln Ala Leu Asn Glu Ile Phe Tyr Pro Thr Val Ala Cys Val Val
305                 310                 315                 320

Leu Ala Tyr Pro Lys Ser Glu Phe Leu Tyr Asp Met Lys Gly Phe Gly
                325                 330                 335

Asn Leu Ile Pro Arg Thr Glu Gly Val Arg Thr Leu Gly Thr Ile Trp
                340                 345                 350

Ser Ser Ser Leu Phe Ser Gly Arg Ala Pro Ala Gly Trp Gln Leu Leu
            355                 360                 365

Leu Asn Phe Ile Gly Gly Thr Leu Asp Pro Ala Leu Ala His Leu Ser
            370                 375                 380

Glu Ala Glu Ile Ile Ala Ala Val His Gln Asp Leu Lys Lys Thr Ile
385                 390                 395                 400

Leu Arg Pro Asp Thr Lys Val Ser Pro Lys Ala Ile Ala Val His Val
                405                 410                 415

Trp Asp Lys Ala Ile Pro Gln Tyr Glu Ile Gly His Leu Glu Arg Leu
                420                 425                 430

Ala Thr Val Glu Ala Glu Leu Gln Lys Ser Ser Gly Leu Tyr Val Ser
                435                 440                 445

Ala Asn Phe Ile Gly Gly Val Ala Leu Gly Asp Cys Ile Lys Arg Ser
            450                 455                 460

Leu Gln Glu Ala His Lys Ile Ala Ala Phe Leu Glu Thr Ile
465                 470                 475
```

```
<210> SEQ ID NO 46
<211> LENGTH: 479
<212> TYPE: PRT
<213> ORGANISM: Artificial Sequence
<220> FEATURE:
<223> OTHER INFORMATION: Synthetic_PPO of Pseudanabaena sp. (HBC40803.1)

<400> SEQUENCE: 46
```

```
Met Thr Ser Ala Gln Thr Thr Glu Val Asn Gln Pro Leu Asp Val Leu
1               5                   10                  15

Val Val Gly Ala Gly Ile Ser Gly Leu Ala Ile Ala His Glu Leu Ala
                20                  25                  30

Ile Ala Lys Asn Tyr Arg Val Leu Val Ala Glu Ala Gln Asp Arg Val
                35                  40                  45

Gly Gly Ala Ile Thr Ser Asn Arg Asn Asp Asp Gly Tyr Leu Trp Glu
            50                  55                  60

Glu Gly Pro Asn Ser Phe Gln Pro Ala Pro Glu Leu Leu Arg Leu Ala
65                  70                  75                  80

Val Glu Val Gly Leu Lys Asp Glu Leu Val Leu Ala Asp Gly Lys Leu
                85                  90                  95

Pro Arg Phe Val Phe Leu Asn Gly Lys Leu Asn Ala Leu Pro Met Ser
```

```
            100             105             110
Pro Pro Thr Ala Ile Ala Ser Lys Ile Leu Thr Trp Gly Gly Lys Ile
        115             120             125

Arg Leu Ala Leu Gly Ala Leu Gly Phe Ala Arg Pro Ala Met Ser Gly
    130             135             140

Glu Glu Ser Val Asp Gln Phe Phe Ser Arg Leu Leu Gly Lys Gln Ala
145             150             155             160

Val Glu Arg Leu Val Ala Pro Phe Ile Ser Gly Val Tyr Ala Gly Asp
            165             170             175

Pro Lys Arg Leu Ser Ala Arg Ala Ala Phe Ser Lys Ile Phe Arg Leu
            180             185             190

Glu Asn Gly Tyr Gly Gly Leu Leu Thr Gly Ala Ile Leu Thr Ala Lys
            195             200             205

Asp Arg Lys Ala Gln Lys Leu Asn Asp Pro Asn Ile Pro Lys Val Lys
        210             215             220

Ser Gly Glu Leu Gly Ser Phe Arg Gln Gly Ile Lys Met Leu Pro Glu
225             230             235             240

Ala Ile Ala Thr Lys Leu Arg Asp Gln Gly Thr Ala Val Lys Gln Gln
            245             250             255

Trp Thr Leu Arg Ser Leu Glu Lys Gln Gly Glu Ile Tyr Val Ser Gln
            260             265             270

Phe Gly Thr Pro Thr Gly Thr Glu Thr Ile Thr Ser Arg Ser Val Val
            275             280             285

Leu Thr Thr Pro Ala Tyr Val Ser Ala Lys Leu Leu Gln Gly Tyr Leu
        290             295             300

Pro Ala Ala Ser Gln Ala Leu Ser Glu Ile Phe Tyr Pro Thr Val Ala
305             310             315             320

Cys Val Val Leu Ala Tyr Pro Lys Ser Glu Phe Ala Tyr Asp Met Lys
            325             330             335

Gly Phe Gly Asn Leu Ile Pro Arg Thr Gln Gly Val Arg Thr Leu Gly
            340             345             350

Thr Ile Trp Ser Ser Ser Leu Phe Ala Gly Arg Ala Pro Asp Gly Trp
            355             360             365

Gln Leu Leu Leu Asn Phe Ile Gly Gly Thr Leu Asp Pro Asp Leu Ala
        370             375             380

Asn Leu Ser Glu Ala Lys Ile Val Gln Ala Val His Gln Asp Leu Lys
385             390             395             400

Lys Thr Leu Leu Arg Pro Asp Ser Lys Val Glu Pro Lys Val Ile Ala
            405             410             415

Val His Val Trp Asp Lys Ala Ile Pro Gln Tyr Glu Ile Gly His Leu
            420             425             430

Glu Arg Leu Ala Thr Ile Glu Thr Glu Leu Gln Lys Ser Gln Gly Leu
            435             440             445

Tyr Val Ser Ala Asn Phe Ile Gly Gly Val Ala Leu Gly Asp Cys Ile
        450             455             460

Lys Arg Ser Leu Gln Glu Ala Asp Lys Ile Ala Ala Phe Leu Lys
465             470             475
```

<210> SEQ ID NO 47
<211> LENGTH: 511
<212> TYPE: PRT
<213> ORGANISM: Artificial Sequence
<220> FEATURE:
<223> OTHER INFORMATION: Synthetic_PPO of Synechoccus sp.
     JA-2-3B'a(2-13) (WP_049749573)

-continued

<400> SEQUENCE: 47

```
Met Asn Ser Ser Val Glu His Phe Ser Gly Thr Gln Ser Leu Gln Ala
1               5                   10                  15

Glu Val Val Val Val Gly Ala Gly Ile Ser Gly Leu Thr Leu Ala Leu
            20                  25                  30

Arg Leu Gln Gln Gly Leu Ser Pro Lys Asp Glu Ser Thr Gln Pro Leu
        35                  40                  45

Leu Leu Ala Glu Ala Ser Ser Arg Val Gly Gly Cys Ile Ser Thr Gln
    50                  55                  60

Ser Lys Asp Ser Tyr Arg Trp Glu Glu Gly Pro Asn Ser Phe Thr Pro
65                  70                  75                  80

Val Pro Ala Leu Leu Asn Leu Ile Ala Glu Val Gly Leu Ala Glu His
            85                  90                  95

Leu Val Leu Ala Asp Ala Lys Leu Pro Arg Tyr Ile Tyr Trp Glu Lys
            100                 105                 110

Glu Leu Leu Pro Val Pro Leu Ser Pro Ser Ala Ala Ile Gly Ser Arg
        115                 120                 125

Leu Leu Ser Val Gly Gly Lys Leu Arg Ala Leu Arg Gly Leu Leu Gly
    130                 135                 140

Phe Val Ala Pro Pro Pro Gly Gly Glu Glu Thr Val Arg Gln Phe Phe
145                 150                 155                 160

Arg Arg Gln Leu Gly Ser Glu Val Val Glu Arg Leu Val Glu Pro Phe
            165                 170                 175

Thr Ser Gly Val Tyr Ala Gly Asp Pro Asp Gln Leu Ser Ala Leu Ala
            180                 185                 190

Ala Phe Pro Arg Ile Ala Gly Leu Glu Glu Arg Tyr Gly Ser Leu Phe
        195                 200                 205

Ala Gly Ala Val Gln Ala Leu Arg Ser Arg Tyr Arg Tyr Ala Thr Leu
    210                 215                 220

Pro Arg Thr Arg His Gln Asp Ser Ala Asn Ser Pro Ile Gln Pro Pro
225                 230                 235                 240

Pro Lys Arg Gly Gln Leu Gly Asn Leu Arg Gln Gly Leu Gln Gln Leu
            245                 250                 255

Pro Glu Ala Ile Ala Gln Lys Leu Gly Ser Ala Leu Arg Leu Gly Trp
            260                 265                 270

Arg Ala Val His Leu Lys Arg Asp Glu Thr Gly Tyr Arg Val Gly Phe
            275                 280                 285

Val Ile His Asp Ser Gly Ala Glu His Thr Ala Pro Glu Glu Ile His
    290                 295                 300

Trp Val Ala Ala Gln Gln Val Val Leu Thr Leu Pro Ala Tyr Ala Ala
305                 310                 315                 320

Ala Thr Leu Leu Gln Asp Leu Asn Pro Gln Ala Ser Arg Leu Leu Arg
            325                 330                 335

Glu Ile Pro Tyr Pro Pro Val Ala Val Val Ala Leu Ala Tyr Pro Glu
            340                 345                 350

Glu Ala Leu Pro Gln Pro Leu Arg Gly Phe Gly His Leu Ile Pro Arg
            355                 360                 365

Ser Gln Gly Leu Arg Thr Leu Gly Thr Ile Trp Ala Ser Ser Leu Phe
    370                 375                 380

Pro Glu Arg Ala Pro Gln Gly Tyr His Cys Leu Ile Ser Phe Ile Gly
385                 390                 395                 400

Gly Ala Thr Asp Ala Ala Phe Ala Arg Gln Lys Gly Ile Pro Pro Ile
```

```
                    405              410              415

Thr Ala Leu Ser Pro Asp Glu Arg Ala Gln Ile Val His Ala Glu Leu
            420              425              430

Ser Gln Ile Leu Leu Thr Arg Pro Val Glu Pro Ile Arg Leu Gly Glu
            435              440              445

Arg Leu Trp Pro Gln Ala Ile Pro Gln Tyr Thr Leu Gly His Arg Gln
    450              455              460

Arg Ile Ala Gln Leu Gln Ala Ser Leu Ala Asp Gln Thr Pro Gly Val
465              470              475              480

Trp Val Cys Ala Asn Tyr Leu Asp Gly Val Ala Leu Gly Asp Cys Val
            485              490              495

Arg Arg Ala Glu Ala Leu Ala Gln Gln Ile Leu Ser Val Arg Arg
            500              505              510
```

```
<210> SEQ ID NO 48
<211> LENGTH: 479
<212> TYPE: PRT
<213> ORGANISM: Artificial Sequence
<220> FEATURE:
<223> OTHER INFORMATION: Synthetic_PPO of Pseudanabaena biceps
      (WP_009629673)

<400> SEQUENCE: 48

Met Thr Ser Ala Gln Ile Pro Glu Val Asn Pro Leu Asp Val Leu Val
1               5               10              15

Val Gly Ala Gly Ile Ser Gly Leu Thr Ile Ala His Glu Leu Ala Ile
            20              25              30

Ala Lys Asn Tyr Arg Val Leu Val Ala Glu Ala Gln Asp Arg Val Gly
            35              40              45

Gly Ala Ile Thr Ser Ala Lys Asn Asp Glu Gly Tyr Gln Trp Glu Glu
    50              55              60

Gly Pro Asn Ser Phe Gln Pro Ala Pro Glu Leu Leu Arg Leu Ala Val
65              70              75              80

Glu Val Gly Leu Lys Asp Glu Leu Val Leu Ala Asp Gly Lys Leu Pro
            85              90              95

Arg Phe Val Phe Leu Asn Gly Lys Leu Asn Ala Leu Pro Met Ser Pro
            100             105             110

Pro Thr Ala Ile Ala Ser Gln Ile Leu Thr Trp Gly Gly Lys Ile Arg
            115             120             125

Leu Ala Leu Gly Ala Met Gly Phe Ala Arg Pro Ala Met Ala Gly Glu
    130             135             140

Glu Ser Val Asp Arg Phe Phe Ser Arg Leu Leu Gly Arg Gln Ala Val
145             150             155             160

Asp Arg Leu Val Ala Pro Phe Ile Ser Gly Val Tyr Ala Gly Asp Pro
            165             170             175

Lys Arg Leu Ser Ala Lys Ala Ala Phe Ala Lys Ile Ala Lys Leu Glu
            180             185             190

Thr Tyr Gly Gly Leu Leu Ala Gly Ala Ile Leu Ser Ser Lys Glu Arg
            195             200             205

Lys Ala Gln Lys Leu Asn Asp Pro Arg Ile Pro Lys Thr Lys Ala Gly
    210             215             220

Glu Leu Gly Ser Phe Arg Glu Gly Ile Lys Met Leu Pro Glu Ala Ile
225             230             235             240

Thr Ala Lys Leu Arg Ala Gln Gly Thr Ala Val Lys Gln Gln Trp Thr
            245             250             255
```

Leu Gln Ser Leu Glu Lys Gln Gly Glu Ile Tyr Val Ser Lys Phe Ala
            260                 265                 270

Thr Pro Thr Gly Glu Glu Ile Val Thr Ser Arg Ser Val Val Leu Ser
            275                 280                 285

Thr Pro Ala Tyr Val Thr Ala Lys Leu Leu Gln Asp Tyr Leu Pro Ala
            290                 295                 300

Ala Ser Gln Ala Leu Asn Glu Ile Phe Tyr Pro Thr Val Ala Cys Val
305                 310                 315                 320

Val Leu Ala Tyr Pro Lys Ser Glu Phe Arg Tyr Asp Met Lys Gly Phe
                325                 330                 335

Gly Asn Leu Ile Pro Arg Thr Glu Gly Val Arg Thr Leu Gly Thr Ile
            340                 345                 350

Trp Ser Ser Ser Leu Phe Ala Gly Arg Ala Pro Ala Gly Trp Gln Leu
            355                 360                 365

Leu Leu Asn Phe Ile Gly Gly Thr Leu Asp Pro Ala Leu Ala His Leu
            370                 375                 380

Ser Glu Ala Glu Ile Ile Ala Ala Val His Gln Asp Leu Lys Lys Thr
385                 390                 395                 400

Ile Leu Arg Pro Asp Thr Lys Val Ser Pro Lys Ala Ile Ala Val His
                405                 410                 415

Val Trp Asp Lys Ala Ile Pro Gln Tyr Glu Ile Gly His Leu Glu Arg
                420                 425                 430

Leu Ala Thr Val Glu Ala Glu Leu Gln Lys Ser Ser Gly Leu Tyr Ile
            435                 440                 445

Ser Ala Asn Phe Ile Gly Gly Val Ala Leu Gly Asp Cys Ile Lys Arg
            450                 455                 460

Ser Leu Gln Glu Ala His Lys Ile Ala Ala Phe Leu Glu Thr Ile
465                 470                 475

<210> SEQ ID NO 49
<211> LENGTH: 478
<212> TYPE: PRT
<213> ORGANISM: Artificial Sequence
<220> FEATURE:
<223> OTHER INFORMATION: Synthetic_PPO of Pseudanabaena sp. (PZV12410)

<400> SEQUENCE: 49

Met Thr Leu Thr Pro Ser Ser Glu Glu Asn Gln Pro Leu Asp Thr Leu
1               5                   10                  15

Ile Ile Gly Ala Gly Ile Ser Gly Leu Thr Ile Ala His Glu Leu Val
                20                  25                  30

Ile Ala Lys Asn Tyr Arg Ile Leu Val Ala Glu Ala Gln Asp Arg Val
            35                  40                  45

Gly Gly Ala Ile Thr Ser Ala Lys Asn Asp Glu Gly Tyr Leu Trp Glu
        50                  55                  60

Glu Gly Pro Asn Ser Phe Gln Pro Ala Pro Glu Leu Leu Arg Leu Ala
65                  70                  75                  80

Val Gln Val Gly Leu Lys Asp Glu Leu Val Leu Ala Asp Gly Lys Leu
                85                  90                  95

Pro Arg Phe Val Phe Leu Asn Gly Lys Leu Asn Ala Leu Pro Met Ser
            100                 105                 110

Pro Pro Thr Ala Ile Thr Ser Lys Ile Leu Thr Trp Gly Gly Lys Ile
        115                 120                 125

Arg Leu Ala Leu Gly Ala Ile Gly Phe Ala Arg Pro Ala Met Ala Gly
        130                 135                 140

-continued

```
Glu Glu Ser Val Asp Gln Phe Phe Ser Arg Ile Leu Gly Lys Gln Ala
145             150                 155                 160

Val Glu Arg Leu Val Ala Pro Phe Ile Ser Gly Val Tyr Ala Gly Asp
                165                 170                 175

Pro Lys Arg Leu Ser Ala Lys Ala Ala Phe Ser Lys Ile Ala Lys Leu
            180                 185                 190

Glu Thr Tyr Gly Gly Leu Leu Ser Gly Ala Ile Leu Ser Ser Lys Glu
            195                 200                 205

Arg Lys Ala Gln Lys Leu Asn Glu Pro Asn Ile Pro Lys Thr Lys Ala
    210                 215                 220

Gly Glu Leu Gly Ser Phe Arg Gln Gly Ile Gln Met Leu Pro Glu Ala
225                 230                 235                 240

Ile Ala Ser Lys Leu Arg Glu Thr Gly Thr Ala Val Lys Gln Lys Trp
                245                 250                 255

Thr Leu Arg Ser Leu Glu Lys Gln Gly Asp Ile Tyr Ile Ser Lys Phe
            260                 265                 270

Asp Thr Pro Ser Gly Glu Glu Thr Val Thr Ser Arg Ser Val Val Leu
            275                 280                 285

Thr Thr Pro Ala Tyr Val Thr Ala Lys Leu Leu Glu Asp Tyr Leu Pro
    290                 295                 300

Ala Ala Ser Gln Ala Leu Asn Glu Ile Phe Tyr Pro Thr Val Ala Cys
305                 310                 315                 320

Val Val Leu Ala Tyr Pro Lys Ser Glu Phe Ala His Asp Met Lys Gly
                325                 330                 335

Phe Gly Asn Leu Ile Pro Arg Thr Gln Gly Val Arg Thr Leu Gly Thr
            340                 345                 350

Ile Trp Ser Ser Ser Leu Phe Ala Gly Arg Ala Pro Glu Gly Trp Gln
            355                 360                 365

Leu Leu Leu Asn Phe Ile Gly Gly Thr Leu Asp Pro Ala Leu Ala Lys
    370                 375                 380

Leu Ser Glu Ser Glu Ile Ile Ala Ala Val His Ala Asp Leu Lys Lys
385                 390                 395                 400

Thr Ile Leu Arg Pro Asp Thr Lys Ala Glu Pro Lys Ala Ile Ala Val
                405                 410                 415

His Val Trp Asp Lys Ala Ile Pro Gln Tyr Glu Ile Gly His Leu Asp
                420                 425                 430

Arg Leu Ala Thr Val Glu Ala Glu Leu Gln Lys Ser Gln Gly Leu Tyr
            435                 440                 445

Val Ser Ala Asn Phe Ile Gly Gly Val Ala Leu Gly Asp Cys Ile Lys
    450                 455                 460

Arg Ser Leu Gln Glu Ala Asn Lys Ile Asp Ala Phe Leu Lys
465                 470                 475
```

```
<210> SEQ ID NO 50
<211> LENGTH: 502
<212> TYPE: PRT
<213> ORGANISM: Artificial Sequence
<220> FEATURE:
<223> OTHER INFORMATION: Synthetic_PPO of Pseudanabaena sp. PCC 7367
      (WP_015165508)

<400> SEQUENCE: 50
```

```
Met Ser Asn His Asn His Ala Gly Ser Pro Ile Asp Leu Leu Val Val
1               5                   10                  15

Gly Ala Gly Ile Ser Gly Leu Thr Val Ala His Asp Leu Ala Ser Asn
                20                  25                  30
```

```
Ser Val Ala Glu Ala Asn Gly Ser Asn Gln Leu Arg Ile Ile Val Thr
        35                  40                  45

Glu Ala Gln Asn Arg Val Gly Gly Ala Ile Val Ser Gln Arg Asp Glu
    50                  55                  60

Val Gly Phe Gln Trp Glu Glu Gly Pro Asn Ser Phe Gln Pro Ala Pro
65                  70                  75                  80

Glu Leu Leu Lys Leu Ala Ala Ala Val Gly Leu Lys Asp Glu Leu Val
                85                  90                  95

Phe Ala Asp Gly Lys Leu Pro Arg Phe Val Phe Trp Asn Gly Lys Leu
                100                 105                 110

Asn Ala Leu Pro Met Ser Pro Gln Leu Leu Thr Lys Phe Asn Leu Leu
                115                 120                 125

Thr Ile Lys Gly Lys Leu Arg Ala Phe Leu Gly Ala Ile Gly Phe Val
        130                 135                 140

Arg Pro Ala Ala Ala Gly Glu Glu Thr Val Ala Gln Phe Phe Lys Arg
145                 150                 155                 160

His Leu Gly Gln Glu Val Val Asp Arg Leu Val Val Pro Phe Ile Ser
                165                 170                 175

Gly Val Tyr Ala Gly Asn Thr Asp Lys Leu Ser Ala Ala Ala Ala Phe
                180                 185                 190

Gly Lys Ile Phe Arg Leu Glu Lys Asn Tyr Asn Gly Leu Val Ala Gly
                195                 200                 205

Ala Ile Leu Ser Arg Leu Ala Lys Arg Lys Gln Glu Lys Ala Gln Thr
        210                 215                 220

Asn Gln Pro Ala Asn Ile Tyr Asp Arg Gln Glu Ile Pro Lys Thr Lys
225                 230                 235                 240

Pro Gly Gln Leu Gly Ser Phe Lys Asn Gly Ile Glu Ala Leu Pro Arg
                245                 250                 255

Ala Ile Ala Glu Asp Leu Ile Asp Lys Gly His Glu Val Arg Leu Gln
                260                 265                 270

Trp Arg Leu Asp Lys Ile Gln Pro Asn Ser Asp Gly Thr Tyr Ser Ala
        275                 280                 285

Thr Tyr Glu Thr Pro His Gly Ile Glu Thr Ile Thr Ala Arg Ala Leu
        290                 295                 300

Leu Leu Thr Thr Pro Ala Tyr Val Ser Ser Met Leu Leu Gln Asp Ile
305                 310                 315                 320

Ala Pro Asp Ala Ala Gln Ser Leu Gly Glu Ile Tyr Tyr Pro Pro Val
                325                 330                 335

Ala Cys Val Val Leu Gly Tyr Pro Asp Ala Ala Met Lys Arg Asp Met
                340                 345                 350

Asn Gly Phe Gly Asn Leu Ile Pro Arg Ser Gln Gly Ile Arg Thr Leu
                355                 360                 365

Gly Thr Ile Trp Gly Ser Ser Leu Phe Ser Asp Arg Ala Pro Ala Gly
        370                 375                 380

Tyr His Leu Leu Leu Asn Phe Ile Gly Gly Ser Leu Asp Thr Gly Ile
385                 390                 395                 400

Ala Asp Leu Ser Glu Pro Glu Ile Ala Gln Ala Val His Ser Asp Leu
                405                 410                 415

Lys Gln Thr Leu Leu Lys Pro Asp Thr Thr Ile Glu Pro Lys Val Leu
                420                 425                 430

Ala Val His Leu Trp Gln Arg Ala Ile Pro Gln Tyr Glu Val Gly His
        435                 440                 445
```

```
Leu Asp Arg Leu Ala Arg Val Glu Arg Asp Leu Ala Asn His Pro Gly
    450             455             460

Leu Phe Val Ser Ala Asn Phe Ile Gly Gly Val Ala Leu Gly Asp Cys
465             470             475             480

Val Lys Arg Ser Phe Gly Thr Ala Glu Gln Ile Lys Gly Phe Leu Asn
                485             490             495

Leu Ser Thr Lys Lys Lys
            500

<210> SEQ ID NO 51
<211> LENGTH: 479
<212> TYPE: PRT
<213> ORGANISM: Artificial Sequence
<220> FEATURE:
<223> OTHER INFORMATION: Synthetic_PPO of Pseudanabaena sp. SR411
      (WP_094530677)

<400> SEQUENCE: 51

Met Ser Leu Thr Pro Ser Ser Ala Thr Asn Gln Pro Leu Asp Val Leu
1               5               10              15

Val Val Gly Ala Gly Ile Ser Gly Leu Thr Ile Ala His Glu Leu Ala
                20              25              30

Ile Ala Lys Lys Tyr Arg Val Leu Val Ala Glu Ala Gln Asp Arg Val
            35              40              45

Gly Gly Ala Ile Thr Ser Ala Lys Asn Asp Glu Gly Tyr Gln Trp Glu
    50              55              60

Glu Gly Pro Asn Ser Phe Gln Pro Ala Pro Glu Leu Leu Arg Leu Ala
65              70              75              80

Val Gln Val Gly Leu Lys Asp Glu Leu Val Leu Ala Asp Gly Lys Leu
                85              90              95

Pro Arg Phe Val Phe Leu Asn Gly Lys Leu Asn Ala Leu Pro Met Ser
            100             105             110

Pro Pro Thr Ala Ile Ala Ser Lys Ile Leu Thr Trp Gly Gly Lys Ile
            115             120             125

Arg Leu Ala Leu Gly Ala Ile Gly Phe Ala Arg Pro Ala Met Ala Gly
    130             135             140

Glu Glu Ser Val Asp Gln Phe Phe Ser Arg Leu Leu Gly Lys Gln Ala
145             150             155             160

Val Glu Arg Leu Val Ala Pro Phe Ile Ser Gly Val Tyr Ala Gly Asp
            165             170             175

Pro Lys Arg Leu Ser Ala Lys Ala Ala Phe Ala Lys Ile Phe Arg Leu
            180             185             190

Glu Asn Ser Tyr Asn Gly Leu Leu Ala Gly Ala Ile Leu Ser Ala Lys
            195             200             205

Glu Arg Lys Ala Gln Lys Leu Ser Asp Pro Asn Ile Pro Lys Val Lys
    210             215             220

Ala Gly Glu Leu Gly Ser Phe Arg Gln Gly Ile Lys Met Leu Pro Glu
225             230             235             240

Ala Ile Ala Thr Lys Leu Arg Asp Gln Gly Thr Ala Val Lys Gln Gln
            245             250             255

Trp Thr Leu Arg Ser Leu Glu Lys Gln Asp Glu Ile Tyr Ile Ser Lys
            260             265             270

Phe Asp Thr Pro Thr Gly Glu Glu Thr Val Arg Ser Arg Ser Val Val
            275             280             285

Leu Ser Thr Pro Ala Tyr Val Thr Ala Lys Leu Leu Gln Asp Tyr Leu
    290             295             300
```

-continued

```
Pro Ala Ala Ser Gln Ala Leu Asn Glu Ile Phe Tyr Pro Thr Val Ala
305                 310                 315                 320

Cys Val Val Met Ala Tyr Pro Lys Ser Glu Phe Ala Tyr Asp Met Lys
                325                 330                 335

Gly Phe Gly Asn Leu Ile Pro Arg Thr Gln Gly Val Arg Thr Leu Gly
            340                 345                 350

Thr Ile Trp Ser Ser Ser Leu Phe Ala Gly Arg Ala Pro Glu Gly Trp
            355                 360                 365

Gln Leu Leu Leu Asn Phe Ile Gly Gly Thr Leu Asp Pro Ala Leu Ala
        370                 375                 380

Lys Leu Ser Glu Pro Glu Ile Ile Ala Ala Val His Gln Asp Leu Lys
385                 390                 395                 400

Lys Thr Ile Leu Arg Pro Asp Thr Lys Ala Glu Pro Lys Ala Ile Ala
                405                 410                 415

Val His Val Trp Asp Lys Ala Ile Pro Gln Tyr Glu Ile Gly His Leu
                420                 425                 430

Asp Arg Leu Ala Thr Val Glu Lys Glu Leu Gln Lys Ser Gln Gly Leu
            435                 440                 445

Tyr Ile Ser Ala Asn Phe Ile Gly Gly Val Ala Leu Gly Asp Cys Ile
        450                 455                 460

Lys Arg Ser Leu Gln Glu Ala Thr Lys Ile Asp Ala Phe Leu Lys
465                 470                 475

<210> SEQ ID NO 52
<211> LENGTH: 483
<212> TYPE: PRT
<213> ORGANISM: Artificial Sequence
<220> FEATURE:
<223> OTHER INFORMATION: Synthetic_PPO of Pseudanabaena frigida
      (PZO41121)

<400> SEQUENCE: 52

Met Thr Thr Ser Gln Glu Thr Lys Ala Ser Gln Pro Leu Asp Val Leu
1               5                   10                  15

Val Val Gly Ala Gly Ile Ser Gly Leu Thr Ile Ala His Glu Leu Ala
            20                  25                  30

Ile Ala Lys His Arg His Val Leu Val Ala Glu Ala Gln Asp Arg Val
        35                  40                  45

Gly Gly Ala Ile Thr Thr Ala Ser Asn Asn Glu Gly Tyr Leu Trp Glu
    50                  55                  60

Glu Gly Pro Asn Ser Phe Gln Pro Ala Pro Glu Leu Leu Arg Leu Ala
65                  70                  75                  80

Val Glu Val Gly Leu Lys Asp Glu Leu Val Leu Ala Asp Gly Lys Leu
                85                  90                  95

Pro Arg Phe Val Phe Leu Asn Gly Lys Leu Asn Ala Leu Pro Met Ser
                100                 105                 110

Pro Pro Thr Ala Ile Ala Ser Lys Ile Leu Ser Trp Gly Gly Lys Ile
            115                 120                 125

Arg Leu Ala Leu Gly Ala Leu Gly Phe Ala Arg Pro Ala Met Ala Gly
        130                 135                 140

Glu Glu Ser Val Asp Arg Phe Phe Ser Arg Leu Leu Gly Lys Gln Ala
145                 150                 155                 160

Val Glu Arg Leu Val Ala Pro Phe Ile Ser Gly Val Tyr Ala Gly Asp
                165                 170                 175

Pro Lys Arg Leu Ser Ala Lys Ala Ala Phe Ser Lys Ile Ala Lys Leu
```

-continued

```
                180              185              190

Glu Thr Tyr Gly Gly Leu Leu Ala Gly Ala Ile Leu Ser Ser Lys Glu
        195              200              205

Arg Lys Ala Gln Lys Leu Asn Asp Pro Asn Ile Pro Lys Thr Lys Ala
    210              215              220

Gly Glu Leu Gly Ser Phe Arg Gln Gly Ile Lys Met Leu Pro Glu Ala
225              230              235              240

Ile Ala Ala Lys Leu Arg Ala Gln Gly Thr Pro Val Lys Gln Gln Trp
            245              250              255

Thr Leu Arg Ser Leu Gln Lys Gln Asp Glu Ile Tyr Ile Ala Lys Phe
            260              265              270

Asp Thr Pro Thr Gly Glu Glu Val Val Thr Ser Lys Ser Val Val Leu
        275              280              285

Ser Thr Pro Ala Tyr Val Ser Ala Lys Leu Leu Gln Asp Tyr Leu Pro
    290              295              300

Ala Ala Ser Gln Ala Leu Ser Glu Ile Phe Tyr Pro Thr Val Ala Cys
305              310              315              320

Val Val Leu Ala Tyr Pro Lys Ser Ala Phe Ala Tyr Asp Met Lys Gly
            325              330              335

Phe Gly Asn Leu Ile Pro Arg Thr Gln Gly Val Arg Thr Leu Gly Thr
            340              345              350

Ile Trp Ser Ser Ser Leu Phe Ala Gly Arg Ala Pro Asp Gly Trp Gln
            355              360              365

Leu Leu Leu Asn Phe Ile Gly Gly Thr Leu Asp Pro Ala Leu Ala Gln
    370              375              380

Leu Ser Glu Ser Glu Ile Ile Gln Ala Val His Gln Asp Leu Lys Lys
385              390              395              400

Thr Ile Leu Arg Pro Asp Thr Gln Val Glu Pro Lys Thr Ile Ala Val
            405              410              415

His Val Trp Asp Lys Ala Ile Pro Gln Tyr Glu Ile Gly His Leu Gln
            420              425              430

Arg Leu Ala Thr Ile Lys Ala Glu Leu Gln Lys Ser Gln Gly Leu Tyr
        435              440              445

Ile Ser Ala Asn Phe Ile Gly Gly Val Ala Leu Gly Asp Cys Ile Lys
    450              455              460

Arg Ser Leu Gln Glu Ser Ile Glu Ile Asp Glu Phe Leu Ser Arg Thr
465              470              475              480

Asn Ser Leu
```

```
<210> SEQ ID NO 53
<211> LENGTH: 481
<212> TYPE: PRT
<213> ORGANISM: Artificial Sequence
<220> FEATURE:
<223> OTHER INFORMATION: Synthetic_PPO of Pseudanabaena sp. (PZU98053)

<400> SEQUENCE: 53

Met Asn Gln Leu Ala Asp Arg Pro Ser Gly Glu Gln Thr Leu Asp Val
1               5                10               15

Leu Val Val Gly Ala Gly Ile Ser Gly Leu Thr Ile Ala Tyr Asp Leu
            20               25               30

Ala Ile Asn Gln His Arg Gln Val Leu Val Ala Glu Ala Gln Asp Arg
        35               40               45

Val Gly Gly Ala Ile Val Ser Lys Gln Asn Asp Glu Gly Tyr Leu Trp
    50               55               60
```

```
Glu Glu Gly Pro Asn Ser Phe Gln Pro Thr Pro Glu Leu Leu Arg Leu
65              70                  75                  80

Ala Val Asn Val Gly Leu Glu Asp Gln Leu Val Leu Ala Asn Gly Lys
                85                  90                  95

Leu Pro Arg Phe Val Phe Leu Lys Gly Lys Leu Asn Ala Leu Pro Met
            100                 105                 110

Ser Pro Pro Ala Ala Ile Ala Thr Pro Leu Leu Asp Trp Gly Ser Lys
            115                 120                 125

Ile Arg Leu Ala Leu Gly Ala Ile Gly Phe Ala Arg Pro Ala Met Ala
        130                 135                 140

Gly Glu Glu Ser Val Asp Gln Phe Phe Ser Arg Leu Leu Gly Lys Gln
145                 150                 155                 160

Ala Val Ala Arg Leu Val Ala Pro Phe Ile Ser Gly Val Tyr Ala Gly
                165                 170                 175

Asp Pro Lys Arg Leu Ser Ala Arg Ala Ala Phe Ala Lys Ile Phe Arg
            180                 185                 190

Leu Glu Asn Asn Tyr Gly Gly Leu Val Ala Gly Ala Ile Leu Ser Gly
            195                 200                 205

Lys Asp Arg Gln Ala Gln Lys Ala Lys Asn Ala Asp Leu Pro Lys Val
        210                 215                 220

Lys Ala Gly Glu Leu Gly Ser Phe Lys Gln Gly Ile Lys Met Leu Pro
225                 230                 235                 240

Glu Ala Ile Ala Thr Lys Leu Arg Ser Gln Gly Thr Ala Val Lys Gln
                245                 250                 255

Gln Trp Thr Leu Arg Ser Leu Asp Arg Gln Gly Asp His Tyr Ile Ala
            260                 265                 270

Lys Phe Asp Thr Pro Thr Gly Glu Glu Thr Val Met Ser Arg Ala Val
            275                 280                 285

Val Leu Ala Thr Pro Ala Tyr Val Thr Ala Asn Leu Leu Lys Asp Tyr
        290                 295                 300

Leu Pro Ser Ala Ser Gln Ala Leu Arg Lys Ile Phe Tyr Pro Thr Val
305                 310                 315                 320

Ala Cys Val Val Leu Ala Tyr Pro Lys Thr Glu Phe Ala Tyr Asp Met
                325                 330                 335

Gln Gly Phe Gly Asn Leu Ile Pro Arg Thr Glu Gly Val Arg Thr Leu
            340                 345                 350

Gly Thr Ile Trp Ser Ser Ser Leu Phe Ala Gly Arg Ala Pro Gln Gly
            355                 360                 365

Trp Gln Leu Leu Leu Asn Phe Ile Gly Gly Thr Leu Asp Pro Ala Leu
        370                 375                 380

Ala Gln Leu Ser Glu Ala Glu Ile Ile Gln Ala Val His Gln Asp Leu
385                 390                 395                 400

Lys Lys Thr Ile Leu Arg Pro Asp Thr Lys Ala Glu Pro Lys Ala Ile
                405                 410                 415

Ala Val His Arg Trp Asp Lys Ala Ile Pro Gln Tyr Glu Ile Gly His
            420                 425                 430

Leu Gln Leu Leu Ala Thr Val Glu Ala Glu Leu Gln Lys Ser Gln Gly
        435                 440                 445

Leu Tyr Ile Ser Ala Asn Phe Ile Gly Gly Val Ala Leu Gly Asp Cys
        450                 455                 460

Ile Lys Arg Ser Leu Gln Glu Ala Ile Lys Ile Glu Gln Phe Leu Ala
465                 470                 475                 480
```

-continued

Lys

<210> SEQ ID NO 54
<211> LENGTH: 488
<212> TYPE: PRT
<213> ORGANISM: Artificial Sequence
<220> FEATURE:
<223> OTHER INFORMATION: Synthetic_PPO of Oscillatoriales cyanobacterium
      CG2_30_44_21 (OIP76421)

<400> SEQUENCE: 54

Met Pro Ser Pro Gln Ser Ala Thr Asn Gln Ser Asp Asp Arg Pro Ser
1               5                   10                  15

Gly Gly Gln Pro Ile Asp Val Leu Val Val Gly Ala Gly Val Ser Gly
            20                  25                  30

Leu Thr Ile Ala His Asp Leu Ala Ile Asn Tyr Gln Arg Gln Val Leu
        35                  40                  45

Val Ala Glu Ala Gln Asp Arg Val Gly Gly Ala Ile Ile Ser Arg Gln
    50                  55                  60

Asn Asn Glu Gly Tyr Leu Trp Glu Glu Gly Pro Asn Ser Phe Gln Pro
65                  70                  75                  80

Ala Pro Glu Leu Leu Arg Leu Ala Val Asn Val Gly Leu Glu Asp Gln
                85                  90                  95

Leu Val Leu Ala Asn Gly Lys Leu Pro Arg Phe Val Phe Leu Lys Gly
            100                 105                 110

Lys Leu Asn Ala Ile Pro Met Ser Pro Pro Ala Ala Ile Ala Thr Pro
        115                 120                 125

Leu Leu Asp Trp Gly Ser Lys Ile Arg Leu Ala Leu Gly Ala Ile Gly
    130                 135                 140

Phe Ala Arg Pro Ala Met Ala Gly Glu Glu Ser Val Asp Gln Phe Phe
145                 150                 155                 160

Ser Arg Leu Leu Gly Lys Gln Ala Val Ala His Leu Val Ala Pro Phe
                165                 170                 175

Ile Ser Gly Val Tyr Ala Gly Asp Pro Lys Arg Leu Ser Ala Arg Ala
            180                 185                 190

Ala Phe Ala Lys Ile Phe Arg Leu Glu Asn Asn Tyr Gly Gly Leu Val
        195                 200                 205

Ala Gly Ala Ile Leu Ser Gly Lys Asp Arg Gln Ala Gln Lys Ala Lys
    210                 215                 220

Asn Thr Asp Leu Pro Gln Val Lys Ala Gly Glu Leu Gly Ser Phe Lys
225                 230                 235                 240

Gln Gly Ile Lys Met Leu Pro Glu Ala Ile Ala Thr Lys Leu Arg Ser
                245                 250                 255

Gln Gly Thr Pro Val Lys Gln Gln Trp Thr Leu Arg Ser Leu Asn Arg
            260                 265                 270

Gln Asp Asp Ile Tyr Ile Ala Lys Phe Asp Thr Pro Thr Gly Glu Glu
        275                 280                 285

Ile Val Met Ser Arg Ala Met Val Met Ala Thr Pro Ala Tyr Val Thr
    290                 295                 300

Ala Asp Leu Leu Lys Asp Tyr Leu Pro Ser Ala Ser Gln Ala Leu Ser
305                 310                 315                 320

Lys Ile Phe Tyr Pro Thr Val Ala Cys Val Val Leu Ala Tyr Pro Lys
                325                 330                 335

Thr Glu Phe Ala Tyr Asp Met Gln Gly Phe Gly Asn Leu Ile Pro Arg
            340                 345                 350

```
Thr Glu Gly Val Arg Thr Leu Gly Thr Ile Trp Ser Ser Ser Leu Phe
        355                 360             365

Ala Gly Arg Ala Pro Gln Gly Trp Gln Leu Leu Leu Asn Phe Ile Gly
        370             375         380

Gly Thr Leu Asp Pro Ala Leu Ala Lys Leu Ser Asp Ser Glu Ile Ile
385                 390             395                 400

Gln Ala Val His Gln Asp Leu Lys Lys Thr Ile Leu Arg Pro Asp Thr
            405             410             415

Lys Ala Glu Pro Lys Ala Ile Ala Val His Arg Trp Asp Lys Ala Ile
            420             425             430

Pro Gln Tyr Glu Ile Gly His Leu Gln Leu Leu Ala Thr Val Glu Ala
        435             440             445

Glu Leu Lys Lys Ser Gln Gly Leu Tyr Ile Ser Ala Asn Phe Ile Gly
        450             455             460

Gly Val Ala Leu Gly Asp Cys Ile Lys Arg Ser Leu Gln Glu Ala Ile
465                 470             475                 480

Lys Ile Glu Gln Phe Leu Ala Lys
            485

<210> SEQ ID NO 55
<211> LENGTH: 563
<212> TYPE: PRT
<213> ORGANISM: Artificial Sequence
<220> FEATURE:
<223> OTHER INFORMATION: Synthetic_PPO of Chlamydomonas reinhardtii
      (AF068635.1)

<400> SEQUENCE: 55

Met Met Leu Thr Gln Thr Pro Gly Thr Ala Thr Ala Ser Ser Arg Arg
1               5               10              15

Ser Gln Ile Arg Ser Ala Ala His Val Ser Ala Lys Val Ala Pro Arg
            20              25              30

Pro Thr Pro Phe Ser Val Ala Ser Pro Ala Thr Ala Ala Ser Pro Ala
        35              40              45

Thr Ala Ala Ala Arg Arg Thr Leu His Arg Thr Ala Ala Ala Ala Thr
    50              55              60

Gly Ala Pro Thr Ala Ser Gly Ala Gly Val Ala Lys Thr Leu Asp Asn
65              70              75              80

Val Tyr Asp Val Ile Val Val Gly Gly Gly Leu Ser Gly Leu Val Thr
            85              90              95

Gly Gln Ala Leu Ala Ala Gln His Lys Ile Gln Asn Phe Leu Val Thr
        100             105             110

Glu Ala Arg Glu Arg Val Gly Gly Asn Ile Thr Ser Met Ser Gly Asp
        115             120             125

Gly Tyr Val Trp Glu Glu Gly Pro Asn Ser Phe Gln Pro Asn Asp Ser
        130             135             140

Met Leu Gln Ile Ala Val Asp Ser Gly Cys Glu Lys Asp Leu Val Phe
145             150             155             160

Gly Asp Pro Thr Ala Pro Arg Phe Val Trp Trp Glu Gly Lys Leu Arg
                165             170             175

Pro Val Pro Ser Gly Leu Asp Ala Phe Thr Phe Asp Leu Met Ser Ile
            180             185             190

Pro Gly Lys Ile Arg Ala Gly Leu Gly Ala Ile Gly Leu Ile Asn Gly
        195             200             205

Ala Met Pro Ser Phe Glu Glu Ser Val Glu Gln Phe Ile Arg Arg Asn
    210             215             220
```

```
Leu Gly Asp Glu Val Phe Phe Arg Leu Ile Glu Pro Phe Cys Ser Gly
225                 230                 235                 240

Val Tyr Ala Gly Asp Pro Ser Lys Leu Ser Met Lys Ala Ala Phe Asn
                245                 250                 255

Arg Ile Trp Ile Leu Glu Lys Asn Gly Gly Ser Leu Val Gly Gly Ala
            260                 265                 270

Ile Lys Leu Phe Gln Glu Arg Gln Ser Asn Pro Ala Pro Pro Arg Asp
            275                 280                 285

Pro Arg Leu Pro Pro Lys Pro Lys Gly Gln Thr Val Gly Ser Phe Arg
        290                 295                 300

Lys Gly Leu Lys Met Leu Pro Asp Ala Ile Glu Arg Asn Ile Pro Asp
305                 310                 315                 320

Lys Ile Arg Val Asn Trp Lys Leu Val Ser Leu Gly Arg Glu Ala Asp
                325                 330                 335

Gly Arg Tyr Gly Leu Val Tyr Asp Thr Pro Glu Gly Arg Val Lys Val
                340                 345                 350

Phe Ala Arg Ala Val Ala Leu Thr Ala Pro Ser Tyr Val Val Ala Asp
            355                 360                 365

Leu Val Lys Glu Gln Ala Pro Ala Ala Ala Glu Ala Leu Gly Ser Phe
        370                 375                 380

Asp Tyr Pro Pro Val Gly Ala Val Thr Leu Ser Tyr Pro Leu Ser Ala
385                 390                 395                 400

Val Arg Glu Glu Arg Lys Ala Ser Asp Gly Ser Val Pro Gly Phe Gly
                405                 410                 415

Gln Leu His Pro Arg Thr Gln Gly Ile Thr Thr Leu Gly Thr Ile Tyr
            420                 425                 430

Ser Ser Ser Leu Phe Pro Gly Arg Ala Pro Glu Gly His Met Leu Leu
            435                 440                 445

Leu Asn Tyr Ile Gly Gly Thr Thr Asn Arg Gly Ile Val Asn Gln Thr
        450                 455                 460

Thr Glu Gln Leu Val Glu Gln Val Asp Lys Asp Leu Arg Asn Met Val
465                 470                 475                 480

Ile Lys Pro Asp Ala Pro Lys Pro Arg Val Val Gly Val Arg Val Trp
                485                 490                 495

Pro Arg Ala Ile Pro Gln Phe Asn Leu Gly His Leu Glu Gln Leu Asp
            500                 505                 510

Lys Ala Arg Lys Ala Leu Asp Ala Ala Gly Leu Gln Gly Val His Leu
            515                 520                 525

Gly Gly Asn Tyr Val Ser Gly Val Ala Leu Gly Lys Val Val Glu His
        530                 535                 540

Gly Tyr Glu Ser Ala Ala Asn Leu Ala Lys Ser Val Ser Lys Ala Ala
545                 550                 555                 560

Val Lys Ala
```

```
<210> SEQ ID NO 56
<211> LENGTH: 565
<212> TYPE: PRT
<213> ORGANISM: Artificial Sequence
<220> FEATURE:
<223> OTHER INFORMATION: Synthetic_PPO of Volvox carteri f. nagariensis
      hypothetical protein (XM_002955148.1)

<400> SEQUENCE: 56
```

```
Met Leu Thr Ser His Ala Thr Asn Ile Tyr Ala Asn Ser Lys Ala Arg
1               5                   10                  15
```

-continued

```
Leu Gln Ile Arg Glu Ile Ala Arg Pro Thr Val Thr Gly Val Ser Arg
        20                  25                  30

Ser Gly Val Leu Gln Asp Val Ala Ser Pro Leu Pro Arg Gln Ile Pro
        35                  40                  45

Arg Pro Ala Gln Arg Ala Ala Arg Pro Thr Ser Ala Thr Ala Thr Ser
    50                  55                  60

Ser Gly Val Pro Thr Ala Asp Ser Ala Arg Gly Thr Lys Ile Val Asp
65                  70                  75                  80

Asn Val Tyr Asp Val Ile Val Val Gly Gly Gly Leu Ser Gly Leu Val
                85                  90                  95

Thr Gly Gln Ala Leu Ser Ala Gln His Gly Val Asn Asn Phe Leu Val
            100                 105                 110

Thr Glu Ala Arg Glu Arg Val Gly Gly Asn Ile Thr Ser Met Ser Gly
            115                 120                 125

Asp Gly Tyr Val Trp Glu Glu Gly Pro Asn Ser Phe Gln Pro Asn Asp
    130                 135                 140

Ser Met Leu Gln Val Ala Val Asp Ala Gly Val Glu Lys Asp Leu Val
145                 150                 155                 160

Leu Gly Asp Pro Lys Ala Pro Arg Phe Val Tyr Trp Gln Asn Lys Leu
                165                 170                 175

Arg Pro Val Pro Ser Gly Pro Asp Ala Leu Thr Phe Asp Leu Met Ser
            180                 185                 190

Leu Pro Gly Lys Ile Arg Ala Gly Leu Gly Ala Ile Gly Leu Ile Asn
            195                 200                 205

Gly Ala Met Pro Asn Phe Glu Glu Ser Val Glu Gln Phe Ile Arg Arg
    210                 215                 220

Asn Leu Gly Asp Glu Val Phe Glu Arg Leu Ile Glu Pro Phe Cys Ser
225                 230                 235                 240

Gly Val Tyr Ala Gly Asp Pro Ser Lys Leu Ser Met Lys Ala Ala Phe
            245                 250                 255

Asn Arg Ile Trp Ile Leu Glu Lys Asp Gly Ser Ser Leu Val Gly Gly
            260                 265                 270

Ala Leu Lys Leu Phe Gln Glu Arg Arg Lys Asn Pro Pro Pro Pro Arg
            275                 280                 285

Asp Pro Arg Leu Pro Pro Lys Pro Lys Gly Gln Thr Val Gly Ser Phe
    290                 295                 300

Arg Leu Gly Leu Lys Met Leu Pro Glu Ala Ile Glu Arg Arg Ile Lys
305                 310                 315                 320

Asp Gln Val Arg Val Asn Trp Lys Leu Val Ser Leu Thr Arg Asp Gly
                325                 330                 335

Asp Arg Tyr Ser Leu Val Tyr Asp Thr Pro Glu Gly Arg Val Gln Cys
            340                 345                 350

Tyr Ser Arg Ala Val Ala Leu Thr Ala Pro Ser Tyr Val Val Ala Asp
            355                 360                 365

Leu Ile Lys Ala Glu Val Pro Ala Ala Ala Glu Ala Leu Ser Ser Phe
    370                 375                 380

Asp Tyr Pro Pro Val Gly Ala Val Thr Leu Ser Tyr Pro Leu Ser Ala
385                 390                 395                 400

Ile Arg Asp Asp Arg Lys Asp Ala Gln Gly Asn Val Pro Gly Phe Gly
                405                 410                 415

Gln Leu His Pro Arg Ser Gln Gly Val Thr Thr Leu Gly Thr Ile Tyr
            420                 425                 430
```

-continued

```
Ser Ser Ser Leu Phe Pro Gly Arg Ala Pro Pro Gly His Met Leu Leu
    435             440             445

Leu Asn Tyr Ile Gly Gly Ala Thr Asn Arg Gly Ile Val Asn Gln Thr
    450             455             460

Gln Glu Gln Leu Val Ala Gln Val Asp Lys Asp Leu Arg Leu Met Val
465             470             475             480

Leu Lys Pro Asp Ala Pro Ala Pro Arg Val Val Gly Val Arg Val Trp
                485             490             495

Pro Arg Ala Ile Pro Gln Phe Asn Ile Gly His Leu Glu Leu Leu Asp
                500             505             510

Lys Ala Arg Gly Ala Leu Glu Ala Lys Gly Trp Asn Gly Val Phe Leu
            515             520             525

Gly Gly Asn Tyr Val Ser Gly Val Ala Leu Gly Lys Val Val Glu Tyr
        530             535             540

Gly Tyr Glu Ser Ala Ala Lys Leu Ala Lys His Leu Thr Ala Ala Gln
545             550             555             560

Lys Gln Val Ala Val
            565
```

<210> SEQ ID NO 57
<211> LENGTH: 493
<212> TYPE: PRT
<213> ORGANISM: Artificial Sequence
<220> FEATURE:
<223> OTHER INFORMATION: Synthetic_PPO of Chondrus crispus
      (CHC_T00000813001) (XM_005718155.1)

<400> SEQUENCE: 57

```
Met Ala Val Ala Glu Gly Ala Thr Pro Ala Pro Ala Ala Ala Ser Ala
1               5               10              15

Thr Pro Ser Glu Val Asp Ala Leu Val Ile Gly Ser Gly Ile Ser Gly
            20              25              30

Ser Ser Leu Ala Phe Thr Leu Ser Gln Ala Ser Pro Ala Thr Ser Leu
        35              40              45

Leu Leu Thr Glu Ala Arg Pro Val Val Gly Gly Asn Val Ile Ser Arg
    50              55              60

Asn Glu Arg Gly Tyr Thr Trp Glu Glu Gly Pro Asn Thr Phe Gln Pro
65              70              75              80

Ala Pro His Ile Ile Arg Met Ala Val Asp Leu Gly Leu Arg Asp Asp
                85              90              95

Ile Val Leu Ala Asp His Thr Leu Pro Arg Phe Val Tyr Trp Asp Gln
            100             105             110

Arg Leu Phe Ala Leu Pro Leu Ser Pro Asn Asp Ile Pro Thr Phe Arg
        115             120             125

Leu Leu Ser Leu Pro Gly Ala Ile Arg Ala Gly Leu Gly Ala Ala Gly
    130             135             140

Phe Val Met Pro Pro Pro Lys Gly Arg Glu Glu Ser Ile Lys Asp Phe
145             150             155             160

Ile Thr Arg His Leu Gly Ala Glu Val Phe Gln Lys Met Ile Asp Pro
                165             170             175

Phe Val Ser Gly Val Tyr Ala Gly Asp Pro Ser Lys Leu Ser Met Ser
            180             185             190

Ala Ala Phe Lys Lys Ile Tyr Ala Leu Gln Glu Leu Gly Met Thr Gln
        195             200             205

Gly Ile Val Glu Gly Ala Ile Ile Arg Ile Gln Gln Lys Lys Lys Glu
    210             215             220
```

-continued

Ala Pro Pro Pro Asp Pro Glu Leu Pro Thr Trp Lys Gly Gly Ala Leu
225             230             235             240

Gly Ser Phe Arg Lys Gly Leu Gly Met Leu Pro Gln Ala Val Ala Glu
                245             250             255

Arg Leu Gly Asp Arg Val Lys Leu Ser Trp Lys Leu Val Ser Leu Gly
            260             265             270

Lys Glu Ser Asp Gly Arg Tyr Arg Ala Thr Tyr Glu Thr Pro Glu Gly
        275             280             285

Thr Lys Thr Val Ile Ala Arg Ser Val Ala Ile Thr Ala Pro Ala Asn
    290             295             300

Ala Thr Ala Gly Ile Leu Gly Asp Leu Ala Pro Gly Ile Lys Ala Ile
305             310             315             320

Glu Glu Ile Asn Tyr Pro Thr Val Trp Ser Ile Thr Leu Ala Tyr Pro
                325             330             335

Lys Asn Glu Phe Arg Glu Pro Leu Ser Gly Phe Gly Asn Leu Ile Pro
            340             345             350

Arg Ser Met Gly Ile Arg Thr Leu Gly Thr Ile Trp Ser Ser Cys Leu
        355             360             365

Phe Pro Gly Arg Ala Pro Glu Gly Met Glu Leu Leu Leu Ser Tyr Ile
    370             375             380

Gly Gly Ala Gln Asp Ala Ala Ile Lys Glu Leu Thr Glu Asp Glu Val
385             390             395             400

Val Ala Thr Val Asp Ala Asp Ile Lys Lys Ile Leu Met Lys Asp Gly
                405             410             415

Ser Glu Val Lys Pro Val Val Val Gly Ala Arg Lys Trp Asp Arg Ala
            420             425             430

Ile Pro Gln Tyr Asn Ile Gly Tyr Trp Asp Ile Met Gly Lys Ala Glu
        435             440             445

Glu Ala Val Lys Glu His Pro Gly Ile Phe Leu Gly Gly Asn Tyr Thr
    450             455             460

Ser Gly Val Ala Phe Gly Asp Cys Val Gln Trp Gly Ile Asp Thr Ala
465             470             475             480

Pro Lys Val Ala Glu Tyr Val Ala Ala Gln Ala Ala Val
            485             490

<210> SEQ ID NO 58
<211> LENGTH: 570
<212> TYPE: PRT
<213> ORGANISM: Artificial Sequence
<220> FEATURE:
<223> OTHER INFORMATION: Synthetic_PPO of Galdieria sulphuraria
      (XM_005708373.1)

<400> SEQUENCE: 58

Met Ser Ser Gly Phe Leu Cys Phe Cys Pro Asn Ala Val Ile Lys Ala
1               5               10              15

Ala Gln Tyr Val Arg Pro Lys Asn Thr Phe Ser Cys Lys His Tyr Thr
                20              25              30

Cys Lys Asn Arg Asn Ser Trp Phe Tyr Gly Asn Glu Leu Tyr Ile Lys
            35              40              45

Arg Arg Lys Val Val Glu Gln Gln Arg Thr Thr Ser His Val Ser Lys
        50              55              60

Leu Pro Phe Arg Gln Thr Trp Lys Ala Val Ser Ala Gln His Thr Glu
65              70              75              80

Asp Gly Glu Cys Ser Val Leu Ile Ile Gly Ser Gly Val Thr Gly Ser

-continued

```
                85                  90                  95

Thr Ala Ala Phe Gln Leu Ala Glu Ser Gly Ile Asp Val Leu Val Ala
            100                 105                 110

Glu Lys Asn Glu Gln Val Gly Gly Asn Ile Ile Ser Arg Lys Glu Gln
            115                 120                 125

Gly Phe Ile Trp Glu Glu Gly Pro Asn Thr Phe Gln Pro Thr Pro Asp
            130                 135                 140

Ile Leu Val Met Ile Glu Lys Leu Gly Leu Val Asp Lys Leu Val Leu
145                 150                 155                 160

Ala Asp Ala Lys Leu Pro Arg Tyr Val Phe Tyr Gln Asp Lys Leu His
            165                 170                 175

Lys Ile Pro Ser Ser Pro Phe Glu Ala Cys Gln Phe Ser Leu Leu Ser
            180                 185                 190

Thr Arg Gly Lys Leu Arg Ala Phe Leu Gly Ala Ile Gly Phe Ala Pro
            195                 200                 205

Met Asn Leu Lys Lys Lys Glu Glu Thr Val Arg Asp Phe Val Thr Arg
            210                 215                 220

His Leu Gly Glu Glu Val Tyr Glu Arg Leu Val Asp Pro Phe Ile Ser
225                 230                 235                 240

Gly Val Tyr Ala Gly Asp Pro Ser Lys Leu Ser Met Lys Ala Ala Phe
            245                 250                 255

Lys Arg Val Gln Ala Leu Glu Glu Lys Gly Val Thr Gln Ser Leu Ile
            260                 265                 270

Glu Gly Ala Ile Ile Arg Met Phe Glu Thr Lys Asn Ser Lys Gly Lys
            275                 280                 285

Lys Glu Thr Lys Gly Ser Leu Lys Val Pro Arg Gly Ser Leu Gly Ser
            290                 295                 300

Phe Lys Asp Gly Leu Gln Met Tyr Pro Gln Ser Val Gln Ser Lys Leu
305                 310                 315                 320

Ser Asn Lys Val Lys Thr Gly Trp Lys Leu Ile Arg Leu Glu Lys Ser
            325                 330                 335

Gly Asn Gly Ser Ser His Gln Ser Cys Glu Asp Tyr Phe Ala Val Phe
            340                 345                 350

Gln Ile Pro Asn Gly Ile Thr Lys Val Ile Arg Thr Lys Ala Leu Ile
            355                 360                 365

Phe Thr Ser Pro Ala Tyr Ile Thr Ala Ser Leu Leu Arg Pro Phe Ile
            370                 375                 380

Pro Asn Ala Ser Asp Leu Leu Glu Gln Ile Tyr Tyr Pro Cys Val Val
385                 390                 395                 400

Ser Val Ser Leu Ala Tyr Pro Ser Ser Ser Phe Arg Phe Pro Leu Ser
            405                 410                 415

Gly Phe Gly His Leu Ile Pro Arg Ser Thr Lys Ile Arg Thr Leu Gly
            420                 425                 430

Thr Ile Trp Ser Ser Ser Leu Phe Pro Tyr Arg Val Pro Glu Gly Tyr
            435                 440                 445

His Leu Leu Ser Ser Tyr Ile Gly Gly Ala Gln Asp Thr Asp Ile Ala
            450                 455                 460

Ser Leu Ser Glu Asp Gln Val Val Lys Gln Val Asp Ser Asp Ile Arg
465                 470                 475                 480

Lys Ile Leu Leu Arg Gln Asp Ala Ala Leu Pro Lys Val Leu Gly Val
            485                 490                 495

Arg His Trp Asn Lys Ala Ile Pro Gln Tyr Glu Leu Gly His Leu Ser
            500                 505                 510
```

-continued

```
Arg Met Glu Thr Ile Gln Ser Gln Val Ser Glu Thr Leu Pro Gly Val
        515             520             525

Phe Leu Gly Gly Asn Tyr Val Ser Gly Ile Ser Phe Gly Asp Cys Val
        530             535             540

Ser Phe Gly Met Gln Leu Ala Asp Gln Ala Ser Tyr Tyr Ile Lys Glu
545             550             555             560

Asn Thr Glu Leu Leu Ser Ser Thr Val Val
            565             570

<210> SEQ ID NO 59
<211> LENGTH: 482
<212> TYPE: PRT
<213> ORGANISM: Artificial Sequence
<220> FEATURE:
<223> OTHER INFORMATION: Synthetic_PPO of Pseudanabaena sp. ABRG5-3
      (WP_126386150.1)

<400> SEQUENCE: 59

Met Thr Ser Ala Gln Pro Thr Glu Val Asn Gln Pro Leu Asp Val Leu
1               5               10              15

Val Val Gly Ala Gly Ile Ser Gly Leu Ala Ile Ala His Glu Leu Ala
            20              25              30

Ile Ala Lys Asn Tyr Arg Val Leu Val Ala Glu Ala Gln Asp Arg Val
        35              40              45

Gly Gly Ala Ile Thr Ser Asn Arg Asn Asp Glu Gly Tyr Leu Trp Glu
    50              55              60

Glu Gly Pro Asn Ser Phe Gln Pro Ala Pro Glu Leu Leu Arg Leu Ala
65              70              75              80

Val Gln Val Gly Leu Lys Asp Glu Leu Val Leu Ala Asp Gly Lys Leu
            85              90              95

Pro Arg Phe Val Phe Leu Asn Gly Lys Leu Asn Ala Leu Pro Met Ser
            100             105             110

Pro Pro Thr Ala Ile Ala Ser Lys Ile Leu Thr Trp Gly Gly Lys Ile
        115             120             125

Arg Leu Ala Leu Gly Ala Leu Gly Phe Ala Arg Pro Ala Met Ser Gly
    130             135             140

Glu Glu Ser Val Asp Gln Phe Phe Ser Arg Leu Leu Gly Lys Gln Ala
145             150             155             160

Val Glu Arg Leu Val Ala Pro Phe Ile Ser Gly Val Tyr Ala Gly Asp
            165             170             175

Pro Lys Arg Leu Ser Ala Arg Ala Ala Phe Ser Lys Ile Phe Arg Leu
        180             185             190

Glu Asn Gly Tyr Gly Gly Leu Leu Ala Gly Ala Leu Leu Thr Ala Lys
        195             200             205

Glu Arg Lys Ala Gln Lys Leu Asn Asp Pro Asn Ile Pro Lys Val Lys
    210             215             220

Ser Gly Glu Leu Gly Ser Phe Arg Gln Gly Ile Lys Met Leu Pro Glu
225             230             235             240

Ala Ile Ala Thr Lys Leu Arg Asp Gln Gly Thr Ala Val Lys Gln Gln
            245             250             255

Trp Thr Leu Arg Ser Leu Glu Lys Gln Gly Asp Ile Tyr Ile Ser Gln
            260             265             270

Phe Asp Thr Pro Thr Gly Ala Glu Thr Ile Thr Ser Arg Ser Val Val
        275             280             285

Leu Thr Thr Pro Ala Tyr Val Ser Ala Lys Leu Leu Gln Asp Tyr Leu
```

-continued

```
           290                  295                  300

Pro Ala Ala Ser Gln Ala Leu Ser Glu Ile Phe Tyr Pro Thr Val Ala
305                  310                  315                  320

Cys Val Val Leu Ala Tyr Pro Lys Ser Glu Phe Ala Tyr Asp Met Lys
                     325                  330                  335

Gly Phe Gly Asn Leu Ile Pro Arg Thr Gln Gly Val Arg Thr Leu Gly
                     340                  345                  350

Thr Ile Trp Ser Ser Ser Leu Phe Ala Gly Arg Ala Pro Asp Gly Trp
                     355                  360                  365

Gln Leu Leu Leu Asn Phe Ile Gly Gly Thr Leu Asp Pro Ala Leu Ala
                     370                  375                  380

Lys Leu Ser Glu Ala Glu Ile Val Gln Ala Val His Gln Asp Leu Lys
385                  390                  395                  400

Lys Thr Ile Leu Arg Pro Asp Thr Lys Ala Glu Pro Lys Ala Ile Ala
                     405                  410                  415

Val His Val Trp Asp Lys Ala Ile Pro Gln Tyr Glu Ile Gly His Leu
                     420                  425                  430

Glu Arg Leu Ala Thr Ile Glu Ala Glu Leu Gln Lys Ser Gln Gly Leu
                     435                  440                  445

Tyr Val Ser Ala Asn Phe Ile Gly Gly Val Ser Leu Gly Asp Cys Ile
                     450                  455                  460

Lys Arg Gly Leu Gln Glu Ala Ser Lys Ile Asp Val Phe Leu Ser Ser
465                  470                  475                  480

Gln Gly
```

```
<210> SEQ ID NO 60
<211> LENGTH: 483
<212> TYPE: PRT
<213> ORGANISM: Artificial Sequence
<220> FEATURE:
<223> OTHER INFORMATION: Synthetic_PPO of Arthrospira platensis YZ
      (WP_014277531.1)

<400> SEQUENCE: 60

Met Thr Asn Leu Val Asp Ser Leu Ile Val Gly Ala Gly Ile Ser Gly
1                5                   10                  15

Leu Ser Leu Ala His Ser Leu Asn Arg Glu Lys Asn Pro Arg Ser Pro
                20                  25                  30

Leu Lys Val Leu Val Thr Glu Ser Gln Asn Arg Val Gly Gly Asn Ile
            35                  40                  45

Thr Thr Gly Arg Ala Ser Asp Phe Leu Trp Glu Glu Gly Pro Asn Ser
        50                  55                  60

Phe Ala Pro Thr Pro Glu Leu Leu Gly Leu Ala Val Asp Leu Gly Leu
65                  70                  75                  80

Lys Gln Glu Leu Ile Phe Ala Asp Arg Lys Leu Pro Arg Tyr Val Tyr
                85                  90                  95

Trp Asn His Lys Leu His Pro Val Pro Met Thr Pro Pro Ala Leu Leu
                100                 105                 110

Ser Ser Gln Leu Ile Ser Pro Arg Gly Lys Leu Arg Ala Ala Leu Gly
            115                 120                 125

Ala Ile Gly Phe Val Pro Pro Val Gly Ala His Leu Ser Gln Gln
            130                 135                 140

Arg Gly Glu Glu Thr Ile Thr Gln Phe Phe His Arg His Leu Gly Ser
145                 150                 155                 160

Glu Val Leu Glu Arg Leu Val Gln Pro Phe Val Ser Gly Val Tyr Ala
```

```
                      165               170               175

Gly Asp Pro Gln Gln Leu Ala Val Arg Ser Ala Phe Ser Arg Leu Val
                180               185               190

Ala Ala Glu Asp Ala Gly Gly Ala Leu Leu Pro Gly Phe Val Arg Ser
                195               200               205

Arg Leu Asn Lys Lys Thr Thr Lys Asp Thr Thr Pro Asp Pro Asn Ile
        210               215               220

Pro Lys Thr Arg Pro Gly Glu Leu Gly Ser Phe Arg Tyr Gly Leu Glu
225               230               235               240

Thr Leu Pro Glu Thr Leu Ala Ser Lys Leu Gly Asp Arg Val Lys Leu
                245               250               255

Asn Trp Thr Leu Asp Arg Phe Tyr Pro Thr Pro His Gln Thr Tyr Ile
                260               265               270

Ala Glu Phe Ser Thr Pro Asp Gly Pro Gln Gln Val Glu Thr Arg Thr
                275               280               285

Leu Ala Leu Met Thr Pro Ala His Val Ser Ala Arg Leu Leu Gln Pro
        290               295               300

Leu His Ser Gln Ile Ala Ser Ala Leu Ser Gln Ile Pro Tyr Pro Pro
305               310               315               320

Val Ala Cys Val Val Leu Ala Tyr Pro Lys Ser Ala Leu Lys Gln Gln
                325               330               335

Leu Lys Gly Phe Gly Asn Leu Ile Pro Arg His Gln Gly Ile Arg Thr
                340               345               350

Leu Gly Thr Ile Trp Thr Ser Ser Leu Phe Pro Gly Arg Ala Pro Glu
                355               360               365

Ser Trp Gln Val Leu Ser Asn Tyr Ile Gly Gly Ala Thr Asp Pro Glu
        370               375               380

Ile Gly Glu Met Asp Asp Asp Gln Ile Val Ala Ala Val His Gln Asp
385               390               395               400

Leu Arg Gln Ile Leu Leu Ala Glu Asp Val Pro Pro Lys Val Leu Ala
                405               410               415

Val His Leu Trp Arg Arg Ala Ile Pro Gln Tyr Thr Leu Gly His Gln
                420               425               430

Asp Arg Leu Asn Ser Ile Asn Ala Gly Leu Arg Ser Leu Pro Gly Leu
        435               440               445

Tyr Leu Cys Ser Asn Tyr Ile Asp Gly Val Ser Val Gly Asp Cys Val
        450               455               460

Arg Arg Gly Gln Gln Trp Ala Ser Gln Ile Gln Ser His Leu His Pro
465               470               475               480

Thr Ala Asn
```

```
<210> SEQ ID NO 61
<211> LENGTH: 469
<212> TYPE: PRT
<213> ORGANISM: Artificial Sequence
<220> FEATURE:
<223> OTHER INFORMATION: Synthetic_PPO of Gloeobacter kilaueensis JS1
      (WP_023175091)

<400> SEQUENCE: 61

Met Gly Arg Met Ser Val Ala Ala Glu Pro Leu Asp Val Leu Val Val
1               5                 10                15

Gly Ala Gly Leu Ser Gly Leu Ala Leu Ala Trp His Leu Gln Arg Ser
                20                25                30

Gly Arg Arg Val Leu Val Cys Glu Ala Thr Glu Arg Val Gly Gly Ala
```

-continued

```
          35                    40                    45
Ile Ser Ser Glu Leu Ile Asp Gly Phe Thr Cys Glu Gly Gly Pro Asn
      50                    55                    60

Ser Phe Gln Ser Thr Arg Pro Leu Gln Glu Leu Leu Val Glu Leu Gln
65                    70                    75                    80

Leu Glu Glu Arg Leu Val Phe Ala Glu Glu Arg Leu Ala Arg Phe Val
                  85                    90                    95

Trp Trp Glu Asn Arg Leu Arg Pro Val Pro Met Ser Pro Ala Gln Phe
                 100                   105                   110

Val Arg Ala Asp Leu Leu Ser Trp Pro Gly Lys Leu Arg Cys Leu Ser
                 115                   120                   125

Glu Phe Phe Val Pro Pro Leu Ser Glu Pro Arg Glu Glu Thr Val Ala
      130                   135                   140

Glu Phe Val Leu Arg Arg Phe Gly Asp Glu Ala Leu Asn Arg Leu Ile
145                   150                   155                   160

Glu Pro Phe Ile Ala Gly Val Phe Ala Gly Asp Ala Gly Gln Leu Ser
                 165                   170                   175

Ala Asp Ala Ala Leu Ala Pro Leu Val Glu Leu Glu Arg Gln Ala Gly
                 180                   185                   190

Ser Val Leu Arg Gly Leu Trp Gln Arg Arg Asn Arg Gly Val Leu Thr
                 195                   200                   205

Pro Gln Arg Leu Cys Thr Leu Arg Gly Gly Ile Glu Gln Leu Pro Arg
      210                   215                   220

Ala Ile Ala Arg Arg Leu Gln Ser Gln Leu Arg Phe Gln Ser Arg Leu
225                   230                   235                   240

Glu Ala Leu Glu Pro Leu Ala Gly Gly Trp Gln Ala Ile Val Leu Asp
                 245                   250                   255

Gly Arg Gly Glu Ala Gln Ala Ile Ser Ala Arg Ser Val Ala Leu Ala
                 260                   265                   270

Ala Pro Ala Trp Ala Ile Ala Pro Val Leu Ala Arg Leu Asp Pro Ser
                 275                   280                   285

Leu Gly Arg Ala Leu Glu Ser Ile Tyr Tyr Pro Pro Val Ala Ala Val
      290                   295                   300

Ser Leu Gly Tyr Ser Lys Ser Gln Leu Pro Asn Leu Ser Glu Gly Phe
305                   310                   315                   320

Gly His Leu Ile Pro Arg Gly Gln Ser Leu Arg Ser Leu Gly Val Ile
                 325                   330                   335

Tyr Asn Ser Cys Leu Phe Arg His Ala Ala Pro Thr Ser Trp Arg Leu
                 340                   345                   350

Phe Thr Cys Phe Leu Gly Gly Thr Thr Asp Pro Leu Ile Ala Asp Leu
                 355                   360                   365

Ser Asp Gly Glu Leu Ala Asn Leu Ala His Arg Glu Leu Gln Ala Val
      370                   375                   380

Leu Asp Phe Gln Ser Ser Tyr Gln Leu Leu Arg Val Ala Arg Trp Pro
385                   390                   395                   400

Arg Ala Ile Pro Gln Tyr Ala Leu Gly His Ile Thr Lys Gln Glu Arg
                 405                   410                   415

Ile Glu Arg Tyr Leu Ala Glu Leu Pro Gly Leu Phe Leu Val Gly Asn
                 420                   425                   430

Tyr Phe Gly Gly Ile Ser Val Gly Asp Cys Val Arg Gln Ala Arg Leu
                 435                   440                   445

Lys Ala Asp Ser Val Leu Gln Phe Leu Thr Arg Thr Ala Ala Asn Gly
      450                   455                   460
```

```
Arg Leu Asn Leu Ala
465

<210> SEQ ID NO 62
<211> LENGTH: 466
<212> TYPE: PRT
<213> ORGANISM: Artificial Sequence
<220> FEATURE:
<223> OTHER INFORMATION: Synthetic_PPO of Gloeobacter violaceus PCC 7421
      (WP_011140945)

<400> SEQUENCE: 62

Met Asn Thr Ala Glu Glu Leu Leu Asp Val Leu Val Val Gly Ala Gly
1               5                   10                  15

Leu Ser Gly Leu Ala Leu Ala Trp Lys Leu Lys Arg Ala Gly Cys Thr
            20                  25                  30

Phe Leu Val Cys Gln Ala Gly Glu Arg Val Gly Gly Ala Ile Thr Thr
        35                  40                  45

Ala Ile Ala Asp Gly Phe Val Cys Glu Gly Gly Pro Asn Ser Phe Gln
    50                  55                  60

Glu Ser Pro Pro Leu Ile Glu Leu Leu Thr Gln Leu Gln Leu Glu Asp
65                  70                  75                  80

Gln Ile Val Thr Ala Asp Pro Arg Leu Ala Arg Phe Val Trp Trp Glu
                85                  90                  95

Asn Arg Leu Arg Ser Val Pro Leu Thr Pro Ala Gln Leu Val Arg Ser
            100                 105                 110

Asp Leu Leu Ser Trp Ser Gly Lys Ala Arg Leu Leu Trp Glu Leu Phe
            115                 120                 125

Val Pro Ala Leu Gly Glu Pro Arg Glu Glu Thr Val Ala Glu Phe Val
    130                 135                 140

Leu Arg Arg Phe Gly Glu Glu Val Leu Ser Arg Leu Val Asp Pro Leu
145                 150                 155                 160

Val Ser Gly Met Cys Ala Gly Asp Val Gly Gln Leu Ser Ile Glu Ala
                165                 170                 175

Thr Phe Glu Arg Leu Val Asp Leu Glu Arg Arg His Gly Gly Val Leu
            180                 185                 190

Arg Gly Leu Trp Arg Thr Ala Arg Thr Arg Pro Pro Phe Lys Arg Leu
            195                 200                 205

Cys Thr Leu Arg Gly Gly Leu Glu Gln Leu Pro Gln Ala Leu Ala Gln
    210                 215                 220

Arg Leu Gln Pro Gln Ile Leu Leu Ser His Arg Leu Glu Ala Leu Glu
225                 230                 235                 240

His Leu Ala Gly Asp Arg Trp Arg Ala Val Val Ala Gly Pro Gln Gly
                245                 250                 255

Glu Pro Val Ala Ile Ala Ala Arg Thr Val Ile Leu Ser Gly Ser Ala
            260                 265                 270

His Ala Met Ala Ser Val Leu Arg Pro Leu Asp Ala Gly Leu Gly Arg
            275                 280                 285

Ala Leu Glu Ser Ile Tyr Tyr Pro Pro Val Val Ser Ile Ser Leu Ala
    290                 295                 300

Tyr Ser Lys Ser Gln Val Pro Asn Ala Pro Glu Gly Phe Gly His Leu
305                 310                 315                 320

Ile Pro Arg Asn Gln Thr Leu Arg Ser Leu Gly Val Ile Trp Asn Ser
            325                 330                 335

Ser Leu Phe Pro His Thr Ala Pro Pro Asn Trp Arg Leu Tyr Thr Cys
```

-continued

```
                340             345             350
Phe Val Gly Gly Thr Thr Asp Pro Ala Thr Pro Asn Leu Ser Asp Thr
        355             360             365

Glu Leu Ala Ser Leu Ala His Arg Glu Leu Gln Thr Val Leu Gly Phe
    370             375             380

Gln Ala Gly Tyr Gln Leu Leu Arg Val Thr Arg Trp Pro Gln Ala Ile
385             390             395             400

Pro Gln Tyr Ala Leu Gly His Pro Ser Lys Gln Glu Arg Val Glu Arg
            405             410             415

Ala Leu Leu Gly Leu Pro Gly Leu Phe Leu Val Gly Asn Tyr Phe Gly
        420             425             430

Gly Ile Ser Leu Gly Asp Cys Val Arg His Ser Gly Ala Val Ala Ser
        435             440             445

Arg Val Leu Gln Phe Leu Thr Thr Val Ala Ser Asn Gly Ser Leu Arg
    450             455             460

Pro Ala
465

<210> SEQ ID NO 63
<211> LENGTH: 538
<212> TYPE: PRT
<213> ORGANISM: Artificial Sequence
<220> FEATURE:
<223> OTHER INFORMATION: Synthetic_PPO of Panicum hallii var. hallii
      (PUZ57154.1)

<400> SEQUENCE: 63

Met Val Ala Ala Ala Ala Ala Ala Met Ala Thr Ala Ala Ser Ala Gly
1               5               10              15

Val Pro Pro Leu Ser Gly Pro Arg Gly Pro Ala Arg Leu Arg Ser Arg
        20              25              30

Gly Val Ile Val Arg Cys Ala Ala Val Ala Gly Gly Ala Ala Glu Ala
        35              40              45

Pro Thr Ser Thr Gly Ala Arg Val Ser Ala Asp Cys Val Val Val Gly
    50              55              60

Gly Gly Ile Ser Gly Leu Cys Thr Ala Gln Ala Leu Ala Thr Lys His
65              70              75              80

Gly Val Gly Asp Val Leu Val Thr Glu Ala Arg Ala Arg Pro Gly Gly
            85              90              95

Asn Ile Thr Thr Val Glu Arg Pro Glu Glu Gly Tyr Leu Trp Glu Glu
        100             105             110

Gly Pro Asn Ser Phe Gln Pro Ser Asp Pro Val Leu Thr Met Ala Val
        115             120             125

Asp Ser Gly Leu Lys Asp Asp Leu Val Phe Gly Asp Pro Asn Ala Pro
    130             135             140

Arg Phe Val Leu Trp Glu Gly Lys Leu Arg Pro Val Pro Ser Lys Pro
145             150             155             160

Ala Asp Leu Pro Phe Phe Asp Leu Met Ser Ile Pro Gly Lys Leu Arg
            165             170             175

Ala Gly Phe Gly Ala Leu Gly Ile Arg Pro Pro Pro Gly Arg Glu
        180             185             190

Glu Ser Val Glu Glu Phe Val Arg Arg Asn Leu Gly Ala Glu Val Phe
        195             200             205

Glu Arg Leu Ile Glu Pro Phe Cys Ser Gly Val Tyr Ala Gly Asp Pro
    210             215             220
```

```
Ser Lys Leu Ser Met Lys Ala Ala Phe Gly Lys Val Trp Arg Leu Glu
225                 230                 235                 240

Glu Ala Gly Gly Ser Ile Ile Gly Gly Thr Ile Lys Thr Ile Gln Glu
                245                 250                 255

Arg Gly Lys Asn Pro Lys Pro Pro Arg Asp Pro Arg Leu Pro Lys Pro
                260                 265                 270

Lys Gly Gln Thr Val Ala Ser Phe Arg Lys Gly Leu Ala Met Leu Pro
                275                 280                 285

Asn Ala Ile Thr Ser Ser Leu Gly Ser Lys Val Lys Leu Ser Trp Lys
            290                 295                 300

Leu Thr Ser Ile Thr Lys Ser Asp Gly Lys Gly Tyr Val Leu Val Tyr
305                 310                 315                 320

Glu Thr Pro Glu Gly Val Val Ser Val Gln Ala Lys Ser Val Ile Met
                325                 330                 335

Thr Ile Pro Ser Tyr Val Ala Ser Asp Ile Leu Arg Pro Leu Ser Ser
                340                 345                 350

Asp Ala Ala Asp Ala Leu Ser Arg Phe Tyr Tyr Pro Pro Val Ala Ala
            355                 360                 365

Val Thr Ile Ser Tyr Pro Lys Glu Ala Ile Arg Lys Glu Cys Leu Ile
            370                 375                 380

Asp Gly Glu Leu Gln Gly Phe Gly Gln Leu His Pro Arg Ser Gln Gly
385                 390                 395                 400

Val Glu Thr Leu Gly Thr Ile Tyr Ser Ser Ser Leu Phe Pro Asn Arg
                405                 410                 415

Ala Pro Ala Gly Arg Val Leu Leu Leu Asn Tyr Ile Gly Gly Ala Thr
                420                 425                 430

Asn Thr Gly Ile Val Tyr Lys Ser Glu Ser Glu Leu Val Glu Ala Val
            435                 440                 445

Asp Arg Asp Leu Arg Lys Met Leu Ile Asn Pro Arg Ala Val Asp Pro
            450                 455                 460

Leu Val Leu Gly Val Arg Val Trp Pro Gln Ala Ile Pro Gln Phe Leu
465                 470                 475                 480

Val Gly His Leu Asp Leu Leu Glu Ala Ala Lys Ser Ala Leu Gly Arg
                485                 490                 495

Gly Gly Tyr Asp Gly Leu Phe Leu Gly Gly Asn Tyr Val Ala Gly Val
                500                 505                 510

Ala Leu Gly Arg Cys Val Glu Gly Ala Tyr Glu Ser Ala Ser Gln Ile
            515                 520                 525

Ser Asp Phe Leu Thr Lys Tyr Ala Tyr Lys
    530                 535
```

<210> SEQ ID NO 64
<211> LENGTH: 563
<212> TYPE: PRT
<213> ORGANISM: Artificial Sequence
<220> FEATURE:
<223> OTHER INFORMATION: Synthetic_PPO of Porphyra umbilicalis
      (OSX75961.1)

<400> SEQUENCE: 64

```
Met Ala Ala Phe Val Pro Ala Ala Ala Ala Pro Trp Thr Ala Arg
1               5                   10                  15

Arg Ser Ala Phe Ala Gly Ala Pro Ala Ala Ala Gly Ser Arg Arg Pro
                20                  25                  30

Ala Met Ala Gly Ala Ala Ala Pro Leu Arg Ser Leu Val Pro Arg Ala
            35                  40                  45
```

-continued

```
Ile Pro Pro Pro Gly Ala Ala Arg Arg Ala Ala Pro Ser Pro Arg Met
    50              55              60

Ala Ala Gly Gly Ala Pro Asp Glu Val Val Asp Ala Leu Val Val Gly
65              70              75              80

Ser Gly Val Ser Gly Ser Thr Leu Ala Tyr Arg Leu His Ser Arg Gly
            85              90              95

Val Ser Met Leu Leu Thr Glu Ala Arg Asp Val Val Gly Gly Asn Val
        100             105             110

Ile Ser Arg Ser Ala Asn Gly Tyr Thr Trp Glu Glu Gly Pro Asn Thr
    115             120             125

Phe Gln Pro Ala Pro His Ile Leu Arg Leu Ala Val Asp Val Gly Leu
    130             135             140

Lys Asp Asp Leu Val Phe Ala Asp His Thr Leu Pro Arg Phe Val Tyr
145             150             155             160

Trp Asn Gly Asn Leu Phe Ala Leu Pro Met Gly Pro Ala Asp Ile Pro
            165             170             175

Lys Phe Arg Leu Leu Ser Pro Leu Gly Ala Val Arg Ala Gly Leu Gly
        180             185             190

Ala Ala Gly Phe Val Trp Pro Asn Trp Ser Gly Lys Glu Glu Ser Val
        195             200             205

Lys Glu Phe Ile Thr Arg His Leu Gly Ala Glu Val Phe Ala Lys Met
    210             215             220

Ile Asp Pro Phe Val Ser Gly Val Tyr Ala Gly Asp Pro Ser Ser Leu
225             230             235             240

Ala Ile Arg Gly Ala Phe Gly Lys Ile Tyr Ala Leu Gln Asn Leu Gly
            245             250             255

Ile Thr Gln Gly Ile Val Glu Gly Ala Ile Ile Arg Leu Arg Gln Arg
        260             265             270

Lys Ala Glu Ala Gly Glu Pro Asp Pro Glu Leu Pro Val Val Lys Gly
        275             280             285

Gly Ala Leu Gly Ser Phe Arg Glu Gly Leu Gly Met Leu Pro Lys Ala
    290             295             300

Val Ala Ala Lys Leu Gly Asp Ala Val Arg Leu Gly Trp Thr Leu Thr
305             310             315             320

Glu Leu Arg Lys Leu Pro Gly Ser Ala Pro Gly Tyr Glu Ala Val Tyr
            325             330             335

Ser Thr Pro Asp Gly Pro Arg Thr Val His Ala Lys Thr Val Ser Leu
            340             345             350

Thr Ala Pro Ala Gly Ala Ala Ser Ser Ile Leu Gly Gly Met Leu Pro
        355             360             365

Ala Ala Lys Ala Leu Asp Asp Val Tyr Tyr Pro Cys Val Trp Ser Val
    370             375             380

Thr Leu Ser Tyr Pro Thr Ala Ala Phe Lys Arg Pro Leu Lys Gly Phe
385             390             395             400

Gly Asn Leu Ile Pro Arg Ser Met Gly Val Arg Thr Leu Gly Thr Ile
            405             410             415

Trp Ser Ser Ser Leu Phe Pro Gly Arg Ala Pro Pro Gly Arg Glu Leu
            420             425             430

Leu Leu Ser Tyr Ile Gly Gly Ala Gln Asp Lys Gly Ile Ala Asp Leu
        435             440             445

Ser Glu Glu Glu Val Val Ala Ala Val Asp Gly Asp Ile Lys Ala Leu
    450             455             460
```

-continued

```
Leu Leu Ser Glu Gly Ala Ala Asp Glu Val Pro Val Val Val Gly Val
465             470             475             480

Arg Lys Trp Pro Arg Ala Ile Pro Gln Tyr Val Arg Gly His Leu Glu
            485             490             495

Leu Val Ala Gly Val Arg Glu Ala Ala Ala Glu Cys Pro Gly Leu
            500             505             510

Phe Leu Gly Gly Asn Tyr Ala Ser Gly Val Ala Phe Gly Asp Cys Val
            515             520             525

Ala Trp Gly Asp Lys Ala Ala Ala Glu Val Val Ala Thr Leu Gly Asp
            530             535             540

Met Pro Glu Thr Gly Ala Pro Met Ala Met Pro Glu Thr Ala Thr Pro
545             550             555             560

Ala Ser Val

<210> SEQ ID NO 65
<211> LENGTH: 533
<212> TYPE: PRT
<213> ORGANISM: Artificial Sequence
<220> FEATURE:
<223> OTHER INFORMATION: Synthetic_PPO of Ostreococcus tauri
      (XP_003079975.1)

<400> SEQUENCE: 65

Met Ser Arg Ala Gln Val Ser Leu Ala Pro Ala Arg Val Ala Asp Arg
1               5               10              15

Arg Arg Val Gly Arg Thr Arg Ala Ala Arg Arg Ala Val Ala Val Arg
            20              25              30

Ala Ser Thr Val Glu Arg Asp Val Val Ile Val Gly Ala Gly Val Ser
            35              40              45

Gly Leu Ser Thr Ala Phe Thr Leu Ala Lys Lys Thr Met Pro Asn Ala
    50              55              60

Ser Val Met Val Thr Glu Ala Arg Asp Arg Val Gly Gly Asn Ile Thr
65              70              75              80

Ser Lys Ser Asp Gly Thr Tyr Thr Trp Glu Glu Gly Pro Asn Ser Tyr
            85              90              95

Gln Pro Gly Asp Ala Ile Leu Thr Leu Ala Cys Asp Ala Gly Met Arg
            100             105             110

Asp Asp Ile Leu Leu Ala Asp Pro Ala Ser Asn Arg Tyr Val Leu Trp
            115             120             125

Asp Gly Lys Leu Arg Ile Leu Pro His Ser Ile Glu Ser Ala Val Leu
            130             135             140

Gly Asp Phe Leu Thr Trp Pro Gly Lys Ile Arg Ala Gly Leu Gly Ala
145             150             155             160

Ile Gly Ile Arg Pro Pro Ala Pro Gly Lys Glu Glu Ser Val Lys Glu
            165             170             175

Phe Val Ser Arg Asn Leu Gly Thr Glu Ala Phe Glu Arg Leu Ile Glu
            180             185             190

Pro Phe Cys Ser Gly Val Tyr Ala Gly Asp Pro Ala Ser Leu Ser Ser
            195             200             205

Val Ala Ala Thr Gly Arg Val Gln Arg Leu Glu Pro Leu Gly Gly Ser
            210             215             220

Leu Val Val Gly Ala Leu Lys Ala Gln Ala Glu Ala Ala Lys Ala Lys
225             230             235             240

Lys Glu Ser Gly Phe Lys Arg Asp Pro Arg Leu Pro Glu Val Lys Gly
            245             250             255
```

-continued

```
Gln Thr Val Gly Ser Phe Arg Gly Gly Leu Lys Thr Phe Pro Glu Gly
            260                 265                 270

Leu Ala Lys Gln Leu Gly Asp Asp Val Val Lys Cys Asn Trp Lys Leu
        275                 280                 285

Val Asn Val Asn Lys Ala Ala Glu Gly Gly Tyr Thr Cys Glu Tyr Asp
        290                 295                 300

Thr Pro Glu Gly Arg Arg Thr Val Ile Ala Lys Cys Leu Leu Leu Thr
305                 310                 315                 320

Ala Pro Ala Tyr Val Thr Ala Glu Ile Val Lys Asp Met Ala Pro Ala
                325                 330                 335

Ala Ser Thr Ala Leu Asn Lys Phe Tyr Tyr Pro Pro Val Ala Ser Val
            340                 345                 350

Thr Val Ser Tyr Lys Lys Asp Ser Phe Arg Leu Asp Gly Thr Ser Ala
            355                 360                 365

Leu Pro Glu Gly Gly Leu Thr Gly Phe Gly Gln Leu His Pro Arg Ser
        370                 375                 380

Gln Gly Ile Arg Thr Leu Gly Thr Ile Tyr Ser Ser Ser Leu Phe Lys
385                 390                 395                 400

Asp Asp Lys Arg Gln Pro Asp Asp Glu Phe Met Ile Leu Asn Tyr Ile
                405                 410                 415

Gly Gly Ala Arg Asp Val Ala Ile Lys Asp Leu Ser Glu Asp Glu Leu
            420                 425                 430

Val Gln Gln Val His Glu Asp Ala Leu Lys Thr Ile Leu Lys Pro Gly
        435                 440                 445

Thr Pro Leu Pro Lys Val Val Gly Val Lys Leu Trp Glu Lys Ala Ile
        450                 455                 460

Pro Gln Phe Asn Leu Gly His Leu Asp Val Leu Ala Glu Ala Glu Asn
465                 470                 475                 480

Ala Leu Glu Ala Ala Ala Cys Gly Glu Lys Asp Gly Leu Phe Leu Gly
                485                 490                 495

Gly Asn Tyr Thr Ala Gly Val Ala Leu Gly Arg Cys Val Glu Phe Gly
            500                 505                 510

Val Glu Gln Ala Asp Glu Val Ala Thr Phe Leu Lys Ser Ala Lys Lys
        515                 520                 525

Leu Thr Ala Ala Val
    530

<210> SEQ ID NO 66
<211> LENGTH: 551
<212> TYPE: PRT
<213> ORGANISM: Artificial Sequence
<220> FEATURE:
<223> OTHER INFORMATION: Synthetic_PPO of Ectocarpus siliculosus
      (CBJ31610.1)

<400> SEQUENCE: 66

Met Leu Ala Ala Val Gly Thr Ala Ala Gly Leu Leu Ala Val Ala Gly
1               5                   10                  15

Ile Thr Pro Ala Tyr Gly Phe Val Thr Pro Ser Thr Ala Trp Asn Thr
            20                  25                  30

Ala Arg Gly Ser Gly His Gly Thr Ala Ser Arg Ala Ala Thr Thr Met
        35                  40                  45

Ala Ala Asp Ile Phe Lys Ala Gly Pro Val Glu Lys Val Asp Cys Ala
        50                  55                  60

Val Val Gly Ser Gly Ile Ser Gly Ser Thr Leu Gly Phe Tyr Leu Asp
65                  70                  75                  80
```

-continued

```
Lys Lys Gly Val Asp Cys Val Val Leu Glu Ala Arg Asp Gln Val Gly
                85              90              95

Gly Asn Val Ile Ser Lys Lys Glu Asp Gly Phe Leu Trp Glu Glu Gly
            100             105             110

Pro Asn Ser Phe Gln Pro Thr Pro Tyr Ile Met Arg Thr Thr Val Asp
            115             120             125

Leu Gly Leu Lys Glu Asp Leu Val Leu Ala Asp Pro Thr Leu Pro Arg
    130             135             140

Phe Val Phe Trp Glu Gly Gly Leu Phe Pro Leu Pro Ser Ser Leu Gln
145             150             155             160

Ser Ile Ile Thr Asp Phe Trp Leu Leu Ser Trp Pro Gly Lys Ile Arg
                165             170             175

Ala Gly Leu Gly Ala Ile Gly Leu Val Leu Pro Pro Pro Ser Asp Tyr
            180             185             190

Glu Glu Ser Val Lys Glu Phe Val Thr Arg His Leu Gly Pro Glu Ala
            195             200             205

Phe Glu Arg Leu Ile Asp Pro Phe Val Ser Gly Val Tyr Ala Gly Asp
    210             215             220

Pro Ser Lys Leu Ala Ile Lys Ala Ala Leu Lys Lys Val Ala Arg Leu
225             230             235             240

Glu Val Leu Gly Gly Pro Gly Leu Ile Asp Gly Ala Ile Leu Arg Leu
            245             250             255

Lys Glu Arg Ala Arg Gln Glu Lys Glu Leu Pro Glu Pro Leu Gln Ser
            260             265             270

Glu Asp Leu Pro Thr Tyr Gln Gly Gly Ser Leu Gly Ser Phe Arg Glu
            275             280             285

Gly Leu Gln Met Leu Pro Asn Ala Ala Leu Lys Ala Met Gly Lys Asp
    290             295             300

Lys Met Arg Thr Ser Trp Val Met Lys Gly Ile Lys Arg Ser Glu Asp
305             310             315             320

Gly Gly Tyr Leu Leu Ala Phe Asp Thr Pro Lys Gly Pro Lys Arg Leu
            325             330             335

Gln Ala Lys Val Ala Val Cys Thr Ala Pro Ala His Arg Leu Ala Ser
            340             345             350

Val Glu Gly Leu Arg Asp Ile Val Pro Glu Ala Ala Arg Leu Asp Glu
            355             360             365

Val Tyr Tyr Pro Pro Val Ala Ser Val Thr Leu Ala Tyr Pro Lys Ser
    370             375             380

Ser Phe Lys Val Asp Leu Thr Gly Phe Gly Asn Leu Ile Pro Arg Lys
385             390             395             400

Met Lys Ile Arg Thr Leu Gly Thr Ile Trp Ser Ser Ser Leu Phe Pro
            405             410             415

Gly Arg Ala Pro Glu Gly Tyr Ala Met Leu Leu Asn Tyr Ile Gly Gly
            420             425             430

Ala Gln Asp Pro Ala Ile Lys Asp Leu Ser Asp Asp Glu Ile Val Ala
            435             440             445

Glu Cys Asp Arg Asp Ile Arg Thr Ile Leu Leu Lys Asp Asp Ala Pro
    450             455             460

Pro Pro Lys Val Leu Gly Cys Arg Leu Trp Lys Thr Ala Ile Pro Gln
465             470             475             480

Tyr Gln Arg Gly His Leu Ala Ile Leu Glu Glu Leu Gln Glu Gly Leu
            485             490             495
```

-continued

```
Lys Ala Ala Pro Gly Leu Arg Met Gly Gly Asn Tyr Ile Thr Gly Val
                500                 505                 510

Ala Phe Gly Asp Cys Val Gln Tyr Gly Tyr Glu Glu Ala Glu Arg Ile
                515                 520                 525

Glu Glu Met Leu Lys Ser Gly Ala Leu Asp Gly Gln Gln Ser Val Ser
            530                 535                 540

Asp Lys Glu Ala Val Ala Ala
545                 550

<210> SEQ ID NO 67
<211> LENGTH: 473
<212> TYPE: PRT
<213> ORGANISM: Artificial Sequence
<220> FEATURE:
<223> OTHER INFORMATION: Synthetic_PPO of Nannochloropsis gaditana
      CCMP526 (XM_005854685.1)

<400> SEQUENCE: 67

Met Glu Glu Thr Asp Val Leu Val Val Gly Ser Gly Ile Ser Gly Ser
1               5                   10                  15

Thr Thr Ala Phe Tyr Leu Asn Lys Ala Gly Val Lys Cys Leu Leu Thr
                20                  25                  30

Glu Ala Lys Pro Val Val Gly Gly Asn Val Ile Ser Lys Ser Glu Ser
            35                  40                  45

Gly Phe Leu Trp Glu Glu Gly Pro Asn Ser Phe Gln Pro Thr Tyr Pro
        50                  55                  60

Leu Met Gln Ala Thr Val Asp Met Gly Leu Ala Asp Glu Leu Val Leu
65                  70                  75                  80

Ala Asp Ala Ser Leu Pro Arg Phe Val Tyr Trp Lys Glu Lys Leu Tyr
                85                  90                  95

Ala Leu Pro Gly Gly Leu Gly Asp Ile Pro Phe Phe Asn Leu Leu Ser
            100                 105                 110

Ile Pro Gly Arg Ile Arg Ala Gly Leu Gly Ala Leu Gly Phe Ile Arg
        115                 120                 125

Gly Pro Pro Lys Asp Lys Glu Glu Ser Val Lys Glu Phe Val Thr Arg
        130                 135                 140

His Leu Gly Ala Glu Thr Phe Glu Arg Ile Ile Asp Pro Phe Val Ser
145                 150                 155                 160

Gly Val Tyr Ala Gly Asp Pro Ser Lys Leu Ser Met Lys Ala Ala Leu
                165                 170                 175

Lys Lys Val Lys Arg Leu Glu Glu Leu Gly Gly Arg Gly Ile Leu Asp
            180                 185                 190

Gly Ala Leu Leu Arg Ile Gln Glu Ile Gln Arg Thr Lys Pro Pro Val
        195                 200                 205

Val Pro Glu His Pro Val Tyr Lys Gly Gly Gln Leu Gly Ser Phe Lys
        210                 215                 220

Arg Gly Leu Gln Ser Met Pro Leu Ala Ala Ala Lys Ala Leu Gly Lys
225                 230                 235                 240

Glu Lys Val Arg Leu Ser His Lys Leu Leu Ser Val Val Glu Gly Lys
                245                 250                 255

Gly Pro Lys Gly Gly Tyr Glu Ala Val Phe Gln Thr Pro Gln Gly Arg
            260                 265                 270

Lys Arg Ile Lys Cys Gln Ala Leu Ala Ile Thr Ala Pro Ala His Val
        275                 280                 285

Val His Lys Leu Leu Arg Pro Leu Val Pro Glu Ala Ala Arg Leu Ala
        290                 295                 300
```

```
Asp Val Tyr Tyr Pro Pro Val Ala Ser Val Thr Leu Ala Tyr Pro Lys
305             310             315             320

Thr Ala Phe Arg Glu Pro Leu Arg Gly Phe Gly Asn Leu Ile Pro Arg
                325             330             335

Ser Met Lys Ile Arg Thr Leu Gly Thr Ile Trp Ser Ser Ser Leu Phe
            340             345             350

Pro Gly Gly Pro Pro Asp Tyr Asn Met Leu Leu Ser Tyr Ile Gly Gly
        355             360             365

Ala Gln Asp Pro Gly Ile Ala Glu Leu Ser Ser Gln Gln Ile Val Lys
    370             375             380

Glu Val Asp Arg Asp Ile Lys Lys Val Leu Leu Lys Pro Asp Ala Pro
385             390             395             400

Ala Pro Lys Ile Leu Gly Val Arg Leu Trp Pro Thr Ala Ile Pro Gln
            405             410             415

Tyr Asn Lys Gly His Leu Asp Ile Leu Ala Ser Val Glu Ala Gly Val
            420             425             430

Lys Lys His Pro Gly Leu Phe Leu Gly Gly Asn Tyr Arg Thr Gly Val
        435             440             445

Ala Phe Gly Asp Cys Val Thr Tyr Gly Met Glu Glu Ala Gly Arg Ile
    450             455             460

Gln Ser Tyr Leu Ala Ala Lys Ala Pro
465             470
```

```
<210> SEQ ID NO 68
<211> LENGTH: 472
<212> TYPE: PRT
<213> ORGANISM: Artificial Sequence
<220> FEATURE:
<223> OTHER INFORMATION: Synthetic_PPO of Ostreococcus lucimarinus
      CCE9901 (XM_001418241.1)

<400> SEQUENCE: 68
```

```
Met Lys Lys Met Arg Glu Ala Thr Val Leu Val Thr Glu Ala Arg Glu
1               5               10              15

Arg Val Gly Gly Asn Val Thr Ser Arg Ser Asp Gly Thr Tyr Thr Trp
            20              25              30

Glu Glu Gly Pro Asn Ser Tyr Gln Pro Gly Asp Ala Ile Leu Thr Leu
        35              40              45

Ala Cys Asp Ala Gly Met Arg Asp Asp Ile Leu Leu Ala Asp Pro Ala
    50              55              60

Ser Asn Arg Tyr Val Leu Trp Asp Gly Lys Leu Arg Ile Leu Pro His
65              70              75              80

Ser Ile Glu Ser Ala Val Leu Gly Asp Phe Leu Thr Trp Pro Gly Lys
            85              90              95

Ile Arg Ala Gly Leu Gly Ala Ile Gly Ile Arg Pro Pro Ala Pro Gly
            100             105             110

Lys Glu Glu Ser Val Lys Glu Phe Val Ser Arg Asn Leu Gly Thr Glu
        115             120             125

Ala Phe Glu Arg Leu Ile Glu Pro Phe Cys Ser Gly Val Tyr Ala Gly
    130             135             140

Asp Pro Ala Ala Leu Ser Ser Val Ala Ala Thr Gly Arg Val Gln Arg
145             150             155             160

Leu Glu Pro Leu Gly Gly Ser Leu Val Ala Gly Ala Ile Met Ala Gln
            165             170             175

Lys Glu Ala Ala Gln Asn Lys Lys Pro Arg Asp Pro Arg Leu Pro Glu
```

-continued

```
              180              185              190
Val Lys Gly Gln Thr Val Gly Ser Phe Arg Gly Gly Leu Lys Thr Phe
        195              200              205

Pro Glu Gly Leu Ala Lys Gln Leu Gly Asp Asp Val Val Lys Cys Asn
        210              215              220

Trp Lys Leu Val Gly Val Ser Lys Ser Ala Glu Gly Gly Tyr Glu Cys
225              230              235              240

Ala Tyr Asp Thr Pro Glu Gly Pro Gln Thr Val Arg Thr Lys Cys Leu
            245              250              255

Leu Leu Thr Ala Pro Ala Tyr Val Ala Ala Glu Met Val Lys Asp Met
            260              265              270

Ala Pro Ala Ala Ala Thr Ala Leu Asn Lys Phe Tyr Tyr Pro Pro Val
        275              280              285

Ala Ser Val Thr Ile Ser Tyr Lys Lys Asp Ser Phe Arg Leu Asp Gly
        290              295              300

Thr Ser Ala Leu Pro Glu Gly Gly Leu Thr Gly Phe Gly Gln Leu His
305              310              315              320

Pro Arg Ser Gln Gly Ile Arg Thr Leu Gly Thr Ile Tyr Ser Ser Ser
            325              330              335

Leu Phe Lys Asp Asp Lys Arg Gln Pro Asp Asp Glu Phe Met Ile Leu
            340              345              350

Asn Tyr Ile Gly Gly Ala Arg Asp Val Ala Ile Lys Asp Leu Ser Glu
        355              360              365

Glu Glu Leu Val Lys Gln Val His Glu Asp Ala Leu Lys Thr Ile Leu
        370              375              380

Lys Pro Gly Thr Pro Leu Pro Lys Val Val Gly Val Lys Val Trp Glu
385              390              395              400

Lys Ala Ile Pro Gln Phe Asn Leu Gly His Leu Asp Val Leu Ala Glu
            405              410              415

Ala Glu Asn Ala Leu Thr Ala Ala Asp Cys Gly Glu Lys Asp Gly Leu
            420              425              430

Phe Leu Gly Gly Asn Tyr Thr Ala Gly Val Ala Leu Gly Arg Cys Val
            435              440              445

Glu Phe Gly Ile Glu Gln Ala Asp Glu Val Val Ala Tyr Leu Asn Ala
        450              455              460

Ala Ser Lys Lys Ala Val Ala Val
465              470
```

```
<210> SEQ ID NO 69
<211> LENGTH: 570
<212> TYPE: PRT
<213> ORGANISM: Artificial Sequence
<220> FEATURE:
<223> OTHER INFORMATION: Synthetic_PPO of Guillardia theta CCMP2712
     (XM_005821253.1)

<400> SEQUENCE: 69

Met Val Thr Met Ala Ala Val Arg Thr Lys Ala Trp Val Thr Ser Pro
1               5                10               15

Ser Met Leu Ser Ser Pro Ala Leu Leu Arg Met Pro Ser Cys Ser Trp
            20               25               30

Thr Gly Lys Ser Ser Val Arg Gly Ala Arg Asp Ser Ser Val Gln Phe
        35               40               45

Arg Gly Arg Ser Ala Arg Phe Gly Ala Gly Val Arg Gly Met Gln Ser
    50               55               60
```

```
Ala Gly Gly Trp Gly Ala Gly Ser Met Glu Lys Tyr Asp Thr Leu Val
65              70              75              80

Ile Gly Ser Gly Val Ser Gly Ser Ser Leu Gly Phe Ser Leu Phe Gln
                85              90              95

Lys Gly Val Asn Val Leu Val Thr Glu Ala Arg Asp Val Val Gly Gly
            100             105             110

Asn Val Ile Thr Arg Glu Gln Asp Gly Phe Leu Trp Glu Glu Gly Pro
        115             120             125

Asn Thr Phe Gln Pro Thr Arg Gln Ile Met Arg Leu Ala Val Asp Leu
    130             135             140

Gly Leu Lys Asp Glu Leu Val Phe Ala Asp His Thr Leu Pro Arg Cys
145             150             155             160

Val Tyr Trp Glu Lys Glu Leu Phe Pro Leu Pro Ser Lys Pro Glu Asp
            165             170             175

Ala Pro Phe Phe Arg Leu Leu Ser Ile Pro Glu Lys Ile Arg Ala Gly
        180             185             190

Ile Gly Ala Ile Gly Leu His Ala Pro Lys Pro Asp Tyr Glu Glu Ser
        195             200             205

Val Lys Asp Phe Ile Glu Arg His Leu Gly Glu Ala Val Phe Lys Lys
    210             215             220

Met Ile Asp Pro Phe Val Ser Gly Val Tyr Ala Gly Asp Pro Thr Lys
225             230             235             240

Leu Ser Met Ala Ser Ala Phe Lys Lys Ile Tyr Ala Leu Glu Asp Leu
            245             250             255

Gly Met Thr Pro Ser Leu Ile Glu Gly Gly Ile Ile Arg Gln Ala Glu
            260             265             270

Arg Ala Lys Glu Ala Arg Glu Asn Tyr Asp Pro Glu Leu Pro Thr Tyr
        275             280             285

Lys Gly Gly Ala Leu Gly Ser Phe Arg Lys Gly Leu Val Ser Leu Pro
    290             295             300

Lys Ala Ala Gln Glu Lys Leu Gly Asp Arg Leu Arg Thr Ser Trp Lys
305             310             315             320

Val Glu Ser Ile Ser Lys Gly Glu Asp Gly Gly Tyr Val Thr Lys Phe
            325             330             335

Ser Thr Pro Gln Gly Ser Lys Glu Val Trp Ser Lys Thr Val Ala Val
            340             345             350

Thr Ala Pro Ala His Ala Thr Val Gly Met Leu Ser Glu Leu Val Pro
        355             360             365

Glu Cys Lys Ala Leu Glu Glu Ile His Tyr Pro Cys Val Tyr Ser Val
    370             375             380

Thr Leu Ala Tyr Pro Lys Glu Cys Leu Lys Asp Glu Val Arg Lys Glu
385             390             395             400

Arg Pro Gly Leu Gly Lys Arg Leu Phe Gly Phe Gly Asn Leu Ile Pro
            405             410             415

Arg Ser Met Gly Ile Arg Thr Leu Gly Thr Ile Trp Ser Ser Ser Leu
        420             425             430

Phe Pro Tyr Arg Ala Pro Glu Gly Tyr Glu Met Met Leu Ser Tyr Ile
        435             440             445

Gly Gly Ala Gln Asp Pro Leu Arg Tyr Asn Pro Pro Ile Ala Glu Leu
    450             455             460

Ser Glu Glu Glu Val Ala Lys Ile Val His Gly Asp Val Ser Lys Ile
465             470             475             480

Leu Leu Lys Glu Gly Ala Pro Glu Pro Lys Val Leu Gly Val Arg Lys
```

```
                          485                 490                 495
Trp Pro Lys Ala Ile Pro Gln Tyr Asn Lys Gly Tyr Ser Glu Ile Met
              500                 505                 510

Gly Lys Val Asn Ser Gly Leu Ser Lys Cys Pro Gly Leu Tyr Leu Gly
              515                 520                 525

Gly Asn Tyr Val Ser Gly Val Ala Phe Gly Asp Cys Val Gln Trp Gly
              530                 535                 540

Val Asp Thr Ala Pro Lys Val Lys Glu Phe Leu Asp Ser Val Pro Ser
545                 550                 555                 560

Ser Glu Lys Ala Ala Asn Ala Ala Leu Val
              565                 570

<210> SEQ ID NO 70
<211> LENGTH: 575
<212> TYPE: PRT
<213> ORGANISM: Artificial Sequence
<220> FEATURE:
<223> OTHER INFORMATION: Synthetic_PPO of Cyanidioschyzon merolae strain
      10D (XM_005535077.1)

<400> SEQUENCE: 70

Met Leu Arg Trp Ser Gly Ser Gln Gln Val Thr Asp Arg Asn Arg Ala
1               5                   10                  15

Glu Gln His Gly Leu Val Val Ala Phe Ala Phe Pro Ala Arg Ala Pro
              20                  25                  30

Arg His Ser Glu Ala Thr His Glu Arg Trp Thr Gly Leu Ala Gln Arg
          35                  40                  45

Glu Arg Gly Leu Cys Val Pro Leu Lys Ala Thr Lys Trp Lys Arg Asp
      50                  55                  60

Leu Trp His Ser Arg Lys Leu Gln Met Gln Glu Pro Ala Gln Arg Asn
65                  70                  75                  80

Arg Glu Gln Val Gln Ala Leu Val Val Gly Ser Gly Val Thr Gly Ser
                  85                  90                  95

Ser Phe Ala Phe Leu Leu Gln His Ala Gly Ile Ser Asp Val Ile Cys
              100                 105                 110

Thr Glu Ala Arg Gly Glu Val Gly Gly Asn Leu Ile Ser Arg Ser Lys
          115                 120                 125

Asp Gly Tyr Leu Trp Glu Glu Gly Pro Asn Thr Phe Gln Pro Thr Pro
      130                 135                 140

Val Ile Leu Lys Leu Ala Arg Asp Ala Gly Leu Glu Ser Glu Leu Val
145                 150                 155                 160

Phe Ala Asp Ala Lys Leu Pro Arg Tyr Val Tyr Trp Glu Gly Val Leu
              165                 170                 175

His Ala Leu Pro Ser Ser Pro Ala Asp Leu Ile Thr Gly Arg Phe Arg
          180                 185                 190

Leu Leu Ser Asn Ala Gly Lys Ala Arg Ala Ala Leu Gly Ala Leu Gly
          195                 200                 205

Phe Val Gly Ala Pro Lys Arg Val Ala Arg Gln Ala Gly Pro Glu Pro
      210                 215                 220

Ser Glu Asp Ala Asp Leu Ala Asp Glu Ser Val Glu Glu Phe Val Thr
225                 230                 235                 240

Arg His Leu Gly Arg Glu Val Phe Leu Lys Ile Ile Asp Pro Phe Val
              245                 250                 255

Ser Gly Val Tyr Ala Gly Asp Pro Ser Lys Leu Ser Met Ala Ala Ala
          260                 265                 270
```

Phe Lys Arg Val Tyr Ala Leu Glu Gln Leu Gly Gly Thr Arg Gly Ile
        275                 280                 285

Leu Glu Gly Ala Leu Ile Arg Leu Gln Gln Arg Arg Arg Glu Arg Gln
        290                 295                 300

Arg Trp Ala Ala Glu Asn Leu Pro Lys Val Lys Ala Gly Ala Leu Gly
305                 310                 315                 320

Ser Phe Arg Glu Gly Leu Gln Gln Leu Pro Leu Thr Val Ala Thr Arg
                325                 330                 335

Leu Gly Pro Glu Arg Met Arg Thr Arg Tyr Ala Leu Arg Gln Ile Glu
                340                 345                 350

Tyr Asn Gly Ala Lys Arg Gly Lys Arg Arg Tyr Thr Ala Arg Phe Glu
                355                 360                 365

Thr Pro Asp Gly Glu Arg Val Ile Glu Thr Asp Ala Leu Ile Leu Thr
        370                 375                 380

Ile Pro Ala His Ala Ala Ser Pro Leu Leu Gln Gly Leu Gly Val Ser
385                 390                 395                 400

Gly Ser Glu Leu Leu Gln Glu Ile Asp Phe Pro Pro Val Tyr Ser Val
                405                 410                 415

Thr Leu Ala Tyr Pro Lys Phe Ala Ala Arg Phe Pro Leu Asn Gly Phe
                420                 425                 430

Gly Asn Leu Ile Pro Arg Ser Ala Gly Ile Arg Thr Leu Gly Met Val
        435                 440                 445

Trp Ser Ser Ser Leu Phe Pro Glu Arg Ala Pro Pro Asp Met Asn Met
        450                 455                 460

Val Leu Ser Tyr Ile Gly Gly Ala Arg Asp Pro Gly Ile Arg Glu Cys
465                 470                 475                 480

Thr Pro Asp Glu Val Ala Ala Leu Val Asp Ala Asp Met Arg Arg Val
                485                 490                 495

Leu Leu Arg Ala Asp Ala Pro Ser Pro Gln Val Leu Gly Val Arg Leu
                500                 505                 510

Trp Pro Arg Ala Ile Pro Gln Tyr Asn Arg Gly His Leu Arg Arg Leu
                515                 520                 525

Glu Ala Cys Asn Gln Gly Leu Gln Gly Phe Pro Gly Leu Phe Leu Gly
        530                 535                 540

Gly Asn Tyr Leu Ser Gly Val Ser Phe Gly Asp Cys Val Gln Trp Ala
545                 550                 555                 560

Tyr Asp Asn Val Pro Arg Val Leu Thr Phe Leu Gln Glu Thr Ala
                565                 570                 575

<210> SEQ ID NO 71
<211> LENGTH: 559
<212> TYPE: PRT
<213> ORGANISM: Artificial Sequence
<220> FEATURE:
<223> OTHER INFORMATION: Synthetic_PPO of Bathycoccus prasinos
    (XM_007513261.1)

<400> SEQUENCE: 71

Met Thr Met Thr Thr Gly Ile Ser Ser Ile Gly Thr Lys Lys Asn Ser
1               5                   10                  15

Ile Asn Arg Ala Lys Val Ser Ser Thr Arg Arg Thr Arg Arg Val Arg
                20                  25                  30

Ala Ala Leu Ser Ser Ser Gly Ser Lys Gly Ser Asn Phe Val Val Arg
        35                  40                  45

Ala Ser Ser Ser Ser Ser Ser Pro Ser Asp Asp Glu Asn Asn Ser Leu
        50                  55                  60

```
Gly Ile Lys Asp Thr Ile Ile Val Gly Gly Gly Val Ser Gly Leu Ser
65              70              75              80

Thr Ala Phe Thr Met Lys Ser Lys Asn Ala Ser Cys Asp Ile Met Val
                85              90              95

Thr Glu Ile Arg Asp Arg Val Gly Gly Asn Val Thr Ser Lys Asn Asp
            100             105             110

Gly Gln Tyr Ile Trp Glu Glu Gly Pro Asn Ser Tyr Gln Pro Gly Asp
            115             120             125

Ala Val Leu Lys Leu Ala Cys Asp Ala Gly Met Lys Glu Asp Ile Val
            130             135             140

Leu Ala Asn Pro Asp Ser Asp Arg Tyr Val Leu Trp Asp Gly Glu Leu
145             150             155             160

Arg Ala Leu Pro Lys Asp Ile Pro Thr Ala Val Leu Gly Asp Phe Leu
                165             170             175

Thr Trp Pro Gly Lys Ile Arg Ala Gly Leu Gly Ala Val Gly Ile Arg
                180             185             190

Met Pro Lys Glu Glu Gly Lys Glu Glu Thr Val Lys Glu Phe Val Ser
            195             200             205

Arg Asn Leu Gly Glu Glu Ala Phe Gln Arg Leu Ile Glu Pro Phe Cys
            210             215             220

Ser Gly Val Tyr Ala Gly Asp Pro Ala Met Leu Ser Ala Glu Ala Ala
225             230             235             240

Thr Gly Arg Val Ser Val Leu Glu Asn Lys Gly Pro Trp Pro Gly Leu
                245             250             255

Phe Pro Gly Ala Leu Lys Ala Gln Tyr Glu Gly Ala Lys Lys Lys Lys
                260             265             270

Glu Asn Pro Arg Asp Pro Arg Leu Pro Val Ile Glu Gly Gln Thr Val
            275             280             285

Gly Ser Phe Lys Gly Gly Leu Gln Thr Leu Pro Glu Gly Leu Ala Lys
            290             295             300

Gln Leu Gly Glu Gly Ile Val Lys Leu Gln Trp Lys Leu Ile Lys Thr
305             310             315             320

Glu Lys Thr Glu Asp Gly Leu Phe Ser Leu Thr Tyr Glu Thr Pro Glu
                325             330             335

Gly Glu Lys Lys Val Lys Ala Lys Ser Val Val Phe Thr Gln Pro Ala
                340             345             350

Tyr Val Val Ala Asp Thr Val Arg Ser Ile Ala Pro Glu Ala Ala Lys
            355             360             365

Ser Phe Glu Lys Phe Tyr Tyr Pro Pro Val Ala Ser Val Thr Val Ala
            370             375             380

Tyr Lys Arg Asp Ala Phe Lys Leu Asp Gly Arg Ser Ala Leu Pro Glu
385             390             395             400

Gly Gly Leu Thr Gly Phe Gly Gln Leu His Pro Arg Thr Gln Lys Val
                405             410             415

Arg Thr Leu Gly Thr Ile Tyr Ser Ser Tyr Leu Trp Ala Asp Asp Gly
                420             425             430

Arg Cys Pro Lys Asp Glu Phe Met Ile Leu Asn Tyr Ile Gly Gly Ala
            435             440             445

Arg Asp Val Glu Ile Gln Lys Leu Asn Glu Asp Glu Leu Val Gln Ala
            450             455             460

Val His Ala Asp Ala Leu Lys Thr Ile Leu Lys Pro Asp Thr Pro Leu
465             470             475             480
```

```
Pro Lys Lys Val Gly Val Arg Met Trp Ser Lys Ala Ile Pro Gln Phe
                485                 490                 495

Asn Leu Gly His Trp Lys Leu Leu Asp Glu Ala Lys Glu Leu Leu Lys
            500                 505                 510

Lys Glu Lys Cys Ser Glu Glu Asp Gly Leu Phe Leu Gly Gly Asn Tyr
        515                 520                 525

Val Ala Gly Val Ala Phe Gly Arg Cys Val Glu Tyr Gly Val Asp Gln
    530                 535                 540

Ala Ser Asp Val Leu Asn Phe Leu Asp Lys Gln Arg Arg Thr Val
545                 550                 555

<210> SEQ ID NO 72
<211> LENGTH: 471
<212> TYPE: PRT
<213> ORGANISM: Artificial Sequence
<220> FEATURE:
<223> OTHER INFORMATION: Synthetic_PPO of Myxococcus xanthus
      (AY916795.1)

<400> SEQUENCE: 72

Met His His Met Pro Arg Thr Thr Gly Met Asn Val Ala Val Val Gly
1               5                   10                  15

Gly Gly Ile Ser Gly Leu Ala Val Ala His His Leu Arg Ser Arg Gly
            20                  25                  30

Thr Asp Ala Val Leu Leu Glu Ser Ser Ala Arg Leu Gly Gly Ala Val
        35                  40                  45

Gly Thr His Ala Leu Ala Gly Tyr Leu Val Glu Gln Gly Pro Asn Ser
    50                  55                  60

Phe Leu Asp Arg Glu Pro Ala Thr Arg Ala Leu Ala Ala Ala Leu Asn
65                  70                  75                  80

Leu Glu Gly Arg Ile Arg Ala Ala Asp Pro Ala Ala Lys Arg Arg Tyr
                85                  90                  95

Val Tyr Thr Arg Gly Arg Leu Arg Ser Val Pro Ala Ser Pro Pro Ala
            100                 105                 110

Phe Leu Ala Ser Asp Ile Leu Pro Leu Gly Ala Arg Leu Arg Val Ala
        115                 120                 125

Gly Glu Leu Phe Ser Arg Arg Ala Pro Glu Gly Val Asp Glu Ser Leu
    130                 135                 140

Ala Ala Phe Gly Arg Arg His Leu Gly His Arg Ala Thr Gln Val Leu
145                 150                 155                 160

Leu Asp Ala Val Gln Thr Gly Ile Tyr Ala Gly Asp Val Glu Gln Leu
                165                 170                 175

Ser Val Ala Ala Thr Phe Pro Met Leu Val Lys Met Glu Arg Glu His
            180                 185                 190

Arg Ser Leu Ile Leu Gly Ala Ile Arg Ala Gln Lys Ala Gln Arg Gln
            195                 200                 205

Ala Ala Leu Pro Ala Gly Thr Ala Pro Lys Leu Ser Gly Ala Leu Ser
    210                 215                 220

Thr Phe Asp Gly Gly Leu Gln Val Leu Ile Asp Ala Leu Ala Ala Ser
225                 230                 235                 240

Leu Gly Asp Ala Ala His Val Gly Ala Arg Val Glu Gly Leu Ala Arg
                245                 250                 255

Glu Asp Gly Gly Trp Arg Leu Ile Ile Glu Glu His Gly Arg Arg Ala
            260                 265                 270

Glu Leu Ser Val Ala Gln Val Val Leu Ala Ala Pro Ala His Ala Thr
            275                 280                 285
```

```
Ala Lys Leu Leu Arg Pro Leu Asp Asp Ala Leu Ala Ala Leu Val Ala
    290             295             300

Gly Ile Ala Tyr Ala Pro Ile Ala Val Val His Leu Gly Phe Asp Ala
305             310             315             320

Gly Thr Leu Pro Ala Pro Asp Gly Phe Gly Phe Leu Val Pro Ala Glu
                325             330             335

Glu Gln Arg Arg Met Leu Gly Ala Ile His Ala Ser Thr Thr Phe Pro
                340             345             350

Phe Arg Ala Glu Gly Gly Arg Val Leu Tyr Ser Cys Met Val Gly Gly
            355             360             365

Ala Arg Gln Pro Gly Leu Val Glu Gln Asp Glu Asp Ala Leu Ala Ala
    370             375             380

Leu Ala Arg Glu Glu Leu Lys Ala Leu Ala Gly Val Thr Ala Arg Pro
385             390             395             400

Ser Phe Thr Arg Val Phe Arg Trp Pro Leu Gly Ile Pro Gln Tyr Asn
                405             410             415

Leu Gly His Leu Glu Arg Val Ala Ala Ile Asp Ala Ala Leu Gln Arg
            420             425             430

Leu Pro Gly Leu His Leu Ile Gly Asn Ala Tyr Lys Gly Val Gly Leu
            435             440             445

Asn Asp Cys Ile Arg Asn Ala Ala Gln Leu Ala Asp Ala Leu Val Ala
    450             455             460

Gly Asn Thr Ser His Ala Pro
465             470

<210> SEQ ID NO 73
<211> LENGTH: 469
<212> TYPE: PRT
<213> ORGANISM: Artificial Sequence
<220> FEATURE:
<223> OTHER INFORMATION: Synthetic_PPO of Myxococcus virescens
      (WP_090484749.1)

<400> SEQUENCE: 73

Met His His Met Gln Arg Thr His Arg Met Asn Val Ala Val Val Gly
1               5               10              15

Gly Gly Ile Ser Gly Leu Ala Ile Ala His Gly Leu Arg Ser Arg Gly
            20              25              30

Thr Ala Ala Val Leu Leu Glu Thr Ser Ala Arg Leu Gly Gly Ala Val
        35              40              45

Gly Thr His Ala Arg Ala Gly Tyr Leu Val Glu Gln Gly Pro Asn Ser
    50              55              60

Phe Leu Asp Arg Glu Pro Ala Thr Arg Glu Leu Ala Ala Ala Leu Asn
65              70              75              80

Leu Glu Gly Arg Ile Arg Val Ala Asp Pro Ser Ala Lys Arg Arg Tyr
            85              90              95

Val Tyr Thr Arg Gly Arg Leu Arg Ser Val Pro Ala Ser Pro Pro Ala
            100             105             110

Phe Leu Ala Ser Asp Ile Leu Pro Leu Gly Ala Arg Leu Arg Val Ala
        115             120             125

Gly Glu Leu Phe Ser Arg Arg Ala Pro Glu Gly Thr Asp Glu Ser Leu
    130             135             140

Ala Ala Phe Gly Arg Arg His Leu Gly Arg Ala Ala Thr Arg Val Leu
145             150             155             160

Leu Asp Ala Val Gln Thr Gly Ile Tyr Ala Gly Asp Val Glu Gln Leu
```

```
                   165              170              175
Ser Val Glu Ala Thr Phe Pro Met Leu Val Lys Leu Glu Arg Glu His
               180              185              190

Arg Ser Leu Ile Leu Gly Ala Ile Arg Ala Gln Lys Ala Gln Arg Lys
           195              200              205

Ala Leu Pro Ala Gly Asp Ala Pro Lys Leu Ser Gly Ala Leu Ser Thr
       210              215              220

Phe Asp Gly Gly Leu Gln Val Leu Ile Asp Ala Leu Ala Ala Ser Leu
225              230              235              240

Gly Asp Thr Ala His Val Ser Ala Arg Val Glu Gly Leu Thr Arg Val
               245              250              255

Asp Gly Gly Trp Lys Leu Ala Val Glu Glu His Gly Arg Arg Ala Glu
               260              265              270

Leu Thr Ala Asn His Val Val Leu Ala Val Pro Ala Phe Val Ala Ala
               275              280              285

Gln Leu Leu Arg Pro Leu Asp Asp Ala Leu Ala Glu Gln Val Ser Arg
       290              295              300

Ile Glu Tyr Ala Pro Ile Ala Val Val His Leu Gly Phe Asp Ala Gly
305              310              315              320

Ala Leu Pro Ala Pro Asp Gly Phe Gly Phe Leu Val Pro Phe Glu Glu
               325              330              335

Lys Arg Arg Leu Leu Gly Ala Ile His Ala Ser Thr Thr Phe Pro Phe
               340              345              350

Arg Val Glu Gly Gly Arg Val Leu Tyr Thr Cys Met Val Gly Gly Ala
               355              360              365

Arg Gln Pro Asp Leu Val Lys Arg Asp Glu Ala Ala Leu Ala Ala Leu
       370              375              380

Ala Leu Glu Glu Leu Gln Ala Leu Thr Gly Val Thr Ala Arg Pro Thr
385              390              395              400

Phe Thr Glu Val Phe Arg Trp Pro Arg Gly Ile Pro Gln Tyr Asn Val
               405              410              415

Gly His Leu Ala Arg Met Ala Gly Ile Asp Ala Ala Leu Gln Arg Trp
               420              425              430

Pro Gly Leu His Leu Ala Gly Asn Ala Tyr Lys Gly Ile Gly Leu Asn
           435              440              445

Asp Cys Ile Arg Asn Ala Ala Arg Leu Ala Thr Ala Leu Ala Asp Glu
       450              455              460

Glu Ser Val Arg Lys
465
```

```
<210> SEQ ID NO 74
<211> LENGTH: 463
<212> TYPE: PRT
<213> ORGANISM: Artificial Sequence
<220> FEATURE:
<223> OTHER INFORMATION: Synthetic_PPO of Myxococcus macrosporus DSM
      14697 (ATB45699.1)

<400> SEQUENCE: 74

Met Asn Val Ala Val Val Gly Gly Gly Ile Ser Gly Leu Ala Val Ala
1               5               10              15

His Gly Leu Arg Ser Arg Gly Thr Ala Ala Val Leu Leu Glu Thr Ser
           20              25              30

Ala Arg Leu Gly Gly Ala Val Gly Thr His Ala Arg Ala Gly Tyr Leu
       35              40              45
```

-continued

```
Val Glu Gln Gly Pro Asn Ser Phe Leu Asp Arg Glu Pro Ala Thr Arg
    50              55              60

Ala Leu Ala Ala Ala Leu Asn Leu Glu Gly Arg Ile Arg Val Ala Asp
65              70              75              80

Ala Ser Ala Lys Arg Arg Tyr Val Tyr Thr Arg Gly Arg Leu Arg Ser
            85              90              95

Val Pro Ala Ser Pro Pro Ala Phe Leu Thr Ser Asp Ile Leu Pro Leu
            100             105             110

Gly Ala Arg Leu Arg Val Met Gly Glu Leu Phe Ser Ser Arg Ala Pro
            115             120             125

Glu Gly Thr Asp Glu Ser Leu Ala Ala Phe Gly Arg Arg His Leu Gly
    130             135             140

Pro Val Ala Thr Arg Val Leu Leu Asp Ala Val Gln Thr Gly Ile Tyr
145             150             155             160

Ala Gly Asp Val Glu Arg Leu Ser Val Glu Ala Thr Phe Pro Leu Leu
            165             170             175

Val Lys Leu Glu Arg Glu His Arg Ser Leu Ile Leu Gly Ala Ile His
            180             185             190

Ala Gln Lys Ala Gln Ala Arg Ala Lys Ala Leu Leu Pro Pro Gly Asp
            195             200             205

Ala Pro Lys Leu Thr Gly Ala Leu Ser Thr Phe Asp Gly Gly Leu Gln
    210             215             220

Val Leu Ile Asp Ala Leu Ala Ser Ser Leu Gly Asp Ala Ala His Val
225             230             235             240

Gly Ala Arg Val Glu Gly Leu Thr Arg Val Asp Gly Gly Trp Arg Leu
            245             250             255

Ala Val Glu Glu His Gly Gln Arg Ala Glu Leu Ser Ala Ser His Val
            260             265             270

Val Leu Ala Val Pro Ala His Val Ala Ala Glu Leu Leu Gln Pro Leu
    275             280             285

Asp Asp Ala Leu Ala Ala Gln Val Ser Arg Ile Glu Tyr Ala Pro Ile
    290             295             300

Ala Val Val His Leu Gly Phe Asp Ala Gly Thr Leu Pro Ala Pro Asp
305             310             315             320

Gly Phe Gly Phe Leu Val Pro Phe Glu Glu Gln Arg Arg Leu Leu Gly
            325             330             335

Ala Ile His Ala Ser Thr Thr Phe Pro Phe Arg Val Glu Gly Gly Arg
            340             345             350

Val Leu Tyr Thr Cys Met Val Gly Gly Ala Arg Gln Pro Asp Leu Val
            355             360             365

Gln Arg Asp Glu Ala Glu Leu Ala Ala Leu Ala Leu Glu Glu Leu Arg
    370             375             380

Ala Leu Ala Gly Val Thr Ala Arg Pro Thr Phe Thr Gln Val Phe Arg
385             390             395             400

Trp Pro Arg Gly Ile Pro Gln Tyr Asn Val Gly His Leu Glu Arg Met
            405             410             415

Ala Gly Ile Asp Ala Ala Leu Gln Arg Trp Pro Gly Leu His Leu Ala
            420             425             430

Gly Asn Ala Tyr Lys Gly Ile Gly Leu Asn Asp Cys Ile Arg Asn Ala
            435             440             445

Ala Arg Leu Ala Ala Ala Leu Ser Asp Glu Glu Asn Val Arg Lys
    450             455             460
```

<210> SEQ ID NO 75
<211> LENGTH: 469
<212> TYPE: PRT
<213> ORGANISM: Artificial Sequence
<220> FEATURE:
<223> OTHER INFORMATION: Synthetic_PPO of Myxococcus hansupus
      (WP_044889345)

<400> SEQUENCE: 75

Met His His Met Pro Arg Thr His Gly Met Asn Val Ala Val Val Gly
1               5                   10                  15

Gly Gly Ile Ser Gly Leu Ala Val Ala His Arg Leu Arg Ser Arg Gly
            20                  25                  30

Thr Asp Ala Val Leu Leu Glu Thr Ser Gly Arg Leu Gly Gly Ala Val
        35                  40                  45

Gly Thr His Ala Arg Asp Gly Tyr Leu Val Glu Gln Gly Pro Asn Ser
    50                  55                  60

Phe Leu Asp Arg Glu Pro Ala Thr Arg Glu Leu Ala Ala Ala Leu Asn
65                  70                  75                  80

Leu Glu Gly Arg Ile Arg Val Ala Asp Pro Leu Ala Lys Arg Arg Tyr
                85                  90                  95

Val Tyr Thr Arg Gly Arg Leu Arg Ser Val Pro Ser Ser Pro Pro Ala
            100                 105                 110

Phe Leu Ala Ser Asp Ile Leu Pro Leu Gly Ala Arg Leu Arg Val Ala
            115                 120                 125

Gly Glu Leu Phe Ser Gly Arg Ala Pro Thr Gly Ile Asp Glu Ser Leu
    130                 135                 140

Ala Glu Phe Gly Arg Arg His Leu Gly Arg Thr Ala Thr Gln Val Leu
145                 150                 155                 160

Leu Asp Ala Val Gln Thr Gly Ile Tyr Ala Gly Asp Val Glu Gln Leu
                165                 170                 175

Ser Val Ala Ala Thr Phe Pro Met Leu Val Asp Leu Glu Arg Lys His
            180                 185                 190

Arg Ser Leu Ile Leu Gly Ala Ile Arg Ala Gln Gln Val Gln Arg Arg
            195                 200                 205

Ala Leu Ser Ala Gly Gly Thr Pro Lys Leu Ser Gly Ala Leu Ser Thr
    210                 215                 220

Phe Asp Gly Gly Leu Gln Val Leu Ile Asp Ala Leu Ala Thr Ser Leu
225                 230                 235                 240

Gly Asp Ala Ala His Val Gly Ala Gln Val Glu Cys Leu Thr Arg Val
            245                 250                 255

Asp Gly Gly Trp Lys Leu Met Val Glu Glu Arg Gly Gln Arg Ala Glu
            260                 265                 270

Leu Ser Ala Ser Gln Val Val Leu Ala Val Pro Ala His Val Ala Ala
    275                 280                 285

Glu Leu Leu Arg Pro Leu Asp Asp Ala Leu Ala Ala Gln Val Ala Arg
    290                 295                 300

Ile Asp Tyr Ala Pro Ile Ala Val Val His Leu Gly Phe Asp Ala Gly
305                 310                 315                 320

Thr Leu Pro Ala Pro Asp Gly Phe Gly Phe Leu Val Pro Ser Gly Glu
            325                 330                 335

Lys Arg Arg Leu Leu Gly Ala Ile His Ala Ser Thr Thr Phe Pro Phe
            340                 345                 350

Arg Val Glu Gly Gly Arg Val Leu Tyr Thr Cys Met Val Gly Gly Ala
            355                 360                 365

-continued

```
Arg Gln Pro Glu Leu Val Arg Gln Asp Glu Ala Ala Leu Ala Ala Leu
    370             375             380

Ala Leu Glu Glu Leu Arg Ala Leu Ala Gly Val Thr Ala Gln Pro Thr
385             390             395             400

Phe Thr Gln Val Tyr Arg Trp Gln Arg Gly Ile Pro Gln Tyr Asn Val
            405             410             415

Gly His Leu Glu Arg Met Ala Gly Ile Asp Ala Ala Leu Gln Arg Trp
        420             425             430

Pro Gly Leu His Leu Ala Gly Asn Ala Tyr Lys Gly Ile Gly Leu Asn
        435             440             445

Asp Cys Ile Arg Asn Ala Ala Arg Leu Ala Asp Ala Leu Thr Asp Glu
    450             455             460

Glu Ser Val Arg Lys
465

<210> SEQ ID NO 76
<211> LENGTH: 461
<212> TYPE: PRT
<213> ORGANISM: Artificial Sequence
<220> FEATURE:
<223> OTHER INFORMATION: Synthetic_PPO of Myxococcus fulvus
      (WP_046711394.1)

<400> SEQUENCE: 76

Met Thr Val Ala Val Val Gly Gly Gly Ile Ser Gly Leu Val Val Ala
1               5               10              15

Trp Arg Leu Arg Ser Arg Gly Arg Asp Ala Val Leu Leu Glu Thr Thr
            20              25              30

Ser Arg Leu Gly Gly Ala Val Gly Thr Arg Ala Gln Arg Gly Phe Leu
        35              40              45

Leu Glu Thr Gly Pro Asn Ser Phe Leu Asp Arg Glu Pro Ala Met Arg
    50              55              60

Glu Leu Ala Ser Ala Leu Asn Leu Glu His Arg Ile Arg Ala Ala Asp
65              70              75              80

Gly Ala Ala Lys Arg Arg Tyr Val Tyr Thr Arg Gly Lys Leu Arg Ser
            85              90              95

Val Pro Ala Ser Pro Pro Ala Phe Leu Lys Ser Asp Ile Leu Pro Phe
            100             105             110

Gly Ala Lys Leu Arg Val Met Gly Glu Leu Phe Ser Gly Arg Ala Ala
        115             120             125

Pro Gly Val Asp Glu Ser Leu Ala Asp Phe Gly Arg Arg His Leu Gly
    130             135             140

Ala Thr Ala Thr Arg Val Leu Leu Asp Ala Val Gln Thr Gly Ile Phe
145             150             155             160

Ala Gly Asp Val Glu Lys Leu Ser Val Gly Ala Thr Phe Pro Pro Leu
            165             170             175

Val Lys Leu Glu Arg Glu His Arg Ser Leu Leu Leu Gly Ala Ile Gln
            180             185             190

Ala Gln Lys Ala Gln Lys Ala Arg Ala Lys Ala Leu Pro Ala Gly Ser
        195             200             205

Thr Ala Pro Lys Leu Ser Gly Ala Leu Ser Thr Phe Glu Gly Gly Leu
    210             215             220

Gly Thr Leu Ile Asp Ala Leu Gly Thr Ala Leu Gly Asp Ala Ala Arg
225             230             235             240

Thr Gly Ala Thr Val Glu Gly Leu Thr Arg Gly Asp Asp Gly Trp Arg
            245             250             255
```

```
Leu Ala Val Ser Glu Arg Gly Gln Arg Ser Glu Leu Lys Ala Ser Ser
        260                 265                 270

Val Val Leu Ala Ala Pro Ala Tyr Val Thr Arg Gly Leu Leu Glu Pro
        275                 280                 285

Leu Asp Ala Glu Leu Ala Ala Arg Val Gly Gly Ile Asp Tyr Ala Pro
        290                 295                 300

Ile Ala Val Val His Leu Gly Phe Asp Ala Gly Thr Thr Pro Ala Pro
305                 310                 315                 320

Asp Gly Phe Gly Phe Leu Val Pro Pro Met Glu Lys Arg Arg Leu Leu
                325                 330                 335

Gly Ala Ile His Ala Ser Thr Val Phe Pro Phe Arg Val Glu Ala Gly
                340                 345                 350

Arg Val Leu Tyr Thr Cys Met Val Gly Gly Ala Thr Arg Pro Asp Leu
                355                 360                 365

Val Ala Leu Asp Glu Ala Glu Leu Val Ala Leu Ala Arg Glu Glu Leu
        370                 375                 380

Lys Ala Leu Ala Gly Val Thr Ala Thr Pro Thr Leu Thr Glu Val Phe
385                 390                 395                 400

Arg Trp Lys Arg Gly Ile Pro Gln Tyr Asn Leu Gly His Leu Glu Arg
                405                 410                 415

Met Asp Gly Val Asp Arg Ala Leu Thr Arg Leu Pro Gly Leu His Leu
                420                 425                 430

Ala Gly Asn Ala Tyr Lys Gly Val Gly Leu Asn Asp Cys Ile Arg Asn
        435                 440                 445

Gly Leu Ala Leu Ala Asp Ala Leu Val Asp Ala Gly Ala
        450                 455                 460

<210> SEQ ID NO 77
<211> LENGTH: 461
<212> TYPE: PRT
<213> ORGANISM: Artificial Sequence
<220> FEATURE:
<223> OTHER INFORMATION: Synthetic_PPO of Myxococcus fulvus
      (WP_074949681.1)

<400> SEQUENCE: 77

Met Thr Val Ala Val Val Gly Gly Gly Ile Ser Gly Leu Val Val Ala
1               5                   10                  15

Trp Arg Leu Arg Ser Arg Gly Arg Asp Ala Val Leu Leu Glu Thr Thr
                20                  25                  30

Ser Arg Leu Gly Gly Ala Val Gly Thr Arg Ala Gln Arg Gly Phe Leu
        35                  40                  45

Leu Glu Thr Gly Pro Asn Ser Phe Leu Asp Arg Glu Pro Ala Met Arg
        50                  55                  60

Glu Leu Ala Ser Ala Leu Asn Leu Glu His Arg Ile Arg Ala Ala Asp
65                  70                  75                  80

Gly Ala Ala Lys Arg Arg Tyr Val Tyr Thr Arg Gly Lys Leu Arg Ser
                85                  90                  95

Val Pro Ala Ser Pro Pro Ala Phe Leu Lys Ser Asp Ile Leu Pro Phe
                100                 105                 110

Gly Ala Lys Leu Arg Val Met Gly Glu Leu Phe Ser Gly Arg Ala Ala
        115                 120                 125

Pro Gly Val Asp Glu Ser Leu Ala Asp Phe Gly Arg Arg His Leu Gly
        130                 135                 140

Ala Thr Ala Thr Arg Val Leu Leu Asp Ala Val Gln Thr Gly Ile Phe
```

-continued

```
         145              150              155              160

Ala Gly Asp Val Glu Lys Leu Ser Val Gly Ala Thr Phe Pro Pro Leu
             165              170              175

Val Lys Leu Glu Arg Glu His Arg Ser Leu Leu Leu Gly Ala Ile Gln
             180              185              190

Ala Gln Lys Ala Gln Lys Ala Arg Ala Lys Ala Leu Pro Ala Gly Ser
         195              200              205

Thr Gly Pro Lys Leu Ser Gly Ala Leu Ser Thr Phe Glu Gly Gly Leu
    210              215              220

Gly Thr Leu Ile Asp Ala Leu Gly Thr Ala Leu Gly Asp Ala Ala Arg
225              230              235              240

Thr Gly Ala Thr Val Glu Gly Leu Thr Arg Gly Asp Asp Gly Trp Arg
             245              250              255

Leu Ala Val Ser Glu Arg Gly Gln Arg Ser Glu Leu Lys Ala Ser Ser
             260              265              270

Val Val Leu Ala Ala Pro Ala Tyr Val Thr Arg Gly Leu Leu Glu Pro
             275              280              285

Leu Asp Ala Glu Leu Ala Ala Arg Val Gly Gly Ile Asp Tyr Ala Pro
    290              295              300

Ile Ala Val Val His Leu Gly Phe Asp Ala Gly Thr Thr Pro Ala Pro
305              310              315              320

Asp Gly Phe Gly Phe Leu Val Pro Pro Met Glu Lys Arg Arg Leu Leu
             325              330              335

Gly Ala Ile His Ala Ser Thr Val Phe Pro Phe Arg Val Glu Ala Gly
             340              345              350

Arg Val Leu Tyr Thr Cys Met Val Gly Gly Ala Thr Arg Pro Asp Leu
             355              360              365

Val Ala Leu Asp Glu Ala Glu Leu Val Ala Leu Ala Arg Glu Glu Leu
    370              375              380

Lys Ala Leu Ala Gly Val Thr Ala Thr Pro Thr Leu Thr Glu Val Phe
385              390              395              400

Arg Trp Lys Arg Gly Ile Pro Gln Tyr Asn Leu Gly His Leu Glu Arg
             405              410              415

Met Asp Gly Val Asp Arg Ala Leu Thr Arg Leu Pro Gly Leu His Leu
             420              425              430

Ala Gly Asn Ala Tyr Lys Gly Val Gly Leu Asn Asp Cys Ile Arg Asn
         435              440              445

Gly Leu Ala Leu Ala Asp Ala Leu Val Asp Ala Gly Ala
    450              455              460
```

<210> SEQ ID NO 78
<211> LENGTH: 459
<212> TYPE: PRT
<213> ORGANISM: Artificial Sequence
<220> FEATURE:
<223> OTHER INFORMATION: Synthetic_PPO of Myxococcus stipitatus
      (WP_015346914.1)

<400> SEQUENCE: 78

```
Met Thr Val Ala Val Val Gly Gly Gly Ile Ser Gly Leu Val Val Ala
1               5               10              15

Trp Arg Leu Arg Ser Arg Gly Lys Ala Ala Val Val Leu Glu Thr Thr
             20              25              30

Ser Arg Leu Gly Gly Ala Val Gly Thr Arg Ala Lys Gln Gly Phe Leu
         35              40              45
```

```
Leu Glu Thr Gly Pro Asn Ser Phe Leu Asp Arg Glu Pro Ala Thr Arg
    50                  55                  60

Glu Leu Ala Gly Ala Leu Asn Leu Glu His Arg Ile Arg Ala Ala Asp
65                  70                  75                  80

Ala Ala Ala Lys Arg Arg Tyr Val Tyr Thr Arg Gly Gln Leu Arg Ser
                85                  90                  95

Val Pro Ala Ser Pro Pro Ala Phe Leu Gly Ser Asp Ile Leu Pro Trp
                100                 105                 110

Ser Ala Lys Leu Arg Val Met Gly Glu Leu Phe Thr Gly Arg Ala Ala
            115                 120                 125

Pro Gly Ile Asp Glu Ser Leu Ala Ala Phe Gly Arg Arg His Leu Gly
            130                 135                 140

Ala Thr Ala Thr Arg Val Leu Leu Asp Ala Val Gln Thr Gly Ile Phe
145                 150                 155                 160

Ala Gly Asp Val Glu Arg Leu Ser Val Gly Ala Thr Phe Pro Pro Leu
                165                 170                 175

Val Lys Leu Glu His Glu His Arg Ser Leu Ile Leu Gly Ala Ile Arg
            180                 185                 190

Thr Gln Gln Ala Arg Arg Lys Ala Leu Pro Ala Gly Ala Ser Ala Ala
            195                 200                 205

Pro Glu Leu Ser Gly Ala Leu Ser Thr Phe Glu Gly Gly Leu Gln Thr
    210                 215                 220

Leu Ile Asp Ala Leu Ser Ala Ser Leu Gly Glu Asp Ala Arg Val Asn
225                 230                 235                 240

Ala Thr Val Glu Gly Leu Thr Arg Val Gly Asp Gly Trp Arg Leu Ala
                245                 250                 255

Val Ser Glu Lys Gly Gln Arg Ser Glu Leu Asp Ala Ser His Val Val
                260                 265                 270

Leu Ala Ala Pro Ala Tyr Val Thr Gln Lys Leu Leu His Pro Leu Asp
            275                 280                 285

Ala Glu Leu Ala Ala Arg Val Gly Gly Ile Glu Tyr Ala Pro Ile Ala
    290                 295                 300

Val Val Gln Leu Gly Phe Asp Val Gly Thr Thr Pro Ala Pro Asp Gly
305                 310                 315                 320

Phe Gly Phe Leu Val Pro Pro Ser Glu Gly Arg Arg Leu Leu Gly Ser
                325                 330                 335

Ile His Ala Ser Thr Val Phe Pro Phe Arg Val Glu Pro Gly Arg Val
            340                 345                 350

Leu Tyr Thr Cys Met Val Gly Gly Ala Lys Arg Pro Asp Leu Val Gly
            355                 360                 365

Leu Asp Glu Pro Ala Leu Val Ala Leu Ala Arg Glu Glu Leu Lys Ala
    370                 375                 380

Leu Ala Gly Val Thr Ala Thr Pro Ser Leu Thr Glu Val Phe Arg Trp
385                 390                 395                 400

Pro Leu Gly Ile Pro Gln Tyr Asn Val Gly His Leu Ala Arg Met Ala
                405                 410                 415

Ala Val Asp Gln Ala Leu Thr Arg Arg Pro Gly Leu Ser Leu Thr Gly
            420                 425                 430

Asn Ala Tyr Lys Gly Val Gly Leu Asn Asp Cys Ile Arg Asn Gly Leu
            435                 440                 445

Gln Leu Ala Asp Ala Leu Val Thr Ala Ala Gly
    450                 455
```

-continued

```
<210> SEQ ID NO 79
<211> LENGTH: 458
<212> TYPE: PRT
<213> ORGANISM: Artificial Sequence
<220> FEATURE:
<223> OTHER INFORMATION: Synthetic_PPO of Hyalangium minutum
      (WP_044193071.1)

<400> SEQUENCE: 79

Met Thr Val Ile Ala Val Ile Gly Gly Gly Ile Ser Gly Leu Thr Leu
1               5                   10                  15

Thr His Cys Leu Arg Ser Arg Gly Lys Asp Ala Leu Leu Leu Glu Ala
            20                  25                  30

Ser Ser Arg Leu Gly Gly Asn Ile Glu Thr Arg Gln Arg Asp Gly Phe
        35                  40                  45

Leu Ile Glu Thr Gly Pro Asn Ser Phe Leu Asp Arg Glu Pro Ala Thr
    50                  55                  60

Arg Glu Leu Ala Ala Gly Val Gly Val Glu Asp Arg Ile Arg Ser Ala
65                  70                  75                  80

Asp Pro Ala Ala Lys Ala Arg Tyr Leu Tyr Thr Arg Gly Arg Leu Arg
                85                  90                  95

Pro Val Pro Ser Ser Pro Pro Ala Phe Leu Lys Ser Asp Ile Leu Pro
            100                 105                 110

Leu Gly Ala Arg Leu Arg Val Met Ala Glu Leu Phe Thr Gly Arg Ala
        115                 120                 125

Pro Glu Gly Val Asp Glu Ser Leu Ala Ala Phe Gly Arg Arg His Leu
    130                 135                 140

Gly Pro Ala Ala Thr Ala Val Leu Leu Asp Ala Val Gln Thr Gly Ile
145                 150                 155                 160

Tyr Ala Gly Asn Met Glu Thr Leu Ser Val Asp Ala Thr Phe Pro Gln
                165                 170                 175

Leu Thr Lys Leu Glu Arg Glu His Arg Ser Leu Ile Leu Gly Ala Ile
            180                 185                 190

Arg Ser Gln Lys Ala Gln Arg Lys Ala Leu Pro Ala Gly Ala Ala Gly
        195                 200                 205

Ser Pro Glu Lys Leu Arg Gly Thr Leu Cys Thr Phe Asp Gly Gly Leu
    210                 215                 220

Gln Thr Leu Val Asp Gly Leu Ala Arg Glu Leu Gly Pro Ala Ala His
225                 230                 235                 240

Thr Asn Ala Lys Val Glu Gly Leu Gln Pro Ser His Gly Gly Trp Arg
                245                 250                 255

Val Ser Val Arg Glu Asn Gly Gly Gln Ala Glu Leu Leu Ala Ser Gln
            260                 265                 270

Val Val Leu Ala Thr Pro Ala Phe Val Ala Ala Gly Leu Met Arg Pro
        275                 280                 285

Leu Asp Glu Pro Leu Ala Ala Leu Val Glu Gly Ile Ala Tyr Ala Pro
    290                 295                 300

Ile Ala Val Val His Leu Gly Phe Ala Pro Gly Ser Thr Pro Ala Pro
305                 310                 315                 320

Asp Gly Phe Gly Phe Leu Val Pro Gly Leu Glu Lys Arg Arg Leu Leu
                325                 330                 335

Gly Ala Ile His Ala Ser Thr Val Phe Pro Phe Arg Thr Glu Gly Gly
            340                 345                 350

Arg Val Leu Tyr Thr Cys Met Val Gly Gly Ala Arg Gln Pro Asp Leu
        355                 360                 365
```

-continued

```
Val Lys Leu Asp Glu Glu Ala Leu Val Ala Leu Ala Arg Glu Glu Leu
    370             375             380

Lys Glu Leu Ala Gly Val Thr Ala Ser Pro Ser Phe Thr Glu Val Ile
385             390             395             400

Arg Trp Thr Arg Gly Ile Pro Gln Tyr Asn Val Gly His Leu Glu Arg
                405             410             415

Val Ala Ala Ile Asp Ala Ala Leu Lys Arg Trp Pro Gly Leu His Leu
            420             425             430

Thr Gly Asn Ala Tyr Lys Gly Val Gly Ile Asn Asp Cys Ile Arg Asn
        435             440             445

Ala Phe Ala Leu Gly Asp Ala Leu Ala Ala
    450             455
```

```
<210> SEQ ID NO 80
<211> LENGTH: 1404
<212> TYPE: DNA
<213> ORGANISM: Artificial Sequence
<220> FEATURE:
<223> OTHER INFORMATION: Synthetic_Gene encoding SEQ ID NO: 1

<400> SEQUENCE: 80
atgagtgagg tagatgtcgc aattgtcggt ggtggcctca gtggcctgag tctggcttgg        60
cggttgcagc aaagcgcccc ccagtacagc gtggttcttt tagaggccag cgatcgcctt       120
gggggcaata ttacgacgca aacagcagag ggctttgtct gggaactagg tcccaatagt       180
tttgcaccga cccccgccct gttgcaactc attgctgagg tgggcttgca gtcggaactc       240
attcggggcg atcgccacct gccgcgctac atctactggc ggggacaact ctaccccta       300 caacccacc gtcctcttgc cttagccacc tcaaacctcc tcagtccttg gggaaaagtg        360
cgggcagccc ttggtgccct tgggtttgtg ccccccatt taggcagcgg cgatgagtca        420
gtcaattcat ttttccgtcg ccatttgggg caagaggtag ctgaacgact ggtggcgccc        480
tttgtctctg gggtttatgc gggtgatcca caacaactga gtgctgctgc tgctttttcgc       540 cgtattgctc aattggaaaa acttgggggt ggcctcattg ctggtgccct gcacctacgg        600
cgtcaacaag ccccaaacc caagccgcct acaagtgtgc agatgcgacc gggggaactt        660
ggttccttta aggaaggcct agccgcgcta cctcgggcga tcgcccaaca actgaaggca        720
ccgattcacc tgcaaacccc tgttcaagaa atcaccccag accctaaggg tgggtacctg        780
ctgcgcagtg gtgagcaaac gtggcgcgcc cgcagtgtgg tttttggcaac gcctgcctat        840 caaaccgcag agttagtggc acccttcag ccagcgatcg cccgtgtttt ggccaccatt        900
ccctatccca ccgtggcctg tgtggtcttg gcctatcctg ctggacttgg gcgcagtgtc        960
cgccccggct ttggcgtact gattcctcgc agtcagggca tccgcaccct tggcaccatt       1020
tggtcgtcct gtctctttcc ccaacgcacc cccgccggtt ggcaagtctt tacgagtttt       1080
attggcggtg ctacggatcc tgatttggca agcctgagcg aagaagccat tgttcagcag       1140
gtgcagcagg atttgaaccg actccttgat ttacccgcag ccaaggcacg cttactcggt       1200
atgaaggttt ggcgacgggc gattccccaa tatatggtgg gctaccctga gcagtggcag       1260
caggtgaccc catgccctcag tcaaaccccc ggccttttcc tgtgtagtaa ttatgctgag       1320
ggtgtcgcct tgggcgatcg cgtcgaacat ggcaatcgaa ccgctgctgc tgttgctgcc       1380 taccttttcag gaggccagcc ctag                                           1404
```

```
<210> SEQ ID NO 81
<211> LENGTH: 1398
```

-continued

```
<212> TYPE: DNA
<213> ORGANISM: Artificial Sequence
<220> FEATURE:
<223> OTHER INFORMATION: Synthetic_Gene encoding SEQ ID NO: 2

<400> SEQUENCE: 81
atgatggagg tagatgtcgc aattgttggg ggtggtctca gtggcctgag tgttgcttgg      60
cggttgcagc agagcgcccc gcagtacagt ggggttcttt tagaggctag cgatcgcctg     120 gggggggaata tcacgaccca aggggcggag ggttttgtct gggaactggg tcccaatagc     180
tttgcaccca cccctgccct cctacaactc attgctgagg tgggcttgca ctcagagcta     240
attcggggcg atcgccacct accgcgctac atctactggc gggggggaact ctaccccctc     300 gaacccaccc gtccccttgc tttggccacc tcaaatttac tcagcccttg gggaaaagtg     360
cgggcagccc ttggtgcctt ggggtttgtg ccccccatc tgggcagtgg ggatgagtcg     420
gttaattcat ttttccgtcg ccatttgggg caagaggtgg ctgaacgact ggtggccccc     480
tttgtctctg gggtttacgc cggtgatccg caacaattga gtgccgctgc tgcttttcgt     540
cgtattgccc aactggaaaa actaggggt gggctcattg ccggcgccct gcgcctgcgg     600
cgccaacaac ctcctaaacc aaggccacct gcagaggtgc aaatgcgacc aggggaactg     660
ggctccttta aggaaggctt ggctgctctg ccgcgggcga tcgcccaaca attgaaggca     720
ccggttcacc tgcaaacccc cgttgaagca atcaccccag aacccaatgg tggctatctg     780
ctgcgcagtg gtgagcaaac gtggcaggcc cgcagtgtgg tcttggcaac gcctgcctat     840
caaaccgcgg cgttggtagc gccctttcag ccagcgatcg cccgtgtttt ggctgccatc     900
ccctatccca ccgtggcctg tgtggtcttg gcctaccccg cgggactggg acgcagtgta     960
cgccccggat ttggcgtact gattcctcgt ggccagggca tccgtaccct tggcaccatt    1020
tggtcgtcct gtctttttcc ccaacgcacc cccgccggct ggcaagtctt tacaagtttt    1080
attggcggtg ccacggatcc tgatttggct agccttaggg aagaagccat tgtccagcaa    1140
gtgcagcagg atttgacccg cctccttgat ttacccgccg ccaaggcacg attactcggt    1200
atgaaagttt ggcgacgggc gattccccaa tatcttgtgg gctaccctca gcagtggcag    1260
caggtgaccc atgccctcag ccacacccct gggcttttcc tgtgtagtaa ctatgcggag    1320
ggggtggcct tgggcgatcg cgtcgaacat ggcaatcgaa ccgctgctgc tgttgctgcc    1380
tacctttcag gaggttaa                                                 1398

<210> SEQ ID NO 82
<211> LENGTH: 1404
<212> TYPE: DNA
<213> ORGANISM: Artificial Sequence
<220> FEATURE:
<223> OTHER INFORMATION: Synthetic_Gene encoding SEQ ID NO: 3

<400> SEQUENCE: 82
atgattgagg tagatgtcgc aattgttggg ggtggtctca gtggcctcag tgttgcttgg      60
cggttgcagc ggagcgcccc tcactacagt ggcgttcttt tagaggccag cgatcgcctg     120
gggggcaata tcacgaccca agcggcggag ggctttgtct gggaactggg tcccaatagc     180
tttgccccca cccctgccct cctacaactc attgccgagg tgggcttgca ctcagagctc     240
attcggggcg atcgccacct accgcgctac atctactggc gggggggaact ctaccccctc     300 gaacccaccc gtcccctggc cttggccact tcaaatttgc tcagcccttg gggaaaagta     360
cgggcagccc ttggtgcctt ggggtttgtg cctccctatc tgggcagtgg ggacgagtca     420
```

-continued

```
gttgattcat ttttccggcg ccatttgggg caagaggttg ctgaacgact agtggccccc      480
tttgtctctg gggtttatgc cggtgatccg caacaattga gtgccgctgc cgctttccgt      540
cgtattgccc aactggaaaa actaggggt agcctcattg ccggggctct cgcctgcgg      600 cgtcaacaac cccctcaacc aaaacccct gcacaggtgc aaatgcgacc aggggagctt      660
ggctccttta gggaaggttt ggctgctctg ccgcgggcga tcgcccaaca attgaaggca      720 cccttcacc tgcaaacccc tgttgaagca atcacccag aacccaaggg tggctacctg      780
ctgcgcagtg gtgagcaaac gtggcatgcc cgcagtgtgg tcttggcaac gcctgcctat      840
caaagcgcag agttagtcgc tcccttccag ccagcgatcg cccgtgcttt ggcgaccatc      900
ccctatccca ccgtggcctg tgtggtgttg gcctaccctg ccggactggg acgcagtgta      960
cgccccggat ttggagtact ggttcctcgt ggtcagggca tccgtaccct gggcaccatt     1020
tggtcgtcct gtcttttttcc ccaacgcacc cccgccggtt ggcaagtctt caccagtttt     1080
attggcggtg ctacggatcc cgatttggct agccttaggg aagaagcgat tgtcgagcaa     1140
gtgcagcagg atttgacccg cctccttgat ttacccgcag ccaaggcacg attactcggt     1200
atgaaagttt ggcgacgggc gattccccaa tatattgtgg gctaccctca gcagtggcag     1260
cagctgaccc atgccctcac ccaaacccct gggcttttcc tgtgtagtaa ctatgctgag     1320
ggtgtggcct tgggcgatcg cgtcgaacac ggcaatcgaa ccgctgctgc cgtggctgcc     1380
tatcttgcag gaggccagtc ctag                                           1404
```

```
<210> SEQ ID NO 83
<211> LENGTH: 1431
<212> TYPE: DNA
<213> ORGANISM: Artificial Sequence
<220> FEATURE:
<223> OTHER INFORMATION: Synthetic_Gene encoding SEQ ID NO: 4

<400> SEQUENCE: 83
```

```
atgagtgaac ctattgtcgt agatgttgct gttgttgggg cggggttaag cggcctgagt       60
gttgcatggc ggttgcaaca ggtggcaccg cagtacaagg tggtggtgct ggaggccagc      120
gatcgcctag gcgggaacat cacgaccgaa gcgcgggacg gctttgtgtg ggaattgggc      180
cccaatagtt ttgcgcccac ccctgccctg ctgcacctta ttgccgaggt ggggcttcag      240
gatcaactgc tgcggggcga tcgccgcctg ccccgttaca tttattggcg cggcaagctc      300
caccctttag agcctacccg cccccctcgcc ctcgccacga gcgggttact tagcccttgg      360
ggaaaactgc gagccgcctt aggtgccttt ggctttgtcc cgccctacct tagggatgcc      420
gatgaatccg ttagctcgtt ttttcagcgc cacttaggga aagaggtagc cgagcgattg      480
gttgcgccct ttgtgtctgg ggtttatgct ggcgatccac aacaactgag tgcagcggcg      540
gcctttcggc gcattgtcca actggagcag ctcggcggtg ctctcatacc gggtgcccta      600
cggctacggc ggcagcagcc ccccaagccc acccccccaa agggactcga gatgcgtcca      660
ggggaactgg ggtcgtttca ggagggatta agtgccctcc cgcgggcgat cgcccaccac      720
ttagcagcac ccattcactt acaaacggca ctgcatcagc ttaccccccga actcagcggc      780 ggctatacccc taagcgccac caccctgat ggcgagcaag catggcgtgc ccgtagtgtg      840
gtgctggcca ccccgccta tgtcaccgca gacctcctgc ggccatggca acccacaatt      900
gctgccggtc tagaggccat tccctaccca gcgtggcct gcgtggtctt ggcctatcct      960
gccgcggtgg gggtaaccgc tcgtcccggc tttggggtac tgattccccg cactcaagga     1020
ttacgcaccc ttggcacaat ttggtcatct tgcttgtttc ccgagcgcac gccgtctggc     1080
```

-continued

```
tggcaagtgt ttaccagctt tattggtggg gcaacggatc ctgaattggc gacgcttgaa      1140
cccgaggcca ttgtccagca ggtgcagcag gatttagagc acatgcttgc cttacccca       1200 gccaaagccc gcttattggg gatgaaactg tggcggcgag ccattcccca atacaccctt      1260
ggctatccgc agcagtggca gcagatcacc cacgccctga agcacctgcc cggcctattc      1320
ctgtgtagta attacgcggc tggcgttgcc ctaggcgatc gcgtcgaaca tgggtataac      1380
actgctgctg cggtggatgc ctacttagga gggacgtatg gctctgtcta a              1431
```

<210> SEQ ID NO 84
<211> LENGTH: 1455
<212> TYPE: DNA
<213> ORGANISM: Artificial Sequence
<220> FEATURE:
<223> OTHER INFORMATION: Synthetic_Gene encoding SEQ ID NO: 5

<400> SEQUENCE: 84

```
atgacgaacg tagtagatac tttgattgtg ggtgcaggta ttagcggttt gagtctggcc        60
cacgcacttc agaagcaagc taagactgcg cctcccctga agattttagt cgctgagagt       120
cagggacggg tgggcgggaa tatcacaact cagacagatg gagggtttct ctgggaggag       180
ggcccgaata gttttgcgcc gacaccggaa ttgatgaagt tggctgtgga tgtggggctg       240
aagcaggagt tgattttgc cgatcgcaaa ttgcctcgtt atgtttattg gcaagggaag        300
ctgcaaccgg tgccgatgac tccgcaggcg atgattcagt cccagttact gagttttccg       360
gggaaactgc gggcgcttgt cggggctttg ggctttgtgg ggccggcgat gggttctcaa       420
ttgtcgcagc agggtggaga ggaaactgtt tctcaatttt tccgacgcca tcttggtacg       480
gaagtgatgc agcgattggt ggaacctttt gtttctgggg tttatgcggg cgatccgcaa       540
cagttgagtg cggcggctgc ttttggccgg gtaactcaga tggctgatgt gggtggcggc       600
ctagtggcgg gcgcgctgct ttctgctaga aaaaggccga agaaattgcc cgtagacccg       660
aatattcctc agactaagcc gggggagttg ggttcgttta aacaggggtt gaaggctctg       720
ccagaggcga tcgctgctca attgggcgat cggctcaaac tcaattggca cttgactcgc       780
ctccaacgca cggaacgcca aacttacatt gcggaatttg ctacacctga cggccagcaa       840
caagttgagg cgcgcaccgt cgtttttgaca actcccgcct acatcacagc ggagttgttg      900
gcacctctcc aaccggaagt tagcagcgct ttacaagctg ttacttatcc tacggttgcc       960
tgcgttgtct tagcatatcc gctgtcggat gtcaagggta aattagtggg ttttggaaat      1020
ttaattccga gggccagggg aattcgcacc ctggggacgt tttggacatc gagcttattt      1080
cccgatcgcg cccctgctgg ttggcaaact ctcagcaatt acatcggtgg ggcaacagac      1140
tcggatatcg ccaatcttga ccccgaacaa atcgttgggg aggtacatcg agatttatct      1200
cggattttgc tgaagcctct ggcggcgcag cccaaagttt tggctgtgaa cctgtggaag      1260
cgggcgattc ctcagtacaa tttggggcat ctccgcgcc tgcaacaggt cgagaacggc      1320
ttaaaatcct tgccgggggt gtatttgtgc agcaactacg ttggcggggt ggctttggga      1380
gattgcgtgc ggtggggttt tgagcgggcg atcgaagtca gcgagtattt gcaagaaaca      1440
gggcataggg catag                                                       1455
```

<210> SEQ ID NO 85
<211> LENGTH: 1431
<212> TYPE: DNA
<213> ORGANISM: Artificial Sequence
<220> FEATURE:

-continued

```
<223> OTHER INFORMATION: Synthetic_Gene encoding SEQ ID NO: 6
<220> FEATURE:
<221> NAME/KEY: misc_feature
<222> LOCATION: (153)
<223> OTHER INFORMATION: n is a, c, g, or t
<220> FEATURE:
<221> NAME/KEY: misc_feature
<222> LOCATION: (154)
<223> OTHER INFORMATION: n is a, c, g, or t

<400> SEQUENCE: 85
atgacgaaca tagtagatac tttgattgtg ggtgcaggta ttagcggttt gagtctggcc      60
cacgcactcc agaaacaagc taagactgcg cctcccctga agattttagt cgctgagagt     120
cggggacgag tgggcgggaa tatcacaact cannggggagg agggcccgaa tagttttatg    180
ccaacaccgg aattgatgaa gttggctgtg gatgtggggc tgaagcagga gttgattttt     240
gccgatcgaa aattgcctcg ttatatttat tggcaaggga aactgcaacc agtgccgatg     300
actccccagg cgatgattca gtcccagttg ctgagttttc cggggaaact gcgggcgctg     360
ttcggggctt tggggtttgt ggggtcggcg atgggttctc aattgtcgca gcagggtgga     420
gaggaaactg tttctcaatt tttccgacgc catcttggta cggaagtgat gcagcgattg     480
gtggaacctt ttgtttctgg ggtttatgcg ggtgatccgc aacagttgag tgcggcggct     540 gctttttggcc gggtaactca gatggctgat gtgggtggcg gcctagtggc gggcgcgctg    600
ctttctgcta gaaaaaggcc gaagaaattg cccgtagacc cgaatattcc tcagactaag     660 ccggggggagt tgggttcgtt taaacagggg ttgaaggctc tgccagaggc gatcgctgct    720
caattaggcg atcggctcaa actcaattgg cacttaactc gcctccaacg cacggaacgc     780
caaacttaca ttgcggaatt tgctacacct gacggccagc aacaagttga ggcgcgcacc     840
gtcgttttga caactcccgc ctacatcaca gcggagttgt tggcacctct ccaaccggaa     900
gttagcagcg ctttacaagc tgttacttat cctacggttg cctgcgttgt attagcatat     960
ccgctgtcgg atgtcaaggg taaattagtg ggttttggaa atttaattcc gaggggccag    1020
ggaattcgca ccctggggac gatttggact tcgagcttat ttcccgatcg cgcccctgct    1080
ggttggcaaa ctctcagcaa ttacatcggt ggggcaacag actcggatat cgccaatctt    1140
gaccccgaac aaatcgttgg ggaggtacat cgagatttat ctcggatgtt gctgaagcct    1200
ctggtggcgc agcccaaagt tttggctgtg aacctgtgga agcgggcgat tcctcagtac    1260
aatttgggtc atattcagcg cctgcaacag gtcgagaacg gcttaaaatc cttgccgggg    1320
gtgtatttgt gcagcaacta cgttggcggt attgctttgg gtgattgcgt gcggtggggt    1380
tttgagcggg cgatcgaagt cagcgagtat ttgcaagaaa cagggcgcta g             1431

<210> SEQ ID NO 86
<211> LENGTH: 1476
<212> TYPE: DNA
<213> ORGANISM: Artificial Sequence
<220> FEATURE:
<223> OTHER INFORMATION: Synthetic_Gene encoding SEQ ID NO: 7

<400> SEQUENCE: 86
atggaagttt tagatacctt gattgtgggt gcgggggatta gcggtttgag tttggcacac      60
gcacttcaaa aggaagccag gatcgcatcg ccacgggcga ttttggtcgc tgagagtcag     120
ggacgtgtgg gcgggaatat tacgactgcg acagggggagg ggtttctctg gaggagggc     180 ccgaatagtt tttcgccgac gccggagttg ctgaagttgg ctgtggatgt gggtttgaag     240
caggagttga ttttttgccga tcgcaagttg ccgcgttatg tttattggga taagaagctg     300
```

-continued

```
caaccggtgc cgatgactcc tggggcgatg attcagtctg ggttgctgag ttttccgggg    360
aaactgcggg cgctgttcgg ggctttgggg tttgtggcgc ctgcaatggg ttctcaactt    420
tcgcagcagg gtgatgagga aactgtttct caattttttcc gccgtcatct ggggaaggaa    480
gtgatgcagc gcttggtgga accttttgtg tctggggtgt atgcggggga tccccaacaa    540
cttagcgcgg cggcggcttt tggccgggta acaaagatgg ctgatgcggg gggctctctg    600
gtggcggggg cgctgctttc tgctaggaaa aaaaaacccc aacccccct tggtaaaggg     660 gggctaaatg ctcttgcaga cccgaatatt ccgaagacta agcgggggga gttgggttcg    720
tttaaagggg ggttgaaggc tctgccagag gcgatcgctg cttcttgggg cgatcgagtg    780
aaactcaact ggcatttgac taggctcgat cgcactgaac gggaaactta cattgctgta    840
ttttcaacac ccgacggaca gcaggaaatt gaggcgcgca cggtggtttt gacgaccccg    900
gcttacgtga cagcggagtt gttgcagcct ctgcaaccgt ccgttagcag cgctttacaa    960
gcttttactt atcctacggt tgcatcggtt gtattagcat atccgatgtc ggatgtcaag   1020
ggcaaattag tgggatttgg aaatttaatt ccgagagggc agggaattcg cactctgggg   1080
acgatttgga catcgagttt atttcccgat cgcgcgcctg cgggctggca aactctcacc   1140
agttatattg gcggagcaac tgattcggga attggcaatc ttgacgccga acaaattgtt   1200
ggggaggtgc accgagattt gtctaggatt ttgctgaagc cggaggcggc gcagccgaaa   1260
gttttgactg tgaaactttg gaagcgggcg attcctcagt acaatttggg ttatttcgat   1320
cgcctgcaac agatcgatcg gggtttaaaa tctttgcccg ggctgtattt gtgcagcaac   1380
tacttaggcg gggtggcttt gggagattgc gtgcgcaggg gctttgagcg agcgcaagaa   1440
gtgggcgagt atttgaacga tagtttttgag ttttga                            1476
```

```
<210> SEQ ID NO 87
<211> LENGTH: 1404
<212> TYPE: DNA
<213> ORGANISM: Artificial Sequence
<220> FEATURE:
<223> OTHER INFORMATION: Synthetic_Gene encoding SEQ ID NO: 8

<400> SEQUENCE: 87
atggacgatc gccaagggga gccaaccgag gttttggtgg tgggggccgg catttgcggc     60
ttgacggtgg cccatggctt ggcgcagcgg ggtgtggcct gtcgggtggt ggaagccagt    120
gaccgcgtgg ggggcgcgat cgtcacccgg cgggagcatg gctttcagtg ggaggagggc    180
cccaacagct tttcgcccac cccggagttg ttggctttgg cgatcgccat gggtttgcgg    240
gacgagttga ttttggctga ccggcggttg ccccggtatg tgtggtggca aaaccgtttg    300
caggcggtac ccatggcccc accgggtctc ctgacgacgg gtttgttgtc gccgtggggc    360
aaattgcggg cggcggtggg ggccttgggg tttgtgcccc ccagctttgc ggcggatgag    420
acggtgggga gttttttccg gcggcatttg gggccgaggg ttttgacgcg gttggcggca    480
ccgtttgtat cgggggtgta tgccggcgat cccgaagccc tctccattgg cgcggctttt    540
ccccgggtga cggcgatcga agcgatgggg ggcggcctgg tggcggggtt tatccaggcc    600
ctgcggcagc gggggggcccc cgatccccat ttgccccaga ccaagccggg ggagttgggt    660
tccttccggg aagggatcga ggctttgccc cgggcgatcg ccgccgattt agcccaacgg    720
ggggtgaccc taaccttgaa ccaagcctta acccgattgg aacccacggg cgatcgctgg    780
cgggcggtgt tggccagcgg cgaggaattg gaagcccgga gtgtggtgtt ggcggtgccg    840
```

```
gcgtgggcgg cggcgaaaat tctccagcaa accccagaaa ccgccgattg ggtggcggat      900
ttggagagaa ttccctatcc ggcggtggcc tgtgcggtgt tggcctatcc cgacggggat      960
ttgcggcagc cgttgcgggg atttgggcac ttggtgccgc gggggcaagg cattcgcacc     1020
ctgggcacca tttgggcatc cagtttgttt ccggggcggg cccccgccgg atacaccctc     1080
ctgctgaatt tcattggcgg caccaccgat cccacactgg cgcagttgga cgcaggggcg     1140
atcgcccaag cggtccacca ggacttgcga caaattttgg ttcaaccgac ggcggcgccc     1200
cccaaagtat tggcggtgaa cctgtggcgg cgggcgatcc cgcagtttac ggtggggcac     1260
caagggcgct tggcgcggct ggcggcgggg ttaccaccgg ggttggtttt ggccgggaat     1320
tatcgggggg gggtggccct cggcgattgc gtgcggcacg ggctggcggt ggcggcccaa     1380
gttgcggctt ttcttgagag ataa                                           1404
```

<210> SEQ ID NO 88
<211> LENGTH: 1410
<212> TYPE: DNA
<213> ORGANISM: Artificial Sequence
<220> FEATURE:
<223> OTHER INFORMATION: Synthetic_Gene encoding SEQ ID NO: 9

<400> SEQUENCE: 88

```
atgctggata cgctcgtagt tggggcaggt ttgagcggat tgagcgtcgc gcgatcgctc       60
caaatggcag ggcgcaatgt gctggttgcc gaggcgcagg agcgtgttgg cggtaacatt      120
ctcacgcagc agagcgatga tgggtttcag tgggaggagg ggccaaatag cttctcgcca      180
aaccgcgaac tgctcgaact cgcagtcggt gtggggctca gggacaagct gattttttgca      240 gatcgccgtt tgccgcgttt tgtttactgg cgcaatagtt tgcatccggt cccaatgagc      300
ccgccgcgag cagtgacgac atcgctattg agtcccttag gtaaattacg cgcggtagcc      360
ggcgcgatcg gatttgtgcc cccagcgctc tccgacgagg agtccgttgc cgagttcttc      420
acgcgccatt tggggtccga agttgccgaa cgactggttg cgcctttcgt ttcggggggtt      480 tacgcaggtg atgtcgagcg attgagtgtc agctcagcct tccggcaagt cgctaagctg      540
tccgaggtcg gtgtgcgggtt gcttgctgga gcactcctga cgcgccgtgg taaatccggc      600
cctcctcaaa agctccctcc aagggttgac cccaatttgc cgcgcgtcca acgcggtgag      660
ttggggtctt tcgtcggcgg gttaaaaatg ctgcccgagg cgatcgccgc taaactcggc      720
accaagctta agctgcactg gaccctagaa cacttagttc gctgcgaggg cggctatcgc      780
gccgaattcg caactccgga ggggcaacag cagatcgagg tgcgttcgct ggtattggca      840
acacctgctt acagatgcgc gcgggtattg caatcgctcg ctccttcggc ttgccaagcg      900
ctatccgaaa tgccttatcc agcagtagcg tgcgtagtgc tggcgtatcc gagctcggcg      960
ttttcctctc ctttacaagg gtttggcaat ttgattcccc gcggacaagg tattcgcacg     1020
ctgggtacaa tttggtcgtc ggcacttttc cctgggcgaa cgccgccagg ctgggagatc     1080
ttaacgagtt ttattggcgg cgcgaccgac cccgaactcg gtacgctgtc cgcacagcaa     1140
atcgtggcag aggtccgtcg cgacctgcag cgggtgttgg tcgataaaga acccaacacc     1200
gaaccgcgcg tcctggcagc taaggtttgg ccgcgcgcga tccctcagta cgtgctcggt     1260
catagcgatc gcctcaaccg catccaaatc gacctcgacc ggctgcccgg cttatatttg     1320
tgcagcaact tcaccgatgg cgtagcgctc ggcgactgcg tgcggcgggg cttcgagact     1380
gctgaggcga tcggacagta cctcaactga                                     1410
```

```
<210> SEQ ID NO 89
<211> LENGTH: 1416
<212> TYPE: DNA
<213> ORGANISM: Artificial Sequence
<220> FEATURE:
<223> OTHER INFORMATION: Synthetic_Gene encoding SEQ ID NO: 10
<220> FEATURE:
<221> NAME/KEY: misc_feature
<222> LOCATION: (95)
<223> OTHER INFORMATION: n is a, c, g, or t
<220> FEATURE:
<221> NAME/KEY: misc_feature
<222> LOCATION: (1385)
<223> OTHER INFORMATION: n is a, c, g, or t

<400> SEQUENCE: 89
atgctaaagt tggcggtaga tgttggcctt aaacaggatt taattttttgc agatcgtaag      60 ctacctcgct atgtttattg gaatggtcaa ttacntttag ttgctgagag ccaaaatcga     120 gtaggggta atattacaac tgtttctcaa ggagattta tttgggaaga aggtcctaat     180 agttttctc ctacacctga actgctaaag ttggcggtag atgttggcct taaacaggat     240 ttaattttttg cagatcgtaa gctacctcgc tatgtttatt ggaatggtca attactacca     300
gtgccaatgg gtccaacggc gatgttacag tctaagctac tgagtgattc tggaaagtta     360
cgcgctttag ttggtgcttt gggttttgtg ccacctgctg tgggtactgg tctgtctcag     420
caagggggag aagaaactgt atctcaattt ttccaaagac atctgggtgt ggaggtgatg     480
cagcgattgg tagaaccttt tgtttctggc gtttatgctg gagaccctag tcaacttagt     540
gctactgctg cttttctag agtagcgaga atggccgata ttggtggtgg acttttggct     600
ggtgctgttt tgtctgctaa aagaaatcct aagtcaaagg ttgctgccga tcctaatatt     660
cccaagacta aacctggaga gctaggttct ttccgggtg gtttggaggc attgccaaag     720
gcgatcgcta cttatttagg agaagcggta aaactaaatt ggcatctcat tggtattcgt     780
cgtacagaac aacaaactta tatagcagaa ttttctactc ccaacggttc tgagcaaata     840
gaaactcgta ctattgctct atctactcct gcttattttt gttctgaatt atttaaacct     900
ttattgcctg aaattgcttc tactttcgat gaatttttatt atcctactgt tgcttgtgta     960
gttttggcat atcctgtttc ttctattaag gcaaagatag atggctttgg taatttaatt    1020
cctagaggtc aaggtatcag gactcttggt actatttggt cttctgcttt gtttcctggt    1080
agaacacctc caggatggca agtttttact aattttattg ggggtgcaac agacccagga    1140
atttctcagt tagatagtga ggcgatcgtt tcacgagtac atcaagacct tgggcaaact    1200
ttattaaagc aagatgcgga acaaccaaaa gttctggctg tacatttatg gtctcgtgct    1260
attcctcagt ataatttagg tcataattct aggctggatc agattaatca tggtttaaaa    1320
tcttggcctg gtgtgtatct ttgtagtaat tatattggtg gtgtagcttt gggagattgt    1380
gttcngtaca tcaagacctt gggcaaactt tattaa                             1416

<210> SEQ ID NO 90
<211> LENGTH: 1464
<212> TYPE: DNA
<213> ORGANISM: Artificial Sequence
<220> FEATURE:
<223> OTHER INFORMATION: Synthetic_Gene encoding SEQ ID NO: 11

<400> SEQUENCE: 90
atggaagttt tagatacctt gattgtgggt gcggggatta gcggtttgag tttggcgcac      60
gcacttcaaa aagaagcaac gagtgcatcg ccacgggcga ttttggtggc tgagagtcag     120
```

-continued

```
ggacgtgtgg gcgggaatat cacgactgcg acaggggagg ggtttctctg ggaggagggc      180
ccgaatagtt tttcgccgac gccggagttg ctgaagttgg ctgtggatgt cggtttgaag      240
caggagttga tttttgccga tcgcaaattg cctcgttatg tttattggga aaagaagctg      300
caaccggtgc cgatgactcc tggggcgatg attcagtctc agttgctgag ttttccgggg      360
aaactgcggg cgctgttcgg ggctttgggg tttgtggggc cggcaatggg ttctcaactt      420
tcgcagcagg gtgatgagga aactgtttct caatttttcc gccgtcatct gggaaaggaa      480
gtgatgcagc gcttggtgga accttttgtg tctgggtttt atgcggggga tccccaacaa      540
cttagcgcgg cggctgcttt tggccgggta acaaagatgg ctgatgcggg tggcgggctg      600
gtggcggggg cgctgctttc tgctaggaaa agacccccccc aacccccccct taccaagggg     660 gggctaaaga ctgttgcaga cccgaatatt ccgaagacta agccgggggga gttgggttcg      720 tttaaagggg ggttgcaggc tctgccagag gcgatcgctg cgaacttggg cgatcgactg      780
aaactcaact ggcacctgac tcgactcgat cgcacggaac gcgacactta catagctgta      840
ttttctacgc ccgacggaca gcaggaagtt gaggcccgaa ccgtagtttt gacaacaccg      900
gcctatgtta cagccgagtt gttggagcct ctgcaaccgt ccgttagcag cgctttacaa      960
gcttttactt atcctacggt tgcctccgtt gtattggcat atccgatgtc ggatctcaag     1020
ggtaaattag tgggatttgg aaatttaatt ccgaggggggc agggaattcg cactctgggg     1080
acgatttgga catcgagttt atttgccgat cgcgcgcctg cgggctggca aactctcacc     1140
agttatatcg gcggggctac tgattcggga attggcaatc ttgacgccga acaaattgtt     1200
ggggaggtgc accgagattt gtctcagatt ttgctgaagc cggaggcggc gcagccgaaa     1260
gtgttgactg tgaaaatttg gaagcgggcg attcctcagt acaatttggg tcatttcgat     1320
cgcctgcaac agatcgatcg gggcttaaaa tctttgccgg ggctgtattt gtgcaccaac     1380
tactttggcg gtgtggcttt gggagattgc gtgcggagag gttttgagcg ggctcaagaa     1440
gtggacgagt atttgaacgg atag                                            1464
```

<210> SEQ ID NO 91
<211> LENGTH: 1428
<212> TYPE: DNA
<213> ORGANISM: Artificial Sequence
<220> FEATURE:
<223> OTHER INFORMATION: Synthetic_Gene encoding SEQ ID NO: 12

<400> SEQUENCE: 91

```
atggtagata tctctaatcat tggtgccgga ataagcggtc ttagcctagc ctacgcctta      60
catcaagacg ggcgaaaagt tttgctgtgc gaacgtcaag aacgagttgg cggaaatatt      120
acaacaggta aggcgggtgg gtttctttgg gaagaagggc caaccagctt tacaccaaca      180
ccagcactgc taaagctggc agtagatgtg gggttgagag aggagttggt gttagcagac      240
caccgcttac ctcgttttgt ctactggaaa ggtcagctac ttcctgtacc gatgagtcca      300
ccatcggctg tcacatccaa gttactaagc ttgtcaggca gtttagggc tttagtaggt      360 gcttttagggt ttatcccacc agcaataggc aaccacttat ctcagcaagg aggcgaggaa      420
acagttgctc agtttttaa gcgccattta gggacagaag tggcagaaag attggtagcg      480
ccgtttgtct ctggtgtcta tgctggtgat gtgcatcaac tcagcgcccg ttcagctttt      540
cggcggatcg ctcaactaga aaatgtgggc gggggactgg tatctggggc aatattgtca      600
cggaagcaac gccagcaaca gaaaccgcca acagatccca gtttgcctac tgttcgccgt      660
ggtgaattag gctcgtttaa agagggttta caatctctac caaaagcgat cgcatcccat      720
```

```
ctgggtgaaa atattaaact aaattggact ttgactgagc ttcgtcaaac agccaatcaa      780
acttatattg cagaatttc taccccagaa ggtagtcagc aggtagaagc gcgtactgtt      840
gttctaacta ccccagctta tgtaaccgcc gaattgctgc ataatctagc accaaatgcg      900
agtattgcct taaaagaaat tccttatccc tcagtagctt gcgttgtctt agcttatcca      960
gacgatgcct taaaatttcc cctaaaaggc tttggaaact taattccacg aggtcaaggt     1020
attcggactc taggcacaat ttggtcttct agcttatttc caggacgtgc gccgcaaggt     1080
tggcaaatgc taactaattt tattggtggg gctacagatc cagaagtagg taatctagac     1140
aacgagcaat tagttcaagc agtccataaa gacttcagc gcgttcttct taaaaaagat     1200
gtacctccaa aagcgatcgc agtacattta tggaaacggg caattcctca atatacttta     1260
ggtcatcatc tgcgtttagc ccaaatcaat caagatttgg cacaactacc tggtttatat     1320
ctatgtagta actacactga tggcgtttct ttaggtgatt gtgtgcaacg cgcctacgat     1380
caattaccaa ttatcaataa acaactatca attatcaatg acaattag               1428
```

<210> SEQ ID NO 92
<211> LENGTH: 1464
<212> TYPE: DNA
<213> ORGANISM: Artificial Sequence
<220> FEATURE:
<223> OTHER INFORMATION: Synthetic_Gene encoding SEQ ID NO: 13

<400> SEQUENCE: 92

```
atggaagttt tagatacctt gattgtgggt gcggggatta gcggtttgag tttggcgcac       60
gcacttcaaa aagaagcaac gagtgcatcg ccacgggcga ttttggtggc tgagagtcag      120
ggacgtgtgg gcgggaatat cacgactgcg acaggggagg ggtttctctg ggaggagggc      180
ccgaatagtt tttcgccgac gccggagttg ctgaagttgg ctgtggatgt cggtttgaag      240
caggagttga ttttttgccga tcgcaaattg cctcgttttg tttattggga aaagaagctg      300
caaccggtgc cgatgactcc tggggcgatg attcagtctc agttgctgag ttttccgggg      360
aaactgcggg cgctgttcgg ggctttgggg tttgtggggc cggcaatggg ttctcaactt      420
tcgcagcagg gtgatgagga aactgtttct caatttttcc gccgtcatct gggaaaggaa      480
gtgatgcagc gcttggtgga accttttgtg tctgggtttt atgcggggga tccccaacaa      540
cttagcgcgg cggctgcttt tggccgggta acaaagatgg ctgatgcggg tggcgggctg      600
gtggcggggg cgctgctttc tgctaggaaa agacccccc aacccccct taccaagggg       660 gggctaaaga ctgttgcaga cccgaatatt ccgaagacta agccggggga gttgggttcg      720
tttaaagggg ggttgcaggc tctgccagag gcgatcgctg cgaacttggg cgatcgactg      780
aaactcaact ggcacctgac tcgactcgat cgcacggaac gcgacactta catagctgta      840
ttttctacgc ccgacggaca gcaggaagtt gaggcccgaa ccgtagtttt gacaacaccg      900
gcctatgtta cagccgagtt gttggagcct ctgcaaccgt ccgttagcag cgctttacaa      960 gctttactt atcctacggt tgcctccgtt gtattggcat atccgatgtc ggatctcaag     1020
ggtaaattag tgggatttgg aaatttaatt ccgaggggc agggaattcg cactctgggg     1080
acgatttgga catcgagttt atttgccgat cgcgcgcctg cgggctggca aactctcacc     1140
agttatatcg gcggggctac tgattcggga attggcaatc ttgacgccga acaaattgtt     1200
ggggaggtgc accgagattt gtctcagatt ttgctgaagc cggaggcggc gcagccgaaa     1260
gtgttgactg tgaaaatttg gaagcgggcg attcctcagt acaatttggg tcatttcgat     1320
```

```
cgcctgcaac agatcgatcg gggcttaaaa tctttgccgg ggctgtattt gtgcaccaac    1380
tactttggcg gtgtggcttt gggagattgc gtgcggagag gttttgagcg ggctcaagaa    1440
gtggacgagt atttgaacgg atag                                           1464
```

```
<210> SEQ ID NO 93
<211> LENGTH: 1464
<212> TYPE: DNA
<213> ORGANISM: Artificial Sequence
<220> FEATURE:
<223> OTHER INFORMATION: Synthetic_Gene encoding SEQ ID NO: 14

<400> SEQUENCE: 93
atggaagttt tagatacctt gattgtgggt gcggggatta gcggtttgag tttggcgcac      60
gcacttcaaa aggaagcgag gagtgcatcg cctcgggcga ttttggtggc tgagagtcag     120
ggacgtgtgg gcggaaatat cacgactgcg acaggggagg ggtttctctg ggaggagggc     180
ccgaatagtt tttcgccgac gccggagttg ctgaagttgg ctgtggatgt cggtttgaag     240
caggagttga tttttgccga tcgcaaattg cctcgttttg tttattggga aaagaagctg     300
caaccggtgc cgatgactcc tggggcgatg attcagtctc agttgctgag ttttccgggg     360
aaactgcggg cgctgttcgg ggcttttggg tttgtggggc cggcaatggg ttctcaactt     420
tcgcagcagg gtgatgagga aactgtttct caattttttcc gccgtcatct gggaaaggaa     480
gtgatgcagc gcttggtgga accttttgtg tctggggttt atgcggggga tccccaacaa     540
cttagcgcgg cggctgcttt tggccgggta acaaagatgg ctgatgcggg tggcgggctg     600
gtggcggggg cgctgctttc tgctaggaaa agacccccccc aaccccccct taccaagggg     660
gggctaaaga ctgttgcaga cccgaatatt ccgaagacta agccggggga gttgggctcg     720
tttaaagggg ggttgaaggc tctgccagag gcgatcgctg cgaacttggg cgatcgactg     780
aaactcaact ggcacctgac tcgactcgat cgcacggaac gcgacactta catagctgta     840
ttttctacgc ccgacggaca gcaggaagtt gaggcccgaa ccgtagtttt gacaacaccg     900
gcctatgtta cagcggagtt gttggagcct ctgcaacctt ccgttagcag cgctttacaa     960 gctttttactt atcctacggt tgcctccgtt gtattggcat atccgatgtc ggatctcaag    1020
ggtaaattag tgggatttgg aaatttaatt ccgaggggggc agggaattcg cactctgggg    1080
acgatttgga catcgagttt atttgccgat cgcgcccctg cgggctggca aactctcacc    1140
agttatatcg gcggggctac tgattcggga attggcaatc ttgacgccga acaaattgtt    1200
ggggaggtgc accgagattt gtctcagatt ttgctgaagc cggaggcggc gcagccgaaa    1260
gtgttgactg tgaaaatttg gaagcgggcg attcctcagt acaatttggg tcatttcgat    1320
cgcctggaac agatcaatcg gggcttaaaa tctttgccgg ggctgtattt gtgcaccaac    1380
tactttggcg gtgtggcttt gggagattgc gtgcggagag gttttgagcg ggctcaagaa    1440
gtggacgagt atttgaacgg atag                                           1464
```

```
<210> SEQ ID NO 94
<211> LENGTH: 1437
<212> TYPE: DNA
<213> ORGANISM: Artificial Sequence
<220> FEATURE:
<223> OTHER INFORMATION: Synthetic_Gene encoding SEQ ID NO: 15

<400> SEQUENCE: 94
atgctggatg cgttagtcgt gggcgctggc atcagcggtt tgagcttggg gcgcaccctg      60
cagcagcagc agcactcgct gctcgtggcc gagcgccaac cccaggttgg gggcaacatt     120
```

```
accaccagca gcactggcga gttttgtgg gaggaagggc ccaacagctt ctcgccggcg      180
cgagagctgc ttgagcttgc cgtcgatgct ggcctgcgcg aggagctcgt gctggccgac      240
cgacagctgc cgcgctacat ctactggcgg gggcgactgc agccggtgcc catgcgccct      300
tcggccgcgc tcaaaacgca gctgctgagc cctagcggca agctgcgagc gctggccggg      360
gcgctgggat ttgtcccccc ggcggtgggc gaggcggtat cgcagcaagg cggcgaggaa      420
acggtcgcgc agttttttcca acgccatctg gggcgcgagg ttaccgagcg tttggtcgcc      480
ccgttcgtct cgggcgttta cgccggcgac gtccgccagt tgagcgccca ggccgccttc      540
cggcgcgtca cgcagctcgc cgatcgcggc ggcggcctgc tccccggagc gcttctgggg      600
cggcaggcgg ccccgcaacg cccggctacc agccagacgc agctcccca aacccaaagt       660 ggggagctgg gctcgttccg cacgggcttg caggcgcttc ccaacgccat tgccgagcgc      720
ttgggggatg ccctgcgctg caactgggcg ctatcgcagc tgcagcgcac cgagcgcgac      780
agctatttgg ccaccttcca aacgccccag gggccgcagc aggttgaggc gcgtgcggtg      840
gtgctcacca ccccagccta taccagcgcc gagctattgc ccgctgca cgcccgcgcc        900 agccagcggc tggctgccat tccctacccg ccggtggcta gcgtggtgct ggcctacccg      960
cagcaggcgt tgggcggggc cctgcgcggc tttggcaacc tcaacccgcg cggtcaaggc     1020
attcgcaccc tgggcacgat ttggtcgtcg gcgctgtttg ccggccgcgc gccggctggt     1080
tgggaaatcc tgactagctt tattggggc gccactgacc ctgaaatcgc tcgcctggat      1140
gaagatcgca tcgtgcaagc cgtccacgcc gatttgcgcc aggtcctgct ggcgcgctac     1200
gtggcaccca aggtgctggc cgtgcggctc tggcaccgcg ccattccgca gtacgccatc     1260
ggccaccagg cccaaatgca agccctcgaa gccgagctag ccgagctgcc ggggctgttt     1320
ctgtgcagca actacctcga tggggtctcg ctgggcgatt gcatccgccg cggcttcgag     1380
cgggcgcaca cggtttcgca ctacttgcaa gcgcctgcgg cagctccagc ggcctga       1437
```

<210> SEQ ID NO 95
<211> LENGTH: 1440
<212> TYPE: DNA
<213> ORGANISM: Artificial Sequence
<220> FEATURE:
<223> OTHER INFORMATION: Synthetic_Gene encoding SEQ ID NO: 16

<400> SEQUENCE: 95

```
atgactcacg tactcgatag tttgatcgtc ggtgctggca ttagcggcct gagtttagct       60
cattctctcc ttcggaaccc aaaccctcaa ttgtctctca acattctggt gagcgagcat      120
caaggacggg taggaggaaa cataaccaca gtatctcaag agagtttct ctgggaagaa       180 ggccccaata gtttctctcc gacccctgag ttactgaagt tagccgtaga agttggcctc      240
aagtctgagt tcgtctttgc cgatcgcaag ttacctcggt atgtttactg gaatagtcaa      300
cttatgccag tgccgatgag tcctccggct ttgttgagta caaaactctt aagtcctgga      360
ggtaaactcc gagcattaac gggggcatta ggatttgtac ggccggcgat gggacaagcg      420
ttaagtcaac aaaatgggga agaaacgatc tcgcagtttt ttgagcgtca tttgggttca      480
gaagttctca aacgactggt tgaaccattt gtttccgggg tctatgcagg cgatccacag      540
caactcgaaa ttagctcggc ttttgcccga gtcgcacgta tggcttacag tggcggtggg      600
ttagttgccg gagcggtttt atcacgtggt cagaacaaat cttcgcgatc gcctgccgat      660
ccgtctattc cccaaactaa acggggagag ttggggtctt ttcgtcaggg aattggagcc      720
```

```
ttacccaatg cgatcgcgca gcagttaggc gatcaactca aattaaactg gcaactcact      780
cgtcttgaac ggactgaaaa ccaaacttat cgggctgaat tttcgacccc agatggcgtt      840
caacaggtcg aaactcgaac ggtagtgttg acaactccgg cttatgtcac agcagaaatt      900
ctgaaaccgt tgcaactcca agtcagtcaa acgttaaccg aaattcctta tcctccggtg      960
gcttgcgtcg ttttagccta tcccgtttca gctttcaagc agaaattaac cggatttggg      1020
aatttagttc cccgaggaca aggaattcgg acgttaggca cgatttggac ctcaagttta      1080
tttcccggtc gcgcccccca aggctggcaa gttctcacca gttatattgg cggagcgact      1140
gatccagaaa ttggagagtt agaagatgat caaattgttg aggcggttca tcaagatttg      1200
cgtcgcattt tactcaaaga agatatctct cccaaagtgc tagccgtgca tctgtggaaa      1260
cgtgctatcc ctcaatacaa tctcggacac caacaacggt tacaacaggt taatgaaggt      1320
ctagaggcaa tgccagggtt atatctgtgt agcaactata tcgacggtgt agcgttagga      1380
gattgtgtgc gtcgttctat aggacaagct aacgaaattc tcagtttttt ggatcaatag      1440
```

```
<210> SEQ ID NO 96
<211> LENGTH: 1446
<212> TYPE: DNA
<213> ORGANISM: Artificial Sequence
<220> FEATURE:
<223> OTHER INFORMATION: Synthetic_Gene encoding SEQ ID NO: 17

<400> SEQUENCE: 96
```

```
atgacgaatg tagtagatag cttgattgtg ggtgctggta ttactggctt gagtctggcc       60
cacgcacttc ataaggaagc aaagactgga actccggtga agattttggt tgctgagagt      120
ctgggacgtg tggggggaa tatcacaact tgtacaggga atgggtttct gtgggaggag      180
ggcccgaata gttttcgcc gacggtggag ttgatgaagt tggctgtgga tgtgggggctg      240 aaggaggagt tgattttgc cgatcgcaaa ttacctcgtt ttgtatattg gcaaaataag      300
ctgcaaccgg tgccgatgac tccacaggcg atgattcagt cgcaattgtt gagttttccg      360
gggaaactgc gggcgctgtt cggggctttg ggatttgtgg caccggcaat gggtgctaca      420
ctttcgcagc agggtggtca ggaaactatt tctcaatttt tccggcgaca tctgggtacg      480
gaagtgatgc agcgattggt ggaaccgttt gtttctggag tttatgccgg cgatcccgaa      540
caacttagcg cggcggcggc ttttggtcgg gtaacgagga tggctgattt gggtggtgga      600
ctggtggcgg gggcgctgct tggggcgagg aaagggccga agaaaatgcc cgcagacccg      660
aatattccca agactaagcc ggggggagttg ggttcgttta aaggggggtt gaaggctcta      720
ccagaggcga tcgctgctca attaggcgat cgcctgaaac tcaattggca tctcacaggt      780
ttgcaccgta ctgaaaacaa aacttacatt gctgaattct caacgccgga tgggccgcaa      840
caggttgaga ctcgcactgt ggtgttgaca actcctgctt atgtgacagc cgattggttc      900
caatctctgc aaccggaagt gagcacggcc ttacaagctt ttacttaccc tactgttgcc      960
tgcgttgtcc tagcatatcc gaaatcggat gtcaaggaaa agatggtggg ctttggaaat      1020
ttaattccga ggggacaggg aattcggact ctggggacga tttggagttc gagtttattt      1080
gctaatcgtg cgcctgcggg ttggcaaact ttgacgagtt ttatcggcgg ggctactgat      1140
tcgggtattg cgaatcttga cgctgaacaa attgtggccc aggtgcatcg agatttgtct      1200
cggattttgc tgaaaccgga tgtcccacag ccgaaggttt ggcggtgaa ggtgtggaag      1260 caggcgattc tcagtacaa tttggggcat ttcgatcgcc tggaacagat cgatcgaggt      1320
ttaaaatctt tgccgggggt ttatttgtgt agcaattacc ttggtgggggt ggctttggga      1380
```

-continued

```
gattgtgtgc gtctgggttt ggaaagggcg atcgaggtta gtaagtattt gcaagaaacc    1440
agctag                                                               1446

<210> SEQ ID NO 97
<211> LENGTH: 1446
<212> TYPE: DNA
<213> ORGANISM: Artificial Sequence
<220> FEATURE:
<223> OTHER INFORMATION: Synthetic_Gene encoding SEQ ID NO: 18

<400> SEQUENCE: 97
atgacgaacg tagtagatac tttgattgtg ggtgctggta ttactggctt gagtctggcc      60
cacgcacttc agaaggaagc aaagactgga actccggtga agattttggt tgctgagagt     120
ctgggacgtg tggggggggaa tatcacaact tgtacaggga atgggtttct gtgggaggag     180
ggcccgaata gttttttcacc gacggcggag ttgatgaagt tggctgtgga tgtggggctg     240
aaggaggagt tgattttttgc cgatcgcaaa ttgcctcgtt ttgtatattg gcaaaataag     300
ctgcaaccgg tgccgatgac tccgcaggcg atgattcagt cgcaattgtt gagttttccg     360
gggaaactgc gggcgctgtt cggggctttg ggatttgtgg caccggcaat gggtgctaca     420 cttttcgcagc agggtggtca ggagactgtt tctcaatttt tcgggcgaca tctcggtacg     480
gaagtgatgc agcgattggt ggaaccgttt gtttctgggg tttatgcggg cgatcccccaa     540 caacttagcg cggcggcggc ttttggtcgg gtgacgagga tggctgattt gggtggtgga     600
ctggtggcgg gggcgctgct tggggcgagg aaagcgccga agaaaatgcc cgcagacccg     660
aatgttccga agactaagcc ggggggagttg ggttcgttta agggggggggtt gaaggctctg     720 ccagaggcga tcgctgctca attaggcgat cgcctgaaac tcaattggca tctcacaggt     780
ttgcaccgta ctgaaaacaa aacttatatt gctgaattt cgacgccgga tgggccgcaa     840
caggttgaga ctcgcactgt ggtgttgaca actcctgctt atgtgacagc ggatttgttc     900
caatctctgc aaccggaagt tagcagcgcc ttacaagctt ttacttaccc tactgttgcc     960
tgcgttgtct tagcatatcc gaaatcggat gtcaaggaaa agatggtggg atttggaaat    1020
ttaattccga gggggcaggg aattcggact ctggggacga tttggacttc gagtttattt    1080
gctaatcgcg cgcctgcggg ttggcagact ttgacgagtt atatcggtgg ggctactgat    1140
tcggggattg ggaatcttga tgctgaacaa attgttgggg aggtgcatcg agatttgtct    1200
cggattttgc tgaaacctaa tgtgcctcag ccgaaggttt tggcggtgaa ggtgtggaag    1260
caggcgattc ctcagtacaa tttgggggcat ttcgatcgcc tggaacggat cgatcgaggt    1320
ttaaaatctt tgccgggggggt ttatttgtgt agcaactacg ttggtgggggt ggctttggga    1380 gattgtgtgc gtctgggttt tgaaagggcg atcgaggtta gtgagtattt gcaagcaacc    1440
agctag                                                               1446

<210> SEQ ID NO 98
<211> LENGTH: 1401
<212> TYPE: DNA
<213> ORGANISM: Artificial Sequence
<220> FEATURE:
<223> OTHER INFORMATION: Synthetic_Gene encoding SEQ ID NO: 19

<400> SEQUENCE: 98
atgttagata ctttaattgt aggagcagga atcagcggtt taagcacggc ctatcgcctg      60
catcaagggc aacgccagat tttagtcgca gaacagcgcg atcgcgttgg cggcaatatt     120
```

```
gcaacggaac accagggggga attcctctgg gaagaaggcc ccaatagttt ttccccaacg      180
ccggagttat taaaactggc agttgatgcg ggcttaaaaa atgactttgt tttcgctgat      240
cgcaatcttc cccgttacgt ttattggcag ggaaaactgc gtcctgttcc catgagtccc      300
ccagcagcag ttaaatcgca attgcttagc ccttggggaa aactgcgggc attagccggt      360
gccctgggct ttgtttcccc taatgttgaa gggaaggaag agacagttgc cgactttttt      420
acccgtcact tgggagaaga agtggcgcaa cgcctcgtcg ctccctttgt gtctggcgtt      480
tacgccggag atgttcaccg gctcagtgcc caagccgcct ttggccgggt tacgcaattg      540
gctgatgtgg gcggtggact ggttgcaggg gcagtattat cccgcggtaa gagaaagcag      600
tcttcatcga cggtaactga gaatgccgat attcccaaaa ccaagtccgg ggaattggga      660
tcctttcgag aaggcttgca aatgttgccg cgcgcgatcg cgtcaaaact gggcgaatca      720
gttaaattaa actggcagct taacaatatt tctcctcatc ccgaacaagg ctacattgcc      780
gcattttcca ccccggaagg ggaacaaagc gtagaagcta aaagtattgt cctcactaca      840
ccagctcatg tcactgcccc aattattcaa accttatccc cgctaaccag cacagcactc      900
caagatattt cttatccgcc agtagcctgt gttattcttg cctatccaga tgaggcgctg      960
cgcttctcct taaaaggatt tggcaacctg gttccccgca accaaggctt gcgtacgcta     1020
ggcacaattt gggcatcaac gctatttcct gggcgtgccc ctcaaggttg gcacattctg     1080
acaaacttta tcggtggggc aacagatccc gaaattgctc aacttagtga agaacaaatc     1140
atcgaccaag ttcaccagga cttacaaaag gtgttactga aatcggatac gaaccccaaa     1200
cccttagcgg ttcatctgtg gtcaaaagcc attccgcaat atactttagg acatctcgac     1260
cgtttagaaa cgataagaaa tagtctaaaa tcttgtcctg gcctcttttt atgcagcaat     1320
tatcttgatg gggtttcact gggagattgt gtccgtcgcg gcgaagaaac cgctcaagcc     1380
gtgttagatt atttgggtta a                                              1401
```

<210> SEQ ID NO 99
<211> LENGTH: 1449
<212> TYPE: DNA
<213> ORGANISM: Artificial Sequence
<220> FEATURE:
<223> OTHER INFORMATION: Synthetic_Gene encoding SEQ ID NO: 20

<400> SEQUENCE: 99

```
atgactgaaa tattagatgt cttagtcgtg ggtgcaggta tcagtggctt gagtttagcc       60
cataaactga caaaattaag taataattca cccttgaaaa ttttagttgc tgagagccaa      120
aaccgagtcg ggggtaatat cacgacagtt tctcaaggag aatttctttg ggaagaaggt      180
cctaatagtt tttctcccac ccctgagctt ttaaagttgg ctgtagatgt tggcctcaaa      240
gaggatttga tttttgcaga ccgtaagtta cctcgttatg tttattggaa tggtcaatta      300
ctaccagtac caatgagccc aaaggcaatg ttacagtctc aactactgag taatactgga      360
aagttacgcg ctttagttgg tgctttgggt tttgttccac ctgttgttgg tatggatcta      420
tctcaggaag ggggagaaga aactgtatcc caatttttcc aaagacatct tggtaaagag      480
gtaatggaac gattagttga acctttttgtt tctggtgttt acgctggaga ccctagtcaa      540
cttagtgcta ctgctgcttt ttctaaagtg gctcgaatgg ctgaccttgg tggtggactt      600
ttggctggtg ctgttttgtc tgctcaaaga aaccctaagt caaaggctgc tgctaattct      660
aatattccta aaactaaacc tggagagttg ggttctttcc gacgtggttt ggaggtattg      720
ccaaaagcga tcgctactta tttaggacaa gcagtcaagc tcaattggtc tctcgtgggt      780
```

```
cttcgtccga cagaaaaaca gacttatata gcagaatttt cgactcccaa tggttctcag        840
caaatagaaa ctcgtaccat tgccctctcc agccctgctt atgcctgtgc taaattattt        900
agacctttac ttcctgaaat tgctggtact cttgatgaat tctattatcc tactgttgcc        960
tgtgtagttt tggcatatcc tgtttcttct atcaaggcca agatagatgg ctttggtaat       1020
ttgattccta gaggtcaagg cattcggact cttggtacta tttggtcttc tgctttattt       1080
tctggtagaa cacctcttgg atggcaaatt tttactaatt atattggtgg tgcaacagac       1140
ccagaaattt ctcacttaga tagtgaagcc atcgttgcac aagttcatca agacctttgt       1200
caaactctat taaaccagaa tcctgaaaaa ccaaaagttc tggcagtaca tatatggtct       1260
cgtgctattc ctcagtataa tttaggttat agttctaggc tggctcagat taatcatggc       1320
ttaaaatctt ggcctggagt atatctatgt agtaattata ttggtggtgt ggctctggga       1380
gattgtgttc gtcgtagtat agaagtagcg actgatattt attcgggtat ggggtttggg       1440
gagctttaa                                                             1449

<210> SEQ ID NO 100
<211> LENGTH: 1497
<212> TYPE: DNA
<213> ORGANISM: Artificial Sequence
<220> FEATURE:
<223> OTHER INFORMATION: Synthetic_Gene encoding SEQ ID NO: 21

<400> SEQUENCE: 100
atgaatgcca ttgcggaaaa tggaaacgag gcaaacgaag catcgcctgt atgggtagat         60
accttaattg tgggtggtgg tataagcgga ttgagcgtgg ctcatgcttt ggtcaactgc        120
gatcgctcgg tggacaatat tttactggcg gaaagccaac ctcgggtggg aggcagcgta        180
accagtgctt cgagtgaggg attttttgtac gaagaaggtc ccaatagttt ttcgcccaca       240
cccgaactgc tgcaacttgc tgtggatgtc ggtttgaaag atgagttgat tttggctgac        300
cgccgcttgc cgcgctacgt ttactggcaa ggaagattga ttgcactgcc gaacagtccg        360
cccagtgccg ttacttcccc tattttaagt cctgtgggca aactacgggc gctgttgggg        420
gcattgggat ttgtaccgcc ccacgtgacc agcgaaccgg aaagcgtttc cgatttttatc       480 cgccgccacc tgggacctga agtcttgcaa aaattggtgg aaccgtttac ttctgggta        540 tatgctggta accccgacga actggaagcg gcttctgctt ttgcccggat agcacgtttg        600
gaaaaagttg ggggcagctt ggtagcggga gctattttat cgcggcgtca ggcaccaacg        660 cagaaaaaa accgcgatcg caatttgcca aaaacgcaac gcgggcagtt aggttccttt        720
caacggggct tgcagtcttt gccggaagcc attgccggaa aattgggttc gcgagtgcgg        780
gtgaactggc aggcaaaaag catcggtaaa acggaaggtg gcaattattt ggtggaattt        840
gctaccccgc aggggcacca acaggtagaa gcgcgatcgc tggttttggc aacaccggct        900
tacgtaacag ccaacttgct caaatcctac ccccatgtca attcccagca gcaacaagcc        960
atccaagcct tggaaagcat tccctacccg cccgtagctt gtgtggtttt aggctatccc       1020
agcagtgcgt ttaaaaaaca accettacat ggatttggca atttgattcc tcggggtcag       1080
ggcattcgca ctttgggcac catttggggc tctagtctgt ttccggggag ggcaccggaa       1140
ggttgggaat tgctgctgaa ttttattggc ggcaccaccg atccagaaat tgcgaacttg       1200
gatcaagaac aaattgccca actgtacat cgggatttgt gccagaccct gctgcgggaa        1260
gacaaacaac caaaagtact acaggttcac ttgtggaaac aggccatccc tcagtatact       1320
```

-continued

```
atcggtcacg ggagtcggct ggcagccatt gatgcggggg tgcgatcgct accggggttg    1380
tttttgtgca gcaactacag cgatggagtc gccatgggcg attgtgcccg acgcggctac    1440
gaactggcac cacgggtggc tgagtatttg caaccgggat cctataaatt cgtttga      1497

<210> SEQ ID NO 101
<211> LENGTH: 1491
<212> TYPE: DNA
<213> ORGANISM: Artificial Sequence
<220> FEATURE:
<223> OTHER INFORMATION: Synthetic_Gene encoding SEQ ID NO: 22

<400> SEQUENCE: 101
atggttgtgg caacaccggg cgcggttgaa agcagtgtgg cgcgatcaaa cccgatcgac      60
ctgttgatcg tggggcagg cttgacgggg ttgagcgcgg cccagcggtt tgtgcgccag      120
tcgccggggc gatcgtgcct ggtggtggag gcccaagatc gggtcggcgg caacatcacc      180
acgcgatcgg gcaatggctt tttgtgggaa gaaggcccca acagctttgc ccccacgccg      240
gagttgctgc aactggcggt ggaagtgggt ctcaaggatc agttggtgtt tgctgatggc      300
aagttgcccc gctttgtcta ttgggacggg cgcttgcagg caattcccat gagtccaggg      360
gcattttgga attcgacctt gttgagcgat cggggcaagg cgcggctgct gttggggcg       420 gccggatttg tgccgccgat cctgggggcc acggtgcagg cccggggcgg cgaagaaacc      480
gtgcgggaat tttttacccg acatctgggc caagaaacca tggagcggat ggttgatccg      540
tttatttccg gggtctatgc cggcgatccc gatgccctga gcgcttcggc ggccttccgc      600
aagatggcgc ctatgcaggc agcgggcggg ggactggcgg ccggggcgat tcggacgttg      660
ctggccaagc ggcgggcggc caaaaccgcg cccccggctg acccgaattt gcccaagcca      720
aaatccggtg aactggggtc gttccgggaa ggcttgcaaa tgctgccgga agcggtggcc      780
aaggaactgg gcgatcgcgt gaagctgggc tggcgggtgg aggcgatcgc ccgatcaagc      840
aatggcgact acaccgtgga cttggcaacc cccgatgggc cgcgccaaat cacgactcgg      900
gcgatcgtcc tggccacccc cgctccagcc acggcgaacc tgttgcaacc cctggctccg      960
gccgccagcg ccgccctgca cgcaattccc tatccggcgg tagcttgcgt gattttggcc     1020
tatcccgaaa cggcctttgc ccaatccctg cgcggctttg gcaacttgat ccccgtagc      1080 ttggggctgc aaaccttggg cacgatttgg gcttctagcc tgtttgcggg ccgtgcgccc     1140
cagggttggg cccacctgat caacttcatc ggtggcgcgc aaaatcctgg gctaatcaac     1200
aaaaccgagg cggaaattgc agatatcgtc catgggatg tgcggcgcat tctgctgaag     1260
gaagacgtag ctcccaaggt gctgtcggtg aagctgtggc ggcgggcgat tcctcagtac     1320
acgatcggcc atgccgatcg cctggccaca ctgcatcggg aattggccgc ctggccgggg     1380
ctgttcccct gcagcaacta cgaaggcggt gtggccctgg gtgactgtgt gcgccacggt     1440
tgggatcaag cggctgaggt cgatcgctac ctggcccaac tgcccgttta g            1491

<210> SEQ ID NO 102
<211> LENGTH: 1446
<212> TYPE: DNA
<213> ORGANISM: Artificial Sequence
<220> FEATURE:
<223> OTHER INFORMATION: Synthetic_Gene encoding SEQ ID NO: 23

<400> SEQUENCE: 102
atgacgaacc gagtagacac cttgattgtg ggtgctggta ttaccggctt gagtctggcc      60
cacgcgctgc acaaggaagc aaagactgga gaacccctga agattttagt tgctgagagt     120
```

```
cagggacgtg tgggcgggaa tatcacaact tctacagggc atgggtttct gtgggaggag      180
ggcccgaata gtttttcgcc gacgccggaa ttgatgaagt tggctgtgga tgtgggctg       240 aagcaggagt tgatgtttgc cgatcgccaa ttgcctcgtt ttgtatattg gcaaaataag      300
ctgcaaccgg tgccgatgac tcctggggcg atgattcagt ctgggttgct gagttttccg      360
gggaaactgc gggctctgtt cggggctttg gggtttgtgg ctccggtaat gggtgctaca      420
ctttcgcagc agggtgagga ggaaactgtt tctcaatttt tccggcgaca tttgggtacg      480
gaagtgatgc agcgattggt ggagcccttt gtgtctgggg tttatgccgg cgatcctcaa      540
caacttagcg ccgcggcggc tttttgggcgg gtgacaaaga tggctgatgc tggtggcggg      600
ctggtggccg gggcgctgct ttctgccagg aaacggccca aaaaaatgcc cccagacccg      660
aatattcctc agactaagcc gggggagctg ggttcgttta aaggggggct gatggctctg      720
ccagaggcga tcgctgcttc tttgggcgat cgcctgaaac tgaattggca tctgactggt      780
ttgcaccgta ctgaaaataa aacctatatt gcggaattct caacccccca tgggccgcaa      840
caaattgaga ctcggactgt ggtgctgaca acgcctgctt atgtggcagc ggatttgttg      900
caatctctgc aaccggaagt tagcagcact ttacaaggtt ttacttaccc tactgttgcc      960
tgtgtggtct tagcatatcc gctgtcggat gtcaagggta aattggtggg atttggaaat     1020
ttaattccga gggggcaggg aattcgcact ctgggaacga tttggacttc gagtttattt     1080
gccgatcgcg cgccggcggg ttggcaaact ctgacgagtt acatcggtgg ggctacggat     1140
tcgggtattg gcaatcttga ccccgaagaa attgtggccg aggtgcatcg agatttgtct     1200
cgcatcttgc tcaaaccgaa tgtgccacag ccgaaggtgt tggcggtgaa gctctggaaa     1260
caggcgattc ctcagtataa tttggggcat ctcgatcgcc tccaacagat cgatcgaggc     1320
ttaaaatctt tgccagggat gtatttgtgt agtaattacg ttggcggggt ggctttggga     1380
gattgtgtgc ggctgggttt ggaaaaggcg atcgcagtta gcaaatattt acaagaaacc     1440
agctaa                                                                  1446
```

<210> SEQ ID NO 103
<211> LENGTH: 1446
<212> TYPE: DNA
<213> ORGANISM: Artificial Sequence
<220> FEATURE:
<223> OTHER INFORMATION: Synthetic_Gene encoding SEQ ID NO: 24

<400> SEQUENCE: 103

```
atgacgaacc gagtagacac cttgattgtg ggtgctggta ttaccggctt gagtctggcc       60
cacgcgctgc acaaggaagc aaagactgga gaacccctga agattttagt tgctgagagt      120
cagggacgtg tgggcgggaa tatcacaact tctacagggc atgggtttct gtgggaggag      180
ggcccgaata gtttttcgcc gacgccggaa ttgatgaagt tggctgtgga tgtgggctg       240 aagcaggagt tgatgtttgc cgatcgccaa ttgcctcgtt ttgtatattg gcaaaataag      300
ctgcaaccgg tgccgatgac tcctggggcg atgattcagt ctgggttgct gagttttccg      360
gggaaactgc gggctctgtt cggggctttg gggtttgtgg ctccggtaat gggtgctaca      420
ctttcgcagc agggtgagga ggaaactgtt tctcaatttt tccggcgaca tttgggtacg      480
gaagtgatgc agcgattggt ggagcccttt gtgtctgggg tttatgccgg cgatcctcaa      540
caacttagcg ccgcggcggc tttttgggcgg gtgacaaaga tggctgatgc tggtggcggg      600
ctggtggccg gggcgctgct ttctgccagg aaacggccca aaaaaatgcc cccagacccg      660
```

-continued

```
aatattcctc agactaagcc gggggagctg ggttcgttta aagggggggct gatggctctg      720 ccagaggcga tcgctgcttc tttgggcgat cgcctgaaac tgaattggca tctgactggt      780
ttgcaccgta ctgaaaataa aacctatatt gcccaattct caacccccga tgggcctcaa      840
caaattgaga ctcggactgt ggtgctgaca acgcctgctt atgtggcagc ggatttgttg      900
caatctctgc aaccggaagt tagcagcact ttacaaggtt ttacttaccc tactgttgcc      960
tgtgtggtct tagcatatcc gctgtcggat gtcaagggta aattggtggg atttggaaat     1020
ttaattccga gggggcaggg aattcgcact ctgggaacga tttggacttc gagtttatt     1080 gccgatcgcg cgccggcggg ttggcaaact ctgacgagtt acatcggtgg ggctacggat     1140
tcgggtattg gcaatcttga ccccgaagaa attgtggccg aggtgcatcg agatttgtct     1200
cgcatcttgc tcaaaccgaa tgtgccacag ccgaaggtgt tggcggtgaa gctctggaaa     1260
caggcgattc ctcagtataa tttgggggcat ctcgatcgcc tccaacagat cgatcgaggc     1320
ttaaaatctt tgccagggat gtatttgtgt agtaattacg ttggcggggt ggctttggga     1380
gattgtgtgc ggctgggttt ggaaaaggcg atcgcagtta gcaaatattt acaagaaacc     1440
agctaa                                                                 1446
```

<210> SEQ ID NO 104
<211> LENGTH: 1440
<212> TYPE: DNA
<213> ORGANISM: Artificial Sequence
<220> FEATURE:
<223> OTHER INFORMATION: Synthetic_Gene encoding SEQ ID NO: 25

<400> SEQUENCE: 104

```
atggatgtgt tgattgtcgg cgcgggttta acgggcttga gcgctgccca ccgcttggtt       60
aatcacccgg gcaaccgagg gcgatcgacc ctggtggtgg aagcgcaaaa ccgtgtgggc      120
ggcaacatca ccacccgatc ggccgatggg ttcctgtggg aagaggggcc caacagcttc      180
gcccccacgc cagagctgct gaaactcgcc gtggaagtgg ggttgaagga tgagctggtg      240
tttgcggatg gcaagctgcc ccgatttgtc tactgggacg gtcggttaca agccattccc      300
atgagtcccg gcgcatttttg gaattccacc ttgctgagcg atcggggcaa agccagactg      360
ctgttaggtg cggcgggttt tgtgcccccg atcgtgggtg cagccatttc ggcaaggggc      420
ggcgaagaaa ccgtccgtga attcttcact cgccacctgg gtcaagaagc catggagcgc      480
ctcgtggatc cctttatctc ggggggtttat gccggagatc ccaatgccct cagtgcttcg      540
gcggccttcc gcaaaatggc cgccatgcaa gcggccggtg gtggcttggg agccgggggcg      600 gcgcggattc tctgggccaa acgccaagcg gccaaacaag cacccccagc cgatccccgc      660
ttacccaagc ccagtccggg ggagttggga tccttccgcg agggactgca agctttgccg      720
gaagcggtgg caagcggttt gggcgatcgg gtcaagttgg gttggcaggt ggaagcgatc      780
gcccgtgatc cccaaggcgt ttaccaggtt gcgatcgcca gccccgatgg cccccaacag      840
atcacggctc gatcgatcat tctggccacc ccggctccgg tcacggctca actgttggaa      900
cccctcgccc ccgagccag caccgccctc aacgccattc cctacccccgc cgttgcctgc      960 gtaattttgg cctatcccga aaccgccttt tcccagtccc tgcgcggctt tggcaacctg     1020
attccccgca gcctgggcct gcaaactcta ggaaccattt gggcttccag cctgtttgcg     1080
ggacgcgctc cccaaggttg ggcccaccta atcaacttca ttggcggcgc acaaaacccc     1140
accctgatcc acaaaaccga agacgaaatc gcccaaatgg ttcatgcgga cgtgcggcgg     1200
attttgctga aacaggacgt gccgcccaag gtgctgtcgg tcaaactctg cggcggggcg     1260
```

-continued

```
atcccgcaat acacgatcgg gcatgggtct cgcctggcca ccttgcacca ggagcttcag    1320
cattggcctg gcctctttgc ttgcagcaac tatgaaggcg gcgtagcgct gggtgattgc    1380
gtgcgccatg gttgggaaca ggccgacgcg atcgagcagt tcctcggcag tcgagtctag    1440
```

```
<210> SEQ ID NO 105
<211> LENGTH: 1473
<212> TYPE: DNA
<213> ORGANISM: Artificial Sequence
<220> FEATURE:
<223> OTHER INFORMATION: Synthetic_Gene encoding SEQ ID NO: 26

<400> SEQUENCE: 105
atgaattcca ccgatttagc caatccatct actacccttg ataccttaat cgtcggtgca      60
gggattacgg gtcttagtct cgcccaagca cttcagcaag accgcaagcg cggtcgccaa     120
tcagggcaga ttttattgac agaaagtcaa gaaagggtag gggggcgcat tgttacacaa     180
tcgcaagacg gatttctctg ggaagaaggt cccaatagtt gcttaccaac ccctgagttt     240
ctcaagttgg cggtggatgt gggattaaaa gatgagttgg tgctggctga ccgtcgtctt     300
cctcggtatg tttatttaca gggagagtta atcccagtgc cgatgagtcc gccagcattt     360
tttcagacga agttactcag cgattggggt aagttacgcg cgatcgccgg ggctttgggt     420
tttgtgcctc ccgctatcgg tgccacccta tccgcccaag gggatgaaga aaccgtagcc     480
cagttctttg gtcgtcacct ggggcaggaa gtcttggaac gtctggtaca gccctttgtg     540
tctggagtct atgcgggaga tcccaatcaa ctcagtgcca gcgccgcttt tgggaaagtc     600
actaaaatgg ccgatatcgg cggtggactg gcggctgggg cgattttatc tttagcgaaa     660
aatgggagag cgaaaaagac ggtggatccg agtctgccca aagtccagcg cggggaatta     720
gcttcatttc gtcaaggtct ggaagcttta cccaaggcga tcgcggctca attgggcgat     780
gtagtcaagt taggctggca tttaatccaa attaaaccca cagaacacca aacttatctg     840
gccgaatttt ccaccccca aggtccagcc agaattgaaa ctcgcagtat ggttctgacc     900 accccagct atgtctccgc tgacttgtta gccaatcttt gcccagtggc gagtcaaggg     960
ttagccaaaa ttccttatcc agcggtcgct tgcgtggtct taggctatcc tgaaagcgcc    1020
tttaaaacca gtgtatcatc gggttttggc aacttaatcc ccagaggtca aggaatacgc    1080
accttgggta cgatctggtc ttcgagttta tttcccaatc gcgctccgc tggatggcgc    1140 ttattgctta attttatcgg tggcaccacg gatctggcga tcgctcagtt aagccaagaa    1200
gaaatcgtcc aaatcgtaca cagagatctg caaaaaccc tgctcaaaca ggacatccca    1260
ccgaaagtcc tggcggtgca tttatggaag cgggcaattc cccaatatcc cctcggccat    1320
catcaaaacc tggcacaaat tcatcactct ttgcaacaac ggcctggatt atttttatgt    1380
ggcaactata cggatggggt tgccgtaggc gactgtattc gccgtggcca agaatgtgcc    1440
gctgacgtgg tgaaatattt agatcaaggc taa                                1473
```

```
<210> SEQ ID NO 106
<211> LENGTH: 1440
<212> TYPE: DNA
<213> ORGANISM: Artificial Sequence
<220> FEATURE:
<223> OTHER INFORMATION: Synthetic_Gene encoding SEQ ID NO: 27

<400> SEQUENCE: 106
atggatgtgt tgattgtcgg cgcgggttta acgggcttga gcgctgccca ccgcttggtt      60
```

-continued

```
aatcacccgg gcaaccgggg gcgatcgacc ctggtggtgg aagcgcaaaa ccgtgtgggc     120
ggcaacatca ccacccgatc ggccgatggg ttcctgtggg aagaggggcc caacagcttc     180
gcccccacgc cagagctgct gaaactctcc gtggaagtgg gtttgcagga tgagctggtg     240
tttgcggatg gcaagctccc ccgatttgtc tattgggacg gtcggttaca agccattccc     300
atgagtcccg gcgcattttg gaattccact ctgctgagcg atcggggcaa agccagactg     360
ctgctaggcg cggcgggttt tgtgcccccg atcgtgggtg cagccatttc agcaaggggc     420
ggtgaagaaa ccgtccgtga attcttcact cgccacctgg gccaagaagc catggagcgc     480
ctcgtggatc cctttatctc gggggtttat gccggagatc ccaacgccct cagcgcttcg     540
gcggccttcc gcaaaatggc cgccatgcaa gcggccggtg gtggcttggg agccggagct     600
gcgcggattc tctgggccaa acgccaagcg gccaagcaag cgcccccagc cgatccccgc     660
ttacccaagc ccaagtccgg ggagttggga tccttccgcg agggactgca agccttgccg     720
gaagcggtag caagcggttt gggcgatcgg gtcaagttgg gttggcaggt ggaggcgatc     780
gcccgtgatc cccaaggcac ttaccaggtt acgatcgcca gccccgatgg cccccaacgg     840
atcaccgcgc gatcgatcat tctggctacc ccggctcccg tcacggccca actgctcgaa     900
cccctcgccc cccgagccag caccgccctc aacgccattc cctaccccgc cgttgcctgc     960
gtgattttgg cctatcccga aaccgccttt gcccagtccc tgcgcggctt tggcaacctg    1020
attccccgca gcctgggcct gcaaacccta ggaaccattt gggcttccag cctgtttgcg    1080
ggacgcgctc cccaaggttg ggcccacctg atcaacttca ttggcggcgc acaaaacccc    1140
accctgatcc acaaaaccga agacgaaatc gcccagatgg ttcatgcgga cgtgcggcag    1200
attttgctga acaggacgt accgcccaag gtgctgtcgg tcaagctctg gcgacgggcg    1260
atcccgcaat acacgatcgg gcatgggtct cgcttggcca ccttgcacca ggagttgcaa    1320
cattggcctg gcctctttgc ttgcagcaac tatgaaggcg gcgtagcgct gggtgattgc    1380
gtgcgccatg gttgggaaca ggccgacgcg atcgagcagt tcctcggcag tcgagtctag    1440
```

```
<210> SEQ ID NO 107
<211> LENGTH: 1437
<212> TYPE: DNA
<213> ORGANISM: Artificial Sequence
<220> FEATURE:
<223> OTHER INFORMATION: Synthetic_Gene encoding SEQ ID NO: 28

<400> SEQUENCE: 107
```

```
atgactgaag ttttagatgt cttagttgtt ggcgcaggta ttagtgggtt aagtttagcc      60
catgcactga caaaattagg taataattcc ccgttaaaga ttttagttgc agaaagccaa     120
aatcgagtgg ggggaaatat cacaacagtt tctttaggag actttctttg ggaagaaggg     180
ccaaatagtt tttctccgac accggaattt ttaaagttgg ctgtagatgt tggcctgaag     240
caggagctag ttttttgccga tcgcaaactg cctcgctatg tttattggaa tggtcaatta     300
ttaccagtgc ccatgagtcc aacagctatg ctacagtcta aattactgag tgatgctggt     360
aagctacgcg ctttagttgg cgctttgggt tttgtctcac ctgccattgg taatttatca     420
ggacaaggag gagaagaaac tgtatcccaa ttttttccaga gacatcttgg tcctgaagta     480
atgcagcgac tggtggaacc tttcgtttct ggtgtttatg caggagaccc tagtcaactg     540
agtgcttctg ctgcttttgc taaagtggct cgaatggctg acttaggtgg tggacttgta     600
gctggtgctt tgctgtctgc taaaaaaaat cgtaagttta aggttgctcc cgaccctaat     660
attcctaaga ctaagactgg tgaattgggt tcttttcgag gtggtttgga ggcattacca     720
```

-continued

```
aaagcgatcg cctcttattt aggagaagca gttaaattaa attggcatct tactaatatt      780
cgtcggactg aacaacaaac ttatatagca gaattttcta ctcccaatgg tcctgagcaa      840
atagaaactc gtactatttc cctttctact cccgctcgtg tttgtgcaga attattcaaa      900
actttgcaac cggaaattgc ttctatattt aatgaatttt attatcctcc tgttgcctgt      960
gtagtcttgg catatcctga tacttctatc aaggttaaga tagatggctt tggtaatttg     1020
attcctagag gtcaaggtat ccggactctt ggtagtattt ggtcttctac tttattttct     1080
ggtagaacac ctccaggatg gcaaattttt actaattta ttggtggtgc aacagacccg      1140
gaaattgcga acttagatag tgaagcgata gtgcaacagg tacatcaaga tctttgtcaa      1200
actctgttaa aacagaatgc tgaacaacca aaagttcttg cggtgcattt atggtctcgt      1260
gctattcctc aatataattt aggccataat tctaaattgg aggagattaa taatggctta      1320
aaatctttgc ctggtctata tctgtgcagt aattatattg gtggtatagc tttgggagat      1380
tgtgttcgcc gtggcacaga agtagcgact gaaatttatc aaggtttgca gacttga       1437
```

```
<210> SEQ ID NO 108
<211> LENGTH: 1435
<212> TYPE: DNA
<213> ORGANISM: Artificial Sequence
<220> FEATURE:
<223> OTHER INFORMATION: Synthetic_Gene encoding SEQ ID NO: 29

<400> SEQUENCE: 108
```

```
atgactgaag ttttagatgt cttagttgtt ggcgcaggta ttagtgggtt aagtttagcc       60
catgcactga caaaattagg taataattcc ccgttaaaga ttttagttgc agaaagccaa      120
aatcgagtgg ggggaaatat cacaacagtt tctttaggag actttctttg ggaagaaggg      180
ccaaatagtt tttctccgac accggaattt ttaaagttgg ctgtagatgt tggcctaaag      240
gaggagctaa tctttgccga tcgcaaactg cctcgctatg tttattggaa tggtcaatta      300
ttgccagtac ctatgagtcc aaaagctatg ctacagtcta agttactgag tgatggtggt      360
aagttacgcg ccctagttgg tgctttgggt tttgtatcgc ctgctattgg cgatctgtca      420
gagcaagggg gagaagaaac tgtatcccaa tttttccaga gacatcttgg tgctgaagtg      480
atgcagcgac tggtggaacc tttttgtttct ggtgtttatg caggagatcc tggtcaactg      540
agtgctaatg cggcttttgc taaagtggct cgaatggctg acttaggtgg tggacttgtc      600
gctggtgctt tgttgtctgc caaaaaaaat cgtaagttca aggttgctcc cgatcctaat      660
attcctaaga ctaaaactgg cgaattgggt tcttttcgag gtggtttgga ggcattacca      720
aaagcgatcg cttcttattt aggagaagca gttaaattaa attggcatct tactggtatt      780
cgccgcactg aacaacaaac ttatatagca gaattttcga ctcccaatgg tactgagcaa      840
atagaaactc gtactatttc tctttctact cctgctcgtg tttgttcaga gttattcaca      900
actttgcaac ctgaaattgc ttctatattt aatgagtttt attatcctac tgttgcctgt      960
gtagtcttgg catatcctga tacttctatc aaggttaaga tagatggctt tggtaatttg     1020
attcctagag gtcaaggtat ccggactctt ggtagtattt ggtcttctac tttattttct     1080
ggtagaacac ctccaggatg gcaaattttt actaattta ttggtggtgc aacagacccg      1140
gaaattgcga acttagatag tgaagcgata gtgcaacagg tacatcaaga cctttgtcaa      1200
actctgttaa aacagaatgc tgaacaacca aaagttcttg cggtgcattt atggtctcgt      1260
gctattcctc aatataattt aggccataat tctaaattgg aggagattaa taatggctta      1320
```
aaatctttgc ctggtctata tctgtgcagt aattatattg gtggtatagc tttgggagat    1380
tgtgttcgca gtgggacaga agtagctact aagatttatc aaggtttaca agtga    1435

<210> SEQ ID NO 109
<211> LENGTH: 1473
<212> TYPE: DNA
<213> ORGANISM: Artificial Sequence
<220> FEATURE:
<223> OTHER INFORMATION: Synthetic_Gene encoding SEQ ID NO: 30

<400> SEQUENCE: 109
atgtctttca ccgatctggc cactccatct cacccccttg atacgctcgt tattggggca      60
ggaattagcg gtttaagtct tgcctttacc ttgcaacaac ggcagaccca agtattagtc     120
tgcgaaagtc aaaaccgcat tgggggggaat atcacaacgg gtcaggcgga tggttttctg     180
tgggaggaag ggccgaacag tttcgcgccg acacccgctc ttttaaggct aattgtcgat     240
gctggattag agaaagacat gattcttgcc gaccggcgct taccgcgttt tgtgtacagg     300
caagggcgct tgcaagcgat tcccatgagt cccccgcgg cgattgggac gccgttactc      360
agttggccgg gtaaactcag ggctggattg ggtgccatcg gttttgtccg cccccgttg      420 ggcgagcagt tttctcaaca aggctcagaa gagacggtgg ctcaattttt ccagcgccac     480
ctcggtgaag aggtgatgga aaggctggta acgccgtttg tctctggcgt gtatgccgga     540
gatgtgaatc aattgagtgc ggcggcagcc tttcggagaa ttgctcagtt agagggcgtt     600
ggcggcggtt tagtggccgg ggcgattctc tcgcggatga aggccaaatc tcagccgcaa     660
gtcccggtcg atccaagctt acctaaaacg cgacctgggg agttagggtc atttcaacaa     720
gggttacaaa tgctacccca agcgctggcg gccaaattag gcgatgcggt gcggttgaat     780
tggcggttgc tgcaaattac cccaacaacg cgccaaagct atattgcaga attcggtacc     840
ccagagggaa cgcagattgt agaagctcgc catgtggtgt tgacaacgcc tgcttatatt     900
accgcagaga ttgtagaggc gatcgcgccc cttgccagcc aagctttgcg agcgattgag     960
tatcccccgg tggcaaacgt cgtcttagcc tacccagaat cagccttgaa gcagccttta    1020
aagggatttg ggcatttgat tccgcgtagc gaaggaatcc gcactctagg gacaatctgg    1080
tcgtctagcc tgtttcccgg acgagtcccc ccaggctggc agttactcac caattatatt    1140
ggcggcgcaa ccgatccagg catttttagac ttagaccgcg attcgcgaag caatctcgac    1200
gggaatccca ttgctcaagc cgttcaccaa gatatccgcc gcatcctcct ccagcaagag    1260
gttcagccca aggtgctagc ggttcatctg tggaagcggg cgattcccca atataatcta    1320
ggtcatcacc agcgcttgca aaccattttc caaagtttgg ccccgttccc cggtttgcat    1380
atttgcagca actataccga tggggtagcc ctcggagatt gcgtccgcag agcgcaagaa    1440
ctcgctgata tcttaacccca aaaaactcgg tag                                1473

<210> SEQ ID NO 110
<211> LENGTH: 1470
<212> TYPE: DNA
<213> ORGANISM: Artificial Sequence
<220> FEATURE:
<223> OTHER INFORMATION: Synthetic_Gene encoding SEQ ID NO: 31

<400> SEQUENCE: 110
atggaagcgg cagtgaatcc tgcaactcct gaacccctta acgcggaggt ggtggtcatt      60
ggggcgggca tcagcggcct gacgctggcc tggcgcctgc agcagggttt atcggctagg     120
gggggatccc ctcaagcggt gctcctggcg gaggccagct cccgcgtcgg cggctgcatt     180

```
tccacccagt ccaaagacgg ctactgctgg gaggaaggcc ccaacagctt taccccacc      240 cctgccctgc tcaacctcat tgctgaggtg ggcctgaccg accaactggt gctggccgat      300
gccaagctgc cccgctacat ctactgggag aaagagctgc tgccggtgcc gcttagcccc      360
gcggcagccc tgagctcccg gctgctcagt gtgggcggca agctgcgggc tctgcagggc      420
ctgctggggt ttgtcccgcc gccgccagga cgcgaggaaa cggtgcggca gttttttccgg     480 cgacaactgg gatccgaagt ggccgagcgc ctggtggagc cctttacctc gggggtttat      540 gcggggggatc cggatcagct cagcgccgtg gcggctttcc ctcgcgtggc gggcctggag     600
gagcgctatg gcagcctctt tgccggccgcc ctgcaggctc tgcgccaaag accccagcct     660
tctcctgcgg ccatccaacc cccgcccaaa cggggccaac tgggcaatct gaggcagggg     720
ctgcagcagt tgccagaggc cctagcccaa aagctgggcg acagcctgcg gctgggctgg     780
cgagcggtgc agcttaagcg ggagggagag ctctattggg tgggctttga gacgccagag     840
ggatcccgct gggtggctgc ccgccaggtg gtgctggccc tccccgccta cgaggctgcc     900
gcgctgctac aggagctcaa cccccccggcc agccagctct tggccgagat cctctatccg     960
ccggtggcgg tggtggctct ggcctatccc caagaggccc tgccccagcc gctgcggggc    1020
tttggccacc tcatcccccg ttcccagggc ctgcgcaccc tgggcacgat ctgggcctcc    1080 tgccttttttc cagagcgggc tccccagggc taccacagct tcctcagctt cctgggcggc    1140
gccaccgatg cggccttggc ccgccggcgg gggatcccgc ccatccctgc gctgtctcct    1200
gaggagcgag cgcaaattgc ccacgccgag cttagccagg ttctgctcac ccgccgcgtc    1260
gagcccatct acctcgggga acgcctatgg ccccgcgcca tcccccagta caccccttggc   1320 caccggcaac gcatagccca ggtgcaggcc cacctggcct cccagacgcc agggatctgg    1380
gtatgcgcca actacctcga tggcgtggcc ctgggcgatt gcgtgcggcg ggccgaggcg    1440
ctggcgcagc agctgttgtc ccaggtctag                                      1470
```

<210> SEQ ID NO 111
<211> LENGTH: 1470
<212> TYPE: DNA
<213> ORGANISM: Artificial Sequence
<220> FEATURE:
<223> OTHER INFORMATION: Synthetic_Gene encoding SEQ ID NO: 32

<400> SEQUENCE: 111

```
atggaagcgg cagtgaatcc tgcaacccct gaacccctta acgcggaggt ggtggtcatt       60
ggggcgggca tcagcggcct gacgctggcc tggcgcctgc agcagggttt atcggctagg      120
gggggatccc ctcaagcggt gctcctggcg gaggccagct cccgcgtcgg cggctgcatt      180
tccacccagt ccaaagacgg ctaccgctgg gaggaaggcc ccaatagctt taccccacc      240 cctgccctgc tcaacctcat tgctgaggtg ggcctgaccg accaactggt gctggccgat      300
gccaagctgc cccgctacat ctactgggaa ggagcgctgt tgccggtgcc tctgagcccc      360
gcggcagccc tgggatcacg gctgctcagc gtgggcggca agctgcgggc tctgcagggc      420
ctgctggggt ttgtcccgcc gccgccagga cgcgaggaaa cggtgcggca gttttttccgg     480 cgacaactgg gatccgaagt ggccgagcgc ctggtggagc ccttcacctc aggagtctat      540
gccggcgacc cagatcaact cagcgccgtg gcggctttcc ctcgcgtggc gggcctggag     600
gagcgctatg gcagcctctt tgccggccgcc ctgcaggctc tgcgccaaag accccagcct     660
tctcctgcgg ccatccaacc cccgcccaaa cggggccaac tgggcaatct gaggcagggg     720
```

-continued

```
ctgcagcagt tgccagaggc cctagcccaa aagctgggcg acagcctgcg gctgggctgg      780
cgagcgctgc agctgaagcg ggcgggagag ctctattggg tgggctttga gacgccagag      840
ggatcccgct gggtggctgc tcgccaggtg gtgctggccc tccccgccta cgaggctgcc      900
gcgctgctac aggagctcaa cccccgggcc agccagctct tggccgagat cctctatccg      960
ccggtggcgg tggtggctct ggcctatccc caagaggccc tgccccagcc gctgcggggc     1020
tttggccacc tcatcccccg ttcccagggc ctgcgcaccc tgggcacgat ctgggcctcc     1080
tgcctttttc cagagcgggc tccccagggc taccacagct tcctcagctt cctgggcggc     1140
gccaccgatg cggccttggc ccgccagcaa gggatcccac ccatccctgc gctgtctcct     1200
gaggagcgag cgcaaattgc ccacgccgag cttagccagg ttctgctcac ccgccgcgcc     1260
gagcccgtct acctgggcga acgtctctgg ccccgcgcca tcccccagta cacccttggc     1320
caccggcaac gcatagccca ggtgcaggcc cacctggcct cccagacgcc ggggatctgg     1380
gtgtgtgcca actacctgga tggcgtggcc ctgggcgatt gcgtgcggcg ggccgaggcg     1440
ctggcgcagc agctgttgtc ccaggtctag                                      1470
```

```
<210> SEQ ID NO 112
<211> LENGTH: 1470
<212> TYPE: DNA
<213> ORGANISM: Artificial Sequence
<220> FEATURE:
<223> OTHER INFORMATION: Synthetic_Gene encoding SEQ ID NO: 33

<400> SEQUENCE: 112
```

```
atggaagcgg cagtgaatcc tgcaaccccct gaaccccctta acgcggaggt ggtggtcatt       60
ggggcgggca tcagcggcct gacgctggcc tggcgcctgc agcagggttt atcggctagg      120
gggggatccc ctcaagcggt gctcctggcg gaggccagct cccgcgtcgg cggctgcatt      180
tccacccagt ccaaagacgg ctaccgctgg gaggaaggcc ccaatagctt taccccccacc      240 cctgccctgc tcaacctcat tgctgaggtg ggcctggccg accaactggt gctggccgat      300
gccaagctgc cccgctacat ctactgggaa ggagcgctgt tgccggtgcc tctgagcccc      360
gcggcagccc tgggatcacg gctgctcagc gtgggcggca agctgcgggc tctgcagggc      420
ttgttggggt ttgtcccgcc gccgccagga cgcgaggaaa cggtgcggca gtttttccgg      480
cgacaactgg gatccgaagt ggccgagcgc ctggtggagc ccttcacctc aggagtctat      540
gccggcgacc cagatcaact cagcgccgtg gcggctttcc ctcgcgtggc gggcctggag      600
gagcgctatg gcagcctctt tgccggcgcc ctgcaggctc tgcgccaacg accccagcct      660
tctcctgcgg ccatccaacc cccgcccaaa cggggccaac tgggcaatct gaggcagggg      720
ctgcagcagt tgccagaggc cctagcccaa aagctgggcg acagcctgcg gctgggctgg      780
cgagcgctgc agctgaagcg ggcgggagag ctctattggg tgggctttga gacgccagag      840
ggatcccgct gggtggctgc tcgccaggtg gtgctggccc tccccgccta cgaggctgcc      900
gcgctgctac aggagctcaa cccccgggcc agccagctct tggccgagat cctctatccg      960
ccggtggcgg tggtggctct ggcctatccc caagaggccc tgccccagcc gctgcggggc     1020
tttggccacc tcatcccccg ttcccagggc ctgcgcaccc tgggcacgat ctgggcctcc     1080
tgcctttttc cagagcgggc tccccagggc taccacagct tcctcagctt cctgggcggc     1140
gccaccgatg cggccttggc ccgccagcaa gggatcccac ccatccctgc gctgtctcct     1200
gaggagcgag cgcaaattgc ccacgccgag cttagccagg ttctgctcac ccgccgcgcc     1260
gagcccgtct acctgggcga acgtctctgg ccccgcgcca tcccccagta cacccttggc     1320
```

-continued

```
caccggcaac gcatagccca ggtgcaggcc cacctggcct cccagacgcc ggggatctgg      1380
gtgtgtgcca actacctgga tggcgtggcc ctgggcgatt gcgtgcggcg ggccgaggcg      1440
ctggcgcagc agctgttctc ccaggtctag                                       1470

<210> SEQ ID NO 113
<211> LENGTH: 1470
<212> TYPE: DNA
<213> ORGANISM: Artificial Sequence
<220> FEATURE:
<223> OTHER INFORMATION: Synthetic_Gene encoding SEQ ID NO: 34

<400> SEQUENCE: 113
atggaagcgg cagtgaatcc tgcaacccct gaacccctta acgcggaggt ggtggtcatt        60
ggggcgggca tcagcggcct gacgctggcc tggcgcctgc agcagggttt atcggctagg       120
gggggatccc ctcaagcggt gctcctggcg gaggccagct cccgcgtcgg cggctgcatt       180
tccacccagt ccaaagacgg ctaccgctgg gaggaaggcc ccaatagctt taccccccacc      240 cctgccctgc tcaacctcat tgctgaggtg ggcctggccg accaactggt gctggccgat       300
gccaagctgc cccgctacat ctactgggaa ggagcgctgt tgccggtgcc tctgagcccc       360
gcggcagccc tgggatcacg gctgctcagc gtgggcggca agctgcgggc tctgcagggc       420
ttgttggggt ttgtcccgcc gccgccagga cgcgaggaaa cggtcgggca gtttttccgg       480
cgacaactgg gatccgaagt ggccgagcgc ctggtggagc cctttacctc gggggtttat       540 gcggggatc cggatcagct cagcgccgtg gcggctttcc ctcgcgtggc gggcctggag       600
gagcgctatg gcagcctctt tgccggcgcc ctgcaggctc tgcgccaaag accccagcct       660
tctcctgcgg ccatccaacc cccgcccaaa cggggccaac tgggcaatct gaggcagggg       720
ctgcagcagt tgccagaggc cctagcccaa aagctgggcg acagcctgcg gctgggctgg       780
cgagcgctgc agctgaagcg ggcggggagag ctctattggg tgggctttga cacgccagag      840
ggatcccgct gggtggctgc ccgccaggtg gtgctggccc tccccgccta cgaggctgcc       900
gcgctgctac aggagctcaa cccccgggcc agccagctct tggccgagat cctctatccg       960
ccggtggcgg tggtggctct ggcctatccc caagaggccc tgccccagcc gctgcggggc       1020
tttggccacc tcatcccccg ttcccagggc ctgcgcaccc tgggcacgat ctgggcctcc      1080
tgcctttttc cagagcgggc tccccagggc taccacagct tcctcagctt cctgggcggc      1140
gccaccgatg cggccttggc ccgccggcgg gggatcccgc ccatccctgc gctgtctcct      1200
gaggagcgag cgcaaattgc ccacgccgag cttagccagg ttctgctcac ccgccgcgcc      1260
gagcccgtct acctgggcga acgtctctgg ccccgcgcca tccccagta caccctttggc      1320 caccggcaac gcatagccca ggtgcaggcc cacctggcct cccagacgcc ggggatctgg      1380
gtgtgtgcca actacctgga tggcgtggcc ctgggcgatt gcgtgcggcg ggccgaggcg      1440
ctggcgcagc agctgttctc ccaggtctag                                       1470

<210> SEQ ID NO 114
<211> LENGTH: 1470
<212> TYPE: DNA
<213> ORGANISM: Artificial Sequence
<220> FEATURE:
<223> OTHER INFORMATION: Synthetic_Gene encoding SEQ ID NO: 35

<400> SEQUENCE: 114
atggaagcgg cagtgaatcc tgcaactcct gaacccctta acgcggaggt ggtggtcatt        60
```

-continued

```
ggggcgggca tcagcggcct gacgctggcc tggcgcctgc agcagggttt atcggctagg    120
gggggatccc ctcaagcggt gctcctggcg gaggccagct cccgcgtcgg cggctgcatt    180
tccacccagt ccaaagacgg ctaccgctgg gaggaaggcc ccaatagctt tacccccacc    240
cctgccctgc tcaacctcat tgctgaggtg ggcctgaccg accaactggt gctggccgat    300
gccaagctgc cccgctacat ctactgggaa ggagcgctgt tgccggtgcc tctgagcccc    360
gcggcagccc tgggatcacg gctgctcagc gtgggcggca agctgcgggc tctgcagggc    420
ctgctggggt ttgtcccgcc gccgccagga cgcgaggaaa cggtgcggca gttttttcgg    480
cgacaactgg gatccgaagt ggccgagcgc ctggtggagc ccttcacctc aggagtctat    540
gccggcgacc cagatcaact cagcgccgtg gcggctttcc ctcgcgtggc gggcctggag    600
gagcgctatg gcagcctctt tgccggccgcc ctgcaggctc tgcgccaaag accccagcct    660
tctcctgcgg ccatccaacc cccgcccaaa cggggccaac tgggcaatct gaggcagggg    720
ctgcagcagt tgccagaggc cctagcccaa aagctgggcg acagcctgcg gctgggttgg    780
cgagcgctgc agctgaagcg ggcgggagag ctctattggg tgggctttga gacgccagag    840
ggatcccgct gggtggctgc cgccaggtg gtgctggccc tccccgccta cgaggctgcc    900
gcgctgctac aggagctcaa cccccccggcc agccagctct tggccgagat cctctatccg    960
ccggtggcgg tggtggctct ggcctatccc caagaggccc tgccccagcc gctgcggggc    1020
tttggccacc tcatcccccg ttcccagggc ctgcgcaccc tgggcacgat ctgggcctcc    1080
tgcctttttc cagagcgggc tccccagggc taccacagct tcctcagctt cctgggcggc    1140
gccaccgatg cggccttggc ccgccggcgg gggatcccgc ccatccctgc gctgtctcct    1200
gaggagcgag cgcaaattgc ccacgccgag cttagccagg ttctgctcac ccgccgcgcc    1260
gagcccgtct acctgggcga acgtctctgg ccccgcgcca tccccagta caccccttggc    1320 caccggcaac gcatagccca ggtgcaggcc cacctggcct cccagacgcc ggggatctgg    1380
gtgtgtgcca actacctgga tggcgtggcc ctgggcgatt gcgtgcggcg ggccgaggcg    1440
ctggcgcagc agctgttctc ccaggtctag                                      1470
```

```
<210> SEQ ID NO 115
<211> LENGTH: 1458
<212> TYPE: DNA
<213> ORGANISM: Artificial Sequence
<220> FEATURE:
<223> OTHER INFORMATION: Synthetic_Gene encoding SEQ ID NO: 36

<400> SEQUENCE: 115
```

```
atgagtgaac cagcgaatcc atctaccttta ctcgataccc tcgtcgtcgg tgcgggcatt    60
acgggcctga cgcttgcatt cgacttgcaa cagaaatcga gcggcaccgc ccattcagcg    120
aaagttctcg tcgccgaaag tcaagctcgg gtgggaggtc gcatcgttac cgcatcggga    180
gatggttttc tctgggaaga aggccccaac agttttgcgc cgaccccaga gttattacaa    240
ttagccgttg aagtcggctt aaaagataaa ttagtcttcg ccgacggcaa actccctcgc    300
ttcgtctact ggcagggaga attaatgccc gttcccatga gtcccctgc catcattagc    360 tcaaaactgc ttacttggcg ggggaaactg cgcgcattct tcggtgcttt ggggtttgtc    420
cccccggcaa tggccgatgt gggttccgag gaaactgtcg cctccttctt cgagcgccat    480
ttgggccgcg aagtgctgca cgcgcttagtc gaaccgttcg tgtccggggt ctatgccgga    540
gatccgcgac agttaagcgc ccgagcggca tttgggcgtg tggcgcgcat ggcagaagca    600 ggggcggac tggttgcggg agcagtccgc acgagccgcc agaaaccgaa aacgaaagtc    660
```

```
accccagatc cgaacgtccc gcagcccaaa cggggacagc tcggttcttt tcgtcaagga      720
ttggcgactt tgcccgaggc gatcgccgat cgcctcggag acgcagtcca actcaactgg      780
cacttaattc gcgtgcgccc caccgaacga cacacctaca ttgccgagtt ttcgacgccg      840
gacggtccga agcgggtaga agcgcgcagt gtggtcttga ccaccccaac ttacgtgacg      900
gctgatttat tcgatcccct ccacggggag attgcccggg ccttacgggg atttgtctat      960
ccgtcagtgg cttgtgtggt gttgggatat cccacttcgg cgttgaaacg cccgttaaat     1020
ggttttggga atttgattcc ccgaaatcag gggattcgca ccctggggac gatttggtct     1080
tcgtccttgt tttccgggcg ggcgccggag ggttggaatt tgttgattaa ttttattggg     1140
ggcacggggg atccggcgat cgccgagtta gagaaagacg agatcgttcg ggtcgtgcat     1200
cgagatttac tcaaaacgct gctcgcgcga gatgtagacc cgaaggtgtt ggcagttcat     1260
ctctggaagc gggcaattcc ccaatattgc ttgggtcacc accagcgctg ggagcagatc     1320
gatcgcggct tgcaggagtt tcccggtctt tacttgtgtg ggaattacag tgacggggta     1380
gcggtgggcg attgcgttcg tcgcgcgcga gatcgcgctg cggagatccg ccaatatttg     1440
gcctcggcga cggtctaa                                                    1458
```

<210> SEQ ID NO 116
<211> LENGTH: 1407
<212> TYPE: DNA
<213> ORGANISM: Artificial Sequence
<220> FEATURE:
<223> OTHER INFORMATION: Synthetic_Gene encoding SEQ ID NO: 37

<400> SEQUENCE: 116

```
atgttagaca gtctgattgt gggggccggt ctcagtggct tgaccgttgc ccataccttg       60
cagcagcgcg atcgcaatat tctcgtcgcg gaagctagcc ccgatgtggg gggcaatatt      120
attagccgcc aacagggtga atttctctgg gaggagggcc caaacagttt tcaaccgaat      180
ccgaccctgc tcaaattggc ggtggatgtg ggactaaagg atgacctcgt ctttgccgat      240
cgcaaactgc cccgctgggt ctattggcaa ggtcgtctct tggctgtacc catgagtccg      300
gggactgcgg tgcgatcgcc cctgctgagt gtgccgggga aactgcgggc cctgttcggg      360
gcgctggggt ttgtgccgcc cttggtcgga agccacattc aggcccaagg cggcgatgaa      420
accatttggc aatttattaa ccgtcattta ggcccagaag tggccgagcg gctgatttcg      480
ccctttgtgt cggggtcta tgctggggat gtccacgccc tgagtatggc ggcagccttt      540
cggaaaattt atcgcctcga aaccctgggc ggtggccttg tggcggggc gatgcgatcg      600 cggcggcaag gtaaagccga tcgccccgct gttgatccca atctgcccac cacgaagccg      660
ggccagttgg ggtcatttcg cgagggcatg gtgatgctac ccaacgcgat cgctgctcga      720
ttgggcgatc gcctccgctg ccgctggacg ctgacccaga tcgaaccgtt ggaacagggc      780
tatcgcgccc attttgacac ccccgacggc ggccaaacca tcgagacgcg caccctcgtt      840
ttggcgattc ctgcccatcg agtggccccc ctcctcgcgc ccctgatgcc ggagttaagc      900
accacattac aagcgattcc ctatcctgcc gtagcctgta ccgtgatggc ctatcccaaa      960
acggcgttgg tgcgatcgct ccacggcttt ggcaacctca accccgcag ccaaggtatc     1020 cgcacccttg gcaccatctg gtcatccacc ctcttccccg gtcgtgcgcc cgaaggttgg     1080
gtgatgttga gtagttttat cggtggctcc actgatccgg cggtggcgac gatggatgaa     1140
ggcgcgatcg cccaagccgt ccaccaagac ctcagtaaca ttctcgtcaa acccgacagc     1200
```

-continued

```
accccgaaag tcctcgccgt caaactctgg tcaaaagcga ttccccaata caccctaggg    1260
cattgcgatc gcctctccgt catggccgaa cacctcaaag cccaccccca cctcacccta    1320
tgcagcaact acaccgacgg tgtcgccctc ggtgactgca tccgacgcgg catcgaagcg    1380
ggagaagcga tcgatcagca actctaa                                       1407

<210> SEQ ID NO 117
<211> LENGTH: 1392
<212> TYPE: DNA
<213> ORGANISM: Artificial Sequence
<220> FEATURE:
<223> OTHER INFORMATION: Synthetic_Gene encoding SEQ ID NO: 38

<400> SEQUENCE: 117
atggtagaga ctttaattgt cggagcagga attagtggtt tgaccactgc ttatcggtta      60
catgagcaac aacatgaggt gatggtagcc gaaaagaacg atcgagcagg gggaaacatt     120
accagcaaag ccagtggggg tttcctctgg gaagaaggac ccaatagctt ttctccgacc     180
ccagaattgc taaaactggc ggtagatgtc gggttaaaag atgagttcgt atttgccgat     240
ccgacgcttc cccgttatgt ttattggcag gggaaactac ttcctgttcc catgagtccc     300
ccatcggcgg taaaatcaca gttgttgagt ccattgggga aactgcgagc gttaacgggt     360
gcgatcgggt ttgttccccc aaaggtggcg actgaagaag aaacagtggc ggaattttc     420 acccgtcatt tgggttcgga agtggcgcag cgattggtga gtccttttgt ttctggggtg     480
tatgctggag atgtggcaaa cttgagtgct tcggcagctt ttggacgagt gacgcaattg     540
gcggatgtgg gaggcggact ggttgctggg gcaattttat ctcgtggcaa gaaaaaaaag     600
gcaaccactg aggttgatcc agagattccc aaaacgcgat cgggagaatt aggatcattt     660
cgagaagggt tacagcaatt accaagctcg atcgcccgta aattaggaga ggcggtaaaa     720
ttcaattggg aactaaaaca gatttcccag acttcagaag cgggctacat tgccactttt     780
tccaccccag aaggagaaca aaacgtggaa gcgcagcaaa tcatcctcac gactcctgct     840
tatgttagcg ctccaatttt acaagactta tccccagaag cgagtcaagc gctgagagaa     900
atttattatc cgccagtagc ttgtgtggtt ctcgcgtatc ccgatgaagc cttcagtgtg     960
ccattagacg ggtttggtaa tctcaatccg cgtagtgaag gagtccgtac tttaggaaca    1020
atttggtctt ctactttgtt ttctggacgt actcctcaag gttggcagat tctgactaat    1080
tttatcggcg gcgcaactga tcctgaaatt gctcaactca gtgaagaaga gattgttcaa    1140
caagtccatc aagacttaca gaaaaccata gttaaaccga atacgacacc gaaacccta    1200 gcggttcatt tatggtcgca agcgattcct caatataccc ttggacatct cgatcgaatc    1260
gcgagaatta aagagagttt gaaaccgttt tcggggctat ttttatcgag taactatctt    1320
gatggcgttg cgttaggaga ttgtgtgcgg cgcggggaag aaacagcagc ccagattctt    1380
aataaaaagt ag                                                       1392

<210> SEQ ID NO 118
<211> LENGTH: 1386
<212> TYPE: DNA
<213> ORGANISM: Artificial Sequence
<220> FEATURE:
<223> OTHER INFORMATION: Synthetic_Gene encoding SEQ ID NO: 39

<400> SEQUENCE: 118
atggtagaga ctttaattgt cggagcagga attagtggtt tgaccactgc ttatcggtta      60
catgagcaac aacatgaggt gatggtagcc gaaaagaacg atcgagcagg gggaaacatt     120
```

-continued

```
accagcaaag ccagtggggg tttcctctgg gaagaaggac ccaatagctt ttccccgacc      180
ccagaattgc taaaactggc ggtagatgtg gggttaaaag atgagttcgt atttgccgat      240
ccgacgcttc cccgttatgt ttattggcag gggaaactac ttcctgttcc catgagtccc      300
ccagcggcgg taaaatcgca actactgagt ccattgggga aactgcgagc gttaacgggt      360
gcgatcgggt ttgttccccc aaaggtggcg actgaagaag aaacagtggc ggaatttttc      420
acccgtcatt taggctcgga agtggcgcag cgattggtga gtccttttgt ttctggggtg      480
tatgctggag atgtggcaaa cttgagcgct tcggcagctt ttgcacgagt gacgcaattg      540
gcggatgtgg gaggcggatt ggttgctggg gcaattttat ctcgtggcaa gaaaaaaaag      600
gcaaccactg aggttaattc agagattccc aaaacgcgat cgggagaatt aggatcattt      660
cgagaagggt tacagcaatt accaagctcg atcgcccgta aattaggaga ggcggtaaaa      720
ttcaattggg aactaaaaca gatttcccag acttcagaag cgggctacat tgccactttt      780 tccacccccag aaggagaaca aaacgtggaa gcgcagcaaa tcatcctcac gactcctgct      840
tatgttaacg ctccaatttt acaagactta tccccagaag cgagtcaagc gctgagagaa      900
attgattatc cgccagtggc ttgtgtggtt ctcgcgtatc ccgatgaagc cttcagtgtg      960
ccattagacg ggtttggtaa tctcaatccg cgtagtgaag gagtccgtac tttaggaaca     1020
atttggtctt ctactttgtt ttctggacgt actcctcaag gttggcagat tctgactaat     1080
tttatcggcg gcgcaactga tcctgaaatt gctcaactca gtgaagaaga gattgttcaa     1140
caagtccatc aagacttaca gaaaaccata gttaaaccga atacgacacc gaaacccta      1200 gcggttcatt tatggtcgca agcgattcct caatataccc ttggacatct cgatcgaatc     1260
gcgagaatta aagagagttt gaaaccgttt tcggggctat ttttatccag caactatctt     1320
gatggcgttg cgttaggaga ttgtgtgcgg cgcggggaag aaacagcagc ccagattctt     1380
agataa                                                                 1386
```

```
<210> SEQ ID NO 119
<211> LENGTH: 1404
<212> TYPE: DNA
<213> ORGANISM: Artificial Sequence
<220> FEATURE:
<223> OTHER INFORMATION: Synthetic_Gene encoding SEQ ID NO: 40

<400> SEQUENCE: 119
```

```
atgggctccc acacccccga tattttgatt ctcggcgcag gcatcagtgg cctatccgct       60
gccttccgac tccaccaaca gcaacaagat ctattggtgg ccgagcgcgc cgagcgcgtt      120
ggcggcgtca tcaccacccg cgctcaagac ggctttcgct gggaagaagg ccccaacagc      180 ttcacccccct ccccgccct cctcaacctc atcgccgacg caggcattgc cgatcgcctc      240
ctgtgggcag atggcaagtt accccgcttc gtctacctcg aaggcaaact caccctcgtt      300
cccatgactc ccccagactt aatcaagtcc aacctgctca gctttggggc taagctgcgc      360
gccttattgg gcattctcgg ctttacagcc aaagcccccg acaaagaaga gaccgtcgaa      420
gaattctttg cccgccaact ggggcctcag gtggtcgagc gcttggtcgg cccccttcacc      480 tccggcgtct atgcaggcga cacgcagcaa ctgagcgcca cagccgcgtt ctccaaagtg      540
gcggatctag aacgtaaata cggcagcatt attgccggca tcatccgctc ccccaaatcc      600
cccaaacccc ccatctccgc aaaaatcgac ccccctgccca aacgcggcca gctcggtaat      660
tttgtggagg gattgcagga attgcccgac gcgatcgccc agcagctcgg cgatgccgtc      720
```

-continued

```
aagctgcagt gggaagcggc tgagattgtc aaagaaggcg atcgctaccg caccactttc      780
caaaccccca gtggcccca aaccgtctcc tccaaagcca tcctgctcgc cgtccctgcc      840
taccgtgccg ccccctact caaatccctc gacactgccc ttgccgacga actcgctgcc      900
attccctatc cccacgttgg ggccgttacc ctggcctacc ccgccgatgc cctgcctcaa      960
cctttcgccg gattcggcca actcttcccg cgcggccaag gcatccgcac cctcggcacc     1020
atctggacct ccagcctctt ccccggccgc gccccggcag gctatcaatg caccctcagc     1080
tacatcggcg gtgccaccga ccctgacatt gctcaaatga cggacgaagc cttagctcga     1140
acggtccacc aagacctgag caaaactctg ttggtgaaag aagctgaacc gcgcgtcatg     1200
ggcgtacgcc gctggccccg cgccattcct caatacaccc tcggtcaccg acagcgcctt     1260 gccccgcattg acgaattgct cgcagactat tccggcttgg tgttgtgtac caattacttg     1320
gatggcgtgg cattgggcga ttgtgtcagg cgaggagagg ctcgggcagc ggatttggtg     1380
gaatggctgg cacaagctga gtag                                            1404
```

<210> SEQ ID NO 120
<211> LENGTH: 1455
<212> TYPE: DNA
<213> ORGANISM: Artificial Sequence
<220> FEATURE:
<223> OTHER INFORMATION: Synthetic_Gene encoding SEQ ID NO: 41

<400> SEQUENCE: 120

```
atgacaaacc tagttgatag ccttattgtt ggtgctggta ttagtgggct gagtttagcc       60
tatagtctta accgtgaaaa aagtgtgcgc gaacctctaa aggttttggt tacagaaagc      120
cagaaccgag tcgggggaaa tattacaacc ggacgggctg atgatttttt atgggaagaa      180
ggccctaaca gttttgcccc cacccctgaa ttactcggac tagccgtaga tttagggctc      240
aaagaagaat tgattttgc cgatcgcaaa ctacccgtt atgtgtactg gaacctaatg       300
ttacatccag tacccatgaa cccccccgcc ctactctcct ccgaactcat cagcgccaga      360
ggtaaactcc gcgccgcatt aggagccata ggatttgtgc cacccccagt aggcgctcac      420
ctctctcaac agggaggaga agaaactatc acccagtttt tcgatcgcca tttaggttca      480
gaagtcctag aacgtctcgt ccagcccttc gtttcagggg tttatgctgg cgaccctcaa      540
cagttagcag tccgttccgc tttttagtcgc atagtagccg ctgaggaggc tggggggggg      600
ctactacctg gatttgtgcg atcgcgtctg aataaaaaag ccccgtctc taccccgac       660 cccaacattc ccaaaactcg ccccggtgaa ttagggtcct tccgttatgg tctgcaaact      720
ctaccagaaa ccttagccag caaattaggc gatcgagtta agttaaattg gactatcgac      780 cgttttttatc ccaccgatca tcaaacctat attgctgaat tttccacccc agacggtcct      840
cagcaagtag aagcccgaac ccttgcctta atgaccccg cccatgttag cgctcgcctg       900
ttgcaacccc tacactctcc catcgctacc gcattaagcc aaattcccta tccccccgtc      960
gcttgtgtag tcctcgccta tcccaaatca gccttaaaac aacaactcaa aggctttggt     1020
aatttaattc cccgccgtca aggaatccgt acccttggca ctatttggac ctcaagttta     1080
tttcccggtc gcgccccaga atcttggcaa gtcctcagca attatattgg gggtgcaaca     1140
gacccggaaa ttggcgaaat ggatgatgat caaattgtcg ccgccgttca tcaagaccta     1200
cgccaaattc tgctggctga agatgtcccc cccaaggtct tagctgttca tctttggcgg     1260
cgcgctatcc cacaatatac tctcggtcat cagaaccgcc taaattgcat cgatgctgga     1320
ttgcgatcgy ttcccggact ttatctgtgt agcaactata ttgatggggt ttccgtcgga     1380
```

-continued

```
gactgtgtga ggcgcggtca gcaatgggca tctaaaattc agtcccatct tcatgactgc   1440
caaacagcca actaa                                                     1455

<210> SEQ ID NO 121
<211> LENGTH: 1455
<212> TYPE: DNA
<213> ORGANISM: Artificial Sequence
<220> FEATURE:
<223> OTHER INFORMATION: Synthetic_Gene encoding SEQ ID NO: 42

<400> SEQUENCE: 121
atgacaaacc tagttgatag ccttattgtt ggtgctggta ttagtgggct gagtttagcc     60
tatagtctta accgtgaaaa aagtgtgcgc gaacctctaa aggtttttggt tacagaaagc    120 cagaaccgag tcgggggaaa tattacaacc ggacgggctg atgatttttt atgggaagaa    180
ggccctaaca gttttgcccc cacccctgaa ttactcggac tagccgtaga tttagggctc    240
aaagaagaat tgattttttgc cgatcgcaaa ctaccccgtt atgtgtactg gaacctaatg    300
ttacatccag tacccatgaa ccccccccgcc ctactctcct ccgaactcat cagcgccaga    360
ggtaaactcc gcgccgcatt aggagccata ggatttgtgc cacccccagt aggcgctcac    420
ctctctcaac agggaggaga agaaactatc acccagtttt tcgatcgcca tttaggttca    480
gaagtcctag aacgtctcgt ccagcccttc gtttcagggg tttatgctgg cgaccctcaa    540
cagttagcag tccgttccgc ttttagtcgc atagtagccg ctgaggaggc tgggggggggg    600 ctactacctg gatttgtgcg atcgcgtctg aataaaaaag ccccgtctc taccccccgac    660 cccaacattc ccaaaactcg ccccggtgaa ttagggtcct tccgttatgg tctgcaaact    720
ctaccagaaa ccttagccag caaattaggc gatcgagtta agttaaattg gactatcgac    780
cgtttttatc ccaccgatca tcaaacctat attgctgaat tttccacccc agacggtcct    840
cagcaagtag aagcccgaac ccttgcctta atgacccccg cccatgttag cgctcgcctg    900
ttgcaacccc tacactctcc catcgctacc gcattaagcc aaattcccta tccccccgtc    960
gcttgtgtag tcctcgccta tcccaaatca gccttaaaac aacaactcaa aggctttggt   1020
aatttaattc cccgccatca aggaatccgt accccttggca ctatttggac ctcaagttta   1080
tttcccggtc gcgccccaga atcttggcaa gtcctcagca attatattgg gggtgcaaca   1140
gacccggaaa ttggcgaaat ggatgatgat caaattgtcg ccgccgttca tcaagaccta   1200
cgccaaattc tgctggctga agatgtcccc cccaaggtct tagctgttca tctttggcgg   1260
cgcgctatcc cacaatatac tctcggtcat cagaaccgcc taaattgcat cgatgctgga   1320
ttgcgatcgc ttcccggact ttatctgtgt agtaactata ttgatggggt ttccgtcgga   1380
gactgtgtga ggcgcggcca gcaatgggca tctaaaattc agtcccacct tcatgactgc   1440
caaacagcca actaa                                                     1455

<210> SEQ ID NO 122
<211> LENGTH: 1452
<212> TYPE: DNA
<213> ORGANISM: Artificial Sequence
<220> FEATURE:
<223> OTHER INFORMATION: Synthetic_Gene encoding SEQ ID NO: 43

<400> SEQUENCE: 122
atgacaaacc tagttgatag ccttatagtt ggtgctggta ttagcgggct aagtttagcc     60
catagcctga accgtgaaaa aaaccccccgc tcacccctaa aagtttttggt cacagaaagc    120
```

-continued

```
cagaaccgag tcggggggaaa tattacgacc ggacgcgcat ctgatttttt atgggaagaa      180
ggccctaaca gttttgcccc cacccctgaa ttactcggac tagccgtaga tttggggctt      240
aaacaagaat tgatttttgc cgatcgcaaa ctaccccgtt atgtctactg gaaccataag      300
ttacatccag tacccatgac ccccccccgcc ctactctcct cccaactaat cagccccaga      360
ggtaaactcc gcgccgcctt gggagccata ggatttgtgc cacccccagt aggcgctcac      420
ctctctcaac agcgaggaga agaaactatt acccagtttt tccatcgcca tttaggttca      480
gaagtcctag aacgtctcgt ccagcccttc gtttctgggg tttatgctgg cgaccctcaa      540
cagttagcag tgcgttccgc ctttagtcga ttagtagccg ccgaagacgc agggggtgcg      600
ctactacctg gatttgtgcg atcgcgcctt aataaaaaag ccaccaaaga caccaccgcc      660
gaccccaata ttcccaaaac tcgccccggt gaattagggt ccttccgtta tggcctggaa      720
actctgcccg aaaccttggc cagtaaatta ggcgatcgag ttaagttaaa ttggaccctc      780
gaccgttttt atcccaccga tcatcaaacc tatattgctg aattttccac cccagacggc      840
ccccagcaag tagaaacccg aaccctcgct ttaatgaccc ccgcccatgt tagcgctcgc      900
ctcttgcaac ccctacactc tcaaatcgct tccgcattaa gccaaattcc ttatccccccc      960 gtcgcttgtg tcgtactcgc ctatcctaaa tcagccttaa aacaacaact caaaggcttt     1020
ggtaatttaa ttccccgcca tcaaggaatc cgtaccctcg gcactatttg gacctccagt     1080
ttattccccg gtcgcgcccc agaatcttgg caagtcctca gcaattatat tgggggtgct     1140
acagaccctg aaattggcga aatggatgat gatcaaattg tcgccgccgt tcatcaagac     1200
ctacgccaaa ttctgctggc tgaagatgtc cccccccaaag tcttggctgt ccatctctgg     1260
cggcgcgcta tcccacaata tactctcggt catcaagatc gcctaaattc catcaatgct     1320
ggattgcgat cgcttcccgg actttatctg tgtagcaact atattgatgg ggtttccgtc     1380
ggtgactgtg tgaggcgcgg tcagcaatgg gcatcgcaaa ttcagtccca ccttcatcca     1440
acagccaact aa                                                          1452
```

```
<210> SEQ ID NO 123
<211> LENGTH: 1437
<212> TYPE: DNA
<213> ORGANISM: Artificial Sequence
<220> FEATURE:
<223> OTHER INFORMATION: Synthetic_Gene encoding SEQ ID NO: 44

<400> SEQUENCE: 123
```

```
atgaccatca cgccaccctc tgagaacaat caacccatag atgtccttgt cgttggggca       60
ggaatctcag gattaacgat cgcccatgaa ctagcgatct ctaaaaaata tagcgtcttg      120
gtagcagaag cacaggatcg tgtgggtgga gccataacca gtgccaaaaa tgacgaaggt      180
tatcaatggg aagagggccc aaatagtttc caacccgctc ctgaactatt gcgtctagcg      240
gtacaggtag gactcaagga tgaattggtg ctagctgatg gcaaattacc ccgtttcgtt      300
tttctaaatg ggaagttaaa cgccttaccg atgactccag cgagtgcgat cgcatctaaa      360
atattgactt ggggcggcaa gattcgtcta gctctaggtg caatcggctt tgcgcgtcca      420
gccatggctg gagaagaatc cgttgatcaa ttcttttcac gtttgctagg cagacaagca      480
gttgaaagat tagttgcacc gtttatctca ggtgtatacg caggcgatcc caagcgactc      540
agtgccaagg ctgcctttttc taagattgct cgtctagaaa cctatggtgg gttaatcgca      600
ggcgcaatat tatctagcaa acaacggaaa gccgaaaaga ttaatgatcc gaatattccc      660
aaaactaaag ctggtgaact aggttcattt cgtcaaggta taaaaatgct gcctgaagcg      720
```

-continued

```
atcgctacca agttaagaga gcaaggttca gccatcaaac aacaatggac tttgcgatcg     780
ctggaaaaac aaggcgaagt ctatatttct aagttcgata cacccacggg tgaagaaact     840
gtgacatcgc gatcgattgt tctcgctacc ccagcctatg tcacggcaaa attactgcaa     900
gattacttgc cagccgccag tcaagccttg aatgagattt ctatccgac cgttgcttgt      960 gtggtacttg cttatcctaa gagcgaattt gcctatgata tgaagggctt tggcaatctg    1020 attcccgca ctcaaggagt aagaacttta ggcactatct ggtcatcgag cctatttact     1080
ggacgtgctc cagaaggttg gcaactatta ctaaacttta ttggcggcac gcttgatccc    1140
gctctagcca aactttcgga accagaaatc attgccgctg tgcatcaaga tttaaagaaa    1200
acaattcttc gacctgacac gaaagccgaa ccaaaagcga tcgcagttca tgtatgggat    1260
aaagcgatcc cccaatacga aatcggacat ttagaaaggc ttgccattgt ggaagcagaa    1320
ttacagaaat ctcaaggact ttatgtcagt gccaatttta tcggaggtgt ggctctaggt    1380
gactgcatca agcgtagttt gcaagaagcc aataaaattg atgcatatct aaagtaa       1437
```

```
<210> SEQ ID NO 124
<211> LENGTH: 1437
<212> TYPE: DNA
<213> ORGANISM: Artificial Sequence
<220> FEATURE:
<223> OTHER INFORMATION: Synthetic_Gene encoding SEQ ID NO: 45

<400> SEQUENCE: 124
```

```
atgacctccg cccagattcc tgaagttaat ccattagatg ttcttgtcgt tggggcaggg      60
atttcaggtt taacgatcgc ccatgaatta gcgatcgcta aaaactatcg cgtcttggtg     120
gcggagacac aggatcgggt gggcggcgca attactagcg ccaaaaatga cgatggctat     180
caatgggagg aaggacctaa tagcttccag ccagcccccg aattattacg tttagccgta     240
gaagtcggac tcaaggatga attggtgctt gcggatggca aactaccccg tttttgtattt     300 ctcaacggca agttaaacgc tttgcccatg tctccgccaa cggcgatcgc ttcccgaatt     360
ttgacttggg gaggcaaaat ccgtctcgct ttaggggcaa tgggttttgc acgtcctgca     420
atggcgggag aagaatccgt cgatcgcttc ttttcgcgcc tgttaggcag acaagcggtc     480
gatcgcttgg ttgcccctt catttctgga gtatatgcgg gcgatcccaa gcggctcagt      540
gccaaggctg cctttgccaa aatcgccaag ctggaaacct atggcggttt gcttgctggg     600
gcaatattat cgagtaaaga gcgcaaacaa aaacttaacg atcctcgcat tccgaaaacg     660
aaggcagggg agttaggttc ctttcgcgag ggcataaaga tgctccctga agcgatcgcc     720
gctaaattaa gggcacaggg tacagccgtt aaacaacaat ggactctgcg atcgctagag     780
aagcaaggcg aatctatat ttccaaattt gatacccca cgggcgaaga aattgtgacc       840
tcgcgatcgg tcgttctttc cacccctgcc tatgtcactg caaaattatt acaagattat     900
ttacccgccg ccagccaagc cttaaatgag attttttatc cgacggtagc ctgtgtcgtg     960
cttgcctatc ccaaaagcga atttctctat gacatgaaag ctttggcaa tttgattcct     1020 cggacagagg gagttagaac cctagggaca atttggtcat ctagcctctt ttcaggacgc    1080
gcccccgcag gttggcaact attgctcaat tttatcggtg gcaccctcga tcccgcacta    1140
gcccatttat ctgaagccga aatcattgct gccgtgcatc aagatctcaa aaaaacgatt    1200
cttcgccccg atacgaaggt atctcccaaa gcgatcgccg ttcatgtgtg ggataaggct    1260
attcctcaat acgaaatcgg gcatttagag cgccttgcca cggtggaagc cgaattgcaa    1320
```

-continued

```
aaatcctcag ggctatatgt cagtgctaat tttattggcg gagtcgcctt aggtgactgc   1380
atcaagcgca gcttgcaaga agctcataaa attgcggctt ttttagaaac catttag      1437

<210> SEQ ID NO 125
<211> LENGTH: 1440
<212> TYPE: DNA
<213> ORGANISM: Artificial Sequence
<220> FEATURE:
<223> OTHER INFORMATION: Synthetic_Gene encoding SEQ ID NO: 46

<400> SEQUENCE: 125
atgacttctg ctcaaaccac cgaagttaat caacccttag atgttcttgt tgttgggggca    60 ggaatttctg gtttagcgat cgcccatgaa ctcgcgattg ccaaaaatta ccgtgtttta   120
gtagcagaag ctcaagatcg cgttggtggt gcaattacca gtaaccgtaa tgatgacggc   180
tatctctggg aagagggggcc caatagcttt cagcctgcac cagagttatt gcgtctagcc   240
gtagaggtag ggctcaagga tgaattggta cttgccgatg gtaagttgcc gcgatttgta   300
tttctcaatg gcaagttaaa tgcgttgccg atgagtccac ctaccgcgat cgcctccaaa   360
atcctgactt ggggcggcaa gattcgccta gctctgggtg cattaggttt tgcgcgtcct   420
gccatgagtg gtgaggaatc tgttgaccaa ttttttttcgc gcctcttagg taagcaagca   480
gtggagcgct tagttgcccc ttttatctct ggggtctatg cgggtgatcc aaagcgtctc   540
agtgctagag ctgcattttc taaaattttc cgtctcgaga atggctatgg tggtttgctc   600 acagggggcaa tcctgacggc aaaagatcgc aaagcccaaa agctgaacga tccgaatatt   660
cccaaggtga agtctggtga actaggttct ttccgacaag gcattaaaat gctgcccgaa   720
gcgatcgcaa ccaaactcag agatcaaggt acggctgtca aacaacaatg gactttgcga   780
tcgctagaaa agcaaggcga aatctatgtt tctcagtttg gtacgcctac tggtacagaa   840
acaattactt cgcgatctgt ggtattgact accccagcct atgtgagcgc caagttattg   900
cagggctatt tacctgctgc aagccaagcc ctgagcgaga ttttctatcc gaccgtggca   960
tgtgtcgtac ttgcctatcc caaaagcgaa tttgcttatg acatgaaggg attcggtaat  1020
ctcattcccc gcacgcaagg tgtaagaact cttggaacaa tttggtcatc cagtctattt  1080
gcagggcggg ctcctgatgg ttggcaatta ttgctgaact ttataggtgg tactcttgat  1140
ccagatttag caaatctttc ggaagcgaag atcgttcaag cagtacatca agatctcaag  1200
aaaaccctgc tacgtcctga tagcaaagtc gaacccaagg tgatcgctgt acatgtgtgg  1260
gacaaggcaa ttcctcagta tgaaatcgga catttagagc gtcttgccac tatcgaaact  1320
gaattgcaaa agtcacaggg tttgtatgtc agcgcgaatt ttattggtgg tgttgcgctt  1380
ggtgattgca ttaagcgtag cctccaagaa gcagataaaa ttgcagcatt tttgaagtaa  1440

<210> SEQ ID NO 126
<211> LENGTH: 1536
<212> TYPE: DNA
<213> ORGANISM: Artificial Sequence
<220> FEATURE:
<223> OTHER INFORMATION: Synthetic_Gene encoding SEQ ID NO: 47

<400> SEQUENCE: 126
atgaactctt ctgttgagca cttttagcggg acgcagtcct tgcaggccga ggtggtggtg    60 gtggggcgg gcatcagcgg cctaacgttg gccttgcgat tacaacaggg cttatccccc   120
aaggatgaat ccacccagcc gctgctcctg gccgaggcca gctcccgcgt ggggggctgt   180
atctccaccc aatccaaaga cagctatcgc tgggaagagg gccccaacag ctttaccccc   240
```

-continued

```
gtccccgccc tgcttaacct cattgccgag gtgggcttgg cggagcacct ggtgctggcc    300
gatgccaagc tgccccgcta catctactgg gaaaaagagc tgctgccggt gcccctgagc    360
ccttctgcag ccattggctc gcggctgttg agcgtgggcg gcaagttgcg ggccttacgt    420
gggttgttgg ggtttgtcgc gccgccgcca ggcggagagg aaacggtgcg gcaattcttc    480
cggcggcaac tgggatccga ggtggtggaa cggctggtcg aacctttcac ctcaggggtg    540
tatgccgggg atccggatca gctcagcgcc ttggcagcct tcccccgcat tgccggcttg    600
gaagaacgct acggcagcct ctttgccggt gctgtgcagg ctttgcgcag ccgttatcgc    660
tacgcgacgc tcccgcgaac ccgtcaccag gacagcgcca actcccccat ccagcctcct    720
cccaagcggg gccaactggg taacctgcgg caggggttgc agcagctacc tgaggcgatt    780
gcccagaaac tgggcagtgc gctgcggctg ggctggcggg ctgtgcatct caagcgggat    840
gagacgggct accgggtggg cttcgtcata cacgacagcg gcgcggagca cacggcccca    900
gaagaaatcc actgggtggc ggctcaacag gtggtgctca ccctccctgc ctacgctgct    960
gccaccctcc tgcaggatct caacccccag gccagccggc tgctgaggga aatcccctac    1020
ccgcctgtgg cggtggtggc tttggcctat ccagaagaag ccctcccccca accgctgcga    1080 gggtttggcc atctgatccc tcgctctcag ggcctgcgca ccctgggcac catctgggcc    1140
tcctccctct tcccagagcg ggctcctcag ggctatcact gcctgatcag cttcatcggg    1200
ggagctaccg atgcggcttt tgcccgccag aaagggatcc cgcccattac ggcgctctcc    1260
cctgacgagc gggcccaaat tgtgcatgca gaactcagcc agatcctgct cacccgccct    1320
gtcgaaccca tccgcctggg agagcgcctg tggccccagg ctatcccgca atatacgctt    1380
ggccaccggc agcggattgc ccaattgcag gccagcctgg ccgaccaaac cccagggggtg    1440 tgggtgtgtg ccaactacct ggatggcgtg gccttgggag attgtgtgcg gcgggccgag    1500
gccctagccc agcagatcct gtccgtccgg cgttag                             1536
```

```
<210> SEQ ID NO 127
<211> LENGTH: 1440
<212> TYPE: DNA
<213> ORGANISM: Artificial Sequence
<220> FEATURE:
<223> OTHER INFORMATION: Synthetic_Gene encoding SEQ ID NO: 48

<400> SEQUENCE: 127
```

```
atgacctccg cccagattcc tgaagttaat ccattagatg ttcttgtcgt tggggcaggg     60
atttcaggtt taacgatcgc ccacgaacta gcgatcgcta aaaactatcg cgtcttggtg    120
gcggaggcac aggatcgcgt gggcggcgcg attactagcg caaaaaatga cgagggctat    180
caatgggagg aaggtcccaa tagtttccag ccagcccccg aattattacg tttagccgta    240
gaagtcggac tcaaggatga attggtgctt gcggatggca aactaccccg ctttgtattt    300
ctcaacggca agttaaacgc tttgcccatg tctccgccaa cggcgatcgc ctcccaaatt    360
ttgacttggg gtggcaaaat ccgtctcgct ttgggggcaa tgggttttgc acgccctgcg    420
atggcgggag aagaatccgt tgatcgcttc ttttcgcgcc tgttaggcag acaagcggtt    480
gatcgcttgg ttgctccctt catttctgga gtatatgcgg gcgatcccaa gcggctcagt    540
gcgaaggctg cttttgcaaa aattgccaag ctggaaacct atggtggttt gcttgctggg    600
gcaatattat caagtaaaga gcgcaaagcc caaaaactta cgatcctcg cattccgaaa    660 acgaaggctg gggagttggg ttcctttcgc gagggaataa aaatgctccc tgaagcgatc    720
```

-continued

```
accgctaaat taagggcgca gggtacagcc gtcaaacaac aatggactct gcaatcgcta     780
gagaagcaag gcgaaatcta tgtttccaaa ttcgctaccc ccacgggcga agaaattgtg     840
acctcgcgat cggtcgttct ttccaccccc gcctatgtca ctgcaaaatt attacaagat     900
tatttgcccg ccgctagcca agccttaaat gagatttttt atccaactgt tgcctgtgtg     960
gtacttgcct accccaaaag cgaatttcgc tatgacatga aaggctttgg caatttgatt    1020
cctcggacag agggagttag aaccctagga acaatttggt catctagtct ctttgcagga    1080
cgcgcccccg caggttggca actattgctc aattttatcg gcggcacgct tgatcccgca    1140
ctagcccatt tatcagaagc agaaattatt gctgccgtgc atcaagatct caaaaaaaca    1200
attcttcgcc ccgatacgaa ggtatctccc aaagcgatcg ccgttcatgt gtgggataag    1260
gctattcctc aatacgaaat cgggcattta gagcgacttg ccacggtaga agctgaattg    1320
caaaaatctt cagggctata tatcagtgct aattttattg gcggagtcgc cttaggtgac    1380
tgcatcaagc gtagcttgca agaagctcat aaaattgcgg cttttttaga aaccatttag    1440
```

```
<210> SEQ ID NO 128
<211> LENGTH: 1437
<212> TYPE: DNA
<213> ORGANISM: Artificial Sequence
<220> FEATURE:
<223> OTHER INFORMATION: Synthetic_Gene encoding SEQ ID NO: 49

<400> SEQUENCE: 128
```

```
atgaccctca cgccatcttc tgaagaaaat cagccattag ataccctaat cattggggca      60
ggaatctcag gattaacgat cgctcatgag ctagtgatcg ctaaaaacta ccgcattttg     120
gttgcggagg cacaggatcg cgtgggtggt gccataacta gcgccaaaaa tgacgaaggc     180
tatctatggg aagagggccc aaatagtttt caacccgcac ctgagctatt gcgcttagcg     240
gtacaagtgg gactcaagga tgaattggtt ctagccgatg gcaaattgcc ccgttttgtc     300
tttttgaatg gcaagttaaa tgccttgcca atgagtccac cgaccgcgat tacttccaaa     360
atcctgactt ggggcggcaa gattcgtctg gctttggggg cgatcggctt tgctcgtcca     420
gcgatggctg gggaagaatc tgtcgatcaa ttcttttcac gtatattagg caagcaagca     480
gttgaaagat tggttgcgcc gtttatatct ggtgtgtatg caggtgatcc caagcgactc     540
agtgccaagg ctgctttttc aaagattgcc aaactagaaa cctatggagg cttgctctca     600
ggagcaatat tatccagcaa agaacgtaaa gcccaaaagc tcaacgaacc gaatattccc     660
aaaactaaag ctggtgaatt aggatcgttt cgacaaggca tccagatgct gccagaagcg     720
atcgcgtcaa agttaaggga gacaggtaca gcagtcaagc aaaaatggac tttgagatcg     780
ctagaaaaac aaggcgatat ctatatttct aagttcgata caccctcagg tgaagaaact     840
gtgacatcgc gatcggtggt tttgactacc cccgcctatg tcaccgccaa acttttggaa     900
gattatttgc cagccgctag ccaagctctg aatgagattt tctatcctac tgttgcttgc     960
gtggtgcttg cctatccaaa gagcgaattt gcccatgaca tgaagggctt tggcaacctg    1020
attccccgca ctcaaggagt gagaacgtta ggcacaatct ggtcatcaag tttatttgct    1080
ggacgtgccc ctgaaggttg gcaactatta ctaaactttta tcggcggcac tctcgatcct    1140
gccctagcca agctttcaga atcggaaatt attgctgctg ttcatgcaga tctaaagaaa    1200
acaattctcc gacctgatac taaagccgaa ccgaaggcga tcgcagttca tgtatgggat    1260
aaggcaattc cacaatacga aatcggacat ttagatcgac ttgccacagt ggaagcagaa    1320
ttacagaaat cacaaggact gtatgtaagc gcaaacttta tcggaggtgt ggctcttggt    1380
```

-continued

```
gattgcatca agcggagctt gcaagaagcc aataaaatcg atgcattttt aaaatga          1437

<210> SEQ ID NO 129
<211> LENGTH: 1509
<212> TYPE: DNA
<213> ORGANISM: Artificial Sequence
<220> FEATURE:
<223> OTHER INFORMATION: Synthetic_Gene encoding SEQ ID NO: 50

<400> SEQUENCE: 129
atgtccaacc ataatcatgc tggctcaccg atcgacctgt tggtagttgg cgctgggatc           60
agtggcctca ccgtggctca tgacctggcc agcaattctg tcgctgaggc taatgggtca          120
aaccagctca ggattatcgt caccgaggca caaaatcggg tgggcggggc gatcgtctcg          180
cagcgggatg aagtaggttt tcaatgggaa gaagggccca atagctttca gccagcccca          240
gagctactca aactggcggc ggcggtgggg ctaaaggatg aattagtatt tgcggatggc          300
aagttgccca ggtttgtgtt ctggaatggg aagttaaatg ctctgcccat gtcaccgcag          360
ctgctaacca aatttaattt attaacgatc aagggcaagc taagggcttt cctgggggcg          420
atcggctttg tgcgaccagc ggcagcgggg gaagaaactg tggcgcagtt ttttaagcgg          480
catctggggc aagaggtggt cgatcggctg gtagtaccgt tcatctctgg ggtttatgca          540
ggcaatacgg acaagctgag tgcggcggcg gcatttggca agattttccg gttagaaaaa          600
aactacaatg gtctggtggc gggggcgatc ctgtcgcggt tggccaagcg caagcaagag          660
aaggcgcaaa ccaaccagcc agcaaatatt tacgatcgcc aggagatccc caaaaccaag          720
ccaggacagt tgggatcatt taaaaatggg attgaggctc tgcccagggc gatcgccgaa          780
gatttaatcg acaaaggtca tgaggtgcga ttgcaatggc ggttggacaa aatccagccc          840
aactctgatg ggacatatag cgccacctat gagacacccc acgggatcga aacgatcacg          900
gcgcgggctt tgctccttac tacgcctgcc tatgtttcca gtatgctgct gcaagatatt          960
gcccctgatg cagctcaatc tttgggtgag atttattacc cgccagtggc ctgtgtggtg         1020
ttggggtatc cggatgcggc gatgaaacgg gatatgaatg ggtttggtaa tttgatcccg         1080
cgtagtcagg gcatccgtac gttgggcacg atctggggat cgagtttgtt tagcgatcgc         1140
gctccggctg gctatcatct gctgctgaat tttattggtg ggtcgttgga tactggcatt         1200
gccgatctat ctgaacctga aatagctcag gcggtgcata gtgacctgaa gcaaacgttg         1260
ctgaaaccag acaccacgat cgaaccgaag gtgttggcgg tgcatttgtg gcaacgggcg         1320
atcccgcagt atgaggtcgg tcacctcgat cgattggcgc gggttgaaag ggatctggct         1380
aatcatcctg ggttgtttgt gagtgctaat tttattggtg gcgtggcgct gggggattgt         1440
gtgaagagga gttttggtac ggctgaacaa attaaggggg ttttaaatct gtctactaaa         1500
aaaaaataa                                                                 1509

<210> SEQ ID NO 130
<211> LENGTH: 1440
<212> TYPE: DNA
<213> ORGANISM: Artificial Sequence
<220> FEATURE:
<223> OTHER INFORMATION: Synthetic_Gene encoding SEQ ID NO: 51

<400> SEQUENCE: 130
atgtccctaa caccttcctc tgcaaccaat caacccttag atgttcttgt cgttggcgca           60
gggatatcag gcttaacgat cgcccatgaa ctggcgatcg ccaaaaaata tcgcgtcttg          120
```

-continued

```
gttgcggaag cacaggatcg ggtgggcggt gcgatcacca gcgctaaaaa tgatgaaggt      180
tatcaatggg aagagggtcc aaatagtttt cagcctgcgc ctgagctatt gcgtttagca      240
gtacaggtgg gactaaagga cgaattggta ttagctgatg gcaaattgcc ccgttttgtc      300
tttctcaatg gcaagttaaa cgctttaccc atgagtccac cgacagcgat cgcctccaaa      360
attttgactt ggggaggcaa aattcgtctg gctttaggtg cgatcggctt tgcgcgtccc      420
gcaatggctg gcgaagaatc cgttgatcaa ttcttttcgc gccttctagg taaacaagcg      480
gttgaaagat tagttgcacc gtttatctca ggtgtatacg caggtgatcc taaacgactc      540
agtgccaagg cagcctttgc caaaatcttt cggttagaaa atagctataa cggtttgctc      600
gcaggcgcga ttctttcggc aaaggaacgt aaagcccaaa agctgagtga tcccaatatt      660
cctaaagtta aagctggtga attgggttca tttcggcaag ggattaagat gttgcctgag      720
gcgatcgcca cgaaattgcg agatcaaggt acagccgtca agcagcaatg gactttgcga      780
tcgctagaaa agcaagacga aatctatatt tctaagtttg atacgcctac gggtgaagaa      840
acggtgcgat cgcgatcggt agtactcagt acccccgcct atgtcactgc taagctattg      900
caagactatc taccagcagc tagccaagcc ttaaacgaga tttttttatcc gactgtagcc      960 tgtgtagtga tggcatatcc taagagcgaa tttgcctatg acatgaaagg atttggcaat     1020
ctcattcccc gcactcaagg cgtgagaact ctaggcacaa tctggtcatc cagtctattt     1080
gcaggacgcg cccctgaagg ttggcaactg ttattaaact ttatcggcgg cacgctcgat     1140
cctgctttag ctaagctatc agaacctgaa atcattgctg ccgttcatca agatctcaag     1200
aaaaccatcc tgcgtcctga tacaaaagcc gaaccgaagg cgatcgcagt ccatgtttgg     1260
gataaagcca ttcctcaata cgagattgga catttagacc gccttgcgac ggtagaaaaa     1320
gaattacaaa aatctcaagg cttgtatatc agtgccaact ttattggcgg tgtggcttta     1380
ggtgattgca tcaagcggag tttgcaagaa gctactaaaa ttgatgcatt cttaaaataa     1440
```

```
<210> SEQ ID NO 131
<211> LENGTH: 1452
<212> TYPE: DNA
<213> ORGANISM: Artificial Sequence
<220> FEATURE:
<223> OTHER INFORMATION: Synthetic_Gene encoding SEQ ID NO: 52

<400> SEQUENCE: 131
```

```
atgaccacct ctcaagaaac taaagctagt caaccgttag atgttcttgt cgttggggca       60
ggaatatcgg gtttaacgat cgcccacgaa ctggcgatcg ctaagcacag acatgtctta      120
gttgctgaag cacaggatcg agtgggtggt gcgattacca cggctagcaa taacgagggt      180
tatctttggg aagaagggcc caacagtttt caacctgcac ccgaactatt gcgcctagcg      240
gtagaggttg ggcttaaaga tgaattggta ctggcagatg gcaaattacc aagattcgtg      300
tttctcaatg gcaagttaaa tgctctacca atgagtccac cgacggcgat cgcctccaag      360
atcttgagtt ggggaggcaa aatccgtcta gctttaggtg ctcttggctt tgcgcgtcca      420
gcgatggctg gcgaagaatc tgtcgatcga ttcttttcgc gtttattggg gaaacaggct      480
gttgaaagat tggttgcccc ctttatctct ggtgtctatg caggcgatcc gaagcggctc      540
agtgcgaagg cagcctttttc caaaattgcc aaactcgaaa cctatggagg cttgctcgca      600
ggagcaatat tgtcgagcaa agagcggaaa gcccaaaagc tcaatgaccc taatattccc      660
aaaactaagg ctggtgaact tggctctttt cgccaaggga ttaaaatgct acccgaagcg      720
atcgctgcta agttaagagc gcaagggaca ccagttaagc agcaatggac gttgcgatcg      780
```

```
ctccagaagc aagatgaaat ttatatcgct aagttcgata cgccaacggg tgaagaggtc       840
gtcacatcga agtctgtggt tctcagtaca ccagcctatg tttccgccaa actactgcaa       900
gattatttgc ctgctgccag tcaagcgttg agcgagattt tttatcccac tgttgcttgc       960
gtggtgcttg cttatcctaa gagtgcattt gcctatgaca tgaaaggctt tggcaacttg      1020
attcctcgca ctcaaggcgt gagaactctc ggcacaattt ggtcatcaag tctatttgct      1080
ggacgcgctc ccgatggctg gcaactgtta cttaacttta tcggcggtac gctcgatcct      1140
gctctagctc aactttcgga atctgaaatc attcaagccg tacatcaaga tctcaagaaa      1200
acaattctcc gtcctgatac gcaagtggaa ccaaagacga tcgccgttca tgtatgggat      1260
aaggcaattc cacagtacga gatcggtcat ttacaacgcc ttgcaaccat caaagcagaa      1320
ttacaaaaat ctcaaggatt gtacatcagc gctaatttta tcggcggtgt agctctaggc      1380
gattgcataa agcgtagtct gcaagaatcg atcgaaattg atgagtttct atcgagaaca      1440
aactctcttt aa                                                          1452
```

<210> SEQ ID NO 132
<211> LENGTH: 1446
<212> TYPE: DNA
<213> ORGANISM: Artificial Sequence
<220> FEATURE:
<223> OTHER INFORMATION: Synthetic_Gene encoding SEQ ID NO: 53

<400> SEQUENCE: 132

```
atgaaccaat tagccgatcg cccatcaggt gagcaaactt tggatgtgct tgtggtggga        60
gcaggaattt caggcttgac gatcgcctat gatttggcaa ttaatcagca tcggcaggtt       120
ttagtcgctg aagcgcaaga tcgcgttggt ggggcaatcg tctctaaaca aaatgacgaa       180
ggctatcttt gggaagaagg acctaatagc tttcagccca cacccgaact gctgcgccta       240
gcagtcaatg tgggacttga ggatcaattg gtgctagcca atggcaagtt accgcgcttt       300 gtattttaa agggcaaact aaacgctttg cctatgagtc cccccgccgc gatcgccaca       360
ccattattgg attggggtag caagattcgc ttggcactag gggcgatcgg ttttgcccgt       420
cccgccatgg ctggcgaaga gtcggtggat cagttcttta gcagactgtt gggcaagcaa       480
gcggtggcgc gtttggtagc accgtttatt tcaggagtat atgcaggtga tcccaagcga       540
ctaagtgcta gggctgcttt tgccaaaata tttcgcctcg aaaataatta tggcggctta       600
gtggcaggtg caattttatc aggtaaagat cgccaagctc aaaaggctaa aaatgccgat       660
ctgcctaagg tcaaggcagg tgaactaggg tcatttaaac aggggattaa gatgttgcca       720
gaggcgatcg ccactaagct gcgatcgcaa ggcacagcag ttaaacagca atggactttg       780
cgatcgctag atcggcaagg tgatcattac atcgccaagt ttgacacccc cacgggcgaa       840
gaaacggtca tgtcccgtgc tgtagtactg gctacccccg cctatgtgac agccaactta       900
ttaaaagact atttgccatc ggcaagccaa gccctccgca aaatctttta tccaaccgtt       960
gcctgtgtgg tgctggctta ccctaaaacc gaatttgcct atgatatgca gggctttggc      1020
aacctcatcc cgcgtacgga aggagtccgc accctcggta cgatctggtc atcgagttta      1080
tttgcaggac gcgccccca aggttggcaa ctactgctca acttcatcgg cggcacctta      1140
gatccagccc tagcacagct ttctgaggca gaaattatcc aagctgtgca tcaggatttg      1200
aaaaaaacta tccttcgtcc tgataccaaa gcagaaccca aggcgatcgc tgtgcatcga      1260
tgggacaagg cgattccgca gtatgaaatt gggcatttac aacttctcgc caccgtggaa      1320
```

```
gcggagttac aaaagtctca aggtttatac atcagcgcca attttattgg tggagttgcc    1380
ctcggtgact gcatcaagcg cagcttgcag gaagctatta aaattgagca attttttagcc   1440 aaataa                                                              1446
```

<210> SEQ ID NO 133
<211> LENGTH: 1467
<212> TYPE: DNA
<213> ORGANISM: Artificial Sequence
<220> FEATURE:
<223> OTHER INFORMATION: Synthetic_Gene encoding SEQ ID NO: 54

<400> SEQUENCE: 133

```
atgccctcac cccaatctgc tacgaaccaa tcagatgatc gcccatcagg tgggcaacct      60
atagatgtgc tggtagtggg cgcaggagtt tcaggtctga cgatcgccca tgatttggca     120
attaattacc agcgccaagt tttggtggcg gaggcgcaag atcgcgtggg cggagcgatt     180
atctcaagac aaaataatga aggttatctc tgggaagaag gtcccaatag ctttcagcct     240
gctcccgaac ttttgcgtct agcggtcaat gtcggacttg aggatcaatt agtgctagcc     300
aatggcaagt tgccgcgctt tgtatttttg aagggcaaat aaacgccat ccccatgagt      360 cccccgccg cgatcgccac accattgttg gattgggggta gcaaaattcg cttggcgctg     420
ggggcgatcg gctttgcccg tcccgcgatg gcgggtgagg agtcggtgga tcaatttttt     480
agcaggctat gggtaagca agccgtagcg catctagttg cgccatttat ctcaggcgta      540
tatgcaggtg atccgaagcg attgagtgct agggctgcct ttgccaaaat atttcgcctt     600
gaaaataact atggcggtct agtggcaggc gcaattttat caggtaagga tcgccaagct     660
cagaaagcca aaaatacgga tctgcctcag gttaaggcag gtgagctagg gtcatttaag     720
caaggaatca gatgttgcc agaggcgatc gctacgaagc tgcgatcgca aggcacgccc      780
gtcaaacaac aatggactct gcgatcgcta atcgacaag acgatattta cattgccaaa      840
tttgacacgc ccactggcga agaaatagtt atgtcccgcg ccatggtaat ggctacacct     900
gcctatgtga ctgccgactt attaaaagac tatttaccat cggcaagcca agccctcagc     960
aaaatctttt atccaaccgt tgcctgtgtg gtgctggctt accctaaaac tgaatttgcc    1020
tatgatatgc agggctttgg taatttgatc ccgcgtacgg aaggagtccg cacccttggt    1080
actatctggt catcaagttt atttgcagga cgcgctcccc aaggttggca actactactc    1140
aacttcatcg gtggcacatt agatccagct ctagccaagt tatccgactc agagatcatc    1200
caagctgtgc atcaggattt aaaaaaaact atccttcgtc ctgatactaa agcggaaccc    1260
aaggcgatcg cagtgcatcg atgggataag gcaattccgc agtatgaaat cggacattta    1320
caactcctcg ccactgtgga agctgaattg aaaaagtctc aaggtctata cattagcgcc    1380
aattttatcg gcggcgttgc tctcggtgac tgcatcaagc gcagcttgca agaagctatt    1440
aaaattgagc aatttttagc caagtaa                                       1467
```

<210> SEQ ID NO 134
<211> LENGTH: 1692
<212> TYPE: DNA
<213> ORGANISM: Artificial Sequence
<220> FEATURE:
<223> OTHER INFORMATION: Synthetic_Gene encoding SEQ ID NO: 55

<400> SEQUENCE: 134

```
atgatgttga cccagactcc tgggaccgcc acggcttcta gccggcggtc gcagatccgc      60
tcggctgcgc acgtctccgc caaggtcgcg cctcggccca cgccattctc ggtcgcgagc     120
```

-continued

```
cccgcgaccg ctgcgagccc cgcgaccgcg gcggcccgcc gcacactcca ccgcactgct      180
gcggcggcca ctggtgctcc cacggcgtcc ggagccggcg tcgccaagac gctcgacaat      240
gtgtatgacg tgatcgtggt cggtggaggt ctctcgggcc tggtgaccgg ccaggccctg      300
gcggctcagc acaaaattca gaacttcctt gttacggagg ctcgcgagcg cgtcggcggc      360
aacattacgt ccatgtcggg cgatggctac gtgtgggagg agggcccgaa cagcttccag      420
cccaacgata gcatgctgca gattgcggtg gactctggct gcgagaagga ccttgtgttc      480
ggtgacccca cggctccccg cttcgtgtgg tgggagggca agctgcgccc cgtgccctcg      540
ggcctggacg ccttcacctt cgacctcatg tccatccccg gcaagatccg cgccgggctg      600
ggcgccatcg gcctcatcaa cggagccatg ccctccttcg aggagagtgt ggagcagttc      660
atccgccgca acctgggcga tgaggtgttc ttccgcctga tcgagccctt ctgctccggc      720
gtgtacgcgg gcgacccctc caagctgtcc atgaaggcgg ccttcaacag gatctggatt      780
ctggagaaga acggcggcag cctggtggga ggtgccatca agctgttcca ggaacgccag      840
tccaacccgg ccccgccgcg ggacccgcgc ctgccgccca gcccaagggg ccagacggtg      900
ggctcgttcc gcaagggcct gaagatgctg ccggacgcca ttgagcgcaa catccccgac      960
aagatccgcg tgaactggaa gctggtgtct ctgggccgcg aggcggacgg gcggtacggg     1020
ctggtgtacg acacgcccga gggccgtgtc aaggtgtttg cccgcgccgt ggctctgacc     1080
gcgcccagct acgtggtggc ggacctggtc aaggagcagg cgcccgccgc cgccgaggcc     1140
ctgggctcct cgactacccc gccggtgggc gccgtgacgc tgtcgtaccc gctgagcgcc     1200
gtgcgggagg agcgcaaggc ctcggacggg tccgtgccgg gcttcggtca gctgcacccg     1260
cgcacgcagg gcatcaccac tctgggcacc atctacagct ccagcctgtt ccccggccgc     1320
gcgcccgagg gccacatgct gctgctcaac tacatcggcg gcaccaccaa ccgcggcatc     1380
gtcaaccaga ccaccgagca gctggtggag caggtggaca aggacctgcg caacatggtc     1440
atcaagcccg acgcgcccaa gccccgtgtg gtgggcgtgc gcgtgtggcc gcgcgccatc     1500
ccgcagttca acctgggcca cctggagcag ctggacaagg cgcgcaaggc gctggacgcg     1560
gcggggctgc agggcgtgca cctgggggggc aactacgtca gcggtgtggc cctgggcaag     1620
gtggtggagc acggctacga gtccgcagcc aacctggcca agagcgtgtc caaggccgca     1680
gtcaaggcct aa                                                         1692
```

```
<210> SEQ ID NO 135
<211> LENGTH: 1698
<212> TYPE: DNA
<213> ORGANISM: Artificial Sequence
<220> FEATURE:
<223> OTHER INFORMATION: Synthetic_Gene encoding SEQ ID NO: 56

<400> SEQUENCE: 135
```

```
atgctgacta gccatgccac taacatctac gcgaactcaa aggccaggct tcagatccgc       60
gagatcgctc ggccgacggt gaccggtgtc tcgaggtcag gcgttcttca ggatgtcgcc      120
tctccgctcc cacggcagat tccgaggcca gctcaacgtg ctgcgcgtcc tacttctgct      180
acggccactt caagtggggt acccacggcg gacagtgccc gtggcacgaa gatcgttgac      240
aatgtgtatg acgtgattgt ggttggcggt ggcctctccg ggctcgttac gggtcaagcc      300
ctctcggcgc aacatggtgt taataacttc ctcgttaccg aggctcgcga gcgcgtcggc      360
ggcaacatta cgtccatgtc gggcgatggc tacgtgtggg aggaaggccc aaacagcttc      420
```

```
cagccaaatg atagtatgtt acaagtagct gtggatgccg gggtggagaa ggacctggtg      480
ttgggagacc ccaaggcacc ccgatttgtg tactggcaga acaagctccg tcccgtcccc      540
agcggccctg atgcgctcac ctttgacctc atgtcccttc cggggaagat ccgagctggt      600
ctcggagcca ttggcctgat caacggagcc atgcctaact ttgaggagag cgtggagcag      660
ttcatccgtc ggaacctggg tgacgaggtg ttcgagcgcc tcattgagcc gttctgctcg      720
ggggtgtacg cgggagatcc atccaagcta tccatgaagg cagcgtttaa caggatctgg      780
attttggaga aggacggcag cagtctggtg ggggtgcgt tgaagctgtt tcaggagcgc       840
cgcaagaacc cgccgccacc tcgcgatccc cgcctgccgc ctaaacccaa gggccaaacg      900
gtgggttctt tccgtctcgg tctcaagatg ttgcccgagg cgattgagcg gcgtatcaag      960
gaccaagtca gggtcaactg gaagctggtg tcgttgacgc gcgacggcga tcgctacagc     1020
ctggtgtacg acacgccgga gggccgagtg caatgctaca gccgtgcggt ggcgctgacg     1080
gcaccgtcgt atgttgtggc ggatcttatc aaggctgagg tgccagccgc tgcggaggct     1140
ctgtcctcgt tcgactaccc cccggtgggg gccgtcactc tgagctaccc cctgtcagcc     1200
atacgggatg atcggaagga cgcgcagggc aacgtgccgg gtttcggaca gctccacccc     1260
cgctcgcagg gcgtgacgac tctgggcacc atctacagct cctccctgtt cccgggtcgg     1320
gctccccggg ggcacatgct gctgctcaac tacatcggag gggccacgaa ccgagggata     1380
gtcaaccaga cgcaagagca gcttgtggcg caggtggaca aggacttgcg gttgatggtg     1440
ctcaagcccg acgcgccggc tccacgtgtg gtgggcgtgc gggtttggcc ccgtgccatt     1500
ccccagttca acatcgggca cttggagctg ctggataagg cccgggggggc gctggaggcc     1560 aagggctgga atggcgtctt ccttggcggg aactacgtct cggggggttgc cttgggcaag     1620 gtggtggagt acgggtacga gagcgcggcc aaacttgcaa agcacctcac agccgctcag     1680
aagcaggtgg cggtgtaa                                                 1698
```

<210> SEQ ID NO 136
<211> LENGTH: 1482
<212> TYPE: DNA
<213> ORGANISM: Artificial Sequence
<220> FEATURE:
<223> OTHER INFORMATION: Synthetic_Gene encoding SEQ ID NO: 57

<400> SEQUENCE: 136

```
atggccgtcg cggagggcgc cacacccgcg ccggccgcgg cgtccgccac cccgtcggaa       60
gtcgacgcgc tagtaatcgg ctcgggcatc tccggctcgt cgctggcctt tacgctgtcg      120
caggcctcgc ccgccacgtc gctgctgctc acggaggcgc gccccgtcgt gggcggcaac      180
gtcatctcgc gcaacgagcg cggctacacg tgggaggagg gccccaacac cttccagccg      240
gccccgcaca tcatccgcat ggccgtcgac ctcggcctca gggacgacat cgtcctggct      300
gaccacaccc tgccccgctt cgtgtactgg gatcagcgcc tgttcgccct gccgctctcg      360
ccgaacgaca tccccacctt ccgcctgctc tcgctgcccg cgccatccg cgccggcctg       420 ggcgccgcgg gctttgtcat gcccccgccc aaggggaggg aggagagcat caaggacttt      480
atcacccgcc acttgggcgc cgaggtcttc cagaagatga tcgacccgtt cgtgtccggc      540
gtgtacgcgg gcgacccgag caagctcagc atgtcggccg ccttcaagaa gatctacgcc      600
ctgcaggagc taggcatgac gcagggcatt gtgagggcg ccatcattcg catccagcag       660
aagaagaagg aggccccgcc gccggacccc gagctgccca cgtggaaggg cggcgcgctg      720
ggctcgttcc gcaaggggct gggcatgctg ccgcaggccg tggcggagcg gctgggcgac      780
```

-continued

```
cgcgtcaagt tgtcgtggaa gctggtgtcg ctgggcaagg agagcgacgg gcggtatcgg       840
gcgacgtacg agacgcccga ggggacgaag acggtgattg cgcggagcgt ggcgatcacg       900
gcgccggcga acgcgacggc tgggatcctg ggggaccttg cgccgggcat caaggcgatc       960
gaggagatca actacccgac ggtgtggtcg atcacgctgg cgtacccgaa gaacgagttc      1020
cgcgagccgc tgagcgggtt tggaaacctg atcccgcgca gcatggggat ccggacgctc      1080
gggacgatct ggtcgagctg cctgttcccg gggcgcgcgc cggagggcat ggagctgctg      1140
ctgtcgtaca tcggcggcgc gcaggacgcc gcgattaagg agctgacgga ggacgaggtg      1200
gtggccacgg tggacgcgga tatcaagaag attttgatga aggacgggag cgaggttaag      1260
cccgtggtgg tcggggcgcg gaagtgggat cgcgcgattc cgcagtataa tatcgggtac      1320
tgggatatca tgggcaaggc tgaggaggcg gtcaaggagc accccggcat cttcttgggc      1380
ggcaactata cgagcggcgt cgcgttcggg gattgcgtgc aatggggcat tgatacggca      1440
cccaaggttg cagagtatgt cgccgcgcag gcggcggtct aa                        1482
```

<210> SEQ ID NO 137
<211> LENGTH: 1713
<212> TYPE: DNA
<213> ORGANISM: Artificial Sequence
<220> FEATURE:
<223> OTHER INFORMATION: Synthetic_Gene encoding SEQ ID NO: 58

<400> SEQUENCE: 137

```
atgagcagtg gattcttgtg tttttgtcca aacgcggtta tcaaagcagc tcagtatgtg        60
agacctaaaa acacttttc gtgtaagcac tatacctgca aaaatagaaa tagttggttt       120
tacggcaatg agttgtatat aaagagacgt aaagtggtcg aacagcagag aacaactagc       180
cacgtttcta agttgccttt tcgtcaaaca tggaaagctg tttcagctca gcacacggaa       240
gatggcgaat gtagtgtatt gattattggt tctggcgtca caggaagtac tgctgctttt       300
caattggccg aaagtggcat tgatgtctta gtagctgaga aaaatgaaca agtcggagga       360
aatatcattt ctagaaagga gcaaggtttc atttgggaag aaggtccaaa tacattccaa       420
cctactccag atattcttgt tatgatcgaa aagttaggtt tggtagacaa actggtctta       480
gctgatgcaa agctgccacg atatgtgttc taccaggata aacttcataa gattccttca       540
agtccttttg aagcctgcca attttctctg ttgtcgacaa gaggaaaatt gcgtgccttt       600
ctaggagcta ttggctttgc tccaatgaat ctcaaaaaga aagaggaaac cgtaagagat       660
tttgtaacga gacatttggg ggaagaggta tatgaacggc ttgtggatcc ttttattagt       720
ggagtatatg ctggtgatcc ttccaagctg agtatgaaag cagcattcaa acgagttcaa       780
gccttggaag aaaaaggtgt tacccaaagc cttattgaag gtgctattat tcgaatgttt       840
gaaacaaaga acagtaaagg aaagaaagaa acaaaaggtt ctctcaaggt tccaagaggc       900
tctcttggtt cattcaaaga tggcttacaa atgtacccc aatcagtaca gtcgaagctt       960
tcgaacaaag tgaagactgg atggaagttg ataagactgg agaagagcgg aaatggaagc      1020
agtcatcagt catgtgagga ttactttgca gtgtttcaaa tacccaatgg aatcaccaaa      1080
gtaatacgta cgaaggcatt gatatttact agtcctgctt atatcactgc atctcttttg      1140
agacctttca ttcccaatgc atcagatctg ttggagcaaa tctattatcc ttgtgtagta      1200
tcagtatcct tagcgtatcc ctcttcatct tttcgatttc ctttatctgg ttttggtcat      1260
ttgattccaa gaagtacaaa aattcgtact ttgggtacca tttggtcgag tagtctattt      1320
```

-continued

```
ccatatcgag tacctgaagg ttatcatctt ttatcctctt acattggagg tgctcaggat      1380
acggatattg cttcgctatc tgaagaccaa gttgtgaaac aagttgattc tgatataagg      1440
aaaatacttt taaggcaaga tgcagctctt ccaaaggttt tgggagtacg tcattggaac      1500
aaggccattc cgcaatatga actaggtcat ctctctcgaa tggaaactat tcaaagtcaa      1560
gtcagtgaaa ctcttccagg tgtgtttttg ggtggtaatt atgtcagcgg aatttctttt      1620
ggagattgtg tgtcatttgg tatgcaactt gctgatcaag catcttacta tatcaaagaa      1680
aatacagaat tgctttcttc gacagtcgtt tga                                   1713

<210> SEQ ID NO 138
<211> LENGTH: 1449
<212> TYPE: DNA
<213> ORGANISM: Artificial Sequence
<220> FEATURE:
<223> OTHER INFORMATION: Synthetic_Gene encoding SEQ ID NO: 59

<400> SEQUENCE: 138
atgacttctg ctcaacccac cgaagttaat caacccttag atgttcttgt cgttggtgca        60
ggaatttctg gcttagcgat cgcccatgaa ctagcgatcg ccaaaaatta ccgtgtttta       120
gtagcagaag ctcaggatcg cgtgggtggt gcaattacca gtaatcgcaa tgatgaaggc       180
tatctctggg aagagggccc taatagcttt caaccagcac cagagttatt acgtctcgcc       240
gtacaggtcg gtctcaagga tgaattggta cttgccgatg ggaaattacc gcgatttgta       300
tttctcaatg gcaagttaaa tgctttgccg atgagtccac ctacagcgat cgcctccaaa       360
atcttgactt ggggtggcaa aattcgtcta gcgctaggtg cattaggttt tgcacgtcct       420
gcgatgagtg gtgaagaatc cgttgatcaa ttcttttcgc gcctactagg taagcaagcc       480
gtggagcgct tagttgcgcc ttttatctct ggagtctatg caggcgatcc taaacgcctc       540
agtgctagag ccgcattttc taaaattttc cgtctagaaa atggctatgg tggattgctt       600
gcaggggcgc tcctgacagc caaagaacgc aaagcccaaa agctgaatga tcccaatatt       660
cccaaggtga gtctggcga actgggatct ttccgccaag gtattaaaat gctgcccgaa        720
gcgatcgcta ccaaactcag agatcaaggt acggctgtca aacaacaatg gactttgcga       780
tcgctagaaa agcaaggcga catctatatt tctcagtttg atacgcctac gggtgcagaa       840
actattacat cgcgatcggt agttctgacc acacctgcct atgtgagcgc taagttattg       900
caagactatt acccgccgc tagccaagcc ctgagcgaga ttttctatcc gacagttgcc        960
tgtgtcgtac ttgcctatcc caaaagcgaa tttgcctatg acatgaaggg attcggcaat      1020
ctcattcctc gcactcaagg cgtaagaacc ctcggtacaa tttggtcatc gagtttgttt      1080
gcaggacgcg cccctgatgg ttggcaacta ttacttaact ttatcggtgg cacactcgat      1140
cctgctttgg caaaactttc agaagccgag attgttcaag cggtacacca agatctcaag      1200
aaaacaattt tgcgccctga tacgaaagcc gaacctaaag cgatcgcagt ccatgtgtgg      1260
gacaaggcaa ttcctcagta cgagatcgga catttagagc gtctggcgac gatagaagcc      1320
gaattacaaa aatcacaggg tctgtatgtc agcgcgaatt ttattggtgg tgtttcgctt      1380
ggtgattgca ttaagcgggg tctacaagaa gctagtaaaa ttgatgtctt tttaagtagc      1440
caaggataa                                                            1449

<210> SEQ ID NO 139
<211> LENGTH: 1452
<212> TYPE: DNA
<213> ORGANISM: Artificial Sequence
```

<220> FEATURE:
<223> OTHER INFORMATION: Synthetic_Gene encoding SEQ ID NO: 60

<400> SEQUENCE: 139

```
atgacaaacc tagttgatag ccttatagtt ggtgctggta ttagcgggct aagtttagcc        60
catagcctga accgtgaaaa aaaccccgc tcacccctaa aagttttggt cacagaaagc        120
cagaaccgag tcgggggaaa tattacgacc ggacgcgcat ctgattttt atgggaagaa        180 ggccctaaca gttttgcccc caccctgaa ttactcggac tagccgtaga tttggggctt        240
aaacaagaat tgattttgc cgatcgcaaa ctaccccgtt atgtctactg gaaccataag        300
ttacatccag tacccatgac ccccccgcc ctactctcct cccaactaat cagccccaga        360
ggtaaactcc gcgccgcctt gggagccata ggatttgtgc caccccagt aggcgctcac        420 ctctctcaac agcgaggaga agaaactatt acccagtttt tccatcgaca tctcggttca        480
gaagtcctag aacgtctcgt ccagcccttc gtttctgggg tttatgctgg cgaccctcaa        540
caattagcag tccgttccgc ttttagtcga ttagtagccg ccgaagacgc aggggggtgcg        600 ctactacctg gatttgtgcg atcgcgcctt aataaaaaaa ccaccaaaga caccacccccc        660 gaccccaata ttcccaaaac tcgccccggt gaattagggt cctttcgtta tggcctggaa        720
actctgcccg aaaccttggc cagtaaatta ggcgatcgag ttaagttaaa ttggaccctc        780 gaccgtttt atcccacccc tcatcaaacc tatattgctg aattttccac cccagacggc        840
ccccagcaag tagaaacccg aaccctcgct ttaatgaccc ccgcccatgt tagcgctcgc        900
ctcttgcaac ccctacactc tcaaatcgct tccgcattaa gccaaattcc ttatcccccc        960
gtcgcttgtg tcgtactcgc ctatcctaaa tcagccttaa aacaacaact caaaggcttt       1020
ggtaatttaa ttccccgcca tcaaggaatc cgtaccctcg gcactatttg gacctccagt       1080
ttattccccg gtcgcgcccc agaatcttgg caagtcctca gcaattatat tgggggtgct       1140
acagaccctg aaattggcga aatggatgat gatcaaattg tcgccgccgt tcatcaagac       1200
ctacgccaaa ttctgctggc tgaagatgtc ccccccaaag tcttggctgt ccatctctgg       1260
cggcgcgcta tcccacaata tactctcggt catcaagatc gcctaaattc catcaatgct       1320
ggattgcgat cgcttcccgg actttatctg tgtagcaact atattgatgg ggtttccgtc       1380
ggtgactgtg tgaggcgcgg ccagcaatgg gcatcgcaaa ttcagtccca ccttcatcca       1440
acagccaact aa                                                            1452
```

<210> SEQ ID NO 140
<211> LENGTH: 1410
<212> TYPE: DNA
<213> ORGANISM: Artificial Sequence
<220> FEATURE:
<223> OTHER INFORMATION: Synthetic_Gene encoding SEQ ID NO: 61

<400> SEQUENCE: 140

```
atgggcagga tgagcgtagc cgcagagccg ctggatgtac tggtagtcgg tgccggcctg        60
agtggtctgg ccctggcctg gcacctccag cgctctggcc ggagggtcct ggtgtgcgag       120
gcgactgagc gggtgggcgg tgcgatcagc tccgaactca tcgatggctt cacctgcgag       180
ggcggtccga acagtttca atcgacccgg ccctgcagg agttgctggt cgaactgcag        240
ctggaggagc ggctggtctt tgccgaggag cggctcgccc gctttgtctg gtgggaaaac        300
cgcctgcggc ccgtgccgat gagccctgcg cagttcgtgc gcgcagatct gctcagctgg        360
ccgggcaaac tgcgctgtct atcggaattt tttgtgccgc ctctttcgga gccgcgcgag        420
```

```
gagacggtag ccgaattcgt gctgcgccgc ttcggcgacg aagcgctcaa tcgcctcatc      480
gaaccgttca tcgccggggt gttcgcaggc gacgccgggc agttgagcgc cgatgcggcc      540
ctcgccccgc tcgtcgaact ggaacgccag gcgggcagcg tgctcagggg gctgtggcag      600
cgccgcaatc gggggggtgct cacaccccag cggctgtgta cgctgcgcgg cggcatcgag      660
cagttgccac gggcaattgc ccggcggttg caatcgcagt tgcgcttcca atcgcgctta      720
gaggcgctgg aaccgctggc aggggggctgg caggcgattg tcctcgatgg gcgggggtgag      780 gcccaggcga tcagtgcccg ctcggtggcg cttgccgccc ccgcttgggc gatcgctccg      840
gtgctggcgc ggctcgatcc gagcctgggc cgcgccctgg agagcatcta ctatccaccg      900
gtggcggcgg tcagcctcgg ctactcaaaa agccagcttc ccaacctgag cgaaggcttc      960
ggccatctca tcccgcgcgg acaatcgctg cgcagcctcg gggtgatcta caacagttgc    1020
ctcttccggc acgccgcccc gacgagctgg cggctttta cctgtttttt aggggggtacg    1080 accgacccgc tcatcgccga tctgagcgac ggtgaactgg ccaatctggc gcaccgcgaa    1140
ctgcaggcgg tcctcgactt tcaatcgagc tatcagctgt tgcgggtggc gcgctggccc    1200
agagcgattc cccagtatgc cctgggccat atcaccaaac aggagcgcat cgagcgctac    1260
ttggcggagc tgccgggatt gtttctggtc ggcaattatt ttggcggcat ctctgtgggc    1320
gactgcgtgc gccaggcccg tctcaaggca gatagcgtgc tgcagtttct cacaagaacc    1380
gctgccaatg gccgcctcaa cctggcctga                                     1410
```

```
<210> SEQ ID NO 141
<211> LENGTH: 1401
<212> TYPE: DNA
<213> ORGANISM: Artificial Sequence
<220> FEATURE:
<223> OTHER INFORMATION: Synthetic_Gene encoding SEQ ID NO: 62

<400> SEQUENCE: 141
```

```
atgaacacgg ccgaggaatt gctggatgta ctggtggtgg gcgctggcct gagcgggctg       60
gcgctcgcct ggaaactcaa gcgggccggc tgcacgttct tggtctgtca ggcgggcgag      120
cgggtgggcg gagcgatcac caccgcgatc gccgacggtt ttgtatgcga ggggggtccg      180
aacagttttc aagaatcccc accctcatc gagctgttga cccagttgca actcgaagat      240
caaatcgtca ccgccgatcc gcgcctggcg cgctttgttt ggtgggagaa ccgcctgcgc      300
tcggtgccgc tcaccccggc gcagctggtg cgctccgact tactcagttg gtccggtaaa      360
gcccggctgc tgtgggagtt gttcgtcccg gccctaggcg agccccgcga ggagacggtg      420
gccgaatttg tcctgcgccg cttcggcgaa gaagtcctct cgcggctggt cgatccgctg      480
gtttcgggga tgtgcgcggg cgatgtcggc cagttgagca tcgaagccac cttcgagcgg      540
ctggtcgatc tggagcgccg ccacggcggg gtgctgcggg gtttgtggcg gactgcccgc      600
acccgcccac ccttcaagcg cctctgcacg ttgcgcggcg gcctggagca gttgcccag      660 gcactcgccc agcgcctgca gccgcaaatc ctgctttccc accgcctcga ggcgcttgaa      720
cacctggccg gggatcgctg gcgggcggtg gtggccggtc cgcagggcga gccggtggca      780
attgcggcgc gcacggtgat tctgtcgggt tccgcccacg ccatggcttc ggtcttgcgt      840
cccctggacg ccggtctcgg acgcgccctt gaaagcattt actacccacc ggtcgtgagc      900
atcagtctcg cctactccaa aagccaggtg cccaacgcgc cggagggctt cgggcatttg      960
attccccgca accagaccct gcgcagtctc ggggtgatct ggaacagcag cctctttccc    1020
cataccgccc cacccaactg gcggctctat acctgttttg tgggcggcac caccgatccg    1080
```

```
gccacccca acctcagcga caccgaactg gccagcctcg cccaccgcga actgcagacg      1140
gtcctcggtt tccaggcggg ctatcaactg ctgcgcgtga cgcgctggcc ccaggccatc      1200
ccccagtacg ccctcggcca tcccagcaag caggagcggg tcgaacgggc gctgttggga      1260
ctgccggggt tgttcctggt cggcaattac ttcggcggca tctccctggg agattgcgtg      1320
cgccattccg gtgcggtcgc ctcccgcgta ctgcagtttt taaccacggt ggccagcaac      1380
ggcagcctgc gcccggcctg a                                                 1401
```

```
<210> SEQ ID NO 142
<211> LENGTH: 1617
<212> TYPE: DNA
<213> ORGANISM: Artificial Sequence
<220> FEATURE:
<223> OTHER INFORMATION: Synthetic_Gene encoding SEQ ID NO: 63

<400> SEQUENCE: 142
atggtcgccg ccgccgccgc cgccatggcc accgccgcgt ccgctggcgt gcctccactc        60
agcgggcccc gcggcccccgc gcggctccgc agccgcggcg tcatcgtacg ctgcgccgcg       120
gtggcgggcg cgccgccga ggcgccgacc tccacgggcg cgcgggtgtc cgcggactgc        180
gtcgtggtgg cggcggcat cagcggcctc tgcaccgcgc aggcgctggc cacgaagcac        240
ggcgtcggcg acgtgctcgt cacggaggcc cgcgcccgcc ccggcggcaa catcaccacc        300
gtcgagcgcc ccgaggaagg gtacctctgg gaggaggggc ccaacagctt ccagccctcc        360
gaccccgtcc tcaccatggc cgtggacagc gggctgaagg acgacttggt gtttggggac        420
ccgaacgcgc cgcggttcgt gctgtgggag gggaagctga ggcccgtgcc atccaagccc        480
gccgacctcc cgttcttcga tctcatgagc atccctggca agctcagggc tggctttggg        540
gccctcggta tcagaccgcc gcctccaggc cgtgaggagt ccgtggaaga gttcgtgcgc        600
cgcaacctcg gggctgaagt cttttgagcgc ctcattgagc ctttctgctc aggtgtctat       660
gctggtgatc cttcgaagct cagtatgaaa gctgcatttg ggaaggtgtg gcgcctggaa        720
gaggctggag gtagtatcat ggtggaacc atcaagacga ttcaggagag gggcaagaat         780
cctaaaccac ctagggatcc ccgccttccg aagccaaagg ggcagacagt tgcatctttc        840
aggaagggtc tcgccatgct tccaaatgcc attacatcca gcttgggtag taaagtcaag        900
ctttcctgga aactcacgag cattacaaag tcagacggca aggatatgt attggtgtat         960 gaaacacctg aagggggttgt ttcagtgcag gctaaaagtg ttatcatgac gattccatca      1020
tatgttgcta gtgacatctt gcgtccactt tcaagtgatg ctgcagatgc cctttcaaga      1080
ttctattatc caccagttgc tgctgtaact atttcatatc caaaggaagc tattaggaaa      1140
gaatgcttaa ttgatgggga gcttcaagga ttcgggcagt tgcatccacg tagtcaagga      1200
gttgagacat taggaacaat atacagctca tcactcttcc caaatcgtgc tcctgctgga      1260
agggtgttac tcctaaacta cataggaggc gctacaaaca caggaattgt ttacaagagt      1320
gaaagtgagc tggtagaagc agttgatcgt gacctcagga aaatgctaat taaccctaga      1380
gcagtggatc ctttagtcct cggtgtccga gtgtggccac aagccatacc tcagttcctg      1440
gtaggacatc ttgatcttct ggaggctgca aaatctgccc tgggccgagg tggctacgat      1500
gggctgttcc ttggagggaa ctatgtagca ggagttgccc tgggccgatg cgtggagggt      1560
gcctatgaga gcgcctcgca aatatctgac ttcctgacca agtatgccta caagtga       1617
```

```
<210> SEQ ID NO 143
```

-continued

```
<211> LENGTH: 1692
<212> TYPE: DNA
<213> ORGANISM: Artificial Sequence
<220> FEATURE:
<223> OTHER INFORMATION: Synthetic_Gene encoding SEQ ID NO: 64

<400> SEQUENCE: 143
atggcagcct ttgtcccggc cgccgcggcc gccccctgga ccgcccgccg cagcgccttt      60
gccggcgccc ccgcggccgc cggcagccgc cgccccgcca tggccggcgc ggcggcgccg     120
ctgcggtcgc tcgtccctcg ggccatcccc ccgccggggg cggcccggcg cgcggcgccg     180
tcgcctcgca tggccgccgg cggcgcgccc gacgaggtcg tcgacgcgct tgtcgtcggc     240
tcgggcgtgt ctggctccac cctcgcctac cgcctgcact ctcgcggcgt ttcaatgctc     300
ctcaccgaag cgcgcgacgt ggtcggcggc aacgtcatct cccgctcggc caatgggtat     360
acgtgggagg agggccccaa caccttccag cccgcgcccc acatcctgcg cctggccgtc     420
gacgtgggcc tcaaggacga cctggttttt gccgaccaca cgctgccccg ctttgtctac     480
tggaatggca acctgtttgc gctgccgatg gggccggcgg acatccccaa gttccgcctc     540
ctctccccgc tcggcgccgt gcgcgcgggc ctcggcgcgg cgggctttgt gtggcccaac     600
tggtccggca aggaggagtc ggtcaaggaa ttcattacgc ggcacctcgg cgcggaagtg     660
tttgccaaga tgatcgaccc gtttgtgtcg ggcgtctacg cggggggaccc gtcgtcgctg     720 gccatccgcg gcgcgtttgg caagatctac gccctccaaa acttgggcat cacgcagggc     780
attgtggagg gcgccatcat ccgcttgcgg cagcgcaagg cagaggcggg ggagccagac     840
ccagagctgc ccgtcgtcaa gggcggcgcg ctcggctcct ttcgagaggg cctcgggatg     900
ctgcccaagg cggtggccgc caagctcggt gacgcggtgc ggctcggctg gacgctcacg     960
gagctgcgca agctcccggg ctcggcgccg ggctatgagg ccgtctactc aacgcccgac    1020
ggcccacgga cggtgcacgc caagaccgtg tcgctgacgg cgcccgccgg cgcggcgtcg    1080
tccatcctcg gcgggatgct ccccgctgcc aaggccctcg acgacgtcta ctacccgtgc    1140
gtttggtcag tcacgctctc ctacccgacg gccgcgttta gcggccgcgct caagggcttt    1200 ggcaacctca tcccgcgctc catgggcgtc cgcacgctcg gcaccatctg gtcctcgtcg    1260
ctcttccccg gccgcgcgcc gcccgggcgg gagctcctcc tctcctacat tgggggcgcg    1320
caggacaagg ggattgccga cttgtcagag gaggaggtgg tggctgccgt ggacggggac    1380
atcaaggcgc tgctgctgtc ggaggggggcg gccgacgaag tgccggtcgt cgtgggcgtc    1440
cgcaagtggc cccgcgccat cccccagtac gtgcggggggc acctcgagtt ggtggcgggc    1500
gtgcgggagg cggccgccgc cgagtgcccg gggctgtttt tgggcggcaa ctacgcgtcg    1560
ggggtggcgt ttgggggattg cgtcgcgtgg ggcgacaagg ccgcggcaga ggtggttgcg    1620
acgctcgggg acatgcccga gacggggggcg cccatggcca tgccagagac ggcgacgccg    1680
gcgagcgtgt ga                                                          1692

<210> SEQ ID NO 144
<211> LENGTH: 1602
<212> TYPE: DNA
<213> ORGANISM: Artificial Sequence
<220> FEATURE:
<223> OTHER INFORMATION: Synthetic_Gene encoding SEQ ID NO: 65

<400> SEQUENCE: 144
atgtcgcgcg cgcaggtctc gctcgcgccc gcgcgcgtcg ccgatcggcg ccgcgtcggg      60
cgcactcgcg ccgcccgacg cgccgtcgcc gtccgcgcgt cgacggtgga acgcgacgtc     120
```

```
gtcatcgtcg gcgcgggcgt cagtggtttg tccaccgcgt tcacgctggc gaagaagacg      180
atgccgaacg cgagcgtgat ggtgaccgaa gccagagatc gcgtcggtgg gaacattacg      240
agtaagagcg atggcacgta cacgtgggag gaggggccga actcgtacca acctggggat      300
gcgatcctca cgctggcgtg cgacgccggc atgcgggacg acatcttatt ggccgatccc      360
gcgagcaatc gatacgtgct gtgggatggg aaattgagaa ttttgccgca cagcatcgag      420
agtgcggttt tggggattt cttgacgtgg ccggggaaga ttcgagccgg tttggggggcg      480 atcggaatca ggccgccggc gccgggtaag gaggagagtg tgaaggaatt cgtgagcaga      540
aatctcggca cggaggcgtt cgagcgattg atcgaaccat tttgctcggg ggtgtacgct      600
ggggatcccg cgagcttgag ctcggtcgcg gcgacggggc gagtgcagcg acttgaaccg      660 ctggggggggt cgctcgtggt gggcgcgctc aaggcgcagg cggaggcggc gaaggcgaag      720
aaggagagcg ggttcaagcg cgatcctcga cttccggaag tgaagggtca aaccgtaggt      780
tcgttccgag gtggtttgaa gacatttcca gagggattag cgaaacaact cggcgacgac      840
gtcgtcaagt gcaactggaa gctcgtcaat gtcaacaagg ctgccgaggg cgggtacacg      900
tgcgagtacg ataccccgga ggggcgacga acggttatcg ccaagtgctt gttgctcacc      960
gctccggcgt acgtcaccgc tgagatcgtc aaggacatgg ctccggcggc ttcgacggcg     1020
ctcaacaagt tttactaccc tccggtggcg tccgtgacgg tttcgtacaa gaaggactcg     1080
ttccgtcttg acggcacttc agcgcttcct gagggtggtc tcactggttt cggtcagctc     1140
cacccgcgct cgcagggcat ccgcacgctc ggcacgattt actcgtcctc gcttttcaag     1200
gacgacaagc gccagccgga tgacgagttc atgatcttga actacatcgg tggcgcccga     1260
gacgtcgcga tcaaggactt gagcgaagat gagctcgttc agcaagtgca cgaggacgcg     1320
ctcaagacga tcctcaagcc cggaacgccc cttcccaagg ttgtcggcgt caagctgtgg     1380
gagaaggcca tcccgcagtt caacctcggc catctcgacg tcttggccga ggccgagaac     1440
gcgctcgagg cggcggcgtg cggcgaaaag gatggtctct ttctgggcgg taactacact     1500
gccggcgtcg ctctcggtag atgcgtcgaa tttggcgttg agcaagccga cgaggtcgcc     1560
acgttcctca agtcggcgaa gaagctaact gccgcggttt aa                        1602
```

<210> SEQ ID NO 145
<211> LENGTH: 1656
<212> TYPE: DNA
<213> ORGANISM: Artificial Sequence
<220> FEATURE:
<223> OTHER INFORMATION: Synthetic_Gene encoding SEQ ID NO: 66

<400> SEQUENCE: 145

```
atgctcgccg ccgttggcac cgccgctggc ctcctagccg tagcggggat cacccccgct       60
tatggtttcg taacgccctc caccgcttgg aacaccgctc gcgggagcgg ccatggaacg      120
gcgtcgagag cagccactac catggcagct gatattttca aggccggccc tgtcgaaaag      180
gtggactgtg cggtggtcgg ctctggcatc agcgggagca cgctggggtt ctacctggac      240
aagaagggcg tggactgcgt ggtgctagag gcccgggatc aagtgggcgg caacgttata      300
tccaagaaag aagacggatt cctgtgggaa gagggcccca actcgttcca gccgacaccc      360
tacatcatgc ggaccacggt cgacctgggc ctcaaggagg acctcgttct ggcggacccc      420
accctgcccc gcttcgtgtt ctgggaggga ggcctgttcc cccttccctc ttccctgcag      480
tcgatcatta cggacttttg gttgctttca tggcccggaa agatcagggc cgggctgggt      540
```

-continued

```
gccatcgggc tggtgctgcc cccccttcg gactacgagg agagcgtaaa agagttcgtt      600
actaggcacc tggggccaga ggcgttcgaa aggctcatcg accccttcgt gagcggggtt      660
tacgcgggtg acccgtccaa gctggccatc aaggccgccc ttaagaaggt cgctcggttg      720
gaagtgttgg gcggtccggg cttgatcgac ggtgctattc tcaggcttaa ggagcgtgca      780
cggcaggaga aggagctccc ggagccgctg caatcggagg accttccac gtaccaggga      840 ggcagcctgg gctctttccg cgaggggctg cagatgctcc ccaacgctgc tcttaaggcc      900
atggggaaag acaagatgcg gacgtcgtgg gtgatgaagg gcatcaagcg gtcagaggac      960
ggcggctacc tcctcgcctt cgacaccccc aagggggcca aacgcctcca ggctaaggtt     1020
gccgtttgca ccgcgccggc ccacaggctg gcctccgtcg agggactgcg ggatattgtg     1080
ccggaagcgg cgcgattgga cgaggtgtac taccccccg tggcgagcgt aaccctggcg     1140
taccccaagt cgtccttcaa ggtcgacctc accgggttcg gcaacctcat cccgaggaag     1200
atgaagatca ggaccttggg cacgatctgg tcatcgtcgc tattcccagg gagagccca     1260 gagggctacg ccatgctgct caactacatc gggggtgccc aagaccccgc gatcaaggac     1320
ctttcggacg atgagatcgt ggcggagtgc gacagggaca tccgcacaat ccttctcaag     1380
gacgatgcgc ctccccgaa ggttctcggc tgccgcttgt ggaaaaccgc catcccgcag     1440
taccagaggg gccacctggc catcctggag gagctgcaag agggactcaa ggccgccccg     1500
gggcttcgta tggggggaaa ctacatcacc ggagtggcct ttggagactg cgtgcagtat     1560
gggtacgaag aggcggagcg gatcgaggag atgctcaaga gcggtgcctt ggacgggcag     1620
cagagcgtgt ccgacaaaga agcagttgca gcgtag                                1656
```

```
<210> SEQ ID NO 146
<211> LENGTH: 1422
<212> TYPE: DNA
<213> ORGANISM: Artificial Sequence
<220> FEATURE:
<223> OTHER INFORMATION: Synthetic_Gene encoding SEQ ID NO: 67

<400> SEQUENCE: 146
```

```
atggaggaaa ccgacgttct ggtggtgggc tctgggatca gtggctcgac caccgcgttt       60
tatctgaaca aagctggagt caagtgtctg ctgacagagg ccaaaccgt ggtgggaggg      120 aacgtgatca gtaaatcgga gtccggcttc ttgtgggagg agggcccgaa ttccttccaa      180
cccacttatc cgctcatgca agcgactgta gacatgggcc tggccgatga actggtcctg      240
gcagacgcga gcttgccccg cttcgtgtat tggaaggaga aactctacgc cctgcctggg      300
ggcttgggtg acatccccct tcttcaatctc ctatccatac ccggacgtat cagggcgggt     360 ctggggctc tgggcttcat tcgaggcccg ccgaaggata aggaggagag cgtcaaggaa      420
ttcgtgaccc ggcatttggg ggcagagacc ttcgagcgga tcatcgaccc cttcgtctcg      480
ggcgtctacg ccggggaccc gagcaagctc tccatgaagg cggccctgaa gaaggtgaaa     540
cgcttggagg agctggagg gagggggcatt ctggacgggg ctttgcttcg catccaggag     600
atccaacgga ccaagccgcc ggtggtgccg gagcaccctg tgtacaaggg cgggcagctg     660
ggttcattca gcgaggctt gcagtcgatg ccctggcgg cggccaaggc gctggggaag     720
gagaaggtcc ggctctccca caagctcttg agcgtggtgg aagggaaagg gccgaagggt     780
ggctacgagg cggttttttca gacccccccag ggacggaaac ggatcaaatg ccaggcccta     840
gccatcaccg ccccgcccca cgttgtgcac aagctcctgc gtcctttggt cccggaggcg     900
gcccgtcttg ccgacgtgta ctatccccg gtcgcctccg tcaccttggc ctacccgaaa      960
```

-continued

```
accgccttc gggagccgtt gcggggtttc ggaaatttga ttccccggag catgaagatc      1020
cgaacgctgg ggaccatctg gtcgtcctcc ctcttcccgg gcggcccccc cgactacaac      1080
atgctgcttt cctacatcgg aggggcccaa gatccgggta tcgcggagct gagcagccag      1140
cagatcgtca aggaggtaga cagggatatc aagaaggtct tgctcaagcc cgacgccccg      1200
gcgcccaaga tcctgggcgt gcggctgtgg cccaccgcca tcccgcagta caacaagggc      1260
cacctggaca tcctcgcgag cgtggaggca ggggtcaaga aacatccggg tctctttttg      1320
ggggggaatt accgaacagg cgtggcgttt ggggactgcg tgacctacgg gatggaggaa      1380
gcgggcagga ttcagagcta cttggctgct aaggctccgt aa                        1422
```

```
<210> SEQ ID NO 147
<211> LENGTH: 1419
<212> TYPE: DNA
<213> ORGANISM: Artificial Sequence
<220> FEATURE:
<223> OTHER INFORMATION: Synthetic_Gene encoding SEQ ID NO: 68

<400> SEQUENCE: 147
```

```
atgaaaaaga tgcgcgaggc gacggtgctc gtcacggagg cgcgcgaacg cgtcggaggg       60
aacgtcacga gtcgatcgga tgggacgtac acgtgggagg agggaccgaa ctcgtatcag      120
ccgggggatg cgatcttgac gctggcgtgc gacgcgggga tgcgcgacga catcttgctg      180
gcggatccgg cgagcaatcg gtacgtgctg tgggacggga agctgcggat tttaccgcac      240
agcattgaga gcgcggtgtt gggggatttt ttgacgtggc cggggaagat tcgggcggga      300
ttgggggcga tcggaatcag gccgccggcg ccgggcaagg aggagagcgt gaaggagttc      360
gtgagcagaa acttggggac ggaggcgttc gaacgtctga tcgaaccgtt ttgctcgggc      420
gtgtacgcgg gtgatcccgc ggcgctgtcg tccgtggcgg cgacggggcg cgtgcaacga      480
ctcgaaccgc tcggcgggtc gctcgtcgcc ggcgccatca tggcgcaaaa ggaggcggcg      540
cagaacaaga aaccgcgcga tccgcgcctt cccgaggtca agggccaaac cgtcggctcg      600
ttccgcggtg gtttgaagac gttcccggag ggtttggcca agcagctcgg cgacgacgtc      660
gtcaagtgca actggaagct cgtcggcgtc tcgaaatccg ccgagggcgg gtacgagtgc      720
gcgtacgaca ccccagaagg gccgcaaacg gtgagaacga agtgtttgtt gctcaccgcg      780
ccggcttacg tcgcggccga gatggttaag gacatggctc ccgcggcggc gacggcgctg      840
aacaagtttt actacccacc cgtcgcgtcg gtgacgattt cctacaagaa ggattcgttc      900
cgcctcgacg gcaccagcgc gttacccgaa ggcggcctca ctggcttcgg tcagctccac      960
ccgcgctcgc aaggcattcg cacgctcggc acgatttata gctcgagcct gttcaaggac     1020
gacaagcgtc aaccggacga cgagttcatg attttgaact acatcggcgg cgcgcgcgac     1080
gtcgcgatta aagacttgag cgaggaggag ctcgtgaagc aagtccacga ggacgccttg     1140
aagacaatct tgaagcccgg tacgccgctt cccaaggttg tcggcgtcaa ggtttgggaa     1200
aaggccatcc cgcaattcaa cctcggccac ttggacgtcc tcgccgaagc cgagaacgcg     1260
ttaaccgccg ccgactgcgg cgaaaaagac ggcttgttcc tcggcggcaa ctacaccgcg     1320
ggcgtcgcgt tgggtcgatg cgtcgagttc ggcatcgagc aagcggacga agtcgtggcg     1380
tacttaaacg ccgcatccaa gaaggccgtc gcggtgtga                            1419
```

```
<210> SEQ ID NO 148
<211> LENGTH: 1713
<212> TYPE: DNA
```

<213> ORGANISM: Artificial Sequence
<220> FEATURE:
<223> OTHER INFORMATION: Synthetic_Gene encoding SEQ ID NO: 69

<400> SEQUENCE: 148
atggtgacga tggcggcggt gaggacgaag gcttgggtga ccagcccgtc catgctgagc      60
tctcctgctc tcctcaggat gccttcctgc tcatggaccg gcaagtcctc tgtaagaggc     120
gctagagaca gctcggtcca gttccgggga aggtcggctc ggttcggagc tggggttcga     180
gggatgcaat ctgcgggagg atggggagcg gggagcatgg agaagtacga cacacttgtt     240
attgggagcg gcgtgagcgg ctcttctctt gggttctccc tgttccagaa gggcgtcaac     300
gtccttgtta ctgaagcaag ggacgtggtg ggaggaaacg tgatcaccag agagcaggac     360
gggtttcttt gggaggaagg acccaacacc ttccagccca ctcgccagat catgcgcctt     420
gctgtcgatc ttggcttgaa ggacgagctt gtgtttgctg accacaccct tcctagatgt     480
gtgtactggg agaaagagct cttcccctc ccctccaagc ccgaggatgc gccgttcttc      540
cgcctgctct ccatccccga gaagatccga gctggaatcg gagcgatcgg cctgcatgcg     600
ccgaagccag actacgagga gtcagtgaag gacttcatcg agcgacacct tggcgaggca     660
gtgttcaaga agatgatcga ccccttcgtg tcggagtgt acgcgggtga ccccaccaag      720
ctctccatgg cctcggcctt caagaagatc tacgcgctcg aggacctcgg catgacccca     780
agcttgatcg agggaggcat catccgccag gcggagaggg ccaaggaggc cagggaaaac     840
tatgaccctg agctgccaac ctacaaggga ggggctctcg gctccttcag gaagggtctt     900
gtcagtctcc ccaaggctgc ccaggagaag ctcggagatc gcctgaggac cagctggaag     960
gttgagtcca tctccaaggg agaggatggg ggatacgtca ccaagttttc gaccccccag    1020
ggttccaagg aggtttggtc caagactgtg gccgtgactg ctcctgctca tgctaccgtg    1080
ggcatgctct ccgagcttgt gcctgagtgc aaggcccttg aagagatcca ctacccgtgc    1140
gtctactccg tcactctcgc ctaccccaag gagtgcctca aggacgaggt tcgcaaagag    1200
agaccgggcc tcggcaagag gctcttcggg ttcggaaacc tcatccccg cagcatgggt     1260 atccgtacct tgggaacgat ctggtcctcc tcgctcttcc cctaccgtgc tcccgagggc    1320
tacgagatga tgttgagcta catcggagga gcccaggacc ctctccgcta caaccctccc    1380
atcgccgagc tctcggagga agaggtggca aagattgtcc atggtgacgt cagcaagatc    1440
ctcctcaagg aaggagctcc tgagccaaag gtcctgggag tgcgcaagtg gcccaaggcc    1500
atcccccagt acaacaaggg atactcggag attatgggca aggtcaacag cggtctcagc    1560
aagtgccctg ggctgtacct tggaggcaac tacgtctctg gcgttgcctt cggcgactgc    1620
gttcagtggg gagtcgacac tgcacccaag gtcaaggagt tcctcgactc cgtcccttcc    1680
tccgagaagg cggccaacgc tgcgctggtg taa                                  1713

<210> SEQ ID NO 149
<211> LENGTH: 1728
<212> TYPE: DNA
<213> ORGANISM: Artificial Sequence
<220> FEATURE:
<223> OTHER INFORMATION: Synthetic_Gene encoding SEQ ID NO: 70

<400> SEQUENCE: 149
atgctcaggt ggtccggatc tcaacaggta accgaccgga accgagccga acagcatggc      60
ctggtcgtgg cgttcgcttt tcctgctcga gcaccgcgcc acagcgaagc aacacacgag     120
cgctggactg ggctggcgca gcgcgaacgc ggcttgtgtg taccgttgaa agcgaccaag     180

```
tggaaacgag acttgtggca ctcgcgaaag cttcaaatgc aggagcctgc acagcggaac      240
agagagcagg tgcaagcgct agtagtaggc tctggagtga ctggctcttc gttcgcgttc      300
ctgctgcagc acgctggaat aagcgatgtg atttgcaccg aggcacgagg tgaagttggt      360
ggaaacctta tttcgcgttc caaagacggc tacctttggg aagaagggcc caacaccttc      420
caaccaacac cggtgattct gaaactcgcg cgagacgcgg gtctcgagtc cgagcttgtc      480
ttcgccgacg ccaaactccc tcgatacgta tactgggagg gggttttgca cgcgctcccg      540
agttcgcctg cagacctgat caccggccgt ttccgcctgt tatcgaatgc ggggaaggct      600
cgggcagcgc tcggagcgct cgggttcgta ggcgcaccca aacgcgtcgc acggcaagct      660
ggacccgagc ccagcgagga tgctgaccta gcagacgagt ctgtagagga attcgtgact      720
cgccatctag gccgcgaagt tttcctgaag attatagacc ccttcgtgag cggtgtgtat      780
gcaggcgatc ccagcaaact ctccatggct gcagctttca agcgcgtgta cgcactcgag      840
cagcttggcg gaacacgcgg gattctcgaa ggggcgctca tccgtctgca acaacgtcga      900
cgggaacgtc aacgctgggc ggcagagaat ctccccaagg tgaaagcggg tgcactgggc      960
tccttccgcg agggcctgca gcagttgccg ctcacagtgg cgactcggct gggccctgag     1020
cgaatgcgaa ctcggtatgc actgcgccaa attgaataca atggagcaaa acgtggaaaa     1080
cgtcgctata ctgcccgctt cgaaacccca gatggcgaac gagttatcga aacagatgcc     1140
ctcattctta cgatccccgc acatgcggcg tcaccgctct tgcaaggtct gggtgtctct     1200
gggagtgagc tgctccagga aatcgacttt ccgccggtat actcggtaac tttggcatac     1260
ccaaagtttg cagcgcggtt tcccctaaac ggtttcggga acctgatacc gcgctctgcc     1320
ggtattcgca ccctcgggat ggtctggtcg tcgagtttgt ttccggaacg agcgcctccc     1380
gatatgaata tggtgctctc atacatcggc ggtgcgcgtg atcctggtat ccgcgaatgc     1440
accccggatg aagtcgctgc cctcgtagac gcggacatgc gtcgcgtcct cctacgtgcc     1500
gatgcacctt cgccgcaagt tcttggtgtg agactttggc cgcgggcgat tccacaatac     1560
aaccggggtc acttgcggcg cttggaagcc tgcaaccagg gtctacaagg ctttcctggt     1620 ctcttttttag gcggaaacta tctgagtggc gtttccttcg gtgactgcgt acagtgggcg     1680
tacgataatg tgcctcgagt gctgacgttt ctgcaggaga cggcttga                  1728
```

```
<210> SEQ ID NO 150
<211> LENGTH: 1680
<212> TYPE: DNA
<213> ORGANISM: Artificial Sequence
<220> FEATURE:
<223> OTHER INFORMATION: Synthetic_Gene encoding SEQ ID NO: 71

<400> SEQUENCE: 150
atgacgatga cgacggggat atcctcgatt ggaaccaaga agaacagcat taaccgcgcg       60
aaggtgtcgt cgacgagaag aacacgaaga gtccgagctg ctctttccag cagcggcagc      120
aaagggagca actttgtggt gcgcgcgtct tcgtcttcgt cttctccttc tgacgacgag      180
aacaactctt tgggtattaa agatacgatc atcgtcggtg gtggtgtctc tgggttgtcc      240
acggcgttta cgatgaaatc gaagaacgca tcgtgcgata tcatggtcac ggaaatccga      300
gaccgcgtcg gagggaacgt gacctcgaag aatgacggtc aatacatatg gaggaagga      360 ccgaactcgt accaaccggg agacgcggtg ttgaagttag cgtgcgacgc cgggatgaag      420
gaggatatcg ttctcgcgaa cccggattcg gataggtacg tgttgtggga tggggagttg      480
```

-continued

```
agagcgttgc caaaggatat accgaccgca gtgctcgggg attttttgac ctggcccggg    540
aagattcgag ctggtttagg ggcggtgggt attcgcatgc cgaaagagga aggtaaggag    600
gaaacggtga aggagtttgt atctagaaat ttaggcgaag aggcgtttca gagattaatt    660
gaaccgtttt gctcgggcgt gtacgccggt gatccggcga tgttgagcgc ggaagccgcg    720
acgggtagag tttcggtatt agagaataaa ggtccgtggc cgggtttgtt tccgggcgcg    780
ttgaaagcgc aatacgaagg cgcgaagaag aagaaggaaa atccgagaga tccgagattg    840
ccggtgattg agggtcaaac ggttgggagt tttaaaggcg gtttgcaaac gttaccggaa    900
ggattggcga agcagttagg agagggcatc gtgaagttgc agtggaagct gatcaaaacg    960
gaaaaaaccg aggacggtct gttctctttg acgtacgaaa ctccagaagg ggagaagaaa   1020
gtgaaggcga aatccgtcgt gtttacgcaa ccggcgtacg tggtcgcgga tacggtgcga   1080
agtatcgcgc cagaagctgc gaaatcgttc gagaagttct actatccacc tgttgcgtct   1140
gtcaccgtcg catacaaacg cgacgcgttt aaattagacg gccgttcagc cttgcctgaa   1200
ggcggcttga ccggtttcgg tcaactccat ccgcgaacgc aaaaagtgcg cacgctaggc   1260
accatctact cctcctactt atgggccgac gacggacgat gccctaaaga cgaattcatg   1320
atcctcaact acatcggcgg cgcccgagac gtcgaaattc aaaaactcaa tgaagacgaa   1380
ctcgtccaag ccgtccacgc cgacgcttta aaaaccatct aaaaccaga cacgccgttg   1440 ccgaaaaaag ttggcgttcg catgtggtcc aaagctatcc cgcagtttaa cctcggtcac   1500
tggaaactct tagacgaagc taaagaactt ttgaaaaaag aaaagtgcag cgaagaggac   1560
ggtttatttt taggcggaaa ctacgtcgcc ggcgtcgcgt ttggccggtg cgtcgaatac   1620
ggcgtcgatc aagcctcgga cgtgttgaac tttttagata gcagagacg aaccgtataa   1680
```

```
<210> SEQ ID NO 151
<211> LENGTH: 1416
<212> TYPE: DNA
<213> ORGANISM: Artificial Sequence
<220> FEATURE:
<223> OTHER INFORMATION: Synthetic_Gene encoding SEQ ID NO: 72

<400> SEQUENCE: 151
atgcatcaca tgccaagaac aactggaatg aatgttgcag tagttggagg tgggatttct     60
ggtttggcag ttcacatca tttgagatct aggggtactg atgcagtact tctcgagtca    120
tctgctagac ttggaggtgc agttggaact catgcacttg ctggatacct agtagaacaa    180
ggtcctaata gttttcttga tcgtgaacca gcaactcgtg ctctagcagc agctcttaat    240
cttgaaggac gaattcgcgc tgctgatcct gctgcaaagc gtcgatatgt atacactcgt    300
ggtagactcc gatctgtacc agcttcacct ccagcatttc ttgcatcaga tattcttcct    360
ctaggtgctc gattgcgtgt tgctggagag ctctttttcac gtagagcacc tgagggtgtt    420
gatgaatctc tagctgcatt tggccgacgt catctaggac ataggctac gcaggtactt     480 ctcgatgcag ttcagactgg tatctacgct ggagatgtgg aacaattgag tgtcgctgca    540
acttttccta tgctggttaa gatggaacgt gaacatcgaa gtcttattct cggtgcaatc    600
cgcgcacaaa aggctcaacg tcaggcagcg ctcccagctg aacagcacc gaaattgtcc    660 ggagcactta gcacgtttga tggtggattg caagtgctca tagatgcgct tgcagcttca    720
ttgggtgatg cagctcatgt aggagcacgc gttgaaggac tagcacgaga ggatggcgga    780
tggagactta ttatcgaaga gcatggtcgt cgcgcagagc tctctgttgc acaagtggta    840
ttggcagctc cagcgcatgc tactgctaaa ttgcttcgtc cactcgatga tgcgctagcg    900
```
gcactcgtag caggtattgc ttatgctcct atcgcagttg ttcatctagg ttttgatgca          960
ggaacacttc cggctcctga tggttttgga ttcctggtgc ctgcagaaga gcaacgtcga         1020
atgcttggtg caattcatgc ttctactact tttccatttc gagctgaagg tggacgtgtt         1080
ctctattctt gtatggtggg aggcgcgcgt caaccaggac tggttgaaca ggatgaggat         1140
gctttggctg cactagcacg agaagaactg aaggcacttg caggcgttac agctcgccct         1200
tcatttactc gagtgtttcg ctggccactt ggtattcctc aatacaatct cggacatctt         1260
gaacgagtgg ctgctattga tgcggcacta caacgtttgc cgggccttca tctaattgga         1320
aatgcataca agggtgttgg actaaatgat tgtattcgca acgcagctca actagcagac         1380
gcgctcgttg ccggtaatac ttctcatgca ccgtag                                   1416

<210> SEQ ID NO 152
<211> LENGTH: 1410
<212> TYPE: DNA
<213> ORGANISM: Artificial Sequence
<220> FEATURE:
<223> OTHER INFORMATION: Synthetic_Gene encoding SEQ ID NO: 73

<400> SEQUENCE: 152
atgcaccaca tgcagaggac acatcggatg aatgtcgccg tcgtgggagg tgggatttcg           60
gggttggcca tcgcgcacgg tttgcggtcg cgcggtacgg ctgccgtgct cctggagaca          120
tccgcacgtc ttggaggcgc ggtgggcacg catgcgcggg ctggctacct ggtggagcag          180
ggccccaaca gcttcctgga ccgcgagccc gcgacgcgag aactcgcggc ggcgctgaac          240
ctggaaggtc gaatccgggt cgccgaccct tcagcgaagc gtcgctatgt ctacacgcga          300
ggccgacttc ggtcggtgcc ggcttcgccg ccggcgtttc tggcttcgga cattcttccg          360
ctgggcgcgc ggctgcgggt cgccggcgag ctgttctctc gccgcgcgcc ggaaggcacg          420
gacgaatcgc tggccgcgtt cggccgccgc cacctgggcc gcgcggcgac gcgggtgctg          480
ctggacgcgg tgcagacggg catctacgcc ggtgacgtgg agcagctcag cgtcgaggcc          540
accttcccga tgctggtgaa gctggagcgc gagcaccgca gcctcatcct gggcgccatc          600
cgcgcgcaga aggcccaacg caaggcgctg cccgcggggg acgcgccgaa gctgtcaggc          660
gcgctgagca cgttcgacgg cggcctccag gtgctcatcg acgcgctggc cgcatcgctg          720
ggtgacacag cgcacgtgag cgcgcggggt gaaggcctga cgcgcgtgga tggcggatgg          780
aagctcgccg tcgaggaaca tggacgccgc gcggagctga ccgcgaacca cgtggtgctg          840
gcggttcccg cgtttgtcgc cgcgcagctg ctgcgccccc tggatgacgc gctggcggag          900
caggtgtccc gaatcgagta cgcgcccatc gcggtggtgc acctgggctt cgacgcgggc          960
gcgcttccgg caccggacgg cttcggcttc ctggtgccct cgaggagaa gcggcggctc          1020 ctgggcgcca tccacgcgtc caccaccttc cccttccgtg tcgagggcgg ccgcgtgctc         1080
tacacctgca tggtgggcgg cgcgcgtcag ccggacctgg tgaagcggga cgaagcagcg         1140
ctcgcggcgc tggcgctcga ggagctgcag gccctgacgg gcgtgacggc ccggcccacc         1200
ttcacggagg tcttccgctg gccgcggggc atcccccagt acaacgtggg gcacctagcg         1260
cggatggcgg gcatcgacgc ggcgctccag cgctggcccg ggctgcacct ggcgggcaac         1320
gcctacaaag gcattggcct caacgactgc atccgtaacg cggcgcggct cgcgactgcc         1380
ctcgcggacg aggaaagcgt tcggaaatag                                           1410

<210> SEQ ID NO 153

<211> LENGTH: 1392
<212> TYPE: DNA
<213> ORGANISM: Artificial Sequence
<220> FEATURE:
<223> OTHER INFORMATION: Synthetic_Gene encoding SEQ ID NO: 74

<400> SEQUENCE: 153

```
atgaatgtcg ccgtcgtggg aggtgggatt tcggggttgg ccgtcgcgca cggtttgcgt        60
tcgcgcggta cggctgccgt gctcctggag acatccgcac gtcttggcgg cgcggtgggc       120
acgcatgcgc gcgctggcta cctggtggag caggggccga acagcttcct ggaccgggag       180
cccgcaacgc gcgccctggc ggcggcgctg aacctggaag gccggattcg cgtcgcggac       240
gcgtcggcga agcgtcgcta tgtctacacg cggggcagac tccggtcggt gcccgcgtca       300
ccgcccgcgt tcctgacttc ggacatcctg ccgctgggcg cgcggctgcg cgtcatgggc       360
gagctgttct ccagccgcgc accggagggc acggacgaat ccctggccgc gttcggccgc       420
cgccacctgg gccccgtggc gacgcgggtg ttgttggacg cggtgcagac gggcatctac       480
gccggggacg tggagcggct cagcgtcgag gccaccttcc ccctgctggt gaagctggag       540
cgcgagcacc gcagcctcat cctgggcgca atccacgcgc agaaggccca ggcgcggggcc      600 aaggccctgc tgccccccgg tgacgcgccg aagctgacgg cgcgctgag caccttcgac        660 ggcggcctcc aggtgctcat cgacgcgctg gcctcgtccc tgggagacgc ggcgcacgtg       720
ggcgcgcggg tggaggggct gacgcgcgtg gacggggggct ggaggctcgc cgtggaggag      780
cacggacagc gcgcggagct gagcgcgtcc cacgtggtgc tggcggtgcc cgcgcacgtc       840
gccgccgagc tgttgcagcc cctggatgac gcgctggcgg cgcaggtgtc ccgcatcgaa       900
tacgcgccca tcgcggtggt gcacctgggc ttcgacgcgg ggacgctccc ggcgccggac      960
ggcttcggct tcctggtgcc cttcgaggag cagcggcggc tgctgggcgc catccacgcg      1020
tccaccacct tcccctttccg cgtcgaaggc ggccgcgtgc tctacacctg catggtgggc     1080
ggcgcgcggg agccggacct ggtgcagcgg gatgaagcgg agctcgcggc gctggcgctg      1140
gaggagctgc gcgccctggc gggggtgacg gcccggccca ccttcaccca ggtgttccgc      1200
tggccgcgcg gcatccccca gtacaacgtg ggccacctgg agcgcatggc cggcatcgac      1260
gcggcgctcc agcgctggcc cggcctgcac ctggcgggga acgcgtacaa gggcattggc      1320
ctcaacgact gcatccgtaa cgcggcgcgg ctcgcggcgg cccttcgga cgaggaaaac       1380 gttcggaaat ag                                                         1392
```

<210> SEQ ID NO 154
<211> LENGTH: 1410
<212> TYPE: DNA
<213> ORGANISM: Artificial Sequence
<220> FEATURE:
<223> OTHER INFORMATION: Synthetic_Gene encoding SEQ ID NO: 75

<400> SEQUENCE: 154

```
atgcaccaca tgccgaggac acacggaatg aatgtcgccg tcgtgggagg tgggatttcg        60
gggttggccg tcgcgcatcg tttgcgttcg cgcggtacgg atgccgtgct tctggagacc       120
tccggccgtc ttggaggcgc ggtgggcacg catgcgcgtg acggctacct ggtggagcag       180
ggccccaaca gcttcctgga ccgcgagccg gccacgcggg aactcgcggc ggcattgaac       240
ctggaaggtc gaatccgggt ggcggacccg ttggcgaagc gtcgctatgt ctacacgcgt       300
gggcgactcc ggtcggtgcc gtcctcgccg cccgcgtttc tcgcatcgga cattcttccg       360
ctgggcgcgc ggctgcgtgt cgcgggtgaa ctgttctccg gccgcgcccc cacgggcatc       420
```

```
gatgaatcac tggccgagtt cggccgccgt caccttggac gcaccgccac gcaggtgctg        480
ctcgacgcgg tgcagacggg catctacgcg ggcgacgtgg agcagctcag cgtcgccgcc        540
acgttcccca tgctggtgga cctggagcgc aagcaccgca gcctcatcct gggcgccatc        600
cgcgcgcagc aggtccaacg ccgggccctc tccgcgggcg gcacgccgaa gctgagcggc        660
gcgttgagca cgttcgacgg tggactccag gtgctcatcg acgcgctggc cacgtcgctg        720
ggggacgcgg cgcacgtggg cgctcaggtg gaatgcctga cgcgcgtgga cggcgggtgg        780
aagttgatgg tcgaggagcg cggccagcgc gcggagctga gcgcatccca ggtggtgctg        840
gcggtgcccg cgcatgtcgc ggcggagctg ctccggccct tggatgacgc gctcgcggcg        900
caggtggcgc gcatcgacta tgcgcccatc gccgtggtgc acctgggctt cgacgcgggg        960
acgctgcccg cgccagacgg cttcggcttc ctggtgccct cgggcgaaaa gcggcggctg       1020
ctgggcgcca tccatgcgtc caccaccttc cccttccgcg tcgagggcgg gcgcgtgctc       1080
tacacgtgca tggtgggcgg cgcgcggcag ccggagctgg tgcggcagga cgaagcggcg       1140
ctcgcggccc tggcgctcga ggagctgcgc gccctggcgg gcgtgacggc gcagcccacc       1200
ttcacgcagg tctaccgctg gcagcgcggc atccccagt acaacgtggg gcacctggaa        1260
cggatggccg gcatcgacgc ggcgcttcaa cgctggcccg ggctgcacct cgcgggaaac       1320
gcgtacaagg gcattggcct caacgactgc attcgcaacg cagcgcggct cgcggatgcc       1380
ctcacggacg aggaaagcgt tcggaaatag                                        1410
```

```
<210> SEQ ID NO 155
<211> LENGTH: 1386
<212> TYPE: DNA
<213> ORGANISM: Artificial Sequence
<220> FEATURE:
<223> OTHER INFORMATION: Synthetic_Gene encoding SEQ ID NO: 76

<400> SEQUENCE: 155
```

```
atgactgtcg ccgtcgtagg aggtgggatt tcaggtctgg tcgtcgcctg gcgattgcgc         60
tcccgcggta gggatgccgt tctcctggag acaacctccc ggctcggcgg cgcggtgggc        120
acgcgcgcgc agcggggctt cctcctggag acgggccgga acagcttcct ggaccgcgag        180
cccgccatgc gagagctggc atccgcgctc aatctggaac acaggattcg cgcggcggat        240
ggggcggcga agcggcggta tgtctacacg cgggggaagc tgcgctcggt gcccgcatcg        300
ccgccggcgt tcctgaagtc ggacatcctc cccttcggcg cgaagctgcg ggtgatgggg        360
gagctgttca gcggccgcgc ggcgcccggc gtggacgaat ccctggcgga cttcgggcgt        420
cggcacctgg gggccacggc gacgcgggtg ctgctggacg cggtgcagac gggcatcttc        480
gcgggcgacg tggagaagct cagcgtgggc gccacgttcc cgccgctcgt gaagctggag        540
cgcgagcacc gcagcctcct gctcggcgcc atccaggccc agaaggccca gaaggcgcgg        600
gcgaaggccc tgcccgcggg cagcaccgcg ccgaagctga gcggcgcgct gagcaccttc        660
gagggcgggc tcggcacgct catcgacgcc ctgggcacgg cgctcgggga cgcggcgcgc        720
acgggcgcca cggtggaggg cctgacgcgg ggagacgacg gctggcggct cgcggtgagt        780
gagcggggac agcgctcgga gctgaaggcc tcctccgtgg tgctggccgc gcccgcatac        840
gtgacgcggg gcctgttgga gccgctggac gcggagctgg ccgcgcgcgt gggcggcatc        900
gactacgcgc ccatcgccgt ggtgcacctg ggcttcgacg cggggacgac gcccgcgccg        960
gacggcttcg gcttcctggt gccgccgatg gagaagcgcc ggctgctcgg cgccatccac       1020
```

-continued

```
gcgtccaccg tgttcccctt ccgcgtggag gcgggccggg tgctgtacac gtgcatggtg      1080
ggcggcgcga cgcggccgga cctcgtggcg ctggacgagg ccgaattggt ggccctggcg      1140
cgcgaggagc tgaaggcgct cgcgggcgtc accgccacgc cgacgctcac cgaggtcttc      1200
cgctggaagc ggggcatccc ccagtacaac ctgggccacc tggagcggat ggacggcgtg      1260
gaccgggcgc tcacgcgcct gccagggctg cacctggcgg ggaacgccta caagggcgtg      1320
ggcctcaacg actgcatccg caacgggctg gcgctcgcgg acgcgctggt ggacgcgggg      1380
gcctga                                                                 1386
```

<210> SEQ ID NO 156
<211> LENGTH: 1386
<212> TYPE: DNA
<213> ORGANISM: Artificial Sequence
<220> FEATURE:
<223> OTHER INFORMATION: Synthetic_Gene encoding SEQ ID NO: 77

<400> SEQUENCE: 156

```
atgactgtcg ccgtcgtagg aggtgggatt tcaggtctgg tcgtcgcctg gcgattgcgc        60
tcccgcggta gggatgccgt tctcctggag acaacctccc ggctcggcgg cgcggtgggc       120
acgcgcgcgc agcggggctt cctcctggag acgggccccca acagcttcct ggaccgcgag      180
cccgccatgc gagagctggc atccgcgctc aatctggaac acaggattcg cgcggcggat       240
ggggcggcga agcggcggta tgtctacacg cgggggaagc tgcgctcggt gcccgcatcg       300
ccgccggcgt tcctgaagtc ggacatcctc cccttcggcg cgaagctgcg ggtgatgggg       360
gagctgttca gcggccgcgc ggcgcccggc gtggacgaat ccctggcgga cttcgggcgt       420
cggcacctgg gggccacggc aacgcgggtg ctgctggacg cggtgcagac gggcatcttc       480
gcgggcgacg tggagaagct cagcgtgggc gccacgttcc cgccgctcgt gaagctggag       540
cgcgagcacc gcagcctcct gctcggcgcc atccaggccc agaaggcgca gaaggcacgg       600
gcgaaggccc tgcccgcggg cagcaccggg ccgaagctga gcggcgcgct gagcaccttc       660
gagggcgggc tcggcacgct catcgacgcc ctgggcacgg cgctcgggga cgcggcgcgc       720
acgggcgcca cggtggaggg cctgacgcgg ggagacgacg gctggcggct cgcggtgagt       780
gagcggggac agcgctcgga gctgaaggcc tcctccgtgg tgctggccgc gcccgcatac       840
gtgacgcggg gcctgttgga gccgctggac gcggagctgg ccgcgcgcgt gggcggcatc       900
gactacgcgc ccatcgccgt ggtgcacctg ggcttcgacg cggggacgac gcccgcgccg       960
gacggcttcg gcttcctggt gccgccgatg gagaagcgcc ggctgctcgg cgccatccac      1020
gcgtccaccg tgttcccctt ccgcgtggag gcgggccggg tgctgtacac gtgcatggtg      1080
ggcggcgcga cgcggccgga cctcgtggcg ctggacgagg ccgaattggt ggccctggcg      1140
cgcgaggagc tgaaggcgct cgcgggcgtc accgccacgc cgacgctcac cgaggtcttc      1200
cgctggaagc ggggcatccc ccagtacaac ctgggccacc tggagcggat ggacggcgtg      1260
gaccgggcgc tcacgcgcct gccagggctg cacctggcgg ggaacgccta caagggcgtg      1320
ggcctcaacg actgcatccg caacgggctg gcgctcgcgg acgcgctggt ggacgcgggg      1380
gcctga                                                                 1386
```

<210> SEQ ID NO 157
<211> LENGTH: 1380
<212> TYPE: DNA
<213> ORGANISM: Artificial Sequence
<220> FEATURE:
<223> OTHER INFORMATION: Synthetic_Gene encoding SEQ ID NO: 78

-continued

<400> SEQUENCE: 157

```
atgactgtcg ccgtcgtagg aggtgggatt tcaggtctgg tcgtcgcctg gcgattgcgc     60
tcgcggggca aggccgccgt tgtcctggag acaacatccc ggctcggcgg cgcggtgggg    120
actcgcgcga aacaaggttt cctccttgaa acaggtccca acagcttcct ggaccgtgag    180
ccggcgacac gcgagctggc cggcgcgctg aatctggaac acaggattcg cgcggcggat    240
gcggcggcga agcggcgata tgtctacacg cgaggacagc tgcgctcggt gcccgcatcg    300
cccccggcgt tcctgggctc ggacatcctg ccgtggagcg cgaagctgcg ggtcatgggt    360
gagctcttca ccggccgcgc cgcgccgggc atcgatgagt cactggcggc cttcggtcgc    420
agacatctgg gcgccaccgc gacacgcgtg ctgctggacg cggtgcagac aggcatcttc    480
gccggagacg tggagcgctt gagcgtgggc gccaccttcc cgccgctggt gaagctggag    540
cacgagcacc gcagcctcat cctcggcgcc atccggacgc agcaggcccg acgaaaggcc    600
ctgcccgcgg gcgcgtccgc cgcgcccgag ctgagcggcg cgctcagcac gttcgagggc    660
ggcttgcaga cgctcatcga cgcgctgagc gcttcgctgg gggaggacgc gcgcgtgaac    720
gcgacggtgg aagggctgac gcgcgtgggg gacgggtggc ggctcgcggt gagcgagaag    780
ggacagcgct ccgagctgga tgcgtcccac gtggtgctgg ccgcgcccgc atacgtgacg    840
cagaagctct tgcatccgct ggacgcggag ctggcggcgc gcgtgggcgg catcgagtac    900
gcgcccatcg ccgtggtgca gctgggcttc gacgtgggca cgacgcccgc accggatggc    960
ttcgggttcc tggtgcctcc ctcggaggga cggcggctct tgggctccat ccacgcctcc   1020
accgtgttcc ccttccgcgt ggagccgggc cgcgtgctgt acacgtgcat ggtgggcggc   1080
gcgaagcggc cggacctggt gggcttggat gagccggcgc tggtggccct ggcgcgcgag   1140
gagctgaagg cgctcgcggg ggtgacggcc acgccgtcgc tcacggaggt cttccgttgg   1200
cccctgggca tcccccagta caacgtggga catctggcgc ggatggccgc cgtcgaccag   1260
gcgctcaccc gccggcctgg gctctccctc acggggaacg cctacaaggg cgtgggcctc   1320
aacgactgca tccgcaacgg gctccagctc gcggatgcgc tcgtcaccgc ggcggggtga   1380
```

<210> SEQ ID NO 158
<211> LENGTH: 1377
<212> TYPE: DNA
<213> ORGANISM: Artificial Sequence
<220> FEATURE:
<223> OTHER INFORMATION: Synthetic_Gene encoding SEQ ID NO: 79

<400> SEQUENCE: 158

```
atgactgtta tcgctgttat cggcggagga atcagcggac tcacgctgac acattgctta     60
cgttctcgcg gcaaggatgc gcttctactg gaagcgagtt ctcggctcgg cggcaacatc    120
gaaacgaggc aacgtgacgg gttcctcatc gagacaggac ccaacagctt cctcgatcgg    180
gagcccgcga cgcgcgagct ggcagcgggc gtcggcgtgg aagatcggat ccgatctgcg    240
gatccggcgg cgaaagcgcg ctacctctac acgcgaggcc gactgcgccc ggtgccatcc    300
tctccgccag cgtttctgaa atcggacatc ctcccgctgg gagcgcgcct gagggtgatg    360
gcggagctct tcacgggccg ggctcccgag ggcgtggacg agtcgctggc agcctttggg    420
cggcggcacc tgggcccggc ggcgacggca gtgctgctgg acgcggtaca gacgggcatc    480
tacgcgggga acatggagac gctgagcgtg gacgccacct tccgcgcagct gacgaagctg    540 gagcgcgagc accgcagcct cattctcgga gccatccgct cgcagaaggc gcagcgcaag    600
```

```
gcgctccctg cgggggcagc gggaagcccg gagaagctgc gcggcacgct gtgcaccttc      660
gatgggggtc tgcagacgct ggtggatggg ctggcacggg agctcgggcc cgcggcgcac      720
acgaacgcga aggtggaggg tctccagccg agccacggtg gctggcgagt ctccgtgcga      780
gagaacgggg gccaggccga gctgctggca tcccaggtgg tgctggcaac gccagccttc      840
gtggcggcgg ggctgatgcg gccgctggac gagccgctcg cggcgctggt ggagggcatt      900
gcctacgcgc ccatcgccgt ggtgcacctg ggattcgcgc cgggcagcac gcccgcgccg      960
gatggcttcg gcttcctggt gccggggctg gagaagcggc ggctgctggg agccatccac     1020
gcctccacgg tgttcccctt ccgcaccgag ggcggacgcg tcctctacac ctgcatggtg     1080
ggtggagcgc ggcagcccga cctggtgaag ctggacgagg aggcgctggt ggcgctcgcg     1140
cgcgaggagc tcaaggagct ggccggagtg acggcgagcc cgagcttcac ggaggtgatc     1200
cgctggactc ggggcattcc tcagtacaac gtggggcacc tggagcgggt ggccgccatt     1260
gacgcggcgc tgaagcggtg gccggggctg cacctgaccg gcaacgcgta caagggcgtg     1320
ggcatcaacg actgcatccg caacgccttc gcgctgggcg acgcgctggc ggcctga        1377
```

```
<210> SEQ ID NO 159
<211> LENGTH: 27
<212> TYPE: DNA
<213> ORGANISM: Artificial Sequence
<220> FEATURE:
<223> OTHER INFORMATION: Synthetic_Cy19 BglII_F primer

<400> SEQUENCE: 159
gaagatctat gagtgaggta gatgtcg                                           27

<210> SEQ ID NO 160
<211> LENGTH: 28
<212> TYPE: DNA
<213> ORGANISM: Artificial Sequence
<220> FEATURE:
<223> OTHER INFORMATION: Synthetic_Cy19 SalI_R primer

<400> SEQUENCE: 160
acgcgtcgac ctagggctgg cctcctga                                         28

<210> SEQ ID NO 161
<211> LENGTH: 28
<212> TYPE: DNA
<213> ORGANISM: Artificial Sequence
<220> FEATURE:
<223> OTHER INFORMATION: Synthetic_Cy20 BglII_F primer

<400> SEQUENCE: 161
gaagatctat gatggaggta gatgtcgc                                         28

<210> SEQ ID NO 162
<211> LENGTH: 31
<212> TYPE: DNA
<213> ORGANISM: Artificial Sequence
<220> FEATURE:
<223> OTHER INFORMATION: Synthetic_Cy20 SalI_R primer

<400> SEQUENCE: 162
acgcgtcgac ttaacctcct gaaaggtagg c                                     31

<210> SEQ ID NO 163
<211> LENGTH: 27
<212> TYPE: DNA
<213> ORGANISM: Artificial Sequence
```

-continued

<220> FEATURE:
<223> OTHER INFORMATION: Synthetic_Cy18 BglII_F primer

<400> SEQUENCE: 163
ccagatctat gattgaggta gatgtcg                                          27

<210> SEQ ID NO 164
<211> LENGTH: 26
<212> TYPE: DNA
<213> ORGANISM: Artificial Sequence
<220> FEATURE:
<223> OTHER INFORMATION: Synthetic_Cy18 SalI_R primer

<400> SEQUENCE: 164
ccgtcgacct aggactggcc tcctgc                                           26

<210> SEQ ID NO 165
<211> LENGTH: 29
<212> TYPE: DNA
<213> ORGANISM: Artificial Sequence
<220> FEATURE:
<223> OTHER INFORMATION: Synthetic_Cy19 XbaI_F primer

<400> SEQUENCE: 165
agtatctaga atgagtgagg tagatgtcg                                        29

<210> SEQ ID NO 166
<211> LENGTH: 28
<212> TYPE: DNA
<213> ORGANISM: Artificial Sequence
<220> FEATURE:
<223> OTHER INFORMATION: Synthetic_Cy19 XhoI_R primer

<400> SEQUENCE: 166
ttaactcgag gggctggcct cctgaaag                                         28

<210> SEQ ID NO 167
<211> LENGTH: 28
<212> TYPE: DNA
<213> ORGANISM: Artificial Sequence
<220> FEATURE:
<223> OTHER INFORMATION: Synthetic_Cy20 XbaI_F primer

<400> SEQUENCE: 167
gctctagaat gatggaggta gatgtcgc                                         28

<210> SEQ ID NO 168
<211> LENGTH: 27
<212> TYPE: DNA
<213> ORGANISM: Artificial Sequence
<220> FEATURE:
<223> OTHER INFORMATION: Synthetic_Cy20 XhoI_R primer

<400> SEQUENCE: 168
ccgctcgaga cctcctgaaa ggtaggc                                          27

<210> SEQ ID NO 169
<211> LENGTH: 27
<212> TYPE: DNA
<213> ORGANISM: Artificial Sequence
<220> FEATURE:
<223> OTHER INFORMATION: Synthetic_Cy18 XbaI_F primer

<400> SEQUENCE: 169
cctctagaat gattgaggta gatgtcg                                          27

<210> SEQ ID NO 170
<211> LENGTH: 27
<212> TYPE: DNA
<213> ORGANISM: Artificial Sequence
<220> FEATURE:
<223> OTHER INFORMATION: Synthetic_Cy18 XhoI_R primer

<400> SEQUENCE: 170
ccctcgaggg actggcctcc tgcaaga                                      27

<210> SEQ ID NO 171
<211> LENGTH: 33
<212> TYPE: DNA
<213> ORGANISM: Artificial Sequence
<220> FEATURE:
<223> OTHER INFORMATION: Synthetic_Cy19 R89A F

<400> SEQUENCE: 171
gatcgccacc tgccggcgta catctactgg cgg                               33

<210> SEQ ID NO 172
<211> LENGTH: 33
<212> TYPE: DNA
<213> ORGANISM: Artificial Sequence
<220> FEATURE:
<223> OTHER INFORMATION: Synthetic_Cy19 R89A R

<400> SEQUENCE: 172
ccgccagtag atgtacgccg gcaggtggcg atc                               33

<210> SEQ ID NO 173
<211> LENGTH: 33
<212> TYPE: DNA
<213> ORGANISM: Artificial Sequence
<220> FEATURE:
<223> OTHER INFORMATION: Synthetic_Cy19 V165C F

<400> SEQUENCE: 173
gtctctgggt gctatgcggg tgatccacaa caa                               33

<210> SEQ ID NO 174
<211> LENGTH: 33
<212> TYPE: DNA
<213> ORGANISM: Artificial Sequence
<220> FEATURE:
<223> OTHER INFORMATION: Synthetic_Cy19 V165C R

<400> SEQUENCE: 174
acccgcatag cacccagaga caaagggcgc cac                               33

<210> SEQ ID NO 175
<211> LENGTH: 33
<212> TYPE: DNA
<213> ORGANISM: Artificial Sequence
<220> FEATURE:
<223> OTHER INFORMATION: Synthetic_Cy19 V165S F

<400> SEQUENCE: 175
ccctttgtct ctgggagtta tgcgggtgat cca                               33

<210> SEQ ID NO 176
<211> LENGTH: 33
<212> TYPE: DNA
<213> ORGANISM: Artificial Sequence
<220> FEATURE:
<223> OTHER INFORMATION: Synthetic_Cy19 V165S R -continued

<400> SEQUENCE: 176
tggatcaccc gcataactcc cagagacaaa ggg                                33

<210> SEQ ID NO 177
<211> LENGTH: 30
<212> TYPE: DNA
<213> ORGANISM: Artificial Sequence
<220> FEATURE:
<223> OTHER INFORMATION: Synthetic_Cy19 A167C F

<400> SEQUENCE: 177
gcgccctttg tctctggggt ttattgcggt                                   30

<210> SEQ ID NO 178
<211> LENGTH: 30
<212> TYPE: DNA
<213> ORGANISM: Artificial Sequence
<220> FEATURE:
<223> OTHER INFORMATION: Synthetic_Cy19 A167C R

<400> SEQUENCE: 178
agcactcagt tgttgtggat caccgcaata                                   30

<210> SEQ ID NO 179
<211> LENGTH: 33
<212> TYPE: DNA
<213> ORGANISM: Artificial Sequence
<220> FEATURE:
<223> OTHER INFORMATION: Synthetic_Cy19 A167L F

<400> SEQUENCE: 179
gtctctgggg tttatctggg tgatccacaa caa                               33

<210> SEQ ID NO 180
<211> LENGTH: 33
<212> TYPE: DNA
<213> ORGANISM: Artificial Sequence
<220> FEATURE:
<223> OTHER INFORMATION: Synthetic_Cy19 A167L R

<400> SEQUENCE: 180
ttgttgtgga tcacccagat aaaccccaga gac                               33

<210> SEQ ID NO 181
<211> LENGTH: 33
<212> TYPE: DNA
<213> ORGANISM: Artificial Sequence
<220> FEATURE:
<223> OTHER INFORMATION: Synthetic_Cy19 A167I F

<400> SEQUENCE: 181
gtctctgggg tttatatcgg tgatccacaa caa                               33

<210> SEQ ID NO 182
<211> LENGTH: 33
<212> TYPE: DNA
<213> ORGANISM: Artificial Sequence
<220> FEATURE:
<223> OTHER INFORMATION: Synthetic_Cy19 A167I R

<400> SEQUENCE: 182
ttgttgtgga tcaccgatat aaaccccaga gac                               33

<210> SEQ ID NO 183

```
<211> LENGTH: 34
<212> TYPE: DNA
<213> ORGANISM: Artificial Sequence
<220> FEATURE:
<223> OTHER INFORMATION: Synthetic_Cy19 V305L F

<400> SEQUENCE: 183
cattccctat cccaccctag cctgtgtggt cttg                              34

<210> SEQ ID NO 184
<211> LENGTH: 34
<212> TYPE: DNA
<213> ORGANISM: Artificial Sequence
<220> FEATURE:
<223> OTHER INFORMATION: Synthetic_Cy19 V305L R

<400> SEQUENCE: 184
caagaccaca caggctaggg tgggataggg aatg                              34

<210> SEQ ID NO 185
<211> LENGTH: 33
<212> TYPE: DNA
<213> ORGANISM: Artificial Sequence
<220> FEATURE:
<223> OTHER INFORMATION: Synthetic_Cy19 V305M F

<400> SEQUENCE: 185
tatcccacca tggcctgtgt ggtcttggcc tat                               33

<210> SEQ ID NO 186
<211> LENGTH: 36
<212> TYPE: DNA
<213> ORGANISM: Artificial Sequence
<220> FEATURE:
<223> OTHER INFORMATION: Synthetic_Cy19 V305M R

<400> SEQUENCE: 186
cacacaggcc atggtgggat agggaatggt ggccaa                            36

<210> SEQ ID NO 187
<211> LENGTH: 30
<212> TYPE: DNA
<213> ORGANISM: Artificial Sequence
<220> FEATURE:
<223> OTHER INFORMATION: Synthetic_Cy19 L327T F

<400> SEQUENCE: 187
agtgtccgcc ccggctttgg cgtaaccatt                                  30

<210> SEQ ID NO 188
<211> LENGTH: 30
<212> TYPE: DNA
<213> ORGANISM: Artificial Sequence
<220> FEATURE:
<223> OTHER INFORMATION: Synthetic_Cy19 L327T R

<400> SEQUENCE: 188
gcggatgccc tgactgcgag gaatggttac                                  30

<210> SEQ ID NO 189
<211> LENGTH: 32
<212> TYPE: DNA
<213> ORGANISM: Artificial Sequence
<220> FEATURE:
<223> OTHER INFORMATION: Synthetic_Cy19 F360I F

<400> SEQUENCE: 189
```

-continued caagtcttta cgagtattat tggcggtgct ac                                          32

<210> SEQ ID NO 190
<211> LENGTH: 32
<212> TYPE: DNA
<213> ORGANISM: Artificial Sequence
<220> FEATURE:
<223> OTHER INFORMATION: Synthetic_Cy19 F360I R

<400> SEQUENCE: 190
gtagcaccgc caataatact cgtaaagact tg                                          32

<210> SEQ ID NO 191
<211> LENGTH: 30
<212> TYPE: DNA
<213> ORGANISM: Artificial Sequence
<220> FEATURE:
<223> OTHER INFORMATION: Synthetic_Cy19 F360L F

<400> SEQUENCE: 191
gtctttacga gtttaattgg cggtgctacg                                             30

<210> SEQ ID NO 192
<211> LENGTH: 30
<212> TYPE: DNA
<213> ORGANISM: Artificial Sequence
<220> FEATURE:
<223> OTHER INFORMATION: Synthetic_Cy19 F360L R

<400> SEQUENCE: 192
cgtagcaccg ccaattaaac tcgtaaagac                                             30

<210> SEQ ID NO 193
<211> LENGTH: 36
<212> TYPE: DNA
<213> ORGANISM: Artificial Sequence
<220> FEATURE:
<223> OTHER INFORMATION: Synthetic_Cy19 F360M F

<400> SEQUENCE: 193
ggcaagtctt tacgagtatg attggcggtg ctacgg                                      36

<210> SEQ ID NO 194
<211> LENGTH: 36
<212> TYPE: DNA
<213> ORGANISM: Artificial Sequence
<220> FEATURE:
<223> OTHER INFORMATION: Synthetic_Cy19 F360M R

<400> SEQUENCE: 194
ccgtagcacc gccaatcata ctcgtaaaga cttgcc                                      36

<210> SEQ ID NO 195
<211> LENGTH: 32
<212> TYPE: DNA
<213> ORGANISM: Artificial Sequence
<220> FEATURE:
<223> OTHER INFORMATION: Synthetic_Cy19 F360V F

<400> SEQUENCE: 195
caagtcttta cgagtgttat tggcggtgct ac                                          32

<210> SEQ ID NO 196
<211> LENGTH: 32
<212> TYPE: DNA

-continued

<213> ORGANISM: Artificial Sequence
<220> FEATURE:
<223> OTHER INFORMATION: Synthetic_Cy19 F360V R

<400> SEQUENCE: 196
gtagcaccgc caataacact cgtaaagact tg                                    32

<210> SEQ ID NO 197
<211> LENGTH: 35
<212> TYPE: DNA
<213> ORGANISM: Artificial Sequence
<220> FEATURE:
<223> OTHER INFORMATION: Synthetic_Cy19 F360T F

<400> SEQUENCE: 197
tttacgagta ctattggcgg tgctacggat cctga                                 35

<210> SEQ ID NO 198
<211> LENGTH: 35
<212> TYPE: DNA
<213> ORGANISM: Artificial Sequence
<220> FEATURE:
<223> OTHER INFORMATION: Synthetic_Cy19 F360T R

<400> SEQUENCE: 198
ccgccaatag tactcgtaaa gacttgccaa ccggc                                 35

<210> SEQ ID NO 199
<211> LENGTH: 33
<212> TYPE: DNA
<213> ORGANISM: Artificial Sequence
<220> FEATURE:
<223> OTHER INFORMATION: Synthetic_Cy19 I408R F

<400> SEQUENCE: 199
gtttggcgac gggcgagacc ccaatatatg gtg                                   33

<210> SEQ ID NO 200
<211> LENGTH: 33
<212> TYPE: DNA
<213> ORGANISM: Artificial Sequence
<220> FEATURE:
<223> OTHER INFORMATION: Synthetic_Cy19 I408R R

<400> SEQUENCE: 200
caccatatat tggggtctcg cccgtcgcca aac                                   33

<210> SEQ ID NO 201
<211> LENGTH: 32
<212> TYPE: DNA
<213> ORGANISM: Artificial Sequence
<220> FEATURE:
<223> OTHER INFORMATION: Synthetic_Cy19 I408W F

<400> SEQUENCE: 201
aggtttggcg acgggcgtgg ccccaatata tg                                    32

<210> SEQ ID NO 202
<211> LENGTH: 32
<212> TYPE: DNA
<213> ORGANISM: Artificial Sequence
<220> FEATURE:
<223> OTHER INFORMATION: Synthetic_Cy19 I408W R

<400> SEQUENCE: 202
catatattgg ggccacgccc gtcgccaaac ct                                    32

-continued

<210> SEQ ID NO 203
<211> LENGTH: 41
<212> TYPE: DNA
<213> ORGANISM: Artificial Sequence
<220> FEATURE:
<223> OTHER INFORMATION: Synthetic_Cy19 V165C+A167C F

<400> SEQUENCE: 203
cctttgtctc tgggtgttat tgcggtgatc cacaacaact g                                       41

<210> SEQ ID NO 204
<211> LENGTH: 41
<212> TYPE: DNA
<213> ORGANISM: Artificial Sequence
<220> FEATURE:
<223> OTHER INFORMATION: Synthetic_Cy19 V165C+A167C R

<400> SEQUENCE: 204
cagttgttgt ggatcaccgc aataacaccc agagacaaag g                                       41

<210> SEQ ID NO 205
<211> LENGTH: 42
<212> TYPE: DNA
<213> ORGANISM: Artificial Sequence
<220> FEATURE:
<223> OTHER INFORMATION: Synthetic_Cy19 V165C+A167L F

<400> SEQUENCE: 205
ggcgcccttt gtctctgggt gctacctggg tgatccacaa ca                                      42

<210> SEQ ID NO 206
<211> LENGTH: 42
<212> TYPE: DNA
<213> ORGANISM: Artificial Sequence
<220> FEATURE:
<223> OTHER INFORMATION: Synthetic_Cy19 V165C+A167L R

<400> SEQUENCE: 206
tgttgtggat cacccaggta gcacccagag acaaagggcg cc                                      42

<210> SEQ ID NO 207
<211> LENGTH: 44
<212> TYPE: DNA
<213> ORGANISM: Artificial Sequence
<220> FEATURE:
<223> OTHER INFORMATION: Synthetic_Cy19 V165S+A167C F

<400> SEQUENCE: 207
ggcgcccttt gtctctggga gctactgcgg tgatccacaa caac                                    44

<210> SEQ ID NO 208
<211> LENGTH: 44
<212> TYPE: DNA
<213> ORGANISM: Artificial Sequence
<220> FEATURE:
<223> OTHER INFORMATION: Synthetic_Cy19 V165S+A167C R

<400> SEQUENCE: 208
gttgttgtgg atcaccgcag tagctcccag agacaaaggg cgcc                                    44

<210> SEQ ID NO 209
<211> LENGTH: 39
<212> TYPE: DNA
<213> ORGANISM: Artificial Sequence
<220> FEATURE:

-continued

<223> OTHER INFORMATION: Synthetic_Cy19 V165C+A167I F

<400> SEQUENCE: 209 ggcgccctttt gtctctgggt gctacatcgg tgatccaca                          39

<210> SEQ ID NO 210
<211> LENGTH: 39
<212> TYPE: DNA
<213> ORGANISM: Artificial Sequence
<220> FEATURE:
<223> OTHER INFORMATION: Synthetic_Cy19 V165C+A167I R

<400> SEQUENCE: 210
tgtggatcac cgatgtagca cccagagaca aagggcgcc                           39

<210> SEQ ID NO 211
<211> LENGTH: 39
<212> TYPE: DNA
<213> ORGANISM: Artificial Sequence
<220> FEATURE:
<223> OTHER INFORMATION: Synthetic_Cy19 V165S+A167I F

<400> SEQUENCE: 211 ggcgccctttt gtctctggga gctacatcgg tgatccaca                          39

<210> SEQ ID NO 212
<211> LENGTH: 39
<212> TYPE: DNA
<213> ORGANISM: Artificial Sequence
<220> FEATURE:
<223> OTHER INFORMATION: Synthetic_Cy19 V165S+A167I R

<400> SEQUENCE: 212
tgtggatcac cgatgtagct cccagagaca aagggcgcc                           39

<210> SEQ ID NO 213
<211> LENGTH: 41
<212> TYPE: DNA
<213> ORGANISM: Artificial Sequence
<220> FEATURE:
<223> OTHER INFORMATION: Synthetic_Cy19 V165S+A167L F

<400> SEQUENCE: 213
cctttgtctc tgggtcttat ctgggtgatc cacaacaact g                        41

<210> SEQ ID NO 214
<211> LENGTH: 41
<212> TYPE: DNA
<213> ORGANISM: Artificial Sequence
<220> FEATURE:
<223> OTHER INFORMATION: Synthetic_Cy19 V165S+A167L R

<400> SEQUENCE: 214
cagttgttgt ggatcaccca gataagaccc agagacaaag g                        41

<210> SEQ ID NO 215
<211> LENGTH: 33
<212> TYPE: DNA
<213> ORGANISM: Artificial Sequence
<220> FEATURE:
<223> OTHER INFORMATION: Synthetic_Cy20 R89A F

<400> SEQUENCE: 215
gatcgccacc taccggcgta catctactgg cgg                                 33

<210> SEQ ID NO 216
<211> LENGTH: 33
<212> TYPE: DNA
<213> ORGANISM: Artificial Sequence
<220> FEATURE:
<223> OTHER INFORMATION: Synthetic_Cy20 R89A R

<400> SEQUENCE: 216
ccgccagtag atgtacgccg gtaggtggcg atc                                    33

<210> SEQ ID NO 217
<211> LENGTH: 33
<212> TYPE: DNA
<213> ORGANISM: Artificial Sequence
<220> FEATURE:
<223> OTHER INFORMATION: Synthetic_Cy20 V165C F

<400> SEQUENCE: 217
ccctttgtct ctgggtgtta cgccggtgat ccg                                    33

<210> SEQ ID NO 218
<211> LENGTH: 33
<212> TYPE: DNA
<213> ORGANISM: Artificial Sequence
<220> FEATURE:
<223> OTHER INFORMATION: Synthetic_Cy20 V165C R

<400> SEQUENCE: 218
cggatcaccg gcgtaacacc cagagacaaa ggg                                    33

<210> SEQ ID NO 219
<211> LENGTH: 33
<212> TYPE: DNA
<213> ORGANISM: Artificial Sequence
<220> FEATURE:
<223> OTHER INFORMATION: Synthetic_Cy20 V165S F

<400> SEQUENCE: 219
ccctttgtct ctgggagtta cgccggtgat ccg                                    33

<210> SEQ ID NO 220
<211> LENGTH: 33
<212> TYPE: DNA
<213> ORGANISM: Artificial Sequence
<220> FEATURE:
<223> OTHER INFORMATION: Synthetic_Cy20 V165S R

<400> SEQUENCE: 220
cggatcaccg gcgtaactcc cagagacaaa ggg                                    33

<210> SEQ ID NO 221
<211> LENGTH: 33
<212> TYPE: DNA
<213> ORGANISM: Artificial Sequence
<220> FEATURE:
<223> OTHER INFORMATION: Synthetic_Cy20 A167C F

<400> SEQUENCE: 221
gtctctgggg tttactgtgg tgatccgcaa caa                                    33

<210> SEQ ID NO 222
<211> LENGTH: 33
<212> TYPE: DNA
<213> ORGANISM: Artificial Sequence
<220> FEATURE:
<223> OTHER INFORMATION: Synthetic_Cy20 A167C R -continued

<400> SEQUENCE: 222
ttgttgcgga tcaccacagt aaaccccaga gac                                          33

<210> SEQ ID NO 223
<211> LENGTH: 33
<212> TYPE: DNA
<213> ORGANISM: Artificial Sequence
<220> FEATURE:
<223> OTHER INFORMATION: Synthetic_Cy20 A167L F

<400> SEQUENCE: 223
gtctctgggg tttacctcgg tgatccgcaa caa                                          33

<210> SEQ ID NO 224
<211> LENGTH: 33
<212> TYPE: DNA
<213> ORGANISM: Artificial Sequence
<220> FEATURE:
<223> OTHER INFORMATION: Synthetic_Cy20 A167L R

<400> SEQUENCE: 224
ttgttgcgga tcaccgaggt aaaccccaga gac                                          33

<210> SEQ ID NO 225
<211> LENGTH: 33
<212> TYPE: DNA
<213> ORGANISM: Artificial Sequence
<220> FEATURE:
<223> OTHER INFORMATION: Synthetic_Cy20 A167I F

<400> SEQUENCE: 225
gtctctgggg tttacattgg tgatccgcaa caa                                          33

<210> SEQ ID NO 226
<211> LENGTH: 33
<212> TYPE: DNA
<213> ORGANISM: Artificial Sequence
<220> FEATURE:
<223> OTHER INFORMATION: Synthetic_Cy20 A167I R

<400> SEQUENCE: 226
ttgttgcgga tcaccaatgt aaaccccaga gac                                          33

<210> SEQ ID NO 227
<211> LENGTH: 34
<212> TYPE: DNA
<213> ORGANISM: Artificial Sequence
<220> FEATURE:
<223> OTHER INFORMATION: Synthetic_Cy20 V305L F

<400> SEQUENCE: 227
catcccctat cccaccctag cctgtgtggt cttg                                         34

<210> SEQ ID NO 228
<211> LENGTH: 34
<212> TYPE: DNA
<213> ORGANISM: Artificial Sequence
<220> FEATURE:
<223> OTHER INFORMATION: Synthetic_Cy20 V305L R

<400> SEQUENCE: 228
caagaccaca caggctaggg tgggataggg gatg                                         34

<210> SEQ ID NO 229
<211> LENGTH: 33

-continued

```
<212> TYPE: DNA
<213> ORGANISM: Artificial Sequence
<220> FEATURE:
<223> OTHER INFORMATION: Synthetic_Cy20 V305M F

<400> SEQUENCE: 229
atcccctatc ccaccatggc ctgtgtggtc ttg                          33

<210> SEQ ID NO 230
<211> LENGTH: 33
<212> TYPE: DNA
<213> ORGANISM: Artificial Sequence
<220> FEATURE:
<223> OTHER INFORMATION: Synthetic_Cy20 V305M R

<400> SEQUENCE: 230
caagaccaca caggccatgg tgggataggg gat                          33

<210> SEQ ID NO 231
<211> LENGTH: 33
<212> TYPE: DNA
<213> ORGANISM: Artificial Sequence
<220> FEATURE:
<223> OTHER INFORMATION: Synthetic_Cy20 L327T F

<400> SEQUENCE: 231
cccggatttg gcgtaacgat tcctcgtggc cag                          33

<210> SEQ ID NO 232
<211> LENGTH: 33
<212> TYPE: DNA
<213> ORGANISM: Artificial Sequence
<220> FEATURE:
<223> OTHER INFORMATION: Synthetic_Cy20 L327T R

<400> SEQUENCE: 232
ctggccacga ggaatcgtta cgccaaatcc ggg                          33

<210> SEQ ID NO 233
<211> LENGTH: 33
<212> TYPE: DNA
<213> ORGANISM: Artificial Sequence
<220> FEATURE:
<223> OTHER INFORMATION: Synthetic_Cy20 I340T F

<400> SEQUENCE: 233
cgtacccttg gcaccacatg gtcgtcctgt ctt                          33

<210> SEQ ID NO 234
<211> LENGTH: 33
<212> TYPE: DNA
<213> ORGANISM: Artificial Sequence
<220> FEATURE:
<223> OTHER INFORMATION: Synthetic_Cy20 I340T R

<400> SEQUENCE: 234
aagacaggac gaccatgtgg tgccaagggt acg                          33

<210> SEQ ID NO 235
<211> LENGTH: 33
<212> TYPE: DNA
<213> ORGANISM: Artificial Sequence
<220> FEATURE:
<223> OTHER INFORMATION: Synthetic_Cy20 F360I F

<400> SEQUENCE: 235
```

```
caagtcttta caagtaccat tggcggtgcc acg                                      33
```

```
<210> SEQ ID NO 236
<211> LENGTH: 33
<212> TYPE: DNA
<213> ORGANISM: Artificial Sequence
<220> FEATURE:
<223> OTHER INFORMATION: Synthetic_Cy20 F360I R

<400> SEQUENCE: 236
cgtggcaccg ccaatggtac ttgtaaagac ttg                                      33

<210> SEQ ID NO 237
<211> LENGTH: 33
<212> TYPE: DNA
<213> ORGANISM: Artificial Sequence
<220> FEATURE:
<223> OTHER INFORMATION: Synthetic_Cy20 F360L F

<400> SEQUENCE: 237
caagtcttta caagtctgat tggcggtgcc acg                                      33

<210> SEQ ID NO 238
<211> LENGTH: 33
<212> TYPE: DNA
<213> ORGANISM: Artificial Sequence
<220> FEATURE:
<223> OTHER INFORMATION: Synthetic_Cy20 F360L R

<400> SEQUENCE: 238
cgtggcaccg ccaatcagac ttgtaaagac ttg                                      33

<210> SEQ ID NO 239
<211> LENGTH: 33
<212> TYPE: DNA
<213> ORGANISM: Artificial Sequence
<220> FEATURE:
<223> OTHER INFORMATION: Synthetic_Cy20 F360M F

<400> SEQUENCE: 239
caagtcttta caagtatgat tggcggtgcc acg                                      33

<210> SEQ ID NO 240
<211> LENGTH: 33
<212> TYPE: DNA
<213> ORGANISM: Artificial Sequence
<220> FEATURE:
<223> OTHER INFORMATION: Synthetic_Cy20 F360M R

<400> SEQUENCE: 240
cgtggcaccg ccaatcatac ttgtaaagac ttg                                      33

<210> SEQ ID NO 241
<211> LENGTH: 33
<212> TYPE: DNA
<213> ORGANISM: Artificial Sequence
<220> FEATURE:
<223> OTHER INFORMATION: Synthetic_Cy20 F360V F

<400> SEQUENCE: 241
caagtcttta caagtgttat tggcggtgcc acg                                      33

<210> SEQ ID NO 242
<211> LENGTH: 33
<212> TYPE: DNA
<213> ORGANISM: Artificial Sequence
```

-continued

```
<220> FEATURE:
<223> OTHER INFORMATION: Synthetic_Cy20 F360V R

<400> SEQUENCE: 242
cgtggcaccg ccaataacac ttgtaaagac ttg                                    33

<210> SEQ ID NO 243
<211> LENGTH: 33
<212> TYPE: DNA
<213> ORGANISM: Artificial Sequence
<220> FEATURE:
<223> OTHER INFORMATION: Synthetic_Cy20 I408R F

<400> SEQUENCE: 243
gtttggcgac gggcgaggcc ccaatatctt gtg                                    33

<210> SEQ ID NO 244
<211> LENGTH: 33
<212> TYPE: DNA
<213> ORGANISM: Artificial Sequence
<220> FEATURE:
<223> OTHER INFORMATION: Synthetic_Cy20 I408R R

<400> SEQUENCE: 244
cacaagatat tggggcctcg cccgtcgcca aac                                    33

<210> SEQ ID NO 245
<211> LENGTH: 33
<212> TYPE: DNA
<213> ORGANISM: Artificial Sequence
<220> FEATURE:
<223> OTHER INFORMATION: Synthetic_Cy20 I408W F

<400> SEQUENCE: 245
gtttggcgac gggcgtggcc ccaatatctt gtg                                    33

<210> SEQ ID NO 246
<211> LENGTH: 33
<212> TYPE: DNA
<213> ORGANISM: Artificial Sequence
<220> FEATURE:
<223> OTHER INFORMATION: Synthetic_Cy20 I408W R

<400> SEQUENCE: 246
cacaagatat tggggccacg cccgtcgcca aac                                    33

<210> SEQ ID NO 247
<211> LENGTH: 39
<212> TYPE: DNA
<213> ORGANISM: Artificial Sequence
<220> FEATURE:
<223> OTHER INFORMATION: Synthetic_Cy20 V165C+A167C F

<400> SEQUENCE: 247
ccctttgtct ctgggtgtta ctgtggtgat ccgcaacaa                              39

<210> SEQ ID NO 248
<211> LENGTH: 39
<212> TYPE: DNA
<213> ORGANISM: Artificial Sequence
<220> FEATURE:
<223> OTHER INFORMATION: Synthetic_Cy20 V165C+A167C R

<400> SEQUENCE: 248
ttgttgcgga tcaccacagt aacacccaga gacaaaggg                              39
```

-continued

```
<210> SEQ ID NO 249
<211> LENGTH: 39
<212> TYPE: DNA
<213> ORGANISM: Artificial Sequence
<220> FEATURE:
<223> OTHER INFORMATION: Synthetic_Cy20 V165C+A167I F

<400> SEQUENCE: 249
ccctttgtct ctgggtgtta cattggtgat ccgcaacaa                         39

<210> SEQ ID NO 250
<211> LENGTH: 39
<212> TYPE: DNA
<213> ORGANISM: Artificial Sequence
<220> FEATURE:
<223> OTHER INFORMATION: Synthetic_Cy20 V165C+A167I R

<400> SEQUENCE: 250
ttgttgcgga tcaccaatgt aacacccaga gacaaaggg                         39

<210> SEQ ID NO 251
<211> LENGTH: 39
<212> TYPE: DNA
<213> ORGANISM: Artificial Sequence
<220> FEATURE:
<223> OTHER INFORMATION: Synthetic_Cy20 V165C+A167L F

<400> SEQUENCE: 251
ccctttgtct ctgggtgtta cctcggtgat ccgcaacaa                         39

<210> SEQ ID NO 252
<211> LENGTH: 39
<212> TYPE: DNA
<213> ORGANISM: Artificial Sequence
<220> FEATURE:
<223> OTHER INFORMATION: Synthetic_Cy20 V165C+A167L R

<400> SEQUENCE: 252
ttgttgcgga tcaccgaggt aacacccaga gacaaaggg                         39

<210> SEQ ID NO 253
<211> LENGTH: 39
<212> TYPE: DNA
<213> ORGANISM: Artificial Sequence
<220> FEATURE:
<223> OTHER INFORMATION: Synthetic_Cy20 V165S+A167C F

<400> SEQUENCE: 253
ccctttgtct ctgggagtta ctgtggtgat ccgcaacaa                         39

<210> SEQ ID NO 254
<211> LENGTH: 39
<212> TYPE: DNA
<213> ORGANISM: Artificial Sequence
<220> FEATURE:
<223> OTHER INFORMATION: Synthetic_Cy20 V165S+A167C R

<400> SEQUENCE: 254
ttgttgcgga tcaccacagt aactcccaga gacaaaggg                         39

<210> SEQ ID NO 255
<211> LENGTH: 39
<212> TYPE: DNA
<213> ORGANISM: Artificial Sequence
<220> FEATURE:
<223> OTHER INFORMATION: Synthetic_Cy20 V165S+A167I F
```

<400> SEQUENCE: 255
ccctttgtct ctgggagtta cattggtgat ccgcaacaa                              39

<210> SEQ ID NO 256
<211> LENGTH: 39
<212> TYPE: DNA
<213> ORGANISM: Artificial Sequence
<220> FEATURE:
<223> OTHER INFORMATION: Synthetic_Cy20 V165S+A167I R

<400> SEQUENCE: 256
ttgttgcgga tcaccaatgt aactcccaga gacaaaggg                              39

<210> SEQ ID NO 257
<211> LENGTH: 39
<212> TYPE: DNA
<213> ORGANISM: Artificial Sequence
<220> FEATURE:
<223> OTHER INFORMATION: Synthetic_Cy20 V165S+A167L F

<400> SEQUENCE: 257
ccctttgtct ctgggagtta cctcggtgat ccgcaacaa                              39

<210> SEQ ID NO 258
<211> LENGTH: 39
<212> TYPE: DNA
<213> ORGANISM: Artificial Sequence
<220> FEATURE:
<223> OTHER INFORMATION: Synthetic_Cy20 V165S+A167L R

<400> SEQUENCE: 258
ttgttgcgga tcaccgaggt aactcccaga gacaaaggg                              39

<210> SEQ ID NO 259
<211> LENGTH: 32
<212> TYPE: DNA
<213> ORGANISM: Artificial Sequence
<220> FEATURE:
<223> OTHER INFORMATION: Synthetic_Cy18 R89A F

<400> SEQUENCE: 259
gatcgccacc taccggcata catctactgg cg                                     32

<210> SEQ ID NO 260
<211> LENGTH: 32
<212> TYPE: DNA
<213> ORGANISM: Artificial Sequence
<220> FEATURE:
<223> OTHER INFORMATION: Synthetic_Cy18 R89A R

<400> SEQUENCE: 260
cgccagtaga tgtatgccgg taggtggcga tc                                     32

<210> SEQ ID NO 261
<211> LENGTH: 31
<212> TYPE: DNA
<213> ORGANISM: Artificial Sequence
<220> FEATURE:
<223> OTHER INFORMATION: Synthetic_Cy18 V165C F

<400> SEQUENCE: 261
ccctttgtct ctgggtgtta tgccggtgat c                                      31

<210> SEQ ID NO 262

-continued

```
<211> LENGTH: 31
<212> TYPE: DNA
<213> ORGANISM: Artificial Sequence
<220> FEATURE:
<223> OTHER INFORMATION: Synthetic_Cy18 V165C R

<400> SEQUENCE: 262
gatcaccggc ataacaccca gagacaaagg g                               31

<210> SEQ ID NO 263
<211> LENGTH: 31
<212> TYPE: DNA
<213> ORGANISM: Artificial Sequence
<220> FEATURE:
<223> OTHER INFORMATION: Synthetic_Cy18 V165S F

<400> SEQUENCE: 263
ccctttgtct ctgggagtta tgccggtgat c                               31

<210> SEQ ID NO 264
<211> LENGTH: 31
<212> TYPE: DNA
<213> ORGANISM: Artificial Sequence
<220> FEATURE:
<223> OTHER INFORMATION: Synthetic_Cy18 V165S R

<400> SEQUENCE: 264
gatcaccggc ataactccca gagacaaagg g                               31

<210> SEQ ID NO 265
<211> LENGTH: 31
<212> TYPE: DNA
<213> ORGANISM: Artificial Sequence
<220> FEATURE:
<223> OTHER INFORMATION: Synthetic_Cy18 A167C F

<400> SEQUENCE: 265
gtctctgggg tttattgcgg tgatccgcaa c                               31

<210> SEQ ID NO 266
<211> LENGTH: 31
<212> TYPE: DNA
<213> ORGANISM: Artificial Sequence
<220> FEATURE:
<223> OTHER INFORMATION: Synthetic_Cy18 A167C R

<400> SEQUENCE: 266
gttgcggatc accgcaataa accccagaga c                               31

<210> SEQ ID NO 267
<211> LENGTH: 31
<212> TYPE: DNA
<213> ORGANISM: Artificial Sequence
<220> FEATURE:
<223> OTHER INFORMATION: Synthetic_Cy18 A167L F

<400> SEQUENCE: 267
gtctctgggg tttatctcgg tgatccgcaa c                               31

<210> SEQ ID NO 268
<211> LENGTH: 31
<212> TYPE: DNA
<213> ORGANISM: Artificial Sequence
<220> FEATURE:
<223> OTHER INFORMATION: Synthetic_Cy18 A167L R

<400> SEQUENCE: 268
```

-continued gttgcggatc accgagataa accccagaga c                               31

<210> SEQ ID NO 269
<211> LENGTH: 31
<212> TYPE: DNA
<213> ORGANISM: Artificial Sequence
<220> FEATURE:
<223> OTHER INFORMATION: Synthetic_Cy18 A167I F

<400> SEQUENCE: 269
gtctctgggg tttatatcgg tgatccgcaa c                               31

<210> SEQ ID NO 270
<211> LENGTH: 31
<212> TYPE: DNA
<213> ORGANISM: Artificial Sequence
<220> FEATURE:
<223> OTHER INFORMATION: Synthetic_Cy18 A167I R

<400> SEQUENCE: 270
gttgcggatc accgatataa accccagaga c                               31

<210> SEQ ID NO 271
<211> LENGTH: 34
<212> TYPE: DNA
<213> ORGANISM: Artificial Sequence
<220> FEATURE:
<223> OTHER INFORMATION: Synthetic_Cy18 V305L F

<400> SEQUENCE: 271
catcccctat cccaccctag cctgtgtggt gttg                           34

<210> SEQ ID NO 272
<211> LENGTH: 34
<212> TYPE: DNA
<213> ORGANISM: Artificial Sequence
<220> FEATURE:
<223> OTHER INFORMATION: Synthetic_Cy18 V305L R

<400> SEQUENCE: 272
caacaccaca caggctaggg tgggataggg gatg                           34

<210> SEQ ID NO 273
<211> LENGTH: 34
<212> TYPE: DNA
<213> ORGANISM: Artificial Sequence
<220> FEATURE:
<223> OTHER INFORMATION: Synthetic_Cy18 V305M F

<400> SEQUENCE: 273
catcccctat cccaccatgg cctgtgtggt gttg                           34

<210> SEQ ID NO 274
<211> LENGTH: 34
<212> TYPE: DNA
<213> ORGANISM: Artificial Sequence
<220> FEATURE:
<223> OTHER INFORMATION: Synthetic_Cy18 V305M R

<400> SEQUENCE: 274
caacaccaca caggccatgg tgggataggg gatg                           34

<210> SEQ ID NO 275
<211> LENGTH: 30
<212> TYPE: DNA

-continued

<213> ORGANISM: Artificial Sequence
<220> FEATURE:
<223> OTHER INFORMATION: Synthetic_Cy18 L327T F

<400> SEQUENCE: 275
ccggatttgg agtaacggtt cctcgtggtc                                     30

<210> SEQ ID NO 276
<211> LENGTH: 30
<212> TYPE: DNA
<213> ORGANISM: Artificial Sequence
<220> FEATURE:
<223> OTHER INFORMATION: Synthetic_Cy18 L327T R

<400> SEQUENCE: 276
gaccacgagg aaccgttact ccaaatccgg                                     30

<210> SEQ ID NO 277
<211> LENGTH: 32
<212> TYPE: DNA
<213> ORGANISM: Artificial Sequence
<220> FEATURE:
<223> OTHER INFORMATION: Synthetic_Cy18 F360I F

<400> SEQUENCE: 277
caagtcttca ccagtattat tggcggtgct ac                                  32

<210> SEQ ID NO 278
<211> LENGTH: 32
<212> TYPE: DNA
<213> ORGANISM: Artificial Sequence
<220> FEATURE:
<223> OTHER INFORMATION: Synthetic_Cy18 F360I R

<400> SEQUENCE: 278
gtagcaccgc caataatact ggtgaagact tg                                  32

<210> SEQ ID NO 279
<211> LENGTH: 29
<212> TYPE: DNA
<213> ORGANISM: Artificial Sequence
<220> FEATURE:
<223> OTHER INFORMATION: Synthetic_Cy18 F360L F

<400> SEQUENCE: 279
gtcttcacca gtttgattgg cggtgctac                                      29

<210> SEQ ID NO 280
<211> LENGTH: 29
<212> TYPE: DNA
<213> ORGANISM: Artificial Sequence
<220> FEATURE:
<223> OTHER INFORMATION: Synthetic_Cy18 F360L R

<400> SEQUENCE: 280
gtagcaccgc caatcaaact ggtgaagac                                      29

<210> SEQ ID NO 281
<211> LENGTH: 35
<212> TYPE: DNA
<213> ORGANISM: Artificial Sequence
<220> FEATURE:
<223> OTHER INFORMATION: Synthetic_Cy18 F360M F

<400> SEQUENCE: 281
gcaagtcttc accagtatga ttggcggtgc tacgg                               35

-continued

```
<210> SEQ ID NO 282
<211> LENGTH: 35
<212> TYPE: DNA
<213> ORGANISM: Artificial Sequence
<220> FEATURE:
<223> OTHER INFORMATION: Synthetic_Cy18 F360M R

<400> SEQUENCE: 282
ccgtagcacc gccaatcata ctggtgaaga cttgc                                35

<210> SEQ ID NO 283
<211> LENGTH: 32
<212> TYPE: DNA
<213> ORGANISM: Artificial Sequence
<220> FEATURE:
<223> OTHER INFORMATION: Synthetic_Cy18 F360V F

<400> SEQUENCE: 283
caagtcttca ccagtgttat tggcggtgct ac                                   32

<210> SEQ ID NO 284
<211> LENGTH: 32
<212> TYPE: DNA
<213> ORGANISM: Artificial Sequence
<220> FEATURE:
<223> OTHER INFORMATION: Synthetic_Cy18 F360V R

<400> SEQUENCE: 284
gtagcaccgc caataacact ggtgaagact tg                                   32

<210> SEQ ID NO 285
<211> LENGTH: 42
<212> TYPE: DNA
<213> ORGANISM: Artificial Sequence
<220> FEATURE:
<223> OTHER INFORMATION: Synthetic_Cy18 V165C+A167L F

<400> SEQUENCE: 285
gccccctttg tctctgggtg ctacctcggt gatccgcaac aa                        42

<210> SEQ ID NO 286
<211> LENGTH: 42
<212> TYPE: DNA
<213> ORGANISM: Artificial Sequence
<220> FEATURE:
<223> OTHER INFORMATION: Synthetic_Cy18 V165C+A167L R

<400> SEQUENCE: 286
ttgttgcgga tcaccgaggt agcacccaga gacaaagggg gc                        42

<210> SEQ ID NO 287
<211> LENGTH: 42
<212> TYPE: DNA
<213> ORGANISM: Artificial Sequence
<220> FEATURE:
<223> OTHER INFORMATION: Synthetic_Cy18 V165S+A167C F

<400> SEQUENCE: 287
gccccctttg tctctgggag ctactgcggt gatccgcaac aa                        42

<210> SEQ ID NO 288
<211> LENGTH: 42
<212> TYPE: DNA
<213> ORGANISM: Artificial Sequence
<220> FEATURE:
```

<223> OTHER INFORMATION: Synthetic_Cy18 V165S+A167C R

<400> SEQUENCE: 288
ttgttgcgga tcaccgcagt agctcccaga gacaaagggg gc                    42

<210> SEQ ID NO 289
<211> LENGTH: 37
<212> TYPE: DNA
<213> ORGANISM: Artificial Sequence
<220> FEATURE:
<223> OTHER INFORMATION: Synthetic_Cy18 V165C+A167C F

<400> SEQUENCE: 289
ccccctttgt ctctgggtgc tattgcggtg atccgca                          37

<210> SEQ ID NO 290
<211> LENGTH: 37
<212> TYPE: DNA
<213> ORGANISM: Artificial Sequence
<220> FEATURE:
<223> OTHER INFORMATION: Synthetic_Cy18 V165C+A167C R

<400> SEQUENCE: 290
tgcggatcac cgcaatagca cccagagaca aaggggg                          37

<210> SEQ ID NO 291
<211> LENGTH: 37
<212> TYPE: DNA
<213> ORGANISM: Artificial Sequence
<220> FEATURE:
<223> OTHER INFORMATION: Synthetic_Cy18 V165C+A167I F

<400> SEQUENCE: 291
ccccctttgt ctctgggtgc tacatcggtg atccgca                          37

<210> SEQ ID NO 292
<211> LENGTH: 37
<212> TYPE: DNA
<213> ORGANISM: Artificial Sequence
<220> FEATURE:
<223> OTHER INFORMATION: Synthetic_Cy18 V165C+A167I R

<400> SEQUENCE: 292
tgcggatcac cgatgtagca cccagagaca aaggggg                          37

<210> SEQ ID NO 293
<211> LENGTH: 37
<212> TYPE: DNA
<213> ORGANISM: Artificial Sequence
<220> FEATURE:
<223> OTHER INFORMATION: Synthetic_Cy18 V165S+A167I F

<400> SEQUENCE: 293
ccccctttgt ctctgggagc tacatcggtg atccgca                          37

<210> SEQ ID NO 294
<211> LENGTH: 37
<212> TYPE: DNA
<213> ORGANISM: Artificial Sequence
<220> FEATURE:
<223> OTHER INFORMATION: Synthetic_Cy18 V165S+A167I R

<400> SEQUENCE: 294
tgcggatcac cgatgtagct cccagagaca aaggggg                          37

-continued

```
<210> SEQ ID NO 295
<211> LENGTH: 42
<212> TYPE: DNA
<213> ORGANISM: Artificial Sequence
<220> FEATURE:
<223> OTHER INFORMATION: Synthetic_Cy18 V165S+A167L F

<400> SEQUENCE: 295
gccccctttg tctctgggag ctacctcggt gatccgcaac aa                        42

<210> SEQ ID NO 296
<211> LENGTH: 42
<212> TYPE: DNA
<213> ORGANISM: Artificial Sequence
<220> FEATURE:
<223> OTHER INFORMATION: Synthetic_Cy18 V165S+A167L R

<400> SEQUENCE: 296
ttgttgcgga tcaccgaggt agctcccaga gacaaagggg gc                        42

<210> SEQ ID NO 297
<211> LENGTH: 27
<212> TYPE: DNA
<213> ORGANISM: Artificial Sequence
<220> FEATURE:
<223> OTHER INFORMATION: Synthetic_CyPPO19_XhoI_F

<400> SEQUENCE: 297
ctcgagatgt ctgaggtgga cgttgcc                                         27

<210> SEQ ID NO 298
<211> LENGTH: 27
<212> TYPE: DNA
<213> ORGANISM: Artificial Sequence
<220> FEATURE:
<223> OTHER INFORMATION: Synthetic_CyPPO19_BamHI_R

<400> SEQUENCE: 298
ggatccaggt tggccccecgg aaagata                                        27

<210> SEQ ID NO 299
<211> LENGTH: 27
<212> TYPE: DNA
<213> ORGANISM: Artificial Sequence
<220> FEATURE:
<223> OTHER INFORMATION: Synthetic_CyPPO18_XhoI_F

<400> SEQUENCE: 299
ctcgagatga ttgaagtgga tgtggct                                         27

<210> SEQ ID NO 300
<211> LENGTH: 24
<212> TYPE: DNA
<213> ORGANISM: Artificial Sequence
<220> FEATURE:
<223> OTHER INFORMATION: Synthetic_CyPPO18_BamHI_R

<400> SEQUENCE: 300
ggatcctgat tgtccaccag cgag                                            24

<210> SEQ ID NO 301
<211> LENGTH: 1614
<212> TYPE: DNA
<213> ORGANISM: Artificial Sequence
<220> FEATURE:
<223> OTHER INFORMATION: Synthetic_Gene encoding AtPPO1 of Arabidopsis
      thaliana
```

-continued

<400> SEQUENCE: 301
atggagttat ctcttctccg tccgacgact caatcgcttc ttccgtcgtt ttcgaagccc    60
aatctccgat taaatgttta taagcctctt agactccgtt gttcagtggc cggtggacca    120
accgtcggat cttcaaaaat cgaaggcgga ggaggcacca ccatcacgac ggattgtgtg    180
attgtcggcg gaggtattag tggtctttgc atcgctcagg cgcttgctac taagcatcct    240
gatgctgctc cgaatttaat tgtgaccgag gctaaggatc gtgttggagg caacattatc    300
actcgtgaag agaatggttt tctctgggaa gaaggtccca atagtttca accgtctgat     360 cctatgctca ctatggtggt agatagtggt ttgaaggatg atttggtgtt gggagatcct    420
actgcgccaa ggtttgtgtt gtggaatggg aaattgaggc cggttccatc gaagctaaca    480
gacttaccgt tctttgattt gatgagtatt ggtgggaaga ttagagctgg ttttggtgca    540
cttggcattc gaccgtcacc tccaggtcgt gaagaatctg tggaggagtt tgtacggcgt    600
aacctcggtg atgaggtttt tgagcgcctg attgaaccgt tttgttcagg tgtttatgct    660
ggtgatcctt caaaactgag catgaaagca gcgtttggga aggtttggaa actagagcaa    720
aatggtggaa gcataatagg tggtactttt aaggcaattc aggagaggaa aaacgctccc    780
aaggcagaac gagacccgcg cctgccaaaa ccacagggcc aaacagttgg ttctttcagg    840
aagggacttc gaatgttgcc agaagcaata tctgcaagat taggtagcaa agttaagttg    900
tcttggaagc tctcaggtat cactaagctg gagagcggag gatacaactt aacatatgag    960
actccagatg gtttagtttc cgtgcagagc aaaagtgttg taatgacggt gccatctcat    1020
gttgcaagtg gtctcttgcg ccctctttct gaatctgctg caaatgcact ctcaaaacta    1080
tattacccac cagttgcagc agtatctatc tcgtacccga agaagcaat ccgaacagaa     1140 tgtttgatag atggtgaact aaagggtttt gggcaattgc atccacgcac gcaaggagtt    1200
gaaacattag gaactatcta cagctcctca ctctttccaa atcgcgcacc gcccggaaga    1260
attttgctgt tgaactacat tggcgggtct acaaacaccg gaattctgtc caagtctgaa    1320
ggtgagttag tggaagcagt tgacagagat ttgaggaaaa tgctaattaa gcctaattcg    1380
accgatccac ttaaattagg agttagggta tggcctcaag ccattcctca gtttctagtt    1440
ggtcactttg tatatccttga cacggctaaa tcatctctaa cgtcttcggg ctacgaaggg   1500 ctattttttgg gtggcaatta cgtcgctggt gtagccttag gccggtgtgt agaaggcgca    1560
tatgaaaccg cgattgaggt caacaacttc atgtcacggt acgcttacaa gtaa          1614

<210> SEQ ID NO 302
<211> LENGTH: 155
<212> TYPE: DNA
<213> ORGANISM: Artificial Sequence
<220> FEATURE:
<223> OTHER INFORMATION: Synthetic_Gene encoding Transit Peptide of
      AtPPO1

<400> SEQUENCE: 302
atggagttat tcttctccgt ccgacgactc aatcgcttct tccgtcgttt tcgaagccca    60
atctccgatt aaatgtttat aagcctctta gactccgttg ttcagtggcc ggtggaccaa    120
ccgtcggatc ttcaaaaatc gaaggcggag gaggc                               155

METHODS AND COMPOSITIONS FOR CONFERRING AND/OR ENHANCING HERBICIDE TOLERANCE USING PROTOPORPHYRINOGEN IX OXIDASE OF VARIOUS CYANOBACTERIA OR VARIANT THEREOF

TECHNICAL FIELD

Provided are protoporphyrinogen IX oxidases derived from various organism or variants thereof, and uses of the same for conferring and/or enhancing herbicide tolerance of a plant and/or an alga.

BACKGROUND ART

A porphyrin biosynthetic pathway serves for the synthesis of chlorophyll and heme which play vital roles in plant metabolism, and it takes place in the chloroplast. In this pathway, protoporphyrinogen IX oxidase (hereinafter, referred to as PPO; EC:1.3.3.4) catalyzes the oxidation of protoporphyrinogen IX to protoporphyrin IX. After the oxidation of protoporphyrinogen IX to protoporphyrin IX, protoporphyrin IX binds with magnesium by Mg-chelatase to synthesize chlorophyll, or it binds with iron by Fe-chelatase to synthesize heme.

Therefore, when PPO activity is inhibited, synthesis of chlorophylls and heme is inhibited and the substrate protoporphyrinogen IX leaves the normal porphyrin biosynthetic pathway, resulting in the rapid export of protoporphyrinogen IX from the chloroplast to the cytoplasm, and cytoplasmic accumulation of protoporphyrin IX oxidized by nonspecific peroxidases and auto-oxidation. Accumulated protoporphyrin IX generates highly reactive singlet oxygen ($^1O_2$) in the presence of light and oxygen molecules which destroy cell membrane and rapidly leads to plant cell death. Based on this principle, herbicides inhibiting PPO activity have been developed. Until now, there have been 10 families of PPO-inhibiting herbicides, including pyrimidinediones, diphenyl-ethers, phenylpyrazoles, N-phenylphthalimides, thiadiaz-oles, oxadiazoles, triazinone, triazolinones, oxazolidinediones, and others herbicides, which are classi-fied according to their chemical structures.

Further, in order to prevent effects of these herbicides on the growth of crops while using the herbicides, there is a need to provide herbicide tolerance for the crops.

Meanwhile, algae are photosynthetic organisms that can convert light energy into chemical energy which can be used to synthesize various useful compounds. For example, algae can fix carbon by photosynthesis and convert carbon dioxide into sugar, starch, lipids, fats, or other biomolecules, thereby removing greenhouse gases from the atmosphere. In addi-tion, large-scale cultivation of algae can produce a variety of substances such as industrial enzymes, therapeutic com-pounds and proteins, nutrients, commercial materials and fuel materials.

However, in case of large-scale cultivation of algae in a bioreactor or in an open or enclosed pond, contamination may occur by undesired competent organisms, for example, undesired algae, fungi, rotifer, or zooplankton.

Thus, a technology is needed to harvest desired plants and/or algae on a large scale by treating herbicides at a concentration that would inhibit the growth of competent organisms without herbicide tolerance, after conferring her-bicide tolerance to desired plants and/or algae.

(Patent document 1) U.S. Pat. No. 6,308,458 (2001.10.30)

DISCLOSURE

Technical Problem

In this disclosure, it is found that hemY-type PPO genes derived from prokaryotes and variants thereof show a broad herbicide tolerance to protoporphyrinogen IX oxidase (PPO)-inhibiting herbicides, thereby suggesting that the hemY-type PPO gene can conferr and/or enhance herbicide tolerance when it is introduced in a plant and/or algae.

An embodiment provides a polypeptide comprising an amino acid sequence of SEQ ID NO: 1, SEQ ID NO: 2, or SEQ ID NO: 3.

Another embodiment provides a polypeptide variant com-prising:

(1) an amino acid sequence having modification to SEQ ID NO: 1, wherein the modification comprises deletion and/or substitution with a different amino acid from an original amino acid at one or more amino acids selected from amino acids involved in the interaction of a polypeptide of SEQ ID NO: 1 with a PPO-inhibiting herbicide (e.g., at least one amino acid selected from amino acids positioned on binding sites of the poly-peptide of SEQ ID NO: 1 interacting with PPO-inhib-iting herbicide), or (2) an amino acid sequence having at least 95%, at least 96%, at least 97%, at least 98%, or at least 99% identity with the amino acid sequence (1).

For example, the at least one amino acid selected from the group consisting of amino acids of the polypeptide of SEQ ID NO: 1 involved in the interaction with a PPO-inhibiting herbicide may be at least one amino acid selected from the group consisting of N59, S60, R89, F161, V165, A167, Q184, P303, V305, F324, L327, I340, F360, and I408, of the amino acid sequence of SEQ ID NO: 1.

Another embodiment provides a polypeptide variant com-prising:

(1) an amino acid sequence having modification to SEQ ID NO: 2, wherein the modification comprises deletion and/or substitution with a different amino acid from an original amino acid at one or more amino acids selected from amino acids involved in the interaction of a polypeptide of SEQ ID NO: 2 with a PPO-inhibiting herbicide (e.g., at least one amino acid selected from the amino acids positioned on binding sites of the polypeptide of SEQ ID NO: 2 interacting with PPO-inhibiting herbicide), or (2) an amino acid sequence having at least 95%, at least 96%, at least 97%, at least 98%, or at least 99% sequence identity with the amino acid sequence (1).

For example, the at least one amino acid selected from the group consisting of amino acids of the polypeptide of SEQ ID NO: 2 involved in the interaction with a PPO-inhibiting herbicide may be at least one amino acid selected from the group consisting of N59, S60, R89, F161, V165, A167, Q184, P303, V305, F324, L327, I340, F360, and I408, of the amino acid sequence of SEQ ID NO: 2.

Another embodiment provides a polypeptide variant com-prising:

(1) an amino acid sequence having modification to SEQ ID NO: 3, wherein the modification comprises deletion and/or substitution with a different amino acid from an original amino acid at one or more amino acids selected from amino acids involved in the interaction of a polypeptide of SEQ ID NO: 3 with a PPO-inhibiting herbicide (e.g., at least one amino acid selected from amino acids positioned on binding sites of the polypeptide of SEQ ID NO: 3 interacting with PPO-inhibiting herbicide), or (2) an amino acid sequence having at least 95%, at least 96%, at least 97%, at least 98%, or at least 99% sequence identity with the amino acid sequence (1).

For example, the at least one amino acid selected from the group consisting of amino acids of the polypeptide of SEQ ID NO: 3 involved in the interaction with a PPO-inhibiting herbicide may be at least one amino acid selected from the group consisting of N59, S60, R89, F161, V165, A167, Q184, P303, V305, F324, L327, I340, F360, and I408, of the amino acid sequence of SEQ ID NO: 3.

Another embodiment provides a polynucleotide encoding the polypeptide or the polypeptide variant.

Another embodiment provides a recombinant vector comprising the polynucleotide. The recombinant vector may be used as an expression vector for expressing the polynucleotide in a proper host cell.

Another embodiment provides a recombinant cell comprising the recombinant vector.

Another embodiment provides a composition for conferring and/or enhancing herbicide tolerance of a plant and/or algae, comprising at least one selected from the group consisting of:

(1) at least one selected from the group consisting of a polypeptide of SEQ ID NO: 1, a polypeptide of SEQ ID NO: 2, a polypeptide of SEQ ID NO: 3, a polypeptide variant having modification to SEQ ID NO: 1, a polypeptide variant having modification to SEQ ID NO: 2, a polypeptide variant having modification to SEQ ID NO: 3, and a polypeptide comprising an amino acid sequence having at least 95%, at least 96%, at least 97%, at least 98%, or at least 99% sequence identity with the polypeptide or the polypeptide variant;

(2) a polynucleotide encoding the polypeptide or the polypeptide variant of (1);

(3) a recombinant vector comprising the polynucleotide of (2); and (4) a recombinant cell comprising the recombinant vector of (3).

In a concrete embodiment, the polynucleotide encoding the polypeptide of SEQ ID NO: 1 may comprise the nucleic acid sequence of SEQ ID NO: 80, the polynucleotide encoding the polypeptide of SEQ ID NO: 2 may comprise the nucleic acid sequence of SEQ ID NO: 81; the polynucleotide encoding the polypeptide of SEQ ID NO: 3 may comprise the nucleic acid sequence of SEQ ID NO: 82; but the polynucleotides may not be limited thereto. The polynucleotides may comprise various nucleic acid sequences capable of encoding the amino acid sequence according to codon degeneracy.

The herbicide may be an herbicide inhibiting a protoporphyrinogen IX oxidase activity.

For example, the herbicide may be at least one selected from the group consisting of pyrimidinediones, diphenylethers, phenylpyrazoles, N-phenylphthalimides, phenylesters, thiadiazoles, oxadiazoles, triazinone, triazolinones, oxazolidinediones, and other herbicides, but not be limited thereto.

In a specific embodiment, the herbicide may be at least one selected from the group consisting of tiafenacil, butafenacil, saflufenacil, benzfendizone, fomesafen, oxyfluorfen, aclonifen, acifluorfen, bifenox, ethoxyfen, lactofen, chlomethoxyfen, chlornitrofen, fluoroglycofen-ethyl, halosafen, pyraflufen-ethyl, fluazolate, flumioxazin, cinidon-ethyl, flumiclorac-pentyl, fluthiacet, thidiazimin, oxadiargyl, oxadiazon, carfentrazone, sulfentrazone, trifludimoxazin, azafenidin, pentoxazone, pyraclonil, flufenpyrethyl, profluazol, phenopylate (2,4-dichlorophenyl 1-pyrrolidinecarboxylate), carbamate analogues of phenopylate (for example, O-phenylpyrrolidino- and piperidinocarbamate analoges (refer to "Ujjana B. Nandihalli, Mary V. Duke, Stephen O. Duke, Relationships between molecular properties and biological activities of O-phenyl pyrrolidino- and piperidinocarbamate herbicides., J. Agric. Food Chem., 40(10) 1993-2000, 1992")), agriculturally acceptable salts thereof, and combinations thereof; but not be limited thereto.

The plant may refer to a multicellular eukaryotic organism having photosynthetic capability, which may be a monocotyledonous plant or a dicotyledonous plant, or may be an herbaceous plant or a woody plant. The algae may refer to organisms having photosynthetic capability, which may be eukaryotic algae.

In an embodiment, the plant or algae may be genetically manipulated in order to further comprise a second herbicide tolerance polypeptide or a gene encoding the second herbicide tolerance polypeptide, whereby herbicide tolerance to the second herbicide can be conferred and/or enhanced. The plant or algae, which is genetically manipulated in order to comprise the second herbicide tolerance polypeptide or a gene encoding the second herbicide tolerance polypeptide, may be prepared using the second herbicide tolerance polypeptide or a gene encoding the second herbicide tolerance polypeptide in addition to the above mentioned composition for conferring and/or enhancing herbicide tolerance. Thus, a composition for conferring and/or enhancing tolerance to the herbicide may further comprise the second herbicide tolerance polypeptide or a gene encoding the second herbicide tolerance polypeptide.

Examples of the second herbicide may comprise cell division-inhibiting herbicides, photosynthesis-inhibiting herbicides, amino acid synthesis-inhibiting herbicides, plastid-inhibiting herbicides, cell membrane-inhibiting herbicides, and the like, but not be limited thereto.

In a specific embodiment, the second herbicide may be exemplified by glyphosate, glufosinate, dicamba, 2,4-D (2,4-Dichlorophenoxyacetic acid), isoxaflutole, ALS (acetolactate synthase)-inhibiting herbicide, photosystem II-inhibiting herbicide, or phenylurea-based herbicide, bromoxynil-based herbicide, or combinations thereof, but not be limited thereto.

For example, the second herbicide-tolerant polypeptide may be exemplified by at least one selected from the group consisting of glyphosate herbicide-tolerant EPSPS (glyphosate resistant 5-enolpyruvylshikimate-3-phosphate synthase), GOX (glyphosate oxidase), GAT (glyphosate-N-acetyltransferase) or glyphosate decarboxylase; glufosinate herbicide-tolerant PAT (phosphinothricin-N-acetyltransferase); dicamba herbicide-tolerant DMO (dicamba monooxygenase); 2,4-D herbicide-tolerant 2,4-D monooxygenase or AAD (aryloxyalkanoate dioxygenase); ALS-inhibiting sulfonylurea-based herbicide-tolerant ALS (acetolactate synthase), AHAS (acetohydroxyacid synthase), or AtAHASL (Arabidopsis thaliana acetohydroxyacid synthase large subunit); photosystem II-inhibiting herbicide-tolerant photosystem II protein D1; phenylurea-based herbicide-tolerant cytochrome P450; plastid-inhibiting herbicide-tolerant HPPD (hydroxyphenylpyruvate dioxygenase); bromoxynil herbicide-tolerant nitrilase; and combinations thereof, but not limited thereto.

In addition, the gene encoding the second herbicide-tolerant polypeptide may be exemplified by at least one selected from the group consisting of glyphosate herbicide-tolerant cp4 epsps, mepsps, 2mepsps, goxv247, gat4601 or gat4621 gene; glufosinate herbicide-tolerant bar, pat or pat (SYN) gene; dicamba herbicide-tolerant dmo gene; 2,4-D herbicide-tolerant AAD-1, AAD-12 gene; ALS-inhibiting sulfonylurea-based herbicide-tolerant ALS, GM-HRA, S4-HRA, ZM-HRA, Csr1, Csr1-1, Csr1-2, SurA or SurB; photosystem II-inhibiting herbicide-tolerant psbA gene; phenylurea herbicide-tolerant CYP76B1 gene; isoxaflutole herbicide-tolerant HPPDPF W336 gene and bromoxynil herbicide-tolerant bxn gene; and combinations thereof, but not limited thereto.

Another embodiment provides a transformant of a plant and/or algae having herbicide tolerance, which is transformed with the polynucleotide, or a clone or progeny thereof.

Another embodiment provides a method of preparing a transgenic plant or a transgenic algae having herbicide tolerance or enhanced herbicide tolerance, comprising a step of transforming a plant and/or algae with the polynucleotide.

Another embodiment provides a method of conferring or enhancing herbicide tolerance of a plant and/or algae, comprising a step of transforming a plant and/or algae with the polynucleotide.

The transformation may be performed for an alga, and/or a cell, protoplast, callus, hypocotyl, seed, cotyledon, shoot, or whole body of a plant.

The transformant may be an alga, and/or a cell, protoplast, callus, hypocotyl, seed, cotyledon, shoot, or whole body of a plant. The transformant may comprise a progeny (for example, T1~T8 generations) obtained from the first transformant Another embodiment provides a method of controlling weeds in a cropland comprising:

providing a plant to the cropland, wherein the plant comprises at least one selected from the group consisting of the polypeptide, the polypeptide variant, a polynucleotide encoding the polypeptide, a polynucleotide encoding the polypeptide variant, a recombinant vector comprising the polynucleotide, and a recombinant cell comprising the recombinant vector; and applying an effective amount of a protoporphyrinogen IX oxidase-inhibiting herbicide to the cropland (or to the plant).

In a specific embodiment, the step of applying an effective amount of a protoporphyrinogen IX oxidase-inhibiting herbicide to the cropland (or to the plant) may be performed by applying an effective amount of at least two protoporphyrinogen IX oxidase-inhibiting herbicides sequentially or simultaneously.

In another embodiment, the plant may be genetically manipulated in order to further comprise a second herbicide-tolerant polypeptide or a gene encoding the second herbicide-tolerant polypeptide, and an effective amount of the protoporphyrinogen IX oxidase-inhibiting herbicide and the second herbicide may be applied sequentially or simultaneously.

Another embodiment provides a method of removing an undesired organism from a culture medium, comprising providing an alga to a culture medium, wherein the algae comprises at least one selected from the group consisting of the polypeptide, the variant of the polypeptide, a polynucleotide encoding the polypeptide, a polynucleotide encoding the variant, a recombinant vector comprising the polynucleotide, and a recombinant cell comprising the recombinant vector; and applying an effective amount of a protoporphyrinogen IX oxidase-inhibiting herbicide to the culture medium.

Technical Solution

Provided is a technology of conferring and/or enhancing herbicide tolerance of plants or algae.

As used herein, 'conferring and/or enhancing herbicide tolerance of plants or algae' or 'enhancing herbicide tolerance of plants or algae' may be interpreted as conferring herbicide tolerance to a plant or algae which do not have herbicide tolerance, and/or more strengthening herbicide tolerance of a plant or algae which have herbicide tolerance.

As used herein, 'consisting of a sequence,' consisting essentially of a sequence,' or 'comprising a sequence' may be used in order to cover both cases of comprising described sequence, and/or necessarily comprising the sequence, but it is not intended to exclude comprising further sequence other than the described sequence.

As used herein, the term 'a protein or polypeptide comprising or consisting of an amino acid sequence identified by SEQ ID NO' and 'a gene or polynucleotide comprising or consisting of a nucleic acid sequence identified by SEQ ID NO' may refer to a protein (or polypeptide) or gene (or polynucleotide), which consists essentially of the amino acid sequence or nucleic acid sequence, or which has at least 90%, at least 91%, at least 92%, at least 93%, at least 94%, at least 95%, at least 96%, at least 97%, at least 98%, or at least 99% sequence identity with the amino acid sequence or nucleic acid sequence with maintaining its inherent activity and/or function.

An embodiment provides a polypeptide comprising an amino acid sequence of SEQ ID NO: 1, SEQ ID NO: 2, or SEQ ID NO: 3.

Another embodiment provides a polypeptide variant which is at least one selected from the group consisting of:

a polypeptide variant comprising an amino acid sequence having modification to SEQ ID NO: 1, wherein the modification comprises deletion and/or substitution with a different amino acid from an original amino acid at one or more amino acids selected from amino acids involved in the interaction of a polypeptide of SEQ ID NO: 1 with a PPO-inhibiting herbicide (e.g., at least one amino acid selected from amino acids positioned on binding sites of the polypeptide of SEQ ID NO: 1 interacting with PPO-inhibiting herbicide), or an amino acid sequence having 95% or higher, 96% or higher, 97% or higher, 98% or higher, or 99% or higher sequence identity with the amino acid sequence;

a polypeptide variant comprising an amino acid sequence having modification to SEQ ID NO: 2, wherein the modification comprises deletion and/or substitution with a different amino acid from an original amino acid at one or more amino acids selected from amino acids involved in the interaction of a polypeptide of SEQ ID NO: 2 with a PPO-inhibiting herbicide (e.g., at least one amino acid selected from amino acids positioned on binding sites of the polypeptide of SEQ ID NO: 2 interacting with PPO-inhibiting herbicide), or an amino acid sequence having 95% or higher, 96% or higher, 97% or higher, 98% or higher, or 99% or higher sequence identity with the amino acid sequence; and a polypeptide variant comprising an amino acid sequence having modification to SEQ ID NO: 3, wherein the modification comprises deletion and/or substitution with a different amino acid from an original amino acid at one or more amino acids selected from amino acids involved in the interaction of a polypeptide of SEQ ID NO: 3 with a PPO-inhibiting herbicide (e.g., at least one amino acid selected from amino acids positioned on binding sites of the polypeptide of SEQ ID NO: 3 interacting with PPO-inhibiting herbicide), or an amino acid sequence having 95% or higher, 96% or higher, 97% or higher, 98% or higher, or 99% or higher sequence identity with the amino acid sequence.

In other embodiment, provided is a polynucleotide encoding the polypeptide of SEQ ID NO: 1, 2, or 3, or the polypeptide variant; a recombinant vector comprising the polynucleotide; and a recombinant cell comprising the recombinant vector. The polynucleotide may be designed in order to comprise a codon which is optimized to a cell to be transformed. The optimized codon may be easily known to a person skilled in the art.

Another embodiment provides a composition for conferring and/or enhancing herbicide tolerance of a plant and/or algae, comprising at least one selected from the group consisting of:

(1) at least one selected from the group consisting of a polypeptide of SEQ ID NO: 1, a polypeptide of SEQ ID NO: 2, a polypeptide of SEQ ID NO: 3, a polypeptide variant having modification to SEQ ID NO: 1, a polypeptide variant having modification to SEQ ID NO: 2, a polypeptide variant having modification to SEQ ID NO: 3, and a polypeptide comprising an amino acid sequence having at least 95%, at least 96%, at least 97%, at least 98%, or at least 99% sequence identity with the polypeptide or the polypeptide variant;

(2) a polynucleotide encoding the polypeptide or the polypeptide variant of (1);

(3) a recombinant vector comprising the polynucleotide of (2); and (4) a recombinant cell comprising the recombinant vector of (3).

In a concrete embodiment, the polynucleotide encoding the polypeptide of SEQ ID NO: 1 may comprise the nucleic acid sequence of SEQ ID NO: 80, the polynucleotide encoding the polypeptide of SEQ ID NO: 2 may comprise the nucleic acid sequence of SEQ ID NO: 81; the polynucleotide encoding the polypeptide of SEQ ID NO: 3 may comprise the nucleic acid sequence of SEQ ID NO: 82; but the polynucleotides may not be limited thereto. The polynucleotides may comprise various nucleic acid sequences capable of encoding the amino acid sequence according to codon degeneracy.

In other embodiment, provided is a transformant of a plant and/or algae having herbicide tolerance, the transformant being transformed with a polynucleotide encoding the polypeptide or the polypeptide variant. The polynucleotide may be designed in order to comprise a codon which is optimized to a cell to be transformed. The optimized codon may be easily known to a person skilled in the art.

Another embodiment provides a method of preparing a transgenic plant or a transgenic algae having herbicide tolerance or enhanced herbicide tolerance, comprising a step of transforming a cell, protoplast, callus, hypocotyl, seed, cotyledon, shoot, or whole body of a plant or algae, with the polynucleotide.

Another embodiment provides a method of conferring or enhancing herbicide tolerance of a plant and/or algae, comprising a step of transforming a cell, protoplast, callus, hypocotyl, seed, cotyledon, shoot, or whole body of a plant or algae, with the polynucleotide.

Hereinafter, the present invention is more specifically described:

The polypeptides of SEQ ID NO: 1, 2, and 3 described herein are cyanobacteria-derived PPO proteins having tolerance to a PPO-inhibiting herbicide(s).

Specifically, a PPO protein (comprising GenBank Accession No. CP032152.1) which is derived from *Thermosynechococcus elongatus* PKUAC-SCTE542 strain is provided, and it is designated as CyPPO19 herein, and its amino acid sequence is represented by SEQ ID NO: 1, and a nucleotide sequence of a gene encoding the same is represented by SEQ ID NO: 80.

In addition, a PPO protein (GenBank Accession No. RMH63851.1) which is derived from *Cyanobacteria bacterium* J003 strain is provided, and it is designated as CyPPO20, and its amino acid sequence is represented by SEQ ID NO: 2, and a nucleotide sequence of a gene encoding the same is represented by SEQ ID NO: 81.

In addition, a PPO protein (GenBank Accession No. BAY51976.1) which is derived from *Thermosynechococcus vulcanus* NIES-2134 strain is provided, and it is designated as CyPPO18, and its amino acid sequence is represented by SEQ ID NO: 3, and a nucleotide sequence of a gene encoding the same is represented by SEQ ID NO: 82.

Herein, the polypeptide and variants of polypeptide may also be expressed respectively as herbicide-tolerant PPO protein or herbicide-tolerant PPO protein variant having tolerance to a PPO-inhibiting herbicide(s). In addition, as used herein, the wording "a herbicide-tolerant PPO or its variant" may be used so as to refer to the above herbicide-tolerant PPO protein or herbicide-tolerant PPO protein variant, a herbicide-tolerant PPO protein-coding gene, or a herbicide-tolerant PPO protein variant-coding gene, or a combination thereof.

*Cyanobacteria*-derived PPO proteins may possess excellent enzymatic activities compared to plant-derived PPO proteins, and capable of conferring tolerance to PPO-inhibiting herbicides. In addition, when the cyanobacteria-derived PPO proteins are modified by amino acid mutation (variation) within a range capable of maintaining their overall enzymatic activities, their tolerance to PPO-inhibiting herbicides can be more enhanced compared to those of wild type PPO proteins. Such amino acid mutation may comprise substitution, deletion, addition and/or addition of one or more amino acids selected from amino acid residues of interaction sites of the PPO proteins where the PPO proteins interact with herbicides.

The PPO protein variant will be described in more detail as follows.

An embodiment provides a polypeptide variant, which is a variant of a polypeptide of SEQ ID NO: 1 (CyPPO19), the variant comprising or consisting of an amino acid sequence having modification to SEQ ID NO: 1, wherein the modification comprises deletion and/or substitution with a different amino acid from an original amino acid (i.e., a corresponding amino acid of a wild type) at one or more amino acids selected from amino acids of SEQ ID NO: 1 involved in the interaction with a PPO-inhibiting herbicide (e.g., at least one amino acid selected from the amino acids positioned on binding sites of the polypeptide of SEQ ID NO: 1 interacting with PPO-inhibiting herbicide), or an amino acid sequence having 95% or higher, 96% or higher, 97% or higher, 98% or higher, or 99% or higher sequence identity with the amino acid sequence.

Another embodiment provides a polypeptide variant, which is a variant of a polypeptide of SEQ ID NO: 2 (CyPPO20), the variant comprising or consisting of an amino acid sequence having modification to SEQ ID NO: 2, wherein the modification comprises deletion and/or substitution with a different amino acid from an original amino acid (i.e., a corresponding amino acid of a wild type) at one or more amino acids selected from amino acids of SEQ ID NO: 2 involved in the interaction with a PPO-inhibiting herbicide (e.g., at least one amino acid selected from the amino acids positioned on binding sites of the polypeptide of SEQ ID NO: 2 interacting with PPO-inhibiting herbicide), or an amino acid sequence having 95% or higher, 96% or higher, 97% or higher, 98% or higher, or 99% or higher sequence identity with the amino acid sequence.

Another embodiment provides a polypeptide variant, which is a variant of a polypeptide of SEQ ID NO: 3 (CyPPO18), the variant comprising or consisting of an amino acid sequence having modification to SEQ ID NO: 3, wherein the modification comprises deletion and/or substitution with a different amino acid from an original amino acid (i.e., a corresponding amino acid of a wild type) at one or more amino acids selected from amino acids of SEQ ID NO: 3 involved in the interaction with a PPO-inhibiting herbicide (e.g., at least one amino acid selected from the amino acids positioned on binding sites of the polypeptide of SEQ ID NO: 3 interacting with PPO-inhibiting herbicide), or an amino acid sequence having 95% or higher, 96% or higher, 97% or higher, 98% or higher, or 99% or higher sequence identity with the amino acid sequence.

The amino acid of SEQ ID NO: 1, SEQ ID NO: 2, or SEQ ID NO: 3 (e.g., at least one residue selected from the group consisting of amino acids positioned on binding sites to PPO-inhibiting herbicides of polypeptide of SEQ ID NO: 1, SEQ ID NO: 2, or SEQ ID NO: 3) to be deleted and/or substituted with other amino acid that is different from the original amino acid may be at least one selected from the group consisting of N59 (referring to "N(Asn) at the $59^{th}$ position; the expression of the following amino acid residues is interpreted in this manner), S60, R89, F161, V165, A167, Q184, P303, V305, F324, L327, I340, F360, and I408, for example, at least one, at least two, at least three, at least four, at least five, at least six, or all of R89, V165, A167, V305, L327, F360, and I408, of the amino acid sequence of SEQ ID NO: 1, SEQ ID NO: 2, or SEQ ID NO: 3.

In one specific embodiment, the polypeptide variant may comprise an amino acid sequence having modification to SEQ ID NO: 1, SEQ ID NO: 2, or SEQ ID NO: 3, wherein one or more amino acid residues selected from the group consisting of N59, S60, R89, F161, V165, A167, Q184, P303, V305, F324, L327, I340, F360, and I408 (for example, at least one, at least two, at least three, at least four, at least five, at least six, or all of R89, V165, A167, V305, L327, F360, and I408) of the amino acid sequence of SEQ ID NO: 1, SEQ ID NO: 2, or SEQ ID NO: 3 are respectively and independently deleted or substituted with an amino acid selected from the group consisting of M(Met), V(Val), I(Ile), T(Thr), L(Leu), C(Cys), A(Ala), S(Ser), F(Phe), P(Pro), W(Trp), N(Asn), Q(Gln), G(Gly), Y(Tyr), D(Asp), E(Glu), R(Arg), H(His), K(Lys), and the like, which is different from the amino acid at the corresponding position in the wild type (for example, substituted with an amino acid selected from the group consisting of M(Met), V(Val), I(Ile), T(Thr), L(Leu), C(Cys), A(Ala), S(Ser), R(Arg), W(Trp), and the like, which is different from the amino acid at the corresponding position in the wild type); or an amino acid sequence having at least 95%, at least 96%, at least 97%, at least 98%, or at least 99% sequence identity with the amino acid sequence.

For example, the polypeptide variant may comprise:

(a) an amino acid sequence having modification to SEQ ID NO: 1, SEQ ID NO: 2, or SEQ ID NO: 3, wherein the modification comprises at least one, at least two, at least three, at least four, at least five, at least six, or all of amino acid mutations selected from the group consisting of:

(i) F360M (referring to a variant or mutation wherein "the amino acid residue at the $360^{th}$ position is substituted from F(Phe) to M(Met)"; the expression of the following amino acid mutations is interpreted in this manner), F360V, F360I, F360T, or F360L, (ii) A167C, A167L, or A167I, (iii) V305M or V305L, (iv) R89A, (v) V165S or V165C, (vi) L327T, and (vii) I408R, or I408W, in the amino acid sequence of SEQ ID NO: 1; or (b) an amino acid sequence having at least 95%, at least 96%, at least 97%, at least 98%, or at least 99% sequence identity with the amino acid sequence (a).

More specifically, the variant of polypeptide may comprise an amino acid sequence having modification to SEQ ID NO: 1, SEQ ID NO: 2, or SEQ ID NO: 3, or an amino acid sequence having at least 95%, at least 96%, at least 97%, at least 98%, or at least 99% sequence identity with the amino acid sequence, wherein the modification comprises the following amino acid mutation: R89A, V165C, V165S, A167C, A167I, A167L, V305L, V305M, L327T, F360M, F360I, F360L, F360V, F360T, I408R, I408W, R89A+ V165C (referring to a variant or mutation comprising all of substitution of the $89^{th}$ residue from R to A and substitution of the $165^{th}$ residue from V to C; the expression of the following two or more amino acid mutations is interpreted in this manner), R89A+V165S, R89A+A167C, R89A+ A167I, R89A+A167L, R89A+V305L, R89A+V305M, R89A+L327T, R89A+F360M, R89A+F360I, R89A+F360L, R89A+F360V, R89A+F360T, R89A+I408R, V165C+ A167C, V165C+A167I, V165C+A167L, V165C+V305L, V165C+V305M, V165C+L327T, V165C+F360M, V165C+ F360I, V165C+F360L, V165C+F360V, V165C+F360T, V165C+I408R, V165S+A167C, V165S+A167I, V165S+ A167L, V165S+V305L, V165S+V305M, V165S+L327T, V165S+F360M, V165S+F360I, V165S+F360L, V165S+ F360V, V165S+F360T, V165S+I408W, A167C+V305L, A167C+V305M, A167C+L327T, A167C+F360M, A167C+ F360I, A167C+F360L, A167C+F360V, A167C+F360T, A167C+I408R, A167I+V305L, A167I+V305M, A167I+ L327T, A167I+F360M, A167I+F360I, A167I+F360L, A167I+F360V, A167I+F360T, A167I+I408W, A167L+ V305L, A167L+V305M, A167L+L327T, A167L+F360M, A167L+F360I, A167L+F360L, A167L+F360V, A167L+ F360T, A167L+I408R, V305L+L327T, V305L+F360M, V305L+F360I, V305L+F360L, V305L+F360V, V305L+ F360T, V305L+I408W, V305M+L327T, V305M+F360M, V305M+F360I, V305M+F360L, V305M+F360V, V305M+ F360T, V305M+I408R, L327T+F360M, L327T+F360I, L327T+F360L, L327T+F360V, L327T+F360T, L327T+ I408R, F360M+I408R, F360I+I408R, F360L+I408W, F360V+I408W, F360T+I408W, R89A+V165C+A167C, R89A+V165C+A167I, R89A+V165C+A167L, R89A+ V165C+V305L, R89A+V165C+V305M, R89A+V165C+ L327T, R89A+V165C+F360M, R89A+V165C+F360I, R89A+V165C+F360L, R89A+V165C+F360V, R89A+ V165C+F360T, R89A+V165C+I408R, R89A+V165S+ A167C, R89A+V165S+A167I, R89A+V165S+A167L, R89A+V165S+V305L, R89A+V165S+V305M, R89A+

V165S+L327T, R89A+V165S+F360M, R89A+V165S+
F360I, R89A+V165S+F360L, R89A+V165S+F360V,
R89A+V165S+F360T, R89A+V165S+I408W, R89A+
A167C+V305L, R89A+A167C+V305M, R89A+A167C+
L327T, R89A+A167C+F360M, R89A+A167C+F360I,
R89A+A167C+F360L, R89A+A167C+F360V, R89A+
A167C+F360T, R89A+A167C+I408R, R89A+A167I+
V305L, R89A+A167I+V305M, R89A+A167I+L327T,
R89A+A167I+F360M, R89A+A167I+F360I, R89A+
A167I+F360L, R89A+A167I+F360V, R89A+A167I+
F360T, R89A+A167I+I408W, R89A+A167L+V305L,
R89A+A167L+V305M, R89A+A167L+L327T, R89A+
A167L+F360M, R89A+A167L+F360I, R89A+A167L+
F360L, R89A+A167L+F360V, R89A+A167L+F360T,
R89A+A167L+I408R, R89A+V305L+L327T, R89A+
V305L+F360M, R89A+V305L+F360I, R89A+V305L+
F360L, R89A+V305L+F360V, R89A+V305L+F360T,
R89A+V305L+I408W, R89A+V305M+L327T, R89A+
V305M+F360M, R89A+V305M+F360I, R89A+V305M+
F360L, R89A+V305M+F360V, R89A+V305M+F360T,
R89A+V305M+I408R, R89A+L327T+F360M, R89A+
L327T+F360I, R89A+L327T+F360L, R89A+L327T+
F360V, R89A+L327T+F360T, R89A+L327T+I408R,
R89A+F360M+I408R, R89A+F360I+I408R, R89A+
F360L+I408W, R89A+F360V+I408W, R89A+F360T+
I408W, V165C+A167C+V305L, V165C+A167C+V305M,
V165C+A167C+L327T, V165C+A167C+F360M, V165C+
A167C+F360I, V165C+A167C+F360L, V165C+A167C+
F360V, V165C+A167C+F360T, V165C+A167C+I408R,
V165C+A167I+V305L, V165C+A167I+V305M, V165C+
A167I+L327T, V165C+A167I+F360M, V165C+A167I+
F360I, V165C+A167I+F360L, V165C+A167I+F360V,
V165C+A167I+F360T, V165C+A167I+I408W, V165C+
A167L+V305L, V165C+A167L+V305M, V165C+A167L+
L327T, V165C+A167L+F360M, V165C+A167L+F360I,
V165C+A167L+F360L, V165C+A167L+F360V, V165C+
A167L+F360T, V165C+A167L+I408R, V165C+V305L+
L327T, V165C+V305L+F360M, V165C+V305L+F360I,
V165C+V305L+F360L, V165C+V305L+F360V, V165C+
V305L+F360T, V165C+V305L+F360T, V165C+V305L+
I408W, V165C+V305M+L327T, V165C+V305M+F360M,
V165C+V305M+F360I, V165C+V305M+F360L, V165C+
V305M+F360V, V165C+V305M+F360T, V165C+V305M+
I408R, V165C+L327T+F360M, V165C+L327T+F360I,
V165C+L327T+F360L, V165C+L327T+F360V, V165C+
L327T+F360T, V165C+L327T+I408R, V165C+F360M+
I408R, V165C+F360I+I408R, V165C+F360L+I408W,
V165C+F360V+I408W, V165C+F360T+I408W, V165S+
A167C+V305L, V165S+A167C+V305M, V165S+A167C+
L327T, V165S+A167C+F360M, V165S+A167C+F360I,
V165S+A167C+F360L, V165S+A167C+F360V, V165S+
A167C+F360T, V165S+A167C+I408R, V165S+A167I+
V305L, V165S+A167I+V305M, V165S+A167I+L327T,
V165S+A167I+F360M, V165S+A167I+F360I, V165S+
A167I+F360L, V165S+A167I+F360V, V165S+A167I+
F360T, V165S+A167I+I408W, V165S+A167L+V305L,
V165S+A167L+V305M, V165S+A167L+L327T, V165S+
A167L+F360M, V165S+A167L+F360I, V165S+A167L+
F360L, V165S+A167L+F360V, V165S+A167L+F360T,
V165S+A167L+I408R, V165S+V305L+L327T, V165S+
V305L+F360M, V165S+V305L+F360I, V165S+V305L+
F360L, V165S+V305L+F360V, V165S+V305L+F360T,
V165S+V305L+I408W, V165S+V305M+L327T, V165S+
V305M+F360M, V165S+V305M+F360I, V165S+V305M+
F360L, V165S+V305M+F360V, V165S+V305M+F360T,
V165S+V305M+I408R, V165S+L327T+F360M, V165S+
L327T+F360I, V165S+L327T+F360L, V165S+L327T+

F360V, V165S+L327T+F360T, V165S+L327T+I408R,
V165S+F360M+I408R, V165S+F360I+I408R, V165S+
F360L+I408W, V165S+F360V+I408W, V165S+F360T+
I408W, A167C+V305L+L327T, A167C+V305L+F360M,
A167C+V305L+F360I, A167C+V305L+F360L, A167C+
V305L+F360V, A167C+V305L+F360T, A167C+V305L+
I408W, A167C+V305M+L327T, A167C+V305M+F360M,
A167C+V305M+F360I, A167C+V305M+F360L, A167C+
V305M+F360V, A167C+V305M+F360T, A167C+V305M+
I408R, A167C+L327T+F360M, A167C+L327T+F360I,
A167C+L327T+F360L, A167C+L327T+F360V, A167C+
L327T+F360T, A167C+L327T+I408R, A167C+F360M+
I408R, A167C+F360I+I408R, A167C+F360L+I408W,
A167C+F360V+I408W, A167C+F360T+I408W, A167I+
V305L+L327T, A167I+V305L+F360M, A167I+V305L+
F360I, A167I+V305L+F360L, A167I+V305L+F360V,
A167I+V305L+F360T, A167I+V305L+I408W, A167I+
V305M+L327T, A167I+V305M+F360M, A167I+V305M+
F360I, A167I+V305M+F360L, A167I+V305M+F360V,
A167I+V305M+F360T, A167I+V305M+I408R, A167I+
L327T+F360M, A167I+L327T+F360I, A167I+L327T+
F360L, A167I+L327T+F360V, A167I+L327T+F360T,
A167I+L327T+I408R, A167I+F360M+I408R, A167I+
F360I+I408R, A167I+F360L+I408W, A167I+F360V+
I408W, A167I+F360T+I408W, A167L+V305L+L327T,
A167L+V305L+F360M, A167L+V305L+F360I, A167L+
V305L+F360L, A167L+V305L+F360V, A167L+V305L+
F360T, A167L+V305L+I408W, A167L+V305M+L327T,
A167L+V305M+F360M, A167L+V305M+F360I, A167L+
V305M+F360L, A167L+V305M+F360V, A167L+V305M+
F360T, A167L+V305M+I408R, A167L+L327T+F360M,
A167L+L327T+F360I, A167L+L327T+F360L, A167L+
L327T+F360V, A167L+L327T+F360T, A167L+L327T+
I408R, A167L+F360M+I408R, A167L+F360I+I408R,
A167L+F360L+I408W, A167L+F360V+I408W, A167L+
F360T+I408W, V305L+L327T+F360M, V305L+L327T+
F360I, V305L+L327T+F360L, V305L+L327T+F360V,
V305L+L327T+F360T, V305L+L327T+I408R, V305L+
F360M+I408R, V305L+F360I+I408R, V305L+F360L+
I408W, V305L+F360V+I408W, V305L+F360T+I408W,
V305M+L327T+F360M, V305M+L327T+F360I, V305M+
L327T+F360L, V305M+L327T+F360V, V305M+L327T+
F360T, V305M+L327T+I408R, V305M+F360M+I408R,
V305M+F360I+I408R, V305M+F360L+I408W, V305M+
F360V+I408W, V305M+F360T+I408W, L327T+F360M+
I408R, L327T+F360I+I408R, L327T+F360T+I408R,
L327T+F360L+I408W, L327T+F360V+I408W, L327T+
F360T+I408W, R89A+V165C+A167C+V305L, R89A+
V165C+A167C+V305M, R89A+V165C+A167C+L327T,
R89A+V165C+A167C+F360M, R89A+V165C+A167C+
F360I, R89A+V165C+A167C+F360L, R89A+V165C+
A167C+F360V, R89A+V165C+A167C+F360T, R89A+
V165C+A167C+I408R, R89A+V165C+A167I+V305L,
R89A+V165C+A167I+V305M, R89A+V165C+A167I+
L327T, R89A+V165C+A167I+F360M, R89A+V165C+
A167I+F360I, R89A+V165C+A167I+F360L, R89A+
V165C+A167I+F360V, R89A+V165C+A167I+I408W,
R89A+V165C+A167L+V305L, R89A+V165C+A167L+
V305M, R89A+V165C+A167L+L327T, R89A+V165C+
A167L+F360M, R89A+V165C+A167L+F360I, R89A+
V165C+A167L+F360L, R89A+V165C+A167L+F360V,
R89A+V165C+A167L+I408R, R89A+V165C+V305L+
L327T, R89A+V165C+V305L+F360M, R89A+V165C+
V305L+F360I, R89A+V165C+V305L+F360L, R89A+
V165C+V305L+F360V, R89A+V165C+V305L+I408W,
R89A+V165C+V305M+L327T, R89A+V165C+V305M+
F360M, R89A+V165C+V305M+F360I, R89A+V165C+

V305M+F360L, R89A+V165C+V305M+F360V, R89A+
V165C+V305M+I408R, R89A+V165C+L327T+F360M,
R89A+V165C+L327T+F360I, R89A+V165C+L327T+
F360L, R89A+V165C+L327T+F360V, R89A+V165C+
L327T+I408R, R89A+V165C+F360M+I408R, R89A+
V165C+F360I+I408R, R89A+V165C+F360L+I408W,
R89A+V165C+F360V+I408W, R89A+V165S+A167C+
V305L, R89A+V165S+A167C+V305M, R89A+V165S+
A167C+L327T, R89A+V165S+A167C+F360M, R89A+
V165S+A167C+F360I, R89A+V165S+A167C+F360L,
R89A+V165S+A167C+F360V, R89A+V165S+A167C+
I408R, R89A+V165S+A167I+V305L, R89A+V165S+
A167I+V305M, R89A+V165S+A167I+L327T, R89A+
V165S+A167I+F360M, R89A+V165S+A167I+F360I,
R89A+V165S+A167I+F360L, R89A+V165S+A167I+
F360V, R89A+V165S+A167I+I408W, R89A+V165S+
A167L+V305L, R89A+V165S+A167L+V305M, R89A+
V165S+A167L+L327T, R89A+V165S+A167L+F360M,
R89A+V165S+A167L+F360I, R89A+V165S+A167L+
F360L, R89A+V165S+A167L+F360V, R89A+V165S+
A167L+I408R, R89A+V165S+V305L+L327T, R89A+
V165S+V305L+F360M, R89A+V165S+V305L+F360I,
R89A+V165S+V305L+F360L, R89A+V165S+V305L+
F360V, R89A+V165S+V305L+I408W, R89A+V165S+
V305M+L327T, R89A+V165S+V305M+F360M, R89A+
V165S+V305M+F360I, R89A+V165S+V305M+F360L,
R89A+V165S+V305M+F360V, R89A+V165S+V305M+
I408R, R89A+V165S+L327T+F360M, R89A+V165S+
L327T+F360I, R89A+V165S+L327T+F360L, R89A+
V165S+L327T+F360V, R89A+V165S+L327T+I408R,
R89A+V165S+F360M+I408R, R89A+V165S+F360I+
I408R, R89A+V165S+F360L+I408W, R89A+V165S+
F360V+I408W, R89A+A167C+V305L+L327T, R89A+
A167C+V305L+F360M, R89A+A167C+V305L+F360I,
R89A+A167C+V305L+F360L, R89A+A167C+V305L+
F360V, R89A+A167C+V305L+I408W, R89A+A167C+
V305M+L327T, R89A+A167C+V305M+F360M, R89A+
A167C+V305M+F360I, R89A+A167C+V305M+F360L,
R89A+A167C+V305M+F360V, R89A+A167C+V305M+
I408R, R89A+A167C+L327T+F360M, R89A+A167C+
L327T+F360I, R89A+A167C+L327T+F360L, R89A+
A167C+L327T+F360V, R89A+A167C+L327T+I408R,
R89A+A167C+F360M+I408R, R89A+A167C+F360I+
I408R, R89A+A167C+F360L+I408W, R89A+A167C+
F360V+I408W, R89A+A167I+V305L+L327T, R89A+
A167I+V305L+F360M, R89A+A167I+V305L+F360I,
R89A+A167I+V305L+F360L, R89A+A167I+V305L+
F360V, R89A+A167I+V305L+I408W, R89A+A167I+
V305M+L327T, R89A+A167I+V305M+F360M, R89A+
A167I+V305M+F360I, R89A+A167I+V305M+F360L,
R89A+A167I+V305M+F360V, R89A+A167I+V305M+
I408R, R89A+A167I+L327T+F360M, R89A+A167I+
L327T+F360I, R89A+A167I+L327T+F360L, R89A+
A167I+L327T+F360V, R89A+A167I+L327T+I408R,
R89A+A167I+F360M+I408R, R89A+A167I+F360I+
I408R, R89A+A167I+F360L+I408W, R89A+A167I+
F360V+I408W, R89A+A167L+V305L+L327T, R89A+
A167L+V305L+F360M, R89A+A167L+V305L+F360I,
R89A+A167L+V305L+F360L, R89A+A167L+V305L+
F360V, R89A+A167L+V305L+I408W, R89A+A167L+
V305M+L327T, R89A+A167L+V305M+F360M, R89A+
A167L+V305M+F360I, R89A+A167L+V305M+F360L,
R89A+A167L+V305M+F360V, R89A+A167L+V305M+
I408R, R89A+A167L+L327T+F360M, R89A+A167L+
L327T+F360I, R89A+A167L+L327T+F360L, R89A+
A167L+L327T+F360V, R89A+A167L+L327T+I408R,
R89A+A167L+F360M+I408R, R89A+A167L+F360I+

I408R, R89A+A167L+F360L+I408W, R89A+A167L+
F360V+I408W, R89A+V305L+L327T+F360M, R89A+
V305L+L327T+F360I, R89A+V305L+L327T+F360L,
R89A+V305L+L327T+F360V, R89A+V305L+L327T+
I408R, R89A+V305L+F360M+I408R, R89A+V305L+
F360I+I408R, R89A+V305L+F360L+I408W, R89A+
V305L+F360V+I408W, R89A+V305M+L327T+F360M,
R89A+V305M+L327T+F360I, R89A+V305M+L327T+
F360L, R89A+V305M+L327T+F360V, R89A+V305M+
L327T+I408R, R89A+V305M+F360M+I408R, R89A+
V305M+F360I+I408R, R89A+V305M+F360L+I408W,
R89A+V305M+F360V+I408W, R89A+L327T+F360M+
I408R, R89A+L327T+F360I+I408R, R89A+L327T+
F360L+I408W, R89A+L327T+F360V+I408W, V165C+
A167C+V305L+L327T, V165C+A167C+V305L+F360M,
V165C+A167C+V305L+F360I, V165C+A167C+V305L+
F360L, V165C+A167C+V305L+F360V, V165C+A167C+
V305L+I408W, V165C+A167C+V305M+L327T, V165C+
A167C+V305M+F360M, V165C+A167C+V305M+F360I,
V165C+A167C+V305M+F360L, V165C+A167C+
V305M+F360V, V165C+A167C+V305M+I408R, V165C+
A167C+L327T+F360M, V165C+A167C+L327T+F360I,
V165C+A167C+L327T+F360L, V165C+A167C+L327T+
F360V, V165C+A167C+L327T+I408R, V165C+A167C+
F360M+I408R, V165C+A167C+F360I+I408R, V165C+
A167C+F360L+I408W, V165C+A167C+F360V+I408W,
V165C+A167I+V305L+L327T, V165C+A167I+V305L+
F360M, V165C+A167I+V305L+F360I, V165C+A167I+
V305L+F360L, V165C+A167I+V305L+F360V, V165C+
A167I+V305L+I408W, V165C+A167I+V305M+L327T,
V165C+A167I+V305M+F360M, V165C+A167I+V305M+
F360I, V165C+A167I+V305M+F360L, V165C+A167I+
V305M+F360V, V165C+A167I+V305M+I408R, V165C+
A167I+L327T+F360M, V165C+A167I+L327T+F360I,
V165C+A167I+L327T+F360L, V165C+A167I+L327T+
F360V, V165C+A167I+L327T+I408R, V165C+A167I+
F360M+I408R, V165C+A167I+F360I+I408R, V165C+
A167I+F360L+I408W, V165C+A167I+F360V+I408W,
V165C+A167L+V305L+L327T, V165C+A167L+V305L+
F360M, V165C+A167L+V305L+F360I, V165C+A167L+
V305L+F360L, V165C+A167L+V305L+F360V, V165C+
A167L+V305L+I408W, V165C+A167L+V305M+L327T,
V165C+A167L+V305M+F360M, V165C+A167L+
V305M+F360I, V165C+A167L+V305M+F360L, V165C+
A167L+V305M+F360V, V165C+A167L+V305M+I408R,
V165C+A167L+L327T+F360M, V165C+A167L+L327T+
F360I, V165C+A167L+L327T+F360L, V165C+A167L+
L327T+F360V, V165C+A167L+L327T+I408R, V165C+
A167L+F360M+I408R, V165C+A167L+F360I+I408R,
V165C+A167L+F360L+I408W, V165C+A167L+F360V+
I408W, V165C+V305L+L327T+F360M, V165C+V305L+
L327T+F360I, V165C+V305L+L327T+F360L, V165C+
V305L+L327T+F360V, V165C+V305L+L327T+I408R,
V165C+V305L+F360M+I408R, V165C+V305L+F360I+
I408R, V165C+V305L+F360L+I408W, V165C+V305L+
F360V+I408W, V165C+V305M+L327T+F360M, V165C+
V305M+L327T+F360I, V165C+V305M+L327T+F360L,
V165C+V305M+L327T+F360V, V165C+V305M+L327T+
I408R, V165C+V305M+F360M+I408R, V165C+V305M+
F360I+I408R, V165C+V305M+F360L+I408W, V165C+
V305M+F360V+I408W, V165C+L327T+F360M+I408R,
V165C+L327T+F360I+I408R, V165C+L327T+F360L+
I408W, V165C+L327T+F360V+I408W, V165C+A167C+
V305L+L327T, V165S+A167C+V305L+F360M, V165S+
A167C+V305L+F360I, V165S+A167C+V305L+F360L,
V165S+A167C+V305L+F360V, V165S+A167C+V305L+
I408W, V165S+A167C+V305M+L327T, V165S+A167C+

V305M+F360M, V165S+A167C+V305M+F360I, V165S+A167C+V305M+F360L, V165S+A167C+V305M+F360V, V165S+A167C+V305M+I408R, V165S+A167C+L327T+F360M, V165S+A167C+L327T+F360I, V165S+A167C+L327T+F360L, V165S+A167C+L327T+F360V, V165S+A167C+L327T+I408R, V165S+A167C+F360M+I408R, V165S+A167C+F360I+I408R, V165S+A167C+F360L+I408W, V165S+A167C+F360V+I408W, V165S+A167I+V305L+L327T, V165S+A167I+V305L+F360M, V165S+A167I+V305L+F360I, V165S+A167I+V305L+F360L, V165S+A167I+V305L+F360V, V165S+A167I+V305L+I408W, V165S+A167I+V305M+L327T, V165S+A167I+V305M+F360M, V165S+A167I+V305M+F360I, V165S+A167I+V305M+F360L, V165S+A167I+V305M+F360V, V165S+A167I+V305M+I408R, V165S+A167I+L327T+F360M, V165S+A167I+L327T+F360I, V165S+A167I+L327T+F360L, V165S+A167I+L327T+F360V, V165S+A167I+L327T+I408R, V165S+A167I+F360M+I408R, V165S+A167I+F360I+I408R, V165S+A167I+F360L+I408W, V165S+A167I+F360V+I408W, V165S+A167L+V305L+L327T, V165S+A167L+V305L+F360M, V165S+A167L+V305L+F360I, V165S+A167L+V305L+F360L, V165S+A167L+V305L+F360V, V165S+A167L+V305L+I408W, V165S+A167L+V305M+L327T, V165S+A167L+V305M+F360M, V165S+A167L+V305M+F360I, V165S+A167L+V305M+F360L, V165S+A167L+V305M+F360V, V165S+A167L+V305M+I408R, V165S+A167L+L327T+F360M, V165S+A167L+L327T+F360I, V165S+A167L+L327T+F360L, V165S+A167L+L327T+F360V, V165S+A167L+L327T+I408R, V165S+A167L+F360M+I408R, V165S+A167L+F360I+I408R, V165S+A167L+F360L+I408W, V165S+A167L+F360V+I408W, V165S+V305L+L327T+F360M, V165S+V305L+L327T+F360I, V165S+V305L+L327T+F360L, V165S+V305L+L327T+F360V, V165S+V305L+L327T+I408R, V165S+V305L+F360M+I408R, V165S+V305L+F360I+I408R, V165S+V305L+F360L+I408W, V165S+V305L+F360V+I408W, V165S+V305M+L327T+F360M, V165S+V305M+L327T+F360I, V165S+V305M+L327T+F360L, V165S+V305M+L327T+F360V, V165S+V305M+L327T+I408R, V165S+V305M+F360M+I408R, V165S+V305M+F360I+I408R, V165S+V305M+F360L+I408W, V165S+V305M+F360V+I408W, V165S+L327T+F360M+I408R, V165S+L327T+F360I+I408R, V165S+L327T+F360L+I408W, V165S+L327T+F360V+I408W, A167C+V305L+L327T+F360M, A167C+V305L+L327T+F360I, A167C+V305L+L327T+F360L, A167C+V305L+L327T+F360V, A167C+V305L+L327T+I408R, A167C+V305L+F360M+I408R, A167C+V305L+F360I+I408R, A167C+V305L+F360L+I408W, A167C+V305L+F360V+I408W, A167C+V305M+L327T+F360M, A167C+V305M+L327T+F360I, A167C+V305M+L327T+F360L, A167C+V305M+L327T+F360V, A167C+V305M+L327T+I408R, A167C+V305M+F360M+I408R, A167C+V305M+F360I+I408R, A167C+V305M+F360L+I408W, A167C+V305M+F360V+I408W, A167C+L327T+F360M+I408R, A167C+L327T+F360I+I408R, A167C+L327T+F360L+I408W, A167C+L327T+F360V+I408W, A167I+V305L+L327T+F360M, A167I+V305L+L327T+F360I, A167I+V305L+L327T+F360L, A167I+V305L+L327T+F360V, A167I+V305L+L327T+I408R, A167I+V305L+F360M+I408R, A167I+V305L+F360I+I408R, A167I+V305L+F360L+I408W, A167I+V305L+F360V+I408W, A167I+V305M+L327T+F360M, A167I+V305M+L327T+F360I, A167I+V305M+L327T+F360L, A167I+V305M+L327T+F360V, A167I+V305M+L327T+I408R, A167I+V305M+F360M+I408R, A167I+V305M+F360I+I408R, A167I+V305M+F360L+I408W, A167I+V305M+F360V+

I408W, A167I+L327T+F360M+I408R, A167I+L327T+F360I+I408R, A167I+L327T+F360L+I408W, A167I+L327T+F360V+I408W, A167L+V305L+L327T+F360M, A167L+V305L+L327T+F360I, A167L+V305L+L327T+F360L, A167L+V305L+L327T+F360V, A167L+V305L+L327T+I408R, A167L+V305L+F360M+I408R, A167L+V305L+F360I+I408R, A167L+V305L+F360L+I408W, A167L+V305L+F360V+I408W, A167L+V305M+L327T+F360M, A167L+V305M+L327T+F360I, A167L+V305M+L327T+F360L, A167L+V305M+L327T+F360V, A167L+V305M+L327T+I408R, A167L+V305M+F360M+I408R, A167L+V305M+F360I+I408R, A167L+V305M+F360L+I408W, A167L+V305M+F360V+I408W, A167L+L327T+F360M+I408R, A167L+L327T+F360I+I408R, A167L+L327T+F360L+I408W, A167L+L327T+F360V+I408W, V305L+L327T+F360M+I408R, V305L+L327T+F360I+I408R, V305L+L327T+F360L+I408W, V305L+L327T+F360V+I408W, V305M+L327T+F360M+I408R, V305M+L327T+F360I+I408R, V305M+L327T+F360L+I408W, V305M+L327T+F360V+I408W, R89A+V165C+A167C+V305L+L327T, R89A+V165C+A167C+F360T, R89A+V165C+A167I+F360T, R89A+V165C+A167L+F360T, R89A+V165C+V305L+F360T, R89A+V165C+V305M+F360T, R89A+V165C+L327T+F360T, R89A+V165C+F360T+I408W, R89A+V165S+A167C+F360T, R89A+V165S+A167I+F360T, R89A+V165S+A167L+F360T, R89A+V165S+V305L+F360T, R89A+V165S+V305M+F360T, R89A+V165S+L327T+F360T, R89A+V165S+F360T+I408R, R89A+A167C+V305L+F360T, R89A+A167C+V305M+F360T, R89A+A167C+L327T+F360T, R89A+A167C+F360T+I408W, R89A+A167I+V305L+F360T, R89A+A167I+V305M+F360T, R89A+A167I+L327T+F360T, R89A+A167I+F360T+I408R, R89A+A167L+V305L+F360T, R89A+A167L+V305M+F360T, R89A+A167L+L327T+F360T, R89A+A167L+F360T+I408W, R89A+V305L+L327T+F360T, R89A+V305L+F360T+I408R, R89A+V305M+L327T+F360T, R89A+V305M+F360T+I408W, R89A+L327T+F360T+I408R, V165C+A167C+V305L+F360T, V165C+A167C+V305M+F360T, V165C+A167C+L327T+F360T, V165C+A167C+F360T+I408W, V165C+A167I+V305L+F360T, V165C+A167I+V305M+F360T, V165C+A167I+L327T+F360T, V165C+A167I+F360T+I408R, V165C+A167L+V305L+F360T, V165C+A167L+V305M+F360T, V165C+A167L+L327T+F360T, V165C+A167L+F360T+I408W, V165C+V305L+L327T+F360T, V165C+V305L+F360T+I408R, V165C+V305M+L327T+F360T, V165C+V305M+F360T+I408W, V165C+L327T+F360T+I408R, V165S+A167C+V305L+F360T, V165S+A167C+V305M+F360T, V165S+A167C+L327T+F360T, V165S+A167C+F360T+I408W, V165S+A167I+V305L+F360T, V165S+A167I+V305M+F360T, V165S+A167I+L327T+F360T, V165S+A167I+F360T+I408R, V165S+A167L+V305L+F360T, V165S+A167L+V305M+F360T, V165S+A167L+L327T+F360T, V165S+A167L+F360T+I408W, V165S+V305L+L327T+F360T, V165S+V305L+F360T+I408R, V165S+V305M+L327T+F360T, V165S+V305M+F360T+I408W, V165S+L327T+F360T+I408R, A167C+V305L+L327T+F360T, A167C+V305L+F360T+I408W, A167C+V305M+L327T+F360T, A167C+V305M+F360T+I408R, A167C+L327T+F360T+I408W, A167I+V305L+L327T+F360T, A167I+V305L+F360T+I408R, A167I+V305M+L327T+F360T, A167I+V305M+F360T+I408W, A167I+L327T+F360T+I408R, A167L+V305L+L327T+F360T, A167L+V305L+F360T+I408W, A167L+V305M+L327T+F360T, A167L+V305M+F360T+I408R, A167L+L327T+F360T+I408W, V305L+L327T+F360T+I408R, V305M+L327T+F360T+

I408W, R89A+V165C+A167C+V305L+F360M, R89A+V165C+A167C+V305L+F360I, R89A+V165C+A167C+V305L+F360L, R89A+V165C+A167C+V305L+F360V, R89A+V165C+A167C+V305L+I408W, R89A+V165C+A167C+V305M+L327T, R89A+V165C+A167C+V305M+F360M, R89A+V165C+A167C+V305M+F360I, R89A+V165C+A167C+V305M+F360L, R89A+V165C+A167C+V305M+F360V, R89A+V165C+A167C+V305M+I408R, R89A+V165C+A167C+L327T+F360M, R89A+V165C+A167C+L327T+F360I, R89A+V165C+A167C+L327T+F360L, R89A+V165C+A167C+L327T+F360V, R89A+V165C+A167C+L327T+I408R, R89A+V165C+A167C+F360M+I408R, R89A+V165C+A167C+F360I+I408R, R89A+V165C+A167C+F360L+I408W, R89A+V165C+A167C+F360V+I408W, R89A+V165C+A167I+V305L+L327T, R89A+V165C+A167I+V305L+F360M, R89A+V165C+A167I+V305L+F360I, R89A+V165C+A167I+V305L+F360L, R89A+V165C+A167I+V305L+F360V, R89A+V165C+A167I+V305L+I408W, R89A+V165C+A167I+V305M+L327T, R89A+V165C+A167I+V305M+F360M, R89A+V165C+A167I+V305M+F360I, R89A+V165C+A167I+V305M+F360L, R89A+V165C+A167I+V305M+F360V, R89A+V165C+A167I+V305M+I408R, R89A+V165C+A167I+L327T+F360M, R89A+V165C+A167I+L327T+F360I, R89A+V165C+A167I+L327T+F360L, R89A+V165C+A167I+L327T+F360V, R89A+V165C+A167I+L327T+I408R, R89A+V165C+A167I+F360M+I408R, R89A+V165C+A167I+F360I+I408R, R89A+V165C+A167I+F360L+I408W, R89A+V165C+A167I+F360V+I408W, R89A+V165C+A167L+V305L+L327T, R89A+V165C+A167L+V305L+F360M, R89A+V165C+A167L+V305L+F360I, R89A+V165C+A167L+V305L+F360L, R89A+V165C+A167L+V305L+F360V, R89A+V165C+A167L+V305L+I408W, R89A+V165C+A167L+V305M+L327T, R89A+V165C+A167L+V305M+F360M, R89A+V165C+A167L+V305M+F360I, R89A+V165C+A167L+V305M+F360L, R89A+V165C+A167L+V305M+F360V, R89A+V165C+A167L+V305M+I408R, R89A+V165C+A167L+L327T+F360M, R89A+V165C+A167L+L327T+F360I, R89A+V165C+A167L+L327T+F360L, R89A+V165C+A167L+L327T+F360V, R89A+V165C+A167L+L327T+I408R, R89A+V165C+A167L+F360M+I408R, R89A+V165C+A167L+F360I+I408R, R89A+V165C+A167L+F360L+I408W, R89A+V165C+A167L+F360V+I408W, R89A+V165C+V305L+L327T+F360M, R89A+V165C+V305L+L327T+F360I, R89A+V165C+V305L+L327T+F360L, R89A+V165C+V305L+L327T+F360V, R89A+V165C+V305L+L327T+I408R, R89A+V165C+V305L+F360M+I408R, R89A+V165C+V305L+F360I+I408R, R89A+V165C+V305L+F360L+I408W, R89A+V165C+V305L+F360V+I408W, R89A+V165C+V305M+L327T+F360M, R89A+V165C+V305M+L327T+F360I, R89A+V165C+V305M+L327T+F360L, R89A+V165C+V305M+L327T+F360V, R89A+V165C+V305M+L327T+I408R, R89A+V165C+V305M+F360M+I408R, R89A+V165C+V305M+F360I+I408R, R89A+V165C+V305M+F360L+I408W, R89A+V165C+V305M+F360V+I408W, R89A+V165C+L327T+F360M+I408R, R89A+V165C+L327T+F360I+I408R, R89A+V165C+L327T+F360L+I408W, R89A+V165C+L327T+F360V+I408W, R89A+V165S+A167C+V305L+L327T, R89A+V165S+A167C+V305L+F360M, R89A+V165S+A167C+V305L+F360I, R89A+V165S+A167C+V305L+F360L, R89A+V165S+A167C+V305L+F360V, R89A+V165S+A167C+V305L+I408W, R89A+V165S+A167C+V305M+L327T, R89A+V165S+A167C+V305M+F360M, R89A+V165S+A167C+V305M+F360I, R89A+V165S+A167C+

V305M+F360L, R89A+V165S+A167C+V305M+F360V, R89A+V165S+A167C+V305M+I408R, R89A+V165S+A167C+L327T+F360M, R89A+V165S+A167C+L327T+F360I, R89A+V165S+A167C+L327T+F360L, R89A+V165S+A167C+L327T+F360V, R89A+V165S+A167C+L327T+I408R, R89A+V165S+A167C+F360M+I408R, R89A+V165S+A167C+F360I+I408R, R89A+V165S+A167C+F360L+I408W, R89A+V165S+A167C+F360V+I408W, R89A+V165S+A167I+V305L+L327T, R89A+V165S+A167I+V305L+F360M, R89A+V165S+A167I+V305L+F360I, R89A+V165S+A167I+V305L+F360L, R89A+V165S+A167I+V305L+F360V, R89A+V165S+A167I+V305L+I408W, R89A+V165S+A167I+V305M+L327T, R89A+V165S+A167I+V305M+F360M, R89A+V165S+A167I+V305M+F360I, R89A+V165S+A167I+V305M+F360L, R89A+V165S+A167I+V305M+F360V, R89A+V165S+A167I+V305M+I408R, R89A+V165S+A167I+L327T+F360M, R89A+V165S+A167I+L327T+F360I, R89A+V165S+A167I+L327T+F360L, R89A+V165S+A167I+L327T+F360V, R89A+V165S+A167I+L327T+I408R, R89A+V165S+A167I+F360M+I408R, R89A+V165S+A167I+F360I+I408R, R89A+V165S+A167I+F360L+I408W, R89A+V165S+A167I+F360V+I408W, R89A+V165S+A167L+V305L+L327T, R89A+V165S+A167L+V305L+F360M, R89A+V165S+A167L+V305L+F360I, R89A+V165S+A167L+V305L+F360L, R89A+V165S+A167L+V305L+F360V, R89A+V165S+A167L+V305L+I408W, R89A+V165S+A167L+V305M+L327T, R89A+V165S+A167L+V305M+F360M, R89A+V165S+A167L+V305M+F360I, R89A+V165S+A167L+V305M+F360L, R89A+V165S+A167L+V305M+F360V, R89A+V165S+A167L+V305M+I408R, R89A+V165S+A167L+L327T+F360M, R89A+V165S+A167L+L327T+F360I, R89A+V165S+A167L+L327T+F360L, R89A+V165S+A167L+L327T+F360V, R89A+V165S+A167L+L327T+I408R, R89A+V165S+A167L+F360M+I408R, R89A+V165S+A167L+F360I+I408R, R89A+V165S+A167L+F360L+I408W, R89A+V165S+A167L+F360V+I408W, R89A+V165S+V305L+L327T+F360M, R89A+V165S+V305L+L327T+F360I, R89A+V165S+V305L+L327T+F360L, R89A+V165S+V305L+L327T+F360V, R89A+V165S+V305L+L327T+I408R, R89A+V165S+V305L+F360M+I408R, R89A+V165S+V305L+F360I+I408R, R89A+V165S+V305L+F360L+I408W, R89A+V165S+V305L+F360V+I408W, R89A+V165S+V305M+L327T+F360M, R89A+V165S+V305M+L327T+F360I, R89A+V165S+V305M+L327T+F360L, R89A+V165S+V305M+L327T+F360V, R89A+V165S+V305M+L327T+I408R, R89A+V165S+V305M+F360M+I408R, R89A+V165S+V305M+F360I+I408R, R89A+V165S+V305M+F360L+I408W, R89A+V165S+V305M+F360V+I408W, R89A+V165S+L327T+F360M+I408R, R89A+V165S+L327T+F360I+I408R, R89A+V165S+L327T+F360L+I408W, R89A+V165S+L327T+F360V+I408W, R89A+A167C+V305L+L327T+F360M, R89A+A167C+V305L+L327T+F360I, R89A+A167C+V305L+L327T+F360L, R89A+A167C+V305L+L327T+F360V, R89A+A167C+V305L+L327T+I408R, R89A+A167C+V305L+F360M+I408R, R89A+A167C+V305L+F360I+I408R, R89A+A167C+V305L+F360L+I408W, R89A+A167C+V305L+F360V+I408W, R89A+A167C+V305M+L327T+F360M, R89A+A167C+V305M+L327T+F360I, R89A+A167C+V305M+L327T+F360L, R89A+A167C+V305M+L327T+F360V, R89A+A167C+V305M+L327T+I408R, R89A+A167C+V305M+F360M+I408R, R89A+A167C+V305M+F360I+I408R, R89A+A167C+V305M+F360L+I408W, R89A+A167C+V305M+F360V+I408W, R89A+A167C+

L327T+F360M+I408R, R89A+A167C+L327T+F360I+
I408R, R89A+A167C+L327T+F360L+I408W, R89A+
A167C+L327T+F360V+I408W, R89A+A167I+V305L+
L327T+F360M, R89A+A167I+V305L+L327T+F360I,
R89A+A167I+V305L+L327T+F360L, R89A+A167I+
V305L+L327T+F360V, R89A+A167I+V305L+L327T+
I408R, R89A+A167I+V305L+F360M+I408R, R89A+
A167I+V305L+F360I+I408R, R89A+A167I+V305L+
F360L+I408W, R89A+A167I+V305L+F360V+I408W,
R89A+A167I+V305M+L327T+F360M, R89A+A167I+
V305M+L327T+F360I, R89A+A167I+V305M+L327T+
F360L, R89A+A167I+V305M+L327T+F360V, R89A+
A167I+V305M+L327T+I408R, R89A+A167I+V305M+
F360M+I408R, R89A+A167I+V305M+F360I+I408R,
R89A+A167I+V305M+F360L+I408W, R89A+A167I+
V305M+F360V+I408W, R89A+A167I+L327T+F360M+
I408R, R89A+A167I+L327T+F360I+I408R, R89A+
A167I+L327T+F360L+I408W, R89A+A167I+L327T+
F360V+I408W, R89A+A167L+V305L+L327T+F360M,
R89A+A167L+V305L+L327T+F360I, R89A+A167L+
V305L+L327T+F360L, R89A+A167L+V305L+L327T+
F360V, R89A+A167L+V305L+L327T+I408R, R89A+
A167L+V305L+F360M+I408R, R89A+A167L+V305L+
F360I+I408R, R89A+A167L+V305L+F360L+I408W,
R89A+A167L+V305L+F360V+I408W, R89A+A167L+
V305M+L327T+F360M, R89A+A167L+V305M+L327T+
F360I, R89A+A167L+V305M+L327T+F360L, R89A+
A167L+V305M+L327T+F360V, R89A+A167L+V305M+
L327T+I408R, R89A+A167L+V305M+F360M+I408R,
R89A+A167L+V305M+F360I+I408R, R89A+A167L+
V305M+F360L+I408W, R89A+A167L+V305M+F360V+
I408W, R89A+A167L+L327T+F360M+I408R, R89A+
A167L+L327T+F360I+I408R, R89A+A167L+L327T+
F360L+I408W, R89A+A167L+L327T+F360V+I408W,
R89A+V305L+L327T+F360M+I408R, R89A+V305L+
L327T+F360I+I408R, R89A+V305L+L327T+F360L+
I408W, R89A+V305L+L327T+F360V+I408W, R89A+
V305M+L327T+F360M+I408R, R89A+V305M+L327T+
F360I+I408R, R89A+V305M+L327T+F360L+I408W,
R89A+V305M+L327T+F360V+I408W, V165C+A167C+
V305L+L327T+F360M, V165C+A167C+V305L+L327T+
F360I, V165C+A167C+V305L+L327T+F360L, V165C+
A167C+V305L+L327T+F360V, V165C+A167C+V305L+
L327T+I408R, V165C+A167C+V305L+F360M+I408R,
V165C+A167C+V305L+F360I+I408R, V165C+A167C+
V305L+F360L+I408W, V165C+A167C+V305L+F360V+
I408W, V165C+A167C+V305M+L327T+F360M, V165C+
A167C+V305M+L327T+F360I, V165C+A167C+V305M+
L327T+F360L, V165C+A167C+V305M+L327T+F360V,
V165C+A167C+V305M+L327T+I408R, V165C+A167C+
V305M+F360M+I408R, V165C+A167C+V305M+F360I+
I408R, V165C+A167C+V305M+F360L+I408W, V165C+
A167C+V305M+F360V+I408W, V165C+A167C+L327T+
F360M+I408R, V165C+A167C+L327T+F360I+I408R,
V165C+A167C+L327T+F360L+I408W, V165C+A167C+
L327T+F360V+I408W, V165C+A167I+V305L+L327T+
F360M, V165C+A167I+V305L+L327T+F360I, V165C+
A167I+V305L+L327T+F360L, V165C+A167I+V305L+
L327T+F360V, V165C+A167I+V305L+L327T+I408R,
V165C+A167I+V305L+F360M+I408R, V165C+A167I+
V305L+F360I+I408R, V165C+A167I+V305L+F360L+
I408W, V165C+A167I+V305L+F360V+I408W, V165C+
A167I+V305M+L327T+F360M, V165C+A167I+V305M+
L327T+F360I, V165C+A167I+V305M+L327T+F360L,
V165C+A167I+V305M+L327T+F360V, V165C+A167I+
V305M+L327T+I408R, V165C+A167I+V305M+F360M+
I408R, V165C+A167I+V305M+F360I+I408R, V165C+

A167I+V305M+F360L+I408W, V165C+A167I+V305M+
F360V+I408W, V165C+A167I+L327T+F360M+I408R,
V165C+A167I+L327T+F360I+I408R, V165C+A167I+
L327T+F360L+I408W, V165C+A167I+L327T+F360V+
I408W, V165C+A167L+V305L+L327T+F360M, V165C+
A167L+V305L+L327T+F360I, V165C+A167L+V305L+
L327T+F360L, V165C+A167L+V305L+L327T+F360V,
V165C+A167L+V305L+L327T+I408R, V165C+A167L+
V305L+F360M+I408R, V165C+A167L+V305L+F360I+
I408R, V165C+A167L+V305L+F360L+I408W, V165C+
A167L+V305L+F360V+I408W, V165C+A167L+V305M+
L327T+F360M, V165C+A167L+V305M+L327T+F360I,
V165C+A167L+V305M+L327T+F360L, V165C+A167L+
V305M+L327T+F360V, V165C+A167L+V305M+L327T+
I408R, V165C+A167L+V305M+F360M+I408R, V165C+
A167L+V305M+F360I+I408R, V165C+A167L+V305M+
F360L+I408W, V165C+A167L+V305M+F360V+I408W,
V165C+A167L+L327T+F360M+I408R, V165C+A167L+
L327T+F360I+I408R, V165C+A167L+L327T+F360L+
I408W, V165C+A167L+L327T+F360V+I408W, V165C+
V305L+L327T+F360M+I408R, V165C+V305L+L327T+
F360I+I408R, V165C+V305L+L327T+F360L+I408W,
V165C+V305L+L327T+F360V+I408W, V165C+V305M+
L327T+F360M+I408R, V165C+V305M+L327T+F360I+
I408R, V165C+V305M+L327T+F360L+I408W, V165C+
V305M+L327T+F360V+I408W, V165 S+A167C+V305L+
L327T+F360M, V165 S+A167C+V305L+L327T+F360I,
V165S+A167C+V305L+L327T+F360L, V165 S+A167C+
V305L+L327T+F360V, V165S+A167C+V305L+L327T+
I408R, V165 S+A167C+V305L+F360M+I408R, V165
S+A167C+V305L+F360I+I408R, V165 S+A167C+
V305L+F360L+I408W, V165 S+A167C+V305L+F360V+
I408W, V165 S+A167C+V305M+L327T+F360M, V165
S+A167C+V305M+L327T+F360I, V165 S+A167C+
V305M+L327T+F360L, V165S+A167C+V305M+L327T+
F360V, V165 S+A167C+V305M+L327T+I408R, V165S+
A167C+V305M+F360M+I408R, V165 S+A167C+
V305M+F360I+I408R, V165 S+A167C+V305M+F360L+
I408W, V165 S+A167C+V305M+F360V+I408W, V165S+
A167C+L327T+F360M+I408R, V165 S+A167C+L327T+
F360I+I408R, V165 S+A167C+L327T+F360L+I408W,
V165S+A167C+L327T+F360V+I408W, V165S+A167I+
V305L+L327T+F360M, V165S+A167I+V305L+L327T+
F360I, V165S+A167I+V305L+L327T+F360L, V165S+
A167I+V305L+L327T+F360V, V165S+A167I+V305L+
L327T+I408R, V165S+A167I+V305L+F360M+I408R,
V165S+A167I+V305L+F360I+I408R, V165S+A167I+
V305L+F360L+I408W, V165S+A167I+V305L+F360V+
I408W, V165S+A167I+V305M+L327T+F360M, V165S+
A167I+V305M+L327T+F360I, V165S+A167I+V305M+
L327T+F360L, V165S+A167I+V305M+L327T+F360V,
V165S+A167I+V305M+L327T+I408R, V165S+A167I+
V305M+F360M+I408R, V165S+A167I+V305M+F360I+
I408R, V165S+A167I+V305M+F360L+I408W, V165S+
A167I+V305M+F360V+I408W, V165S+A167I+L327T+
F360M+I408R, V165S+A167I+L327T+F360I+I408R,
V165S+A167I+L327T+F360L+I408W, V165S+A167I+
L327T+F360V+I408W, V165S+A167L+V305L+L327T+
F360M, V165S+A167L+V305L+L327T+F360I, V165S+
A167L+V305L+L327T+F360L, V165S+A167L+V305L+
L327T+F360V, V165S+A167L+V305L+L327T+I408R,
V165S+A167L+V305L+F360M+I408R, V165S+A167L+
V305L+F360I+I408R, V165S+A167L+V305L+F360L+
I408W, V165S+A167L+V305L+F360V+I408W, V165S+
A167L+V305M+L327T+F360M, V165S+A167L+
V305M+L327T+F360I, V165S+A167L+V305M+L327T+
F360L, V165S+A167L+V305M+L327T+F360V, V165S+

A167L+V305M+L327T+I408R, V165S+A167L+V305M+
F360M+I408R, V165S+A167L+V305M+F360I+I408R,
V165S+A167L+V305M+F360L+I408W, V165S+A167L+
V305M+F360V+I408W, V165S+A167L+L327T+F360M+
I408R, V165S+A167L+L327T+F360I+I408R, V165S+
A167L+L327T+F360L+I408W, V165S+A167L+L327T+
F360V+I408W, V165S+V305L+L327T+F360M+I408R,
V165S+V305L+L327T+F360I+I408R, V165S+V305L+
L327T+F360L+I408W, V165S+V305L+L327T+F360V+
I408W, V165S+V305M+L327T+F360M+I408R, V165S+
V305M+L327T+F360I+I408R, V165S+V305M+L327T+
F360L+I408W, V165S+V305M+L327T+F360V+I408W,
A167C+V305L+L327T+F360M+I408R, A167C+V305L+
L327T+F360I+I408R, A167C+V305L+L327T+F360L+
I408W, A167C+V305L+L327T+F360V+I408W, A167C+
V305M+L327T+F360M+I408R, A167C+V305M+L327T+
F360I+I408R, A167C+V305M+L327T+F360L+I408W,
A167C+V305M+L327T+F360V+I408W, A167I+V305L+
L327T+F360M+I408R, A167I+V305L+L327T+F360I+
I408R, A167I+V305L+L327T+F360L+I408W, A167I+
V305L+L327T+F360V+I408W, A167I+V305M+L327T+
F360M+I408R, A167I+V305M+L327T+F360I+I408R,
A167I+V305M+L327T+F360L+I408W, A167I+V305M+
L327T+F360V+I408W, A167L+V305L+L327T+F360M+
I408R, A167L+V305L+L327T+F360I+I408R, A167L+
V305L+L327T+F360L+I408W, A167L+V305L+L327T+
F360V+I408W, A167L+V305M+L327T+F360M+I408R,
A167L+V305M+L327T+F360I+I408R, A167L+V305M+
L327T+F360L+I408W, A167L+V305M+L327T+F360V+
I408W, R89A+V165C+A167C+V305L+F360T, R89A+
V165C+A167C+V305M+F360T, R89A+V165C+A167C+
L327T+F360T, R89A+V165C+A167C+F360T+I408R,
R89A+V165C+A167I+V305L+F360T, R89A+V165C+
A167I+V305M+F360T, R89A+V165C+A167I+L327T+
F360T, R89A+V165C+A167I+F360T+I408W, R89A+
V165C+A167L+V305L+F360T, R89A+V165C+A167L+
V305M+F360T, R89A+V165C+A167L+L327T+F360T,
R89A+V165C+A167L+F360T+I408R, R89A+V165C+
V305L+L327T+F360T, R89A+V165C+V305L+F360T+
I408W, R89A+V165C+V305M+L327T+F360T, R89A+
V165C+V305M+F360T+I408R, R89A+V165C+L327T+
F360T+I408W, R89A+V165S+A167C+V305L+F360T,
R89A+V165S+A167C+V305M+F360T, R89A+V165S+
A167C+L327T+F360T, R89A+V165S+A167C+F360T+
I408R, R89A+V165S+A167I+V305L+F360T, R89A+
V165S+A167I+V305M+F360T, R89A+V165S+A167I+
L327T+F360T, R89A+V165S+A167I+F360T+I408W,
R89A+V165S+A167L+V305L+F360T, R89A+V165S+
A167L+V305M+F360T, R89A+V165S+A167L+L327T+
F360T, R89A+V165S+A167L+F360T+I408R, R89A+
V165S+V305L+L327T+F360T, R89A+V165S+V305L+
F360T+I408W, R89A+V165S+V305M+L327T+F360T,
R89A+V165S+V305M+F360T+I408R, R89A+V165S+
L327T+F360T+I408W, R89A+A167C+V305L+L327T+
F360T, R89A+A167C+V305L+F360T+I408R, R89A+
A167C+V305M+L327T+F360T, R89A+A167C+V305M+
F360T+I408W, R89A+A167C+L327T+F360T+I408R,
R89A+A167I+V305L+L327T+F360T, R89A+A167I+
V305L+F360T+I408W, R89A+A167I+V305M+L327T+
F360T, R89A+A167I+V305M+F360T+I408R, R89A+
A167I+L327T+F360T+I408W, R89A+A167L+V305L+
L327T+F360T, R89A+A167L+V305L+F360T+I408R,
R89A+A167L+V305M+L327T+F360T, R89A+A167L+
V305M+F360T+I408W, R89A+A167L+L327T+F360T+
I408R, R89A+V305L+L327T+F360T+I408W, R89A+
V305M+L327T+F360T+I408R, V165C+A167C+V305L+
L327T+F360T, V165C+A167C+V305L+F360T+I408W,

V165C+A167C+V305M+L327T+F360T, V165C+A167C+
V305M+F360T+I408R, V165C+A167C+L327T+F360T+
I408W, V165C+A167I+V305L+L327T+F360T, V165C+
A167I+V305L+F360T+I408R, V165C+A167I+V305M+
L327T+F360T, V165C+A167I+V305M+F360T+I408W,
V165C+A167I+L327T+F360T+I408R, V165C+A167L+
V305L+L327T+F360T, V165C+A167L+V305L+F360T+
I408W, V165C+A167L+V305M+L327T+F360T, V165C+
A167L+V305M+F360T+I408R, V165C+A167L+L327T+
F360T+I408W, V165C+V305L+L327T+F360T+I408R,
V165C+V305M+L327T+F360T+I408W, V165S+A167C+
V305L+L327T+F360T, V165S+A167C+V305L+F360T+
I408R, V165S+A167C+V305M+L327T+F360T, V165S+
A167C+V305M+F360T+I408W, V165S+A167C+L327T+
F360T+I408R, V165S+A167I+V305L+L327T+F360T,
V165S+A167I+V305L+F360T+I408W, V165S+A167I+
V305M+L327T+F360T, V165S+A167I+V305M+F360T+
I408R, V165S+A167I+L327T+F360T+I408W, V165S+
A167L+V305L+L327T+F360T, V165S+A167L+V305L+
F360T+I408R, V165S+A167L+V305M+L327T+F360T,
V165S+A167L+V305M+F360T+I408W, V165S+A167L+
L327T+F360T+I408R, V165S+V305L+L327T+F360T+
I408W, V165S+V305M+L327T+F360T+I408R, A167C+
V305L+L327T+F360T+I408W, A167C+V305M+L327T+
F360T+I408R, A167I+V305L+L327T+F360T+I408W,
A167I+V305M+L327T+F360T+I408R, A167L+V305L+
L327T+F360T+I408W, A167L+V305M+L327T+F360T+
I408R, R89A+V165C+A167C+V305L+L327T+F360M,
R89A+V165C+A167C+V305L+L327T+F360I, R89A+
V165C+A167C+V305L+L327T+F360L, R89A+V165C+
A167C+V305L+L327T+F360V, R89A+V165C+A167C+
V305L+L327T+I408R, R89A+V165C+A167C+V305L+
F360M+I408R, R89A+V165C+A167C+V305L+F360I+
I408R, R89A+V165C+A167C+V305L+F360L+I408W,
R89A+V165C+A167C+V305L+F360V+I408W, R89A+
V165C+A167C+V305M+L327T+F360M, R89A+V165C+
A167C+V305M+L327T+F360I, R89A+V165C+A167C+
V305M+L327T+F360L, R89A+V165C+A167C+V305M+
L327T+F360V, R89A+V165C+A167C+V305M+L327T+
I408R, R89A+V165C+A167C+V305M+F360M+I408R,
R89A+V165C+A167C+V305M+F360I+I408R, R89A+
V165C+A167C+V305M+F360L+I408W, R89A+V165C+
A167C+V305M+F360V+I408W, R89A+V165C+A167C+
L327T+F360M+I408R, R89A+V165C+A167C+L327T+
F360I+I408R, R89A+V165C+A167C+L327T+F360L+
I408W, R89A+V165C+A167C+L327T+F360V+I408W,
R89A+V165C+A167I+V305L+L327T+F360M, R89A+
V165C+A167I+V305L+L327T+F360I, R89A+V165C+
A167I+V305L+L327T+F360L, R89A+V165C+A167I+
V305L+L327T+F360V, R89A+V165C+A167I+V305L+
L327T+I408R, R89A+V165C+A167I+V305L+F360M+
I408R, R89A+V165C+A167I+V305L+F360I+I408R,
R89A+V165C+A167I+V305L+F360L+I408W, R89A+
V165C+A167I+V305L+F360V+I408W, R89A+V165C+
A167I+V305M+L327T+F360M, R89A+V165C+A167I+
V305M+L327T+F360I, R89A+V165C+A167I+V305M+
L327T+F360L, R89A+V165C+A167I+V305M+L327T+
F360V, R89A+V165C+A167I+V305M+L327T+I408R,
R89A+V165C+A167I+V305M+F360M+I408R, R89A+
V165C+A167I+V305M+F360I+I408R, R89A+V165C+
A167I+V305M+F360L+I408W, R89A+V165C+A167I+
V305M+F360V+I408W, R89A+V165C+A167I+L327T+
F360M+I408R, R89A+V165C+A167I+L327T+F360I+
I408R, R89A+V165C+A167I+L327T+F360L+I408W,
R89A+V165C+A167I+L327T+F360V+I408W, R89A+
V165C+A167L+V305L+L327T+F360M, R89A+V165C+
A167L+V305L+L327T+F360I, R89A+V165C+A167L+

V305L+L327T+F360L, R89A+V165C+A167L+V305L+L327T+F360V, R89A+V165C+A167L+V305L+L327T+I408R, R89A+V165C+A167L+V305L+F360M+I408R, R89A+V165C+A167L+V305L+F360I+I408R, R89A+V165C+A167L+V305L+F360L+I408W, R89A+V165C+A167L+V305L+F360V+I408W, R89A+V165C+A167L+V305M+L327T+F360M, R89A+V165C+A167L+V305M+L327T+F360I, R89A+V165C+A167L+V305M+L327T+F360L, R89A+V165C+A167L+V305M+L327T+F360V, R89A+V165C+A167L+V305M+L327T+I408R, R89A+V165C+A167L+V305M+F360M+I408R, R89A+V165C+A167L+V305M+F360I+I408R, R89A+V165C+A167L+V305M+F360L+I408W, R89A+V165C+A167L+V305M+F360V+I408W, R89A+V165C+A167L+L327T+F360M+I408R, R89A+V165C+A167L+L327T+F360I+I408R, R89A+V165C+A167L+L327T+F360L+I408W, R89A+V165C+A167L+L327T+F360V+I408W, R89A+V165C+V305L+L327T+F360M+I408R, R89A+V165C+V305L+L327T+F360I+I408R, R89A+V165C+V305L+L327T+F360L+I408W, R89A+V165C+V305L+L327T+F360V+I408W, R89A+V165C+V305M+L327T+F360M+I408R, R89A+V165C+V305M+L327T+F360I+I408R, R89A+V165C+V305M+L327T+F360L+I408W, R89A+V165C+V305M+L327T+F360V+I408W, R89A+V165S+A167C+V305L+L327T+F360M, R89A+V165S+A167C+V305L+L327T+F360I, R89A+V165S+A167C+V305L+L327T+F360L, R89A+V165S+A167C+V305L+L327T+F360V, R89A+V165S+A167C+V305L+L327T+I408R, R89A+V165S+A167C+V305L+F360M+I408R, R89A+V165S+A167C+V305L+F360I+I408R, R89A+V165S+A167C+V305L+F360L+I408W, R89A+V165S+A167C+V305L+F360V+I408W, R89A+V165S+A167C+V305M+L327T+F360M, R89A+V165S+A167C+V305M+L327T+F360I, R89A+V165S+A167C+V305M+L327T+F360L, R89A+V165S+A167C+V305M+L327T+F360V, R89A+V165S+A167C+V305M+L327T+I408R, R89A+V165S+A167C+V305M+F360M+I408R, R89A+V165S+A167C+V305M+F360I+I408R, R89A+V165S+A167C+V305M+F360L+I408W, R89A+V165S+A167C+V305M+F360V+I408W, R89A+V165S+A167C+L327T+F360M+I408R, R89A+V165S+A167C+L327T+F360I+I408R, R89A+V165S+A167C+L327T+F360L+I408W, R89A+V165S+A167C+L327T+F360V+I408W, R89A+V165S+A167I+V305L+L327T+F360M, R89A+V165S+A167I+V305L+L327T+F360I, R89A+V165S+A167I+V305L+L327T+F360L, R89A+V165S+A167I+V305L+L327T+F360V, R89A+V165S+A167I+V305L+L327T+I408R, R89A+V165S+A167I+V305L+F360M+I408R, R89A+V165S+A167I+V305L+F360I+I408R, R89A+V165S+A167I+V305L+F360L+I408W, R89A+V165S+A167I+V305L+F360V+I408W, R89A+V165S+A167I+V305M+L327T+F360M, R89A+V165S+A167I+V305M+L327T+F360I, R89A+V165S+A167I+V305M+L327T+F360L, R89A+V165S+A167I+V305M+L327T+F360V, R89A+V165S+A167I+V305M+L327T+I408R, R89A+V165S+A167I+V305M+F360M+I408R, R89A+V165S+A167I+V305M+F360I+I408R, R89A+V165S+A167I+V305M+F360L+I408W, R89A+V165S+A167I+V305M+F360V+I408W, R89A+V165S+A167I+L327T+F360M+I408R, R89A+V165S+A167I+L327T+F360I+I408R, R89A+V165S+A167I+L327T+F360L+I408W, R89A+V165S+A167I+L327T+F360V+I408W, R89A+V165S+A167L+V305L+L327T+F360M, R89A+V165S+A167L+V305L+L327T+F360I, R89A+V165S+A167L+V305L+L327T+F360L, R89A+V165S+A167L+V305L+L327T+F360V, R89A+V165S+A167L+V305L+L327T+I408R, R89A+V165S+A167L+V305L+F360M+I408R, R89A+V165S+A167L+V305L+

F360I+I408R, R89A+V165S+A167L+V305L+F360L+I408W, R89A+V165S+A167L+V305L+F360V+I408W, R89A+V165S+A167L+V305M+L327T+F360M, R89A+V165S+A167L+V305M+L327T+F360I, R89A+V165S+A167L+V305M+L327T+F360L, R89A+V165S+A167L+V305M+L327T+F360V, R89A+V165S+A167L+V305M+L327T+I408R, R89A+V165S+A167L+V305M+F360M+I408R, R89A+V165S+A167L+V305M+F360I+I408R, R89A+V165S+A167L+V305M+F360L+I408W, R89A+V165S+A167L+V305M+F360V+I408W, R89A+V165S+A167L+L327T+F360M+I408R, R89A+V165S+A167L+L327T+F360I+I408R, R89A+V165S+A167L+L327T+F360L+I408W, R89A+V165S+A167L+L327T+F360V+I408W, R89A+V165S+V305L+L327T+F360M+I408R, R89A+V165S+V305L+L327T+F360I+I408R, R89A+V165S+V305L+L327T+F360L+I408W, R89A+V165S+V305L+L327T+F360V+I408W, R89A+V165S+V305M+L327T+F360M+I408R, R89A+V165S+V305M+L327T+F360I+I408R, R89A+V165S+V305M+L327T+F360L+I408W, R89A+V165S+V305M+L327T+F360V+I408W, R89A+A167C+V305L+L327T+F360M+I408R, R89A+A167C+V305L+L327T+F360I+I408R, R89A+A167C+V305L+L327T+F360L+I408W, R89A+A167C+V305L+L327T+F360V+I408W, R89A+A167C+V305M+L327T+F360M+I408R, R89A+A167C+V305M+L327T+F360I+I408R, R89A+A167C+V305M+L327T+F360L+I408W, R89A+A167C+V305M+L327T+F360V+I408W, R89A+A167I+V305L+L327T+F360M+I408R, R89A+A167I+V305L+L327T+F360I+I408R, R89A+A167I+V305L+L327T+F360L+I408W, R89A+A167I+V305L+L327T+F360V+I408W, R89A+A167I+V305M+L327T+F360M+I408R, R89A+A167I+V305M+L327T+F360I+I408R, R89A+A167I+V305M+L327T+F360L+I408W, R89A+A167I+V305M+L327T+F360V+I408W, R89A+A167L+V305L+L327T+F360M+I408R, R89A+A167L+V305L+L327T+F360I+I408R, R89A+A167L+V305L+L327T+F360L+I408W, R89A+A167L+V305L+L327T+F360V+I408W, R89A+A167L+V305M+L327T+F360M+I408R, R89A+A167L+V305M+L327T+F360I+I408R, R89A+A167L+V305M+L327T+F360L+I408W, R89A+A167L+V305M+L327T+F360V+I408W, V165C+A167C+V305L+L327T+F360M+I408R, V165C+A167C+V305L+L327T+F360I+I408R, V165C+A167C+V305L+L327T+F360L+I408W, V165C+A167C+V305L+L327T+F360V+I408W, V165C+A167C+V305M+L327T+F360M+I408R, V165C+A167C+V305M+L327T+F360I+I408R, V165C+A167C+V305M+L327T+F360L+I408W, V165C+A167C+V305M+L327T+F360V+I408W, V165C+A167I+V305L+L327T+F360M+I408R, V165C+A167I+V305L+L327T+F360I+I408R, V165C+A167I+V305L+L327T+F360L+I408W, V165C+A167I+V305L+L327T+F360V+I408W, V165C+A167I+V305M+L327T+F360M+I408R, V165C+A167I+V305M+L327T+F360I+I408R, V165C+A167I+V305M+L327T+F360L+I408W, V165C+A167I+V305M+L327T+F360V+I408W, V165C+A167L+V305L+L327T+F360M+I408R, V165C+A167L+V305L+L327T+F360I+I408R, V165C+A167L+V305L+L327T+F360L+I408W, V165C+A167L+V305L+L327T+F360V+I408W, V165C+A167L+V305M+L327T+F360M+I408R, V165C+A167L+V305M+L327T+F360I+I408R, V165C+A167L+V305M+L327T+F360L+I408W, V165C+A167L+V305M+L327T+F360V+I408W, V165S+A167C+V305L+L327T+F360M+I408R, V165S+A167C+V305L+L327T+F360I+I408R, V165S+A167C+V305L+L327T+F360L+I408W, V165S+A167C+V305L+L327T+F360V+I408W, V165S+A167C+V305M+L327T+F360M+I408R, V165S+A167C+V305M+L327T+F360I+I408R, V165S+A167C+V305M+L327T+F360L+

I408W, V165S+A167C+V305M+L327T+F360V+I408W, V165S+A167I+V305L+L327T+F360M+I408R, V165S+A167I+V305L+L327T+F360I+I408R, V165S+A167I+V305L+L327T+F360L+I408W, V165S+A167I+V305L+L327T+F360V+I408W, V165S+A167I+V305M+L327T+F360M+I408R, V165S+A167I+V305M+L327T+F360I+I408R, V165S+A167I+V305M+L327T+F360L+I408W, V165S+A167I+V305M+L327T+F360V+I408W, V165S+A167L+V305L+L327T+F360M+I408R, V165S+A167L+V305L+L327T+F360I+I408R, V165S+A167L+V305L+L327T+F360L+I408W, V165S+A167L+V305L+L327T+F360V+I408W, V165S+A167L+V305M+L327T+F360M+I408R, V165S+A167L+V305M+L327T+F360I+I408R, V165S+A167L+V305M+L327T+F360L+I408W, V165S+A167L+V305M+L327T+F360V+I408W, R89A+V165C+A167C+V305L+L327T+F360T, R89A+V165C+A167C+V305L+F360T+I408W, R89A+V165C+A167C+V305M+L327T+F360T, R89A+V165C+A167C+V305M+F360T+I408R, R89A+V165C+A167C+L327T+F360T+I408W, R89A+V165C+A167I+V305L+L327T+F360T, R89A+V165C+A167I+V305L+F360T+I408R, R89A+V165C+A167I+V305M+L327T+F360T, R89A+V165C+A167I+V305M+F360T+I408W, R89A+V165C+A167I+L327T+F360T+I408R, R89A+V165C+A167L+V305L+L327T+F360T, R89A+V165C+A167L+V305L+F360T+I408W, R89A+V165C+A167L+V305M+L327T+F360T, R89A+V165C+A167L+V305M+F360T+I408R, R89A+V165C+A167L+L327T+F360T+I408W, R89A+V165C+V305L+L327T+F360T+I408R, R89A+V165C+V305M+L327T+F360T+I408W, R89A+V165S+A167C+V305L+L327T+F360T, R89A+V165S+A167C+V305L+F360T+I408R, R89A+V165S+A167C+V305M+L327T+F360T, R89A+V165S+A167C+V305M+F360T+I408W, R89A+V165S+A167C+L327T+F360T+I408R, R89A+V165S+A167I+V305L+L327T+F360T, R89A+V165S+A167I+V305L+F360T+I408W, R89A+V165S+A167I+V305M+L327T+F360T, R89A+V165S+A167I+V305M+F360T+I408R, R89A+V165S+A167I+L327T+F360T+I408W, R89A+V165S+A167L+V305L+L327T+F360T, R89A+V165S+A167L+V305L+F360T+I408R, R89A+V165S+A167L+V305M+L327T+F360T, R89A+V165S+A167L+V305M+F360T+I408W, R89A+V165S+A167L+L327T+F360T+I408R, R89A+V165S+V305L+L327T+F360T+I408W, R89A+V165S+V305M+L327T+F360T+I408R, R89A+A167C+V305L+L327T+F360T+I408W, R89A+A167C+V305M+L327T+F360T+I408R, R89A+A167I+V305L+L327T+F360T+I408W, R89A+A167I+V305M+L327T+F360T+I408R, R89A+A167L+V305L+L327T+F360T+I408W, R89A+A167L+V305M+L327T+F360T+I408R, V165C+A167C+V305L+L327T+F360T+I408W, V165C+A167C+V305M+L327T+F360T+I408R, V165C+A167I+V305L+L327T+F360T+I408W, V165C+A167I+V305M+L327T+F360T+I408R, V165C+A167L+V305L+L327T+F360T+I408W, V165C+A167L+V305M+L327T+F360T+I408R, V165S+A167C+V305L+L327T+F360T+I408W, V165S+A167C+V305M+L327T+F360T+I408R, V165S+A167I+V305L+L327T+F360T+I408W, V165S+A167I+V305M+L327T+F360T+I408R, V165S+A167L+V305L+L327T+F360T+I408W, V165S+A167L+V305M+L327T+F360T+I408R, R89A+V165C+A167C+V305L+L327T+F360M+I408R, R89A+V165C+A167C+V305L+L327T+F360I+I408R, R89A+V165C+A167C+V305L+L327T+F360L+I408W, R89A+V165C+A167C+V305L+L327T+F360V+I408W, R89A+V165C+A167C+V305M+L327T+F360M+I408R, R89A+V165C+A167C+V305M+L327T+F360I+I408R, R89A+V165C+A167C+V305M+L327T+

F360L+I408W, R89A+V165C+A167I+V305L+L327T+F360V+I408W, R89A+V165C+A167I+V305L+L327T+F360M+I408R, R89A+V165C+A167I+V305L+L327T+F360I+I408R, R89A+V165C+A167I+V305L+L327T+F360L+I408W, R89A+V165C+A167I+V305M+L327T+F360V+I408W, R89A+V165C+A167I+V305M+L327T+F360M+I408R, R89A+V165C+A167I+V305M+L327T+F360I+I408R, R89A+V165C+A167I+V305M+L327T+F360L+I408W, R89A+V165C+A167I+V305M+L327T+F360V+I408W, R89A+V165C+A167L+V305L+L327T+F360M+I408R, R89A+V165C+A167L+V305L+L327T+F360I+I408R, R89A+V165C+A167L+V305L+L327T+F360L+I408W, R89A+V165C+A167L+V305L+L327T+F360V+I408W, R89A+V165C+A167L+V305M+L327T+F360M+I408R, R89A+V165C+A167L+V305M+L327T+F360I+I408R, R89A+V165C+A167L+V305M+L327T+F360L+I408W, R89A+V165C+A167L+V305M+L327T+F360V+I408W, R89A+V165S+A167C+V305L+L327T+F360M+I408R, R89A+V165S+A167C+V305L+L327T+F360I+I408R, R89A+V165S+A167C+V305L+L327T+F360L+I408W, R89A+V165S+A167C+V305M+L327T+F360V+I408W, R89A+V165S+A167C+V305M+L327T+F360M+I408R, R89A+V165S+A167C+V305M+L327T+F360I+I408R, R89A+V165S+A167C+V305M+L327T+F360L+I408W, R89A+V165S+A167I+V305L+L327T+F360V+I408W, R89A+V165S+A167I+V305L+L327T+F360M+I408R, R89A+V165S+A167I+V305L+L327T+F360I+I408R, R89A+V165S+A167I+V305L+L327T+F360L+I408W, R89A+V165S+A167I+V305M+L327T+F360V+I408W, R89A+V165S+A167I+V305M+L327T+F360M+I408R, R89A+V165S+A167I+V305M+L327T+F360I+I408R, R89A+V165S+A167I+V305M+L327T+F360L+I408W, R89A+V165S+A167L+V305L+L327T+F360V+I408W, R89A+V165S+A167L+V305L+L327T+F360M+I408R, R89A+V165S+A167L+V305L+L327T+F360I+I408R, R89A+V165S+A167L+V305L+L327T+F360L+I408W, R89A+V165S+A167L+V305M+L327T+F360V+I408W, R89A+V165S+A167L+V305M+L327T+F360M+I408R, R89A+V165S+A167L+V305M+L327T+F360I+I408R, R89A+V165S+A167L+V305M+L327T+F360L+I408W, R89A+V165C+A167C+V305L+L327T+F360V+I408W, R89A+V165C+A167C+V305M+L327T+F360T+I408R, R89A+V165C+A167I+V305L+L327T+F360T+I408R, R89A+V165C+A167I+V305M+L327T+F360T+I408W, R89A+V165C+A167L+V305L+L327T+F360T+I408R, R89A+V165C+A167L+V305M+L327T+F360T+I408R, R89A+V165S+A167C+V305L+L327T+F360T+I408R, R89A+V165S+A167C+V305M+L327T+F360T+I408W, R89A+V165S+A167I+V305L+L327T+F360T+I408R, R89A+V165S+A167I+V305M+L327T+F360T+I408W, R89A+V165S+A167L+V305L+L327T+F360T+I408R, R89A+V165S+A167L+V305M+L327T+F360T+I408W, or R89A+V165S+A167L+V305M+L327T+F360T+I408R, in the amino acid sequence of SEQ ID NO: 1.

For example, the polypeptide variant may comprise:
an amino acid sequence having modification to SEQ ID NO: 1, wherein the modification may comprise an amino acid mutation of R89A, V165C, V165S, A167C, A167I, A167L, V305M, V305L, L327T, F360M, F360I, F360L, F360V, F360T, I408R, I408W, R89A+F360M, R89A+F360V, R89A+F360I, R89A+F360L, R89A+F360T, V165C+F360I, V165C+F360M, V165C+F360V, V165C+F360L, V165S+F360V, V165S+F360T, V165S+F360I, A167C+F360I, A167L+F360M, A167I+F360I, A167L+F360T, A167C+F360M, A167C+F360L, A167C+F360V, V305M+F360I, V305L+F360M, V305M+F360M, V305M+F360V, V305M+F360L, V305L+F360L, V305M+F360T, L327T+F360I, L327T+F360M, L327T+F360V, L327T+F360L, L327T+F360T, I408W+F360I, I408R+F360M, I408W+F360V, I408R+F360L, I408W+F360T, R89A+V165C+F360I, R89A+V165S+F360M, R89A+V165C+F360V, R89A+A167I+F360V, R89A+A167C+F360L, R89A+A167L+F360T, R89A+V305M+F360I, R89A+V305M+F360V, R89A+V305M+F360T, R89A+L327T+F360I, R89A+L327T+F360M, R89A+L327T+F360T, R89A+I408R+F360M, R89A+I408W+F360V, R89A+I408R+F360L, V165S+A167I+F360M, V165S+A167C+F360L, V165C+A167L+F360T, V165C+V305M+F360I, V165C+V305M+F360V, V165S+V305L+F360L, V165C+L327T+F360I, V165C+L327T+F360V, V165S+L327T+F360T, V165C+I408W+F360V, V165C+I408W+F360T, A167I+V305M+F360L, A167C+V305L+F360V, A167L+V305M+F360T, A167C+L327T+F360I, A167L+L327T+F360M, A167I+L327T+F360V, A167C+I408W+F360I, A167I+I408W+F360V, A167L+I408R+F360L, V305M+L327T+F360I, V305L+L327T+F360V, V305M+L327T+F360T, V305M+I408W+F360I, V305M+I408W+F360V, V305L+I408R+F360L, L327T+I408R+F360M, L327T+I408W+F360V, R89A+V165C+A167C+ F360I, R89A+V165S+V305M+F360M, R89A+ V165C+L327T+F360V, R89A+V165S+I408R+ F360L, R89A+A167L+V305L+F360T, R89A+ A167L+L327T+F360I, R89A+A167C+I408R+ F360M, V165C+A167I+V305M+F360V, V165S+ A167C+L327T+F360M, V165C+A167C+I408W+ F360T, A167I+V305L+L327T+F360V, A167L+ V305M+I408R+F360M, or V305L+L327T+I408W+ F360V, in the amino acid sequence of SEQ ID NO: 1, or an amino acid sequence having at least 95%, at least 96%, at least 97%, at least 98%, or at least 99% sequence identity with the amino acid sequence.

For example, the polypeptide variant may comprise:

an amino acid sequence having modification to SEQ ID NO: 3, wherein the modification may comprise an amino acid mutation of F360M, F360V, F360I, F360L, A167C, A167L, A167I, V305M, R89A, V165S, V165C, L327T, R89A+F360M, A167L+F360M, L327T+F360M, R89A+F360V, A167L+F360I, V305M+F360I, R89A+V165C+F360I, V165C+ A167L+F360I, V165C+A167L+F360M, A167L+ V305M+F360M, V165S+A167L+V305M+F360I, R89A+V165S+V305M+F360I, V165S+A167C+ L327T+F360M, R89A+V165S+A167C+L327T+ F360M, or R89A+V165C+A167L+V305M+F360I, in the amino acid sequence of SEQ ID NO: 3, or an amino acid sequence having at least 95%, at least 96%, at least 97%, at least 98%, or at least 99% sequence identity with the amino acid sequence.

The polypeptide or the polypeptide variant comprising an amino acid sequence having sequence identity (for example, at least 95%, at least 96%, at least 97%, at least 98%, or at least 99% sequence identity) described herein may maintain enzyme activity equivalent to that of a polypeptide having an amino acid sequence which is a standard of identification of sequence identity (for example, the PPO protein having amino acid mutation described above), for example, 5% or higher, 10% or higher, 20% or higher, 30% or higher, 40% or higher, 50% or higher, 60% or higher, 70% or higher, 80% or higher, 90% or higher, or 95% or higher enzyme activity to a polypeptide having an amino acid sequence which is a standard in plants (in a whole plant, in a plant cell or cell culture, in a plant tissue, etc.), in algae, and/or in vitro, and having function to confer herbicide tolerance. The sequence identity description is used in order to clarify that the herbicide-tolerance PPO protein (polypeptide) or its variant described herein may comprise any sequence mutation within the range capable of satisfying the above condition (maintaining enzymatic activity and possessing a function to confer herbicide tolerance).

The amino acids used in the description are summarized as follows:

| Amino acid | 3-letter code | 1-letter code |
| --- | --- | --- |
| Alanine | Ala | A |
| Isoleucine | Ile | I |
| Leucine | Leu | L |
| Methionine | Met | M |
| Phenylalanine | Phe | F |
| Proline | Pro | P |
| Tryptophan | Trp | W |
| Valine | Val | V |
| Aspargine | Asn | N |
| Cysteine | Cys | C |
| Glutamine | Gln | Q |
| Glycine | Gly | G |
| Serine | Ser | S |
| Threonine | Thr | T |
| Tyrosine | Tyr | Y |
| Aspartic acid | Asp | D |
| Glutamic acid | Glu | E |
| Arginine | Arg | R |
| Histidine | His | H |
| Lysine | Lys | K |

The polypeptide variant (herbicide-tolerant PPO protein variant) may maintain its enzymatic activities as a PPO protein, and exhibit increased herbicide tolerance compared to the wild type.

In addition, the polypeptide (herbicide-tolerant PPO protein) and the polypeptide variant (herbicide-tolerant PPO protein variant) may comprise further mutation exhibiting biologically equal activity to a polypeptide consisting of SEQ ID NO: 1, SEQ ID NO: 2, or SEQ ID NO: 3, or an amino acid sequence having amino acid mutation(s) described above. For example, the additional mutation may be amino acid substitution which does not entirely alter molecular activity, and such amino acid substitution may be properly selected by a person skilled in the relevant art. In one example, the additional substitution may be substitution between amino acid residues Ala/Ser, Val/Ile, Asp/Glu, Thr/Ser, Ala/Gly, Ala/Thr, Ser/Asn, Ala/Val, Ser/Gly, Thr/ Phe, Ala/Pro, Lys/Arg, Asp/Asn, Leu/Ile, Leu/Val, Ala/Glu, or Asp/Gly, but not be limited thereto. In some cases, the herbicide-tolerant PPO protein variant may be subjected to at least one modification selected from the group consisting of phosphorylation, sulfation, acylation, glycosylation, methylation, farnesylation, and the like. In addition, the herbicide-tolerant PPO protein variant may be one having increased structural stability to heat, pH, etc. of the protein, or increased protein activity by amino acid variation (mutation) and/or modification.

The term "sequence identity" refers to the degree of similarity to the wild type or reference amino acid sequence or nucleotide sequence, and any protein may be included in the scope of the present invention, as long as it includes amino acid residues having 60% or higher, 65% or higher, 70% or higher, 75% or higher, 80% or higher, 85% or higher, 90% or higher, 95% or higher, 98% or higher, or 99% or higher identity to the amino acid sequence of the herbicide-tolerant PPO protein variant as described above, and retains biological activities equivalent to the herbicide-tolerant PPO protein variant. Such protein homologues may comprise an active site equivalent to that of a targeted protein. Such identity comparison may be conducted visually or with the aid of readily available comparison programs. The identity between two or more sequences can be calculated as a percentage (%) using an online available analysis program. The sequence alignment for sequence comparison may be conducted by any conventional method known in the relevant art, and for example, the conventional method may include, but not be limited thereto, GAP, BESTFIT, BLAST, and Clustal Omega.

The herbicide-tolerant PPO protein or its variant may be obtained by extracting and/or purifying from nature by methods well known in the relevant art. Alternatively, it may be obtained as a recombinant protein using a gene recombination technology. In case of using a gene recombination technology, it may be obtained by a process of introducing a nucleic acid encoding the herbicide-tolerant PPO protein or its variant into an appropriate expression vector, and introducing the expression vector into a host cell in order to express the herbicide-tolerant PPO protein or its variant, and then collecting the expressed herbicide-tolerant PPO protein or its variant from the host cell. After the protein is expressed in a selected host cell, the protein can be separated and/or purified by general biochemical separation techniques, for example, treatment with a protein precipitating agent (salting out), centrifugation, ultrasonic disruption, ultrafiltration, dialysis, chromatography such as molecular sieve chromatography (gel filtration), adsorption chromatography, ion exchange chromatography, affinity chromatography and the like, and in order to separate the protein with a high purity, these methods may be used in combination.

The herbicide-tolerant PPO nucleic acid molecule (polynucleotide encoding the PPO protein or its variant) may be isolated or prepared using standard molecular biological techniques, for example, a chemical synthesis or recombination method, or as the herbicide-tolerant PPO nucleic acid molecule, commercially available one can be used.

In this disclosure, the PPO proteins/nucleic acids or variants thereof were found to exhibit broad herbicide tolerance against representative 10 families of PPO inhibiting herbicides classified according to their chemical structures in a herbicide tolerance test system using PPO-deficient *E. coli* BT3(ΔPPO). It was also found that the proteins may be expressed in the chloroplast of a plant by using a transit peptide (TP). Further, it was found that the PPO proteins/nucleic acids or variants thereof may be also expressed in a monocotyledon, such as *Oryza sativa*, or a dicotyledon, such as, *Arabidopsis thaliana* ecotype Columbia-0 (*A. thaliana*), by a plant expression vector. Even when the transformed plants are treated with PPO-inhibiting herbicides, germination and growth of the plants are observed. Furthermore, it was confirmed, by an inheritance study, that the above herbicide-tolerant traits can be successfully inherited to the next generation.

Therefore, the PPO protein and its variants provided herein may be introduced into a plant or algae, thereby conferring herbicide tolerance to the plant or algae, and/or enhancing herbicide tolerance of the plant or algae.

One embodiment provides a composition for conferring and/or enhancing herbicide tolerance of plants and/or algae, comprising at least one selected from the group consisting of:

(1) at least one selected from the group consisting of a polypeptide of SEQ ID NO: 1, a polypeptide of SEQ ID NO: 2, a polypeptide of SEQ ID NO: 3, a polypeptide variant thereof as described above, and a polypeptide comprising an amino acid sequence having at least 95%, at least 96%, at least 97%, at least 98%, or at least 99% sequence identity with the polypeptide or the polypeptide variant;

(2) a polynucleotide encoding the polypeptide or the polypeptide variant of (1);

(3) a recombinant vector comprising the polynucleotide of (2); and (4) a recombinant cell comprising the recombinant vector of (3).

The herbicide herein refers to an active ingredient that kills, controls, or otherwise adversely modifies the growth of plants or algae. In addition, the herbicide tolerance means that even after treatment of a herbicide which normally kills a normal or wild-type plant or normally inhibits growth thereof, inhibition of the plant growth is weakened or eliminated, compared to that of the normal or wild-type plant, and therefore, the plant continues to grow. The herbicide includes a herbicide inhibiting protoporphyrinogen IX oxidase (PPO) of a plant or an alga. Such PPO-inhibiting herbicide may be classified into pyrimidinediones, diphenyl-ethers, phenylpyrazoles, N-phenylphthalimides, phenylesters, thiadiazoles, oxadiazoles, triazinone, triazolinones, oxazolidinediones, and other herbicides, according to their chemical structures.

As a specific embodiment, the pyrimidinedione-based herbicide may include butafenacil, saflufenacil, benzfendizone, and tiafenacil, but not be limited thereto.

The diphenyl-ether-based herbicide may include fomesafen, oxyfluorfen, aclonifen, acifluorfen, bifenox, ethoxyfen, lactofen, chlomethoxyfen, chlornitrofen, fluoroglycofen-ethyl, and halosafen, but not be limited thereto.

The phenylpyrazole-based herbicide may include pyraflufen-ethyl and fluazolate, but not be limited thereto.

The phenylphthalimide-based herbicide may include flumioxazin, cinidon-ethyl, and flumiclorac-pentyl, but not be limited thereto.

The phenylesters herbicide may include phenopylate (2,4-dichlorophenyl 1-pyrrolidinecarboxylate) and carbamate analogues of phenopylate (for example, O-phenylpyrrolidino- and piperidinocarbamate analoges (refer to "Ujjana B. Nandihalli, Mary V. Duke, Stephen O. Duke, Relationships between molecular properties and biological activities of O-phenyl pyrrolidino- and piperidinocarbamate herbicides., J. Agric. Food Chem., 40(10) 1993-2000, 1992")), and the like, but not be limited thereto. In one specific embodiment, the carbamate analogue of phenopylate may be one or more selected from the group consisting of pyrrolidine-1-carboxylic acid phenyl ester (CAS No. 55379-71-0), 1-pyrrolidinecarboxylicacid, 2-chlorophenyl ester (CAS No. 143121-06-6), 4-chlorophenyl pyrrolidine-1-carboxylate (CAS No. 1759-02-0), carbamic acid, diethyl-,2,4-dichloro-5-(2-propynyloxy)phenyl ester (9CI) (CAS No. 143121-07-7), 1-pyrrolidinecarboxylicacid, 2,4-dichloro-5-hydroxyphenyl ester (CAS No. 143121-08-8), 2,4-dichloro-5-(methoxycarbonyl)phenyl pyrrolidine-1-carboxylate (CAS No. 133636-94-9), 2,4-dichloro-5-[(propan-2-yloxy)carbonyl]phenyl pyrrolidine-1-carboxylate (CAS No. 133636-96-1), 1-piperidinecarboxylic acid, 2,4-dichloro-5-(2-propynyloxy)phenyl ester (CAS No. 87374-78-5), 2,4-dichloro-5-(prop-2-yn-1-yloxy)phenyl pyrrolidine-1-carboxylate (CAS No. 87365-63-7), 2,4-dichloro-5-(prop-2-yn-1-yloxy)phenyl 4,4-difluoropiperidine-1-carboxylate (CAS No. 138926-22-4), 1-pyrrolidinecarboxylicacid, 3,3-difluoro-,2,4-dichloro-5-(2-propyn-1-yloxy)phenyl ester (CAS No. 143121-10-2), 4-chloro-2-fluoro-5-[(propan-2-yloxy)carbonyl]phenyl pyrrolidine-1-carboxylate (CAS No. 133636-98-3), and the like.

The thiadiazole-based herbicide may include fluthiacet and thidiazimin, but not be limited thereto.

The oxadiazole-based herbicide may include oxadiargyl and oxadiazon, but not be limited thereto.

The triazinone-based herbicide may include trifludimoxazin, but not be limited thereto.

The triazolinone-based herbicide may include carfentrazone, sulfentrazone, and azafenidin, but not be limited thereto.

The oxazolidinedione-based herbicide may include pentoxazone, but not be limited thereto.

The other herbicide may include pyraclonil, flufenpyrethyl, and profluazol, but not be limited thereto.

The herbicide-tolerant PPO gene or its variants provided herein may be introduced into a plant or algae by various methods known in the art, and preferably, by using an expression vector for plant or alga transformation.

In case of introducing the gene into a plant, an appropriate promoter which may be included in the vector may be any promoter generally used in the art for introduction of the gene into the plant. For example, the promoter may include an SP6 promoter, a T7 promoter, a T3 promoter, a PM promoter, a maize ubiquitin promoter, a cauliflower mosaic virus (CaMV) 35S promoter, a nopaline synthase (nos) promoter, a figwort mosaic virus 35S promoter, a sugarcane bacilliform virus promoter, a *commelina* yellow mottle virus promoter, a light-inducible promoter from the small subunit of ribulose-1,5-bisphosphate carboxylase (ssRUBISCO), a rice cytosolic triosephosphate isomerase (TPI) promoter, an adenine phosphoribosyltransferae (APRT) promoter of *A. thaliana*, an octopine synthase promoter, and a BCB (blue copper binding protein) promoter, but not be limited thereto.

Further, the vector may include a poly A signal sequence causing polyadenylation of 3'-terminus, and for example, it may include NOS 3'-end derived from a nopaline synthase gene of *Agrobacterium tumefaciens*, an octopine synthase terminator derived from an octopine synthase gene of *Agrobacterium tumefaciens*, 3'-end of protease inhibitor I or II gene of tomato or potato, a CaMV 35S terminator, a rice α-amylase RAmy1 A terminator, and a phaseolin terminator, but not be limited thereto.

In addition, the case of introducing the gene into an alga, chloroplast-specific promoter, nucleus promoter, constitutive promoter, or inducible promoter may be used for introduction of the gene into the algae as a promoter. The herbicide-tolerant PPO gene or its variant provided herein may be designed in order to operationally link to 5' UTR or 3' UTR, thereby expressing function in nucleus of algae. In addition, the vector may further comprise a transcriptional regulatory sequence which is appropriate to transformation of algae. A recombinant gene conferring herbicide tolerance may be integrated to genome of nucleus or genome of chloroplast in a host alga, but not be limited thereto.

In addition, in the vector, a transit peptide required for targeting to chloroplasts may be linked to 5'-end of the PPO gene or its variants in order to express the herbicide-tolerant PPO gene or its variants in the chloroplasts.

In addition, optionally, the vector may further include a gene encoding selectable marker as a reporter molecule, and example of the selectable marker may include a gene having tolerance to an antibiotic (e.g., neomycin, carbenicillin, kanamycin, spectinomycin, hygromycin, bleomycin, chloramphenicol, ampicillin, etc.) or herbicide (glyphosate, glufosinate, phosphinothricin, etc.), but is not limited thereto.

Further, the recombinant vector for plant expression may include an *Agrobacterium* binary vector, a cointegration vector, or a general vector which has no T-DNA region but is designed to be expressed in the plant. Of them, the binary vector refers to a vector containing two separate vector systems harboring one plasmid responsible for migration consisting of left border (LB) and right border (RB) in Ti (tumor inducing) plasmid, and the other plasmid for target gene-transferring, and the vector may include a promoter region and a polyadenylation signal sequence for expression in plants.

When the binary vector or cointegration vector is used, a strain for transformation of the recombinant vector into the plant is preferably *Agrobacterium* (*Agrobacterium*-mediated transformation). For this transformation, *Agrobacterium tumefaciens* or *Agrobacterium rhizogenes* may be used. In addition, when the vector having no T-DNA region is used, electroporation, particle bombardment, polyethylene glycol-mediated uptake, and the like may be used for introduction of the recombinant plasmid into the plant.

The plant transformed with the gene by the above method may be re-differentiated into a plant through callus induction, rhizogenesis, and soil acclimatization, using a standard technique known in the relevant art.

The plant subjected to transformation herein may cover not only a mature plant but also a plant cell (containing a suspension-cultured cell), a protoplast, a callus, a hypocotyl, a seed, a cotyledon, a shoot, and the like, which can grow to a mature plant.

Further, the scope of the transformant may include a transformant which the gene is introduced as well as a clone or progeny thereof ($T_1$ generation, $T_2$ generation, $T_3$ generation, $T_4$ generation, $T_5$ generation, $T_6$ generation, $T_7$ generation, $T_8$ generation, or any subsequent generations). For example, the transformed plant also includes a plant having the inherited herbicide tolerance traits as sexual and asexual progeny of the plant transformed with the gene provided herein. The scope of the present invention also includes all variants and variants showing the characteristics of the initial transformed plant, together with all hybridization and fusion products of the plant transformed with the gene provided herein. Furthermore, the scope of the present invention also includes a part of the plant, such as a seed, a flower, a stem, a fruit, a leaf, a root, a tuber, and/or a tuberous root, which is originated from a transformed plant which is transformed in advance by the method of the present invention, or a progeny thereof, and is composed of at least a part of the transformed cells.

The plant, to which the present invention is applied, is not particularly limited to, but may be at least one selected from the group consisting of monocotyledonous or dicotyledonous plants. Further, the plant may be at least one selected from the group consisting of herbaceous plants and woody plants. The monocotyledonous plant may include plants belonging to families Alismataceae, Hydrocharitaceae, Juncaginaceae, Scheuchzeriaceae, Potamogetonaceae, Najadaceae, Zosteraceae, Liliaceae, Haemodoraceae, Agavaceae, Amaryllidaceae, Dioscoreaceae, Pontederiaceae, Iridaceae, Burmanniaceae, Juncaceae, Commelinaceae, Eriocaulaceae, Gramineae (Poaceae), Araceae, Lemnaceae, Sparganiaceae, Typhaceae, Cyperaceae, Musaceae, Zingiberaceae, Cannaceae, Orchidaceae, and the like, but not be limited thereto.

The dicotyledonous plant may include plants belonging to families Diapensiaceae, Clethraceae, Pyrolaceae, Ericaceae, Myrsinaceae, Primulaceae, Plumbaginaceae, Ebenaceae, Styracaceae, Symplocaceae, Symplocaceae, Oleaceae, Loganiaceae, Gentianaceae, Menyanthaceae, Apocynaceae, Asclepiadaceae, Rubiaceae, Polemoniaceae, Convolvulaceae, Boraginaceae, Verbenaceae, Labiatae, Solanaceae, Scrophulariaceae, Bignoniaceae, Acanthaceae, Pedaliaceae, Orobanchaceae, Gesneriaceae, Lentibulariaceae, Phrymaceae, Plantaginaceae, Caprifoliaceae, Adoxaceae, Valerianaceae, Dipsacaceae, Campanulaceae, Compositae, Myricaceae, Juglandaceae, Salicaceae, Betulaceae, Fagaceae, Ulmaceae, Moraceae, Urticaceae, Santalaceae, Loranthaceae, Polygonaceae, Phytolaccaceae, Nyctaginaceae, Aizoaceae, Portulacaceae, Caryophyllaceae, Chenopodiaceae, Amaranthaceae, Cactaceae, Magnoliaceae, Illiciaceae, Lauraceae, Cercidiphyllaceae, Ranunculaceae, Berberidaceae, Lardizabalaceae, Menispermaceae, Nymphaeaceae, Ceratophyllaceae, Cabombaceae, Saururaceae, Piperaceae, Chloranthaceae, Aristolochiaceae, Actinidiaceae, Theaceae, Guttiferae, Droseraceae, Papaveraceae, Capparidaceae, Cruciferae, Platanaceae, Hamamelidaceae, Crassulaceae, Saxifragaceae, Eucommiaceae, Pittosporaceae, Rosaceae, Leguminosae, Oxalidaceae, Geraniaceae, Tropaeolaceae, Zygophyllaceae, Linaceae, Euphorbiaceae, Callitrichaceae, Rutaceae, Simaroubaceae, Meliaceae, Polygalaceae, Anacardiaceae, Aceraceae, Sapindaceae, Hippocastanaceae, Sabiaceae, Balsaminaceae, Aquifoliaceae, Celastraceae, Staphyleaceae, Buxaceae, Empetraceae, Rhamnaceae, Vitaceae, Elaeocarpaceae, Tiliaceae, Malvaceae, Sterculiaceae, Thymelaeaceae, Elaeagnaceae, Flacourtiaceae, Violaceae, Passifloraceae, Tamaricaceae, Elatinaceae, Begoniaceae, Cucurbitaceae, Lythraceae, Punicaceae, Onagraceae, Haloragaceae, Alangiaceae, Cornaceae, Araliaceae, Umbelliferae (Apiaceae), and the like, but not be limited thereto.

In a specific embodiment, the plant may be at least one selected from the group consisting of food crops such as rice, wheat, barley, corn, soybean, potato, red bean, oat, and sorghum; vegetable crops such as Chinese cabbage, radish, red pepper, strawberry, tomato, watermelon, cucumber, cabbage, oriental melon, pumpkin, welsh anion, anion, and carrot; crops for special use such as *ginseng*, tobacco, cotton, soilage, forage, sesame, sugar cane, sugar beet, *Perilla* sp., peanut, rapeseed, grass, and castor-oil plant; fruit trees such as apple tree, pear tree, jujube tree, peach tree, kiwi fruit tree, grape tree, citrus fruit tree, persimmon tree, plum tree, apricot tree and banana tree; woody plants such as pine, palm oil, and *eucalyptus*; flowering crops such as rose, *gladiolus, gerbera*, carnation, *chrysanthemum*, lily and tulip; and fodder crops such as ryegrass, red clover, orchardgrass, alfalfa, tall fescue and perennial ryegrass, but not be limited thereto. As a specific embodiment, the plant may be at least one selected from the group consisting of dicotyledonous plants such as *arabidopsis*, potato, eggplant, tobacco, red pepper, tomato, burdock, crown daisy, lettuce, balloon flower, spinach, chard, sweet potato, celery, carrot, water dropwort, parsley, Chinese cabbage, cabbage, radish, watermelon, oriental melon, cucumber, pumpkin, gourd, strawberry, soybean, mung bean, kidney bean, and pea; and monocotyledonous plants such as rice, wheat, barley, corn, sorghum, and the like, but not be limited thereto.

The algae, to which the present invention is applied, are not particularly limited to, but may be at least one prokaryotic algae or/and eukaryotic algae. For example, the algae may be at least one selected from the group consisting of cyanobacteria, green algae, red algae, brown algae, macroalgae, microalgae, and the like.

The cyanobacteria may include phylums Chroococcales (e.g., *Aphanocapsa, Aphanothece, Chamaesiphon, Chondrocystis, Chroococcus*, Chroogloeocystis, Crocosphaera, Cyanobacterium, Cyanobium, Cyanodictyon, Cyanosarcina, Cyanothece, Dactylococcopsis, *Gloeocapsa, Gloeothece*, Halothece, *Johannesbaptistia, Merismopedia, Microcystis, Radiocystis, Rhabdoderma*, Snowella, *Synechococcus, Synechocystis, Thermosynechococcus*, Woronichinia), Gloeobacteria, Nostocales (e.g., Microchaetaceae, Nostocaceae, Rivulariaceae, Scytonemataceae), Oscillatoriales (e.g., Arthronema, *Arthrospira*, Blennothrix, Crinalium, Geitlerinema, Halomicronema, Halospirulina, *Hydrocoleum*, Jaaginema, Katagnymene, Komvophoron, *Leptolyngbya*, Limnothrix, *Lyngbya, Microcoleus, Oscillatoria, Phormidium*, Planktothricoides, *Planktothrix, Plectonema, Pseudanabaena, Pseudophormidium, Schizothrix, Spirulina*, Starria, *Symploca, Trichodesmium*, Tychonema), Pleurocapsales (e.g., Chroococcidiopsis, *Dermocarpa*, Dermocarpella, *Myxosarcina, Pleurocapsa*, Solentia, Stanieria, *Xenococcus*), Prochlorales Stigonematales (e.g., *Capsosira, Chlorogloeopsis, Fischerella, Hapalosiphon, Mastigocladopsis, Mastigocladus, Nostochopsis, Stigonema, Symphyonema*, Symphonemopsis, Umezakia, Westiellopsis), and the like.

As another example of algae, Chlorophyta, Chlamydomonas, Volvacales, Dunaliella, Scenedesmus, Chlorella, or Hematococcm may be exemplified.

As other example of algae, Phaeodactylum *tricornutum*, Amphiprora *hyaline, Amphora* spp., *Chaetoceros muelleri, Navicula saprophila, Nitzschia communis, Scenedesmus dimorphus, Scenedesmus obliquus, Tetraselmis suecica, Chlamydomonas reinhardtii, Chlorella vulgaris, Haematococcus pluvialis, Neochloris oleoabundans, Synechococcus elongatus, Botryococcus braunii, Gloeobacter violaceus, Synechocystis, Thermosynechococcus elongatus, Nannochloropsis oculata, Nannochloropsis salina, Nannochloropsis gaditana, Isochrysis galbana, Botryococcus sudeticus, Euglena gracilis, Neochloris oleoabundans, Nitzschia palea, Pleurochrysis carterae, Tetraselmis chuii, Pavlova* spp., *Aphanocapsa* spp., *Synechocystis* spp., *Nannochloris* spp., and the like may be exemplified. However, it is not limited to kinds listed above, and algae belonging to other various genus and family may be comprised.

In an embodiment, the plant or algae with the herbicide-tolerant PPO or its variant provided herein may exhibit tolerance against two or more of PPO-inhibiting herbicides.

Therefore, the technology provided by this disclosure may be used to control weeds or remove undesired aquatic organisms by using at least two PPO-inhibiting herbicides sequentially or simultaneously.

One embodiment provides a method of controlling weeds in a cropland, comprising providing the cropland with a plant comprising the herbicide-tolerant PPO protein, its variant, or a gene encoding the same as described above, and applying an effective dosage of protoporphyrinogen IX oxidase-inhibiting herbicide to the cropland and/or the plant.

Another embodiment provides a method of removing an undesired aquatic organism from a culture medium, comprising:

providing a culture medium with algae comprising the herbicide-tolerant PPO protein, its variant, or a gene encoding the same described above, and applying an effective dosage of protoporphyrinogen IX oxidase-inhibiting herbicide to the culture medium.

In addition, the herbicide-tolerant PPO protein, its variant, or a gene encoding the same provided herein may be used in combination of a second herbicide-tolerant polypeptide or a gene encoding the same.

Therefore, the plant or algae introduced with the herbicide-tolerant PPO provided herein may exhibit tolerance against two or more of herbicides which are different from each other in mechanism of action. In the present invention, two or more of different herbicides including the PPO-inhibiting herbicide, which are different from each other in mechanism of action, may be used sequentially or simultaneously, thereby controlling weeds and/or removing undesired aquatic organisms. Hereinafter, the herbicide which is different from the PPO-inhibiting herbicide in the mechanism of action is called "second herbicide".

One embodiment provides a composition for conferring or enhancing herbicide tolerance of plants or algae, comprising the above-described herbicide-tolerant PPO protein, its variant, or a gene encoding the same; and a second herbicide-tolerant polypeptide or a gene encoding the same.

Another embodiment provides a transformant of plants or algae having herbicide tolerance, or a clone or progeny thereof, comprising the above-described herbicide-tolerant PPO protein, its variant, or a gene encoding the same; and a second herbicide-tolerant polypeptide or a gene encoding the same.

Another embodiment provides a method of preparing plants or algae having herbicide tolerance, comprising a step of introducing the above-described herbicide-tolerant PPO protein, its variant, or a gene encoding the same and a second herbicide-tolerant polypeptide or a gene encoding the same, into an alga, or a cell, protoplast, callus, hypocotyl, seed, cotyledon, shoot, or whole body of a plant.

Another embodiment provides a method of controlling weeds in a cropland, comprising providing the cropland with a plant comprising the above-described herbicide-tolerant PPO protein, its variant, or a gene encoding the same, and a second herbicide-tolerant polypeptide or a gene encoding the same, and applying effective dosages of protoporphyrinogen IX oxidase-inhibiting herbicide and the second herbicide to the cropland simultaneously or sequently in any order.

Another embodiment provides a method of removing an undesired aquatic organism from a culture medium, comprising providing a culture medium with algae comprising the herbicide-tolerant PPO protein, its variant, or a gene encoding the same and a second herbicide-tolerant polypeptide or a gene encoding the same, and applying effective dosages of protoporphyrinogen IX oxidase-inhibiting herbicide and the second herbicide to the culture medium simultaneously or sequently in any order.

For example, the plant or algae may further comprise the second herbicide-tolerance polypeptide or a gene encoding the same, thereby having acquired and/or enhanced tolerance against the second herbicide.

For example, the plant or alga further includes the second herbicide-tolerance polypeptide or a gene encoding thereof, thereby having novel and/or enhanced tolerance against the second herbicide.

For example, the second herbicide may include cell division-inhibiting herbicides, photosynthesis-inhibiting herbicides, amino acid synthesis-inhibiting herbicides, plastid-inhibiting herbicides, cell membrane-inhibiting herbicides, and/or any combinations thereof, but is not limited thereto. The second herbicide may be exemplified by glyphosate, glufosinate, dicamba, 2,4-D (2,4-dichlorophenoxy-acetic acid), ALS (acetolactate synthase)-inhibiting herbicides (for example, imidazolidinone, sulfonylurea, triazole pyrimidine, sulphonanilide, pyrimidine thiobenzoate, etc.), photosystem II-inhibiting herbicides, phenylurea-based herbicides, plastid-inhibiting herbicides, bromoxynil-based herbicides, and/or any combinations thereof, but is not limited thereto.

For example, the second herbicide-tolerant polypeptide may be exemplified as one or more kinds selected from the group consisting of glyphosate herbicide-tolerant EPSPS (glyphosate tolerant 5-enolpyruvylshikimate-3-phosphate synthase), GOX (glyphosate oxidase), GAT (glyphosate-N-acetyltransferase) or glyphosate decarboxylase; glufosinate herbicide-tolerant PAT (phosphinothricin-N-acetyltransferase); dicamba herbicide-tolerant DMO (dicamba monooxygenase); 2,4-D herbicide-tolerant 2,4-D monooxygenase or AAD (aryloxyalkanoate dioxygenase); ALS-inhibiting sulfonylurea-based herbicide-tolerant ALS (acetolactate synthase), AHAS (acetohydroxyacid synthase), or AtAHASL (*Arabidopsis thaliana* acetohydroxyacid synthase large subunit); photosystem II-inhibiting herbicide-tolerant photosystem II protein D1; phenylurea-based herbicide-tolerant cytochrome P450; plastid-inhibiting herbicide-tolerant HPPD (hydroxyphenylpyruvate dioxygenase); bromoxynil herbicide-tolerant nitrilase; and any combinations thereof, but is not limited thereto.

Further, the gene encoding the second herbicide-tolerant polypeptide may be exemplified as one or more kinds selected from the group consisting of glyphosate herbicide-tolerant cp4 epsps, epsps (AG), mepsps, 2mepsps, goxv247, gat4601 or gat4621 gene; glufosinate herbicide-tolerant bar, pat or pat (SYN) gene; dicamba herbicide-tolerant dmo gene; 2,4-D herbicide-tolerant AAD-1 or AAD-12 gene; ALS-inhibiting sulfonylurea-based herbicide-tolerant ALS, GM-HRA, S4-HRA, ZM-HRA, Csr1, Csr1-1, Csr1-2, SurA or SurB; photosystem II-inhibiting herbicide-tolerant psba gene; phenylurea herbicide-tolerant CYP76B1 gene; isoxaflutole herbicide-tolerant HPPDPF W336 gene; bromoxynil herbicide-tolerant bxn gene; and any combinations thereof, but is not limited thereto.

Advantageous Effects

Variants of herbicide-tolerant PPO proteins or genes encoding the same provided herein may be applied to plants or algae, thereby conferring excellent herbicide tolerance traits to the plants or algae and/or enhancing the herbicide tolerance traits of the plants or algae. In addition, a selective control can be performed using herbicides, thereby economically controlling weeds or removing aquatic organisms.

DESCRIPTION OF DRAWINGS

FIG. 1 is a map of pMAL-c2X vector.

FIG. 2 is a map of pET303-CT-His vector.

FIGS. 3 to 30 show cell growth level of PPO-deficient BT3 *E. coli* (ΔPPO) transformed with CyPPO19 wild type gene (indicated by CyPPO19WT), or CyPPO19 variant genes, when treated with various herbicides at various concentrations.

FIGS. 31 and 32 show cell growth level of PPO-deficient BT3 *E. coli* (ΔPPO) transformed with CyPPO18 wild type gene (indicated by CyPPO18WT), or CyPPO18 variant genes, when treated with various herbicides at various concentrations.

FIG. 33 schematically shows a recombinant vector for preparing a fusion protein wherein maltose binding protein (MBP) and PPO protein are fused.

FIGS. 34 and 35 show results observed at the 7$^{th}$ day after spraying 1 µM of tiafenacil or 1 µM of flumioxazin to transgenic *A. thaliana* (T$_2$) transformed with CyPPO19 WT or its variant (F360M, F360V, F360L, V165C+F360M, V165S+F360V) genes compared to wild type *A. thaliana* (Col-0).

FIGS. 36 and 37 show results observed at the 7$^{th}$ day after spraying 5 µM of tiafenacil or 5 µM of flumioxazin to transgenic *A. thaliana* (T$_2$) transformed with CyPPO19

Forward primer (10 µM, refer to Table 1) 1 µl

Reverse primer (10 µM, refer to Table 1) 1 µl

DDW 40 µl

Pfu-X (Solgent, 2.5 units/µl) 1 µl

Total 50 µl

Each PPO gene was designated as CyPPO19 isolated from *Thermosynechococcus elongatus* PKUAC-SCTE542, CyPPO20 from *Cyanobacteria bacterium* J003, and CyPPO18 from *Thermosynechococcus vulcanus* NIES-2134.

TABLE 1

| Strain | Primer | Sequence | SEQ ID NO |
|---|---|---|---|
| *Thermosynechococcus elongatus* PKUAC-SCTE542 | Cy19 BglII_F | GAAGATCTATGAGTGAGGTAGATGTCG | 159 |
|  | Cy19 SalI_R | ACGCGTCGACCTAGGGCTGGCCTCCTGA | 160 |
| *Cyanobacteria bacterium* J003 | Cy20 BglII_F | GAAGATCTATGATGGAGGTAGATGTCGC | 161 |
|  | Cy20 SalI_R | ACGCGTCGACTTAACCTCCTGAAAGGTA GGC | 162 |
| *Thermosynechococcus vulcanus* NIES-2134 | Cy18 BglII_F | CCAGATCTATGATTGAGGTAGATGTC G | 163 |
|  | Cy18 SalI_R | CCGTCGACCTAGGACTGGCCTCCTGC | 164 | variant (F360M, F360V, F360L, V165C+F360M, V165S+F360V) genes compared to wild type *A. thaliana* (Col-0).

FIG. 38 shows a result observed at the 7$^{th}$ day after spraying 1 µM of tiafenacil to transgenic *A. thaliana* (T$_2$) transformed with CyPPO18 WT gene compared to wild type *A. thaliana* (Col-0).

FIG. 39 shows a result observed at the 7$^{th}$ day after spraying 1 µM of tiafenacil to transgenic *A. thaliana* (T$_2$) transformed with CyPPO18 variant (L327T+F360M) gene compared to wild type *A. thaliana* (Col-0).

MODE FOR INVENTION

Hereinafter, the present invention will be described in detail with reference to Examples. However, these Examples are for illustrative purposes only, and the invention is not intended to be limited by these Examples.

Example 1. Isolation of PPO Genes from Prokaryotic Species

PPO sequence information was obtained from Genebank database of species including *Thermosynechococcus elongatus* PKUAC-SCTE542, *Cyanobacteria bacterium* J003, and *Thermosynechococcus vulcanus* NIES-2134. PPO genes were synthesized (Integrated DNA Technologies). PPO genes were amplified under the condition of Table 2 using primers listed in Table 1 to clone them into pMAL-c2X vector (FIG. 1).

PCR mixture:

Template (synthetic DNA of each of CyPPO19, CyPPO20, and CyPPO18) 1 µl

10× buffer 5 µl dNTP mixture (10 mM each) 1 µl

TABLE 2

| PCR Condition | | |
|---|---|---|
| 94° C. | 4 min. | 1 cycle |
| 94° C. | 30 sec. | 25 cycles |
| 56° C. | 30 sec. | |
| 72° C. | 1.5 min. | |
| 72° C. | 5 min. | 1 cycle |
| 4° C. | 5 min. | 1 cycle |

Example 2. Construction of PPO Variants

In order to enhance PPO-inhibiting herbicide tolerance of CyPPO19, CyPPO20, and CyPPO18, a mutation(s) at the position interacting with herbicide was introduced, to prepare variants of CyPPO19, CyPPO20, and CyPPO18.

Detailed experimental procedure was as follows:

Using primers listed in Table 3, PCR was carried out to amplify PPO genes under the conditions shown in Table 4.

PCR reaction mixture:

Template (synthetic DNA of each of CyPPO19, CyPPO20, or CyPPO18) 1 µl

10× buffer 5 µl dNTP mixture (10 mM each) 1 µl

Forward primer (10 µM) 1 µl

Reverse primer (10 µM) 1 µl

DDW 40 µl

Pfu-X (Solgent, 2.5 units/pi) 1 µl

Total 50 µl

TABLE 3

| | | | SEQ ID |
| Strain | Primer | Sequence | NO |
| --- | --- | --- | --- |
| *Thermosynechococcus* | Cy19 | AGTATCTAGAATGAGTGAGGTAGATG | 165 |
| *elongatus* PKUAC- | XbaI_F | TCG | |
| SCTE542 | Cy19 | TTAACTCGAGGGGCTGGCCTCCTGAA | 166 |
| | XhoI_R | AG | |
| *Cyanobacteria* | Cy20 | GCTCTAGAATGATGGAGGTAGATGTCGC | 167 |
| *bacterium* J003 | XbaI_F | | |
| | Cy20 | CCGCTCGAGACCTCCTGAAAGGTAGGC | 168 |
| | XhoI_R | | |
| *Thermosynechococcus* | Cy18 | CCTCTAGAATGATTGAGGTAGATGTC | 169 |
| *vulcanus* NIES-2134 | XbaI_F | G | |
| | Cy18 | CCCTCGAGGGACTGGCCTCCTGCAA | 170 |
| | XhoI_R | GA | |

Amplified PCR products above and pET303-CT His vector (Invitrogen; FIG. 2) were digested with XbaI and XhoI restriction enzymes, and ligated to construct pET303-CyPPO19 pET303-CyPPO20, and pET303-CyPPO18 plasmids using T4 DNA ligase (RBC, 3 units/µl).

Variants of CyPPO19, CyPPO20, and CyPPO18 were constructed using CyPPO19, CyPPO20, and CyPPO18 genes cloned in pET303-CT His vector with primers listed in Tables 5 to 7 under the condition as following.

PCR reaction mixture
Template 1 µl
10× buffer 5 µl
dNTP mixture (10 mM each) 1 µl
forward primer (10 µM) 1 µl
reverse primer (10 µM) 1 µl DDW 40 µl
Pfu-X (Solgent, 2.5 unit/µl) 1 µl
Total 50 µl

TABLE 4

| PCR condition | | |
| --- | --- | --- |
| 94° C. | 4 min. | 1 cycle |
| 94° C. | 30 sec. | 17-25 cycles |
| 56~60° C. | 30 sec. | |
| 72° C. | 3 min. | |
| 72° C. | 5 min. | 1 cycle |
| 4° C. | 5 min. | 1 cycle |

TABLE 5

| Primer list for CyPPO19 variant construction | | |
| --- | --- | --- |
| CyPPO19 mutagenesis | | SEQ ID |
| primer | sequence (5'-> 3') | NO |
| Cy19 R89A F | GATCGCCACCTGCCGGCGTACATCTACTGGCGG | 171 |
| Cy19 R89A R | CCGCCAGTAGATGTACGCCGGCAGGTGGCGATC | 172 |
| Cy19 V165C F | GTCTCTGGGTGCTATGCGGGTGATCCACAACAA | 173 |
| Cy19 V165C R | ACCCGCATAGCACCCAGAGACAAAGGGCGCCAC | 174 |
| Cy19 V165S F | CCCTTTGTCTCTGGGAGTTATGCGGGTGATCCA | 175 |
| Cy19 V165S R | TGGATCACCCGCATAACTCCCAGAGACAAAGGG | 176 |
| Cy19 A167C F | GCGCCCTTTGTCTCTGGGGTTTATTGCGGT | 177 |
| Cy19 A167C R | AGCACTCAGTTGTTGTGGATCACCGCAATA | 178 |
| Cy19 A167L F | GTCTCTGGGGTTTATCTGGGTGATCCACAACAA | 179 |
| Cy19 A167L R | TTGTTGTGGATCACCCAGATAAACCCCAGAGAC | 180 |
| Cy19 A167I F | GTCTCTGGGGTTTATATCGGTGATCCACAACAA | 181 |
| Cy19 A167I R | TTGTTGTGGATCACCGATATAAACCCCAGAGAC | 182 |
| Cy19 V305L F | CATTCCCTATCCCACCCTAGCCTGTGTGGTCTTG | 183 |
| Cy19 V305L R | CAAGACCACACAGGCTAGGGTGGGATAGGGAAT G | 184 |
| Cy19 V305M F | TATCCCACCATGGCCTGTGTGGTCTTGGCCTAT | 185 |

TABLE 5-continued

| Primer list for CyPPO19 variant construction | | |
|---|---|---|
| CyPPO19 mutagenesis primer | sequence (5'-> 3') | SEQ ID NO |
| Cy19 V305M R | CACACAGGCCATGGTGGGATAGGGAATGGTGGCC AA | 186 |
| Cy19 L327T F | AGTGTCCGCCCCGGCTTTGGCGTAACCATT | 187 |
| Cy19 L327T R | GCGGATGCCCTGACTGCGAGGAATGGTTAC | 188 |
| Cy19 F360I F | CAAGTCTTTACGAGTATTATTGGCGGTGCTAC | 189 |
| Cy19 F360I R | GTAGCACCGCCAATAATACTCGTAAAGACTTG | 190 |
| Cy19 F360L F | GTCTTTACGAGTTTAATTGGCGGTGCTACG | 191 |
| Cy19 F360L R | CGTAGCACCGCCAATTAAACTCGTAAAGAC | 192 |
| Cy19 F360M F | GGCAAGTCTTTACGAGTATGATTGGCGGTGCTAC GG | 193 |
| Cy19 F360M R | CCGTAGCACCGCCAATCATACTCGTAAAGACTTG CC | 194 |
| Cy19 F360V F | CAAGTCTTTACGAGTGTTATTGGCGGTGCTAC | 195 |
| Cy19 F360V R | GTAGCACCGCCAATAACACTCGTAAAGACTTG | 196 |
| Cy19 F360T F | TTTACGAGTACTATTGGCGGTGCTACGGATCCTGA | 197 |
| Cy19 F360T R | CCGCCAATAGTACTCGTAAAGACTTGCCAACCGG | 198 |
| Cy19 I408R F | GTTTGGCGACGGGCGAGACCCCAATATATGGTG | 199 |
| Cy19 I408R R | CACCATATATTGGGGTCTCGCCCGTCGCCAAAC | 200 |
| Cy19 I408W F | AGGTTTGGCGACGGGCGTGGCCCCAATATATG | 201 |
| Cy19 I408W R | CATATATTGGGGCCACGCCCGTCGCCAAACCT | 202 |
| Cy19 V165C + A167C F | CCTTTGTCTCTGGGTGTTATTGCGGTGATCCACAA CAACTG | 203 |
| Cy19 V165C + A167C R | CAGTTGTTGTGGATCACCGCAATAACACCCAGAG ACAAAGG | 204 |
| Cy19 V165C + A167L F | GGCGCCCTTTGTCTCTGGGTGCTACCTGGGTGAT CCACAACA | 205 |
| Cy19 V165C + A167L R | TGTTGTGGATCACCCAGGTAGCACCCAGAGACAA AGGGCGCC | 206 |
| Cy19 V165S + A167C F | GGCGCCCTTTGTCTCTGGGAGCTACTGCGGTGAT CCACAACAAC | 207 |
| Cy19 V165S + A167C R | GTTGTTGTGGATCACCGCAGTAGCTCCCAGAGAC AAAGGGCGCC | 208 |
| Cy19 V165C + A167I F | GGCGCCCTTTGTCTCTGGGTGCTACATCGGTGATC CACA | 209 |
| Cy19 V165C + A167I R | TGTGGATCACCGATGTAGCACCCAGAGACAAAG GGCGCC | 210 |
| Cy19 V165S + A167I F | GGCGCCCTTTGTCTCTGGGAGCTACATCGGTGAT CCACA | 211 |
| Cy19 V165S + A167I R | TGTGGATCACCGATGTAGCTCCCAGAGACAAAGG GCGCC | 212 |
| Cy19 V165S + A167L F | CCTTTGTCTCTGGGTCTTATCTGGGTGATCCACAA CAACTG | 213 |
| Cy19 V165S + A167L R | CAGTTGTTGTGGATCACCCAGATAAGACCCAGAG ACAAAGG | 214 |

TABLE 6

| Primer list for CyPPO20 variant construction | | |
|---|---|---|
| CyPPO20 mutagenesis primer | sequence (5'-> 3') | SEQ ID NO |
| Cy20 R89A F | GATCGCCACCTACCGGCGTACATCTACTGGCGG | 215 |
| Cy20 R89A R | CCGCCAGTAGATGTACGCCGGTAGGTGGCGATC | 216 |
| Cy20 V165C F | CCCTTTGTCTCTGGGTGTTACGCCGGTGATCCG | 217 |
| Cy20 V165C R | CGGATCACCGGCGTAACACCCAGAGACAAAGGG | 218 |
| Cy20 V165S F | CCCTTTGTCTCTGGGAGTTACGCCGGTGATCCG | 219 |
| Cy20 V165S R | CGGATCACCGGCGTAACTCCCAGAGACAAAGGG | 220 |
| Cy20 A167C F | GTCTCTGGGGTTTACTGTGGTGATCCGCAACAA | 221 |
| Cy20 A167C R | TTGTTGCGGATCACCACAGTAAACCCCAGAGAC | 222 |
| Cy20 A167L F | GTCTCTGGGGTTTACCTCGGTGATCCGCAACAA | 223 |
| Cy20 A167L R | TTGTTGCGGATCACCGAGGTAAACCCCAGAGAC | 224 |
| Cy20 A167I F | GTCTCTGGGGTTTACATTGGTGATCCGCAACAA | 225 |
| Cy20 A167I R | TTGTTGCGGATCACCAATGTAAACCCCAGAGAC | 226 |
| Cy20 V305L F | CATCCCCTATCCCACCCTAGCCTGTGTGGTCTTG | 227 |
| Cy20 V305L R | CAAGACCACACAGGCTAGGGTGGGATAGGGGATG | 228 |
| Cy20 V305M F | ATCCCCTATCCCACCATGGCCTGTGTGGTCTTG | 229 |
| Cy20 V305M R | CAAGACCACACAGGCCATGGTGGGATAGGGGAT | 230 |
| Cy20 L327T F | CCCGGATTTGGCGTAACGATTCCTCGTGGCCAG | 231 |
| Cy20 L327T R | CTGGCCACGAGGAATCGTTACGCCAAATCCGGG | 232 |
| Cy20 I340T F | CGTACCCTTGGCACCACATGGTCGTCCTGTCTT | 233 |
| Cy20 I340T R | AAGACAGGACGACCATGTGGTGCCAAGGGTACG | 234 |
| Cy20 F360I F | CAAGTCTTTACAAGTACCATTGGCGGTGCCACG | 235 |
| Cy20 F360I R | CGTGGCACCGCCAATGGTACTTGTAAAGACTTG | 236 |
| Cy20 F360L F | CAAGTCTTTACAAGTCTGATTGGCGGTGCCACG | 237 |
| Cy20 F360L R | CGTGGCACCGCCAATCAGACTTGTAAAGACTTG | 238 |
| Cy20 F360M F | CAAGTCTTTACAAGTATGATTGGCGGTGCCACG | 239 |
| Cy20 F360M R | CGTGGCACCGCCAATCATACTTGTAAAGACTTG | 240 |
| Cy20 F360V F | CAAGTCTTTACAAGTGTTATTGGCGGTGCCACG | 241 |
| Cy20 F360V R | CGTGGCACCGCCAATAACACTTGTAAAGACTTG | 242 |
| Cy20 I408R F | GTTTGGCGACGGGCGAGGCCCCAATATCTTGTG | 243 |
| Cy20 I408R R | CACAAGATATTGGGGCCTCGCCCGTCGCCAAAC | 244 |
| Cy20 I408W F | GTTTGGCGACGGGCGTGGCCCCAATATCTTGTG | 245 |
| Cy20 I408W R | CACAAGATATTGGGGCCACGCCCGTCGCCAAAC | 246 |
| Cy20 V165C + A167C F | CCCTTTGTCTCTGGGTGTTACTGTGGTGATCCGCAACAA | 247 |
| Cy20 V165C + A167C R | TTGTTGCGGATCACCACAGTAACACCCAGAGACAAAGGG | 248 |
| Cy20 V165C + A167I F | CCCTTTGTCTCTGGGTGTTACATTGGTGATCCGCAACAA | 249 |

TABLE 6-continued

| Primer list for CyPPO20 variant construction | | |
| --- | --- | --- |
| CyPPO20 mutagenesis primer | sequence (5'-> 3') | SEQ ID NO |
| Cy20 V165C + A167I R | TTGTTGCGGATCACCAATGTAACACCCAGAGACAAAGGG | 250 |
| Cy20 V165C + A167L F | CCCTTTGTCTCTGGGTGTTACCTCGGTGATCCGCAACAA | 251 |
| Cy20 V165C + A167L R | TTGTTGCGGATCACCGAGGTAACACCCAGAGACAAAGGG | 252 |
| Cy20 V165S + A167C F | CCCTTTGTCTCTGGGAGTTACTGTGGTGATCCGCAACAA | 253 |
| Cy20 V165S + A167C R | TTGTTGCGGATCACCACAGTAACTCCCAGAGACAAAGGG | 254 |
| Cy20 V165S + A167I F | CCCTTTGTCTCTGGGAGTTACATTGGTGATCCGCAACAA | 255 |
| Cy20 V165S + A167I R | TTGTTGCGGATCACCAATGTAACTCCCAGAGACAAAGGG | 256 |
| Cy20 V165S + A167L F | CCCTTTGTCTCTGGGAGTTACCTCGGTGATCCGCAACAA | 257 |
| Cy20 V165S + A167L R | TTGTTGCGGATCACCGAGGTAACTCCCAGAGACAAAGGG | 258 |

TABLE 7

| Primer list for CyPPO18 variant construction | | |
| --- | --- | --- |
| CyPPO18 mutagenesis primer | sequence (5'-> 3') | SEQ ID NO |
| Cy18 R89A F | GATCGCCACCTACCGGCATACATCTACTGGCG | 259 |
| Cy18 R89A R | CGCCAGTAGATGTATGCCGGTAGGTGGCGATC | 260 |
| Cy18 V165C F | CCCTTTGTCTCTGGGTGTTATGCCGGTGATC | 261 |
| Cy18 V165C R | GATCACCGGCATAACACCCAGAGACAAAGGG | 262 |
| Cy18 V165S F | CCCTTTGTCTCTGGGAGTTATGCCGGTGATC | 263 |
| Cy18 V165S R | GATCACCGGCATAACTCCCAGAGACAAAGGG | 264 |
| Cy18 A167C F | GTCTCTGGGGTTTATTGCGGTGATCCGCAAC | 265 |
| Cy18 A167C R | GTTGCGGATCACCGCAATAAACCCCAGAGAC | 266 |
| Cy18 A167L F | GTCTCTGGGGTTTATCTCGGTGATCCGCAAC | 267 |
| Cy18 A167L R | GTTGCGGATCACCGAGATAAACCCCAGAGAC | 268 |
| Cy18 A167I F | GTCTCTGGGGTTTATATCGGTGATCCGCAAC | 269 |
| Cy18 A167I R | GTTGCGGATCACCGATATAAACCCCAGAGAC | 270 |
| Cy18 V305L F | CATCCCCTATCCCACCCTAGCCTGTGTGGTGTTG | 271 |
| Cy18 V305L R | CAACACCACACAGGCTAGGGTGGGATAGGGGATG | 272 |
| Cy18 V305M F | CATCCCCTATCCCACCATGGCCTGTGTGGTGTTG | 273 |

TABLE 7-continued

| Primer list for CyPPO18 variant construction | | |
|---|---|---|
| CyPPO18 mutagenesis primer | sequence (5'-> 3') | SEQ ID NO |
| Cy18 V305M R | CAACACCACACAGGCCATGGTGGGATAGGGGATG | 274 |
| Cy18 L327T F | CCGGATTTGGAGTAACGGTTCCTCGTGGTC | 275 |
| Cy18 L327T R | GACCACGAGGAACCGTTACTCCAAATCCGG | 276 |
| Cy18 F360I F | CAAGTCTTCACCAGTATTATTGGCGGTGCTAC | 277 |
| Cy18 F360I R | GTAGCACCGCCAATAATACTGGTGAAGACTTG | 278 |
| Cy18 F360L F | GTCTTCACCAGTTTGATTGGCGGTGCTAC | 279 |
| Cy18 F360L R | GTAGCACCGCCAATCAAACTGGTGAAGAC | 280 |
| Cy18 F360M F | GCAAGTCTTCACCAGTATGATTGGCGGTGCTACGG | 281 |
| Cy18 F360M R | CCGTAGCACCGCCAATCATACTGGTGAAGACTTGC | 282 |
| Cy18 F360V F | CAAGTCTTCACCAGTGTTATTGGCGGTGCTAC | 283 |
| Cy18 F360V R | GTAGCACCGCCAATAACACTGGTGAAGACTTG | 284 |
| Cy18 V165C + A167L F | GCCCCCTTTGTCTCTGGGTGCTACCTCGGTGATCCG CAACAA | 285 |
| Cy18 V165C + A167L R | TTGTTGCGGATCACCGAGGTAGCACCCAGAGACAA AGGGGGC | 286 |
| Cy18 V165S + A167C F | GCCCCCTTTGTCTCTGGGAGCTACTGCGGTGATCCG CAACAA | 287 |
| Cy18 V165S + A167C R | TTGTTGCGGATCACCGCAGTAGCTCCCAGAGACAA AGGGGGC | 288 |
| Cy18 V165C + A167C F | CCCCCTTTGTCTCTGGGTGCTATTGCGGTGATCCGC A | 289 |
| Cy18 V165C + A167C R | TGCGGATCACCGCAATAGCACCCAGAGACAAAGGG GG | 290 |
| Cy18 V165C + A167I F | CCCCCTTTGTCTCTGGGTGCTACATCGGTGATCCGC A | 291 |
| Cy18 V165C + A167I R | TGCGGATCACCGATGTAGCACCCAGAGACAAAGGG GG | 292 |
| Cy18 V165S + A167I F | CCCCCTTTGTCTCTGGGAGCTACATCGGTGATCCGC A | 293 |
| Cy18 V165S + A167I R | TGCGGATCACCGATGTAGCTCCCAGAGACAAAGGG GG | 294 |
| Cy18 V165S + A167L F | GCCCCCTTTGTCTCTGGGAGCTACCTCGGTGATCCG CAACAA | 295 |
| Cy18 V165S + A167L R | TTGTTGCGGATCACCGAGGTAGCTCCCAGAGACAA AGGGGGC | 296 |

Example 3. Verification of PPO-Inhibiting Herbicide Tolerance of PPO Variants (Test in *E. coli*)

To enhance the PPO-inhibiting herbicide resistance of CyPPO19 and CyPPO18, PPO variant genes of the above example 2 were constructed. They were transformed to BT3 (ΔPPO) strain which is deficient of PPO activity and cultured in LB media with PPO-inhibiting herbicide, thereby examining whether growth of transformed BT3 was not inhibited.

Detailed experimental procedure was as follows:

BT3 competent cells were transformed with the pET303-CyPPO19 (wild type), pET303-CyPPO18 (wild type) plasmids, and those with a mutation(s) constructed (refer to example 2) via heat shock method, and were cultured in LB agar media containing ampicillin.

Single colony transformed with each CyPPO gene was cultured in 3 mL of LB broth (LPSS) containing ampicillin for more than 12 hours, and then was subcultured in LB broth until absorbance ($OD_{600}$) reached 0.5 to 1. Then, it was diluted with LB broth to $OD_{600}$=0.5. Again, the diluted solution was serially diluted 4 times by a factor of one tenth.

The LB agar media (LB 25 g/L, Bacto agar 12 g/L) containing ampicillin (100 μg/mL) and 0 to 2,000 μM of various herbicides were prepared. Herbicide solution stocks were all prepared in DMSO.

Then, 10 μL of each diluted solution of *E. coli* was dropped on the plate and cultured at 37° C. under dark for 16-20 hours. PPO-inhibiting herbicide resistance was evaluated with the extent of *E. coli* growth containing each gene was observed.

Herbicides used for tests were listed in Table 8.

TABLE 8

| Family | Herbicide |
| --- | --- |
| Pyrimidinedione herbicide | Tiafenacil |
| | Saflufenacil |
| Diphenyl ether herbicide | Fomesafen |
| | Oxyfluorfen |
| N-phenylphthalimides herbicide | Flumioxazin |
| Triazolinones herbicide | Sulfentrazone |
| | Carfentrazone |

The extent of herbicide resistance was evaluated by the relative growth of variants to that of wild type, and listed in Tables 9 and 10 and FIGS. 3 to 32.

TABLE 9

| No. | Variant | Tiafenacil | Saflufenacil | Flumioxazin | Fomesafen | Sulfentrazone | Oxyfluorfen | Carfentrazone |
| --- | --- | --- | --- | --- | --- | --- | --- | --- |
| 1 | R89A + F360M | ++ | ++++ | +++ | ++ | ++ | + | + |
| 2 | R89A + F360V | ++++ | ++++ | ++++ | + | +++ | + | + |
| 3 | R89A + F360I | +++ | ++++ | +++ | + | +++ | + | + |
| 4 | R89A + F360L | ++ | +++ | ++ | + | ++ | + | + |
| 5 | R89A + F360T | +++ | +++ | +++ | ++ | +++ | + | + |
| 6 | V165C + F360I | ++++ | ++++ | ++++ | + | ++++ | + | + |
| 7 | V165C + F360M | ++++ | ++++ | ++++ | +++ | ++++ | ++ | + |
| 8 | V165C + F360V | ++++ | ++++ | ++++ | + | ++++ | ++ | + |
| 9 | V165C + F360L | ++++ | ++++ | ++++ | +++ | ++++ | ++ | + |
| 10 | V165S + F360V | ++++ | ++++ | ++++ | + | ++++ | ++ | + |
| 11 | V165S + F360L | ++++ | ++++ | ++++ | ++ | +++ | ++ | + |
| 12 | V165S + F360T | ++++ | +++ | +++ | + | ++ | + | + |
| 13 | A167C + F360I | ++++ | +++ | ++++ | + | ++ | + | + |
| 14 | A167L + F360M | ++++ | ++++ | ++++ | ++ | ++ | + | + |
| 15 | A167I + F360L | +++ | +++ | +++ | + | + | + | + |
| 16 | A167L + F360T | +++ | +++ | +++ | + | ++ | + | + |
| 17 | A167C + F360M | ++++ | ++++ | ++++ | + | + | ++ | + |
| 18 | A167C + F360L | +++ | +++ | +++ | + | + | + | + |
| 19 | A167C + F360V | ++++ | +++ | +++ | + | + | + | + |
| 20 | V305M + F360I | ++++ | ++++ | ++++ | + | ++ | + | + |
| 21 | V305L + F360M | +++ | ++++ | ++++ | +++ | + | ++ | + |
| 22 | V305M + F360M | ++++ | ++++ | ++++ | +++ | ++ | ++ | + |
| 23 | V305M + F360V | ++++ | ++++ | ++++ | + | + | ++ | + |

TABLE 9-continued

| No. | Variant | Tiafenacil | Saflufenacil | Flumioxazin | Fomesafen | Sulfentrazone | Oxyfluorfen | Carfentrazone |
|---|---|---|---|---|---|---|---|---|
| 24 | V305M + F360L | ++++ | ++++ | ++++ | ++ | ++ | ++ | + |
| 25 | V305L + F360L | ++++ | ++++ | ++++ | +++ | ++ | ++ | + |
| 26 | V305M + F360T | ++ | ++ | ++ | ++ | + | + | + |
| 27 | L327T + F360I | ++++ | ++ | ++++ | + | +++ | ++ | + |
| 28 | L327T + F360M | +++ | + | +++ | + | + | ++ | + |
| 29 | L327T + F360V | ++++ | ++ | ++++ | + | ++ | ++ | + |
| 30 | L327T + F360L | ++++ | + | ++++ | ++ | ++ | ++ | + |
| 31 | L327T + F360T | ++ | + | + | + | + | + | + |
| 32 | I408W + F360I | ++++ | +++ | +++ | +++ | +++ | ++ | + |
| 33 | I408R + F360M | +++ | ++ | ++ | + | + | + | + |
| 34 | I408W + F360V | ++++ | +++ | ++++ | +++ | +++ | ++ | + |
| 35 | I408R + F360L | ++ | + | + | + | + | + | + |
| 36 | I408W + F360T | ++ | ++ | + | + | + | + | + |
| 37 | R89A + V165C + F360I | ++++ | ++++ | ++++ | ++ | +++ | ++ | + |
| 38 | R89A + V165S + F360M | ++++ | ++++ | ++++ | +++ | +++ | +++ | + |
| 39 | R89A + V165C + F360V | ++++ | ++++ | ++++ | + | +++ | + | + |
| 40 | R89A + A167I + F360V | +++++ | +++++ | +++++ | +++ | +++++ | +++ | + |
| 41 | R89A + A167C + F360L | ++++ | ++++ | ++++ | ++ | ++++ | +++ | ++ |
| 42 | R89A + A167L + F360T | ++++ | ++++ | ++++ | ++ | +++ | ++ | ++ |
| 43 | R89A + V305M + F360I | +++ | +++ | +++ | + | ++ | + | + |
| 44 | R89A + V305M + F360V | +++ | +++ | +++ | + | ++ | + | + |
| 45 | R89A + V305M + F360T | +++++ | +++++ | +++++ | +++ | +++++ | +++ | ++ |
| 46 | R89A + L327T + F360I | ++++ | ++ | ++++ | ++ | +++ | + | + |
| 47 | R89A + L327T + F360M | +++ | ++ | ++++ | +++ | ++ | ++ | + |
| 48 | R89A + L327T + F360T | +++++ | +++++ | +++++ | +++++ | +++++ | +++ | + |
| 49 | R89A + I408R + F360M | +++ | ++++ | ++++ | +++ | +++ | ++ | + |
| 50 | R89A + I408W + F360V | +++++ | +++++ | +++++ | +++++ | +++++ | +++ | + |
| 51 | R89A + I408R + F360L | +++ | +++ | +++ | + | ++ | + | + |
| 52 | V165S + A167I + F360M | +++++ | ++++ | +++++ | ++ | +++ | ++ | + |
| 53 | V165S + A167C + F360L | ++++ | +++ | ++++ | + | ++ | + | + |

TABLE 9-continued

| No. | Variant | Tiafenacil | Saflufenacil | Flumioxazin | Fomesafen | Sulfentrazone | Oxyfluorfen | Carfentrazone |
|---|---|---|---|---|---|---|---|---|
| 54 | V165C + A167L + F360T | ++++ | +++ | +++ | ++ | +++ | + | + |
| 55 | V165C + V305M + F360I | +++++ | +++++ | +++++ | ++ | +++ | ++ | + |
| 56 | V165C + V305M + F360V | +++++ | +++++ | +++++ | ++ | ++++ | +++ | + |
| 57 | V165S + V305L + F360L | +++++ | +++++ | +++++ | +++ | +++++ | +++ | + |
| 58 | V165C + L327T + F360I | +++++ | ++++ | +++++ | ++ | +++++ | +++ | + |
| 59 | V165C + L327T + F360V | +++++ | ++++ | +++++ | + | +++++ | +++ | + |
| 60 | V165S + L327T + F360T | ++++ | ++++ | +++++ | +++ | +++ | ++ | + |
| 61 | V165C + I408W + F360V | ++++ | ++++ | ++++ | +++ | +++ | ++++ | + |
| 62 | V165C + I408W + F360T | ++++ | ++++ | ++++ | + | +++ | ++ | + |
| 63 | A167I + V305M + F360L | +++++ | +++++ | +++++ | +++ | +++++ | +++ | + |
| 64 | A167C + V305L + F360V | ++++ | +++++ | +++++ | + | + | ++ | + |
| 65 | A167L + V305M + F360T | ++++ | +++++ | +++++ | +++ | +++++ | +++ | + |
| 66 | A167C + L327T + F360I | ++++ | +++ | ++++ | ++ | ++++ | +++ | + |
| 67 | A167L + L327T + F360M | +++++ | +++++ | +++++ | +++ | +++++ | +++ | + |
| 68 | A167I + L327T + F360V | +++++ | +++++ | +++++ | +++ | +++++ | +++ | + |
| 69 | A167C + I408W + F360I | +++++ | +++++ | +++++ | +++ | +++++ | +++ | + |
| 70 | A167I + I408W + F360V | ++++ | ++++ | ++++ | + | +++ | ++ | + |
| 71 | A167L + I408R + F360L | ++++ | ++++ | ++++ | +++ | ++++ | +++ | + |
| 72 | V305M + L327T + F360I | ++++ | ++ | ++++ | + | ++ | ++ | + |
| 73 | V305L + L327T + F360V | +++++ | +++ | +++++ | + | ++ | +++ | + |
| 74 | V305M + L327T + F360T | +++ | +++ | +++ | ++ | +++ | ++ | + |
| 75 | V305M + I408W + F360I | +++++ | +++++ | +++++ | +++ | +++ | +++ | + |
| 76 | V305M + I408W + F360V | +++++ | +++++ | +++++ | +++ | ++++ | +++ | + |
| 77 | V305L + I408R + F360L | +++++ | +++++ | ++++ | + | ++ | ++ | + |
| 78 | L327T + I408R + F360M | +++++ | +++ | +++++ | ++ | + | +++ | + |
| 79 | L327T + I408W + F360V | +++++ | +++++ | +++++ | +++++ | ++++ | +++++ | ++ |

TABLE 9-continued

| No. | Variant | Tiafenacil | Saflufenacil | Flumioxazin | Fomesafen | Sulfentrazone | Oxyfluorfen | Carfentrazone |
|---|---|---|---|---|---|---|---|---|
| 80 | R89A + V165C + A167C + F360I | +++ | +++ | +++ | ++ | ++ | + | + |
| 81 | R89A + V165S + V305M + F360M | +++++ | +++++ | +++++ | +++ | +++ | ++ | + |
| 82 | R89A + V165C + L327T + F360V | +++ | +++ | ++++ | + | ++ | + | + |
| 83 | R89A + V165S + I408R + F360L | ++++ | ++++ | ++++ | ++ | +++ | ++ | + |
| 84 | R89A + A167L + V305L + F360T | +++ | +++ | ++ | ++ | ++ | ++ | + |
| 85 | R89A + A167L + L327T + F360I | ++++ | ++++ | ++++ | +++ | ++++ | +++++ | ++ |
| 86 | R89A + A167C + I408R + F360M | +++ | +++ | ++++ | ++ | ++ | ++ | + |
| 87 | V165C + A167I + V305M + F360V | ++ | ++ | ++ | + | + | + | + |
| 88 | V165S + A167C + L327T + F360M | ++++ | ++++ | ++++ | ++ | ++++ | ++ | + |
| 89 | V165C + A167C + I408W + F360T | ++++ | ++++ | ++++ | ++ | +++ | ++ | + |
| 90 | A167I + V305L + L327T + F360V | +++++ | ++++ | +++++ | +++ | ++++ | +++ | + |
| 91 | A167L + V305M + I408R + F360M | +++++ | +++++ | +++++ | +++ | +++++ | +++ | + |
| 92 | 305L + L327T + I408W + F360V | +++++ | +++++ | +++++ | +++ | +++++ | +++ | + |

TABLE 10

| No. | CyPPO18 Variants | Tiafenacil | Saflufenacil | Flumioxazin | Fomesafen | Sulfentrazone | Oxyfluorfen | Carfentrazone |
|---|---|---|---|---|---|---|---|---|
| 1 | R89A + F360V | ++++ | ++++ | ++++ | +++ | ++++ | + | ++ |
| 2 | A167L + F360I | ++++ | ++++ | ++++ | +++ | ++++ | + | ++ |
| 3 | V305M + F360I | ++++ | ++++ | ++++ | ++++ | ++++ | ++ | ++ |
| 4 | L327T + F360M | ++++ | +++ | ++++ | ++++ | ++++ | ++ | ++ |
| 5 | R89A + V165C + F360I | +++++ | +++++ | +++++ | ++++ | +++++ | ++ | ++ |
| 6 | V165C + A167L + F360I | +++++ | +++++ | +++++ | ++++ | +++++ | ++ | ++ |

TABLE 10-continued

| No. | CyPPO18 Variants | Tiafenacil | Saflufenacil | Flumioxazin | Fomesafen | Sulfentrazone | Oxyfluorfen | Carfentrazone |
|---|---|---|---|---|---|---|---|---|
| 7 | A167L + V305M + F360M | +++++ | +++++ | +++++ | +++++ | +++++ | ++ | ++ |
| 8 | V165S + A167L + V305M + F360I | +++++ | +++++ | +++++ | +++++ | +++++ | ++ | ++ |
| 9 | R89A + V165S + V305M + F360I | +++++ | +++++ | +++++ | +++++ | +++++ | ++ | ++ |
| 10 | R89A + V165C + A167L + V305M + F360I | +++++ | +++++ | +++++ | +++++ | +++++ | ++ | ++ |

In Tables 9 and 10, the tolerance level of variants showing equivalent resistance to wild type was presented as '−', and was done as '+' per each 10-fold resistance until '+++++' as maximal resistance.

FIGS. 3 to 30 and FIGS. 31 and 32 show the transformed E. coli growth result of CyPPO19 WT and its variants and CyPPO18 WT and its variants, respectively. The concentrations of herbicides were written above the photographs of tolerance test. A 10-fold dilution series of spots were shown from $OD_{600}$=0.5 of the leftmost spot to $OD_{600}$=0.00005 of the rightmost one.

As shown in Tables 9 and 10 and FIGS. 3 to 32, all the BT3 strains transformed with variants of CyPPO19 or CyPPO18 showed significantly higher (at least 10-fold higher) tolerance level than that of wild type against various PPO-inhibiting herbicides.

Example 4. Measurement of PPO Enzyme Activity and $IC_{50}$ Value for Herbicides The enzyme activities of variants wherein amino acids of certain position of PPO protein mutated were measured and inhibition assay with the PPO-inhibiting herbicides was conducted. Although the solubility of PPO protein is markedly low in aqueous condition, it was greatly increased when maltose binding protein (MBP) was fused to PPO protein. Thus, PPO proteins of wild type and variants were expressed as fused to MBP and were used for experiments (FIG. 33).

In order to express wild type and variant proteins of CyPPO19 and CyPPO18 (refer to Examples 1 and 2), those genes were introduced into pMAL-c2× vector (refer to FIG. 1) and was transformed to BL21 CodonPlus (DE3) E. coli, respectively.

The above transformed E. coli were cultured under the following conditions to express PPO proteins:

Induction: $OD_{600}$=0.2, added with 0.3 mM IPTG (final concentration);

Culturing temperature: 23° C., with shaking at 200 rpm;

Culturing duration: 16 hrs;

Culturing volume: 200 ml/1,000 ml flask.

The cultured transformed E. coli cells were lysed and proteins were extracted as following:

Extraction buffer: Column buffer (50 mM Tris-Cl, pH 8.0, 200 mM NaCl) 5 ml buffer/g cell;

Sonication: SONICS & MATERIALS VCX130 (130 watts);

15 sec ON, 10 sec OFF for 5 min on ice;

Centrifugation at 4° C. for 20 minutes (20,000×g);

The supernatant obtained after the centrifugation was diluted at the ratio of 1:6 with column buffer.

The following process for purification of PPO protein was performed in a 4° C. cold room. Amylose resin (New England Biolabs) was packed to 1.5×15 cm column (Bio-Rad, Econo Columns 1.5×15 cm, glass chromatography column, max. vol), and the obtained protein extracts were loaded to the column at a flow rate of 0.2 ml/min. The column was washed with 3 column volumes of buffer and the presence of protein in the washing solution was examined. When the protein was no longer detected, the washing procedure was terminated. Then, the MBP-PPO protein was eluted with approximately 2 column volumes of buffer containing 20 mM maltose. The protein concentration of each eluent was determined and the elution was stopped when the protein was no longer detected. Ten microliters of each fraction was investigated for protein quantification and SDS-PAGE analysis. The highly pure fractions of PPO protein variants were used for the enzyme assay.

Enzyme activities were measured with purified proteins above of wild type and variants of CyPPO19 and CyPPO18 as following:

Firstly, protoporphyrinogen IX was chemically synthesized in the laboratory. Overall process was performed under nitrogen stream. Six micrograms of protoporphyrin IX was dissolved in 20 ml of 20% (v/v) EtOH, and stirred under dark condition for 30 minutes. The obtained protoporphyrin IX solution was put into a 15 ml screw tube in an amount of 1,000 µl, and flushed with nitrogen gas for 5 minutes. To this, 1 g of sodium amalgam was added and vigorously shaken for 2 minutes. The lid was opened to exhaust hydrogen gas in the tube. Thereafter, the lid was closed and incubated for 3 minutes. The protoporphyrinogen IX solution was filtered using syringe and cellulose membrane filter. To 800 µl of the obtained protoporphyrinogen IX solution, approximately 1,600 µl of 2M MOPS [3-(N-morpholino) propanesulfonic acid] was added to adjust pH to 7.5. To determine the enzyme activity of PPO protein, a reaction mixture was prepared with the following composition (based on 10 ml): 50 mM Tris-Cl (pH 7.5); 50 mM NaCl; 0.04% (v/v) Tween 20; 40 mM glucose (0.072 g); 5 units glucose oxidase (16.6 mg); and 10 units catalase (1 µl).

Hundred and eighty microliters of a reaction mixture were placed in 96 well plates and 20 µl of the purified PPO protein (purified product of the MBP-fused PPO protein) above were added. After 50 µl of the mineral oil was layered, the reaction was initiated by adding the substrate, protoporphyrinogen IX solution, to a final concentration of 50 μM. The reaction proceeded at room temperature for 30 min and the fluorescence of protoporphyrin IX was measured using Microplate reader (Sense, Hidex) (excitation: 405 nm; emission: 633 nm). To calculate the PPO enzyme activity, the protoporphyrinogen IX solution was kept open in the air for more than 12 hours to oxidize the solution. To this, 2.7 N HCl was added, and the absorbance at 408 nm was measured. A standard curve was generated using standard protoporphyrin IX, and PPO activity was measured by calibration of protoporphyrin IX using the standard curve of protoporphyrin IX.

The concentration of the PPO-inhibiting herbicides that inhibits the PPO enzyme activity by 50% ($IC_{50}$) was measured for each herbicide. The final concentrations of each herbicide were as follows:

Concentrations of tiafenacil, saflufenacil, fomesafen, flumioxazin, sulfentrazone, oxyfluorfen, and carfentrazone: 0, 10, 50, 100, 250, 500, 1,000, 2,500, 5,000, 10,000 nM The $IC_{50}$ value, the concentration of the herbicide inhibiting the PPO enzyme activity to 50%, was calculated by adding the herbicide of the above concentrations to the reaction mixture.

The $IC_{50}$ values for each herbicide are shown in the following Tables 11 and 12.

TABLE 11

| CyPPO19 WT and variants | $IC_{50}$ values (nM) of CyPPO19 wild type and variants against various herbicides | | | | | | |
| | $IC_{50}$ (nM) | | | | | | |
| | Tiafenacil | Saflufenacil | Flumioxazin | Fomesafen | Sulfentrazone | Oxyfluorfen | Carfentrazone |
| --- | --- | --- | --- | --- | --- | --- | --- |
| WT | 67 | 158 | 55 | 242 | 516 | 570 | 763 |
| 1 R89A | 113 | 616 | 163 | 2,364 | 1,384 | 602 | 857 |
| 2 V165C | 186 | 280 | 159 | 330 | 2,545 | 3,215 | 3,094 |
| 3 V165S | 269 | 277 | 225 | 348 | 1,213 | 1,667 | 10,000 |
| 4 A167C | 342 | 395 | 197 | 843 | 2,240 | 649 | 3,527 |
| 5 A167I | 248 | 799 | 154 | 899 | 3,521 | 1,331 | 10,000 |
| 6 A167L | 597 | 10,000 | 10,000 | 1,755 | 10,000 | 5,261 | 10,000 |
| 7 V305M | 392 | 435 | 437 | 257 | 693 | 732 | 910 |
| 8 V305L | 1,135 | 1,132 | 367 | 466 | 806 | 793 | 1,329 |
| 9 L327T | 2,614 | 761 | 2,599 | 1,035 | 10,000 | 8,612 | 10,000 |
| 10 F360M | 1,328 | 328 | 1,198 | 584 | 10,000 | 4,895 | 2,507 |
| 11 F360I | 4,863 | 1,109 | 10,000 | 492 | 10,000 | 928 | 10,000 |
| 12 F360L | 4,385 | 10,000 | 3,865 | 851 | 10,000 | 754 | 10,000 |
| 13 F360V | 4,791 | 10,000 | 10,000 | 391 | 10,000 | 638 | 10,000 |
| 14 F360T | 10,000 | 10,000 | 10,000 | 10,000 | 10,000 | 10,000 | 10,000 |
| 15 I408R | 1,039 | 10,000 | 696 | 2,097 | 10,000 | 10,000 | 10,000 |
| 16 I408W | 3,001 | 10,000 | 10,000 | 10,000 | 10,000 | 10,000 | 10,000 |
| 17 R89A + F360M | 3,751 | 10,000 | 2,090 | 10,000 | 10,000 | 5,291 | 6,192 |
| 18 V165C + F360M | 10,000 | 10,000 | 7,763 | 10,000 | 10,000 | 5,266 | 10,000 |
| 19 V165S + F360V | 10,000 | 10,000 | 10,000 | 936 | 10,000 | 2,070 | 10,000 |
| 20 A167C + F360I | 10,000 | 10,000 | 10,000 | 871 | 10,000 | 6,011 | 10,000 |
| 21 A167I + F360L | 10,000 | 10,000 | 10,000 | 1,248 | 10,000 | 10,000 | 10,000 |
| 22 A167L + F360M | 10,000 | 10,000 | 10,000 | 3,151 | 10,000 | 10,000 | 10,000 |
| 23 V305M + F360M | 10,000 | 10,000 | 3,104 | 1,077 | 10,000 | 5,044 | 10,000 |
| 24 L327T + F360M | 10,000 | 1,618 | 10,000 | 2,266 | 10,000 | 10,000 | 10,000 |
| 25 V165C + A167C + F360I | 10,000 | 10,000 | 10,000 | 988 | 10,000 | 10,000 | 10,000 |
| 26 V165S + A167L + F360M | 10,000 | 10,000 | 10,000 | 7,003 | 10,000 | 10,000 | 10,000 |
| 27 R89A + L327T + F360M | 10,000 | 10,000 | 10,000 | 10,000 | 10,000 | 10,000 | 10,000 |
| 28 V165C + L327T + F360I | 10,000 | 10,000 | 10,000 | 10,000 | 10,000 | 10,000 | 10,000 |
| 29 A167I + L327T + F360V | 10,000 | 10,000 | 10,000 | 10,000 | 10,000 | 10,000 | 10,000 |
| 30 V305L + L327T + F360M | 10,000 | 10,000 | 10,000 | 10,000 | 10,000 | 10,000 | 10,000 |

TABLE 11-continued

| IC$_{50}$ values (nM) of CyPPO19 wild type and variants against various herbicides | | | | | | | |
|---|---|---|---|---|---|---|---|
| CyPPO19 WT | IC$_{50}$ (nM) | | | | | | |
| and variants | Tiafenacil | Saflufenacil | Flumioxazin | Fomesafen | Sulfentrazone | Oxyfluorfen | Carfentrazone |
| 31 L327T + I408W + F360V | 10,000 | 10,000 | 10,000 | 10,000 | 10,000 | 10,000 | 10,000 |

TABLE 12

| IC$_{50}$ values (nM) of CyPPO18 wild type and variants against various herbicides | | | | | | | |
|---|---|---|---|---|---|---|---|
| CyPPO18 WT | IC$_{50}$ (nM) | | | | | | |
| and variants | Tiafenacil | Saflufenacil | Flumioxazin | Fomesafen | Sulfentrazone | Oxyfluorfen | Carfentrazone |
| WT | 18 | 32 | 13 | 629 | 27 | 103 | 566 |
| 1 R89A | 98 | 1,231 | 106 | 2,853 | 1,566 | 491 | 872 |
| 2 V165C | 95 | 182 | 29 | 1,739 | 104 | 502 | 1,217 |
| 3 V165S | 119 | 89 | 62 | 1,305 | 185 | 1,487 | 2,229 |
| 4 A167C | 94 | 435 | 65 | 1,209 | 762 | 570 | 1,882 |
| 5 A167L | 813 | 1,933 | 1,288 | 2,681 | 649 | 2,812 | 4,015 |
| 6 A167I | 672 | 1,326 | 231 | 1,377 | 792 | 2,004 | 2,602 |
| 7 V305M | 177 | 132 | 107 | 1,251 | 254 | 355 | 1,613 |
| 8 L327T | 233 | 89 | 108 | 1,789 | 256 | 3,599 | 723 |
| 9 F360M | 130 | 1,618 | 99 | 1,646 | 118 | 329 | 2,181 |
| 10 F360I | 822 | 4,093 | 3,287 | 3,711 | 203 | 455 | 3,928 |
| 11 F360L | 195 | 5,000 | 1,188 | 2,712 | 356 | 538 | 2,512 |
| 12 F360V | 336 | 5,000 | 882 | 1,934 | 175 | 299 | 4,237 |
| 13 R89A + F360M | 1,002 | 5,000 | 1,288 | 5,000 | 5,000 | 5,000 | 5,000 |
| 14 A167L + F360M | 5,000 | 5,000 | 5,000 | 5,000 | 5,000 | 5,000 | 5,000 |
| 15 L327T + F360M | 5,000 | 1,662 | 3,841 | 5,000 | 855 | 5,000 | 5,000 |
| 16 V165C + A167L + F360M | 5,000 | 5,000 | 5,000 | 5,000 | 4,483 | 5,000 | 5,000 |
| 17 V165S + A167C + L327T + F360M | 5,000 | 5,000 | 5,000 | 5,000 | 5,000 | 5,000 | 5,000 |
| 18 R89A + V165S + A167C + L327T + F360M | 5,000 | 5,000 | 5,000 | 5,000 | 5,000 | 5,000 | 5,000 |

(In the above Tables 11 and 12, IC$_{50}$ value '5,000' or IC$_{50}$ value '10,000' means equivalent to or higher than IC$_{50}$ value of 5,000 or IC$_{50}$ value of 10,000 because the enzyme activity was not inhibited by 50% even at each herbicide concentration of 5,000 nM or 10,000 nM)

As shown in the Tables 11 and 12, it was demonstrated that variants of CyPPO proteins showed the significantly increased IC$_{50}$ values against each herbicide compared to the wild type. Such results indicate that herbicide tolerance was increased by amino acid substitutions at specified positions of PPO protein. Although the data showed that CyPPO protein variants possess reduced enzyme activity compared to the wild type, it might be caused by the difference of protein folding and hydrophobicity between proteins. Plant-originated PPO protein is localized in the chloroplast membrane and hydrophobic, however recombinant PPO protein fused to MBP is hydrophilic. Therefore, when PPO variants are properly assembled and expressed in plant chloroplasts, the enzyme activity would not be different between variants and wild type drastically.

Example 5. PPO Protein Variants Originated from Various *Cyanobacteria*, Algae, or Bacteria Based on the mutation positions of CyPPO19 and CyPPO18 whose effect on resistance increase was verified in the examples 3 and 4 above, the mutation sites of PPO proteins originated from various cyanobacteria, algae, or bacteria which have similar effect on herbicide resistance to variants of CyPPO19 and CyPPO18 were analyzed via the analysis of their 3D protein structure and are listed in Table 13:

TABLE 13

| SEQ ID NO | Amino acid after mutation (substitution) at the mutated site | Mutated Site | | | | | | Accession No. |
|---|---|---|---|---|---|---|---|---|
| | | 1 A | 2 C or S | 3 C, I, or L | 4 M or L | 5 T | 6 M, I, L, T, or V | |
| 1 | *Thermosynechococcus elongatus* PKUAC-SCTE542 | R89 | V165 | A167 | V305 | L327 | F360 | CP032152.1 |
| 2 | Cyanobacteria bacterium J003 | R89 | V165 | A167 | V305 | L327 | F360 | RMH63851.1 |
| 3 | *Thermosynechococcus vulcanus* NIES-2134 | R89 | V165 | A167 | V305 | L327 | F360 | BAY51976.1 |
| 4 | *Synechococcus lividus* | R92 | V168 | A170 | V312 | L334 | F367 | WP_099798264.1 |
| 5 | Microcoleaceae bacterium UBA10368 | R93 | V174 | A176 | V319 | L341 | Y374 | HBK97224.1 |
| 6 | Microcoleaceae bacterium UBA11344 | R87 | V168 | A170 | V313 | L335 | Y368 | HAT14741.1 |
| 7 | Oscillatoriales cyanobacterium (TAE85894.1) | R92 | V173 | A175 | V327 | L349 | Y382 | TAE85894.1 |
| 8 | Cyanobacteria bacterium UBA8156 | R92 | V166 | A168 | V309 | L331 | F364 | HAN47127.1 |
| 9 | *Rubidibacter lacunae* | R86 | V160 | A162 | V309 | L331 | F364 | WP_022605844.1 |
| 10 | *Hydrocoleum* sp. CS-953 | R92 | V171 | A173 | V317 | L339 | F372 | WP_094676324.1 |
| 11 | Oscillatoriales cyanobacterium (TAE55813.1) | R92 | V173 | A175 | V327 | L349 | Y382 | TAE55813.1 |
| 12 | *Crinalium epipsammum* | R85 | V166 | A168 | V312 | L334 | F367 | WP_015202233.1 |
| 13 | Oscillatoriales cyanobacterium (TAE70643.1) | R92 | V173 | A175 | V327 | L349 | Y382 | TAE70643.1 |
| 14 | Oscillatoriales cyanobacterium (TAE14532.1) | R92 | V173 | A175 | V327 | L349 | Y382 | TAE14532.1 |
| 15 | Cyanobacteria bacterium QS_8_64_29 | R85 | V166 | A168 | V312 | L334 | F367 | PSP16006.1 |
| 16 | *Lyngbya aestuarii* | R93 | V174 | A176 | V320 | L342 | Y375 | WP_023067908.1 |
| 17 | *Tychonema bourrellyi* | R93 | V174 | A176 | V319 | L341 | F374 | WP_096831359.1 |
| 18 | Oscillatoriales cyanobacterium (TAG91209.1) | R93 | V174 | A176 | V319 | L341 | Y374 | TAG91209.1 |
| 19 | Cyanobacteria bacterium SW_9_44_58 | R85 | V160 | A162 | V308 | L330 | F363 | PSO49761.1 |
| 20 | *Trichodesmium erythraeum* | R92 | V173 | A175 | V319 | L341 | Y374 | WP_011611816.1 |
| 21 | *Geitlerinema* sp. PCC 9228 | R105 | V180 | A182 | V332 | L355 | F388 | WP_071516524.1 |
| 22 | Oscillatoriales cyanobacterium (TAD79992.1) | R104 | V185 | A187 | V334 | L356 | F389 | TAD79992.1 |
| 23 | Oscillatoriales cyanobacterium (TAD82603.1) | R93 | V174 | A176 | V319 | L341 | Y374 | TAD82603.1 |
| 24 | Oscillatoriales cyanobacterium (TAD95528.1) | R93 | V174 | A176 | V319 | L341 | Y374 | TAD95528.1 |
| 25 | *Limnothrix* sp. PR1529 | R88 | V169 | A171 | V318 | L340 | F373 | WP_099534595.1 |
| 26 | *Planktothricoides* sp. SR001 | R102 | V183 | A185 | V329 | L352 | F385 | WP_054468037.1 |
| 27 | *Limnothrix* sp. CACIAM 69d | R88 | V169 | A171 | V318 | L340 | F373 | RFP59749.1 |
| 28 | *Okeania hirsuta* (WP_124155207.1) | R92 | V172 | A174 | V318 | L340 | F373 | WP_124155207.1 |
| 29 | *Okeania hirsuta* (WP_124145785.1) | R92 | V172 | A174 | V318 | L340 | F373 | WP_124145785.1 |

TABLE 13-continued

| SEQ ID NO | Amino acid after mutation (substitution) at the mutated site | Mutated Site | | | | | | Accession No. |
|---|---|---|---|---|---|---|---|---|
| | | 1 A | 2 C or S | 3 C, I, or L | 4 M or L | 5 T | 6 M, I, L, T, or V | |
| 30 | *Desertifilum* sp. IPPAS B-1220 | R96 | V177 | A179 | V324 | L346 | Y379 | WP_069967861.1 |
| 31 | *Synechococcus* sp. 65AY6Li | R105 | V179 | A181 | V322 | L344 | F377 | PIK93057.1 |
| 32 | *Synechococcus* sp. 65AY6A5 | R105 | V179 | A181 | V322 | L344 | F377 | PIK88626.1 |
| 33 | *Synechococcus* sp. 60AY4M2 | R105 | V179 | A181 | V322 | L344 | F377 | PIK94415.1 |
| 34 | *Synechococcus* sp. 63AY4M1 | R105 | V179 | A181 | V322 | L344 | F377 | PIK96673.1 |
| 35 | *Synechococcus* sp. 63AY4M2 | R105 | V179 | A181 | V322 | L344 | F377 | PIK85371.1 |
| 36 | Cyanobacteria bacterium J007 | R100 | V177 | A179 | V323 | L345 | F378 | RMH78328.1 |
| 37 | *Spirulina major* | R85 | V166 | A168 | V311 | L333 | F366 | WP_072619201.1 |
| 38 | *Euhalothece* sp. KZN 001 | R85 | V160 | A162 | V306 | L328 | F361 | PNW65677.1 |
| 39 | *Dactylococcopsis salina* | R85 | V160 | A162 | V306 | L328 | F361 | WP_015230904.1 |
| 40 | *Synechococcus* sp. PCC 7336 | R89 | V163 | A165 | V306 | L328 | Y361 | WP_017328280.1 |
| 41 | *Arthrospira* sp. O9.13F | R93 | V174 | A176 | V320 | L342 | Y375 | WP_111891435.1 |
| 42 | *Arthrospira platensis* (WP_006622155.1) | R93 | V174 | A176 | V320 | L342 | Y375 | WP_006622155.1 |
| 43 | *Arthrospira platensis* (WP_006617829.1) | R93 | V174 | A176 | V321 | L343 | Y376 | WP_006617829.1 |
| 44 | *Pseudanabaena* sp. BC1403 | R98 | V172 | A174 | V318 | L340 | F373 | WP_103669271.1 |
| 45 | *Pseudanabaena* sp. 'Roaring Creek' | R97 | V171 | A173 | V316 | L338 | F371 | WP_055076288.1 |
| 46 | *Pseudanabaena* sp. (HBC40803.1) | R98 | V172 | A174 | V319 | L341 | F374 | HBC40803.1 |
| 47 | *Synechococcus* sp. JA-2-3B'a(2-13) | R106 | V180 | A182 | V343 | L365 | F398 | WP_049749573.1 |
| 48 | *Pseudanabaena biceps* | R97 | V171 | A173 | V317 | L339 | F372 | WP_009629673.1 |
| 49 | *Pseudanabaena* sp. (PZV12410.1) | R98 | V172 | A174 | V318 | L340 | F373 | PZV12410.1 |
| 50 | *Pseudanabaena* sp. PCC 7367 | R104 | V178 | A180 | V336 | L358 | F391 | WP_015165508.1 |
| 51 | *Pseudanabaena* sp. SR411 | R98 | V172 | A174 | V319 | L341 | F374 | WP_094530677.1 |
| 52 | *Pseudanabaena frigida* | R98 | V172 | A174 | V318 | L340 | F373 | PZO41121.1 |
| 53 | *Pseudanabaena* sp. (PZU98053) | R99 | V173 | A175 | V320 | L342 | F375 | PZU98053 |
| 54 | Oscillatoriales cyanobacterium CG2_30_44_21 | R106 | V180 | A182 | V327 | L349 | F382 | OIP76421.1 |
| 55 | *Chlamydomonas reinhardtii* | R167 | V241 | A243 | V389 | L418 | Y451 | AF068635.1 |
| 56 | *Volvox carteri* f. *nagariensis* | R168 | V242 | A244 | V389 | L418 | Y451 | XM_002955148.1 |
| 57 | *Chondrus crispus* (CHC_T00000813001) | R106 | V181 | A183 | V328 | L350 | Y383 | XM_005718155.1 |
| 58 | *Galdieria sulphuraria* | R167 | V242 | A244 | V399 | L421 | Y454 | XM_005708373.1 |
| 59 | *Pseudanabaena* sp. ABRG5-3 | R98 | V172 | A174 | V319 | L341 | F374 | WP_126386150.1 |
| 60 | *Arthrospira platensis* YZ | R93 | V174 | A176 | V321 | L343 | Y376 | WP_014277531.1 |
| 61 | *Gloeobacter kilaueensis* JS1 | R94 | V167 | A169 | V301 | L323 | F356 | WP_023175091 |
| 62 | *Gloeobacter violaceus* PCC 7421 | R91 | M164 | A166 | V298 | L320 | F353 | WP_011140945 |
| 63 | *Panicum hallii* var. *hallii* | R145 | V219 | A221 | V366 | L394 | Y427 | PUZ57154.1 |
| 64 | *Porphyra umbilicalis* | R157 | V232 | A234 | V381 | L403 | Y436 | OSX75961.1 |

TABLE 13-continued

| SEQ ID NO | Amino acid after mutation (substitution) at the mutated site | Mutated Site | | | | | | Accession No. |
|---|---|---|---|---|---|---|---|---|
| | | 1 A | 2 C or S | 3 C, I, or L | 4 M or L | 5 T | 6 M, I, L, T, or V | |
| 65 | *Ostreococcus tauri* | R124 | V198 | A200 | V349 | L380 | Y415 | XP_003079975.1 |
| 66 | *Ectocarpus siliculosus* | R144 | V220 | A222 | V374 | L396 | Y429 | CBJ31610.1 |
| 67 | *Nannochloropsis gaditana* CCMP526 | R87 | V162 | A164 | V311 | L333 | Y365 | XM_005854685.1 |
| 68 | *Ostreococcus lucimarinus* CCE9901 | R67 | V141 | A143 | V288 | L319 | Y354 | XM_001418241.1 |
| 69 | *Guillardia theta* CCMP2712 | R159 | V233 | A235 | V381 | L414 | Y447 | XM_005821253.1 |
| 70 | *Cyanidioschyzon merolae* strain 10D | R168 | V259 | A261 | V413 | L435 | Y468 | XM_005535077.1 |
| 71 | *Bathycoccus prasinos* | R152 | V227 | A229 | V378 | L409 | Y444 | XM_007513261.1 |
| 72 | *Myxococcus Xanthus* Synthetic construct | R94 | I168 | A170 | I311 | L332 | M365 | AY916795.1 |
| 73 | *Myxococcus virescens* | R94 | I168 | A170 | I310 | L331 | M364 | WP_090484749.1 |
| 74 | *Myxococcus macrosporus* DSM 14697 | R86 | I159 | A161 | I304 | L325 | M358 | ATB45699.1 |
| 75 | *Myxococcus hansupus* | R94 | I168 | A170 | I310 | L331 | M364 | WP_044889345.1 |
| 76 | *Myxococcus fulvus* | R85 | I159 | A161 | I305 | L326 | M359 | WP_046711394.1 |
| 77 | *Myxococcus fulvus* | R85 | I159 | A161 | I305 | L326 | M359 | WP_074949681.1 |
| 78 | *Myxococcus stipitatus* | R85 | I159 | A161 | I303 | L324 | M357 | WP_015346914.1 |
| 79 | *Hyalangium minutum* | A86 | I160 | A162 | I305 | L326 | M359 | WP_044193071.1 |

Example 6. Generation of *Arabidopsis thaliana* Transformants Using CyPPOs and Variants, and PPO-Inhibiting Herbicide Tolerance Test 6-1. Construction of *A. thaliana* Transformation Vectors and Generation of *A. thaliana* Transformants

*A. thaliana* was transformed with a binary vector having ORF of a selectable marker, Bar gene (glufosinate-tolerant gene), and ORF of each variant gene of CyPPO19 and CyPPO18. The transgenic plant was examined for cross-tolerance towards glufosinate and PPO-inhibiting herbicides. The bar gene was also used to examine whether the transgene was stably inherited during generations. NOS promoter and E9 terminator were used for bar gene expression.

In order to express proteins of CyPPO19, CyPPO19 variants, CyPPO18, and CyPPO18 variants in plants, a CaMV35S promoter and a NOS terminator were used. Encoding genes of CyPPO19, CyPPO19 variants, CyPPO18, and CyPPO18 variants were amplified by using PCR with primer pairs in Table 14, and then introduced into binary vector using XhoI and BamHI restriction enzymes.

TABLE 14

Primer sequence

| Primer | Sequence (5'→3') | SEQ ID NO |
|---|---|---|
| CyPPO19_XhoI_F | CTCGAGATGTCTGAGGTGGACGTT GCC | 297 |

TABLE 14-continued

Primer sequence

| Primer | Sequence (5'→3') | SEQ ID NO |
|---|---|---|
| CyPPO19_BamHI_R | GGATCCAGGTTGGCCCCCGGAAAG ATA | 298 |
| CyPPO18_XhoI_F | CTCGAGATGATTGAAGTGGATGTG GCT | 299 |
| CyPPO18_BamHI_R | GGATCCTGATTGTCCACCAGCGAG | 300 |

Furthermore, for confirmation of the protein expression, hemagglutinin (HA) tag was fused to the 3'-terminal region of PPO protein coding gene using BamHI and SacI restriction enzymes. A NOS terminator was inserted to 3'-terminus of HA tag, to induce transcription termination of PPO gene. In addition, in order to transit protein to chloroplast, transit peptide (TP) gene (SEQ ID NO: 301) of AtPPO1 gene (SEQ ID NO: 302) was fused to 5'-terminal region of PPO protein coding gene using XbaI and XhoI restriction enzymes.

Each constructed vector was transformed to *Agrobacterium tumefaciens* GV3101 competent cell by freeze-thaw method. *Agrobacterium* GV3101 competent cells were prepared by following procedures, *Agrobacterium* GV3101 strain was cultured in 5 ml LB media at 30° C., 200 rpm for 12 hrs. The cells were subcultured in 200 ml of LB media at 30° C., 200 rpm for 3 to 4 hrs, and centrifuged at 3,000×g at 4° C. for 20 minutes. The cell pellet was washed with sterile distilled water, and then resuspended in 20 ml of LB media. Snap frozen 200 µl aliquots with liquid nitrogen were stored in a deep freezer.

Each transformed *Agrobacterium* was screened in spectinomycin-containing LB media. The screened colony was cultured in LB broth. After *Agrobacterium* cell was harvested from the culture media, it was resuspended in the solution containing 5% sucrose (w/v) and 0.05% Silwet L-77 (v/v) (Momentive Performance Materials Co., Ltd.) at an absorbance ($OD_{600}$) of 0.8. By floral dipping method, *A. thaliana* wild type (Col-0) was transformed, and then the seeds ($T_1$) were harvested after 1 to 2 months.

Transgenic plants were screened with glufosinate tolerance which was conferred by Bar gene expression in the binary vector. The obtained $T_1$ seeds were shown in ½ MS media (2.25 g/l MS salt, 10 g/l sucrose, 7 g/l Agar) supplemented with 50 μM glufosinate, and the surviving plants were selected 7 days after sowing. They were, then, transplanted into soil and grown to obtain $T_1$ plants.

In order to examine PPO-inhibiting herbicide tolerance of the transgenic plants, 3 to 4-week-old plants were evenly sprayed with herbicide (100 ml of 1 μM tiafenacil and 0.05% Silwet L-77 (v/v)) in 40×60 cm area (0.24 m$^2$). While wild type *A. thaliana* (Col-0) completely died within 7 days after treatment of tiafenacil at the same concentration, each transgenic plant showed to PPO-inhibiting herbicide treatment and survived.

The $T_2$ seeds were harvested from tolerant and surviving $T_1$ transgenic plants and were shown to ½ MS media (2.25 g/l MS salt, 10 g/l sucrose, 7 g/l Agar) supplemented with 50 μM glufosinate. One week later, surviving plants were transplanted to soil.

6-2. Verification of Herbicide Tolerance of Transformed *Arabidopsis* Plants ($T_2$)

*Arabidopsis* plants ($T_2$) transformed with genes including CyPPO19, CyPPO19 variants (F360M, F360V, F360L, V165C+F360M, V165S+F360V), CyPPO18, or CyPPO18 variant (L327T+F360M) were tested for their tolerance against herbicides.

In order to examine PPO-inhibiting herbicide tolerance of the transgenic plants, transgenic plants of CyPPO19 WT and its variants (F360M, F360V, F360L, V165C+F360M, V165S+F360V) were evenly sprayed with herbicide (100 ml of 1 μM tiafenacil and 0.05% Silwet L-77 (v/v))/(100 ml of 1 μM flumioxazin and 0.05% Silwet L-77 (v/v)) in 40×60 cm area (0.24 m$^2$). Herbicide tolerance was evaluated 7 days after treatment. Wild type *Arabidopsis* plant (Col-0) was used as a control.

The tolerance evaluation of transgenic *Arabidopsis* ($T_2$) plants after 1 μM tiafenacil or 1 μM flumioxazin treatment was shown in FIGS. 34 and 35.

In order to examine PPO-inhibiting herbicide tolerance of the transgenic plants, transgenic plants of CyPPO19 variants (F360M, F360V, F360L, V165C+F360M, V165S+F360V) were evenly sprayed with herbicide (100 ml of 5 μM tiafenacil and 0.05% Silwet L-77 (v/v))/(100 ml of 5 μM flumioxazin and 0.05% Silwet L-77 (v/v)) in 40×60 cm area (0.24 m$^2$). Herbicide tolerance was evaluated 7 days after treatment. Wild type *Arabidopsis* plant (Col-0) was used as a control.

The tolerance evaluation of transgenic *Arabidopsis* ($T_2$) plants after 5 μM tiafenacil or 5 μM flumioxazin treatment was shown in FIGS. 36 and 37.

In order to examine PPO-inhibiting herbicide tolerance of the transgenic plants, transgenic plants of CyPPO18 wild type were evenly sprayed with herbicide (100 ml of 1 μM tiafenacil and 0.05% Silwet L-77 (v/v)) in 40×60 cm area (0.24 m$^2$). Herbicide tolerance was evaluated 7 days after treatment. Wild type *Arabidopsis* plant (Col-0) was used as a control.

The tolerance evaluation of transgenic *Arabidopsis* ($T_2$) plants after 1 μM tiafenacil treatment was shown in FIG. 38.

In order to examine PPO-inhibiting herbicide tolerance of the transgenic plants, transgenic plants of CyPPO18 variant (L327T+F360M) were evenly sprayed with herbicide (100 ml of 1 μM tiafenacil and 0.05% Silwet L-77 (v/v)) in 40×60 cm area (0.24 m$^2$). Herbicide tolerance was evaluated 7 days after treatment. Wild type *Arabidopsis* plant (Col-0) was used as a control.

The tolerance evaluation of transgenic *Arabidopsis* ($T_2$) plants after 1 μM tiafenacil treatment was shown in FIG. 39.

Based on the results shown in FIGS. 34 to 39, herbicide tolerance of transgenic plants was evaluated with Injury index defined in Table 15.

TABLE 15

| Injury index definition | |
| --- | --- |
| Injury index | Symptom |
| 1 | 1 |
| 0 | No damage |
| 1 | Dried leaf tip |
| 2 | Over 20% and less than 30% of the plant was scorched |
| 2.5 | Over 30% and less than 50% of the plant was scorched |
| 3 | Over 50% and less than 70% of the plant was scorched |
| 4 | Over 70% of the plant was scorched |
| 5 | The whole plant was dried and died |

The tolerance levels of transgenic plants were evaluated according to the injury index definition and were shown in Tables 16 to 19.

TABLE 16

Injury index of transgenic plants of CyPPO19 WT and its variants (F360M, F360V, F360L, V165C + F360M, V165S + F360V) after 1 μM tiafenacil or 1 μM flumioxazin treatment

|  | Injury index | |
| --- | --- | --- |
|  | 1 μM tiafenacil | 1 μM flumioxazin |
| Col-0 | 5 | 5 |
| CyPPO19 WT | 3 | 2 |
| CyPPO19 F360M | 0-1 | 0-1 |
| CyPPO19 F360V | 0-1 | 0-1 |
| CyPPO19 F360L | 1 | 1 |
| CyPPO19 V165C + F360M | 0-1 | 0-1 |
| CyPPO19 V165S + F360V | 0-1 | 0-1 |

TABLE 17

Injury index of transgenic plants of CyPPO19 variants (F360M, F360V, F360L, V165C + F360M, V165S + F360V) after 5 μM tiafenacil or 5 μM flumioxazin treatment

|  | Injury index | |
| --- | --- | --- |
|  | 5 μM tiafenacil | 5 μM flumioxazin |
| Col-0 | 5 | 5 |
| CyPPO19 F360M | 1 | 1 |
| CyPPO19 F360V | 0-1 | 0-1 |
| CyPPO19 F360L | 1 | 1 |
| CyPPO19 V165C + F360M | 0-1 | 0-1 |
| CyPPO19 V165S + F360V | 0-1 | 0-1 |

TABLE 18

Injury index of transgenic plants of CyPPO18 WT after 1 μM tiafenacil treatment

|  | Injury index 1 μM tiafenacil |
| --- | --- |
| Col-0 | 5 |
| CyPPO18 WT | 3-4 |

TABLE 19

Injury index of transgenic plants of CyPPO18 variant (L327T + F360M) after 1 μM tiafenacil treatment

|  | Injury index 1 μM tiafenacil |
| --- | --- |
| Col-0 | 5 |
| CyPPO18 L327T + F360M | 0-1 |

As demonstrated by the above results, transgenic plants transformed with CyPPO19 WT or CyPPO18 WT exhibit increased herbicide tolerance compared to non-transgenic plants. In addition, transgenic plants transformed with CyPPO19 variants or CyPPO18 variant exhibit significantly increased herbicide tolerance compared to non-transgenic plants.

---

The invention claimed is:

1. A polypeptide comprising an amino acid sequence of modified SEQ ID NO: 1, comprising at least one amino acid mutation selected from the group consisting of:

(i) F360M, F360V, F360I, F360T or F360L, (ii) A167C, A167L, or A167I, (iii) V305M or V305L, (iv) R89A, (v) V165S or V165C, (vi) L327T, and (vii) I408R, or I408W, in the amino acid sequence of SEQ ID NO: 1.

2. A polynucleotide encoding the polypeptide of claim 1.

3. A recombinant vector comprising the polynucleotide of claim 2.

4. A recombinant cell comprising the recombinant vector of claim 3.

5. A composition for conferring or enhancing herbicide tolerance of a plant or algae, comprising one or more selected from the group consisting of:

(1) the polypeptide of claim 3;

(2) a polynucleotide encoding the polypeptide of (1);

(3) a recombinant vector comprising the polynucleotide of (2); and (4) a recombinant cell comprising the recombinant vector of (3).

6. The composition of claim 5, wherein the herbicide is an herbicide inhibiting protoporphyrinogen IX oxidase.

7. The composition of claim 5, wherein the herbicide is at least one selected from the group consisting of pyrimidinediones, diphenyl-ethers, phenylpyrazoles, N-phenylphthalimides, phenylesters, thiadiazoles, oxadiazoles, triazinone, triazolinones, oxazolidinediones, pyraclonil, flufenpyrethyl, and profluazol.

8. The composition of claim 5, wherein the herbicide is at least one selected from the group consisting of butafenacil, saflufenacil, benzfendizone, tiafenacil, fomesafen, oxyfluorfen, aclonifen, acifluorfen, bifenox, ethoxyfen, lactofen, chlomethoxyfen, chlorintrofen, fluoroglycofen-ethyl, halosafen, pyraflufen-ethyl, fluazolate, flumioxazin, cinidon-ethyl, flumiclorac-pentyl, fluthiacet, thidiazimin, oxadiargyl, oxadiazon, carfentrazone, sulfentrazone, trifludimoxazin, azafenidin, pentoxazone, pyraclonil, flufenpyrethyl, profluazol, phenopylate, carbamate analogues of phenopylate, and agriculturally acceptable salt thereof.

9. The composition of claim 5, wherein the plant or algae further comprises a second herbicide-tolerant polypeptide or a gene encoding the same, and its tolerance to the second herbicide is conferred or enhanced.

10. The composition of claim 9, wherein the second herbicide is selected from the group consisting of glyphosate, glufosinate, dicamba, 2,4-D (2,4-Dichlorophenoxyacetic acid), isoxaflutole, ALS (acetolactate synthase)-inhibiting herbicide, photosystem II-inhibiting herbicide, phenylurea-based herbicide, bromoxynil-based herbicide, and combinations thereof.

11. The composition of claim 9, wherein the second herbicide-tolerant polypeptide is one or more selected from the group consisting of:

glyphosate herbicide-tolerant EPSPS (glyphosate resistant 5-enolpyruvylshikimate-3-phosphate synthase), GOX (glyphosate (glyphosate-N-acetyltransferase) or glyphosate decarboxylase; oxidase), GAT glufosinate herbicide-tolerant PAT (phosphinothricin-N-acetyltransferase);

dicamba herbicide-tolerant DMO (dicamba monooxygenase);

2,4-D (2,4-dichlorophenoxyacetic acid) herbicide-tolerant 2,4-D monooxygenase or AAD (aryloxyalkanoate dioxygenase);

ALS (acetolactate synthase)-inhibiting sulfonylurea-based herbicide-tolerant ALS (acetolactate synthase), AHAS (acetohydroxyacid synthase) or AtAHASL (*Arabidopsis thaliana* acetohydroxyacid synthase large subunit);

photosystem II-inhibiting herbicide-tolerant photosystem II protein D1;

phenylurea herbicide-tolerant Cytochrome P450;

plastid-inhibiting herbicide-tolerant HPPD (hydroxyphenylpyruvate dioxygenase);

bromoxynil herbicide-tolerant nitrilase; and combinations thereof.

12. The composition of claim 9, wherein the gene encoding the second herbicide-tolerant polypeptide is one or more selected from the group consisting of:

glyphosate herbicide-tolerant cp4 epsps, mepsps, 2mepsps, goxv247, gat4601 or gat4621 gene;

glufosinate herbicide-tolerant BAR or PAT gene;

dicamba herbicide-tolerant dmo gene;

2,4-D (2,4-dichlorophenoxyacetic acid) herbicide-tolerant AAD-1 or AAD-12 gene;

isoxaflutole herbicide-tolerant HPPDPF W336 gene;

sulfonylurea herbicide-tolerant ALS, Csr1, Csr1-1, Csr1-2, GM-HRA, S4-HRA, Zm-HRA, SurA or SurB gene;

photosystem II-inhibiting herbicide-tolerant psbA gene;

phenylurea herbicide-tolerant CYP76B1 gene;

bromoxynil herbicide-tolerant bxn gene; and combinations thereof.

13. A transformant of a plant or algae having herbicide tolerance, or a clone or progeny thereof, comprising (1) the polypeptide of claim 1, or (2) a polynucleotide encoding the polypeptide of (1).

14. The transformant, clone, or progeny thereof of claim 13, wherein the transformant is an alga, or a cell, protoplast, callus, hypocotyl, seed, cotyledon, shoot, or whole body of a plant.

15. A method of preparing a transgenic plant or algae having herbicide tolerance, the method comprising introducing (1) the polypeptide of claim 3, or (2) a polynucleotide encoding the polypeptide of (1), into an alga, or a cell, protoplast, callus, hypocotyl, seed, cotyledon, shoot, or whole body of a plant.

16. A method of conferring or enhancing herbicide tolerance of a plant or algae, the method comprising introducing (1) the polypeptide of claim 3, or (2) a polynucleotide encoding the polypeptide of (1), into an alga, or a cell, protoplast, callus, hypocotyl, seed, cotyledon, shoot, or whole body of a plant.

17. A method of controlling weeds in a cropland, the method comprising:

providing the cropland with a plant comprising (1) the polypeptide of claim 1, or (2) a polynucleotide encoding the polypeptide of (1), and applying an effective dosage of protoporphyrinogen IX oxidase-inhibiting herbicide to the cropland or the plant.

18. The method of claim 17, wherein the step of applying an effective dosage of protoporphyrinogen IX oxidase-inhibiting herbicide to the cropland is performed by applying an effective dosage of two or more kinds of protoporphyrinogen IX oxidase-inhibiting herbicides sequentially or simultaneously.

19. The method of claim 17, wherein the plant further comprises a second herbicide-tolerant polypeptide or a gene encoding the same, and the step of applying an effective dosage of protoporphy-rinogen IX oxidase-inhibiting herbicide to the cropland is performed by applying effective dosages of the protoporphyrinogen IX oxidase-inhibiting herbicide and a second herbicide are applied sequentially or simultaneously.

20. A method of removing an undesired aquatic organism from a culture media, the method comprising:

providing a culture media with algae comprising (1) the polypeptide of claim 1, or (2) a polynucleotide encod-ing the polypeptide of (1), and applying an effective dosage of protoporphyrinogen IX oxidase-inhibiting herbicide to the culture media.

\* \* \* \* \*